United States Patent
Graham et al.

(10) Patent No.: US 11,970,735 B2
(45) Date of Patent: *Apr. 30, 2024

(54) NUCLEOTIDE CLEAVABLE LINKERS AND USES THEREOF

(71) Applicant: Singular Genomics Systems, Inc., La Jolla, CA (US)

(72) Inventors: Ronald Graham, Carlsbad, CA (US); Olga Adelfinskaya, San Marcos, CA (US); Megha Cila, San Diego, CA (US); Rodrigo Rodriguez, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 491 days.

This patent is subject to a terminal disclaimer.

(21) Appl. No.: 17/417,332

(22) PCT Filed: Jan. 7, 2020

(86) PCT No.: PCT/US2020/012595
§ 371 (c)(1),
(2) Date: Jun. 22, 2021

(87) PCT Pub. No.: WO2020/146397
PCT Pub. Date: Jul. 16, 2020

(65) Prior Publication Data
US 2022/0127299 A1  Apr. 28, 2022
US 2022/0332752 A2  Oct. 20, 2022

Related U.S. Application Data

(60) Provisional application No. 62/841,168, filed on Apr. 30, 2019, provisional application No. 62/789,879, filed on Jan. 8, 2019.

(51) Int. Cl.
| | |
|---|---|
| C12Q 1/6869 | (2018.01) |
| C07F 9/655 | (2006.01) |
| C07H 19/06 | (2006.01) |
| C07H 19/10 | (2006.01) |
| C07H 19/14 | (2006.01) |
| C07H 19/16 | (2006.01) |
| C07H 19/20 | (2006.01) |
| C12N 9/12 | (2006.01) |
| C12Q 1/6806 | (2018.01) |

(52) U.S. Cl.
CPC ........ *C12Q 1/6869* (2013.01); *C07F 9/65515* (2013.01); *C07H 19/06* (2013.01); *C07H 19/10* (2013.01); *C07H 19/14* (2013.01); *C07H 19/16* (2013.01); *C07H 19/20* (2013.01); *C12N 9/1241* (2013.01); *C12Q 1/6806* (2013.01); *C12Q 2334/40* (2013.01); *C12Q 2521/101* (2013.01); *C12Q 2525/101* (2013.01); *C12Q 2535/00* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 5,804,386 A | 9/1998 | Ju |
| 5,814,454 A | 9/1998 | Ju |
| 5,876,936 A | 3/1999 | Ju |
| 5,952,180 A | 9/1999 | Ju |
| 6,046,005 A | 4/2000 | Ju et al. |
| 6,485,944 B1 | 11/2002 | Church et al. |
| 6,627,748 B1 | 9/2003 | Ju et al. |
| 6,664,079 B2 | 12/2003 | Ju et al. |
| 7,074,597 B2 | 7/2006 | Ju |
| 7,279,563 B2 | 10/2007 | Kwiatkowski |
| 7,345,159 B2 | 3/2008 | Ju et al. |
| 7,414,116 B2 | 8/2008 | Milton et al. |
| 7,541,444 B2 | 6/2009 | Milton et al. |
| 7,566,537 B2 | 7/2009 | Barnes et al. |
| 7,622,279 B2 | 11/2009 | Ju |
| 7,635,578 B2 | 12/2009 | Ju et al. |
| 7,713,698 B2 | 5/2010 | Ju et al. |
| 7,771,973 B2 | 8/2010 | Milton et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,071,739 B2 | 12/2011 | Milton et al. |
| 8,088,575 B2 | 1/2012 | Ju et al. |
| 8,114,973 B2 | 2/2012 | Siddiqi et al. |
| 8,298,792 B2 | 10/2012 | Ju et al. |
| 8,399,188 B2 | 3/2013 | Zhao et al. |
| 8,597,881 B2 | 12/2013 | Milton et al. |
| 8,796,432 B2 | 8/2014 | Ju et al. |
| 8,889,348 B2 | 11/2014 | Ju |
| 8,900,810 B2 | 12/2014 | Gordon et al. |
| 9,115,163 B2 | 8/2015 | Ju et al. |
| 9,121,060 B2 | 9/2015 | Milton et al. |
| 9,121,062 B2 | 9/2015 | Balasubramanian et al. |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |

(Continued)

FOREIGN PATENT DOCUMENTS

| | | |
|---|---|---|
| EP | 2876166 A1 | 5/2015 |
| EP | 2876166 B1 | 5/2015 |

(Continued)

OTHER PUBLICATIONS

Bentley, D.R. et al. (Nov. 6, 2008). "Accurate whole human genome sequencing using reversible terminator chemistry," *Nature* 456(7218):53-59.

(Continued)

*Primary Examiner* — Layla D Berry
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are compounds, compositions, and methods of use thereof for sequencing a nucleic acid.

20 Claims, 1 Drawing Sheet

(56) References Cited

U.S. PATENT DOCUMENTS

| | | |
|---|---|---|
| 9,388,464 B2 | 7/2016 | Milton et al. |
| 9,410,200 B2 | 8/2016 | Balasubramanian et al. |
| 9,528,151 B2 | 12/2016 | Ju et al. |
| 9,593,373 B2 | 3/2017 | Liu et al. |
| 9,624,539 B2 | 4/2017 | Ju et al. |
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,190,157 B2 | 1/2019 | Wu et al. |
| 10,240,195 B2 | 3/2019 | Fuller et al. |
| 10,246,479 B2 | 4/2019 | Ju et al. |
| 10,260,094 B2 | 4/2019 | Ju et al. |
| 10,273,539 B2 | 4/2019 | Marma et al. |
| 10,336,785 B2 | 7/2019 | Marma et al. |
| 10,738,072 B1 | 8/2020 | Graham et al. |
| 10,822,653 B1 | 11/2020 | Graham et al. |
| 11,085,076 B2 | 8/2021 | Ju et al. |
| 2002/0015961 A1 | 2/2002 | Kwiatkowski |
| 2003/0027140 A1 | 2/2003 | Ju et al. |
| 2004/0023207 A1 | 2/2004 | Polansky |
| 2006/0003383 A1 | 1/2006 | Graham |
| 2006/0057565 A1 | 3/2006 | Ju et al. |
| 2006/0188901 A1 | 8/2006 | Barnes et al. |
| 2006/0252038 A1 | 11/2006 | Ju |
| 2007/0009980 A1 | 1/2007 | Graham |
| 2007/0219367 A1 | 9/2007 | Shchepinov et al. |
| 2009/0047699 A1 | 2/2009 | Graham |
| 2011/0014611 A1 | 1/2011 | Ju et al. |
| 2012/0046177 A1 | 2/2012 | Huang et al. |
| 2012/0142006 A1 | 6/2012 | Ju et al. |
| 2012/0156671 A1 | 6/2012 | Liu et al. |
| 2012/0156680 A1 | 6/2012 | Ju et al. |
| 2013/0137091 A1 | 5/2013 | Gordon et al. |
| 2013/0264207 A1 | 10/2013 | Ju et al. |
| 2013/0280700 A1 | 10/2013 | Ju et al. |
| 2015/0037788 A1 | 2/2015 | Ju |
| 2015/0080232 A1 | 3/2015 | Ju et al. |
| 2015/0140561 A1 | 5/2015 | Bergmann et al. |
| 2015/0197800 A1 | 7/2015 | Ju et al. |
| 2015/0368710 A1 | 12/2015 | Fuller et al. |
| 2016/0002721 A1 | 1/2016 | Liu et al. |
| 2016/0024570 A1 | 1/2016 | Ju et al. |
| 2016/0041179 A1 | 2/2016 | Ju et al. |
| 2016/0108382 A1 | 4/2016 | Efcavitch et al. |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0355541 A1 | 12/2016 | Jain et al. |
| 2016/0369336 A1 | 12/2016 | Stupi et al. |
| 2017/0002407 A1 | 1/2017 | Balasubramanian et al. |
| 2017/0058335 A1 | 3/2017 | Tao et al. |
| 2017/0137869 A1 | 5/2017 | Marma et al. |
| 2017/0166961 A1 | 6/2017 | Liu et al. |
| 2017/0211134 A1 | 7/2017 | Marma et al. |
| 2017/0283451 A1 | 10/2017 | Ju et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0208774 A1 | 7/2018 | Marma et al. |
| 2018/0274024 A1 | 9/2018 | Ju et al. |
| 2018/0274025 A1 | 9/2018 | Marma et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0077726 A1 | 3/2019 | Graham et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |
| 2020/0102609 A1 | 4/2020 | Glezer et al. |

FOREIGN PATENT DOCUMENTS

| | | |
|---|---|---|
| EP | 3356381 A1 | 8/2018 |
| EP | 3356381 A4 | 8/2018 |
| WO | WO-02/022883 A1 | 3/2002 |
| WO | WO-02/029003 A2 | 4/2002 |
| WO | WO-02/029003 A3 | 4/2002 |
| WO | WO-2008/037568 A2 | 4/2008 |
| WO | WO-2008/037568 A3 | 4/2008 |
| WO | WO-2008/144315 A1 | 11/2008 |
| WO | WO-2009/054922 A1 | 4/2009 |
| WO | WO-2012/083249 A2 | 6/2012 |
| WO | WO-2012/083249 A3 | 6/2012 |
| WO | WO-2012/162429 A2 | 11/2012 |
| WO | WO-2012/162429 A3 | 11/2012 |
| WO | WO-2013/154999 A2 | 10/2013 |
| WO | WO-2013/154999 A3 | 10/2013 |
| WO | WO-2013/191793 A1 | 12/2013 |
| WO | WO-2014/144883 A1 | 9/2014 |
| WO | WO-2014/144898 A1 | 9/2014 |
| WO | WO-2015/123430 A2 | 8/2015 |
| WO | WO-2015/123430 A3 | 8/2015 |
| WO | WO-2015/148402 A1 | 10/2015 |
| WO | WO-2016/063059 A1 | 4/2016 |
| WO | WO-2016/144973 A1 | 9/2016 |
| WO | WO-2016/154215 A1 | 9/2016 |
| WO | WO-2017/058953 A1 | 4/2017 |
| WO | WO-2017/079498 A2 | 5/2017 |
| WO | WO-2017/079498 A3 | 5/2017 |
| WO | WO-2017/087887 A1 | 5/2017 |
| WO | WO-2017/176677 A1 | 10/2017 |
| WO | WO-2017/176679 A1 | 10/2017 |
| WO | WO-2017/205336 A1 | 11/2017 |
| WO | WO-2018/165207 A1 | 9/2018 |
| WO | WO-2018/183538 A1 | 10/2018 |
| WO | WO-2019/105421 A1 | 6/2019 |
| WO | WO-2019/164977 A1 | 8/2019 |
| WO | WO-2020/086834 A1 | 4/2020 |
| WO | WO-2020/146397 A1 | 7/2020 |
| WO | WO-2020/146497 A1 | 7/2020 |

OTHER PUBLICATIONS

Bergen, K. et al. (Jun. 17, 2013, e-published Jun. 3, 2013). "Structures of KOD and 9° N DNA polymerases complexed with primer template duplex," *Chembiochem* 14(9):1058-1062.

Bergseid, M. et al. (Nov. 2000). "Small molecule-based chemical affinity system for the purification of proteins," *BioTechniques* 29(5):1126-1133.

Binauld, S. et al. (Mar. 14, 2013). "Acid-degradable polymers for drug delivery: a decade of innovation," *Chem Commun* 49(21):2082-2102.

Blackman, M.L. et al. (Oct. 15, 2008, e-published Sep. 18, 2008). "Tetrazine ligation: fast bioconjugation based on inverse-electron-demand Diels-Alder reactivity," *J Am Chem Soc* 130(41):13518-13519.

Debets, M.F. et al. (Oct. 14, 2013, e-published Aug. 23, 2013). "Bioorthogonal labelling of biomolecules: new functional handles and ligation methods," *Org Biomol Chem* 11(38):6439-6455.

Extended European Search Report mailed on May 10, 2019, for EP Patent Application No. 16852516.0, 7 pages.

Fuller, C.W. et al. (May 10, 2016, e-published Apr. 18, 2016). "Real-time single-molecule electronic DNA sequencing by synthesis using polymer-tagged nucleotides on a nanopore array," *PNAS USA* 113(19):5233-5238.

(56) References Cited

OTHER PUBLICATIONS

Guillier, F. et al. (Jun. 14, 2000). "Linkers and cleavage strategies in solid-phase organic synthesis and combinatorial chemistry," *Chem Rev* 100(6):2091-2158.
Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27):9145-9150.
Hutter, D. et al. (Nov. 2010). "Labeled nucleoside triphosphates with reversibly terminating aminoalkoxyl groups," *Nucleosides Nucleotides Nucleic Acids* 29(11):879-895.
Inoue, T. et al. (Nov. 2015). "Synthesis of trifluoromethyl ethers and difluoro(methylthio)methyl ethers by the reaction of dithiocarbonates with $IF_5$-pyridine-HF," *Journal of Fluorine Chemistry* 179:48-52.
International Search Report dated Dec. 29, 2016, for PCT Application No. PCT/US2016/054236, filed Sep. 28, 2016, 4 pages.
International Search Report dated Jun. 1, 2018 for PCT Application No. PCT/US2018/021219, filed Mar. 6, 2018, 3 pages.
International Search Report dated Jun. 25, 2019, for PCT Application No. PCT/US2019/018810, filed Feb. 20, 2019, 4 pages.
International Search Report dated Jan. 6, 2020 for PCT Application No. PCT/US2019/57842, filed Oct. 24, 2019, 3 pages.
International Search Report dated Apr. 2, 2020 for PCT Application No. PCT/US2020/012595, filed Jan. 7, 2020, 3 pages.
Jewett, J.C. et al. (Mar. 24, 2010). "Rapid Cu-free click chemistry with readily synthesized biarylazacyclooctynones," *J Am Chem Soc* 132(11):3688-3690.
Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.
Kumar, S. et al. (2012, e-published Sep. 21, 2012). "PEG-labeled nucleotides and nanopore detection for single molecule DNA sequencing by synthesis," *Sci Rep* 2:684.
Leicher, T. et al. (Dec. 25, 1998). "Coexpression of the KCNA3B gene product with Kv1.5 leads to a novel A-type potassium channel," *J Biol Chem* 273(52):35095-35101.
Leriche, G. et al. (Jul. 2010). "Optimization of the Azobenzene Scaffold for Reductive Cleavage by Dithionite; Development of an Azobenzene Cleavable Linker for Proteomic Applications," *Eur J Org Chem* 2010(23):4360-4364.
Marcus-Sekura, C.J. et al. (Aug. 1, 1988). "Techniques for using antisense oligodeoxyribonucleotides to study gene expression," *Anal Biochem* 172(2):289-295.
Needleman, S.B .et al. (Mar. 1970). "A general method applicable to the search for similarities in the amino acid sequence of two proteins," *J Mol Biol* 48(3):443-453.
Pearson, W.R. et al. (Apr. 1988). "Improved tools for biological sequence comparison," *PNAS USA* 85(8):2444-2448.
PubChem Compound Summary for CID 121486816 (Aug. 16, 2016). Located at <https:pubchem.ncbi.nlm.nih.gov/compound/121486816> last visited Apr. 22, 2019, 7 pages.

PubChem Compound Summary for CID 69188114 (Nov. 30, 2012). Located at <https:pubchem.ncbi.nlm.nih.gov/compound/69188114> last visited Apr. 22, 2019, 7 pages.
Rathod, K.M. et al. (2013). "Synthesis and Antimicrobial Activity of Azo Compounds Containing m-Cresol Moiety," *Chem Sci Trans* 2(1):25-28.
Rosenblum, B.B. et al. (Nov. 15, 1997). "New dye-labeled terminators for improved DNA sequencing patterns," *Nucleic Acids Res* 25(22):4500-4504.
Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," PNAS USA 102(17):5932-5937.
Schumacher, W. et al. (Jun. 16, 1997). "Redox chemistry of cobalamin and iron-sulfur cofactors in the tetrachloroethene reductase of *Dehalobacter restrictus,*" *FEBS Lett* 409(3):421-425.
Shenoi, R.A. et al. (Sep. 12, 2012, e-published Aug. 30, 2012). "Branched multifunctional polyether polyketals: variation of ketal group structure enables unprecedented control over polymer degradation in solution and within cells," *J Am Chem Soc* 134(36):14945-14957.
Smith T.F. et al. (Dec. 1981). "Comparison of biosequences," *Advances in Applied Mathematics* 2(4):482-489.
Southworth, M.W. et al. (May 28, 1996). "Cloning of thermostable DNA polymerases from hyperthermophilic marine Archaea with emphasis on *Thermococcus* sp. 9° N-7 and mutations affecting 3'-5' exonuclease activity," *PNAS USA* 93(11):5281-5285.
Švagera, Z. et al. (Mar. 2012, e-published Feb. 15, 2012). "Study of disulfide reduction and alkyl chloroformate derivatization of plasma sulfur amino acids using gas chromatography-mass spectrometry," *Anal Bioanal Chem* 402(9):2953-2963.
Tang et al. (Nov. 2014). "Synthesis and Application of Four Fluorescence Labeled Nucleotides Through Disulfide as Reversible Terminators in DNA Sequencing by Synthesis," *Chem. J. Chinese U.* 35(11):2346-2352, including an English language abstract.
Uhlmann, E. et al. (Jun. 1990). "Antisense oligonucleotides: a new therapeutic principle," *Chemical Reviews* 90(4):543-584.
Weintraub, H.M. (Jan. 1990). "Antisense RNA and DNA," *Sci Am* 262(1):40-46.
Written Opinion dated Dec. 29, 2016, for PCT Application No. PCT/US2016/054236, filed Sep. 28, 2016, 4 pages.
Written Opinion dated Jun. 1, 2018 for PCT Application No. PCT/US2018/021219, filed Mar. 6, 2018, 9 pages.
Written Opinion dated Jun. 25, 2019, for PCT Application No. PCT/US2019/018810, filed Feb. 20, 2019, 5 pages.
Written Opinion dated Jan. 6, 2020 for PCT Application No. PCT/US2019/57842, filed Oct. 24, 2019, 11 pages.
Written Opinion dated Apr. 2, 2020 for PCT Application No. PCT/US2020/012595, filed Jan. 7, 2020, 3 pages.
Wu, J. et al. (Oct. 16, 2007, e-published Oct. 8, 2007). "3'-O-modified nucleotides as reversible terminators for pyrosequencing," *PNAS USA* 104(42):16462-16467.
Zhu, Z. et al. (Aug. 25, 1994). "Directly labeled DNA probes using fluorescent nucleotides with different length linkers," *Nucleic Acids Res* 22(16):3418-3422.

NUCLEOTIDE CLEAVABLE LINKERS AND USES THEREOF

CROSS-REFERENCES TO RELATED APPLICATIONS

This application claims the benefit of U.S. Provisional Application No. 62/789,879, filed Jan. 8, 2019; and U.S. Provisional Application No. 62/841,168, filed Apr. 30, 2019; which are incorporated herein by reference in their entirety and for all purposes.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Accordingly, there is a need for modified nucleotides and nucleosides that are effectively recognized as substrates by DNA polymerases, that are efficiently and accurately incorporated into growing DNA chains during SBS. Disclosed herein, inter alia, are solutions to these and other problems in the art.

BRIEF SUMMARY

In an aspect is provided a compound having the formula:

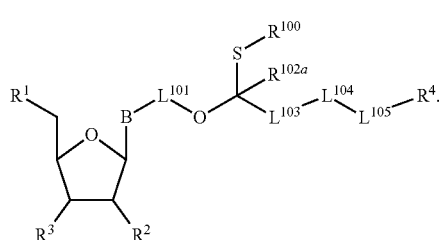

(I)

B is a divalent nucleobase.

$R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

$R^2$ and $R^3$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety.

$L^{101}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; a cleavable linker, a self-immolative linker, a linker capable of dendritic amplification of signal (e.g., capable of increasing fluorescence by releasing fluorophores from the remainder of the linker), a trivalent linker, or a self-immolative dendrimer linker (e.g., capable of increasing fluorescence by releasing fluorophores from the remainder of the linker).

$R^{100}$ is —$SR^{102}$ or —CN.

$R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is a detectable moiety.

In an aspect is provided a nucleic acid polymerase complex, wherein the nucleic acid polymerase is bound (e.g., non-covalently bound) to a compound described herein, including embodiments.

In an aspect is provided a method for sequencing a nucleic acid, including: incorporating in series with a nucleic acid polymerase, within a reaction vessel, one of four different compounds into a primer to create an extension strand, wherein the primer is hybridized to the nucleic acid and wherein each of the four different compounds includes a unique detectable label; detecting the unique detectable label of each incorporated compound, so as to thereby identify each incorporated compound in the extension strand, thereby sequencing the nucleic acid; wherein each of the four different compounds is independently a compound described herein.

In an aspect is provided a method for sequencing a nucleic acid, including: incorporating in series with a nucleic acid polymerase, within a reaction vessel, a compound into a primer to create an extension strand, wherein the primer is hybridized to the nucleic acid and wherein the compound includes a detectable label; detecting the detectable label of the incorporated compound, so as to thereby identify the incorporated compound in the extension strand, thereby sequencing the nucleic acid; wherein the compound is independently a compound described herein.

In an aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein.

DETAILED DESCRIPTION

I. Definitions

Figure 1:
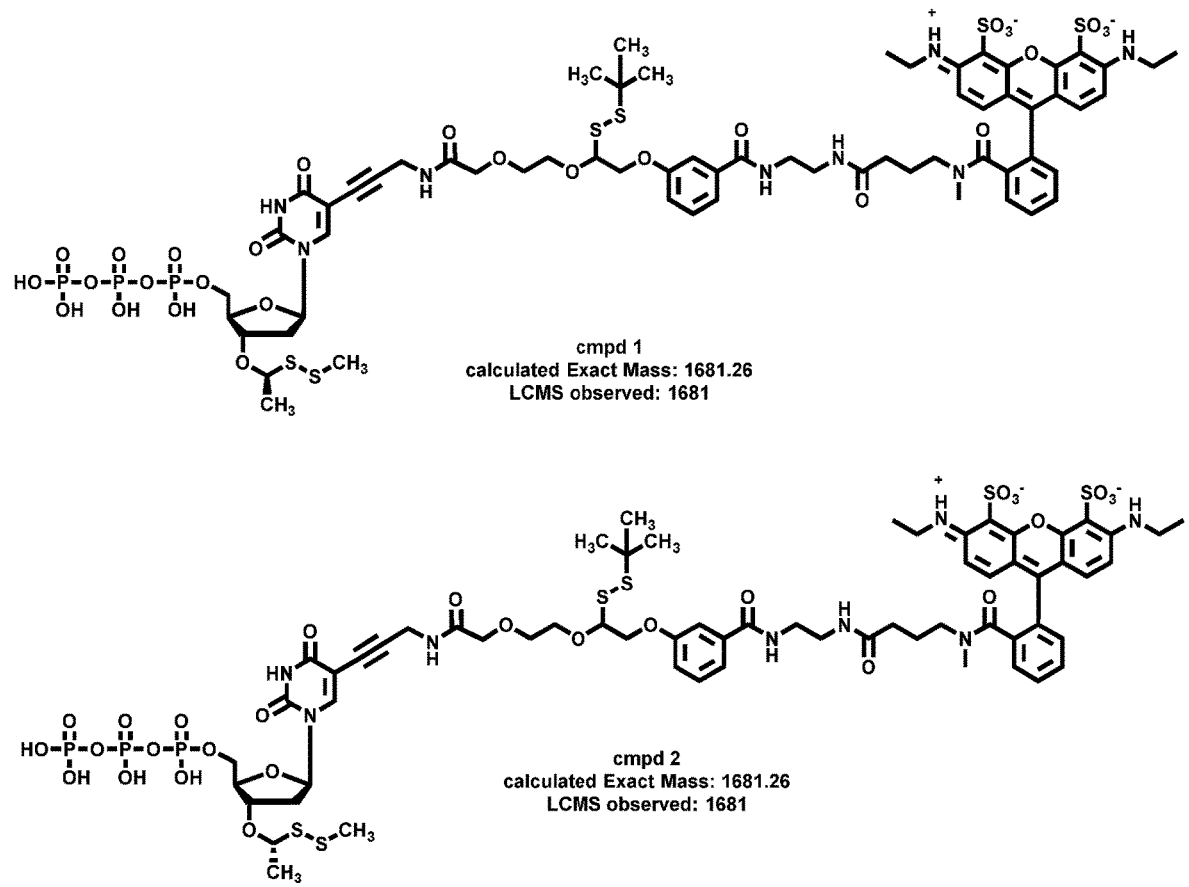
FIG. 1. Structures and LCMS data for compounds containing a thio-trigger containing linker.
Figure 2:
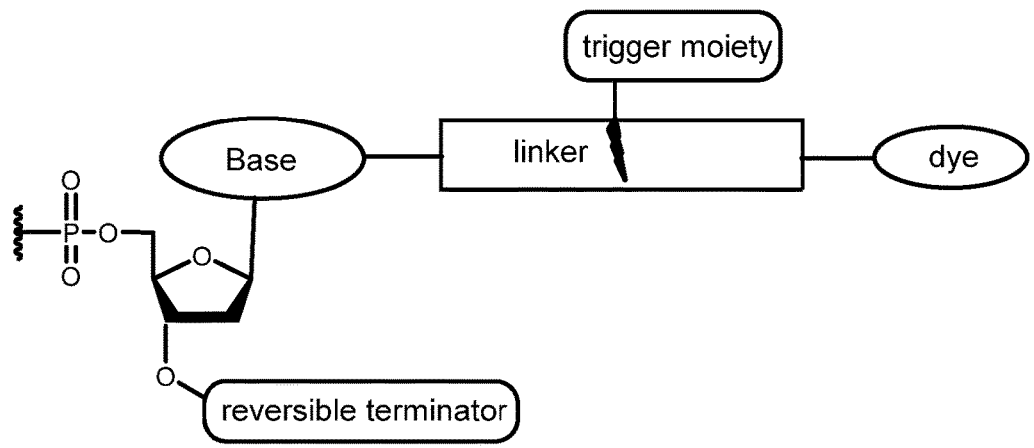
FIG. 2. An illustration of a cleavable fluorescent nucleotide reversible terminator (NRT) that contains a reversible terminator moiety on the 3' oxygen and a dye attached to the base via a linker, wherein the linker includes a trigger moiety (e.g., a thio-trigger moiety, as described herein). In the presence of an appropriate reducing agent (e.g., di-mercaptopropanesulfonate, di-mercaptopropanephosphonate, di-mercaptopropanol, cysteine, cysteamine, dithio-succinic acid, dithiothreitol (DTT), dithiobutylamine, meso-2,5-dimercapto-N,N,N',N'-tetramethyladipamide (DTA), Bis(2-mercaptoethyl)sulfone (BMS), and N,N'-dimethyl, or N,N'-bis(mercaptoacetyl)-hydrazine (DMH)) and suitable reaction conditions (e.g., elevated pH and/or elevated temperature) the trigger moiety breaks the linker (represented as the crack illustration in FIG. 2), thus separating the dye from the nucleotide. Though not shown in FIG. 2, the reducing agent may also remove the reversible terminator simultaneously.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O) NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

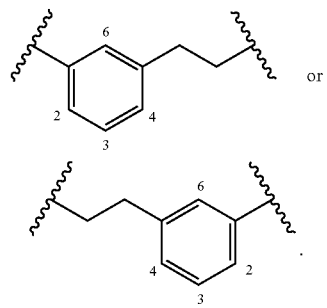

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R" " group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R" " are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent," "detectable compound," "detectable label," or "detectable moiety" is a substance, molecule, or composition detectable by spectroscopic, photochemical, biochemical, immunochemical, chemical, magnetic resonance imaging, or other physical means. For example, detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Ph, $^{111}$Ag, $^{111}$In, $^{123}$I, $^{124}$I, $^{125}$I, $^{131}$I, $^{142}$Pr, $^{143}$P, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g., fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4′,6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup>moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and -6)-Carboxy-2′, 7′-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, *Lucifer* Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the detectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and -6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(µ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, C10H butoxy aza-BODIPY, C10H C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kutzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™ GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP—CO-Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, TRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye®

800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoney-Dew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DUPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DUPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreenl, or ZsYellowl.

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e., cyanine 7 or Cy7).

Descriptions of compounds (e.g., nucleotide analogues) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a target-inhibitor interaction means positively affecting (e.g., increasing) the activity or function of the target (e.g., protein) relative to the activity or function of the target (e.g., protein) in the absence of the activator. In embodiments activation means positively affecting (e.g., increasing) the concentration or levels of the target (e.g., protein) relative to the concentration or level of the target (e.g., protein) in the absence of the activator. The terms may reference activation, or activating, sensitizing, or up-regulating signal transduction or enzymatic activity or the amount of a target (e.g., protein) decreased in a disease. Thus, activation may include, at least in part, partially or totally increasing stimulation, increasing or enabling activation, or activating, sensitizing, or up-regulating signal transduction or enzymatic activity or the amount of a target (e.g., protein) associated with a disease (e.g., a target (e.g., protein) which is decreased in a disease relative to a non-diseased control). Activation may include, at least in part, partially or totally increasing stimulation, increasing or enabling activation, or activating, sensitizing, or up-regulating signal transduction or enzymatic activity or the amount of a target (e.g., protein).

The terms "agonist," "activator," "upregulator," etc. refer to a substance capable of detectably increasing the expression or activity of a given target (e.g., gene or protein). The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition," "inhibit," "inhibiting" and the like in reference to a target-inhibitor interaction means negatively affecting (e.g., decreasing) the activity or function of the target (e.g., protein) relative to the activity or function of the target (e.g., protein) in the absence of the inhibitor. In embodiments inhibition means negatively affecting (e.g., decreasing) the concentration or levels of the target (e.g., protein) relative to the concentration or level of the target (e.g., protein) in the absence of the inhibitor. In embodiments inhibition refers to reduction of a disease or symptoms of disease. In embodiments, inhibition refers to a reduction in the activity of a particular target (e.g., protein). Thus, inhibition includes, at least in part, partially or totally blocking stimulation, decreasing, preventing, or delaying activation, or inactivating, desensitizing, or down-regulating signal transduction or enzymatic activity or the amount of a target (e.g., protein). In embodiments, inhibition refers to a reduction of activity of a target (e.g., protein) resulting from a direct interaction (e.g., an inhibitor binds to the target (e.g., protein)). In embodiments, inhibition refers to a reduction of activity of a target (e.g., protein) from an indirect interaction (e.g., an inhibitor binds to a target (e.g., protein) that activates the target (e.g., protein), thereby preventing target (e.g., protein) activation).

The terms "inhibitor," "repressor," "antagonist," or "downregulator" interchangeably refer to a substance capable of detectably decreasing the expression or activity of a given target (e.g., gene or protein). The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "streptavidin" refers to a tetrameric protein (including homologs, isoforms, and functional fragments thereof) capable of binding biotin. The term includes any recombinant or naturally-occurring form of streptavidin variants thereof that maintain streptavidin activity (e.g., within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. Nucleosides may be modified at the base and/or and the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. In embodiments, when a nucleic acid is to be sequenced, it may be referred to as a template nucleic acid.

"Nucleotide," as used herein, refers to a nucleoside-5'-polyphosphate compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as A, C, G, T, U, or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide").

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of adenine (A), cytosine (C), guanine (G), thymine (T), or uracil (U) (that is, an analogue or derivative of a nucleotide comprising the base adenine (A), cytosine (C), guanine (G), thymine (T), or uracil (U)), comprising a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3-position of deoxyribose. Nucleotide analogues and DNA polymerase-based DNA sequencing are also described in U.S. Pat. No. 6,664,079, which is incorporated herein by reference in its entirety for all purposes.

A "nucleoside" is structurally similar to a nucleotide, but is missing the phosphate moieties. An example of a nucleoside analogue would be one in which the label is linked to the base and there is no phosphate group attached to the sugar molecule.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or "percent identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA*

85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The term "monophosphate" is used in accordance with its ordinary meaning in the arts and refers to a moiety having the formula:

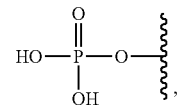

or ionized forms thereof. The term "polyphosphate" refers to at least two phosphate groups, having the formula:

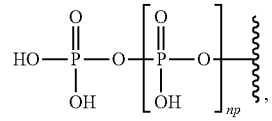

or ionized forms thereof, wherein np is an integer of 1 or greater. In embodiments, np is an integer from 1 to 5. In embodiments, np is an integer from 1 to 2. In embodiments, np is 2. The term "diphosphate" is used in accordance with its ordinary meaning in the arts and refers to a moiety having the formula:

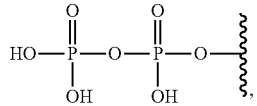 [SMILES: *OP(=O)(O)OP(=O)(O)O]

or ionized forms thereof. The term "triphosphate" is used in accordance with its ordinary meaning in the arts and refers to a moiety having the formula:

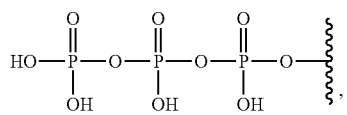

or ionized forms thereof. In embodiments, a polyphosphate is a diphosphate. In embodiments, a polyphosphate is a triphosphate.

The term "nucleobase" or "base" as used herein refers to a divalent purine or pyrimidine compound or a derivative thereof, that may be a constituent of nucleic acid (i.e., DNA or RNA, or a derivative thereof). In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, hypoxanthine, xanthine, theobromine, caffeine, uric acid, or isoguanine, which may be optionally substituted or modified. In embodiments, the base is

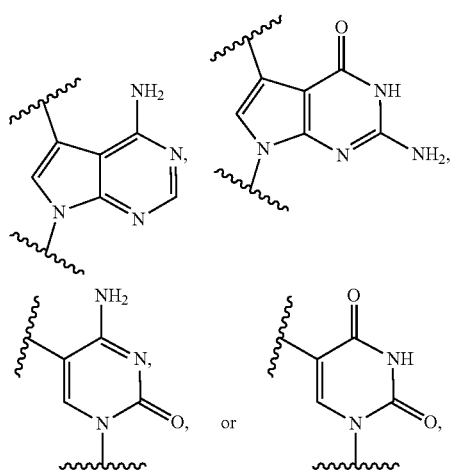

which may be optionally substituted or modified. In embodiments, the base includes

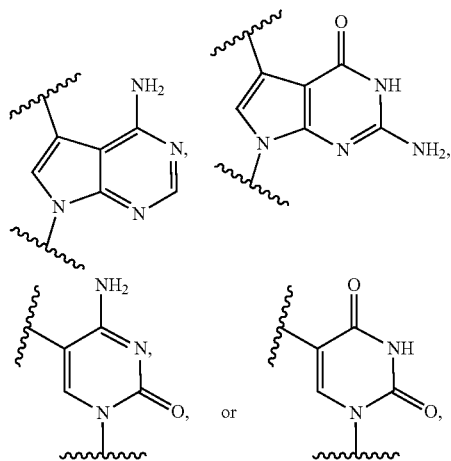

which may be optionally substituted or modified.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group, complementary anchor moiety binder). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) (Blackman, M. L., et al., *J. Am. Chem. Soc.,* 2008, 130, 13518-13519; Debets, M. F., et al. *Org. Biomol. Chem.,* 2013, 11, 6439-6455) and phenyl boric acid (PBA) (Bergseid M., et al., *BioTechniques,* 2000, 29, 1126-1133). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J. C. and Bertozzi C. R. *J. Am. Chem. Soc.,* 2010, 132, 3688-3690), tetrazine (TZ) moiety, salicylhydroxamic acid (SHA) moiety).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/ basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplication of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent (e.g., a reducing agent). In embodiments, the cleaving agent is sodium dithionite ($Na_2S_2O_4$), weak acid, hydrazine ($N_2H_4$), Pd(0), or light-irradiation (e.g., ultraviolet radiation). The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus.

A photocleavable linker (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., tris(3-hydroxypropyl)phosphine). In embodiments, the cleavable linker is a dialkylketal linker (Binaulda S., et al., *Chem. Commun.*, 2013, 49, 2082-2102; Shenoi R. A., et al., *J. Am. Chem. Soc.*, 2012, 134, 14945-14957), an azo linker (Rathod, K. M., et al., *Chem. Sci. Tran.*, 2013, 2, 25-28; Leriche G., et al., *Eur. J. Org. Chem.*, 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

The term "orthogonal detectable label" or "orthogonal detectable moiety" as used herein refer to a detectable label (e.g., fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" as used herein refers to a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is independently —$NH_2$, —CN, —$CH_3$, $C_2$-$C_6$ allyl (e.g., —$CH_2$—CH=$CH_2$), methoxyalkyl (e.g., —$CH_2$—O—$CH_3$), or —$CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with the function of a polymerase (e.g., DNA polymerase, modified DNA polymerase). In embodiments, a polymerase-compatible cleavable moiety is a moiety described herein.

In embodiments, the polymerase-compatible cleavable moiety may be referred to as a "reversible terminator". The terms "reversible terminator" and "reversible terminator moiety" are used in accordance with their plain and ordinary meanings and refers to a cleavable moiety on the 3' position of a nucleotide which does not interfere with the function of a polymerase (e.g., DNA polymerase, modified DNA polymerase). In embodiments, the reversible terminator moiety is

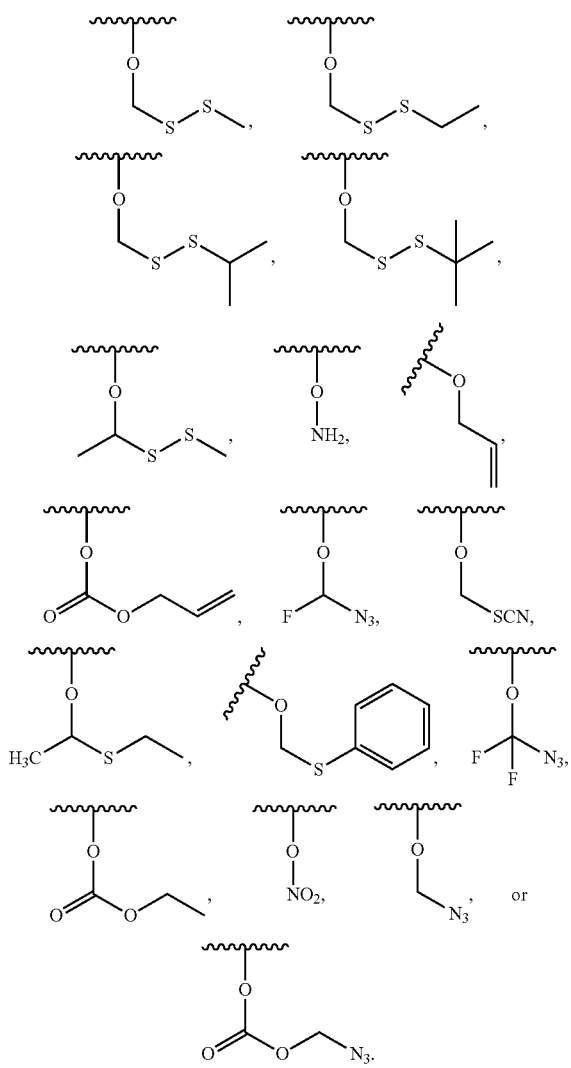

The term "allyl" as described herein refers to an unsubstituted methylene attached to a vinyl group (i.e., —CH=CH$_2$), having the formula

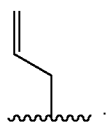

An "allyl linker" refers to a divalent unsubstituted methylene attached to a vinyl group, having the formula

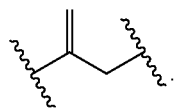

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

The term "polymerase-compatible moiety" as used herein refers a moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) Proc Natl Acad Sci USA 103(52):19635-19640; Ruparel H. et al. (2005) Proc Natl Acad Sci USA 102(17):5932-5937; Wu J. et al. (2007) Proc Natl Acad Sci USA 104(104):16462-16467; Guo J. et al. (2008) Proc Natl Acad Sci USA 105(27): 9145-9150 Bentley D. R. et al. (2008) Nature 456(7218):53-59; or Hutter D. et al. (2010) Nucleosides Nucleotides & Nucleic Acids 29:879-895, which are incorporated herein by reference in their entirety for all purposes. In embodiments, a polymerase-compatible moiety includes hydrogen, —N$_3$, —CN, or halogen. In embodiments, a polymerase-compatible moiety is a moiety on a nucleotide, nucleobase, nucleoside, or nucleic acid that does not interfere with the function of a polymerase (e.g., DNA polymerase, modified DNA polymerase).

The term "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Taq polymerase, Therminator γ, 9° N polymerase (exo-), Therminator II, Therminator III, or Therminator IX).

The term "thermophilic nucleic acid polymerase" as used herein refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M. W., et al. *PNAS.* 1996; 93(11):5281-5285). A thermophilic nucleic acid polymerase is a member of the family B DNA polymerases. Site-directed mutagenesis of the 3'-5' exo motif I (Asp-Ile-Glu) to Asp-Ile-Asp resulted in reduction of 3'-5' exonuclease activity to <1% of wild-type, while maintaining other properties of the polymerase including its high strand displacement activity. Subsequent mutagenesis of key amino acids results in an increased ability of the enzyme to incorporate dideoxynucleotides, ribonucleotides and acyclo-nucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically these enzymes do not have 5'-3' exonuclease activity. Additional information about thermophilic nucleic acid polymerases may be found in (Southworth M W, et al. *PNAS.* 1996; 93(11):5281-5285; Bergen K., et al. *ChemBioChem.* 2013; 14(9):1058-1062; Kumar S., et al. *Scientific Reports.* 2012; 2:684; Fuller C. W., et al. 2016; 113(19): 5233-5238; Guo J., et al. *Proceedings of the National Academy of Sciences of the United States of America.* 2008; 105(27):9145-9150), which are incorporated herein in their entirety for all purposes.

The term "primer," as used herein, is defined to be one or more nucleic acid fragments that specifically hybridize to a nucleic acid template. A primer can be of any length depending on the particular technique it will be used for. For example, PCR primers are generally between 10 and 40 nucleotides in length. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations. The primer permits the addition of a nucleotide residue thereto, or oligonucleotide or polynucleotide synthesis therefrom, under suitable conditions well-known in the art. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target nucleic acid.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology,* ed. Ausubel, et al., supra.

The term "thio-trigger moiety" refers to a substituent having the formula

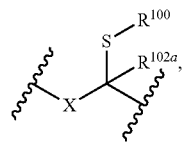

wherein X is —O—, —NH—, or —S—; $R^{100}$ is —$SR^{102}$ or —CN; and $R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the thio-trigger moiety has the formula:

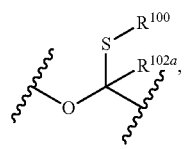

wherein $R^{100}$ and $R^{102a}$ are as described herein.

A "thio-trigger containing linker" refers to a covalent linker that includes a thio-trigger moiety. For example, when a reducing agent (e.g., dithiothreitol, THPP, or TCEP) contacts a thio-trigger containing linker, the heteroatom represented by the symbol X (e.g., oxygen) of the thio-trigger moiety is reduced, and breaks the linker, according to the mechanism:

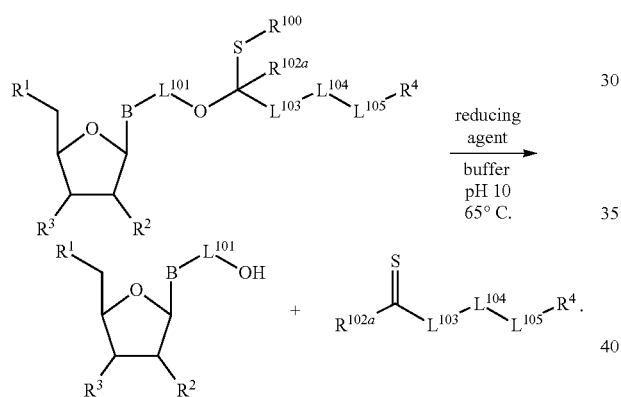

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the term "salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, for example

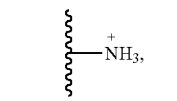

and it is understood an appropriate counter-ion (e.g., chloride ion, fluoride ion, or acetate ion) may also be present, though not explicitly shown. Likewise, for compounds having a negative charge (e.g., 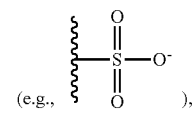 ), it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g., 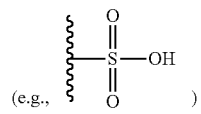 )

or an ionic state (e.g., 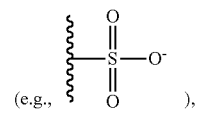 ), and it is understood these are interchangeable. In embodiments, the counter-ion is represented by the symbol M (e.g., M⁺ or M⁻).

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing cycle" is used in accordance with its plain and ordinary meaning and refers to incorporating one or more nucleotides (e.g., a compound described herein) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

II. Compositions

In an aspect is provided a compound having the formula:

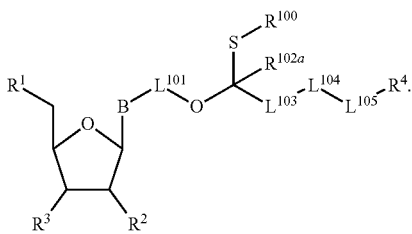

(I)

B is a divalent nucleobase.

$R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

$R^2$ and $R^3$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety.

$L^{101}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; a cleavable linker, a self-immolative linker, a linker capable of dendritic amplification of signal (e.g., capable of increasing fluorescence by releasing fluorophores from the remainder of the linker), a trivalent linker, or a self-immolative dendrimer linker (e.g., capable of increasing fluorescence by releasing fluorophores from the remainder of the linker). In embodiments, $L^{101}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; or a cleavable linker. In embodiments, $L^{101}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^{100}$ is —$SR^{102}$ or —CN.

$R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is a detectable moiety.

In embodiments, $R^{100}$ is —$SR^{102}$. In embodiments, $R^{100}$ is —CN.

In embodiments, the compound has the formula:

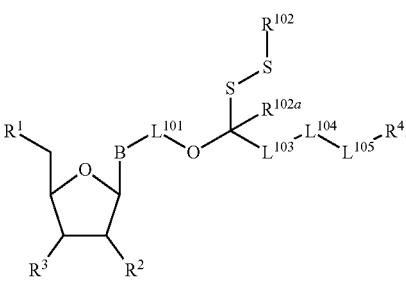

(II)

$R^1$, $R^2$, $R^3$, B, $L^{101}$, $R^{102}$, $R^{102a}$, $L^{103}$, $L^{104}$, $L^{105}$, and $R^4$ are as described herein.

In embodiments, the compound has the formula:

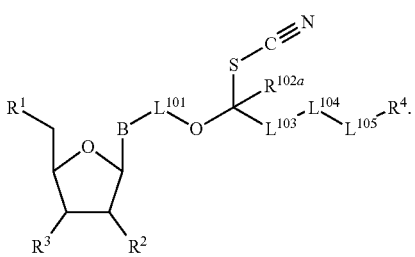

(III)

$R^1$, $R^2$, $R^3$, B, $L^{101}$, $R^{102a}$, $L^{103}$, $L^{104}$, $L^{105}$, and $R^4$ are as described herein.

In embodiments, $R^1$ is independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered), a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite). In embodiments, $R^1$ is independently a 5'-nucleoside protecting group, monophosphate moiety, polyphosphate moiety, or nucleic acid moiety In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group. In embodiments, when $R^1$ is substituted, it is substituted with 1 to 10 substituent groups. In embodiments, when $R^1$ is substituted, it is substituted with 1 to 10 size-limited substituent groups. In embodiments, when $R^1$ is substituted, it is substituted with 1 to 10 lower substituent groups. In embodiments, when $R^1$ is substituted, it is substituted with 1 to 5 substituent groups. In embodiments, when $R^1$ is substituted, it is substituted with 1 to 5 size-limited substituent groups. In embodiments, when $R^1$ is substituted, it is substituted with 1 to 5 lower substituent groups. In embodiments, when $R^1$ is substituted, it is substituted with a substituent group. In embodiments, when $R^1$ is substituted, it is substituted with a size-limited substituent group. In embodiments, when $R^1$ is substituted, it is substituted with a lower substituent group.

In embodiments, $R^1$ is independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —NH₂, —COOH, —CONH₂, —NO₂, —SH, —SO₃H, —SO₂NH₂, —NHNH₂, —NHC(O)NHNH₂, —NHC(O)NH₂, —NHSO₂H, —NHC(O)H, —NHC(O)OH, —NHOH, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a 5'-nucleoside protecting group; or $R^1$ is a monophosphate moiety, polyphosphate moiety, or nucleic acid moiety. In embodiments, $R^1$ is independently hydrogen, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —NH₂, —COOH, —CONH₂, —NO₂, —SH, —SO₃H, —SO₂NH₂, —NHNH₂, —NHC(O)NHNH₂, —NHC(O)NH₂, —NHSO₂H, —NHC(O)H, —NHC(O)OH, —NHOH, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^1$ is a 5'-nucleoside protecting group. In embodiments, $R^1$ is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety.

In embodiments, $R^1$ is hydrogen. In embodiments, $R^1$ is a triphosphate moiety. In embodiments, $R^1$ is —OH.

In embodiments, $R^1$ is hydrogen. In embodiments, $R^1$ is-OH. In embodiments, $R^1$ is a monophosphate moiety. In embodiments, $R^1$ is a polyphosphate moiety. In embodiments, $R^1$ is a triphosphate moiety. In embodiments, $R^1$ is a nucleic acid moiety. In embodiments, $R^1$ is —OH. In embodiments, $R^1$ is a derivative of a monophosphate moiety. In embodiments, $R^1$ is a derivative of a polyphosphate moiety. In embodiments, $R^1$ is a derivative of a triphosphate moiety. In embodiments, $R^1$ is a derivative of a nucleic acid moiety.

In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety. In embodiments, $R^1$ is independently a monophosphate moiety including a phosphodiester derivative. In embodiments, $R^1$ is independently a polyphosphate moiety including a phosphodiester derivative. In embodiments, $R^1$ is independently a nucleic acid moiety including a phosphodiester derivative. In embodiments, $R^1$ is independently a phosphoramidate moiety. In embodiments, $R^1$ is independently a polyphosphate moiety including a phosphoramidate. In embodiments, $R^1$ is independently a nucleic acid moiety including a phosphoramidate. In embodiments, $R^1$ is independently a phosphorothioate moiety. In embodiments, $R^1$ is independently a polyphosphate moiety including a phosphorothioate. In embodiments, $R^1$ is independently a nucleic acid moiety including a phosphorothioate. In embodiments, $R^1$ is independently a phosphorodithioate moiety. In embodiments, $R^1$ is independently a polyphosphate moiety including a phosphorodithioate. In embodiments, $R^1$ is independently a nucleic acid moiety including a phosphorodithioate. In embodiments, $R^1$ is independently an O-methylphosphoroamidite moiety. In embodiments, $R^1$ is independently a polyphosphate moiety including an O-methylphosphoroamidite. In embodiments, $R^1$ is independently a nucleic acid moiety including an O-methylphosphoroamidite. In embodiments, $R^1$ is independently a nucleic acid moiety including a nucleotide analog. In embodiments, $R^1$ is independently a nucleic acid moiety including a plurality of optionally different nucleotide analogs.

In embodiments, $R^1$ is independently a 5'-nucleoside protecting group; and the 5'-nucleoside protecting group is

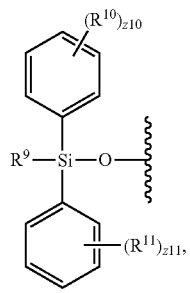

wherein $R^9$ is substituted or unsubstituted $C_1$-$C_4$ alkyl. $R^{10}$ and $R^{11}$ are each independently halogen, —CF$_3$, —Cl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —CHCl$_2$, —OCHI$_2$, —OCHBr$_2$, —OCF$_3$, —OCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. The symbols z10 and z11 are each independently integers from 0 to 5. In embodiments, z10 and z11 are 0.

In embodiments, $R^9$ is substituted (e.g., substituted with a substituent group, size-limited substituent group, or lower substituent group) or unsubstituted $C_1$-$C_4$ alkyl.

In embodiments, a substituted $R^9$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group. In embodiments, when $R^9$ is substituted, it is substituted with 1 to 10 substituent groups. In embodiments, when $R^9$ is substituted, it is substituted with 1 to 10 size-limited substituent groups. In embodiments, when $R^9$ is substituted, it is substituted with 1 to 10 lower substituent groups. In embodiments, when $R^9$ is substituted, it is substituted with 1 to 5 substituent groups. In embodiments, when $R^9$ is substituted, it is substituted with 1 to 5 size-limited substituent groups. In embodiments, when $R^9$ is substituted, it is substituted with 1 to 5 lower substituent groups. In embodiments, when $R^9$ is substituted, it is substituted with a substituent group. In embodiments, when $R^9$ is substituted, it is substituted with a size-limited substituent group. In embodiments, when $R^9$ is substituted, it is substituted with a lower substituent group.

In embodiments, $R^9$ is independently substituted (e.g., substituted with a substituent group, a size-limited substituent group, or lower substituent group) $C_1$-$C_4$ alkyl. In embodiments, $R^9$ is an unsubstituted methyl. In embodiments, $R^9$ is an unsubstituted $C_2$ alkyl. In embodiments, $R^9$ is an unsubstituted $C_3$ alkyl. In embodiments, $R^9$ is an unsubstituted $C_4$ alkyl. In embodiments, $R^9$ is an unsubstituted tert-butyl.

In embodiments, $R^{10}$ and $R^{11}$ are each independently substituted (e.g., substituted with a substituent group, a size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{10}$ and $R^{11}$ are each independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{10}$ and $R^{11}$ are each independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{10}$ and $R^{11}$ are each independently unsubstituted alkyl, unsubstituted heteroalkyl, unsubstituted cycloalkyl, unsubstituted heterocycloalkyl, unsubstituted aryl, or unsubstituted heteroaryl.

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group. In embodiments, when $R^{10}$ is substituted, it is substituted with 1 to 10 substituent groups. In embodiments, when $R^{10}$ is substituted, it is substituted with 1 to 10 size-limited substituent groups. In embodiments, when $R^{10}$ is substituted, it is substituted with 1 to 10 lower substituent groups. In embodiments, when $R^{10}$ is substituted, it is substituted with 1 to 5 substituent groups. In embodiments, when $R^{10}$ is substituted, it is substituted with 1 to 5 size-limited substituent groups. In embodiments, when $R^{10}$ is substituted, it is substituted with 1 to 5 lower substituent groups. In embodiments, when $R^{10}$ is substituted, it is substituted with a substituent group. In embodiments, when $R^{10}$ is substituted, it is substituted with a size-limited substituent group. In embodiments, when $R^{10}$ is substituted, it is substituted with a lower substituent group.

In embodiments, a substituted $R^{11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when $R^{11}$ is substituted, it is substituted with at least one substituent group. In embodiments, when $R^{11}$ is substituted, it is substituted with at least one size-limited substituent group. In embodiments, when $R^{11}$ is substituted, it is substituted with at least one lower substituent group. In embodiments, when $R^{11}$ is substituted, it is substituted with 1 to 10 substituent groups. In embodiments, when $R^{11}$ is substituted, it is substituted with 1 to 10 size-limited substituent groups. In embodiments, when $R^{11}$ is substituted, it is substituted with 1 to 10 lower substituent groups. In embodiments, when $R^{11}$ is substituted, it is substituted with 1 to 5 substituent groups. In embodiments, when $R^{11}$ is substituted, it is substituted with 1 to 5 size-limited substituent groups. In embodiments, when $R^{11}$ is substituted, it is substituted with 1 to 5 lower substituent groups. In embodiments, when $R^{11}$ is substituted, it is substituted with a substituent group. In embodiments, when $R^{11}$ is substituted, it is substituted with a size-limited substituent group. In embodiments, when $R^1$ is substituted, it is substituted with a lower substituent group.

In embodiments, $R^2$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^2$ is independently a polymerase-compatible cleavable moiety. In embodiments, $R^2$ is independently an —O-polymerase-compatible cleavable moiety.

In embodiments, $R^2$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with a substituent group, a size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^2$ is independently a polymerase-compatible cleavable moiety. In embodiments, $R^2$ is independently a —O-polymerase-compatible cleavable moiety.

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group. In embodiments, when $R^2$ is substituted, it is substituted with 1 to 10 substituent groups. In embodiments, when $R^2$ is substituted, it is substituted with 1 to 10 size-limited substituent groups. In embodiments, when $R^2$ is substituted, it is substituted with 1 to 10 lower substituent groups. In embodiments, when $R^2$ is substituted, it is substituted with 1 to 5 substituent groups. In embodiments, when $R^2$ is substituted, it is substituted with 1 to 5 size-limited substituent groups. In embodiments, when $R^2$ is substituted, it is substituted with 1 to 5 lower substituent groups. In embodiments, when $R^2$ is substituted, it is substituted with a substituent group. In embodiments, when $R^2$ is substituted, it is substituted with a size-limited substituent group. In embodiments, when $R^2$ is substituted, it is substituted with a lower substituent group.

In embodiments, $R^2$ is hydrogen. In embodiments, $R^2$ is —OH. In embodiments, $R^2$ is —O-polymerase-compatible cleavable moiety.

In embodiments, $R^2$ is an —O-polymerase-compatible cleavable moiety. In embodiments, the polymerase-compatible cleavable moiety is independently —NH$_2$, —NO$_2$, —CN, —CH$_3$, $C_2$-$C_6$ allyl (e.g., —CH$_2$—CH=CH$_2$), methoxyalkyl (e.g., —CH$_2$—O—CH$_3$), or —CH$_2$N$_3$. In embodiments, the polymerase-compatible cleavable moiety is independently —NH$_2$. In embodiments, the polymerase-compatible cleavable moiety is independently —CN. In embodiments, the polymerase-compatible cleavable moiety is independently —CH$_3$. In embodiments, the polymerase-compatible cleavable moiety is independently $C_2$-$C_6$ allyl (e.g., —CH$_2$—CH=CH$_2$). In embodiments, the polymerase-compatible cleavable moiety is independently methoxyalkyl (e.g., —CH$_2$—O—CH$_3$). In embodiments, the polymerase-compatible cleavable moiety is independently —CH$_2$N$_3$. In embodiments, the polymerase-compatible cleavable moiety is independently —NH$_2$. In embodiments, the polymerase-compatible cleavable moiety is independently —NO$_2$. In embodiments, the polymerase-compatible cleavable moiety is independently —CH$_2$N$_3$. In embodiments, the polymerase-compatible cleavable moiety is independently

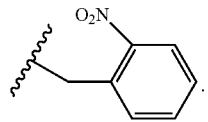

In embodiments, the polymerase-compatible cleavable moiety is independently

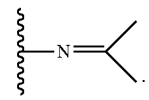

In embodiments, the polymerase-compatible cleavable moiety is independently

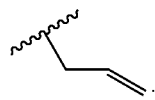 [SMILES: *CC=C]

In embodiments, the polymerase-compatible cleavable moiety is independently

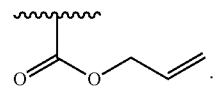

In embodiments, the polymerase-compatible cleavable moiety is independently

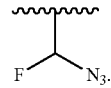

In embodiments, the polymerase-compatible cleavable moiety is independently

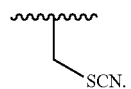

In embodiments, the polymerase-compatible cleavable moiety is independently

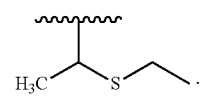

In embodiments, the polymerase-compatible cleavable moiety is independently

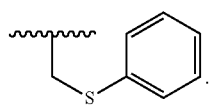

In embodiments, the polymerase-compatible cleavable moiety is independently

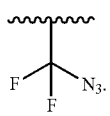

In embodiments, the polymerase-compatible cleavable moiety is independently

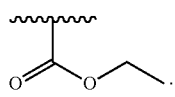 [SMILES: *C(=O)OCC]

In embodiments, the polymerase-compatible cleavable moiety is independently

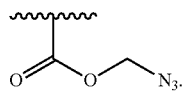

In embodiments, the polymerase-compatible cleavable moiety is independently —CH$_2$—O—CH$_3$. In embodiments, the polymerase-compatible cleavable moiety is independently —NH$_2$, —CH$_2$N$_3$,

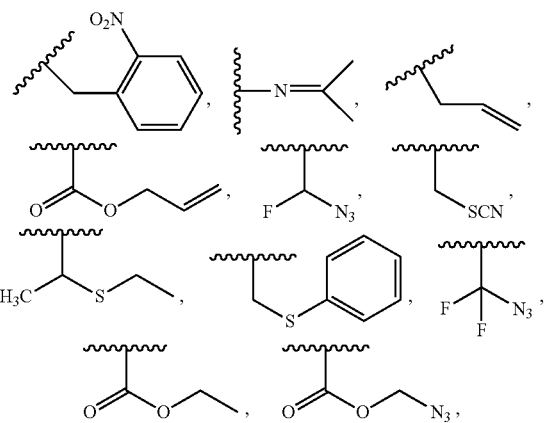

In embodiments, the polymerase-compatible cleavable moiety is independently

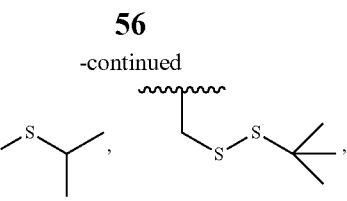

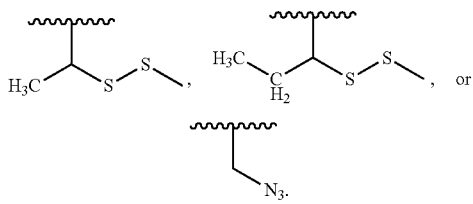

In embodiments, R$^2$ is —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, R$^2$ is —NH$_2$. In embodiments, R$^2$ is —CN. In embodiments, R$^2$ is —CH$_3$. In embodiments, R$^2$ is C$_2$-C$_6$ allyl (e.g., —CH$_2$—CH=CH$_2$). In embodiments, R$^2$ is methoxyalkyl (e.g., —CH$_2$—O—CH$_3$). In embodiments, R$^2$ is —CH$_2$N$_3$. In embodiments, R$^2$ is

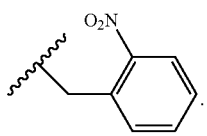

In embodiments, R$^2$ is

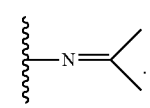

In embodiments, R$^2$ is

In embodiments, R$^2$ is

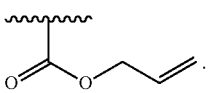

In embodiments, R$^2$ is

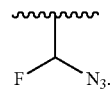

In embodiments R² is

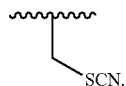

In embodiments R² is

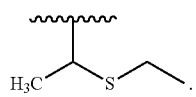

In embodiments, R² is

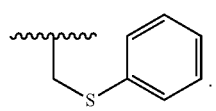

In embodiments, R² is

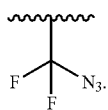

In embodiments, R² is

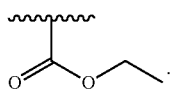

In embodiments, R² is

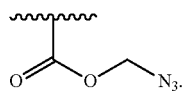

In embodiments, R² is —CH₂—O—CH₃. In embodiments, R² is —NH₂, —CH₂N₃,

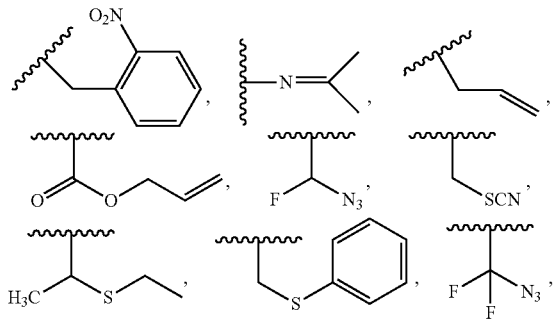

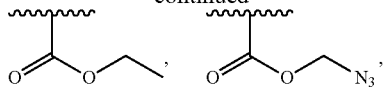

or —CH₂—O—CH₃.

In embodiments, R² is

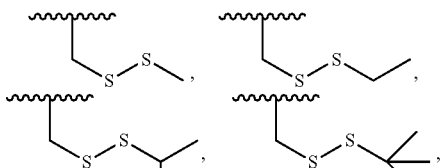

In embodiments, R² is

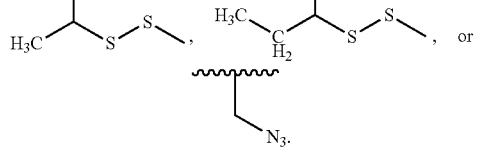

In embodiments, R² is

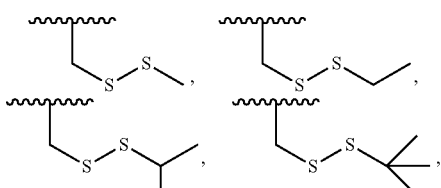

In embodiments, R² is

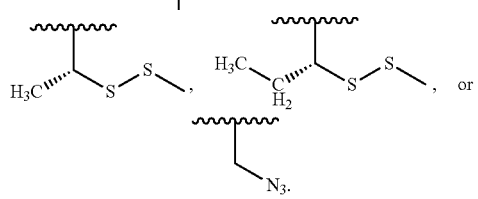

In embodiments, R² is

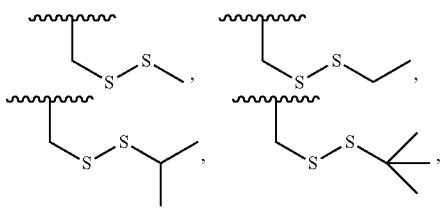

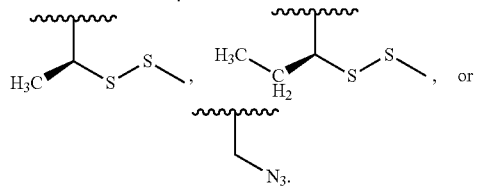

In embodiments, R² is a polymerase-compatible cleavable moiety or an —O-polymerase-compatible cleavable moiety; and the polymerase-compatible cleavable moiety is independently

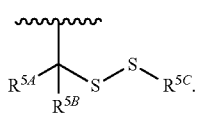

R$^{5A}$ is independently hydrogen, halogen, —CX$^{5A}_3$, —CHX$^{5A}_2$, —CH$_2$X$^{5A}$, —OCX$^{5A}_3$, —OCH$_2$X$^{5A}$, —OCHX$^{5A}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. R$^{5B}$ is independently hydrogen, halogen, —CX$^{5B}_3$, —CHX$^{5B}_2$, —CH$_2$X$^{5B}$, —OCX$^{5B}_3$, —OCH$_2$X$^{5B}$, —OCHX$^{5B}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^-$, —SO$_3^-$, —OPO$_3$H$^-$, —SCN, —ONO$_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, R$^{5A}$ and R$^{5B}$ are combined to form an oxo. R$^{5C}$ is hydrogen, halogen, —CX$^{5C}_3$, —CHX$^{5C}_2$, —CH$_2$X$^{5C}$, —OCX$^{5C}$, —OCH$_2$X$^{5C}$, —OCHX$^{5C}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, substituted (e.g., substituted with a substituent group, size-limited substituent group, or lower substitutent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, R$^{5C}$ is unsubstituted C$_1$-C$_4$ alkyl. In embodiments, R$^{5C}$ is unsubstituted methyl. In embodiments, R$^{5C}$ is unsubstituted tert-butyl. The symbols X$^{5A}$, X$^{5B}$, and X$^{5C}$ are independently —F, —Cl, —Br, or —I.

In embodiments, R$^2$ is a polymerase-compatible cleavable moiety or an —O-polymerase-compatible cleavable moiety; and the polymerase-compatible cleavable moiety is independently

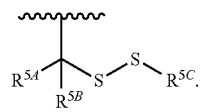

R$^{5A}$ is independently hydrogen, halogen, —CX$^{5A}_3$, —CHX$^{5A}_2$, —CH$_2$X$^{5A}$, —OCX$^{5A}_3$, —OCH$_2$X$^{5A}$, —OCHX$^{5A}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, substituted (e.g., substituted with a substituent group, a size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_8$, C$_3$-C$_6$, C$_4$-C$_6$, or C5-C$_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). R$^{5B}$ is independently hydrogen, halogen, —CX$^{5B}_3$, —CHX$^{5B}_2$, —CH$_2$X$^{5B}$, —OCX$^{5B}_3$, —OCH$_2$X$^{5B}$, —OCHX$^{5B}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, substituted (e.g., substituted with a substituent group, a size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{5A}$ and $R^{5B}$ are combined to form an oxo. $R^{5C}$ is hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^-$, —$SO_3^-$, —$OPO_3H^-$, —SCN, —$ONO_2$, substituted (e.g., substituted with a substituent group, a size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, and $X^{5C}$ are independently —F, —Cl, —Br, or —I.

In embodiments, a substituted $R^{5A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5A}$ is substituted with a plurality of groups selected from substituent groups, size-limited substituent groups, and lower substituent groups; each substituent group, size-limited substituent group, and/or lower substituent group may optionally be different. In embodiments, when $R^{5A}$ is substituted, it is substituted with at least one substituent group. In embodiments, when $R^{5A}$ is substituted, it is substituted with at least one size-limited substituent group. In embodiments, when $R^{5A}$ is substituted, it is substituted with at least one lower substituent group. In embodiments, when $R^{5A}$ is substituted, it is substituted with 1 to 10 substituent groups. In embodiments, when $R^{5A}$ is substituted, it is substituted with 1 to 10 size-limited substituent groups. In embodiments, when $R^{5A}$ is substituted, it is substituted with 1 to 10 lower substituent groups. In embodiments, when $R^{5A}$ is substituted, it is substituted with 1 to 5 substituent groups. In embodiments, when $R^{5A}$ is substituted, it is substituted with 1 to 5 size-limited substituent groups. In embodiments, when $R^{5A}$ is substituted, it is substituted with 1 to 5 lower substituent groups. In embodiments, when $R^{5A}$ is substituted, it is substituted with a substituent group. In embodiments, when $R^{5A}$ is substituted, it is substituted with a size-limited substituent group. In embodiments, when $R^{5A}$ is substituted, it is substituted with a lower substituent group.

In embodiments, a substituted $R^{5B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5B}$ is substituted with a plurality of groups selected from substituent groups, size-limited substituent groups, and lower substituent groups; each substituent group, size-limited substituent group, and/or lower substituent group may optionally be different. In embodiments, when $R^{5B}$ is substituted, it is substituted with at least one substituent group. In embodiments, when $R^{5B}$ is substituted, it is substituted with at least one size-limited substituent group. In embodiments, when $R^{5B}$ is substituted, it is substituted with at least one lower substituent group. In embodiments, when $R^{5B}$ is substituted, it is substituted with 1 to 10 substituent groups. In embodiments, when $R^{5B}$ is substituted, it is substituted with 1 to 10 size-limited substituent groups. In embodiments, when $R^{5B}$ is substituted, it is substituted with 1 to 10 lower substituent groups. In embodiments, when $R^{5B}$ is substituted, it is substituted with 1 to 5 substituent groups. In embodiments, when $R^{5B}$ is substituted, it is substituted with 1 to 5 size-limited substituent groups. In embodiments, when $R^{5B}$ is substituted, it is substituted with 1 to 5 lower substituent groups. In embodiments, when $R^{5B}$ is substituted, it is substituted with a substituent group. In embodiments, when $R^{5B}$ is substituted, it is substituted with a size-limited substituent group. In embodiments, when $R^{5B}$ is substituted, it is substituted with a lower substituent group.

In embodiments, a substituted $R^{5C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5C}$ is substituted with a plurality of groups selected from substituent groups, size-limited substituent groups, and lower substituent groups; each substituent group, size-limited substituent group, and/or lower substituent group may optionally be different. In embodiments, when $R^{5C}$ is substituted, it is substituted with at least one substituent group. In embodiments, when $R^{5C}$ is substituted, it is substituted with at least one size-limited substituent group. In embodiments, when $R^{5C}$ is substituted, it is substituted with at least one lower substituent group. In embodiments, when $R^{5C}$ is substituted, it is substituted with 1 to 10 substituent groups. In embodiments, when $R^{5C}$ is substituted, it is substituted with 1 to 10 size-limited substituent groups. In embodiments, when $R^{5C}$ is substituted, it is substituted with 1 to 10 lower substituent groups. In embodiments, when $R^{5C}$ is substituted, it is substituted with 1 to 5 substituent groups. In embodiments, when $R^{5C}$ is substituted, it is substituted with 1 to 5 size-limited substituent groups. In embodiments, when $R^{5C}$ is substituted, it is substituted with 1 to 5 lower substituent groups. In embodiments, when $R^{5C}$ is substituted, it is substituted with a substituent group. In embodiments, when $R^{5C}$ is substituted, it is substituted with a size-limited substituent group. In embodiments, when $R^{5C}$ is substituted, it is substituted with a lower substituent group.

In embodiments, $R^2$ is a polymerase-compatible cleavable moiety or an —O-polymerase-compatible cleavable moiety; and the polymerase-compatible cleavable moiety is independently

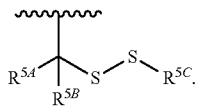

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5D}$-substituted or unsubstituted alkyl, $R^{5D}$-substituted or unsubstituted heteroalkyl, $R^{5D}$-substituted or unsubstituted cycloalkyl, $R^{5D}$-substituted or unsubstituted heterocycloalkyl, $R^{5D}$-substituted or unsubstituted aryl, or $R^{5D}$-substituted or unsubstituted heteroaryl. $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5E}$-substituted or unsubstituted alkyl, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl. $R^{5E}$ is independently halogen, oxo, —$CX^{5E}_3$, —$CHX^{5E}_2$, —$CH_2X^{5E}$, —$OCX^{5E}_3$, —$OCH_2X^{5E}$, —$OCHX^{5E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5F}$-substituted or unsubstituted alkyl, $R^{5F}$-substituted or unsubstituted heteroalkyl, $R^{5F}$-substituted or unsubstituted cycloalkyl, $R^{5F}$-substituted or unsubstituted heterocycloalkyl, $R^{5F}$-substituted or unsubstituted aryl, or $R^{5F}$-substituted or unsubstituted heteroaryl. $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5G}$-substituted or unsubstituted alkyl, $R^{5G}$-substituted or unsubstituted heteroalkyl, $R^{5G}$-substituted or unsubstituted cycloalkyl, $R^{5G}$-substituted or unsubstituted heterocycloalkyl, $R^{5G}$-substituted or unsubstituted aryl, or $R^{5G}$-substituted or unsubstituted heteroaryl. $R^{5G}$ is independently halogen, oxo, —$CX^{5G}_3$, —$CHX^{5G}_2$, —$CH_2X^{5G}$, —$OCX^{5G}_3$, —$OCH_2X^{5G}$, —$OCHX^{5G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5A}$ and $R^{5B}$ are combined to form an oxo. In embodiments, $R^{5C}$ is independently hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5H}$-substituted or unsubstituted alkyl, $R^{5H}$-substituted or unsubstituted heteroalkyl, $R^{5H}$-substituted or unsubstituted cycloalkyl, $R^{5H}$-substituted or unsubstituted heterocycloalkyl, $R^{5H}$-substituted or unsubstituted aryl, or $R^{5H}$-substituted or unsubstituted heteroaryl. $R^{5H}$ is independently halogen, oxo, —$CX^{5H}_3$, —$CHX^{5H}_2$, —$CH_2X^{5H}$, —$OCX^{5H}_3$, —$OCH_2X^{5H}$, —$OCHX^{5H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5I}$-substituted or unsubstituted alkyl, $R^{5I}$-substituted or unsubstituted heteroalkyl, $R^{5I}$-substituted or unsubstituted cycloalkyl, $R^{5I}$-substituted or unsubstituted heterocycloalkyl, $R^{5I}$-substituted or unsubstituted aryl, or $R^{5I}$-substituted or unsubstituted heteroaryl. $R^{5I}$ is independently halogen, oxo, —$CX^{5I}_3$, —$CHX^{5I}_2$, —$CH_2X^{5I}$, —$OCX^{5I}_3$, —$OCH_2X^{5I}$, —$OCHX^{5I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^2$ is a polymerase-compatible cleavable moiety or an —O-polymerase-compatible cleavable moiety; and the polymerase-compatible cleavable moiety is independently

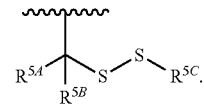

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5D}$-substituted or unsubstituted alkyl (e.g., $C_1$-$C_8$, $C_1$-$C_6$, $C_1$-$C_4$, or $C_1$-$C_2$), $R^{5D}$-substituted or unsubstituted heteroalkyl (e.g., 2 to 8 membered, 2 to 6 membered, 4 to 6 membered, 2 to 3 membered, or 4 to 5 membered), $R^{5D}$-substituted or unsubstituted cycloalkyl (e.g., $C_3$-$C_8$, $C_3$-$C_6$, $C_4$-$C_6$, or C5-$C_6$), $R^{5D}$-substituted or unsubstituted heterocycloalkyl (e.g., 3 to 8 membered, 3 to 6 membered, 4 to 6 membered, 4 to 5 membered, or 5 to 6 membered), $R^{5D}$-substituted or unsubstituted aryl (e.g., $C_6$-$C_{10}$ or phenyl), or $R^{5D}$-substituted or unsubstituted heteroaryl (e.g., 5 to 10 membered, 5 to 9 membered, or 5 to 6 membered). $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5E}$-substituted or unsubstituted alkyl (e.g., $C_1$-$C_8$, $C_1$-$C_6$, $C_1$-$C_4$, or $C_1$-$C_2$), $R^{5E}$-substituted or unsubstituted heteroalkyl (e.g., 2 to 8 membered, 2 to 6 membered, 4 to 6 membered, 2 to 3 membered, or 4 to 5 membered), $R^{5E}$-substituted or unsubstituted cycloalkyl (e.g., $C_3$-$C_8$, $C_3$-$C_6$, $C_4$-$C_6$, or C5-$C_6$), $R^{5E}$-substituted or unsubstituted heterocycloalkyl (e.g., 3 to 8 membered, 3 to 6 membered, 4 to 6 membered, 4 to 5 membered, or 5 to 6 membered), $R^{5E}$-substituted or unsubstituted aryl (e.g., $C_6$-$C_{10}$ or phenyl), or $R^{5E}$-substituted or unsubstituted heteroaryl (e.g., 5 to 10 membered, 5 to 9 membered, or 5 to 6 membered). $R^{5E}$ is independently halogen, oxo, —$CX^{5E}_3$, —$CHX^{5E}_2$, —$CH_2X^{5E}$, —$OCX^{5E}_3$, —$OCH_2X^{5E}$, —$OCHX^{5E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or C5-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H$, —SCN, —$ONO_2$, $R^{5F}$-substituted or unsubstituted alkyl (e.g., $C_1$-$C_8$, $C_1$-$C_6$, $C_1$-$C_4$, or $C_1$-$C_2$), $R^{5F}$-substituted or unsubstituted heteroalkyl (e.g., 2 to 8 membered, 2 to 6 membered, 4 to 6 membered, 2 to 3 membered, or 4 to 5 membered), $R^{5F}$-substituted or unsubstituted cycloalkyl (e.g., $C_3$-$C_8$, $C_3$-$C_6$, $C_4$-$C_6$, or C5-$C_6$), $R^{5F}$-substituted or unsubstituted heterocycloalkyl (e.g., 3 to 8 membered, 3 to 6 membered, 4 to 6 membered, 4 to 5 membered, or 5 to 6 membered), $R^{5F}$-substituted or unsubstituted aryl (e.g., $C_6$-$C_{10}$ or phenyl), or $R^{5F}$-substituted or unsubstituted heteroaryl (e.g., 5 to 10 membered, 5 to 9 membered, or 5 to 6 membered). $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5G}$-substituted or unsubstituted alkyl (e.g., $C_1$-$C_8$, $C_1$-$C_6$, $C_1$-$C_4$, or $C_1$-$C_2$), $R^{5G}$-substituted or unsubstituted heteroalkyl (e.g., 2 to 8 membered, 2 to 6 membered, 4 to 6 membered, 2 to 3 membered, or 4 to 5 membered), $R^{5G}$-substituted or unsubstituted cycloalkyl (e.g., $C_3$-$C_8$, $C_3$-$C_6$, $C_4$-$C_6$, or C5-$C_6$), $R^{5G}$-substituted or unsubstituted heterocycloalkyl (e.g., 3 to 8 membered, 3 to 6 membered, 4 to 6 membered, 4 to 5 membered, or 5 to 6 membered), $R^{5G}$-substituted or unsubstituted aryl (e.g., $C_6$-$C_{10}$ or phenyl), or $R^{5G}$-substituted or unsubstituted heteroaryl (e.g., 5 to 10 membered, 5 to 9 membered, or 5 to 6 membered). $R^{5G}$ is independently halogen, oxo, —$CX^{5G}_3$, —$CHX^{5G}_2$, —$CH_2X^{5G}$, —$OCX^{5G}_3$, —$OCH_2X^{5G}$, —$OCHX^{5G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or C5-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{5A}$ and $R^{5B}$ are combined to form an oxo. In embodiments, $R^{5C}$ is independently hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5H}$-substituted or unsubstituted alkyl (e.g., $C_1$-$C_8$, $C_1$-$C_6$, $C_1$-$C_4$, or $C_1$-$C_2$), $R^{5H}$-substituted or unsubstituted heteroalkyl (e.g., 2 to 8 membered, 2 to 6 membered, 4 to 6 membered, 2 to 3 membered, or 4 to 5 membered), $R^{5H}$-substituted or unsubstituted cycloalkyl (e.g., $C_3$-$C_8$, $C_3$-$C_6$, $C_4$-$C_6$, or $C_5$-$C_6$), $R^{5H}$-substituted or unsubstituted heterocycloalkyl (e.g., 3 to 8 membered, 3 to 6 membered, 4 to 6 membered, 4 to 5 membered, or 5 to 6 membered), $R^{5H}$-substituted or unsubstituted aryl (e.g., $C_6$-$C_{10}$ or phenyl), or $R^{5H}$-substituted or unsubstituted heteroaryl (e.g., 5 to 10 membered, 5 to 9 membered, or 5 to 6 membered). $R^{5H}$ is independently halogen, oxo, —$CX^{5H}_3$, —$CHX^{5H}_2$, —$CH_2X^{5H}$, —$OCX^{5H}_3$, —$OCH_2X^{5H}$, —$OCHX^{5H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5I}$-substituted or unsubstituted alkyl (e.g., $C_1$-$C_8$, $C_1$-$C_6$, $C_1$-$C_4$, or $C_1$-$C_2$), $R^{5I}$-substituted or unsubstituted heteroalkyl (e.g., 2 to 8 membered, 2 to 6 membered, 4 to 6 membered, 2 to 3 membered, or 4 to 5 membered), $R^{5I}$-substituted or unsubstituted cycloalkyl (e.g., $C_3$-$C_8$, $C_3$-$C_6$, $C_4$-$C_6$, or C5-$C_6$), $R^{5I}$-substituted or unsubstituted heterocycloalkyl (e.g., 3 to 8 membered, 3 to 6 membered, 4 to 6 membered, 4 to 5 membered, or 5 to 6 membered), $R^{5I}$-substituted or unsubstituted aryl (e.g., $C_6$-$C_{10}$ or phenyl), or $R^{5I}$-substituted or unsubstituted heteroaryl (e.g., 5 to 10 membered, 5 to 9 membered, or 5 to 6 membered). $R^{5I}$ is independently halogen, oxo, —$CX^{5I}_3$, —$CHX^{5I}_2$, —$CH_2X^{5I}$, —$OCX^{5I}_3$, —$OCH_2X^{5I}$, —$OCHX^{5I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or C5-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{5C}$ is unsubstituted C1-$C_4$ alkyl. In embodiments, $R_{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5D}$-substituted $C_1$-$C_4$ alkyl (e.g., $R^{5D}$-substituted $C_1$-$C_3$ alkyl, $R^{5D}$-substituted $C_1$-$C_2$ alkyl, or $R^{5D}$-substituted methyl) or $R^{5D}$-substituted 2 to 8 membered heteroalkyl (e.g., 2 to 6 membered heteroalkyl, $R^{5D}$-substituted 2 to 5 membered heteroalkyl, or $R^{5D}$-substituted 2 to 4 membered heteroalkyl). In embodiments, $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, or —$ONO_2$. In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5F}$-substituted $C_1$-$C_4$ alkyl, (e.g., $R^{5F}$-substituted $C_1$-$C_3$ alkyl, $R^{5F}$-substituted $C_1$-$C_2$ alkyl, or $R^{5F}$-substituted methyl) or $R^{5F}$-substituted 2 to 8 membered heteroalkyl (e.g., $R^{5F}$-substituted 2 to 6 membered heteroalkyl, $R^{5F}$-substituted 2 to 5 membered heteroalkyl, or $R^{5F}$-substituted 2 to 4 membered heteroalkyl). In embodiments, $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, or —$ONO_2$. In embodiments, $R^{5A}$ and $R^{5B}$ are be combined to form an oxo group. The symbols $X^{5A}$, $X^{5B}$, $X^{5D}$, and $X^{5F}$ are independently —F, —Cl, —Br, or —I.

In embodiments, $R^2$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2A}$-substituted or unsubstituted cycloalkyl (e.g., $C_3$-$C_8$, $C_3$-$C_6$, or $C_5$-$C_6$), $R^{2A}$-substituted or unsubstituted heterocycloalkyl (e.g., 3 to 8 membered, 3 to 6 membered, or 5 to 6 membered), $R^{2A}$-substituted or unsubstituted aryl (e.g., $C_6$-$C_{10}$, $C_{10}$, or phenyl), or $R^{2A}$-substituted or unsubstituted heteroaryl (e.g., 5 to 10 membered, 5 to 9 membered, or 5 to 6 membered), or —$OR^{2A}$. In embodiments, $R^2$ is independently —$OR^{2A}$.

$R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8 membered, 3 to 6 membered, or 5 to 6 membered), $R^{2B}$-substituted or unsubstituted aryl (e.g., $C_6$-$C_{10}$, $C_{10}$, or phenyl), $R^{2B}$-substituted or unsubstituted heteroaryl (e.g., 5 to 10 membered, 5 to 9 membered, or 5 to 6 membered), or a polymerase-compatible cleavable moiety. In embodiments, $R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8 membered, 3 to 6 membered, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10 membered, 5 to 9 membered, or 5 to 6 membered). In embodiments, $R^{2A}$ is independently a polymerase-compatible cleavable moiety.

$R^{2B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, R$^{2C}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{2C}$-substituted or unsubstituted heteroalkyl (e.g., 2 to 20 membered, 8 to 20 membered, 2 to 10 membered, 2 to 8 membered, 2 to 6 membered, or 2 to 4 membered), R$^{2C}$-substituted or unsubstituted cycloalkyl (e.g., C$_3$-C$_8$, C$_3$-C$_6$, or C$_5$-C$_6$), R$^{2C}$-substituted or unsubstituted heterocycloalkyl (e.g., 3 to 8 membered, 3 to 6 membered, or 5 to 6 membered), R$^{2C}$-substituted or unsubstituted aryl (e.g., C$_6$-C$_{10}$, C$_{10}$, or phenyl), or R$^{2C}$-substituted or unsubstituted heteroaryl (e.g., 5 to 10 membered, 5 to 9 membered, or 5 to 6 membered).

R$^{2C}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —NH$_3^+$, —SO$_3^-$, —OPO$_3$H$^-$, —SCN, —ONO$_2$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_{10}$, or phenyl), or unsubstituted heteroaryl (e.g., 5 to 10 membered, 5 to 9 membered, or 5 to 6 membered).

In embodiments, R$^{2A}$ is a polymerase-compatible cleavable moiety; and the polymerase-compatible cleavable moiety is independently

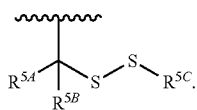

R$^{5A}$, R$^{5B}$, and R$^{5C}$ are as described herein, including in embodiments.

In embodiments, R$^{2A}$ is independently:

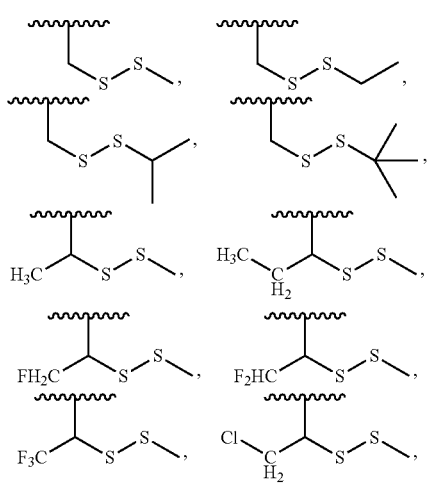

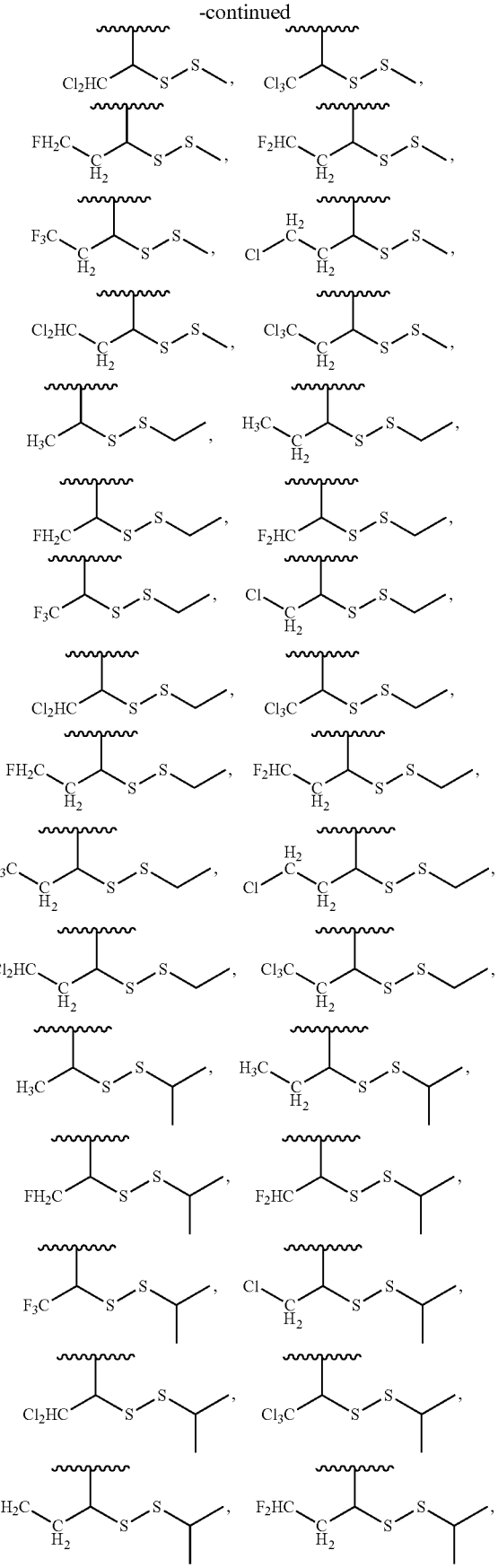

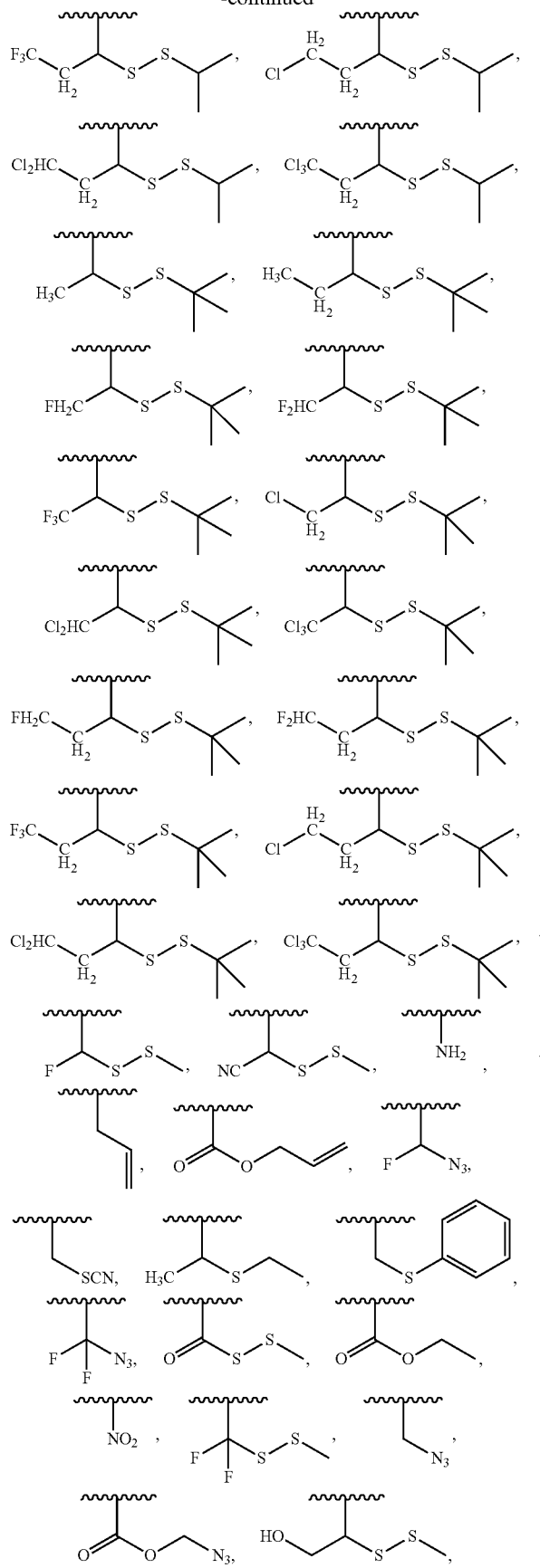
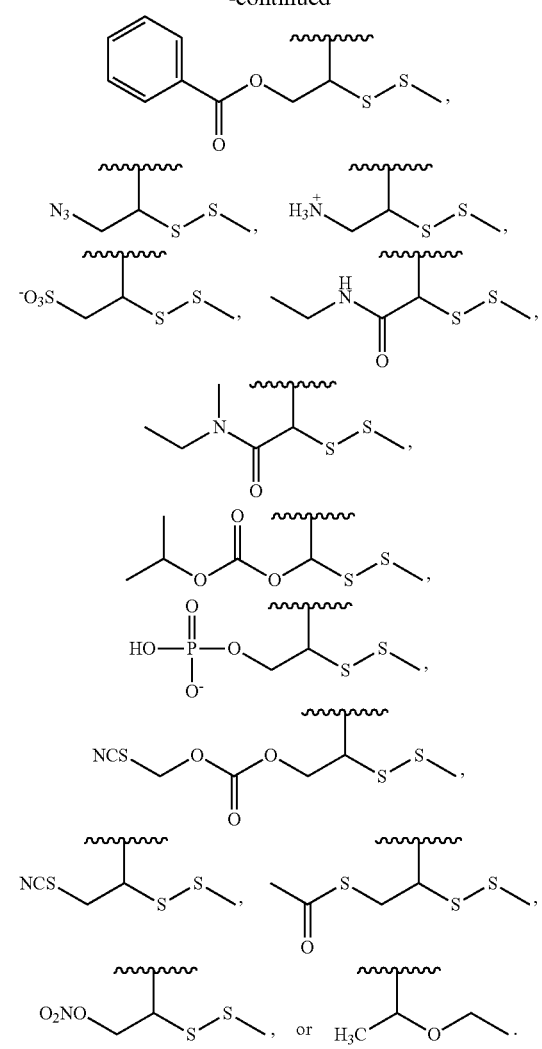
In embodiments, $R^{2A}$ is independently:
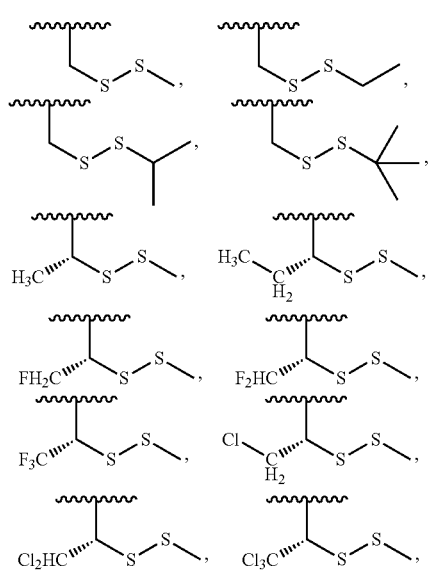

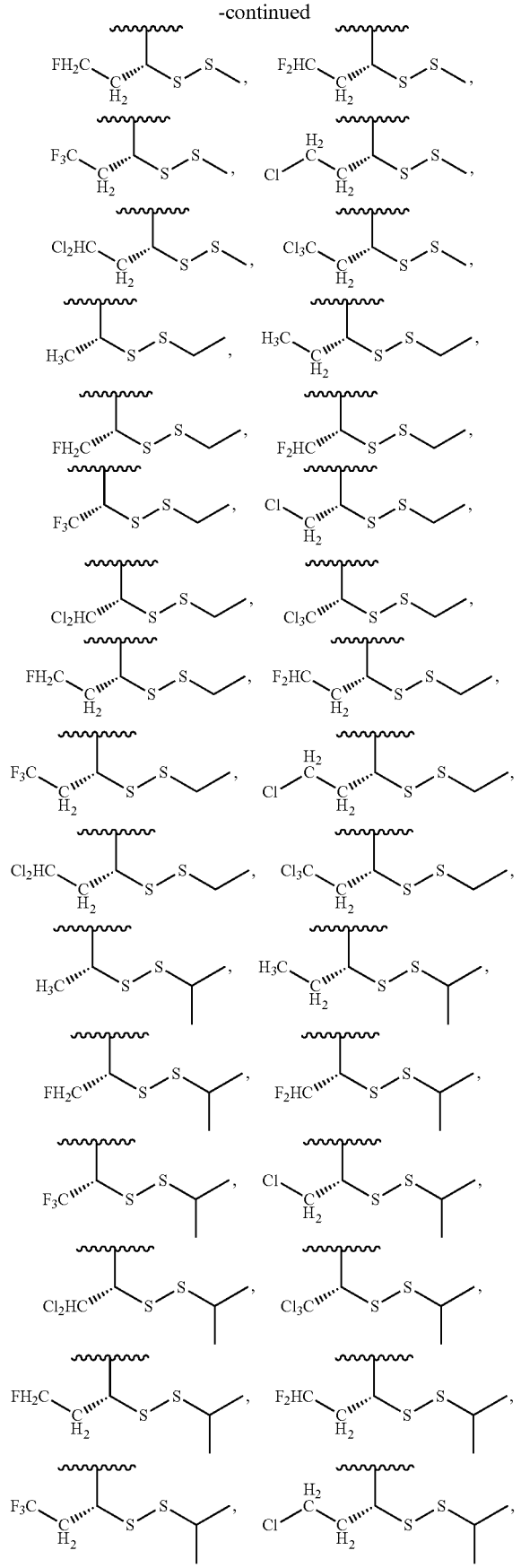

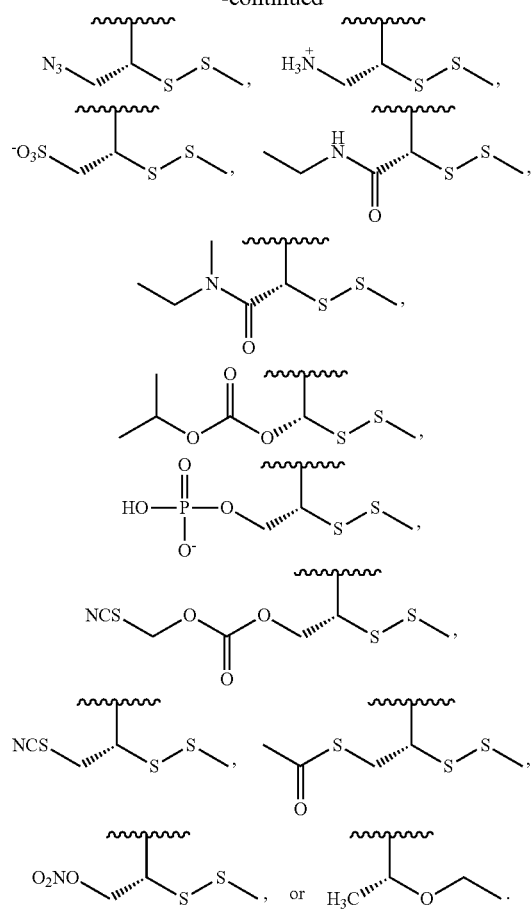
In embodiments, $R^{2A}$ is independently:
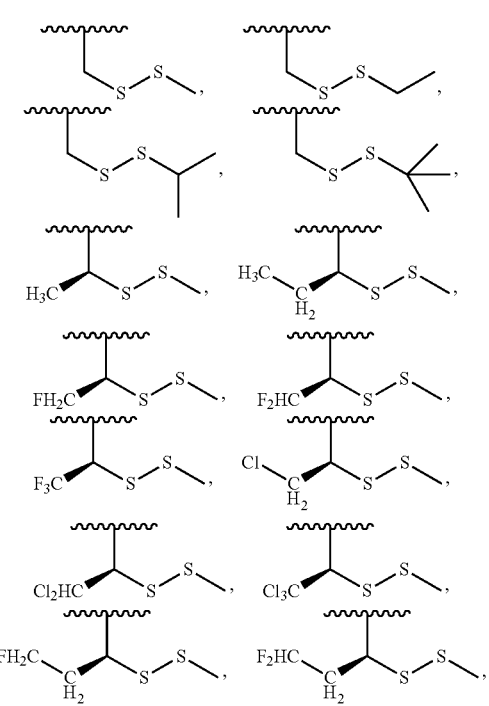
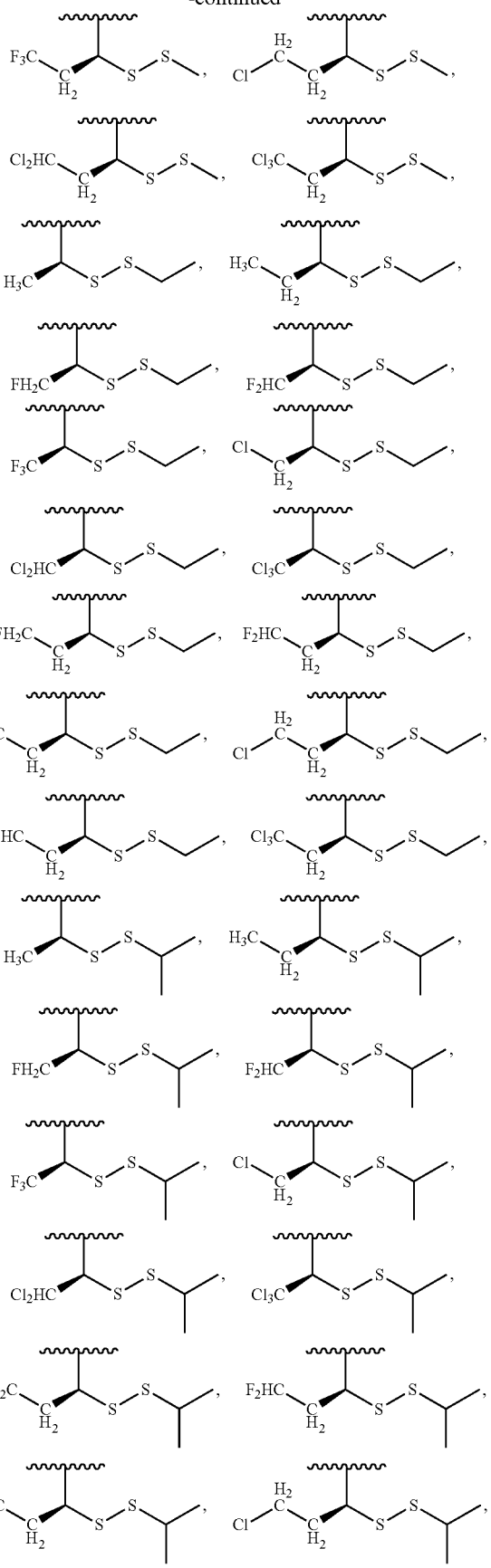

-continued
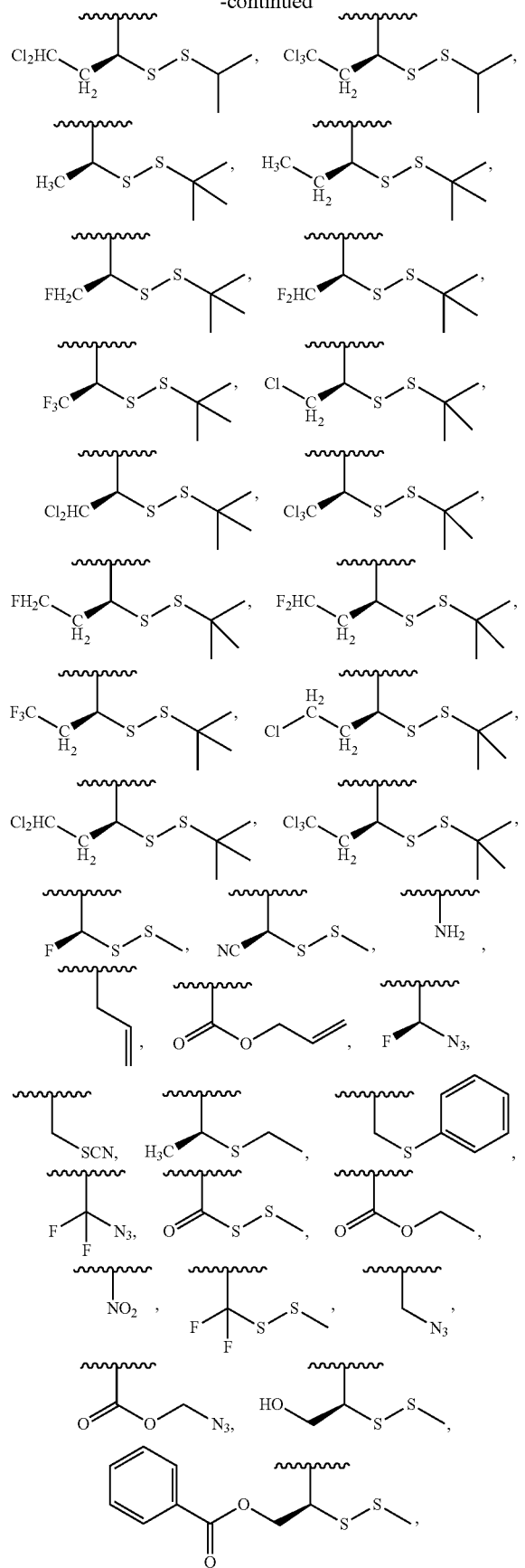
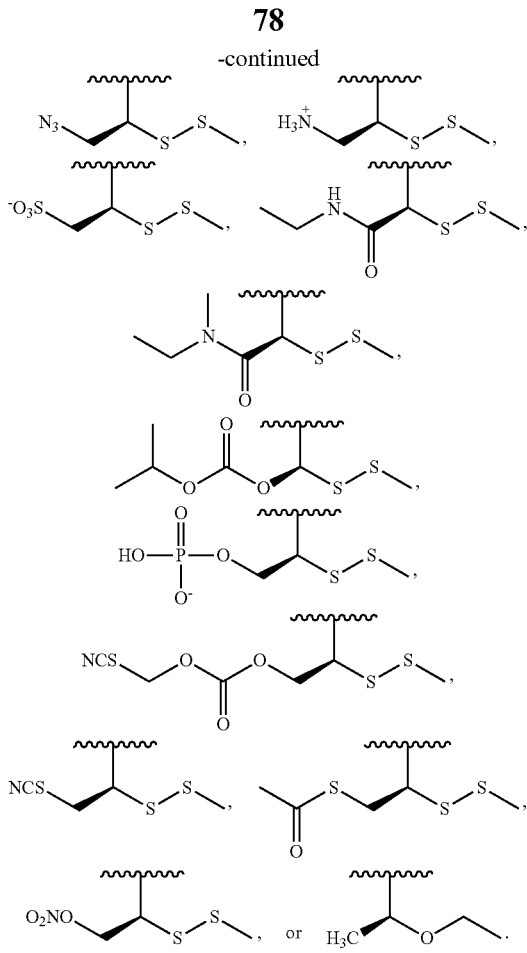
In embodiments, $R^{2A}$ is
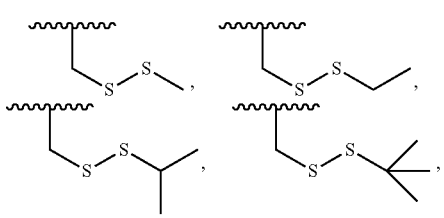
In embodiments, $R^{2A}$ is -continued

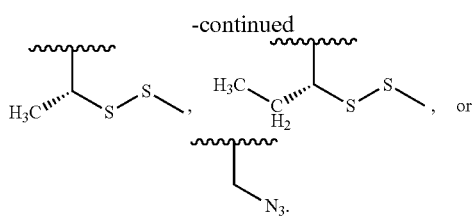

In embodiments, $R^{2A}$ is

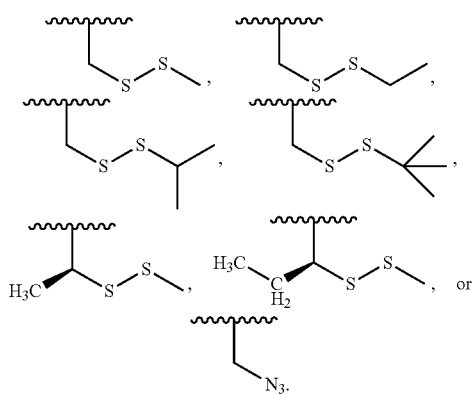

In embodiments, $R^{2A}$ is independently

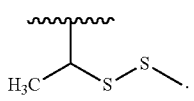

In embodiments, $R^{2A}$ is independently

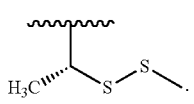

In embodiments, $R^{2A}$ is independently H

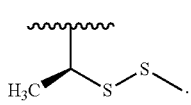

In embodiments, $R^3$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^3$ is independently a polymerase-compatible cleavable moiety. In embodiments, $R^3$ is independently an —O-polymerase-compatible cleavable moiety.

In embodiments, $R^3$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with a substituent group, a size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^3$ is independently a polymerase-compatible cleavable moiety. In embodiments, $R^3$ is independently an —O-polymerase-compatible cleavable moiety.

In embodiments, a substituted $R^3$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group. In embodiments, when $R^3$ is substituted, it is substituted with 1 to 10 substituent groups. In embodiments, when $R^3$ is substituted, it is substituted with 1 to 10 size-limited substituent groups. In embodiments, when $R^3$ is substituted, it is substituted with 1 to 10 lower substituent groups. In embodiments, when $R^3$ is substituted, it is substituted with 1 to 5 substituent groups. In embodiments, when $R^3$ is substituted, it is substituted with 1 to 5 size-limited substituent groups. In embodiments, when $R^3$ is substituted, it is substituted with 1 to 5 lower substituent groups. In embodiments, when $R^3$ is substituted, it is substituted with a substituent group. In embodiments, when $R^3$ is substituted, it is substituted with a size-limited substituent group. In embodiments, when $R^3$ is substituted, it is substituted with a lower substituent group.

In embodiments, $R^3$ is hydrogen. In embodiments, $R^3$ is a polymerase-compatible cleavable moiety. In embodiments, $R^3$ is a polymerase-compatible cleavable moiety including an azido moiety. In embodiments, $R^3$ is a polymerase-compatible cleavable moiety including a dithiol linker. In embodiments, $R^3$ is an —O-polymerase-compatible cleavable moiety; and the polymerase-compatible cleavable moiety is —$CH_2N_3$.

In embodiments, $R^3$ is an —O-polymerase-compatible cleavable moiety. In embodiments, the polymerase-compatible cleavable moiety is independently —$NH_2$, —$NO_2$, —CN, —$CH_3$, $C_2$-$C_6$ allyl (e.g., —$CH_2$—CH=$CH_2$), methoxyalkyl (e.g., —$CH_2$—O—$CH_3$), or —$CH_2N_3$. In embodiments, the polymerase-compatible cleavable moiety is independently —$NH_2$. In embodiments, the polymerase-compatible cleavable moiety is independently —CN. In embodiments, the polymerase-compatible cleavable moiety is independently —$CH_3$. In embodiments, the polymerase-compatible cleavable moiety is independently $C_2$-$C_6$ allyl (e.g., —$CH_2$—CH=$CH_2$). In embodiments, the polymerase-compatible cleavable moiety is independently methoxyalkyl (e.g., —$CH_2$—O—$CH_3$). In embodiments, the polymerase-compatible cleavable moiety is independently —$CH_2N_3$. In embodiments, the polymerase-compatible cleavable moiety is independently —$NH_2$. In embodiments, the polymerase-compatible cleavable moiety is independently —$NO_2$. In embodiments, the polymerase-compatible cleavable moiety is independently —$CH_2N_3$. In embodiments, the polymerase-compatible cleavable moiety is independently

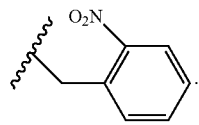

In embodiments, the polymerase-compatible cleavable moiety is independently

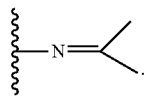

In embodiments, the polymerase-compatible cleavable moiety is independently

In embodiments, the polymerase-compatible cleavable moiety is independently

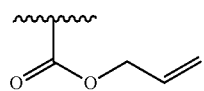

In embodiments, the polymerase-compatible cleavable moiety is independently

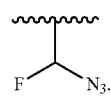

In embodiments, the polymerase-compatible cleavable moiety is independently

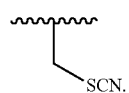

In embodiments, the polymerase-compatible cleavable moiety is independently

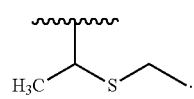

In embodiments, the polymerase-compatible cleavable moiety is independently

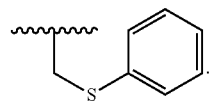

In embodiments, the polymerase-compatible cleavable moiety is independently

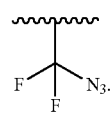

In embodiments, the polymerase-compatible cleavable moiety is independently

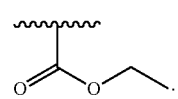 [SMILES: *C(=O)OCC]

In embodiments, the polymerase-compatible cleavable moiety is independently

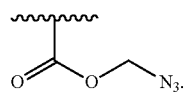

In embodiments, the polymerase-compatible cleavable moiety is independently —$CH_2$—O—$CH_3$. In embodiments, the polymerase-compatible cleavable moiety is independently —$NH_2$, —$CH_2N_3$,

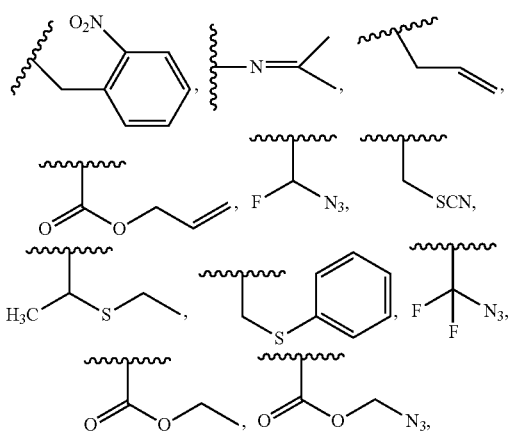

or —CH$_2$—O—CH$_3$.

In embodiments, R$^3$ is —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, R$^3$ is —NH$_2$. In embodiments, R$^3$ is —CN. In embodiments, R$^3$ is —CH$_3$. In embodiments, R$^3$ is C$_2$-C$_6$ allyl (e.g., —CH$_2$—CH=CH$_2$). In embodiments, R$^3$ is methoxyalkyl (e.g., —CH$_2$—O—CH$_3$). In embodiments, R$^3$ is —CH$_2$N$_3$. In embodiments, R$^3$ is

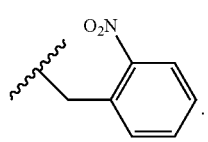

In embodiments, R$^3$ is

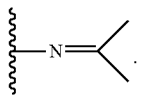

In embodiments R$^3$ is

In embodiments R$^3$ is

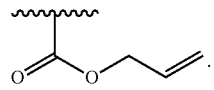 [SMILES: *C(=O)OCC=C]

In embodiments, R$^3$ is

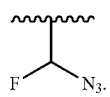

In embodiments R$^3$ is

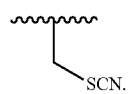

In embodiments, R$^3$ is

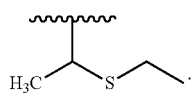

In embodiments, R$^3$ is

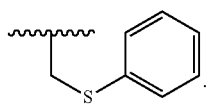

In embodiments, R$^3$ is

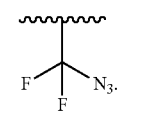

In embodiments, R$^3$ is

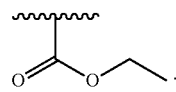 [SMILES: *C(=O)OCC]

In embodiments, R$^3$ is

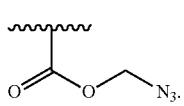

In embodiments, R$^3$ is —CH$_2$—O—CH$_3$. In embodiments, R$^3$ is —NH$_2$, —CH$_2$N$_3$,

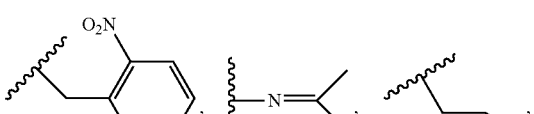

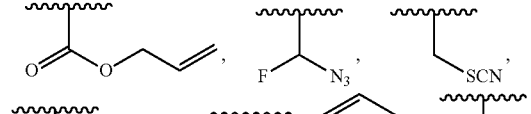

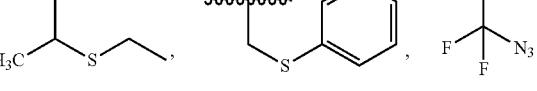

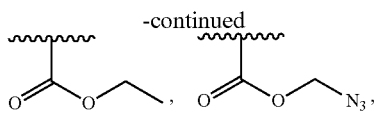
or —CH$_2$—O—CH$_3$.

In embodiments, R$^3$ is

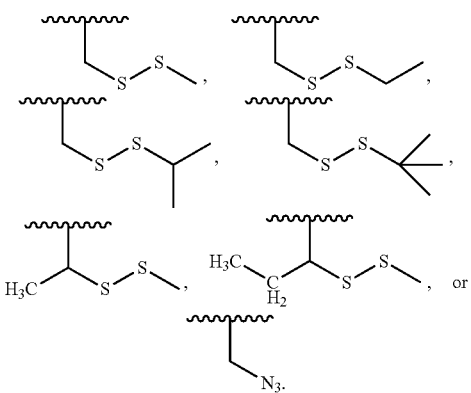

In embodiments, R$^3$ is

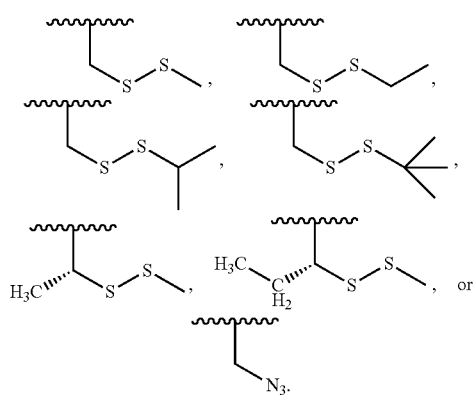

In embodiments, R$^3$ is

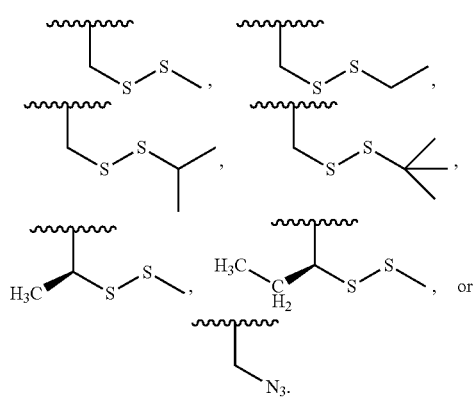

In embodiments, R$^3$ is a polymerase-compatible cleavable moiety or an —O-polymerase-compatible cleavable moiety; and the polymerase-compatible cleavable moiety is independently

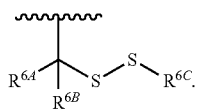

R$^{6A}$ is independently hydrogen, halogen, —CX$^{6A}_3$, —CHX$^{6A}_2$, —CH$_2$X$^{6A}$, —OCX$^{6A}_3$, —OCH$_2$X$^{6A}$, —OCHX$^{6A}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, substituted (e.g., substituted with a substituent group, a size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). R$^{6B}$ is independently hydrogen, halogen, —CX$^{6B}_3$, —CHX$^{6B}_2$, —CH$_2$X$^{6B}$, —OCX$^{6B}_3$, —OCH$_2$X$^{6B}$, —OCHX$^{6B}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, substituted (e.g., substituted with a substituent group, a size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, R$^{6A}$ and R$^{6B}$ are combined to form an oxo. R$^{6C}$ is hydrogen, halogen, —CX$^{6C}_3$, —CHX$^{6C}_2$, —CH$_2$X$^{6C}$, —OCX$^{6C}_3$, —OCH$_2$X$^{6C}$, —OCHX$^{6C}_2$, —CN, —OH, —SH, —NH$_2$, —COOH, —CONH$_2$, —NO$_2$, —SO$_3$H, —SO$_4$H, —SO₂NH₂, —NHNH₂, —ONH₂, —NHC(O)NHNH₂, —NHC(O)NH₂, —NHSO₂H, —NHC(O)H, —NHC(O)OH, —NHOH, —N₃, —SF₅, —NH₃⁺, —SO₃⁻, —OPO₃H⁻, —SCN, —ONO₂, substituted (e.g., substituted with a substituent group, a size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). In embodiments, $R^{6C}$ is unsubstituted $C_1$-$C_4$ alkyl. In embodiments, $R^{6C}$ is unsubstituted methyl. In embodiments, $R^{6C}$ is unsubstituted tert-butyl. The symbols $X^{6A}$, $X^{6B}$, and $X^{6C}$ are independently —F, —Cl, —Br, or —I.

In embodiments, a substituted $R^{6A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6A}$ is substituted with a plurality of groups selected from substituent groups, size-limited substituent groups, and lower substituent groups; each substituent group, size-limited substituent group, and/or lower substituent group may optionally be different. In embodiments, when $R^{6A}$ is substituted, it is substituted with at least one substituent group. In embodiments, when $R^{6A}$ is substituted, it is substituted with at least one size-limited substituent group. In embodiments, when $R^{6A}$ is substituted, it is substituted with at least one lower substituent group. In embodiments, when $R^{6A}$ is substituted, it is substituted with 1 to 10 substituent groups. In embodiments, when $R^{6A}$ is substituted, it is substituted with 1 to 10 size-limited substituent groups. In embodiments, when $R^{6A}$ is substituted, it is substituted with 1 to 10 lower substituent groups. In embodiments, when $R^{6A}$ is substituted, it is substituted with 1 to 5 substituent groups. In embodiments, when $R^{6A}$ is substituted, it is substituted with 1 to 5 size-limited substituent groups. In embodiments, when $R^{6A}$ is substituted, it is substituted with 1 to 5 lower substituent groups. In embodiments, when $R^{6A}$ is substituted, it is substituted with a substituent group. In embodiments, when $R^{6A}$ is substituted, it is substituted with a size-limited substituent group. In embodiments, when $R^{6A}$ is substituted, it is substituted with a lower substituent group.

In embodiments, a substituted $R^{6B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6B}$ is substituted with a plurality of groups selected from substituent groups, size-limited substituent groups, and lower substituent groups; each substituent group, size-limited substituent group, and/or lower substituent group may optionally be different. In embodiments, when $R^{6B}$ is substituted, it is substituted with at least one substituent group. In embodiments, when $R^{6B}$ is substituted, it is substituted with at least one size-limited substituent group. In embodiments, when $R^{6B}$ is substituted, it is substituted with at least one lower substituent group. In embodiments, when $R^{6B}$ is substituted, it is substituted with 1 to 10 substituent groups. In embodiments, when $R^{6B}$ is substituted, it is substituted with 1 to 10 size-limited substituent groups. In embodiments, when $R^{6B}$ is substituted, it is substituted with 1 to 10 lower substituent groups. In embodiments, when $R^{6B}$ is substituted, it is substituted with 1 to 5 substituent groups. In embodiments, when $R^{6B}$ is substituted, it is substituted with 1 to 5 size-limited substituent groups. In embodiments, when $R^{6B}$ is substituted, it is substituted with 1 to 5 lower substituent groups. In embodiments, when $R^{6B}$ is substituted, it is substituted with a substituent group. In embodiments, when $R^{6B}$ is substituted, it is substituted with a size-limited substituent group. In embodiments, when $R^{6B}$ is substituted, it is substituted with a lower substituent group.

In embodiments, a substituted $R^{6C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6C}$ is substituted with a plurality of groups selected from substituent groups, size-limited substituent groups, and lower substituent groups; each substituent group, size-limited substituent group, and/or lower substituent group may optionally be different. In embodiments, when $R^{6C}$ is substituted, it is substituted with at least one substituent group. In embodiments, when $R^{6C}$ is substituted, it is substituted with at least one size-limited substituent group. In embodiments, when $R^{6C}$ is substituted, it is substituted with at least one lower substituent group. In embodiments, when $R^{6C}$ is substituted, it is substituted with 1 to 10 substituent groups. In embodiments, when $R^{6C}$ is substituted, it is substituted with 1 to 10 size-limited substituent groups. In embodiments, when $R^{6C}$ is substituted, it is substituted with 1 to 10 lower substituent groups. In embodiments, when $R^{6C}$ is substituted, it is substituted with 1 to 5 substituent groups. In embodiments, when $R^{6C}$ is substituted, it is substituted with 1 to 5 size-limited substituent groups. In embodiments, when $R^{6C}$ is substituted, it is substituted with 1 to 5 lower substituent groups. In embodiments, when $R^{6C}$ is substituted, it is substituted with a substituent group. In embodiments, when $R^{6C}$ is substituted, it is substituted with a size-limited substituent group. In embodiments, when $R^{6C}$ is substituted, it is substituted with a lower substituent group.

In embodiments, $R^3$ is a polymerase-compatible cleavable moiety or an —O-polymerase-compatible cleavable moiety; and the polymerase-compatible cleavable moiety is independently

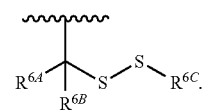

In embodiments, $R^{6A}$ is independently hydrogen, halogen, —$CX^{6A}_3$, —$CHX^{6A}_2$, —$CH_2X^{6A}$, —$OCX^{6A}_3$, —$OCH_2X^{6A}$, —$OCHX^{6A}_2$, —CN, —OH, —SH, —NH₂, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6D}$-substituted or unsubstituted alkyl, R$^{6D}$-substituted or unsubstituted heteroalkyl, R$^{6D}$-substituted or unsubstituted cycloalkyl, R$^{6D}$-substituted or unsubstituted heterocycloalkyl, R$^{6D}$-substituted or unsubstituted aryl, or R$^{6D}$-substituted or unsubstituted heteroaryl. R$^{6D}$ is independently halogen, oxo, —CX$^{6D}_3$, —CHX$^{6D}_2$, —CH$_2$X$^{6D}$—OCX$^{6D}_3$, —OCH$_2$X$^{6D}$, —OCHX$^{6D}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6E}$-substituted or unsubstituted alkyl, R$^{6E}$-substituted or unsubstituted heteroalkyl, R$^{6E}$-substituted or unsubstituted cycloalkyl, R$^{6E}$-substituted or unsubstituted heterocycloalkyl, R$^{6E}$-substituted or unsubstituted aryl, or R$^{6E}$-substituted or unsubstituted heteroaryl. R$^{6E}$ is independently halogen, oxo, —CX$^{6E}_3$, —CHX$^{6E}_2$, —CH$_2$X$^{6E}$, —OCX$^{6E}_3$, —OCH$_2$X$^{6E}$, —OCHX$^{6E}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{6B}$ is independently hydrogen, halogen, —CX$^{6B}_3$, —CHX$^{6B}_2$, —CH$_2$X$^{6B}$, —OCX$^{6B}_3$, —OCH$_2$X$^{6B}$, —OCHX$^{6B}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6F}$-substituted or unsubstituted alkyl, R$^{6F}$-substituted or unsubstituted heteroalkyl, R$^{6F}$-substituted or unsubstituted cycloalkyl, R$^{6F}$-substituted or unsubstituted heterocycloalkyl, R$^{6F}$-substituted or unsubstituted aryl, or R$^{6F}$-substituted or unsubstituted heteroaryl. R$^{6F}$ is independently halogen, oxo, —CX$^{6F}_3$, —CHX$^{6F}_2$, —CH$_2$X$^{6F}$—OCX$^{6F}_3$, —OCH$_2$X$^{6F}$, —OCHX$^{6F}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6G}$-substituted or unsubstituted alkyl, R$^{6G}$-substituted or unsubstituted heteroalkyl, R$^{6G}$-substituted or unsubstituted cycloalkyl, R$^{6G}$-substituted or unsubstituted heterocycloalkyl, R$^{6G}$-substituted or unsubstituted aryl, or R$^{6G}$-substituted or unsubstituted heteroaryl. R$^{6G}$ is independently halogen, oxo, —CX$^{6G}_3$, —CHX$^{6G}_2$, —CH$_2$X$^{6G}$, —OCX$^{6G}_3$, —OCH$_2$X$^{6G}$, —OCHX$^{6G}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{6A}$ and R$^{6B}$ are combined to form an oxo. In embodiments, R$^{6C}$ is independently hydrogen, halogen, —CX$^{6C}_3$, —CHX$^{6C}_2$, —CH$_2$X$^{6C}$, —OCX$^{6C}_3$, —OCH$_2$X$^{6C}$, —OCHX$^{6C}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6H}$-substituted or unsubstituted alkyl, R$^{6H}$-substituted or unsubstituted heteroalkyl, R$^{6H}$-substituted or unsubstituted cycloalkyl, R$^{6H}$-substituted or unsubstituted heterocycloalkyl, R$^{6H}$-substituted or unsubstituted aryl, or R$^{6H}$-substituted or unsubstituted heteroaryl. R$^{6H}$ is independently halogen, oxo, —CX$^{6H}_3$, —CHX$^{6H}_2$, —CH$_2$X$^{6H}$, —OCX$^{6H}_3$, —OCH$_2$X$^{6H}$, —OCHX$^{6H}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6I}$-substituted or unsubstituted alkyl, R$^{6I}$-substituted or unsubstituted heteroalkyl, R$^{6I}$-substituted or unsubstituted cycloalkyl, R$^{6I}$-substituted or unsubstituted heterocycloalkyl, R$^{6I}$-substituted or unsubstituted aryl, or R$^{6I}$-substituted or unsubstituted heteroaryl. R$^{6I}$ is independently halogen, oxo, —CX$^{6I}_3$, —CHX$^{6I}_2$, —CH$_2$X$^{6I}$, —OCX$^{6I}_3$, —OCH$_2$X$^{6I}$, —OCHX$^{6I}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{6C}$ is unsubstituted C$_1$-C$_4$ alkyl. In embodiments, R$^{6C}$ is unsubstituted methyl. In embodiments, R$^{6C}$ is unsubstituted tert-butyl. The symbols X$^{6A}$, X$^{6B}$, X$^{6C}$, X$^{6D}$, X$^{6E}$, X$^{6F}$, X$^{6G}$, X$^{6H}$, and X$^{6I}$ are independently —F, —Cl, —Br, or —I.

In embodiments, R$^3$ is a polymerase-compatible cleavable moiety or an —O-polymerase-compatible cleavable moiety; and the polymerase-compatible cleavable moiety is independently

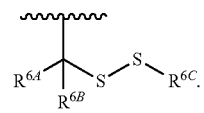

In embodiments, R$^{6A}$ is independently hydrogen, halogen, —CX$^{6A}_3$, —CHX$^{6A}_2$, —CH$_2$X$^{6A}$, —OCX$^{6A}_3$, —OCH$_2$X$^{6A}$, —OCHX$^{6A}_2$, —CN, —OH, —SH, —NH$_2$, —COOH, —CONH$_2$, —NO$_2$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, —SF$_5$, —NH$_3^+$, —SO$_3^-$, —OPO$_3$H$^-$, —SCN, —ONO$_2$, R$^{6D}$-substituted or unsubstituted alkyl (e.g., C$_1$-C$_8$, C$_1$-C$_6$, C$_1$-C$_4$, or C$_1$-C$_2$), R$^{6D}$-substituted or unsubstituted heteroalkyl (e.g., 2 to 8 membered, 2 to 6 membered, 4 to 6 membered, 2 to 3 membered, or 4 to 5 membered), R$^{6D}$-substituted or unsubstituted cycloalkyl (e.g., C$_3$-C$_8$, C$_3$-C$_6$, C$_4$-C$_6$, or C$_5$-C$_6$), R$^{6D}$-substituted or unsubstituted heterocycloalkyl (e.g., 3 to 8 membered, 3 to 6 membered, 4 to 6 membered, 4 to 5 membered, or 5 to 6 membered), R$^{6D}$-substituted or unsubstituted aryl (e.g., C$_6$-C$_{10}$ or phenyl), or R$^{6D}$-substituted or unsubstituted heteroaryl (e.g., 5 to 10 membered, 5 to 9 membered, or 5 to 6 membered). R$^{6D}$ is independently halogen, oxo, —CX$^{6D}_3$, —CHX$^{6D}_2$, —CH$_2$X$^{6D}$, —OCX$^{6D}_3$, —OCH$_2$X$^{6D}$, —OCHX$^{6D}_2$, —CN, —OH, —SH, —NH$_2$, —COOH, —CONH$_2$, —NO$_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6E}$-substituted or unsubstituted alkyl (e.g., $C_1$-$C_8$, $C_1$-$C_6$, $C_1$-$C_4$, or $C_1$-$C_2$), $R^{6E}$-substituted or unsubstituted heteroalkyl (e.g., 2 to 8 membered, 2 to 6 membered, 4 to 6 membered, 2 to 3 membered, or 4 to 5 membered), $R^{6E}$-substituted or unsubstituted cycloalkyl (e.g., $C_3$-$C_8$, $C_3$-$C_6$, $C_4$-$C_6$, or $C_5$-$C_6$), $R^{6E}$-substituted or unsubstituted heterocycloalkyl (e.g., 3 to 8 membered, 3 to 6 membered, 4 to 6 membered, 4 to 5 membered, or 5 to 6 membered), $R^{6E}$-substituted or unsubstituted aryl (e.g., $C_6$-$C_{10}$ or phenyl), or $R^{6E}$-substituted or unsubstituted heteroaryl (e.g., 5 to 10 membered, 5 to 9 membered, or 5 to 6 membered). $R^{6E}$ is independently halogen, oxo, —$CX^{6E}_3$, —$CHX^{6E}_2$, —$CH_2X^{6E}$, —$OCX^{6E}_3$, —$OCH_2X^{6E}$, —$OCHX^{6E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{6B}$ is independently hydrogen, halogen, —$CX^{6B}_3$, —$CHX^{6B}_2$, —$CH_2X^{6B}$, —$OCX^{6B}_3$, —$OCH_2X^{6B}$, —$OCHX^{6B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6F}$-substituted or unsubstituted alkyl (e.g., $C_1$-$C_8$, $C_1$-$C_6$, $C_1$-$C_4$, or $C_1$-$C_2$), $R^{6F}$-substituted or unsubstituted heteroalkyl (e.g., 2 to 8 membered, 2 to 6 membered, 4 to 6 membered, 2 to 3 membered, or 4 to 5 membered), $R^{6F}$-substituted or unsubstituted cycloalkyl (e.g., $C_3$-$C_8$, $C_3$-$C_6$, $C_4$-$C_6$, or $C_5$-$C_6$), $R^{6F}$-substituted or unsubstituted heterocycloalkyl (e.g., 3 to 8 membered, 3 to 6 membered, 4 to 6 membered, 4 to 5 membered, or 5 to 6 membered), $R^{6F}$-substituted or unsubstituted aryl (e.g., $C_6$-$C_{10}$ or phenyl), or $R^{6F}$-substituted or unsubstituted heteroaryl (e.g., 5 to 10 membered, 5 to 9 membered, or 5 to 6 membered). $R^{6F}$ is independently halogen, oxo, —$CX^{6F}_3$, —$CHX^{6F}_2$, —$CH_2X^{6F}$, —$OCX^{6F}_3$, —$OCH_2X^{6F}$, —$OCHX^{6F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6G}$-substituted or unsubstituted alkyl (e.g., $C_1$-$C_8$, $C_1$-$C_6$, $C_1$-$C_4$, or $C_1$-$C_2$), $R^{6G}$-substituted or unsubstituted heteroalkyl (e.g., 2 to 8 membered, 2 to 6 membered, 4 to 6 membered, 2 to 3 membered, or 4 to 5 membered), $R^{6G}$-substituted or unsubstituted cycloalkyl (e.g., $C_3$-$C_8$, $C_3$-$C_6$, $C_4$-$C_6$, or $C_5$-$C_6$), $R^{6G}$-substituted or unsubstituted heterocycloalkyl (e.g., 3 to 8 membered, 3 to 6 membered, 4 to 6 membered, 4 to 5 membered, or 5 to 6 membered), $R^{6G}$-substituted or unsubstituted aryl (e.g., $C_6$-$C_{10}$ or phenyl), or $R^{6G}$-substituted or unsubstituted heteroaryl (e.g., 5 to 10 membered, 5 to 9 membered, or 5 to 6 membered). $R^{6G}$ is independently halogen, oxo, —$CX^{6G}_3$, —$CHX^{6G}_2$, —$CH_2X^{6G}$, —$OCX^{6G}_3$, —$OCH_2X^{6G}$, —$OCHX^{6G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{6A}$ and $R^{6B}$ are combined to form an oxo. In embodiments, $R^{6C}$ is independently hydrogen, halogen, —$CX^{6C}_3$, —$CHX^{6C}_2$, —$CH_2X^{6C}$, —$OCX^{6C}_3$, —$OCH_2X^{6C}$, —$OCHX^{6C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6H}$-substituted or unsubstituted alkyl (e.g., $C_1$-$C_8$, $C_1$-$C_6$, $C_1$-$C_4$, or $C_1$-$C_2$), $R^{6H}$-substituted or unsubstituted heteroalkyl (e.g., 2 to 8 membered, 2 to 6 membered, 4 to 6 membered, 2 to 3 membered, or 4 to 5 membered), $R^{6H}$-substituted or unsubstituted cycloalkyl (e.g., $C_3$-$C_8$, $C_3$-$C_6$, $C_4$-$C_6$, or $C_5$-$C_6$), $R^{6H}$-substituted or unsubstituted heterocycloalkyl (e.g., 3 to 8 membered, 3 to 6 membered, 4 to 6 membered, 4 to 5 membered, or 5 to 6 membered), $R^{6H}$-substituted or unsubstituted aryl (e.g., $C_6$-$C_{10}$ or phenyl), or $R^{6H}$-substituted or unsubstituted heteroaryl (e.g., 5 to 10 membered, 5 to 9 membered, or 5 to 6 membered). $R^{6H}$ is independently halogen, oxo, —$CX^{6H}_3$, —$CHX^{6H}_2$, —$CH_2X^{6H}$, —$OCX^{6H}_3$, —$OCH_2X^{6H}$, —$OCHX^{6H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6I}$-substituted or unsubstituted alkyl (e.g., $C_1$-$C_8$, $C_1$-$C_6$, $C_1$-$C_4$, or $C_1$-$C_2$), $R^{6I}$-substituted or unsubstituted heteroalkyl (e.g., 2 to 8 membered, 2 to 6 membered, 4 to 6 membered, 2 to 3 membered, or 4 to 5 membered), $R^{6I}$-substituted or unsubstituted cycloalkyl (e.g., $C_3$-$C_8$, $C_3$-$C_6$, $C_4$-$C_6$, or $C_5$-$C_6$), $R^{6I}$-substituted or unsubstituted heterocycloalkyl (e.g., 3 to 8 membered, 3 to 6 membered, 4 to 6 membered, 4 to 5 membered, or 5 to 6 membered), $R^{6I}$-substituted or unsubstituted aryl (e.g., $C_6$-$C_{10}$ or phenyl), or $R^{6I}$-substituted or unsubstituted heteroaryl (e.g., 5 to 10 membered, 5 to 9 membered, or 5 to 6 membered). $R^{6I}$ is independently halogen, oxo, —$CX^{6I}_3$, —$CHX^{6I}_2$, —$CH_2X^{6I}$, —$OCX^{6I}_3$, —$OCH_2X^{6I}$, —$OCHX^{612}$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{6C}$ is unsubstituted $C_1$-$C_4$ alkyl. In embodiments, $R^{6C}$ is unsubstituted methyl. In embodiments, $R^{6C}$ is unsubstituted tert-butyl. The symbols $X^{6A}$, $X^{6B}$, $X^{6C}$, $X^{6D}$, $X^{6E}$, $X^{6F}$, $X^{6G}$, $X^{6H}$, and $X^{6I}$ are independently —F, —Cl, —Br, or —I.

In embodiments, $R^{6A}$ is independently hydrogen, halogen, —$CX^{6A}_3$, —$CHX^{6A}_2$, —$CH_2X^{6A}$, —$OCX^{6A}_3$, —$OCH_2X^{6A}$, —$OCHX^{6A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6D}$-substituted $C_1$-$C_4$ alkyl (e.g., $R^{6D}$-substituted $C_1$-$C_3$ alkyl, $R^{6D}$-substituted $C_1$-$C_2$ alkyl, or $R^{6D}$-substituted methyl) or $R^{6D}$-substituted 2 to 8 membered heteroalkyl (e.g., $R^{6D}$-substituted 2 to 6 membered heteroalkyl, $R^{6D}$-substituted 2 to 5 membered heteroalkyl, or $R^{6D}$-substituted 2 to 4 membered heteroalkyl). In embodiments, $R^{6D}$ is independently halogen, oxo, —$CX^{6D}_3$, —$CHX^{6D}_2$, —$CH_2X^{6D}$, —$OCX^{6D}_3$, —$OCH_2X^{6D}$, —$OCHX^{6D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, or —$ONO_2$. In embodiments, $R^{6B}$ is independently hydrogen, halogen, —$CX^{6B}_3$, —$CHX^{6B}_2$, —$CH_2X^{6B}$, —$OCX^{6B}_3$, —$OCH_2X^{6B}$, —$OCHX^{6B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{6F}$-substituted $C_1$-$C_4$ alkyl, (e.g., $R^{6F}$-substituted $C_1$-$C_3$ alkyl, $R^{6F}$-substituted $C_1$-$C_2$ alkyl, or $R^{6F}$-substituted methyl) or $R^{6F}$-substituted 2 to 8 membered heteroalkyl (e.g., $R^{6F}$-substituted 2 to 6 membered heteroalkyl, $R^{6F}$-substituted 2 to 5 membered heteroalkyl, or $R^{6F}$-substituted 2 to 4 membered heteroalkyl). In embodiments, $R^{6F}$ is independently halogen, oxo, —$CX^{6F}_3$, —$CHX^{6F}_2$, —$CH_2X^{6F}$, —$OCX^{6F}_3$, —$OCH_2X^{6F}$ —$OCHX^{6F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, or —$ONO_2$. In embodiments, $R^{6A}$ and $R^{6B}$ are combined to form an oxo. The symbols $X^{6A}$, $X^{6B}$, $X^{6D}$, and $X^{6F}$ are independently —F, —Cl, —Br, or —I.

In embodiments, $R^3$ is independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, —$SF_5$, —$NH_3^+$, —$SO_3^-$, —$OPO_3H^-$, —SCN, —$ONO_2$, $R^{3A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3A}$-substituted or unsubstituted cycloalkyl (e.g., $C_3$-$C_8$, $C_3$-$C_6$, or C5-$C_6$), $R^{3A}$-substituted or unsubstituted heterocycloalkyl (e.g., 3 to 8 membered, 3 to 6 membered, or 5 to 6 membered), $R^{3A}$-substituted or unsubstituted aryl (e.g., $C_6$-$C_{10}$, $C_{10}$, or phenyl), or $R^{3A}$-substituted or unsubstituted heteroaryl (e.g., 5 to 10 membered, 5 to 9 membered, or 5 to 6 membered), or —$OR^{3A}$), or $R^{3A}$-substituted or unsubstituted heteroaryl (e.g., 5 to 10 membered, 5 to 9 membered, or 5 to 6 membered), or —$OR^{3A}$.

In embodiments, $R^3$ is independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, —$SF_5$, —$NH_3^+$, —$SO_3$, —$OPO_3H^-$, —SCN, —$ONO_2$, $R^{3A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3A}$-substituted or unsubstituted cycloalkyl (e.g., $C_3$-$C_8$, $C_3$-$C_6$, or C5-$C_6$), $R^{3A}$-substituted or unsubstituted heterocycloalkyl (e.g., 3 to 8 membered, 3 to 6 membered, or 5 to 6 membered), $R^{3A}$-substituted or unsubstituted aryl (e.g., $C_6$-$C_{10}$, $C_{10}$, or phenyl), or $R^{3A}$-substituted or unsubstituted heteroaryl (e.g., 5 to 10 membered, 5 to 9 membered, or 5 to 6 membered), or —$OR^{3A}$. In embodiments, $R^3$ is independently —$OR^{3A}$. In embodiments, $R^3$ is independently a reversible terminator moiety.

$R^{3A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{3B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3B}$-substituted or unsubstituted cycloalkyl (e.g., $C_3$-$C_8$, $C_3$-$C_6$, or $C_5$-$C_6$), $R^{3B}$-substituted or unsubstituted heterocycloalkyl (e.g., 3 to 8 membered, 3 to 6 membered, or 5 to 6 membered), $R^{3B}$-substituted or unsubstituted aryl (e.g., $C_6$-$C_{10}$, $C_{10}$, or phenyl), $R^{3B}$-substituted or unsubstituted heteroaryl (e.g., 5 to 10 membered, 5 to 9 membered, or 5 to 6 membered), or a polymerase-compatible cleavable moiety. In embodiments, $R^{3A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{3B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3B}$-substituted or unsubstituted cycloalkyl (e.g., $C_3$-$C_8$, $C_3$-$C_6$, or $C_5$-$C_6$), $R^{3B}$-substituted or unsubstituted heterocycloalkyl (e.g., 3 to 8 membered, 3 to 6 membered, or 5 to 6 membered), $R^{3B}$-substituted or unsubstituted aryl (e.g., $C_6$-$C_{10}$, $C_{10}$, or phenyl), or $R^{3B}$-substituted or unsubstituted heteroaryl (e.g., 5 to 10 membered, 5 to 9 membered, or 5 to 6 membered). In embodiments, $R^{3A}$ is independently a polymerase-compatible cleavable moiety.

$R^{3B}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —NH₃⁺, —SO₃⁻, —OPO₃H⁻, —SCN, —ONO₂, $R^{3C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{3C}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{3C}$-substituted or unsubstituted cycloalkyl (e.g., $C_3$-$C_8$, $C_3$-$C_6$, or $C_5$-$C_6$), $R^{3C}$-substituted or unsubstituted heterocycloalkyl (e.g., 3 to 8 membered, 3 to 6 membered, or 5 to 6 membered), $R^{3C}$-substituted or unsubstituted aryl (e.g., $C_6$-$C_{10}$, $C_{10}$, or phenyl), or $R^{3C}$-substituted or unsubstituted heteroaryl (e.g., 5 to 10 membered, 5 to 9 membered, or 5 to 6 membered).

$R^{3C}$ is independently oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, —NH₃⁺, —SO₃⁻, —OPO₃H⁻, —SCN, —ONO₂, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^3$ is an —O-polymerase-compatible cleavable moiety. In embodiments, the -polymerase-compatible cleavable moiety is independently -(substituted or unsubstituted alkylene)-SS-(unsubstituted alkyl). In embodiments, the -polymerase-compatible cleavable moiety is independently -(halo-substituted or unsubstituted $C_1$-$C_3$ alkylene)-SS-(unsubstituted $C_1$-$C_4$ alkyl).

In embodiments, $R^3$ is —$OR^{3A}$. In embodiments, $R^3$ is —OH. In embodiments, $R^{3A}$ is hydrogen. In embodiments, $R^{3A}$ is a polymerase-compatible cleavable moiety. In embodiments, $R^{3A}$ is a polymerase-compatible cleavable moiety including an azido moiety. In embodiments, $R^{3A}$ is a polymerase-compatible cleavable moiety including a dithiol linker. In embodiments, $R^{3A}$ is a polymerase-compatible cleavable moiety; and the polymerase-compatible cleavable moiety is independently —CH₂N₃.

In embodiments, the polymerase-compatible cleavable moiety is independently —NH₂, —NO₂, —CN, —CH₃, $C_2$-$C_6$ allyl (e.g., —CH₂—CH=CH₂), methoxyalkyl (e.g., —CH₂—O—CH₃), or —CH₂N₃. In embodiments, the polymerase-compatible cleavable moiety is independently —NH₂. In embodiments, the polymerase-compatible cleavable moiety is independently —CN. In embodiments, the polymerase-compatible cleavable moiety is independently —CH₃. In embodiments, the polymerase-compatible cleavable moiety is independently $C_2$-$C_6$ allyl (e.g., —CH₂—CH=CH₂). In embodiments, the polymerase-compatible cleavable moiety is independently methoxyalkyl (e.g., —CH₂—O—CH₃). In embodiments, the polymerase-compatible cleavable moiety is independently —CH₂N₃. In embodiments, the polymerase-compatible cleavable moiety is independently —NH₂. In embodiments, the polymerase-compatible cleavable moiety is independently —NO₂. In embodiments, the polymerase-compatible cleavable moiety is independently —CH₂N₃. In embodiments, the polymerase-compatible cleavable moiety is independently

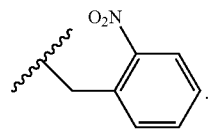

In embodiments, the polymerase-compatible cleavable moiety is independently

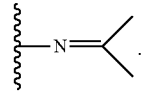

In embodiments, the polymerase-compatible cleavable moiety is independently

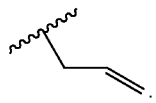 [SMILES: *CC=C ; "."]

In embodiments, the polymerase-compatible cleavable moiety is independently

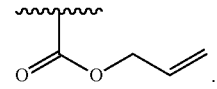 [SMILES: *C(=O)OCC=C]

In embodiments, the polymerase-compatible cleavable moiety is independently

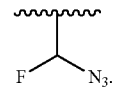

In embodiments, the polymerase-compatible cleavable moiety is independently

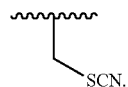

In embodiments, the polymerase-compatible cleavable moiety is independently

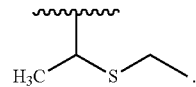

In embodiments, the polymerase-compatible cleavable moiety is independently

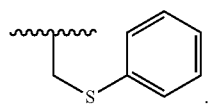

In embodiments, the polymerase-compatible cleavable moiety is independently

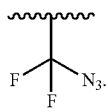

In embodiments, the polymerase-compatible cleavable moiety is independently

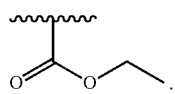 [SMILES: *C(=O)OCC]

In embodiments, the polymerase-compatible cleavable moiety is

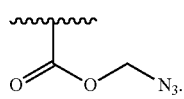

In embodiments, the polymerase-compatible cleavable moiety is independently —CH$_2$—O—CH$_3$. In embodiments, the polymerase-compatible cleavable moiety is independently —NH$_2$, —CH$_2$N$_3$,

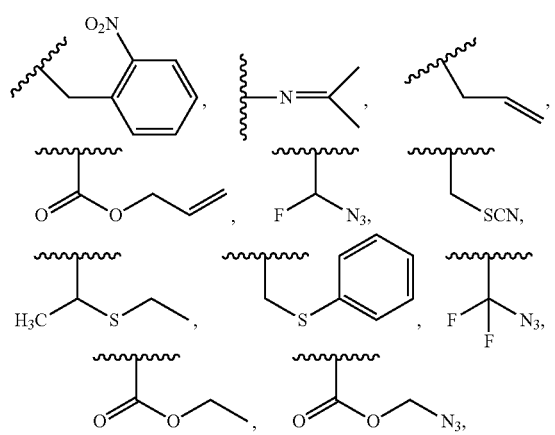

or —CH$_2$—O—CH$_3$.

In embodiments, R$^{3A}$ is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, R$^{3A}$ independently is —NH$_2$. In embodiments, R$^{3A}$ is independently —CN. In embodiments, R$^{3A}$ is independently —CH$_3$. In embodiments, R$^{3A}$ is independently C$_2$-C$_6$ allyl (e.g., —CH$_2$—CH=CH$_2$). In embodiments, R$^{3A}$ independently is methoxyalkyl (e.g., —CH$_2$—O—CH$_3$). In embodiments, R$^{3A}$ is independently —CH$_2$N$_3$. In embodiments, R$^{3A}$ is independently

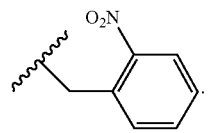 [SMILES: *Cc1ccccc1[N+](=O)[O-]]

In embodiments, R$^{3A}$ is independently

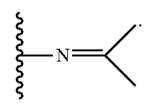

In embodiments, R$^{3A}$ is independently

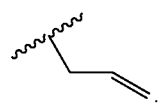

In embodiments, R$^{3A}$ is

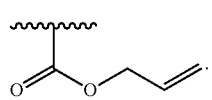 [SMILES: *C(=O)OCC=C]

In embodiments, R$^{3A}$ is

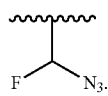

In embodiments, R$^{3A}$ is independently

In embodiments, R$^{3A}$ is independently

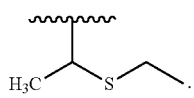

In embodiments, R$^{3A}$ is independently

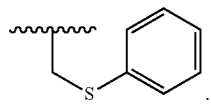

In embodiments, $R^{3A}$ is independently

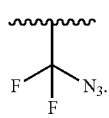

In embodiments, $R^{3A}$ is independently

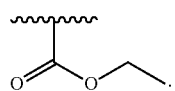 [SMILES: *C(=O)OCC]

In embodiments, $R^{3A}$ is independently

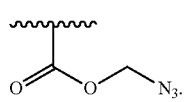

In embodiments, $R^{3A}$ is independently —CH$_2$—O—CH$_3$. In embodiments, $R^{3A}$ is independently —NH$_2$, —CH$_2$N$_3$,

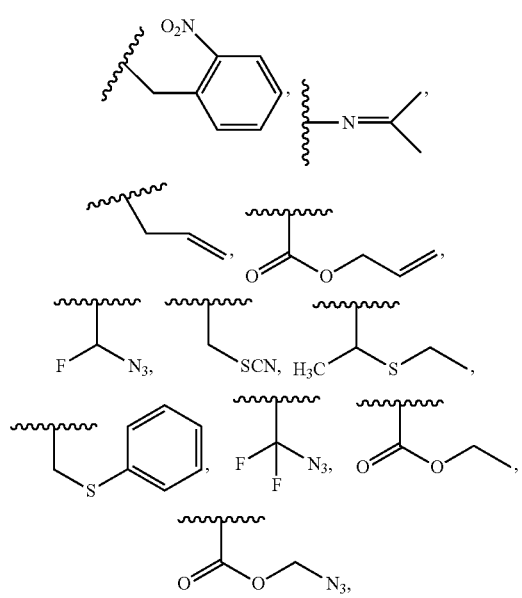

or —CH$_2$—O—CH$_3$.

In embodiments, $R^{3A}$ is a polymerase-compatible cleavable moiety; and the polymerase-compatible cleavable moiety is independently

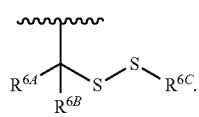

$R^{6A}$, $R^{6B}$, and $R^{6C}$ are as described herein, including in embodiments.

In embodiments, $R^{3A}$ is independently:

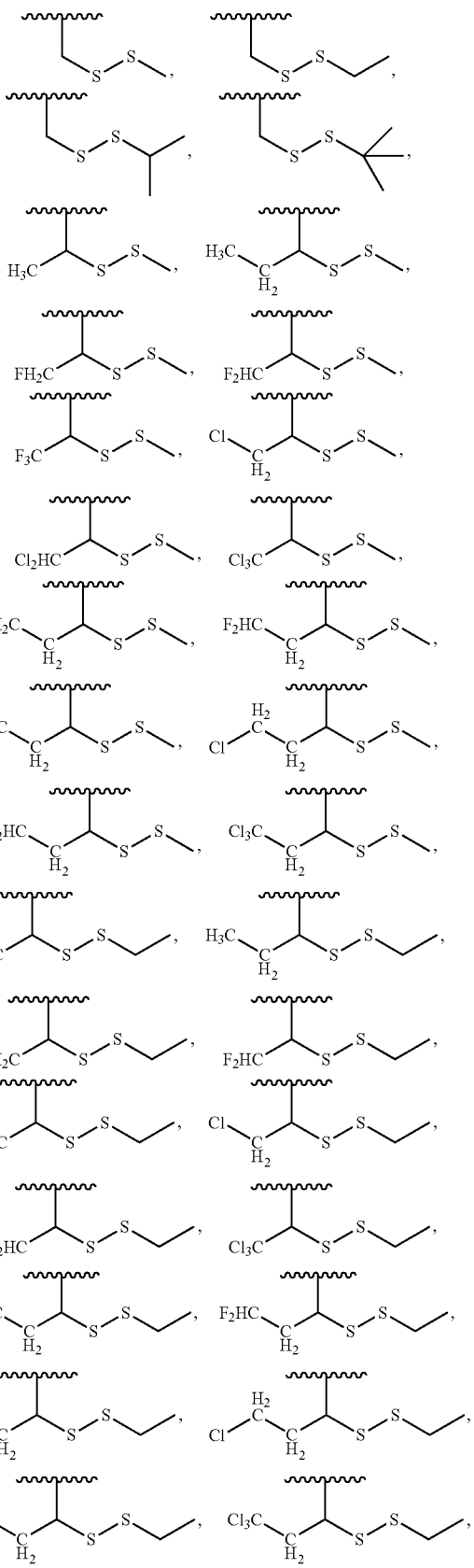

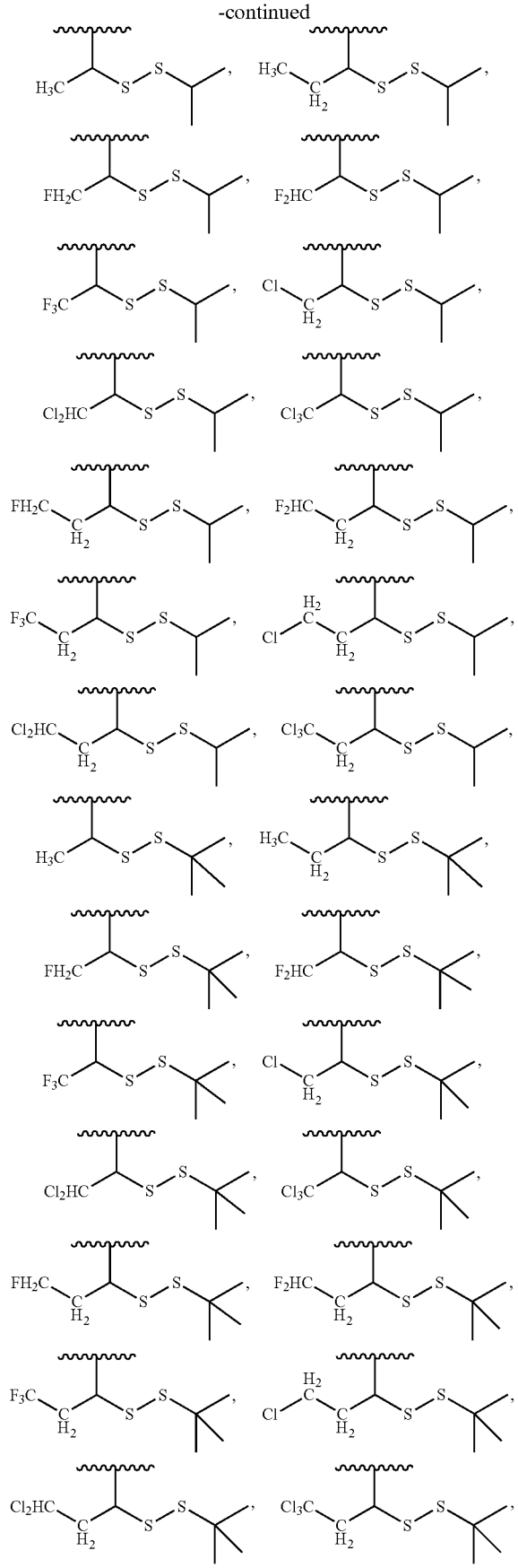
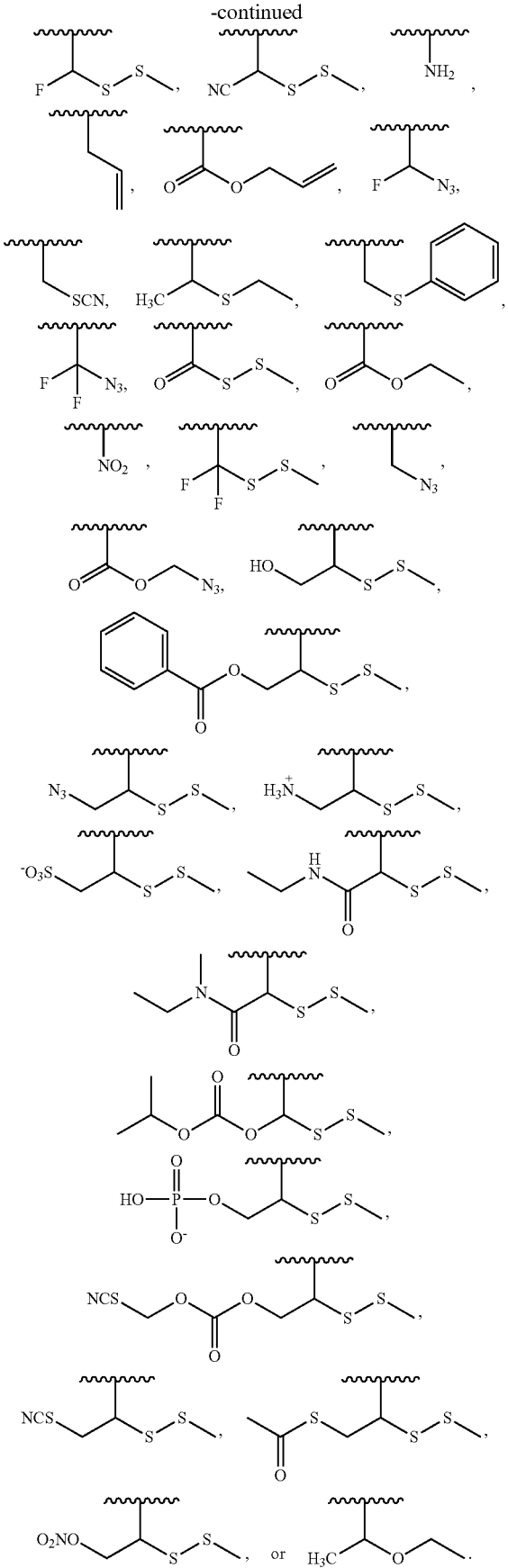

In embodiments, $R^{3A}$ is independently:
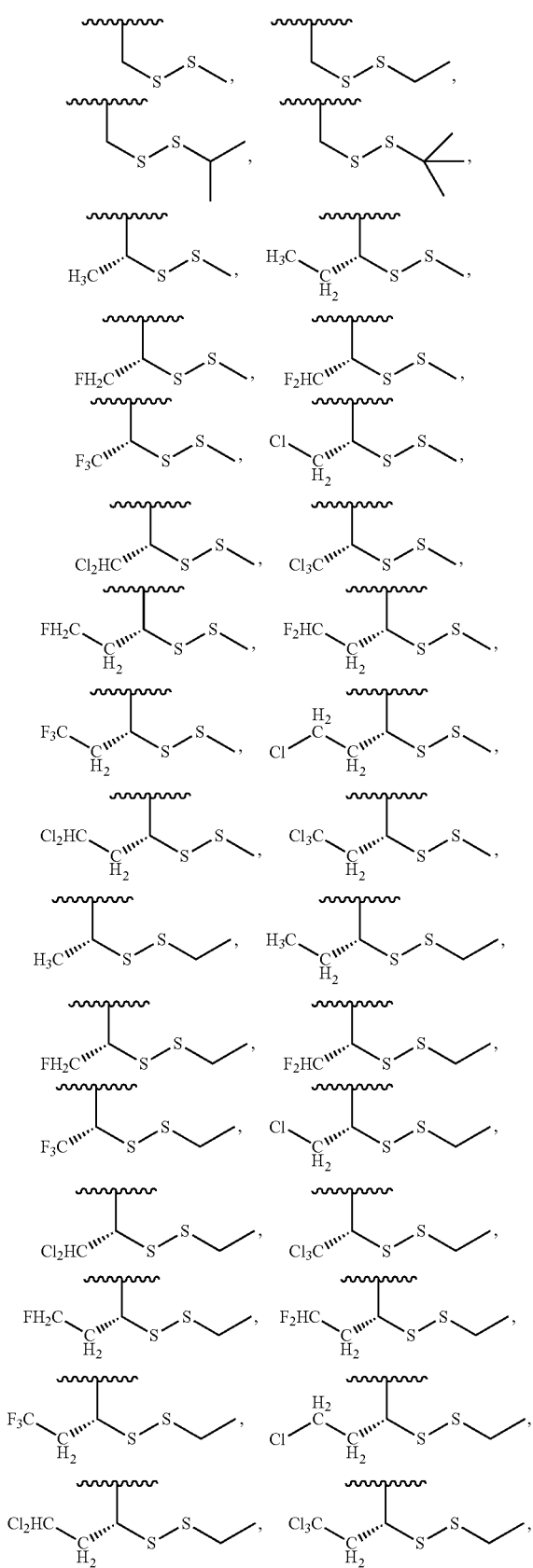
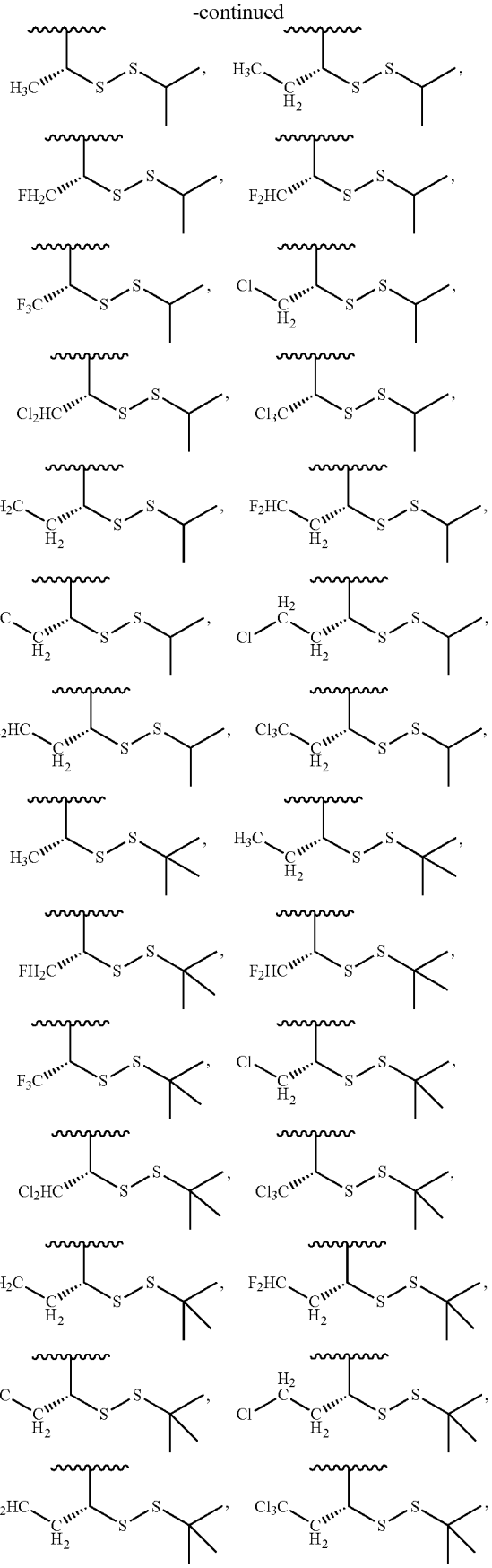

-continued
In embodiments, $R^{3A}$ is independently:
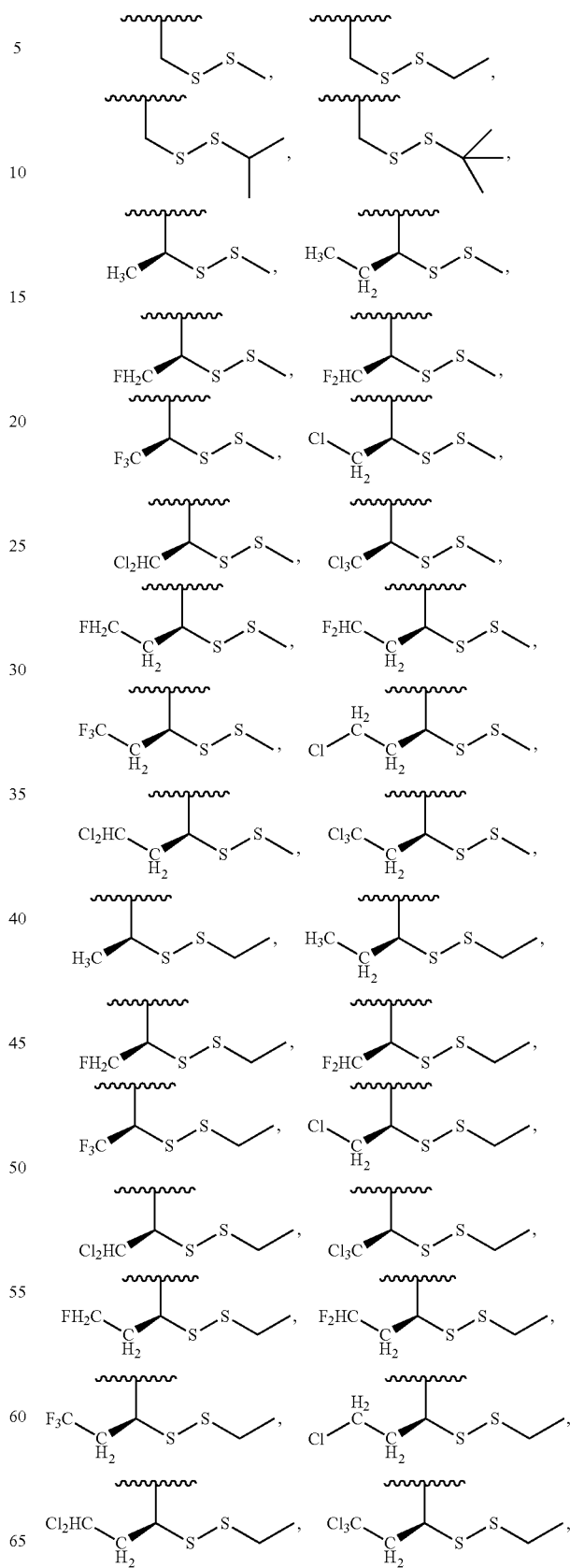

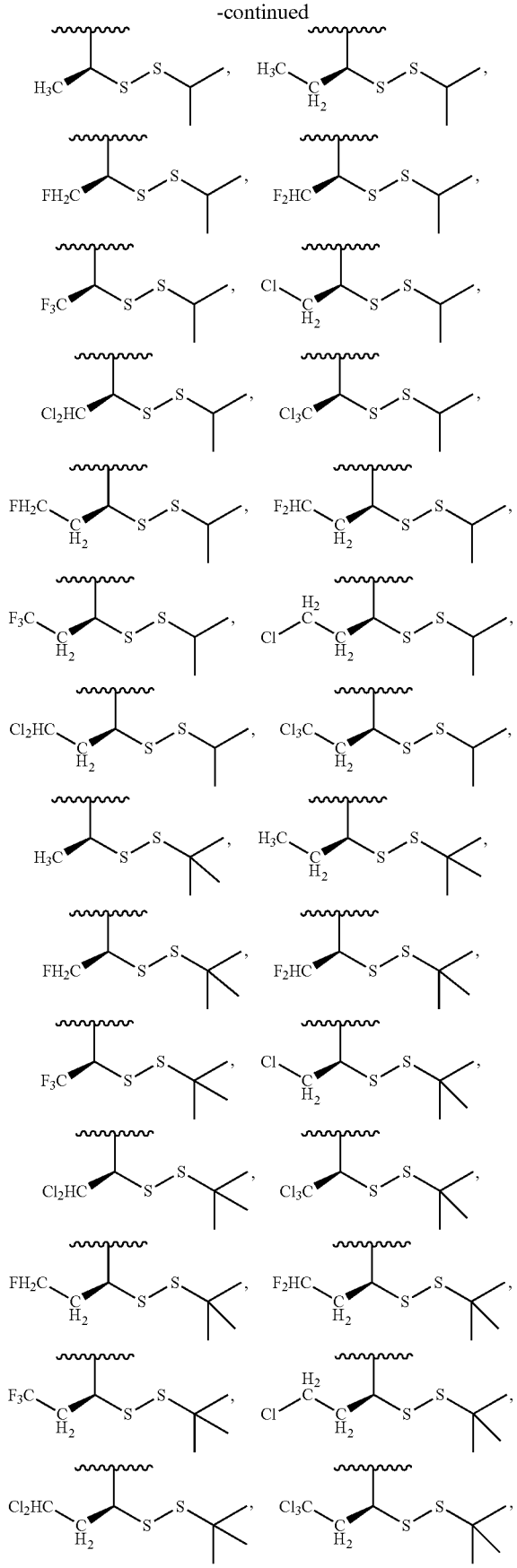
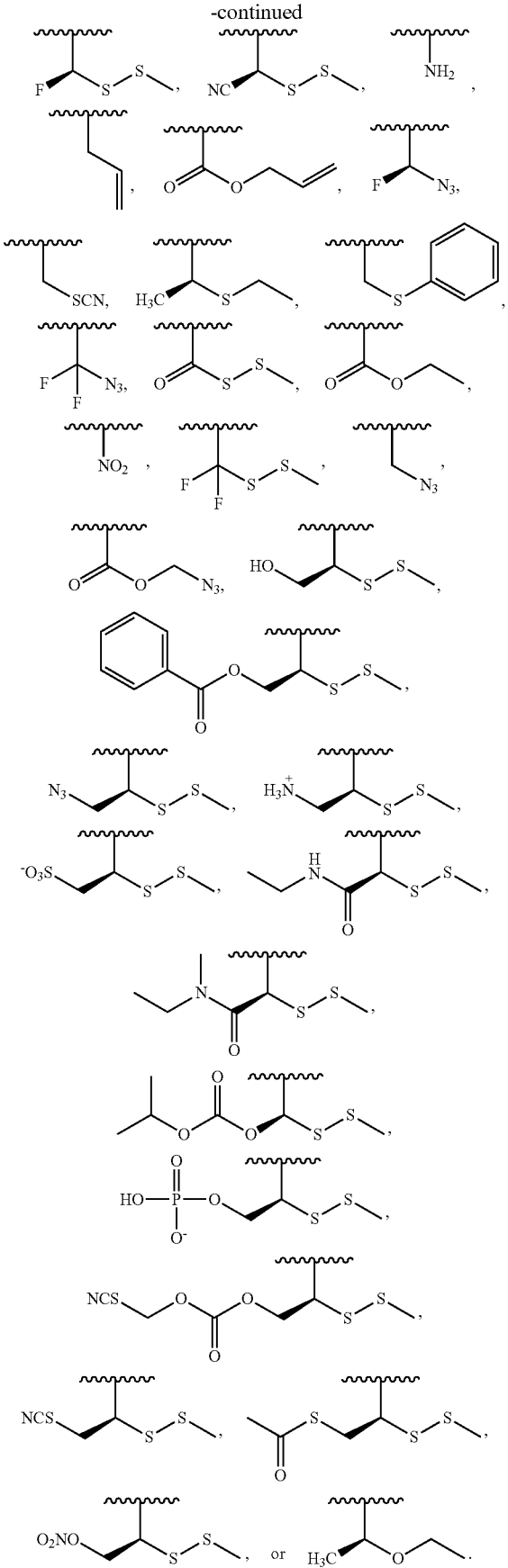

In embodiments, $R^{3A}$ is
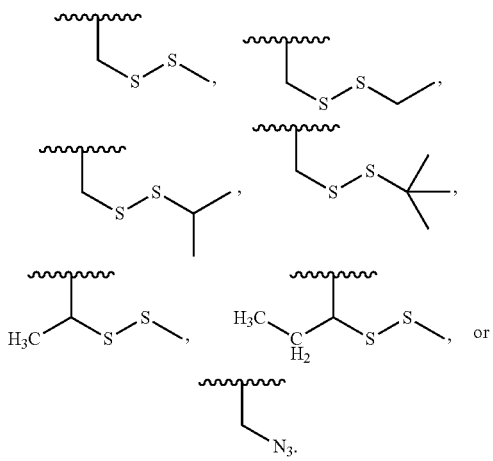
In embodiments, $R^{3A}$ is
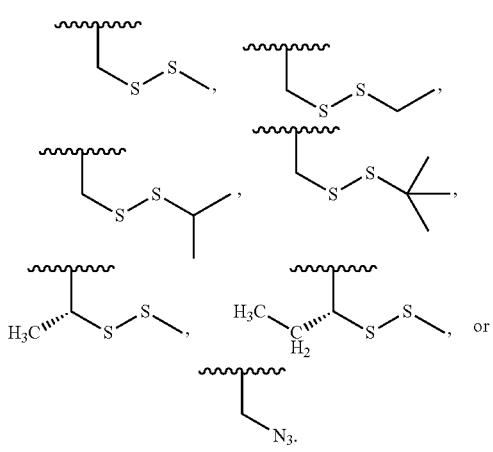
In embodiments, $R^{3A}$ is
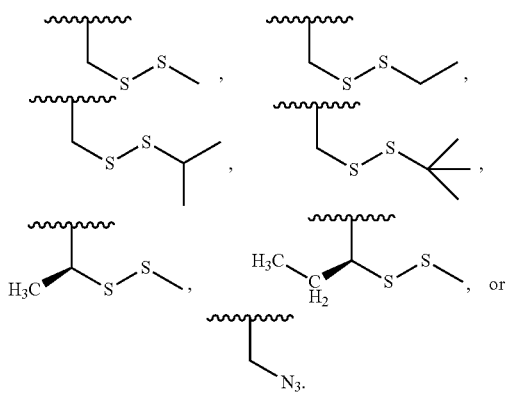
In embodiments, $R^{3A}$ is independently
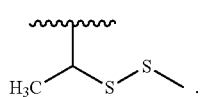
In embodiments, $R^{3A}$ is independently
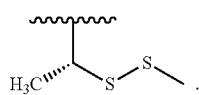
In embodiments, $R^{3A}$ is independently
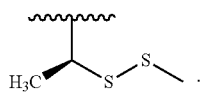
In embodiments, the -polymerase-compatible cleavable moiety is independently:
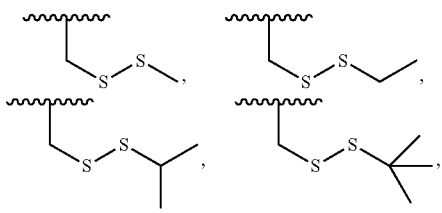
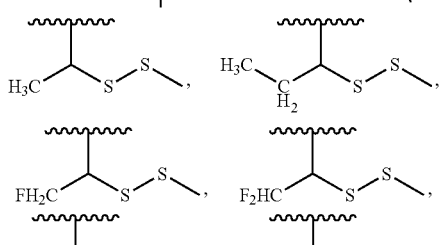
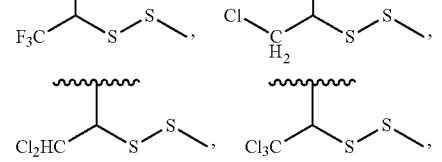
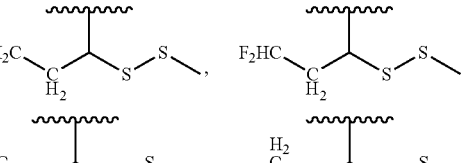
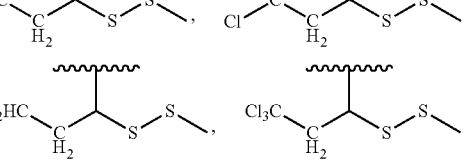
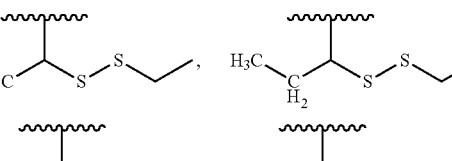
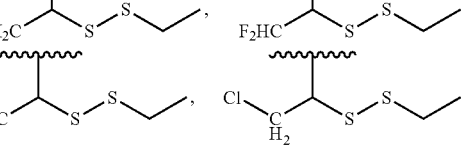

111
-continued
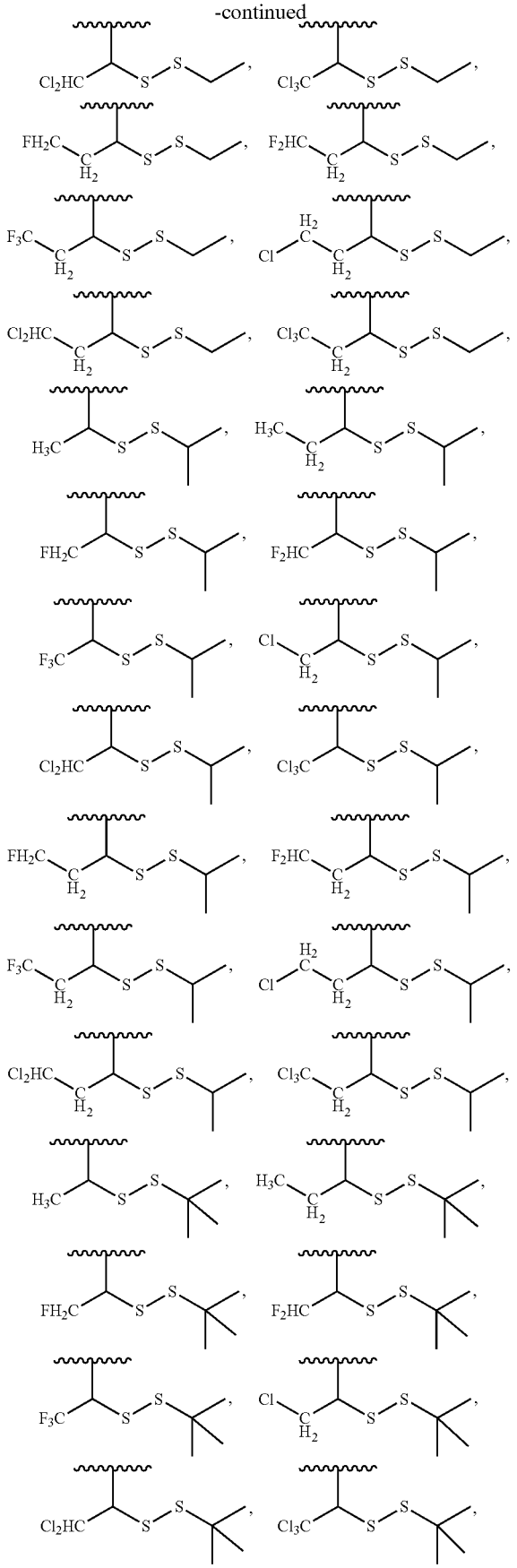
112
-continued
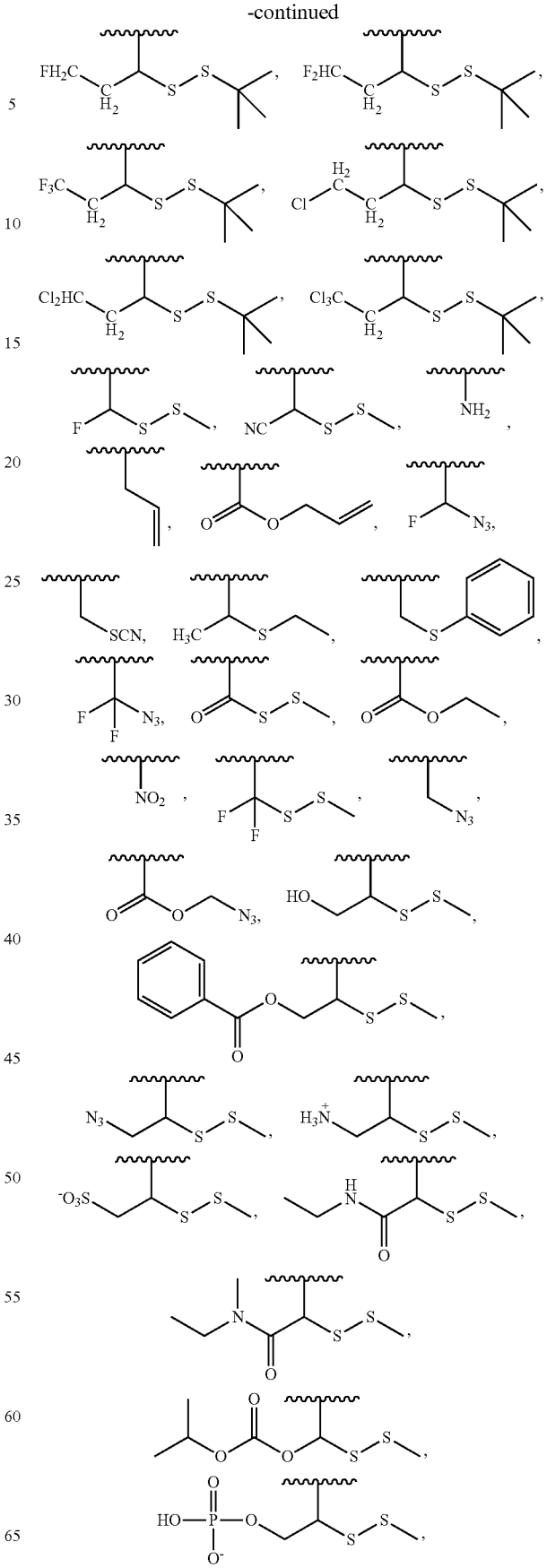

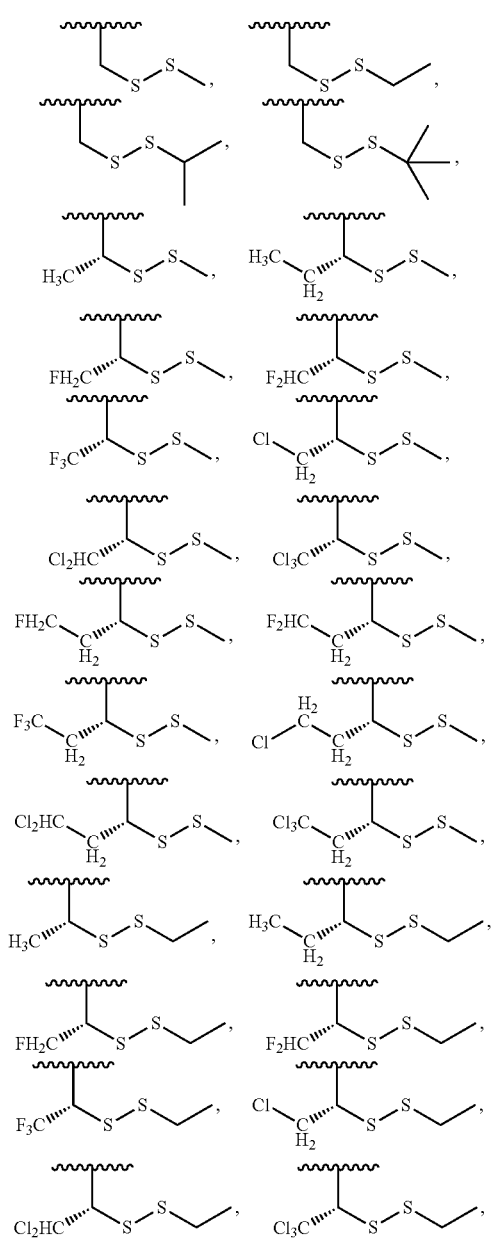

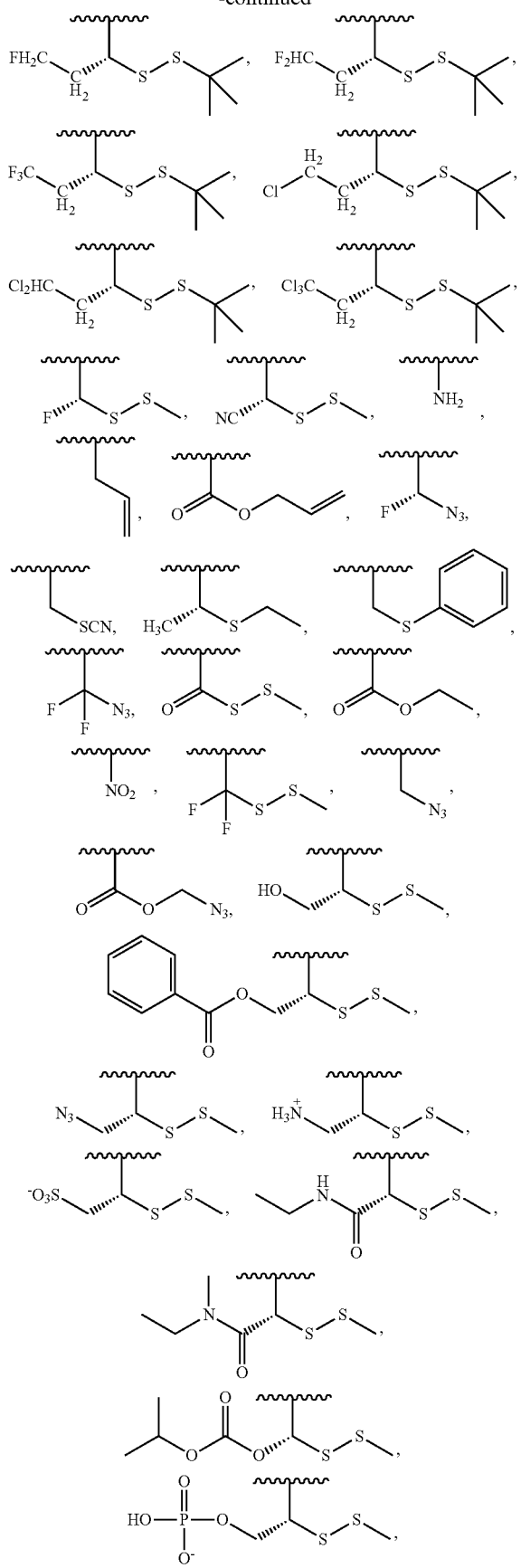
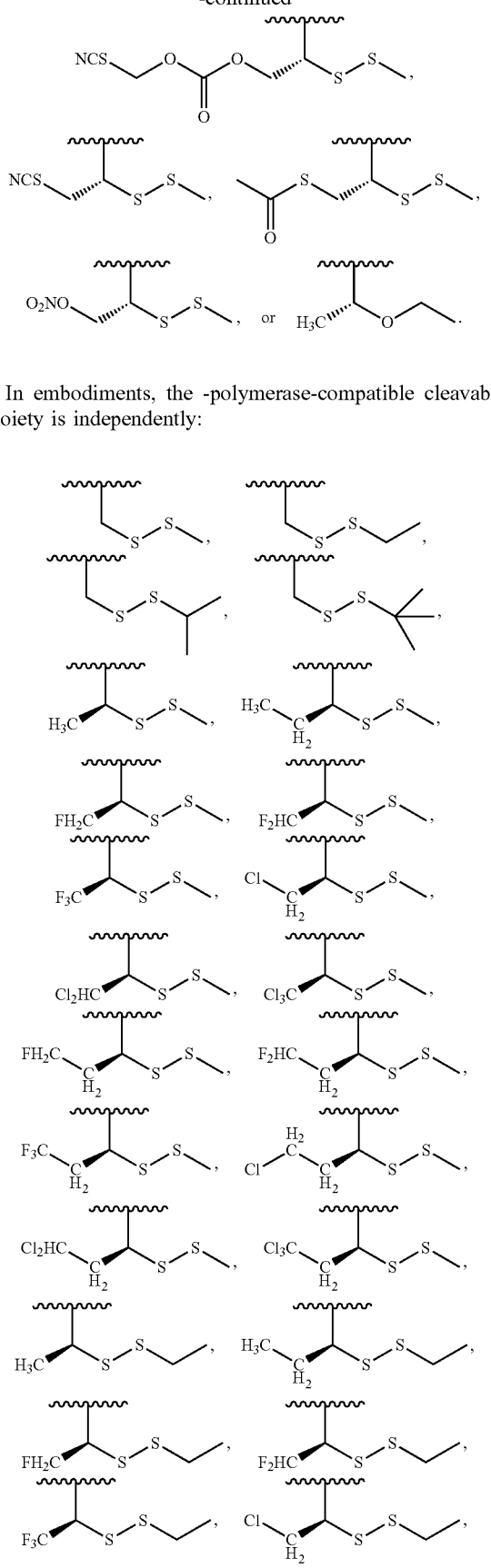
In embodiments, the -polymerase-compatible cleavable moiety is independently:

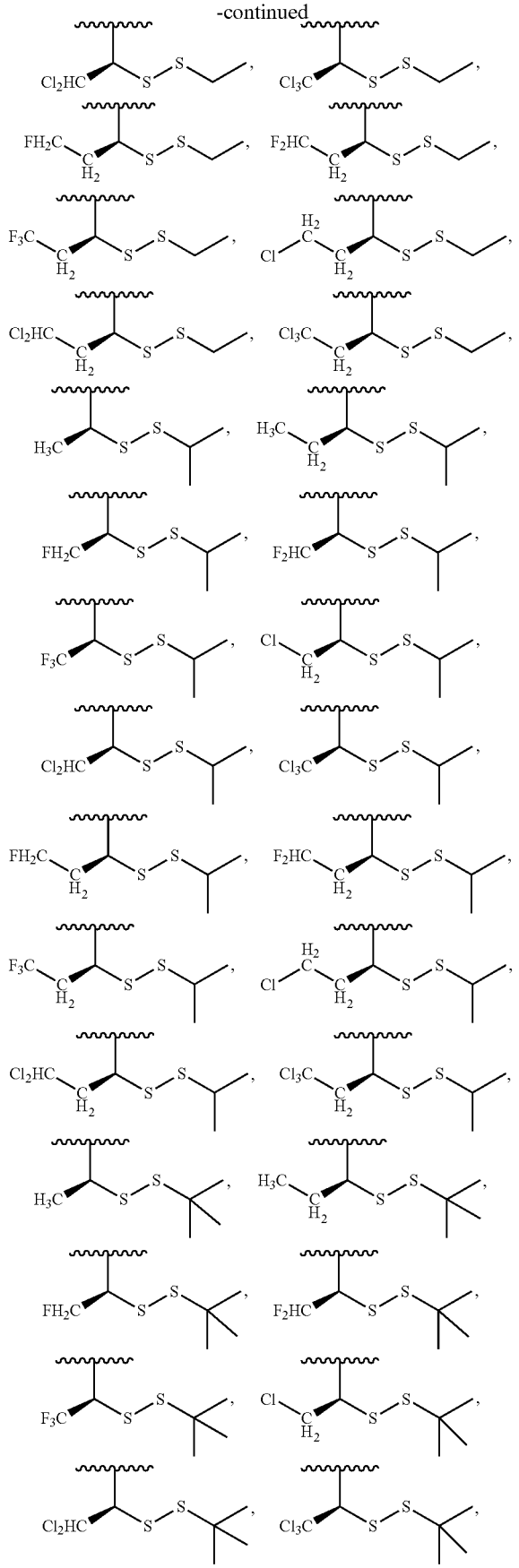
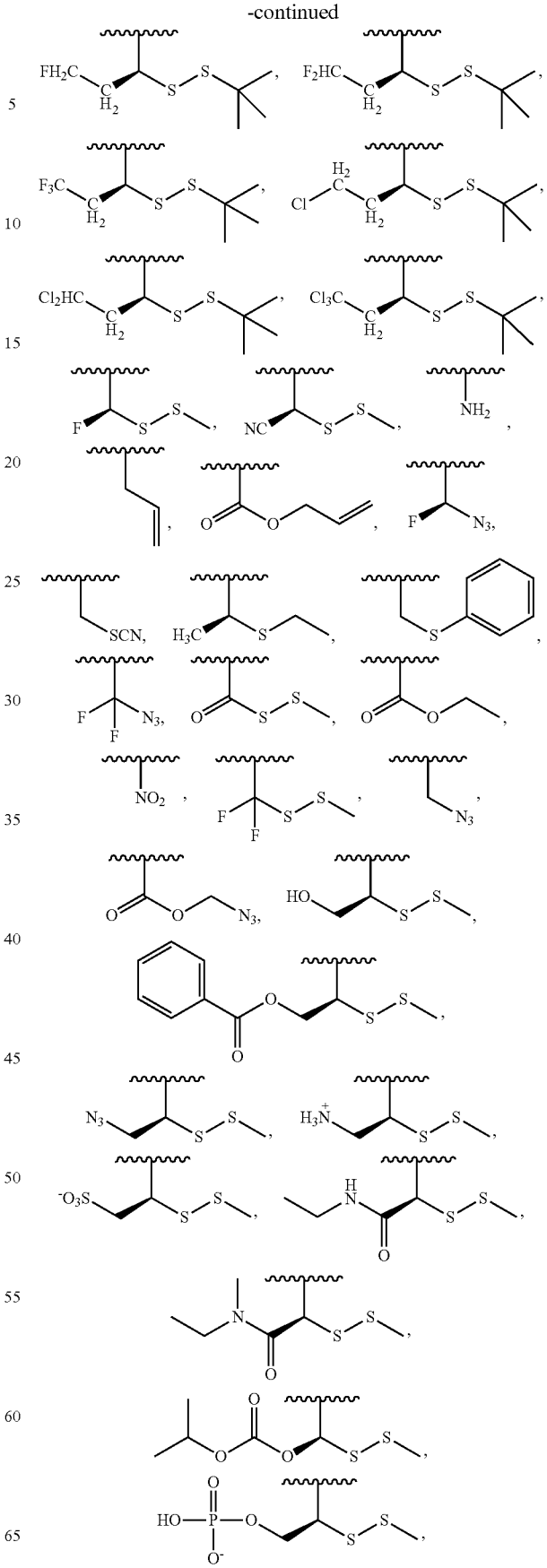

-continued

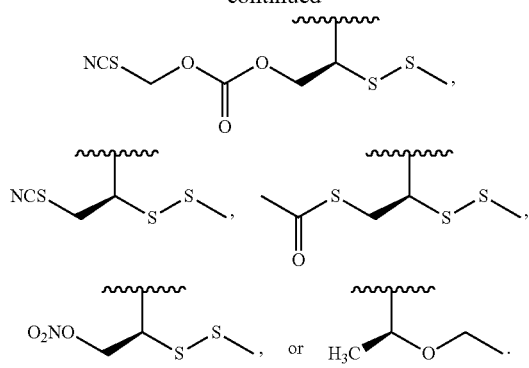

In embodiments, the -polymerase-compatible cleavable moiety is independently:

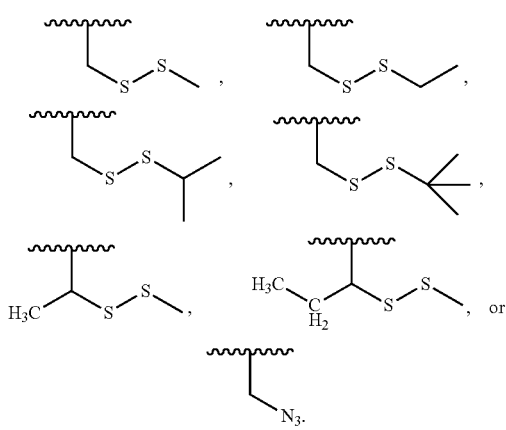

In embodiments, the -polymerase-compatible cleavable moiety is independently:

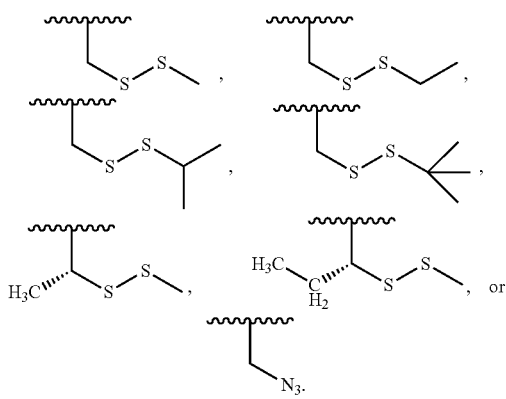

In embodiments, the -polymerase-compatible cleavable moiety is independently:

-continued

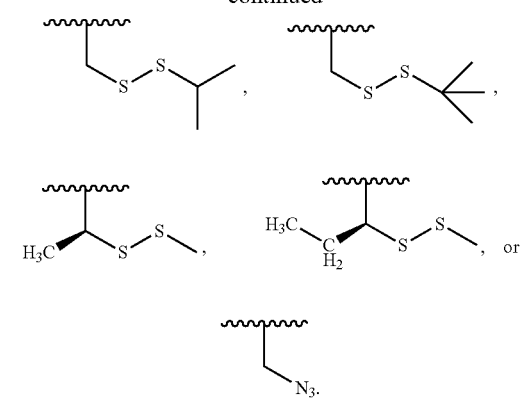

In embodiments, the -polymerase-compatible cleavable moiety is independently:

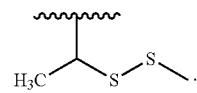

In embodiments, the -polymerase-compatible cleavable moiety is independently:

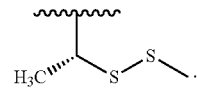

In embodiments, the -polymerase-compatible cleavable moiety is independently:

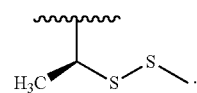

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

In embodiments, B is

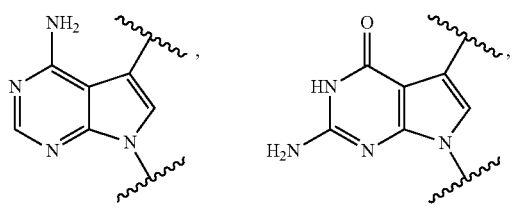

-continued

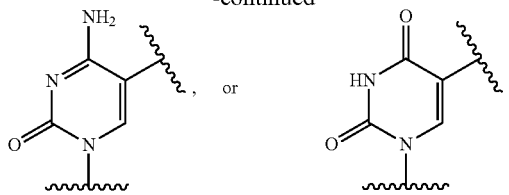

In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof.

In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, B is independently

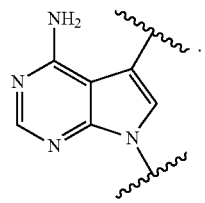

In embodiments, B is independently

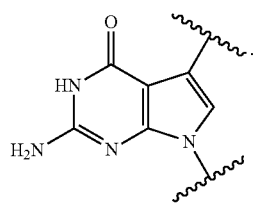 [SMILES: *c1cn(*)c2nc(N)[nH]c(=O)c12]

In embodiments, B is independently

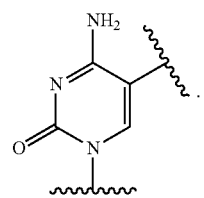 [SMILES: *c1cn(*)c(=O)nc1N]

In embodiments, B is independently

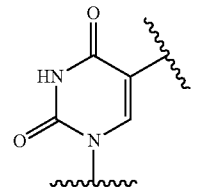

In embodiments, $L^{101}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with a substituent group, size-limited substituent group, or lower substituent group) or unsubstituted alkylene (e.g., $C_1$-$C_{20}$, $C_{10}$-$C_{20}$, $C_1$-$C_8$, $C_1$-$C_6$, or $C_1$-$C_4$), substituted (e.g., substituted with a substituent group, size-limited substituent group, or lower substituent group) or unsubstituted heteroalkylene (e.g., 2 to 20 membered, 8 to 20 membered, 2 to 10 membered, 2 to 8 membered, 2 to 6 membered, or 2 to 4 membered), substituted (e.g., substituted with a substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, or 5 to 6 membered), substituted (e.g., substituted with a substituent group, size-limited substituent group, or lower substituent group) or unsubstituted arylene (e.g., $C_6$-$C_{10}$, $C_{10}$, or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered).

In embodiments, a substituted $L^{101}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{101}$ is substituted with a plurality of groups selected from substituent groups, size-limited substituent groups, and lower substituent groups; each substituent group, size-limited substituent group, and/or lower substituent group may optionally be different. In embodiments, when $L^{101}$ is substituted, it is substituted with at least one substituent group. In embodiments, when $L^{101}$ is substituted, it is substituted with at least one size-limited substituent group. In embodiments, when $L^{101}$ is substituted, it is substituted with at least one lower substituent group. In embodiments, when $L^{101}$ is substituted, it is substituted with 1 to 10 substituent groups. In embodiments, when $L^{101}$ is substituted, it is substituted with 1 to 10 size-limited substituent groups. In embodiments, when $L^{101}$ is substituted, it is substituted with 1 to 10 lower substituent groups. In embodiments, when $L^{101}$ is substituted, it is substituted with 1 to 5 substituent groups. In embodiments, when $L^{101}$ is substituted, it is substituted with 1 to 5 size-limited substituent groups. In embodiments, when $L^{101}$ is substituted, it is substituted with 1 to 5 lower substituent groups. In embodiments, when $L^{101}$ is substituted, it is substituted with a substituent group. In embodiments, when $L^{101}$ is substituted, it is substituted with a size-limited substituent group. In embodiments, when $L^{101}$ is substituted, it is substituted with a lower substituent group.

In embodiments, $L^{101}$ is a bond, —NH—, —NR$^{101}$—, —S—, —O—, —C(O)—, —C(O)O—, —OC(O)—, —NHC(O)—, —C(O)NH—, —NHC(O)NH—, —NHC(NH)NH—, —C(S)—, $R^{101}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{101}$-substituted or unsubstituted heteroalkylene (e.g., 2 to 20 membered, 8 to 20 membered, 2 to 10 membered, 2 to 8 membered, 2 to 6 membered, or 2 to 4 membered), $R^{101}$-substituted or unsubstituted cycloalkylene (e.g., $C_3$-$C_8$, $C_3$-$C_6$, or $C_5$-$C_6$), $R^{101}$-substituted or unsubstituted heterocycloalkylene (e.g., 3 to 8 membered, 3 to 6 membered, or 5 to 6 membered), $R^{101}$-substituted or unsubstituted arylene (e.g., $C_6$-$C_{10}$, $C_{10}$, or phenylene), or $R^{101}$-substituted or unsubstituted heteroarylene (e.g., 5 to 10 membered, 5 to 9 membered, or 5 to 6 membered). In embodiments, $L^{101}$ is a bond. In embodiments, $L^{101}$ is —NH—. In embodiments, $L^{101}$ is —NR$^{101}$—. In embodiments, $L^{101}$ is —S—. In embodiments, $L^{101}$ is —O—. In embodiments, $L^{101}$ is —C(O)—. In embodiments, $L^{101}$ is —C(O)O—. In embodiments, $L^{101}$ is —OC(O)—. In embodiments, $L^{101}$ is —NHC(O)—. In embodiments, $L^{101}$ is —C(O)NH—. In embodiments, $L^{10}$ is —NHC(O)NH—. In embodiments, $L^{101}$ is —NHC(NH)NH—. In embodiments, $L^{101}$ is —C(S)—. In embodiments, $L^{101}$ is $R^{101}$-substituted or unsubstituted $C_1$-$C_{20}$ alkylene. In embodiments, $L^{101}$ is $R^{101}$-substituted or unsubstituted 2 to 20 membered heteroalkylene. In embodiments, $L^{101}$ is $R^{101}$-substituted or unsubstituted $C_3$-$C_5$ cycloalkylene. In embodiments, $L^{101}$ is $R^{101}$-substituted or unsubstituted 3 to 8 membered heterocycloalkylene. In embodiments, $L^{101}$ is $R^{101}$-substituted or unsubstituted $C_6$-$C_{10}$ arylene. In embodiments, $L^{101}$ is $R^{101}$-substituted or unsubstituted 5 to 10 membered heteroarylene.

In embodiments, $L^{101}$ is —(CH$_2$CH$_2$O)$_b$—. In embodiments, $L^{101}$ is —CCCH$_2$(OCH$_2$CH$_2$)$_a$—NHC(O)—(CH$_2$)$_c$(OCH$_2$CH$_2$)$_b$—. In embodiments, $L^{101}$ is —CHCHCH$_2$—NHC(O)—(CH$_2$)$_c$(OCH$_2$CH$_2$)$_b$—. In embodiments, $L^{101}$ is —CCCH$_2$—NHC(O)—(CH$_2$)$_c$(OCH$_2$CH$_2$)$_b$—. In embodiments, $L^{101}$ is —CCCH$_2$—. The symbol a is an integer from 0 to 8. In embodiments, a is 1. In embodiments, a is 0. The symbol b is an integer from 0 to 8. In embodiments, b is 1 or 2. In embodiments, b is an integer from 2 to 8. In embodiments, b is 1. The symbol c is an integer from 0 to 8. In embodiments, c is 3. In embodiments, c is 1. In embodiments, c is 2.

$R^{101}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{101A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{101A}$-substituted or unsubstituted cycloalkyl (e.g., $C_3$-$C_8$, $C_3$-$C_6$, or $C_5$-$C_6$), $R^{101A}$-substituted or unsubstituted heterocycloalkyl (e.g., 3 to 8 membered, 3 to 6 membered, or 5 to 6 membered), $R^{101A}$-substituted or unsubstituted aryl (e.g., $C_6$-$C_{10}$, $C_{10}$, or phenyl), or $R^{101A}$-substituted or unsubstituted heteroaryl (e.g., 5 to 10 membered, 5 to 9 membered, or 5 to 6 membered).

In embodiments, $R^{101}$ is independently —NH$_2$. In embodiments, $R^{101}$ is independently —OH. In embodiments, $R^{101}$ is independently halogen. In embodiments, $R^{101}$ is independently —CN. In embodiments, $R^{101}$ is independently oxo. In embodiments, $R^{101}$ is independently —CF$_3$. In embodiments, $R^{101}$ is independently —COOH. In embodiments, $R^{101}$ is independently —CONH$_2$. In embodiments, $R^{101}$ is independently —F. In embodiments, $R^{101}$ is independently —Cl. In embodiments, $R^{101}$ is independently —Br. In embodiments, $R^{101}$ is independently —I.

$R^{101A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{101B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{101B}$-substituted or unsubstituted cycloalkyl (e.g., $C_3$-$C_8$, $C_3$-$C_6$, or $C_5$-$C_6$), $R^{101B}$-substituted or unsubstituted heterocycloalkyl (e.g., 3 to 8 membered, 3 to 6 membered, or 5 to 6 membered), $R^{101B}$-substituted or unsubstituted aryl (e.g., $C_6$-$C_{10}$, $C_{10}$, or phenyl), or $R^{101B}$-substituted or unsubstituted heteroaryl (e.g., 5 to 10 membered, 5 to 9 membered, or 5 to 6 membered).

$R^{101B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^{102}$ and $R^{102a}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with a substituent group, a size-limited substituent group, or lower substituent group) or unsubstituted alkyl (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{10}$ or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, a substituted R$^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{102}$ is substituted with a plurality of groups selected from substituent groups, size-limited substituent groups, and lower substituent groups; each substituent group, size-limited substituent group, and/or lower substituent group may optionally be different. In embodiments, when R$^{102}$ is substituted, it is substituted with at least one substituent group. In embodiments, when R$^{102}$ is substituted, it is substituted with at least one size-limited substituent group. In embodiments, when R$^{102}$ is substituted, it is substituted with at least one lower substituent group. In embodiments, when R$^{102}$ is substituted, it is substituted with 1 to 10 substituent groups. In embodiments, when R$^{102}$ is substituted, it is substituted with 1 to 10 size-limited substituent groups. In embodiments, when R$^{102}$ is substituted, it is substituted with 1 to 10 lower substituent groups. In embodiments, when R$^{102}$ is substituted, it is substituted with 1 to 5 substituent groups. In embodiments, when R$^{102}$ is substituted, it is substituted with 1 to 5 size-limited substituent groups. In embodiments, when R$^{102}$ is substituted, it is substituted with 1 to 5 lower substituent groups. In embodiments, when R$^{102}$ is substituted, it is substituted with a substituent group. In embodiments, when R$^{102}$ is substituted, it is substituted with a size-limited substituent group. In embodiments, when R$^{102}$ is substituted, it is substituted with a lower substituent group.

In embodiments, a substituted R$^{102a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R$^{102a}$ is substituted with a plurality of groups selected from substituent groups, size-limited substituent groups, and lower substituent groups; each substituent group, size-limited substituent group, and/or lower substituent group may optionally be different. In embodiments, when R$^{102a}$ is substituted, it is substituted with at least one substituent group. In embodiments, when R$^{102a}$ is substituted, it is substituted with at least one size-limited substituent group. In embodiments, when R$^{102a}$ is substituted, it is substituted with at least one lower substituent group. In embodiments, when R$^{102a}$ is substituted, it is substituted with 1 to 10 substituent groups. In embodiments, when R$^{102a}$ is substituted, it is substituted with 1 to 10 size-limited substituent groups. In embodiments, when R$^{102a}$ is substituted, it is substituted with 1 to 10 lower substituent groups. In embodiments, when R$^{102a}$ is substituted, it is substituted with 1 to 5 substituent groups. In embodiments, when R$^{102a}$ is substituted, it is substituted with 1 to 5 size-limited substituent groups. In embodiments, when R$^{102a}$ is substituted, it is substituted with 1 to 5 lower substituent groups. In embodiments, when R$^{6B}$ is substituted, it is substituted with a substituent group. In embodiments, when R$^{102a}$ is substituted, it is substituted with a size-limited substituent group. In embodiments, when R$^{102a}$ is substituted, it is substituted with a lower substituent group.

In embodiments, L$^{103}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., C$_1$-C$_{20}$, C$_{10}$-C$_{20}$, C$_1$-C$_8$, C$_1$-C$_6$, or C$_1$-C$_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8 membered, 3 to 6 membered, or 5 to 6 membered), substituted or unsubstituted arylene (e.g., C$_6$-C$_{10}$, C$_{10}$, or phenylene), or substituted or unsubstituted heteroarylene (e.g., 5 to 10 membered, 5 to 9 membered, or 5 to 6 membered).

In embodiments, L$^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with a group, size-limited substituent group, or lower substituent group) or unsubstituted alkylene (e.g., C$_1$-C$_{20}$, C$_{10}$-C$_{20}$, C$_1$-C$_8$, C$_1$-C$_6$, or C$_1$-C$_4$), substituted (e.g., substituted with a group, size-limited substituent group, or lower substituent group) or unsubstituted heteroalkylene (e.g., 2 to 20 membered, 8 to 20 membered, 2 to 10 membered, 2 to 8 membered, 2 to 6 membered, or 2 to 4 membered), substituted (e.g., substituted with a group, size-limited substituent group, or lower substituent group) or unsubstituted cycloalkylene (e.g., C$_3$-C$_8$, C$_3$-C$_6$, or C$_5$-C$_6$), substituted (e.g., substituted with a group, size-limited substituent group, or lower substituent group) or unsubstituted heterocycloalkylene (e.g., 3 to 8 membered, 3 to 6 membered, or 5 to 6 membered), substituted (e.g., substituted with a group, size-limited substituent group, or lower substituent group) or unsubstituted arylene (e.g., C$_6$-C$_{10}$, C$_{10}$, or phenylene), or substituted (e.g., substituted with a group, size-limited substituent group, or lower substituent group) or unsubstituted heteroarylene (e.g., 5 to 10 membered, 5 to 9 membered, or 5 to 6 membered).

In embodiments, a substituted L$^{103}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{103}$ is substituted with a plurality of groups selected from substituent groups, size-limited substituent groups, and lower substituent groups; each substituent group, size-limited substituent group, and/or lower substituent group may optionally be different. In embodiments, when $L^{103}$ is substituted, it is substituted with at least one substituent group. In embodiments, when $L^{103}$ is substituted, it is substituted with at least one size-limited substituent group. In embodiments, when $L^{103}$ is substituted, it is substituted with at least one lower substituent group. In embodiments, when $L^{103}$ is substituted, it is substituted with 1 to 10 substituent groups. In embodiments, when $L^{103}$ is substituted, it is substituted with 1 to 10 size-limited substituent groups. In embodiments, when $L^{103}$ is substituted, it is substituted with 1 to 10 lower substituent groups. In embodiments, when $L^{103}$ is substituted, it is substituted with 1 to 5 substituent groups. In embodiments, when $L^{103}$ is substituted, it is substituted with 1 to 5 size-limited substituent groups. In embodiments, when $L^{103}$ is substituted, it is substituted with 1 to 5 lower substituent groups. In embodiments, when $L^{103}$ is substituted, it is substituted with a substituent group. In embodiments, when $L^{103}$ is substituted, it is substituted with a size-limited substituent group. In embodiments, when $L^{103}$ is substituted, it is substituted with a lower substituent group.

In embodiments, $L^{103}$ is a bond, —NH—, —NR$^{103}$—, —S—, —O—, —C(O)—, —C(O)O—, —OC(O)—, —NHC(O)—, —C(O)NH—, —NHC(O)NH—, —NHC(NH)NH—, —C(S)—, $R^{103}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{103}$-substituted or unsubstituted heteroalkylene (e.g., 2 to 20 membered, 8 to 20 membered, 2 to 10 membered, 2 to 8 membered, 2 to 6 membered, or 2 to 4 membered), $R^{103}$-substituted or unsubstituted cycloalkylene (e.g., $C_3$-$C_8$, $C_3$-$C_6$, or $C_5$-$C_6$), $R^{103}$-substituted or unsubstituted heterocycloalkylene (e.g., 3 to 8 membered, 3 to 6 membered, or 5 to 6 membered), $R^{103}$-substituted or unsubstituted arylene (e.g., $C_6$-$C_{10}$, $C_{10}$, or phenylene), or $R^{103}$-substituted or unsubstituted heteroarylene (e.g., 5 to 10 membered, 5 to 9 membered, or 5 to 6 membered). In embodiments, $L^{103}$ is a bond. In embodiments, $L^{103}$ is —NH—. In embodiments, $L^{103}$ is —NR$^{103}$—. In embodiments, $L^{103}$ is —S—. In embodiments, $L^{103}$ is —O—. In embodiments, $L^{103}$ is —C(O)—. In embodiments, $L^{103}$ is —C(O)O—. In embodiments, $L^{103}$ is —OC(O)—. In embodiments, $L^{103}$ is —NHC(O)—. In embodiments, $L^{103}$ is —C(O)NH—. In embodiments, $L^{103}$ is —NHC(O)NH—. In embodiments, $L^{103}$ is —NHC(NH)NH—. In embodiments, $L^{103}$ is —C(S)—. In embodiments, $L^{103}$ is $R^{103}$-substituted or unsubstituted $C_1$-$C_{20}$ alkylene. In embodiments, $L^{103}$ is $R^{103}$-substituted or unsubstituted 2 to 20 membered heteroalkylene. In embodiments, $L^{103}$ is $R^{103}$-substituted or unsubstituted $C_3$-$C_8$ cycloalkylene. In embodiments, $L^{103}$ is $R^{103}$-substituted or unsubstituted 3 to 8 membered heterocycloalkylene. In embodiments, $L^{103}$ is $R^{103}$-substituted or unsubstituted $C_6$-$C_{10}$ arylene. In embodiments, $L^{103}$ is unsubstituted phenylene. In embodiments, $L^{103}$ is $R^{103}$-substituted or unsubstituted 5 to 10 membered heteroarylene.

In embodiments, $L^{103}$ is —(CH$_2$CH$_2$O)$_d$—. In embodiments, $L^{103}$ is —(CH$_2$O)$_d$—. In embodiments, $L^{103}$ is —(CH$_2$)$_d$—. In embodiments, $L^{103}$ is —(CH$_2$)$_d$—NH—. In embodiments, $L^{103}$ is -(unsubstituted phenylene)-. In embodiments, $L^{103}$ is

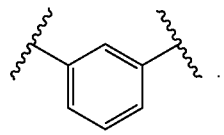

In embodiments, $L^{103}$ is -(unsubstituted phenylene)-C(O)NH—. In embodiments, $L^{103}$ is

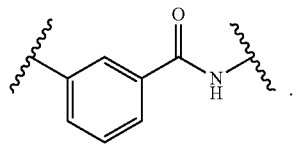 [SMILES: *NC(=O)c1cccc(*)c1]

In embodiments, $L^{103}$ is -(unsubstituted phenylene)-NHC(O)—. In embodiments, $L^{103}$ is

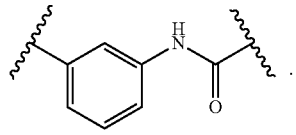 [SMILES: *C(=O)Nc1cccc(*)c1]

The symbol d is an integer from 0 to 8. In embodiments, d is 3. In embodiments, d is 2. In embodiments, d is 1. In embodiments, d is 0.

$R^{103}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{103A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{103A}$-substituted or unsubstituted cycloalkyl (e.g., $C_3$-$C_8$, $C_3$-$C_6$, or $C_5$-$C_6$), $R^{103A}$-substituted or unsubstituted heterocycloalkyl (e.g., 3 to 8 membered, 3 to 6 membered, or 5 to 6 membered), $R^{103A}$-substituted or unsubstituted aryl (e.g., $C_6$-$C_{10}$, $C_{10}$, or phenyl), or $R^{103A}$-substituted or unsubstituted heteroaryl (e.g., 5 to 10 membered, 5 to 9 membered, or 5 to 6 membered).

In embodiments, $R^{103}$ is independently —NH$_2$. In embodiments, $R^{103}$ is independently —OH. In embodiments, $R^{103}$ is independently halogen. In embodiments, $R^{103}$ is independently —CN. In embodiments, $R^{103}$ is independently oxo. In embodiments, $R^{103}$ is independently —CF$_3$. In embodiments, $R^{103}$ is independently —COOH. In embodiments, $R^{103}$ is independently —CONH$_2$. In embodiments, $R^{103}$ is independently —F. In embodiments, $R^{103}$ is independently —Cl. In embodiments, $R^{103}$ is independently —Br. In embodiments, $R^{103}$ is independently —I.

$R^{103A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{103B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{103B}$-substituted or unsubstituted cycloalkyl (e.g., $C_3$-$C_8$, $C_3$-$C_6$, or $C_5$-$C_6$), $R^{103B}$-substituted or unsubstituted heterocycloalkyl (e.g., 3 to 8 membered, 3 to 6 membered, or 5 to 6 membered), $R^{103B}$-substituted or unsubstituted aryl (e.g., $C_6$-$C_{10}$, $C_{10}$, or phenyl), or $R^{103B}$-substituted or unsubstituted heteroaryl (e.g., 5 to 10 membered, 5 to 9 membered, or 5 to 6 membered).

$R^{103B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $L^{104}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{104}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{104}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with a substituent group, size-limited substituent group, or lower substituent group) or unsubstituted alkylene (e.g., $C_1$-$C_{20}$, $C_{10}$-$C_{20}$, $C_1$-$C_8$, $C_1$-$C_6$, or $C_1$-$C_4$), substituted (e.g., substituted with a substituent group, size-limited substituent group, or lower substituent group) or unsubstituted heteroalkylene (e.g., 2 to 20 membered, 8 to 20 membered, 2 to 10 membered, 2 to 8 membered, 2 to 6 membered, or 2 to 4 membered), substituted (e.g., substituted with a substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, or 5 to 6 membered), substituted (e.g., substituted with a substituent group, size-limited substituent group, or lower substituent group) or unsubstituted arylene (e.g., $C_6$-$C_{10}$, $C_{10}$, or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered).

In embodiments, a substituted $L^{104}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{104}$ is substituted with a plurality of groups selected from substituent groups, size-limited substituent groups, and lower substituent groups; each substituent group, size-limited substituent group, and/or lower substituent group may optionally be different. In embodiments, when $L^{104}$ is substituted, it is substituted with at least one substituent group. In embodiments, when $L^{104}$ is substituted, it is substituted with at least one size-limited substituent group. In embodiments, when $L^{104}$ is substituted, it is substituted with at least one lower substituent group. In embodiments, when $L^{104}$ is substituted, it is substituted with 1 to 10 substituent groups. In embodiments, when $L^{104}$ is substituted, it is substituted with 1 to 10 size-limited substituent groups. In embodiments, when $L^{104}$ is substituted, it is substituted with 1 to 10 lower substituent groups. In embodiments, when $L^{104}$ is substituted, it is substituted with 1 to 5 substituent groups. In embodiments, when $L^{104}$ is substituted, it is substituted with 1 to 5 size-limited substituent groups. In embodiments, when $L^{104}$ is substituted, it is substituted with 1 to 5 lower substituent groups. In embodiments, when $L^{104}$ is substituted, it is substituted with a substituent group. In embodiments, when $L^{104}$ is substituted, it is substituted with a size-limited substituent group. In embodiments, when $L^{104}$ is substituted, it is substituted with a lower substituent group.

In embodiments, $L^{104}$ is a bond, —NH—, —$NR^{104}$—, —S—, —O—, —C(O)—, —C(O)O—, —OC(O)—, —NHC(O)—, —C(O)NH—, —NHC(O)NH—, —NHC(NH)NH—, —C(S)—, $R^{104}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{104}$-substituted or unsubstituted heteroalkylene (e.g., 2 to 20 membered, 8 to 20 membered, 2 to 10 membered, 2 to 8 membered, 2 to 6 membered, or 2 to 4 membered), $R^{104}$-substituted or unsubstituted cycloalkylene (e.g., $C_3$-$C_8$, $C_3$-$C_6$, or $C_5$-$C_6$), $R^{104}$-substituted or unsubstituted heterocycloalkylene (e.g., 3 to 8 membered, 3 to 6 membered, or 5 to 6 membered), $R^{104}$-substituted or unsubstituted arylene (e.g., $C_6$-$C_{10}$, $C_{10}$, or phenylene), or $R^{104}$-substituted or unsubstituted heteroarylene (e.g., 5 to 10 membered, 5 to 9 membered, or 5 to 6 membered). In embodiments, $L^{104}$ is a bond. In embodiments, $L^{104}$ is —NH—. In embodiments, $L^{104}$ is —$NR^{104}$—. In embodiments, $L^{104}$ is —S—. In embodiments, $L^{104}$ is —O—. In embodiments, $L^{104}$ is —C(O)—. In embodiments, $L^{104}$ is —C(O)O—. In embodiments, $L^{104}$ is —OC(O)—. In embodiments, $L^{104}$ is —NHC(O)—. In embodiments, $L^{104}$ is —C(O)NH—. In embodiments, $L^{104}$ is —NHC(O)NH—. In embodiments, $L^{104}$ is —NHC(NH)NH—. In embodiments, $L^{104}$ is —C(S)—. In embodiments, $L^{104}$ is $R^{104}$-substituted or unsubstituted $C_1$-$C_{20}$ alkylene. In embodiments, $L^{104}$ is $R^{104}$-substituted or unsubstituted 2 to 20 membered heteroalkylene. In embodiments, $L^{104}$ is $R^{104}$-substituted or unsubstituted $C_3$-$C_8$ cycloalkylene. In embodiments, $L^{104}$ is $R^{104}$-substituted or unsubstituted 3 to 8 membered heterocycloalkylene.

In embodiments, $L^{104}$ is $R^{104}$-substituted or unsubstituted $C_6$-$C_{10}$ arylene. In embodiments, $L^{104}$ is unsubstituted phenylene. In embodiments, $L^{104}$ is $R^{104}$-substituted or unsubstituted 5 to 10 membered heteroarylene.

In embodiments, $L^{104}$ is $-(CH_2CH_2O)_e-$. In embodiments, $L^{104}$ is $-(CH_2O)_e-$. In embodiments, $L^{104}$ is $-(CH_2)_e-$. In embodiments, $L^{104}$ is $-(CH_2)_e-NH-$. In embodiments, $L^{104}$ is -(unsubstituted phenylene)-. In embodiments, $L^{104}$ is

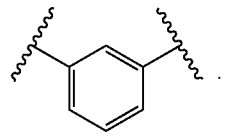 [SMILES: *c1cccc(*)c1]

In embodiments, $L^{104}$ is -(unsubstituted phenylene)-C(O)NH—. In embodiments, $L^{104}$ is

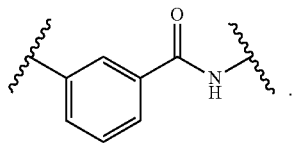 [SMILES: *NC(=O)c1cccc(*)c1]

In embodiments, $L^{104}$ is -(unsubstituted phenylene)-NHC(O)—. In embodiments, $L^{104}$ is

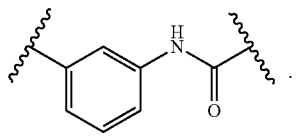 [SMILES: *C(=O)Nc1cccc(*)c1]

The symbol e is an integer from 0 to 8. In embodiments, e is 3. In embodiments, e is 1. In embodiments, e is 2.

$R^{104}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{104A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{104A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{104A}$-substituted or unsubstituted cycloalkyl (e.g., C$_3$-C$_8$, C$_3$-C$_6$, or C$_5$-C$_6$), $R^{104A}$-substituted or unsubstituted heterocycloalkyl (e.g., 3 to 8 membered, 3 to 6 membered, or 5 to 6 membered), $R^{104A}$-substituted or unsubstituted aryl (e.g., C$_6$-C$_{10}$, C$_{10}$, or phenyl), or $R^{104A}$-substituted or unsubstituted heteroaryl (e.g., 5 to 10 membered, 5 to 9 membered, or 5 to 6 membered).

In embodiments, $R^{104}$ is independently —NH$_2$. In embodiments, $R^{104}$ is independently —OH. In embodiments, $R^{104}$ is independently halogen. In embodiments, $R^{104}$ is independently —CN. In embodiments, $R^{104}$ is independently oxo. In embodiments, $R^{104}$ is independently —CF$_3$. In embodiments, $R^{104}$ is independently —COOH. In embodiments, $R^{104}$ is independently —CONH$_2$. In embodiments, $R^{104}$ is independently —F. In embodiments, $R^{104}$ is independently —Cl. In embodiments, $R^{104}$ is independently —Br. In embodiments, $R^{104}$ is independently —I.

$R^{104A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{104B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{104B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{104B}$-substituted or unsubstituted cycloalkyl (e.g., C$_3$-C$_8$, C$_3$-C$_6$, or C$_5$-C$_6$), $R^{104B}$-substituted or unsubstituted heterocycloalkyl (e.g., 3 to 8 membered, 3 to 6 membered, or 5 to 6 membered), $R^{104B}$-substituted or unsubstituted aryl (e.g., C$_6$-C$_{10}$, C$_{10}$, or phenyl), or $R^{104B}$-substituted or unsubstituted heteroaryl (e.g., 5 to 10 membered, 5 to 9 membered, or 5 to 6 membered).

$R^{104B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_{10}$, or phenyl), or unsubstituted heteroaryl (e.g., 5 to 10 membered, 5 to 9 membered, or 5 to 6 membered).

In embodiments, $L^{105}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{105}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., C$_1$-C$_{20}$, C$_{10}$-C$_{20}$, C$_1$-C$_8$, C$_1$-C$_6$, or C$_1$-C$_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8 membered, 3 to 6 membered, or 5 to 6 membered), substituted or unsubstituted arylene (e.g., C$_6$-C$_{10}$, C$_{10}$, or phenylene), or substituted or unsubstituted heteroarylene (e.g., 5 to 10 membered, 5 to 9 membered, or 5 to 6 membered).

In embodiments, $L^{105}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted (e.g., substituted with a substituent group, size-limited substituent group, or lower substituent group) or unsubstituted alkylene (e.g., C$_1$-C$_{20}$, C$_{10}$-C$_{20}$, C$_1$-C$_8$, C$_1$-C$_6$, or C$_1$-C$_4$), substituted (e.g., substituted with a substituent group, size-limited substituent group, or lower substituent group) or unsubstituted heteroalkylene (e.g., 2 to 20 membered, 8 to 20 membered, 2 to 10 membered, 2 to 8 membered, 2 to 6 membered, or 2 to 4 membered), substituted (e.g., substituted with a substituent group, size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, or 5 to 6 membered), substituted (e.g., substituted with a substituent group, size-limited substituent group, or lower substituent group) or unsubstituted arylene (e.g., $C_6$-$C_{10}$, $C_{10}$, or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered).

In embodiments, a substituted $L^{105}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{105}$ is substituted with a plurality of groups selected from substituent groups, size-limited substituent groups, and lower substituent groups; each substituent group, size-limited substituent group, and/or lower substituent group may optionally be different. In embodiments, when $L^{105}$ is substituted, it is substituted with at least one substituent group. In embodiments, when $L^{105}$ is substituted, it is substituted with at least one size-limited substituent group. In embodiments, when $L^{105}$ is substituted, it is substituted with at least one lower substituent group. In embodiments, when $L^{105}$ is substituted, it is substituted with 1 to 10 substituent groups. In embodiments, when $L^{105}$ is substituted, it is substituted with 1 to 10 size-limited substituent groups. In embodiments, when $L^{105}$ is substituted, it is substituted with 1 to 10 lower substituent groups. In embodiments, when $L^{105}$ is substituted, it is substituted with 1 to 5 substituent groups. In embodiments, when $L^{105}$ is substituted, it is substituted with 1 to 5 size-limited substituent groups. In embodiments, when $L^{105}$ is substituted, it is substituted with 1 to 5 lower substituent groups. In embodiments, when $L^{105}$ is substituted, it is substituted with a substituent group. In embodiments, when $L^{105}$ is substituted, it is substituted with a size-limited substituent group. In embodiments, when $L^{105}$ is substituted, it is substituted with a lower substituent group.

In embodiments, $L^{105}$ is a bond, —NH—, —$NR^{105}$—, —S—, —O—, —C(O)—, —C(O)O—, —OC(O)—, —NHC(O)—, —C(O)NH—, —NHC(O)NH—, —NHC(NH)NH—, —C(S)—, $R^{105}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{105}$-substituted or unsubstituted heteroalkylene (e.g., 2 to 20 membered, 8 to 20 membered, 2 to 10 membered, 2 to 8 membered, 2 to 6 membered, or 2 to 4 membered), $R^{105}$-substituted or unsubstituted cycloalkylene (e.g., $C_3$-$C_8$, $C_3$-$C_6$, or $C_5$-$C_6$), $R^{105}$-substituted or unsubstituted heterocycloalkylene (e.g., 3 to 8 membered, 3 to 6 membered, or 5 to 6 membered), $R^{105}$-substituted or unsubstituted arylene (e.g., $C_6$-$C_{10}$, $C_{10}$, or phenylene), or $R^{105}$-substituted or unsubstituted heteroarylene (e.g., 5 to 10 membered, 5 to 9 membered, or 5 to 6 membered). In embodiments, $L^{105}$ is a bond. In embodiments, $L^{105}$ is —NH—. In embodiments, $L^{105}$ is —$NR^{105}$—. In embodiments, $L^{105}$ is —S—. In embodiments, $L^{105}$ is —O—. In embodiments, $L^{105}$ is —C(O)—. In embodiments, $L^{105}$ is —C(O)O—. In embodiments, $L^{105}$ is —OC(O)—. In embodiments, $L^{105}$ is —NHC(O)—. In embodiments, $L^{105}$ is —C(O)NH—. In embodiments, $L^{105}$ is —NHC(O)NH—. In embodiments, $L^{105}$ is —NHC(NH)NH—. In embodiments, $L^{105}$ is —C(S)—. In embodiments, $L^{105}$ is $R^{105}$-substituted or unsubstituted $C_1$-$C_{20}$ alkylene. In embodiments, $L^{105}$ is $R^{105}$-substituted or unsubstituted 2 to 20 membered heteroalkylene. In embodiments, $L^{105}$ is oxo-substituted 2 to 20 membered heteroalkylene. In embodiments, $L^{105}$ is $R^{105}$-substituted or unsubstituted $C_3$-$C_8$ cycloalkylene. In embodiments, $L^{105}$ is $R^{105}$-substituted or unsubstituted 3 to 8 membered heterocycloalkylene. In embodiments, $L^{105}$ is oxo-substituted 3 to 8 membered heterocycloalkylene. In embodiments, $L^{105}$ is $R^{105}$-substituted or unsubstituted $C_6$-$C_{10}$ arylene. In embodiments, $L^{105}$ is $R^{105}$-substituted or unsubstituted 5 to 10 membered heteroarylene. In embodiments, $L^{105}$ is oxo-substituted 5 to 10 membered heteroarylene.

In embodiments, $L^{105}$ is —$(CH_2CH_2O)_f$—. In embodiments, $L^{105}$ is —$(CH_2O)_f$—. In embodiments, $L^{105}$ is —$(CH_2)_f$—. In embodiments, $L^{105}$ is —$(CH_2)_f$—NH—. In embodiments, $L^{105}$ is —C(O)NH$(CH_2)_f$—NH—. In embodiments, $L^{105}$ is —$(CH_2CH_2O)_f$—$(CH_2)_g$—NH—. In embodiments, $L^{105}$ is —$(CH_2)_g$—. In embodiments, $L^{105}$ is —$(CH_2)_g$—NH—. In embodiments, $L^{105}$ is —NHC(O)—$(CH_2)_f$—NH—. In embodiments, $L^{105}$ is —NHC(O)—$(CH_2)_f$—NH—. In embodiments, $L^{105}$ is —NHC(O)—$(CH_2CH_2O)_f$—$(CH_2)_g$—NH—. In embodiments, $L^{105}$ is —NHC(O)—$(CH_2)_g$—. In embodiments, $L^{105}$ is —NHC(O)—$(CH_2)_g$—NH—. In embodiments, $L^{105}$ is —C(O)NH$(CH_2)_f$—NH—. In embodiments, $L^{105}$ is —C(O)NH—$(CH_2CH_2O)_f$—$(CH_2)_g$—NH—. In embodiments, $L^{105}$ is —C(O)NH—$(CH_2)_g$—. In embodiments, $L^{105}$ is —C(O)NH—$(CH_2)_g$—NH—. The symbol f is an integer from 0 to 8. In embodiments, f is 3. In embodiments, f is 1. In embodiments, f is 2. In embodiments, f is 0. The symbol g is an integer from 0 to 8. In embodiments, g is 3. In embodiments, g is 1. In embodiments, g is 2. In embodiments, g is 0.

$R^{105}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{105A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{105A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{105A}$-substituted or unsubstituted cycloalkyl (e.g., $C_3$-$C_8$, $C_3$-$C_6$, or $C_5$-$C_6$), $R^{105A}$-substituted or unsubstituted heterocycloalkyl (e.g., 3 to 8 membered, 3 to 6 membered, or 5 to 6 membered), $R^{105A}$-substituted or unsubstituted aryl (e.g., $C_6$-$C_{10}$, $C_{10}$, or phenyl), or $R^{105A}$-substituted or unsubstituted heteroaryl (e.g., 5 to 10 membered, 5 to 9 membered, or 5 to 6 membered).

In embodiments, $R^{105}$ is independently —$NH_2$. In embodiments, $R^{105}$ is independently —OH. In embodiments, $R^{105}$ is independently halogen. In embodiments, $R^{105}$ is independently —CN. In embodiments, $R^{105}$ is independently oxo. In embodiments, $R^{105}$ is independently —$CF_3$. In embodiments, $R^{105}$ is independently —COOH. In embodiments, $R^{105}$ is independently —$CONH_2$. In embodiments, $R^{105}$ is independently —F. In embodiments, $R^{105}$ is independently —Cl. In embodiments, $R^{105}$ is independently —Br. In embodiments, $R^{105}$ is independently —I.

$R^{105A}$ is independently oxo, halogen, —$CCl_3$, —$CBr_3$, —$CF_3$, —$CI_3$, —CN, —OH, —$NH_2$, —COOH, —$CONH_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, R$^{105B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{105B}$-substituted or unsubstituted heteroalkyl (e.g., 2 to 20 membered, 8 to 20 membered, 2 to 10 membered, 2 to 8 membered, 2 to 6 membered, or 2 to 4 membered), R$^{105B}$-substituted or unsubstituted cycloalkyl (e.g., C$_3$-C$_8$, C$_3$-C$_6$, or C$_5$-C$_6$), R$^{105B}$-substituted or unsubstituted heterocycloalkyl (e.g., 3 to 8 membered, 3 to 6 membered, or 5 to 6 membered), R$^{105B}$-substituted or unsubstituted aryl (e.g., C$_6$-C$_{10}$, C$_{10}$, or phenyl), or R$^{105B}$-substituted or unsubstituted heteroaryl (e.g., 5 to 10 membered, 5 to 9 membered, or 5 to 6 membered).

R$^{105B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_{10}$, or phenyl), or unsubstituted heteroaryl (e.g., 5 to 10 membered, 5 to 9 membered, or 5 to 6 membered).

In embodiments, L$^{101}$, L$^{103}$, L$^{104}$, and L$^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^{101}$, L$^{103}$, L$^{104}$, and L$^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and R$^{102}$ and R$^{102a}$ are independently hydrogen or unsubstituted alkyl.

In embodiments, L$^{101}$ is independently a substituted or unsubstituted C$_1$-C$_4$ alkylene or substituted or unsubstituted 8 to 20 membered heteroalkylene.

In embodiments, L$^{103}$ is independently a bond or substituted or unsubstituted 2 to 10 membered heteroalkylene.

In embodiments, L$^{104}$ is independently a bond, substituted or unsubstituted 4 to 18 membered heteroalkylene, or substituted or unsubstituted phenylene.

In embodiments, L$^{105}$ is independently bond or substituted or unsubstituted 4 to 18 membered heteroalkylene.

In embodiments, L$^{101}$ is independently a substituted or unsubstituted C$_1$-C$_4$ alkylene or substituted or unsubstituted 8 to 20 membered heteroalkylene; L$^{103}$ is independently a bond or substituted or unsubstituted 2 to 10 membered heteroalkylene; L$^{104}$ is independently a bond, substituted or unsubstituted 4 to 18 membered heteroalkylene, or substituted or unsubstituted phenylene; L$^{105}$ is independently bond or substituted or unsubstituted 4 to 18 membered heteroalkylene; and R$^{102}$ is unsubstituted C$_1$-C$_4$ alkyl; and R$^{102a}$ is hydrogen or unsubstituted methyl.

In embodiments, L$^{101}$, L$^{103}$, and L$^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^{104}$ is unsubstituted phenylene.

In embodiments, L$^{101}$, L$^{103}$, and L$^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; L$^{104}$ is unsubstituted phenylene; and R$^{102}$ and R$^{102a}$ are independently hydrogen or unsubstituted alkyl.

In embodiments, L$^{101}$ is independently a substituted or unsubstituted C$_1$-C$_4$ alkylene or substituted or unsubstituted 8 to 20 membered heteroalkylene.

In embodiments, L$^{103}$ is independently a bond or substituted or unsubstituted 2 to 10 membered heteroalkylene.

In embodiments, L$^{104}$ is independently an unsubstituted phenylene.

In embodiments, L$^{105}$ is independently bond or substituted or unsubstituted 4 to 18 membered heteroalkylene.

In embodiments, L$^{101}$ is independently a substituted or unsubstituted C$_1$-C$_4$ alkylene or substituted or unsubstituted 8 to 20 membered heteroalkylene; L$^{103}$ is independently a bond or substituted or unsubstituted 2 to 10 membered heteroalkylene; L$^{104}$ is independently an unsubstituted phenylene; L$^{105}$ is independently bond or substituted or unsubstituted 4 to 18 membered heteroalkylene; and R$^{102}$ is unsubstituted C$_1$-C$_4$ alkyl; and R$^{102a}$ is hydrogen or unsubstituted methyl.

In embodiments, L$^{101}$, L$^{103}$, L$^{104}$, and L$^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and R$^{102}$ is unsubstituted C$_1$-C$_4$ alkyl.

In embodiments, L$^{101}$, L$^{103}$, L$^{104}$, and L$^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, R$^{102}$ is unsubstituted C$_1$-C$_4$ alkyl.

In embodiments, L$^{101}$ is independently a substituted or unsubstituted C$_1$-C$_4$ alkylene or substituted or unsubstituted 8 to 20 membered heteroalkylene; L$^{103}$ is independently a bond or substituted or unsubstituted 2 to 10 membered heteroalkylene; L$^{104}$ is independently a bond, substituted or unsubstituted 4 to 18 membered heteroalkylene, or substituted or unsubstituted phenylene; L$^{105}$ is independently bond or substituted or unsubstituted 4 to 18 membered heteroalkylene; and R$^{102}$ is unsubstituted C$_1$-C$_4$ alkyl. In embodiments, L$^{101}$ is independently a substituted or unsubstituted C$_1$-C$_4$ alkylene or substituted or unsubstituted 8 to 20 membered heteroalkylene. In embodiments, L$^{103}$ is independently a bond or substituted or unsubstituted 2 to 10 membered heteroalkylene. In embodiments, L$^{104}$ is independently a bond, substituted or unsubstituted 4 to 18 membered heteroalkylene, or substituted or unsubstituted phenylene. In embodiments, $L^{105}$ is independently bond or substituted or unsubstituted 4 to 18 membered heteroalkylene.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; and $R^{102}$ is unsubstituted $C_1$-$C_4$ alkyl. In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{104}$ is unsubstituted phenylene.

In embodiments, $R^{102}$ is independently hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{102B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{102B}$-substituted or unsubstituted cycloalkyl (e.g., $C_3$-$C_8$, $C_3$-$C_6$, or $C_5$-$C_6$), $R^{102B}$-substituted or unsubstituted heterocycloalkyl (e.g., 3 to 8 membered, 3 to 6 membered, or 5 to 6 membered), $R^{102B}$-substituted or unsubstituted aryl (e.g., $C_6$-$C_{10}$, $C_{10}$, or phenyl), or $R^{102B}$-substituted or unsubstituted heteroaryl (e.g., 5 to 10 membered, 5 to 9 membered, or 5 to 6 membered).

In embodiments, $R^{102}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102}$ is independently unsubstituted $C_1$-$C_6$ alkyl. In embodiments, $R^{102}$ is independently unsubstituted $C_1$-$C_4$ alkyl. In embodiments, $R^{102}$ is independently unsubstituted methyl. In embodiments, $R^{102}$ is independently unsubstituted ethyl. In embodiments, $R^{102}$ is independently unsubstituted propyl (e.g., n-propyl or isopropyl). In embodiments, $R^{102}$ is independently unsubstituted butyl (e.g., n-butyl, s-butyl, t-butyl, or isobutyl). In embodiments, $R^{102}$ is independently unsubstituted tert-butyl. In embodiments, $R^{102}$ is independently hydrogen.

$R^{102B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{102C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102C}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{102C}$-substituted or unsubstituted cycloalkyl (e.g., $C_3$-$C_8$, $C_3$-$C_6$, or $C_5$-$C_6$), $R^{102C}$-substituted or unsubstituted heterocycloalkyl (e.g., 3 to 8 membered, 3 to 6 membered, or 5 to 6 membered), $R^{102C}$-substituted or unsubstituted aryl (e.g., $C_6$-$C_{10}$, $C_{10}$, or phenyl), or $R^{102C}$-substituted or unsubstituted heteroaryl (e.g., 5 to 10 membered, 5 to 9 membered, or 5 to 6 membered).

$R^{102C}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^{102a}$ is independently hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). In embodiments, $R^{102a}$ is independently hydrogen or unsubstituted alkyl (e.g., $C_1$-$C_{20}$, $C_{10}$-$C_{20}$, $C_1$-$C_8$, $C_1$-$C_6$, or $C_1$-$C_4$).

In embodiments, $R^{102a}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102a}$ is independently unsubstituted $C_1$-$C_6$ alkyl. In embodiments, $R^{102a}$ is independently unsubstituted $C_1$-$C_4$ alkyl. In embodiments, $R^{102a}$ is independently unsubstituted methyl. In embodiments, $R^{102a}$ is independently unsubstituted tert-butyl. In embodiments, $R^{102a}$ is independently hydrogen.

In embodiments, $R^{102}$ and $R^{102a}$ are independently hydrogen or unsubstituted alkyl. In embodiments, $R^{102}$ is unsubstituted $C_1$-$C_4$ alkyl. In embodiments, $R^{102a}$ is hydrogen or unsubstituted methyl.

In embodiments, -($L^{101}$)-OC(SSR$^{102}$)(R$^{102a}$)-($L^{103}$)-($L^{104}$)-($L^{105}$)- is

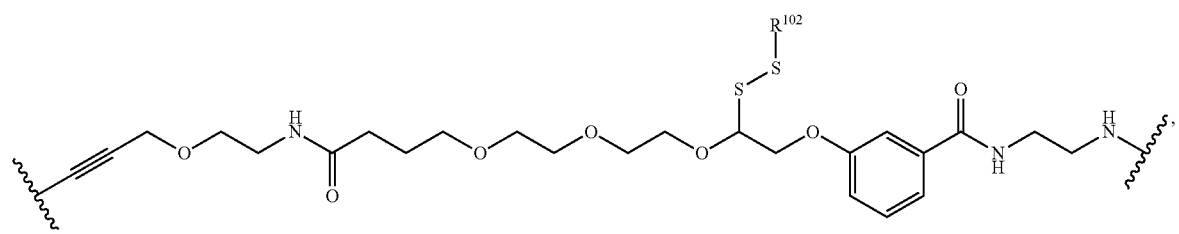

-continued
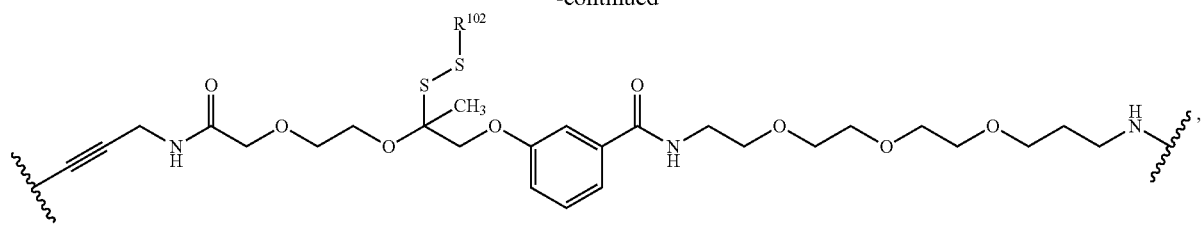
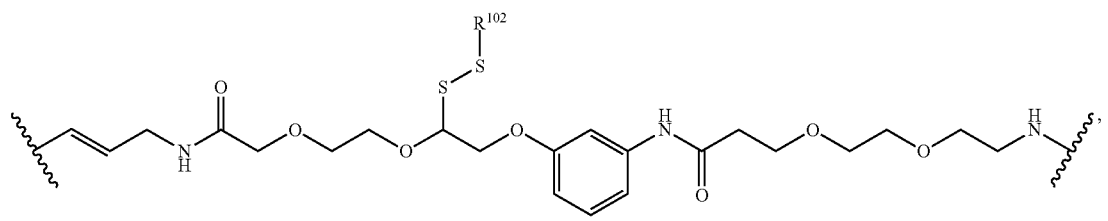
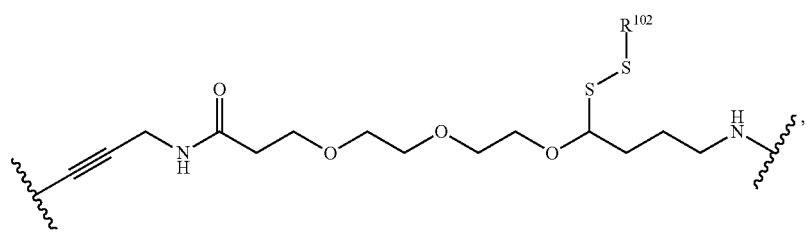
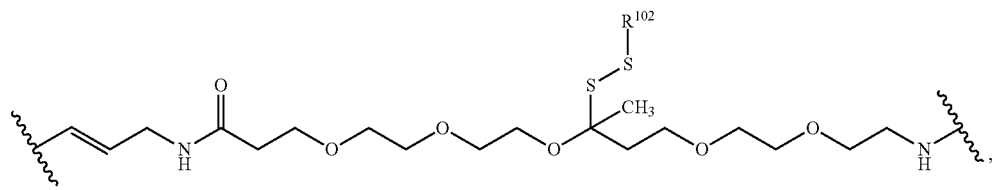
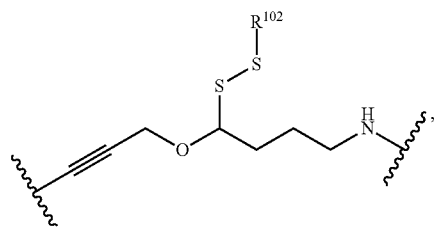
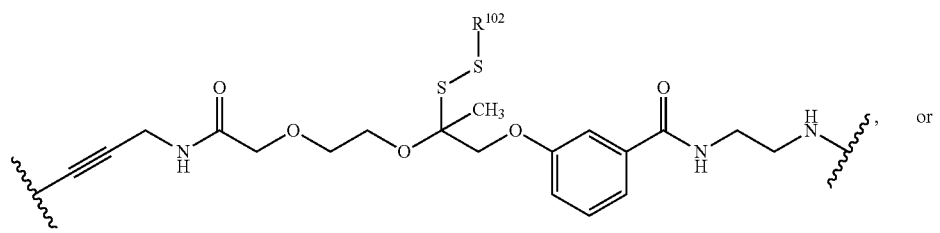, or
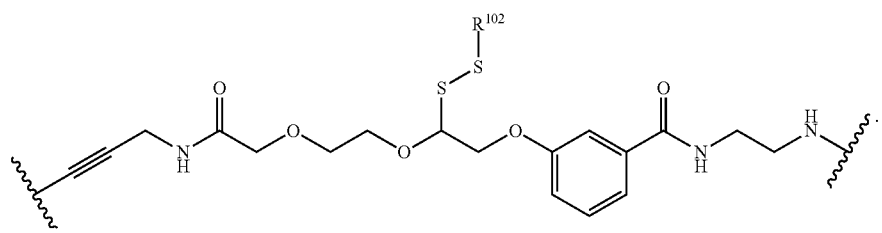

In embodiments, -(L$^{101}$)-OC(SSR$^{102}$)(R$^{102a}$)-(L$^{103}$)-(L$^{104}$)-(L$^{105}$)- is
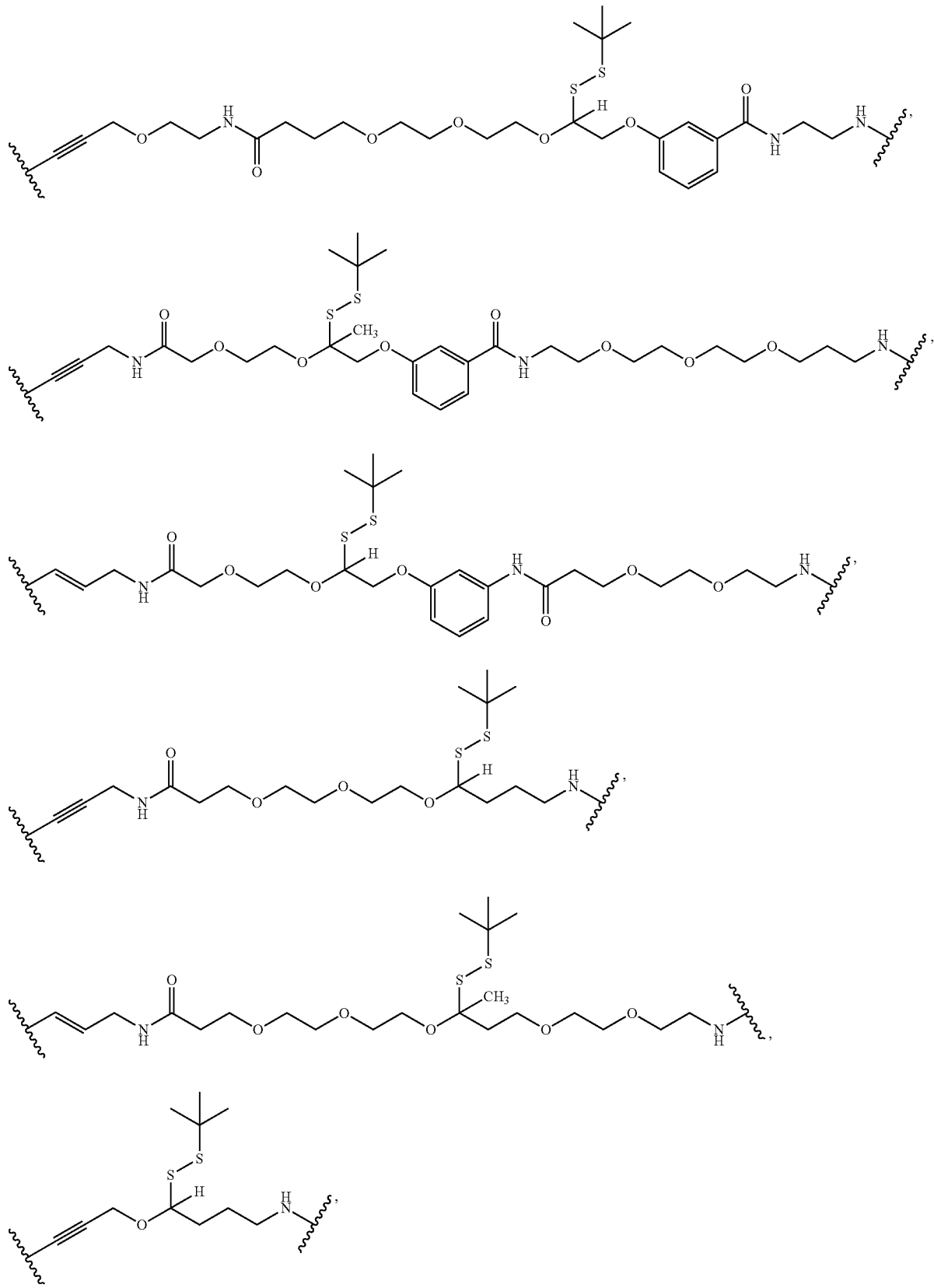

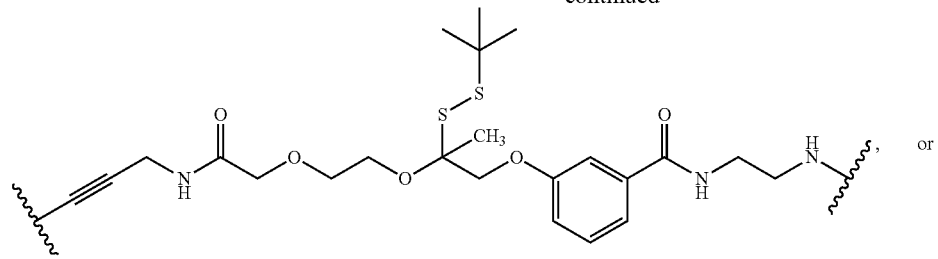
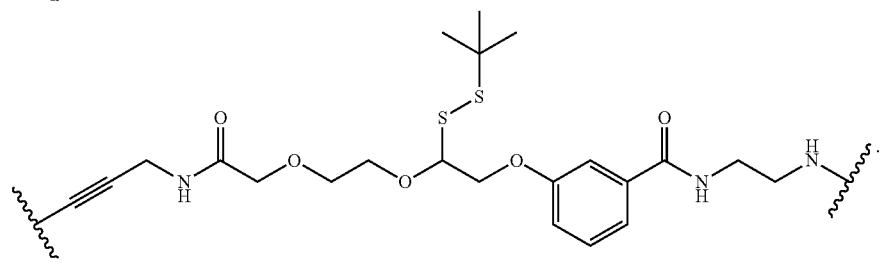
In embodiments, -(L$^{101}$)-OC(SSR$^{102}$)(R$^{102a}$)-(L$^{103}$)-(L$^{104}$)-(L$^{105}$)- is
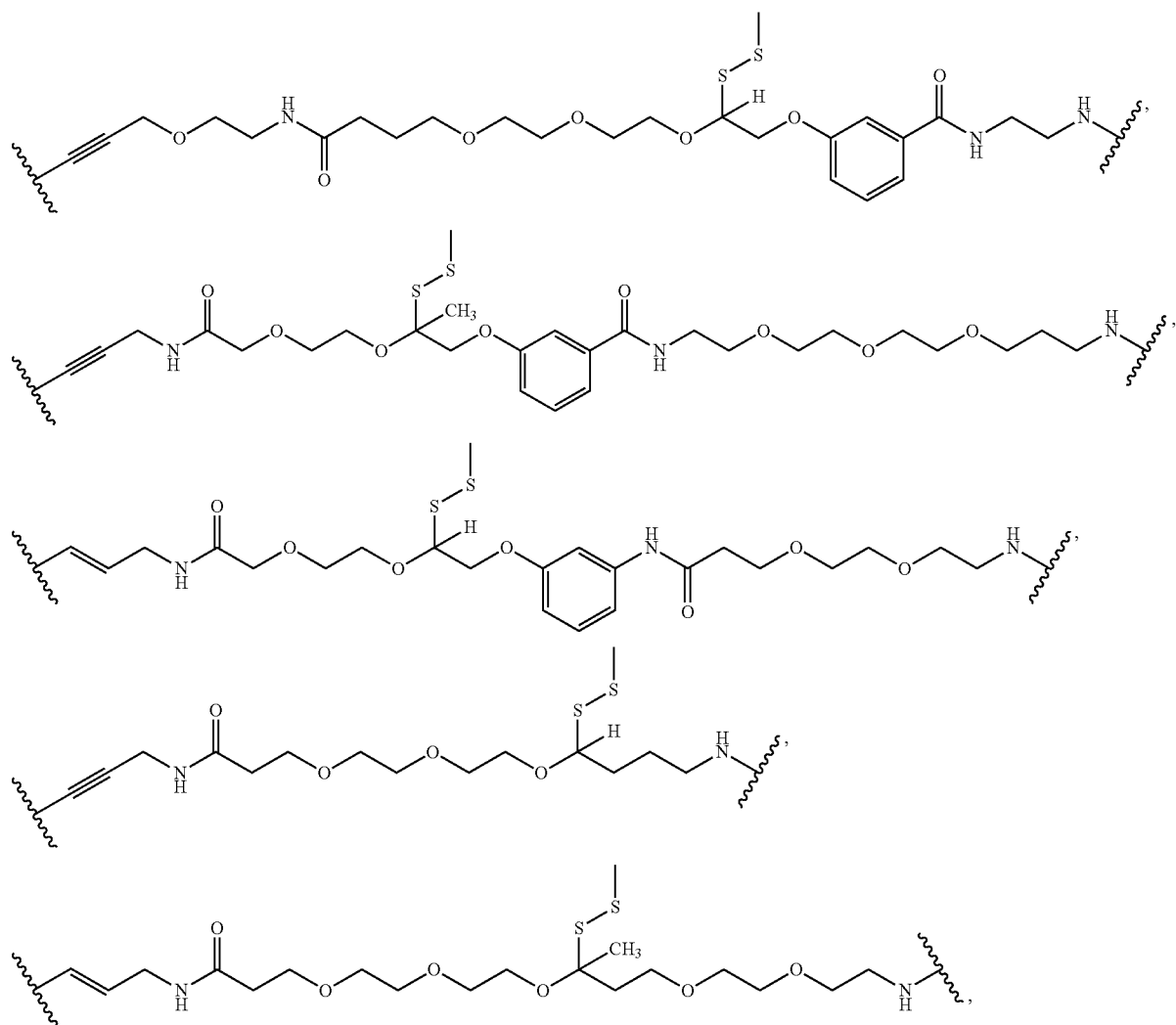

-continued
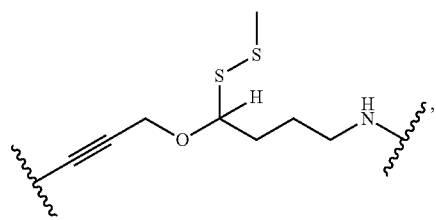
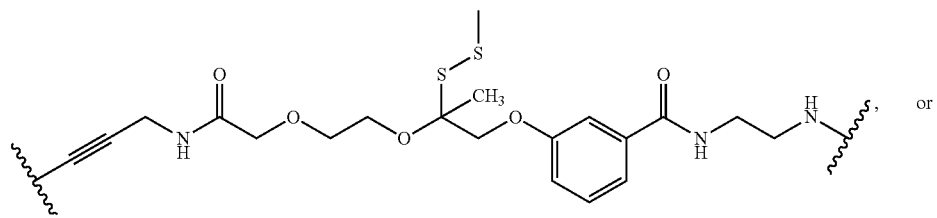
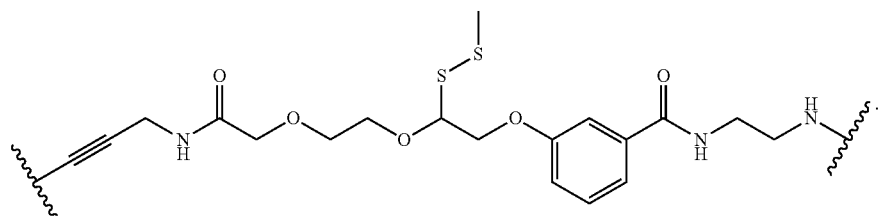
In embodiments, -(L$^{101}$)-OC(SSR$^{102}$)(R$^{102a}$)-(L$^{103}$)-(L$^{104}$)-(L$^{105}$)- is
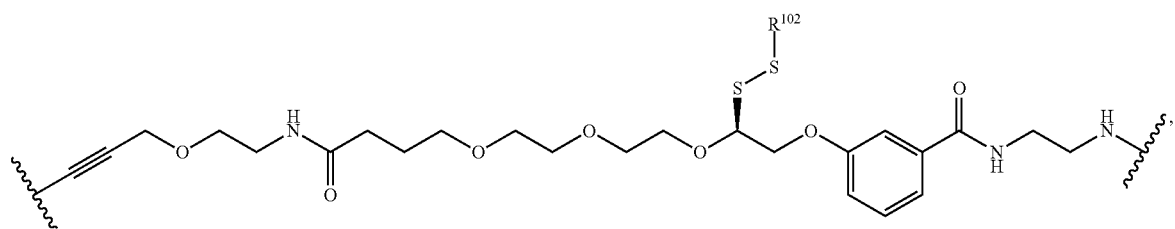
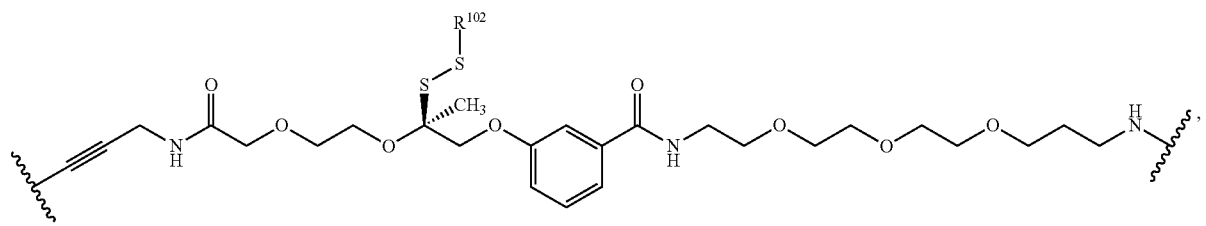
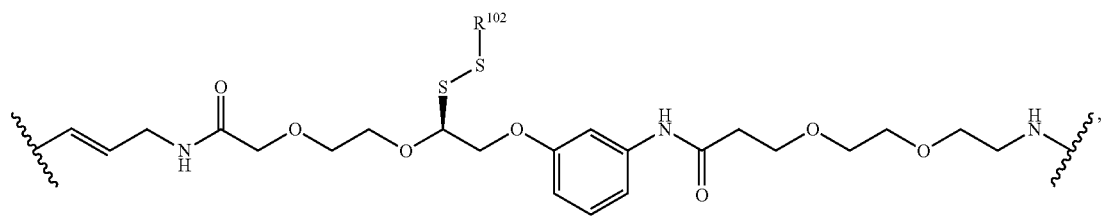

-continued
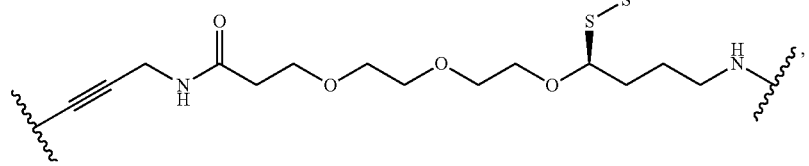
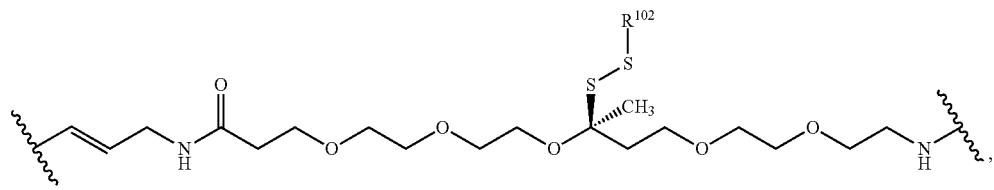
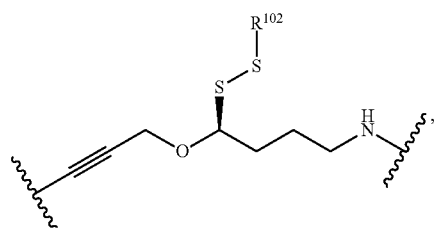
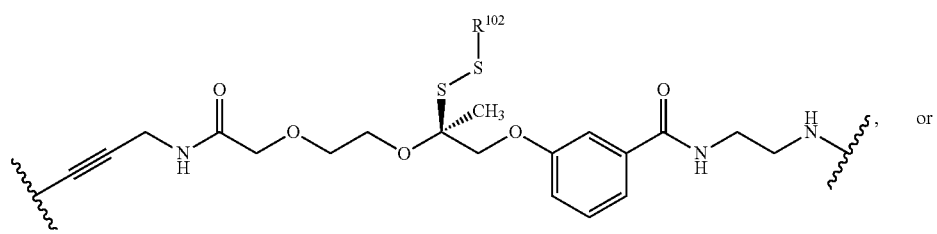
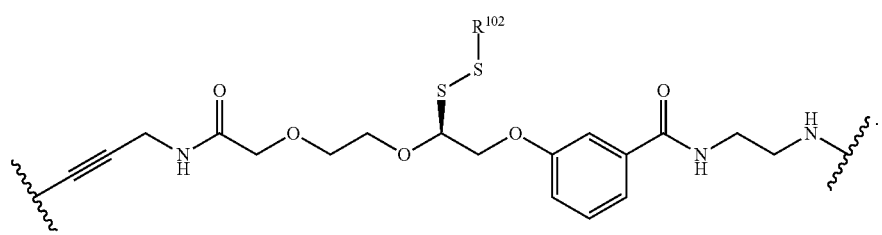
In embodiments, -(L$^{101}$)-OC(SSR$^{102}$)(R$^{102a}$)-(L$^{103}$)-(L$^{104}$)-(L$^{105}$)- is
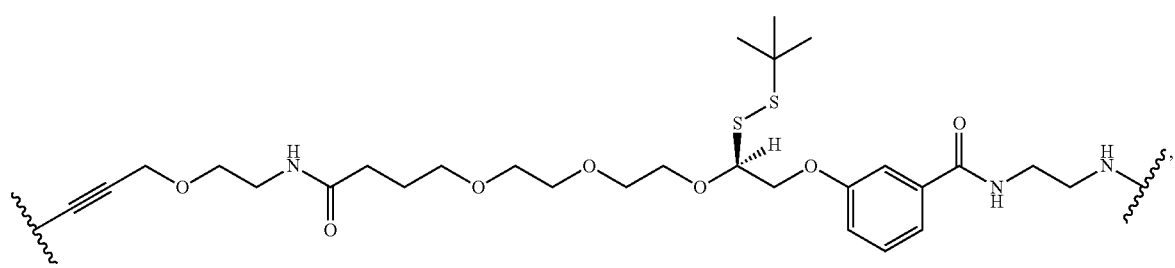

-continued
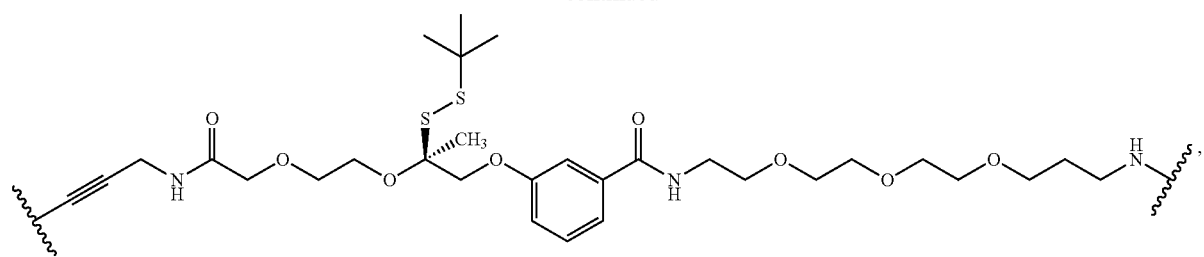
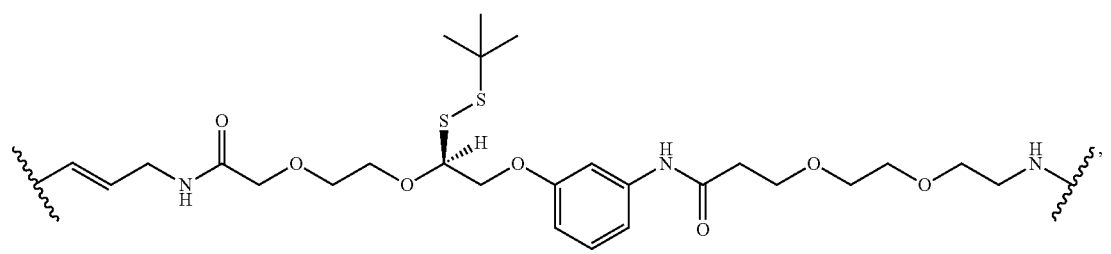
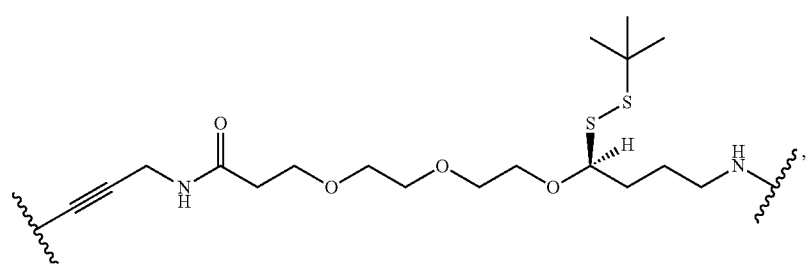
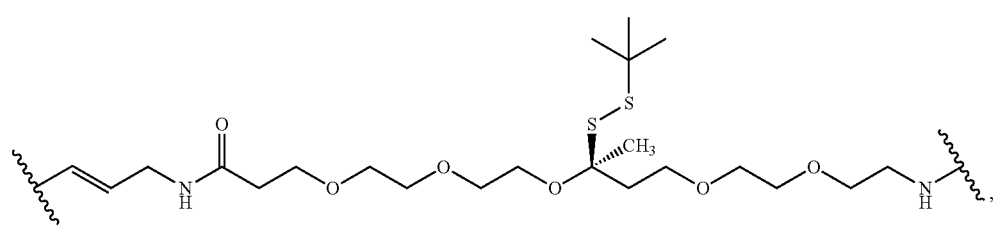
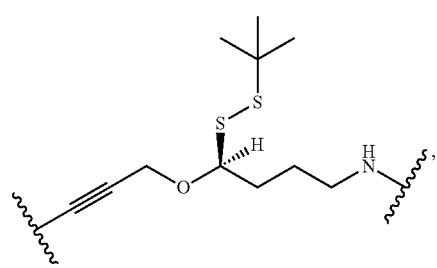
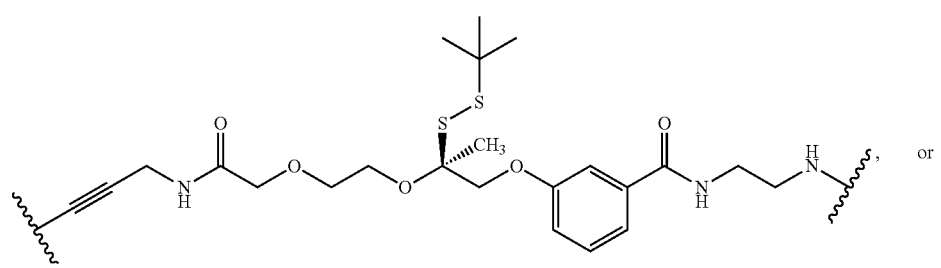, or

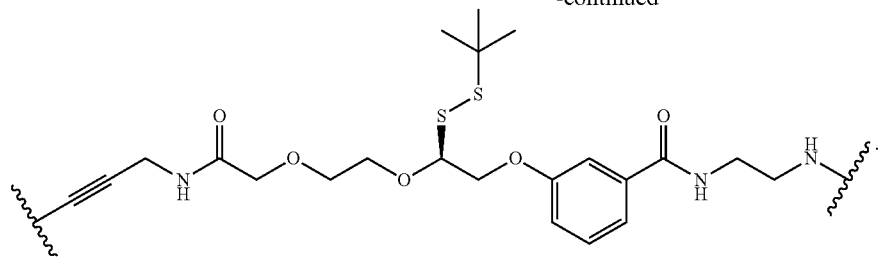
In embodiments, -(L$^{101}$)-OC(SSR$^{102}$)(R$^{102a}$)-(L$^{103}$)-(L$^{104}$)-(L$^{105}$)- is
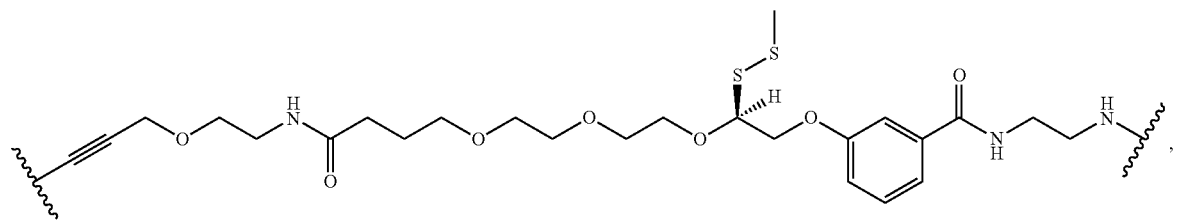
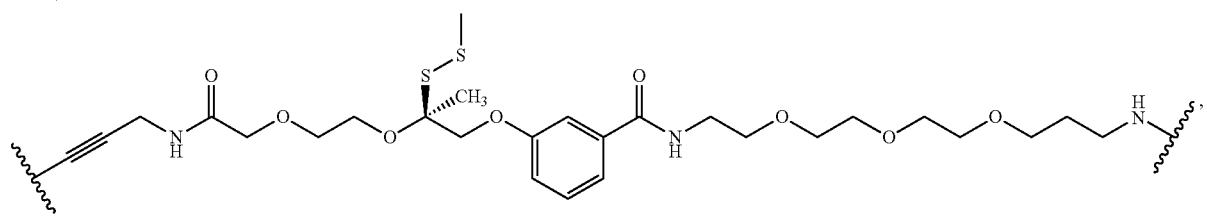
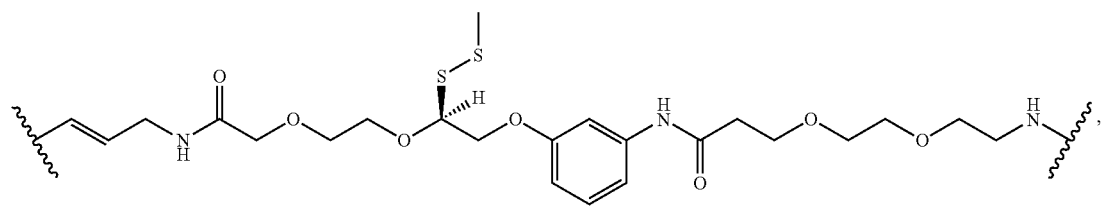
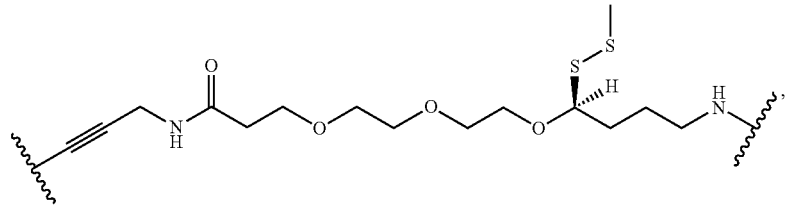
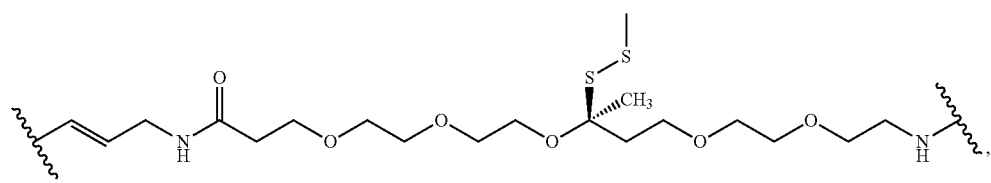
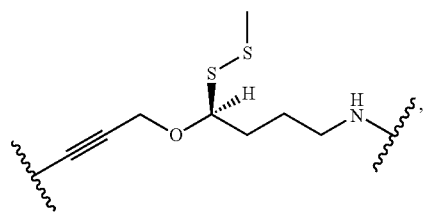

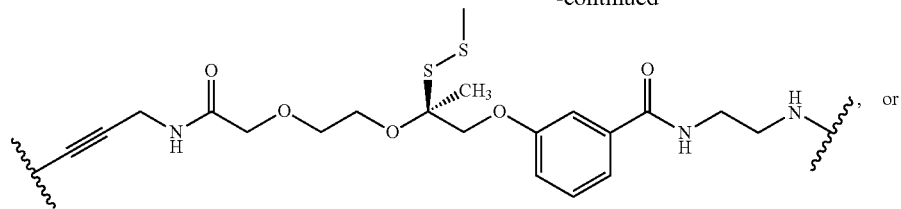
, or
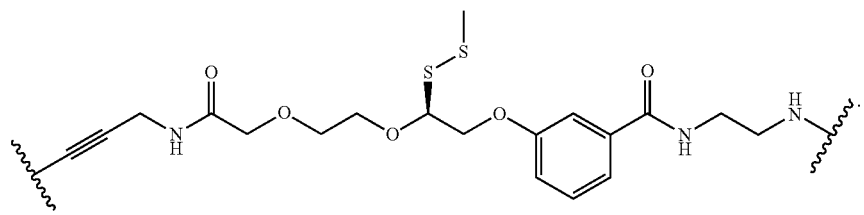
.
In embodiments, $-(L^{101})-OC(SSR^{102})(R^{102a})-(L^{103})-(L^{104})-(L^{105})-$ is
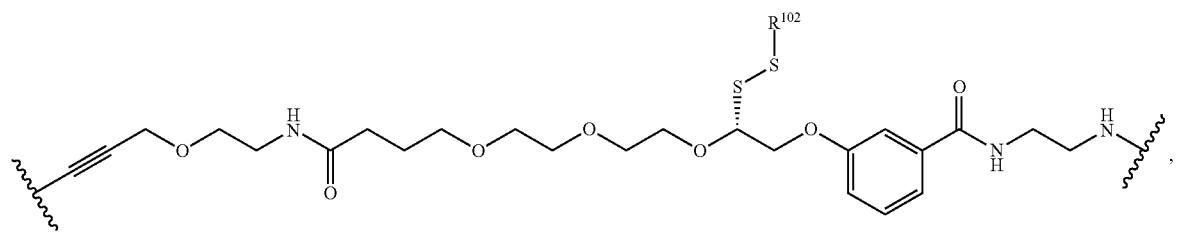
,
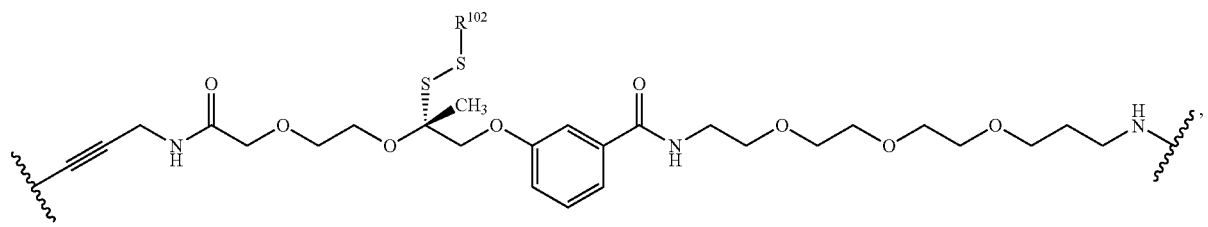
,
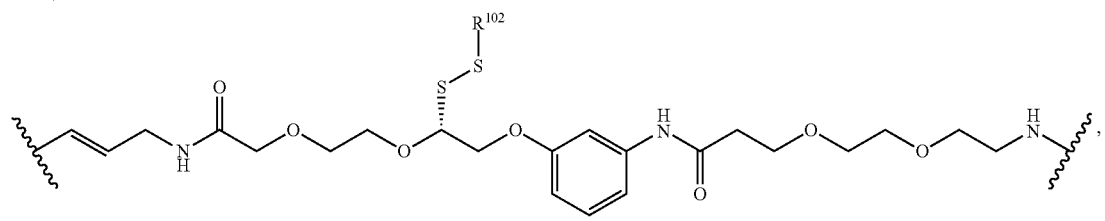
,
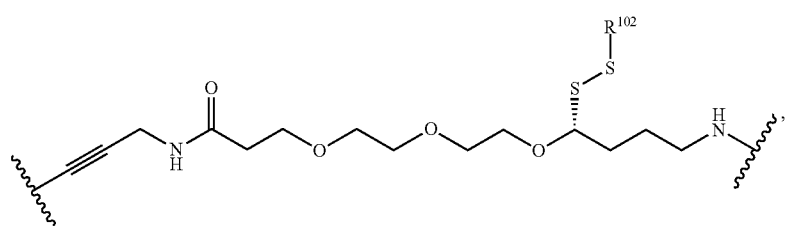
,
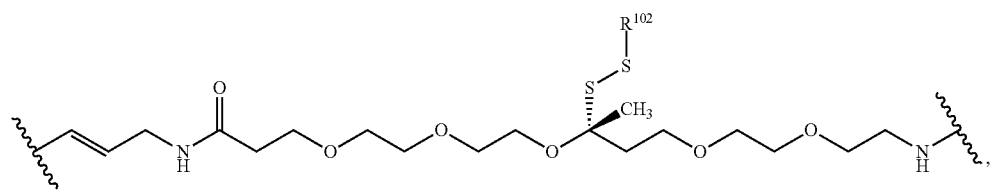
, -continued
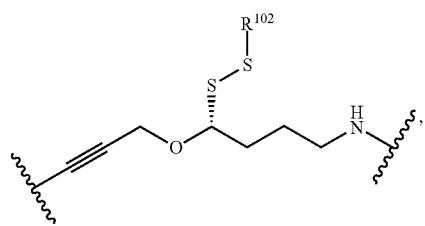
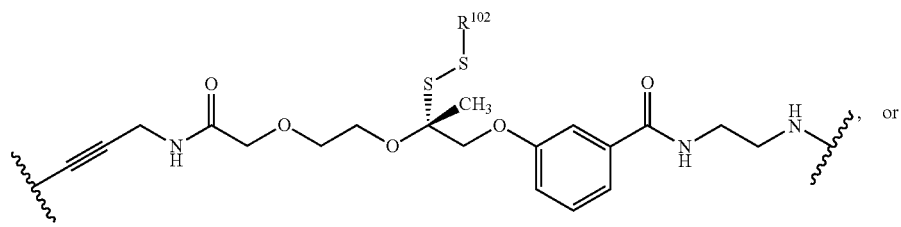, or
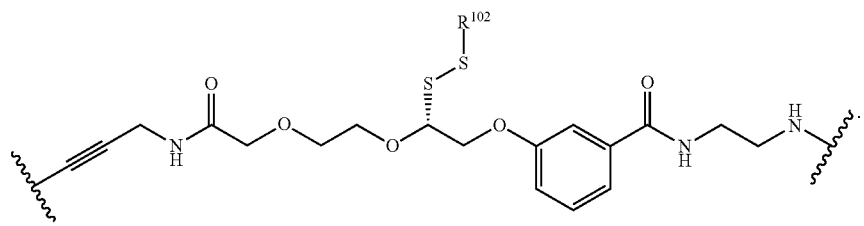
In embodiments, -(L$^{101}$)-OC(SSR$^{102}$)(R$^{102a}$)-(L$^{103}$)-(L$^{104}$)-(L$^{105}$)- is
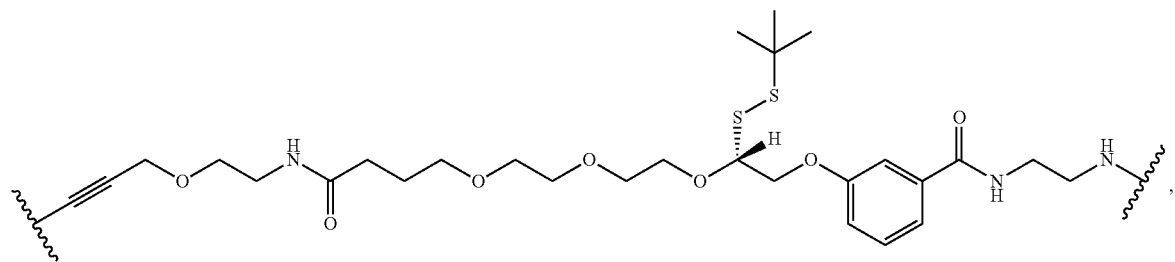,
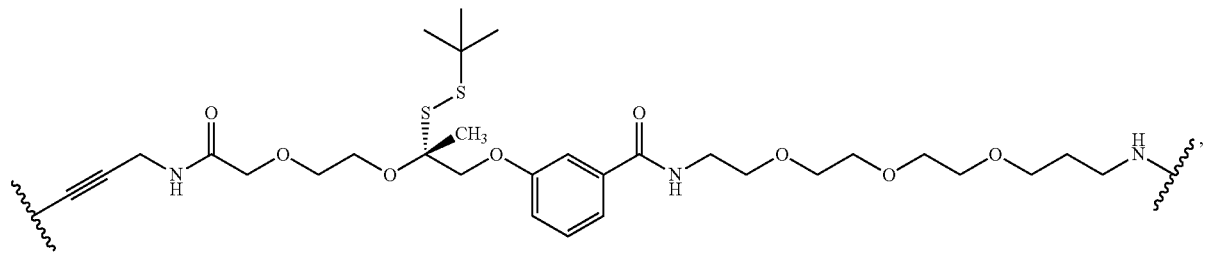,
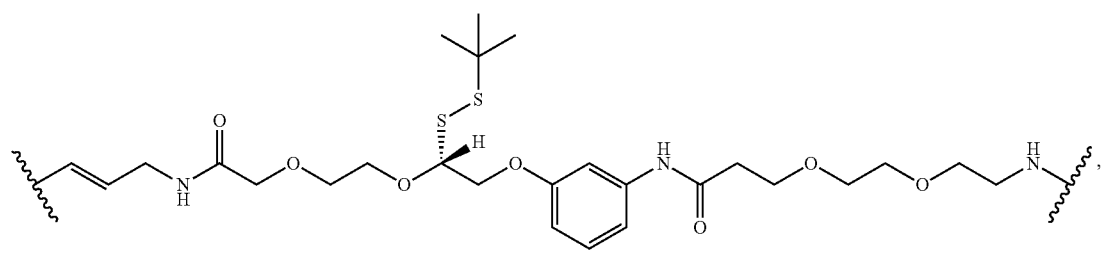,

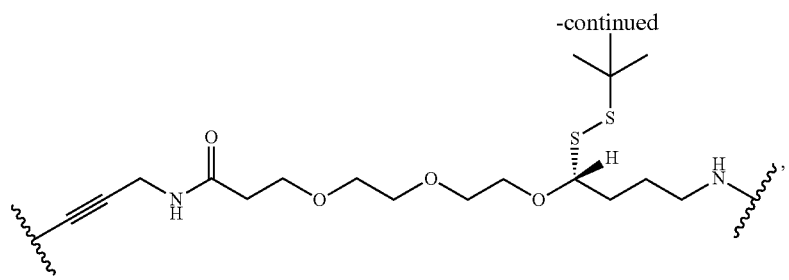
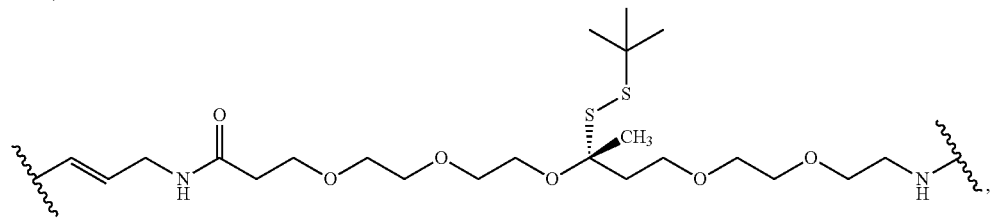
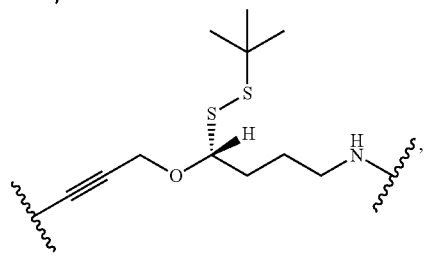
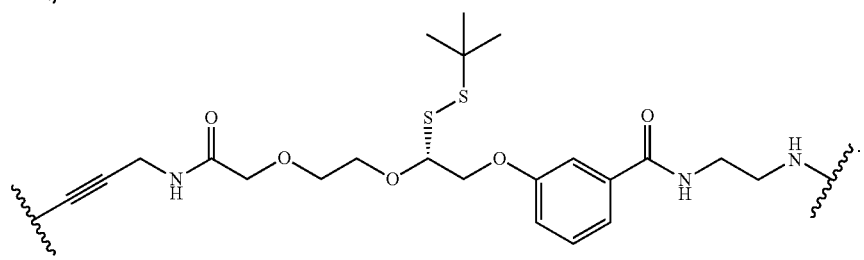
In embodiments, -(L$^{101}$)-OC(SSR$^{102}$)(R$^{102a}$)-(L$^{103}$)-(L$^{104}$)-(L$^{105}$)- is
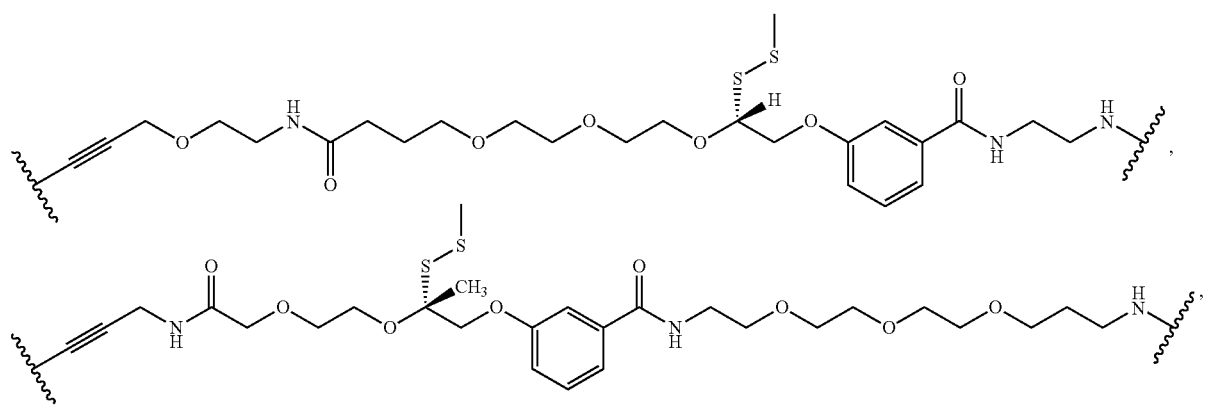

-continued
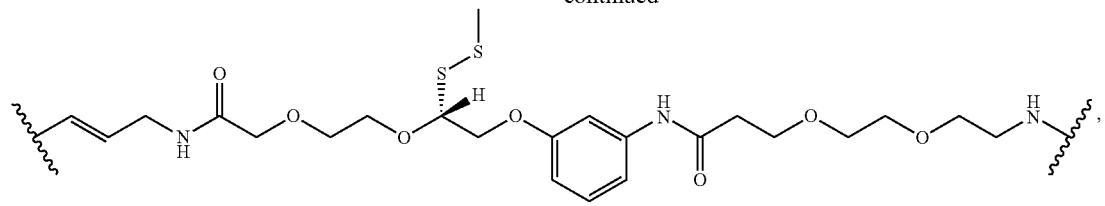
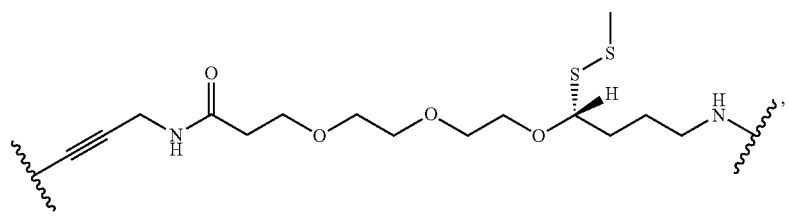
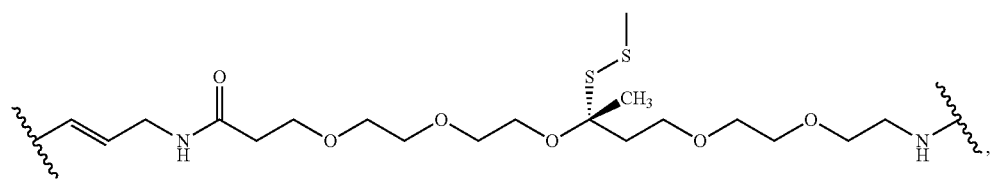
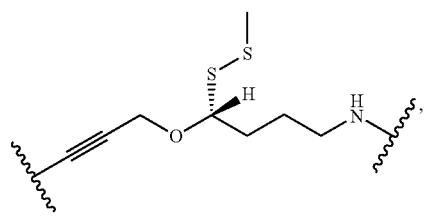
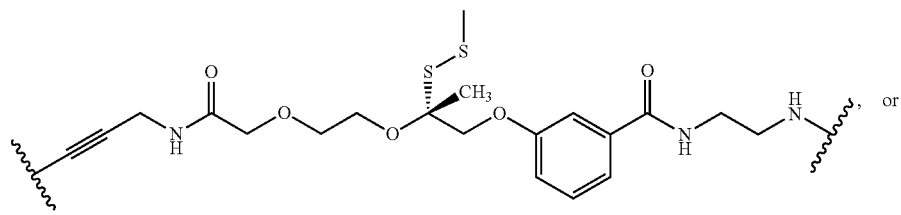
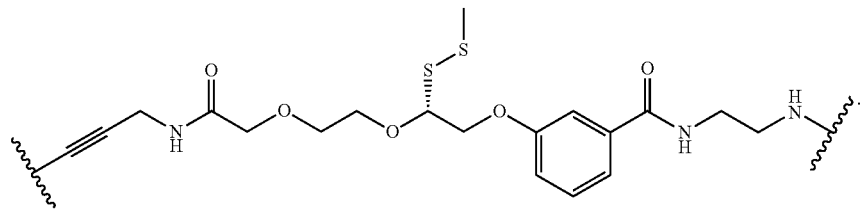
In embodiments, -(L$^{101}$)-OC(SSR$^{102}$)(R$^{102a}$)-(L$^{103}$)-(L$^{104}$)-(L$^{105}$)- is
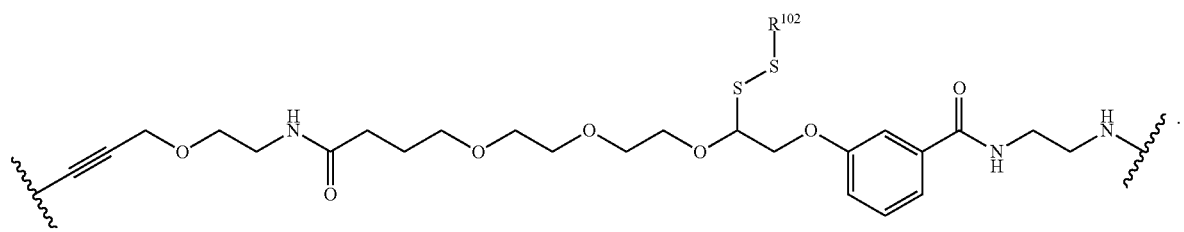

In embodiments, -(L$^{101}$)-OC(SSR$^{102}$)(R$^{102a}$)-(L$^{103}$)-(L$^{104}$)-(L$^{105}$)- is
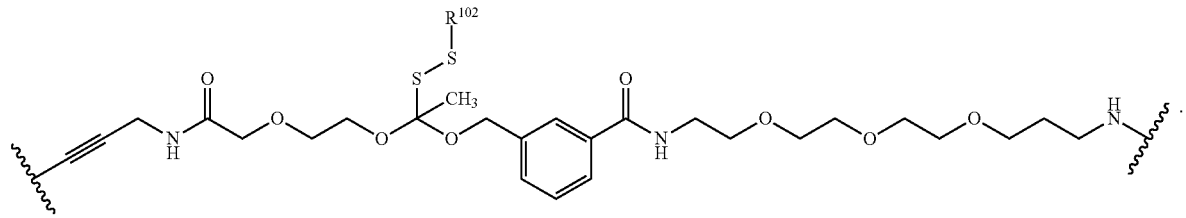
In embodiments, -(L$^{101}$)-OC(SSR$^{102}$)(R$^{102a}$)-(L$^{103}$)-(L$^{104}$)-(L$^{105}$)- is
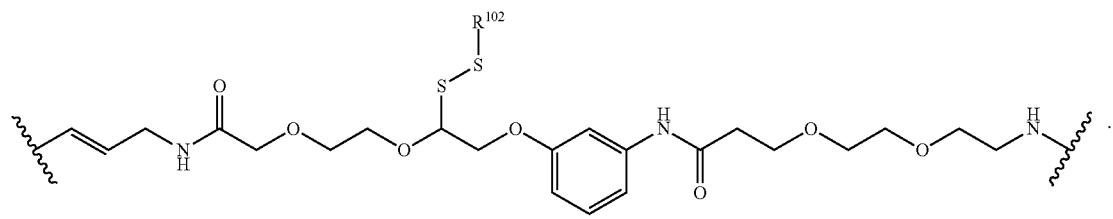
In embodiments, -(L$^{101}$)-OC(SSR$^{102}$)(R$^{102a}$)-(L$^{103}$)-(L$^{104}$)-(L$^{105}$)- is
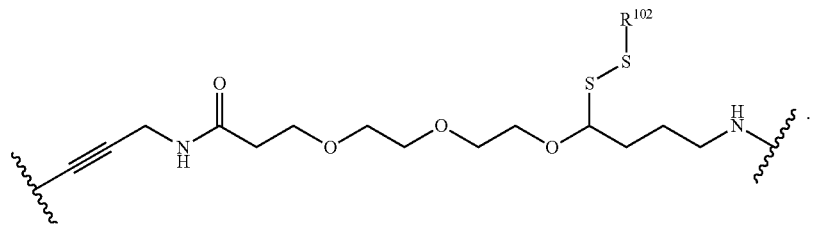
In embodiments, -(L$^{101}$)-OC(SSR$^{102}$)(R$^{102a}$)-(L$^{103}$)-(L$^{104}$)-(L$^{105}$)- is
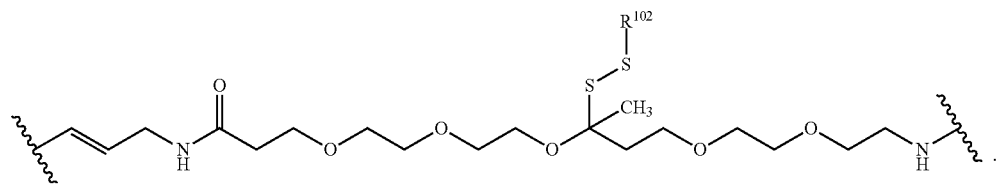
In embodiments, -(L$^{101}$)—OC(SSR$^{102}$)(R$^{102a}$)-(L$^{103}$)-(L$^{104}$)-(L$^{105}$)- is
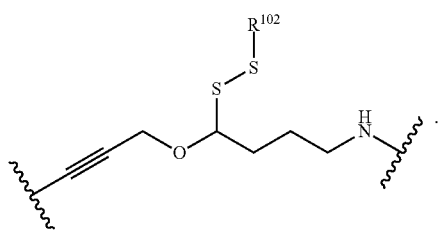

In embodiments, -(L$^{101}$)-OC(SSR$^{102}$)(R$^{102a}$)-(L$^{103}$)-(L$^{104}$)-(L$^{105}$)- is
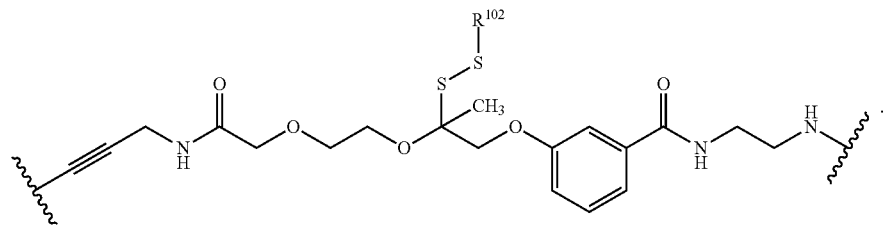
In embodiments, -(L$^{101}$)-OC(SSR$^{102}$)(R$^{102a}$)-(L$^{103}$)-(L$^{104}$)-(L$^{105}$)- is
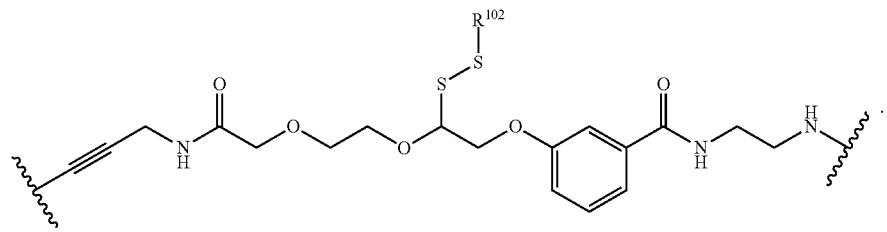
In embodiments, -(L$^{101}$)-OC(SSR$^{102}$)(R$^{102a}$)-(L$^{103}$)-(L$^{104}$)-(L$^{105}$)- is
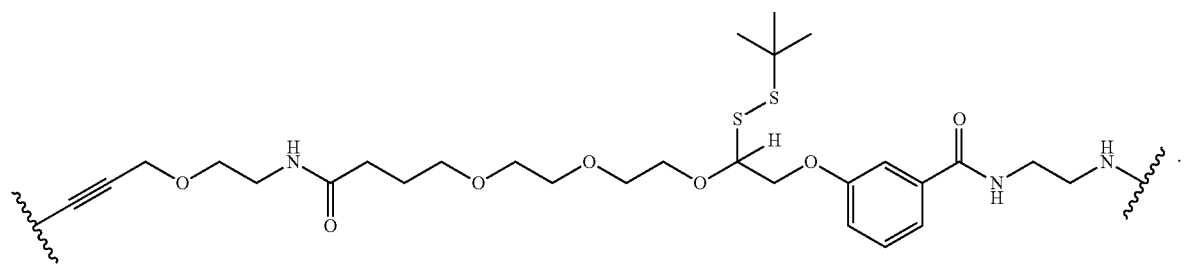 [SMILES: *C#CCOCCNC(=O)CCCOCCOCCOC(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
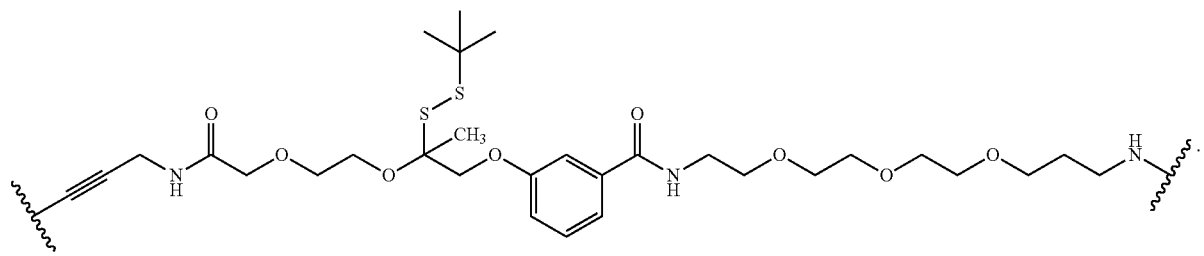 [SMILES: *C#CCNC(=O)COCCOC(C)(COc1cccc(C(=O)NCCOCCOCCOCCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
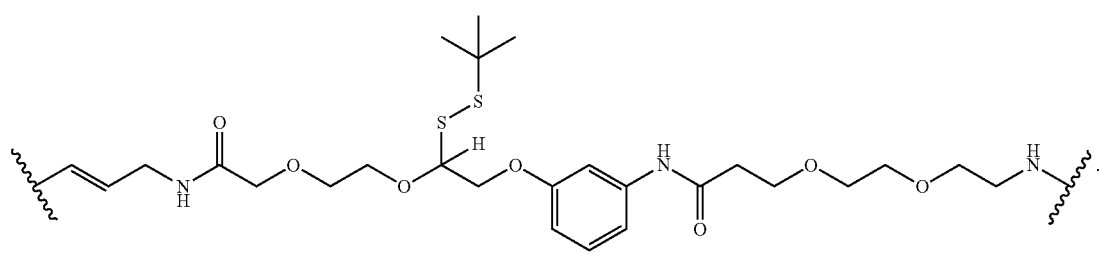 [SMILES: */C=C/CNC(=O)COCCOC(COc1cccc(NC(=O)CCOCCOCCN*)c1)SSC(C)(C)C]

In embodiments, -(L$^{101}$)-OC(SSR$^{102}$)(R$^{102a}$)-(L$^{103}$)-(L$^{104}$)-(L$^{105}$)- is
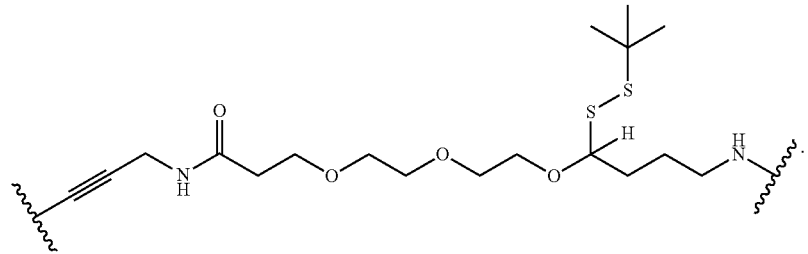 [SMILES: *C#CCNC(=O)CCOCCOCCOC(CCCN*)SSC(C)(C)C]
In embodiments, -(L$^{101}$)—OC(SSR$^{102}$)(R$^{102a}$)-(L$^{103}$)-(L$^{104}$)-(L$^{105}$)- is
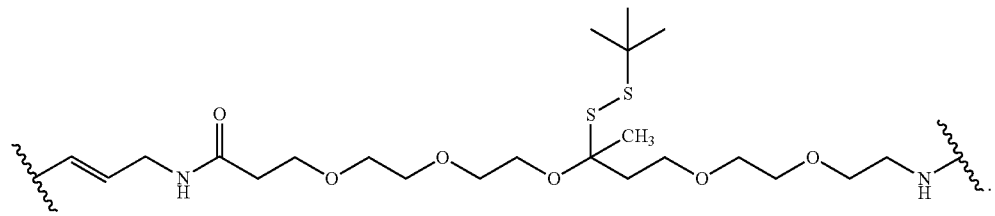 [SMILES: */C=C/CNC(=O)CCOCCOCCOC(C)(CCOCCOCCN*)SSC(C)(C)C]
In embodiments, -(L$^{101}$)-OC(SSR$^{102}$)(R$^{102a}$)-(L$^{103}$)-(L$^{104}$)-(L$^{105}$)- is
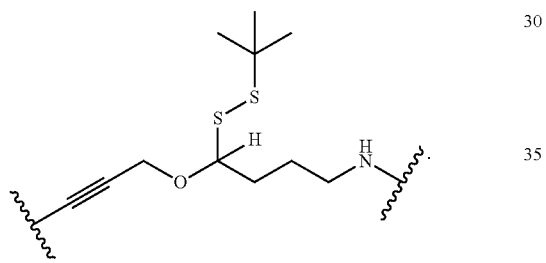
In embodiments, -(L$^{101}$)-OC(SSR$^{102}$)(R$^{102a}$)-(L$^{103}$)-(L$^{104}$)-(L$^{105}$)- is
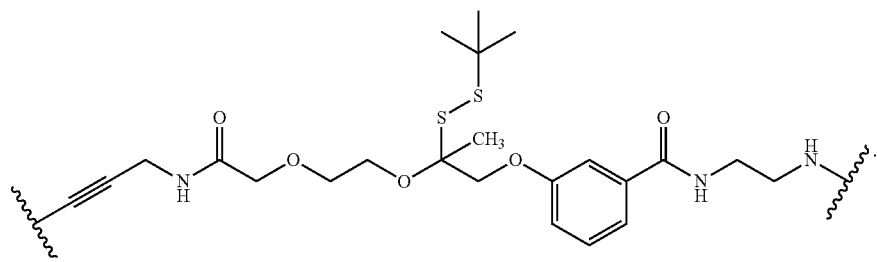 [SMILES: *C#CCNC(=O)COCCOC(C)(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
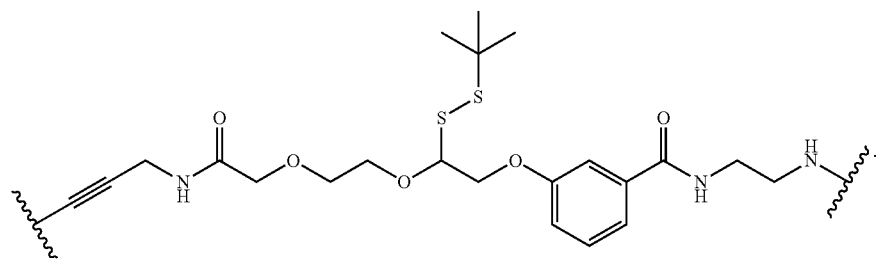 [SMILES: *C#CCNC(=O)COCCOC(COc1cccc(C(=O)NCCN*)c1)SSC(C)(C)C]

In embodiments, -(L$^{101}$)-OC(SSR$^{102}$)(R$^{102a}$)-(L$^{103}$)-(L$^{104}$)-(L$^{105}$)- is
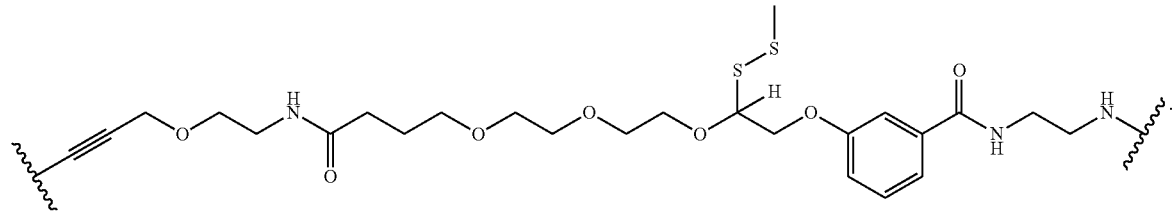 [SMILES: *C#CCOCCNC(=O)CCCOCCOCCOC(COc1cccc(C(=O)NCCN*)c1)SSC]
In embodiments, -(L$^{101}$)-OC(SSR$^{102}$)(R$^{102a}$)-(L$^{103}$)-(L$^{104}$)-(L$^{105}$)- is
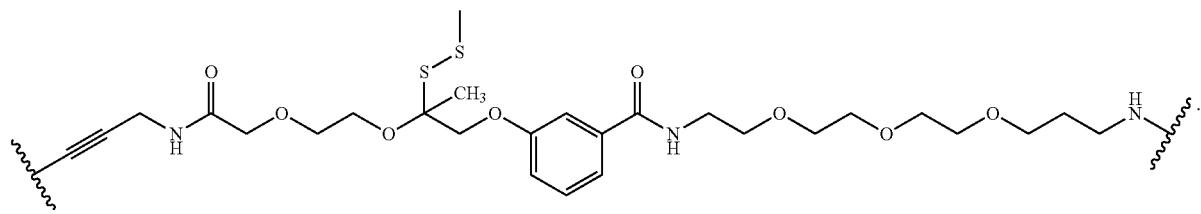 [SMILES: *C#CCNC(=O)COCCOC(C)(COc1cccc(C(=O)NCCOCCOCCOCCCN*)c1)SSC]
In embodiments, -(L$^{101}$)-OC(SSR$^{102}$)(R$^{102a}$)-(L$^{103}$)-(L$^{104}$)-(L$^{105}$)- is
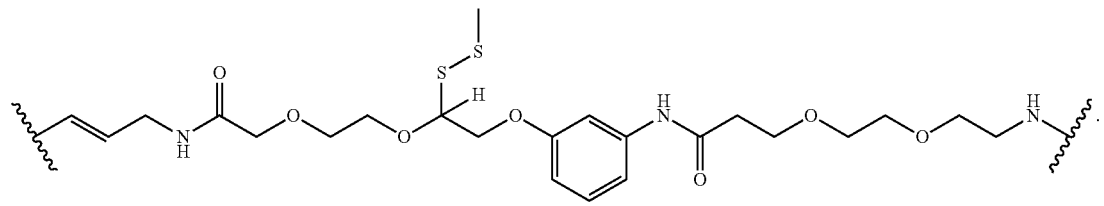 [SMILES: */C=C/CNC(=O)COCCOC(COc1cccc(NC(=O)CCOCCOCCN*)c1)SSC]
In embodiments, -(L$^{101}$)-OC(SSR$^{102}$)(R$^{102a}$)-(L$^{103}$)-(L$^{104}$)-(L$^{105}$)- is
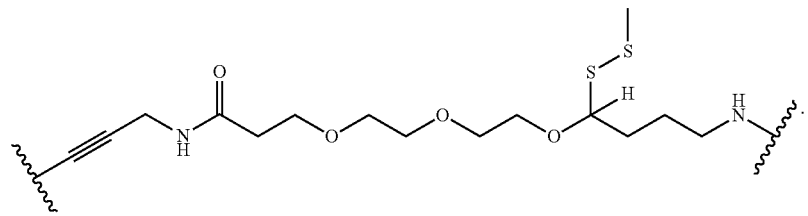 [SMILES: *C#CCNC(=O)CCOCCOCCOC(CCCN*)SSC]
In embodiments, -(L$^{101}$)-OC(SSR$^{102}$)(R$^{102a}$)-(L$^{103}$)-(L$^{104}$)-(L$^{105}$)- is
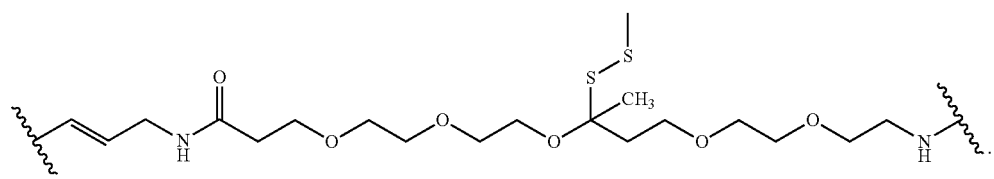 [SMILES: */C=C/CNC(=O)CCOCCOCCOC(C)(CCOCCOCCN*)SSC]

In embodiments, -(L^{101})-OC(SSR^{102})(R^{102a})-(L^{103})-(L^{104})-(L^{105})- is
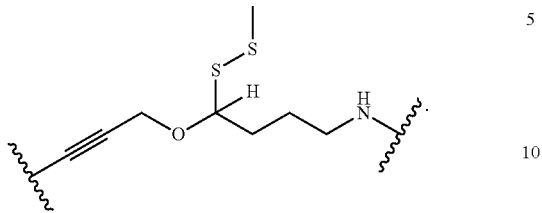
In embodiments, -(L^{101})-OC(SSR^{102})(R^{102a})-(L^{103})-(L^{104})-(L^{105})- is
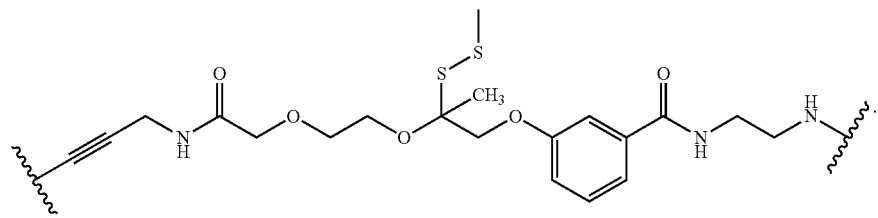 [SMILES: *C#CCNC(=O)COCCOC(C)(COc1cccc(C(=O)NCCN*)c1)SSC]
In embodiments, -(L^{101})-OC(SSR^{102})(R^{102a})-(L^{103})-(L^{104})-(L^{105})- is
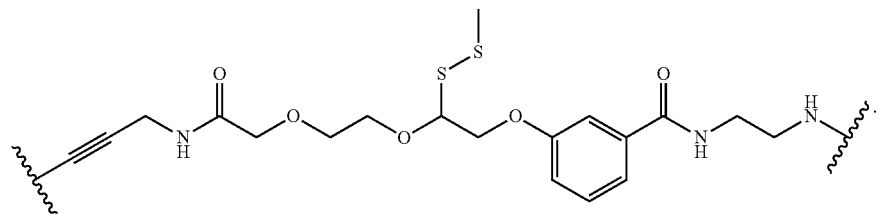 [SMILES: *C#CCNC(=O)COCCOC(COc1cccc(C(=O)NCCN*)c1)SSC]
In embodiments, -(L^{101})-OC(SSR^{102})(R^{102a})-(L^{103})-(L^{104})-(L^{105})- is
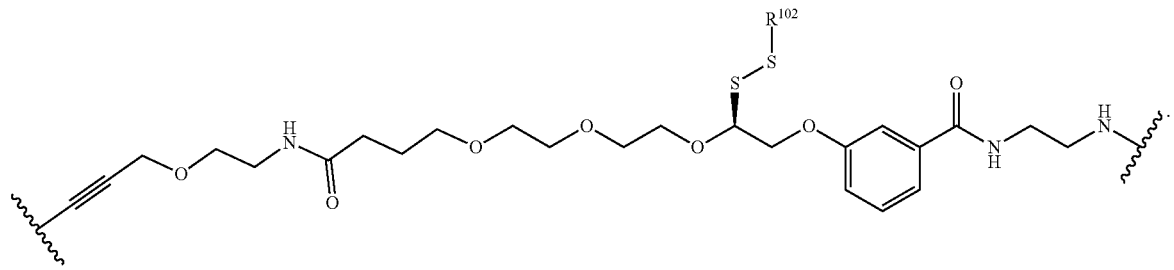
In embodiments, -(L^{101})-OC(SSR^{102})(R^{102a})-(L^{103})-(L^{104})-(L^{105})- is
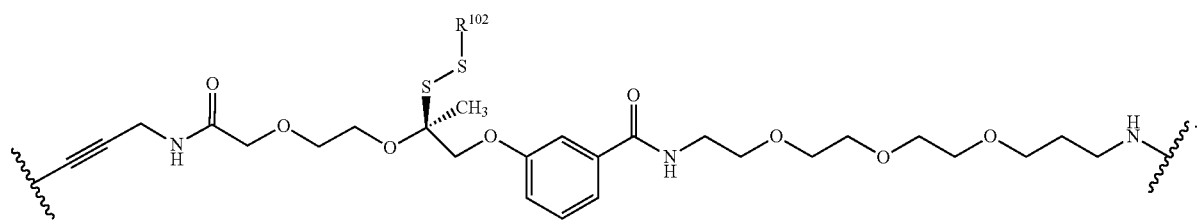

In embodiments, -(L$^{101}$)-OC(SSR$^{102}$)(R$^{102a}$)-(L$^{103}$)-(L$^{104}$)-(L$^{105}$)- is
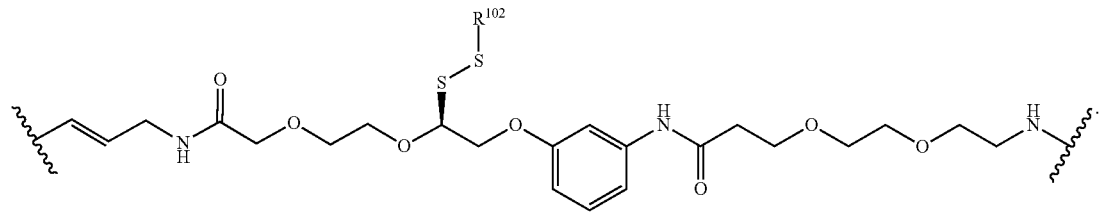
In embodiments, -(L$^{101}$)-OC(SSR$^{102}$)(R$^{102a}$)-(L$^{103}$)-(L$^{104}$)-(L$^{105}$)- is
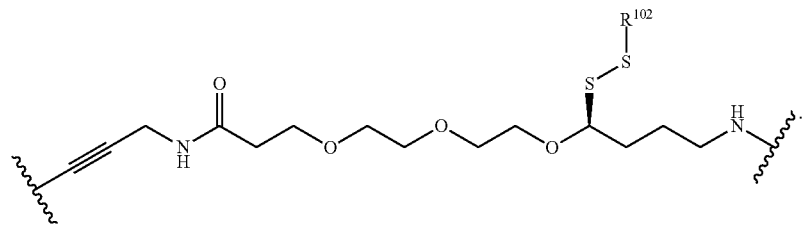
In embodiments, -(L$^{101}$)-OC(SSR$^{102}$)(R$^{102a}$)-(L$^{103}$)-(L$^{104}$)-(L$^{105}$)- is
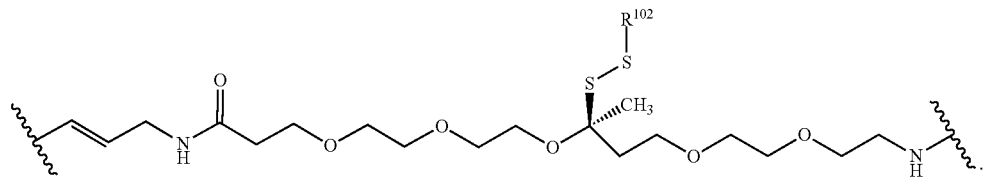
In embodiments, -(L$^{101}$)-OC(SSR$^{102}$)(R$^{102a}$)-(L$^{103}$)-(L$^{104}$)-(L$^{105}$)- is
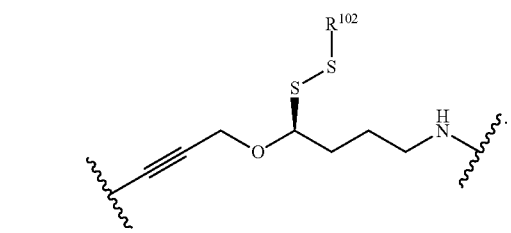
In embodiments, -(L$^{101}$)-OC(SSR$^{102}$)(R$^{102a}$)-(L$^{103}$)-(L$^{104}$)-(L$^{105}$)- is
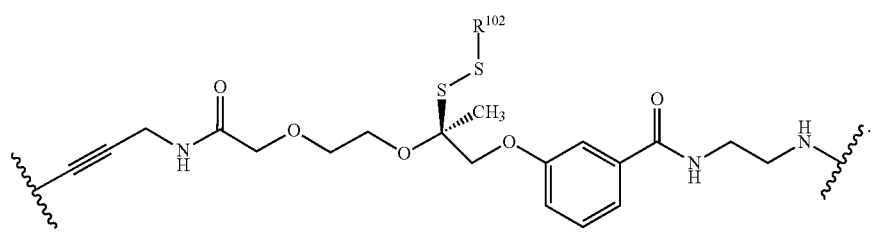

In embodiments, -(L$^{101}$)-OC(SSR$^{102}$)(R$^{102a}$)-(L$^{103}$)-(L$^{104}$)-(L$^{105}$)- is
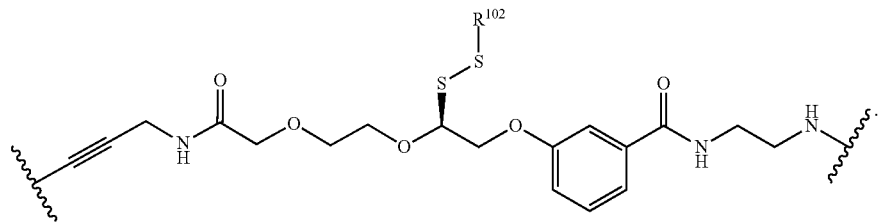
In embodiments, -(L$^{101}$)-OC(SSR$^{102}$)(R$^{102a}$)-(L$^{103}$)-(L$^{104}$)-(L$^{105}$)- is
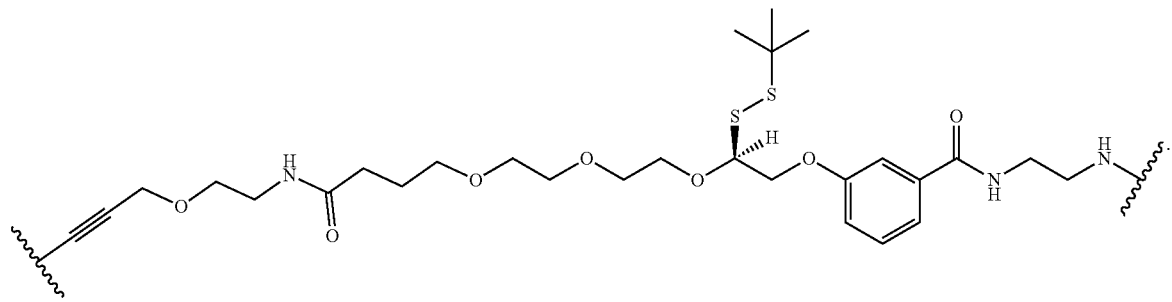 [SMILES: *C#CCOCCNC(=O)CCCOCCOCCO[C@H](COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
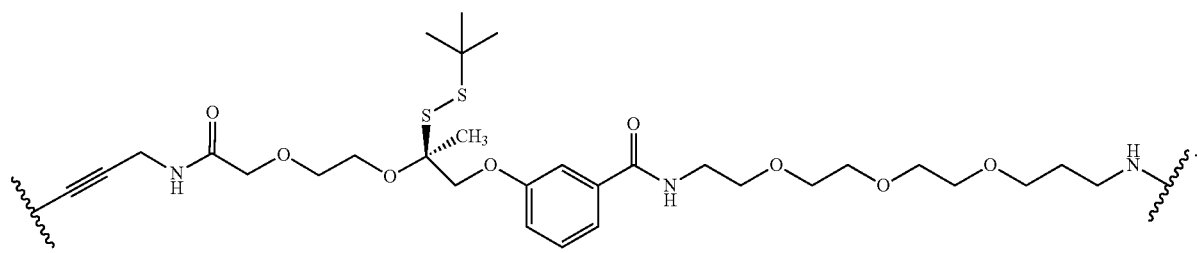 [SMILES: *C#CCNC(=O)COCCO[C@](C)(COc1cccc(C(=O)NCCOCCOCCOCCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
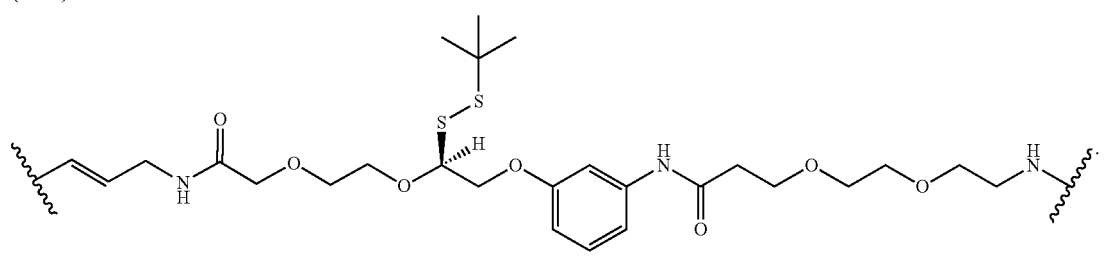
In embodiments, -(L$^{101}$)-OC(SSR$^{102}$)(R$^{102a}$)-(L$^{103}$)-(L$^{104}$)-(L$^{105}$)- is
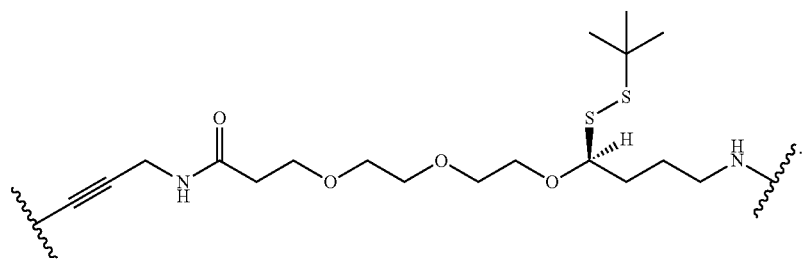 [SMILES: *C#CCNC(=O)CCOCCOCCO[C@H](CCCN*)SSC(C)(C)C]

In embodiments, -(L$^{101}$)-OC(SSR$^{102}$)(R$^{102a}$)-(L$^{103}$)-(L$^{104}$)-(L$^{105}$)- is
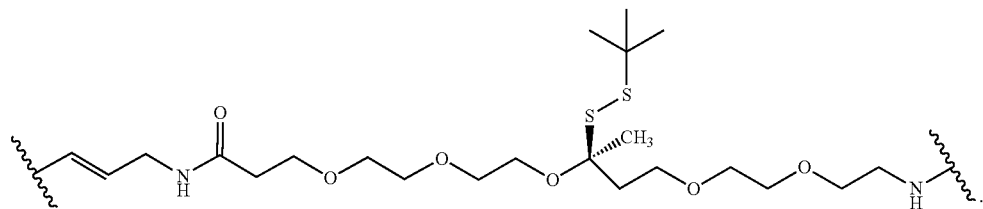 [SMILES: */C=C/CNC(=O)CCOCCOCCO[C@](C)(CCOCCOCCN*)SSC(C)(C)C]
In embodiments, -(L$^{101}$)-OC(SSR$^{102}$)(R$^{102a}$)-(L$^{103}$)-(L$^{104}$)-(L$^{105}$)- is
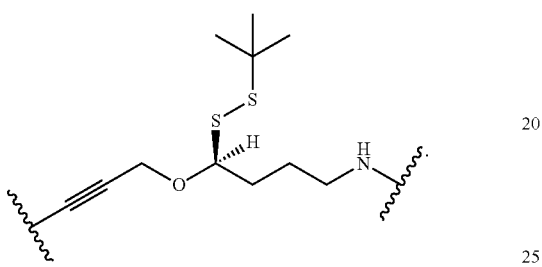
In embodiments, -(L$^{101}$)-OC(SSR$^{102}$)(R$^{102a}$)-(L$^{103}$)-(L$^{104}$)-(L$^{105}$)- is
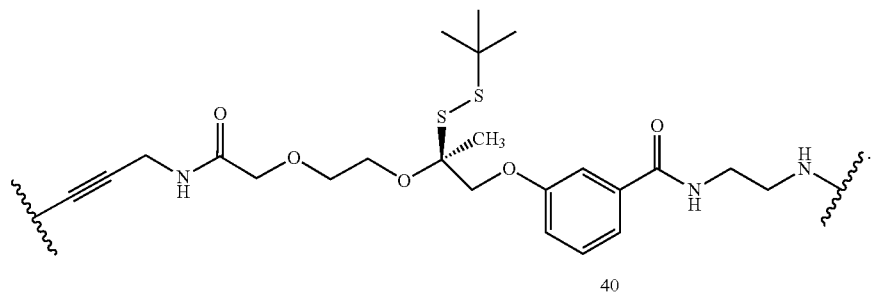
In embodiments, -(L$^{101}$)-OC(SSR$^{102}$)(R$^{102a}$)-(L$^{103}$)-(L$^{104}$)-(L$^{105}$)- is
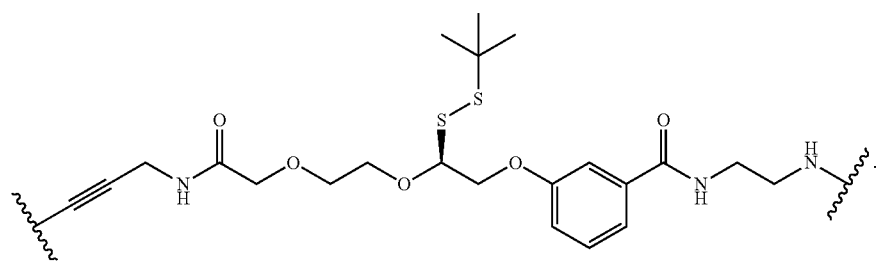
In embodiments, -(L$^{101}$)-OC(SSR$^{102}$)(R$^{102a}$)-(L$^{103}$)-(L$^{104}$)-(L$^{105}$)- is
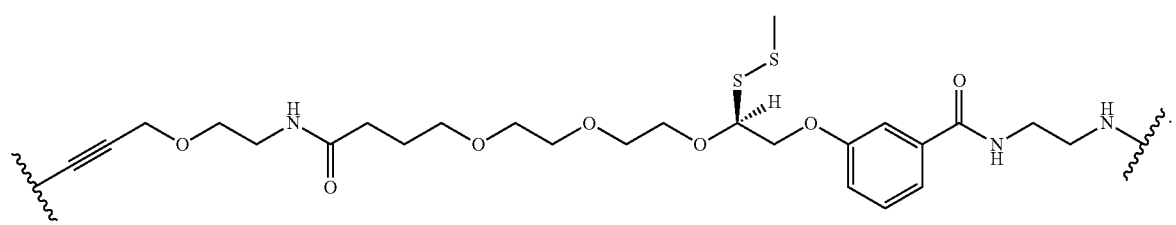 [SMILES: *C#CCOCCNC(=O)CCCOCCOCCO[C@H](COc1cccc(C(=O)NCCN*)c1)SSC]

In embodiments, -(L$^{101}$)-OC(SSR$^{102}$)(R$^{102a}$)-(L$^{103}$)-(L$^{104}$)-(L$^{105}$)- is
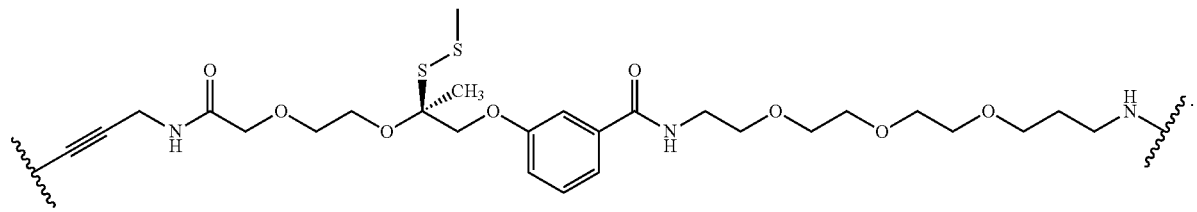
In embodiments, -(L$^{101}$)-OC(SSR$^{102}$)(R$^{102a}$)-(L$^{103}$)-(L$^{104}$)-(L$^{105}$)- is
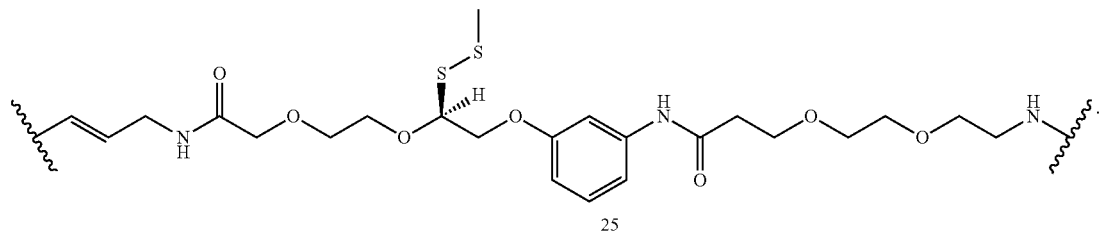
In embodiments, -(L$^{101}$)-OC(SSR$^{102}$)(R$^{102a}$)-(L$^{103}$)-(L$^{104}$)-(L$^{105}$)- is
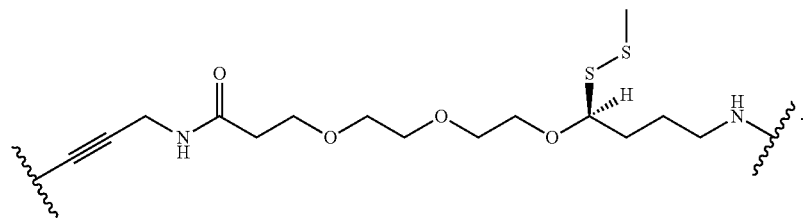 [SMILES: *C#CCNC(=O)CCOCCOCCO[C@H](CCCN*)SSC]
In embodiments, -(L$^{101}$)-OC(SSR$^{102}$)(R$^{102a}$)-(L$^{103}$)-(L$^{104}$)-(L$^{105}$)- is
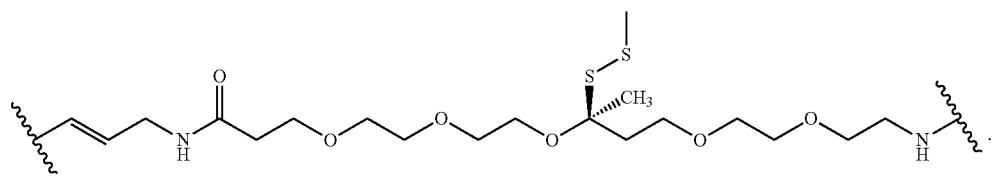 [SMILES: */C=C/CNC(=O)CCOCCOCCO[C@](C)(CCOCCOCCN*)SSC]
In embodiments, -(L$^{101}$)-OC(SSR$^{102}$)(R$^{102a}$)-(L$^{103}$)-(L$^{104}$)-(L$^{105}$)- is
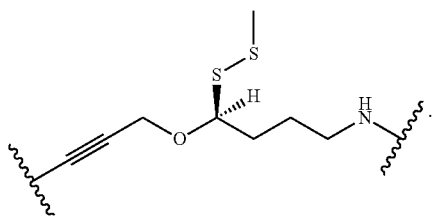 [SMILES: *C#CCO[C@H](CCCN*)SSC]
In embodiments, -(L$^{101}$)-OC(SSR$^{102}$)(R$^{102a}$)-(L$^{103}$)-(L$^{104}$)-(L$^{105}$)- is

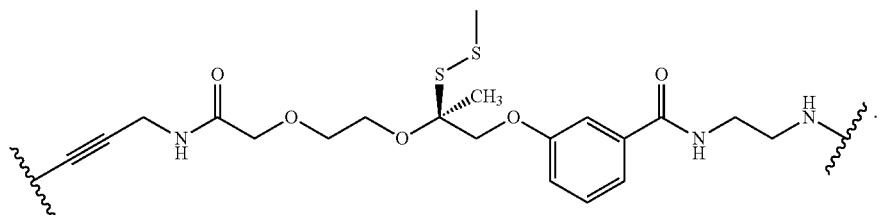 [SMILES: *C#CCNC(=O)COCCO[C@](C)(COc1cccc(C(=O)NCCN*)c1)SSC]
In embodiments, -(L$^{101}$)—OC(SSR$^{102}$)(R$^{102a}$)-(L$^{103}$)-(L$^{104}$)-(L$^{105}$)- is
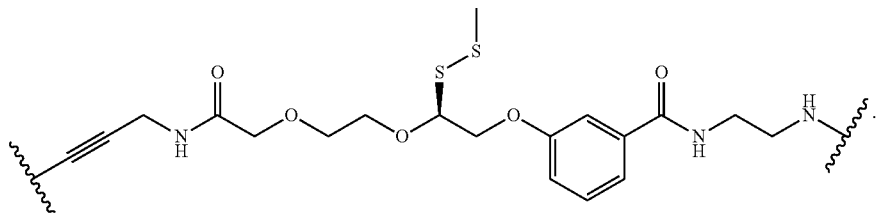 [SMILES: *C#CCNC(=O)COCCO[C@H](COc1cccc(C(=O)NCCN*)c1)SSC]
In embodiments, -(L$^{101}$)-OC(SSR$^{102}$)(R$^{102a}$)-(L$^{103}$)-(L$^{104}$)-(L$^{105}$)- is
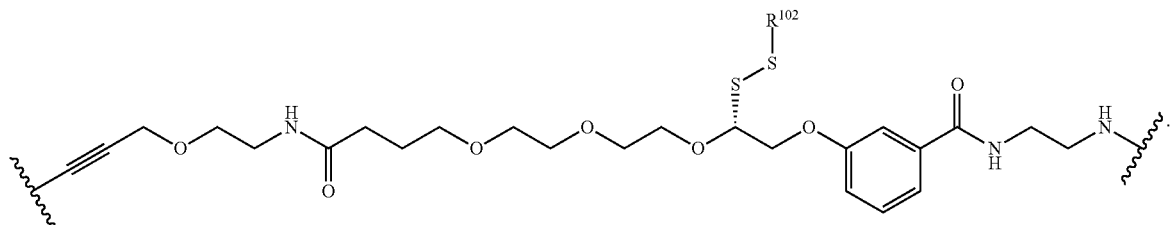
In embodiments, -(L$^{101}$)-OC(SSR$^{102}$)(R$^{102a}$)-(L$^{103}$)-(L$^{104}$)-(L$^{105}$)- is
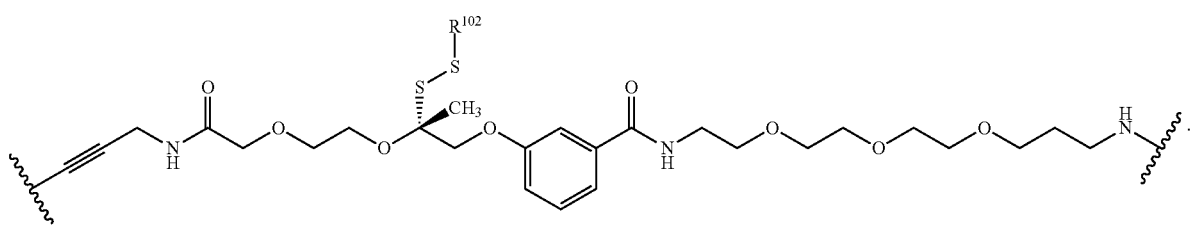
In embodiments, -(L$^{101}$)-OC(SSR$^{102}$)(R$^{102a}$)-(L$^{103}$)-(L$^{104}$)-(L$^{105}$)- is
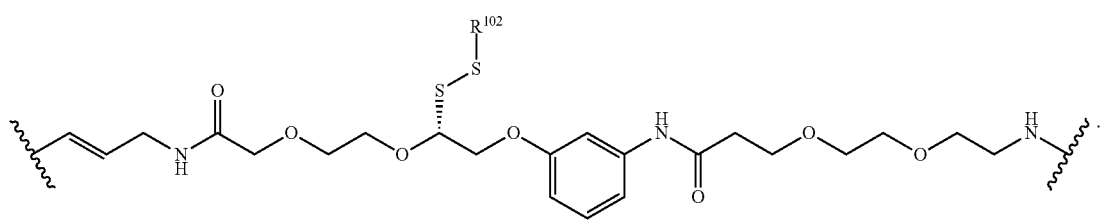

In embodiments, -(L$^{101}$)-OC(SSR$^{102}$)(R$^{102a}$)-(L$^{103}$)-(L$^{104}$)-(L$^{105}$)- is
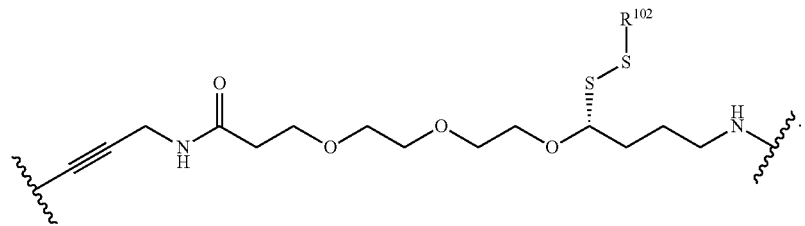
In embodiments, -(L$^{101}$)-OC(SSR$^{102}$)(R$^{102a}$)-(L$^{103}$)-(L$^{104}$)-(L$^{105}$)- is
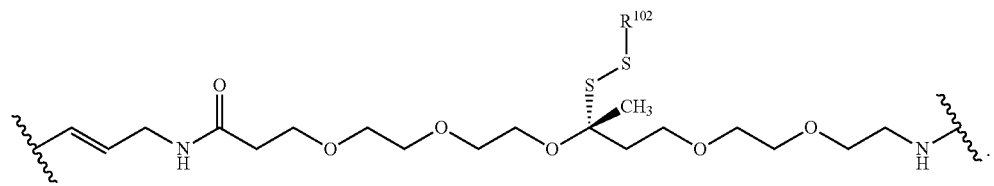
In embodiments, -(L$^{101}$)-OC(SSR$^{102}$)(R$^{102a}$)-(L$^{103}$)-(L$^{104}$)-(L$^{105}$)- is
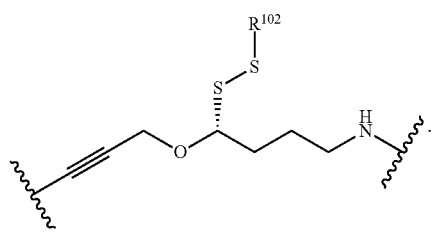
In embodiments, -(L$^{101}$)-OC(SSR$^{102}$)(R$^{102a}$)-(L$^{103}$)-(L$^{104}$)-(L$^{105}$)- is
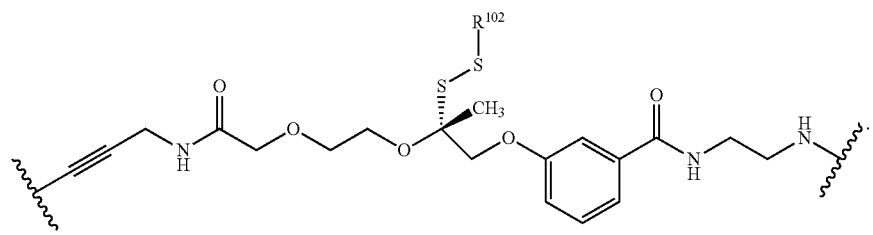
In embodiments, -(L$^{101}$)-OC(SSR$^{102}$)(R$^{102a}$)-(L$^{103}$)-(L$^{104}$)-(L$^{105}$)- is
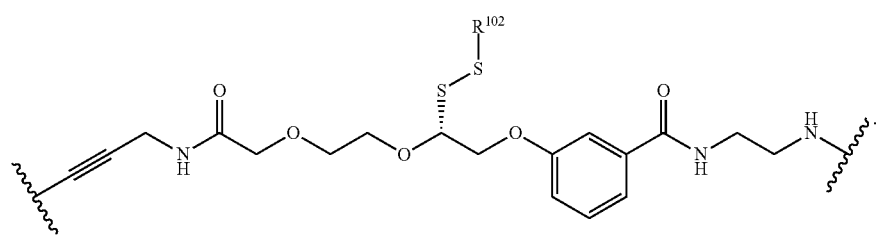

In embodiments, -(L$^{101}$)-OC(SSR$^{102}$)(R$^{102a}$)-(L$^{103}$)-(L$^{104}$)-(L$^{105}$)- is
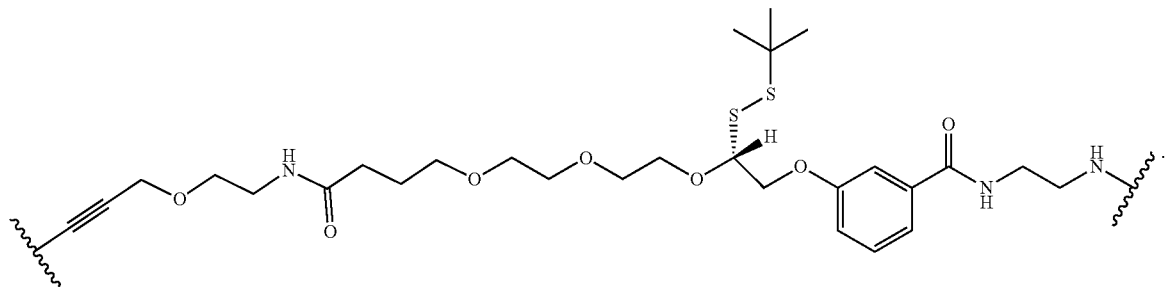 [SMILES: *C#CCOCCNC(=O)CCCOCCOCCO[C@@H](COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
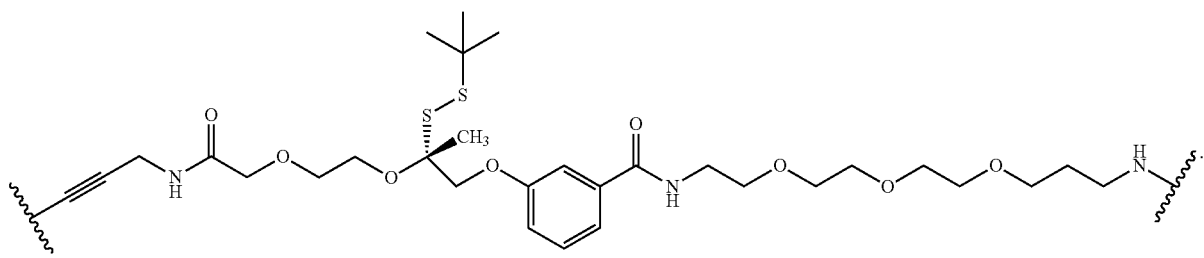 [SMILES: *C#CCNC(=O)COCCO[C@@](C)(COc1cccc(C(=O)NCCOCCOCCOCCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
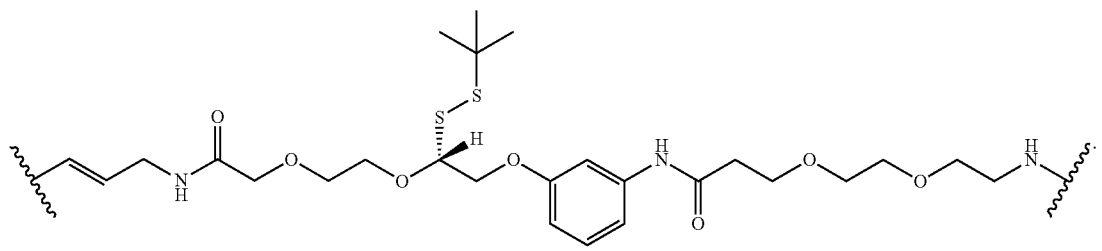 [SMILES: */C=C/CNC(=O)COCCO[C@@H](COc1cccc(NC(=O)CCOCCOCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
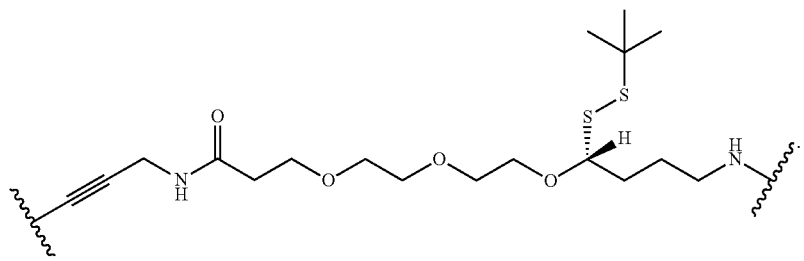 [SMILES: *C#CCNC(=O)CCOCCOCCO[C@@H](CCCN*)SSC(C)(C)C]
In embodiments, -(L$^{101}$)-OC(SSR$^{102}$)(R$^{102a}$)-(L$^{103}$)-(L$^{104}$)-(L$^{105}$)- is
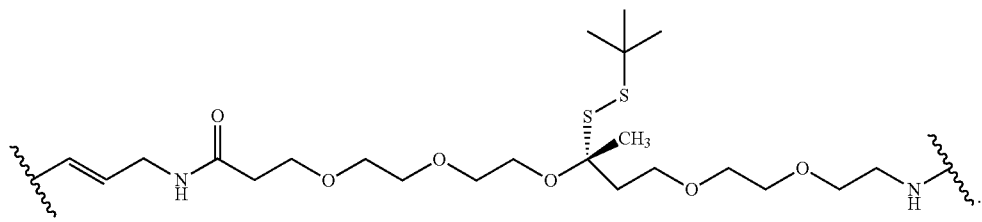 [SMILES: */C=C/CNC(=O)CCOCCOCCO[C@@](C)(CCOCCOCCN*)SSC(C)(C)C]

In embodiments, -(L$^{101}$)-OC(SSR$^{102}$)(R$^{102a}$)-(L$^{103}$)-(L$^{104}$)-(L$^{105}$)- is
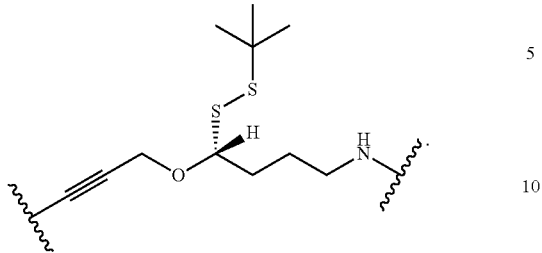
In embodiments, -(L$^{101}$)-OC(SSR$^{102}$)(R$^{102a}$)-(L$^{103}$)-(L$^{104}$)-(L$^{105}$)- is
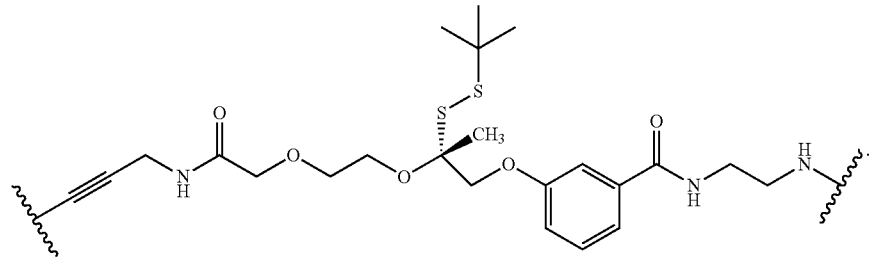 [SMILES: *C#CCNC(=O)COCCO[C@@](C)(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
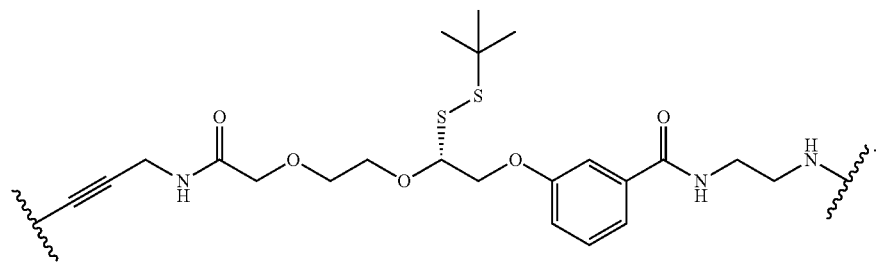 [SMILES: *C#CCNC(=O)COCCO[C@@H](COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
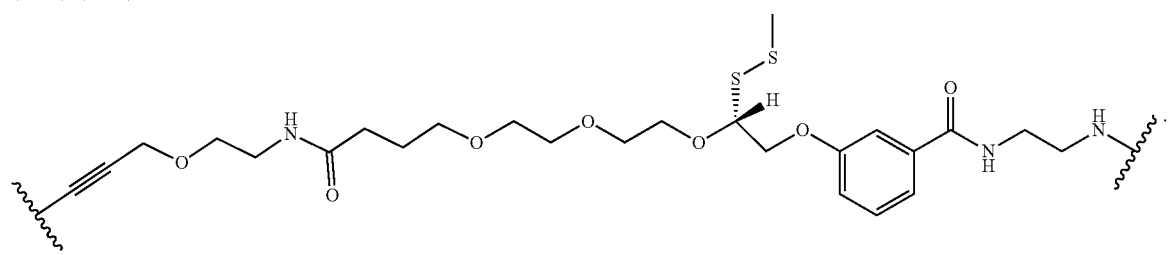 [SMILES: *C#CCOCCNC(=O)CCCOCCOCCO[C@@H](COc1cccc(C(=O)NCCN*)c1)SSC]
In embodiments, -(L$^{101}$)-OC(SSR$^{102}$)(R$^{102a}$)-(L$^{103}$)-(L$^{104}$)-(L$^{105}$)- is
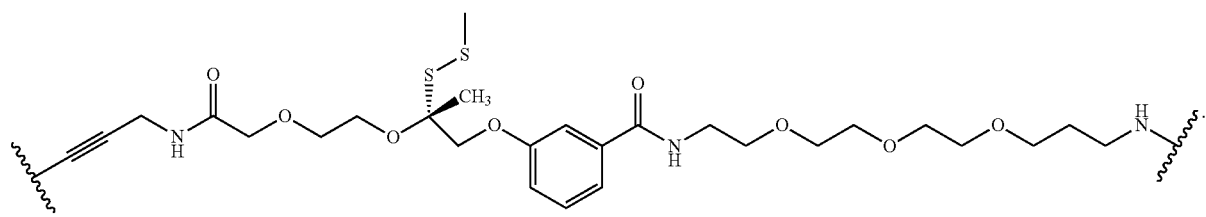 [SMILES: *C#CCNC(=O)COCCO[C@@](C)(COc1cccc(C(=O)NCCOCCOCCOCCCN*)c1)SSC]

In embodiments, -(L$^{101}$)-OC(SSR$^{102}$)(R$^{102a}$)-(L$^{103}$)-(L$^{104}$)-(L$^{105}$)- is
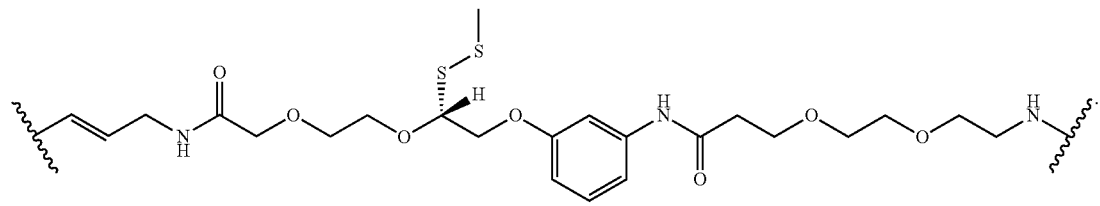 [SMILES: */C=C/CNC(=O)COCCO[C@@H](COc1cccc(NC(=O)CCOCCOCCN*)c1)SSC]
In embodiments, -(L$^{101}$)-OC(SSR$^{102}$)(R$^{102a}$)-(L$^{103}$)-(L$^{104}$)-(L$^{105}$)- is
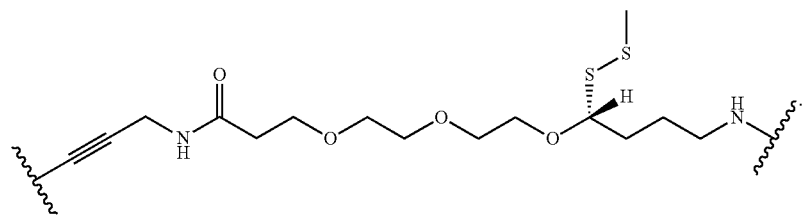 [SMILES: *C#CCNC(=O)CCOCCOCCO[C@@H](CCCN*)SSC]
In embodiments, -(L$^{101}$)-OC(SSR$^{102}$)(R$^{102a}$)-(L$^{103}$)-(L$^{104}$)-(L$^{105}$)- is
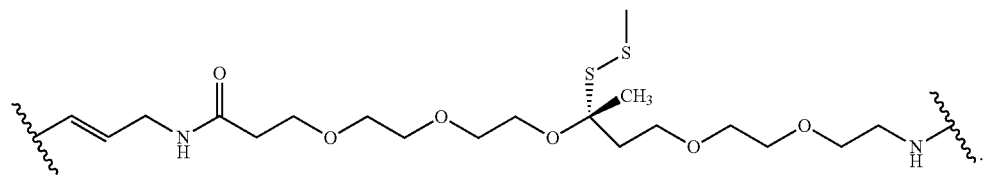 [SMILES: */C=C/CNC(=O)CCOCCOCCO[C@@](C)(CCOCCOCCN*)SSC]
In embodiments, -(L$^{101}$)-OC(SSR$^{102}$)(R$^{102a}$)-(L$^{103}$)-(L$^{104}$)-(L$^{105}$)- is
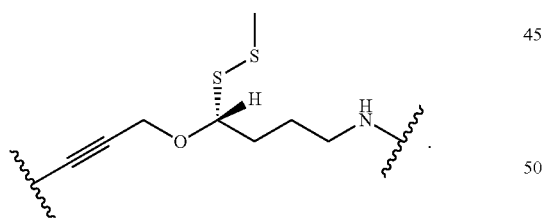
In embodiments, -(L$^{101}$)-OC(SSR$^{102}$)(R$^{102a}$)-(L$^{103}$)-(L$^{104}$)-(L$^{105}$)- is
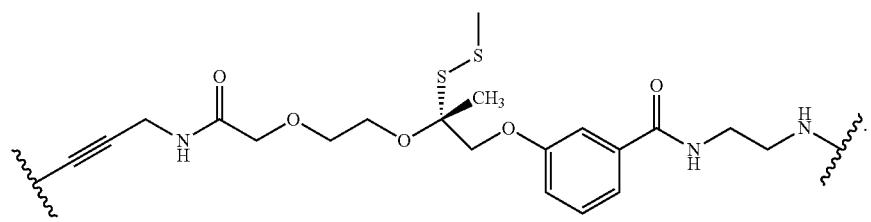 [SMILES: *C#CCNC(=O)COCCO[C@@](C)(COc1cccc(C(=O)NCCN*)c1)SSC]

In embodiments, -(L$^{101}$)-OC(SSR$^{102}$)(R$^{102a}$)-(L$^{103}$)-(L$^{104}$)-(L$^{105}$)- is
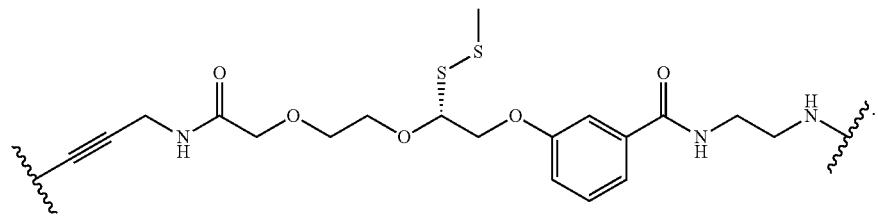
In embodiments, -(L$^{101}$)-OC(SSR$^{102}$)(R$^{102a}$)-(L$^{103}$)-(L$^{104}$)-(L$^{105}$)- is
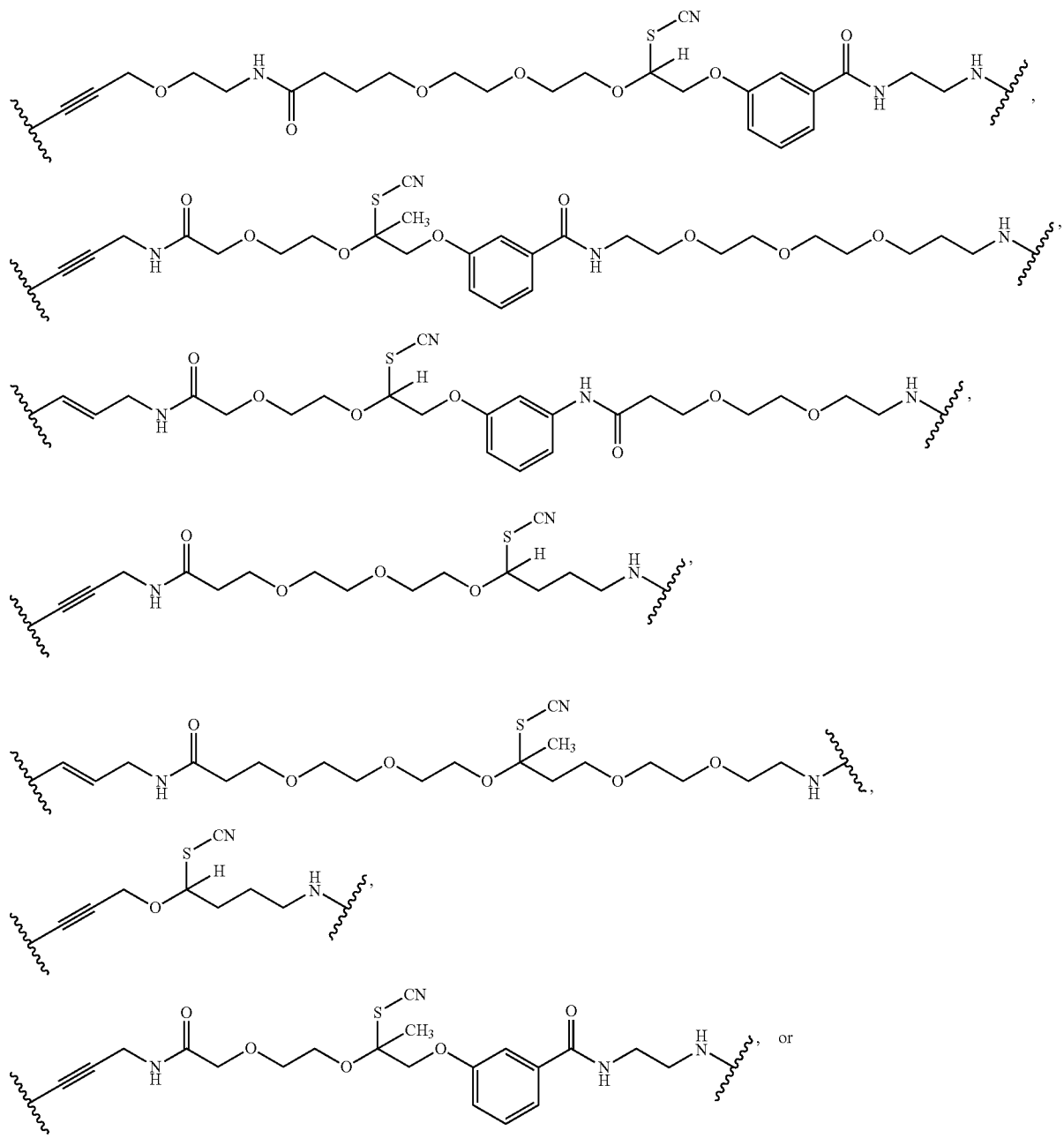

-continued
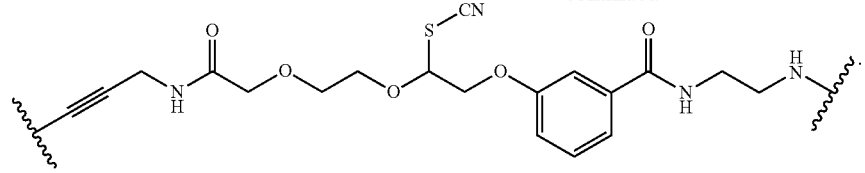
In embodiments, -(L$^{101}$)-OC(SSR$^{102}$)(R$^{102a}$)-(L$^{103}$)-(L$^{104}$)-(L$^{105}$)- is
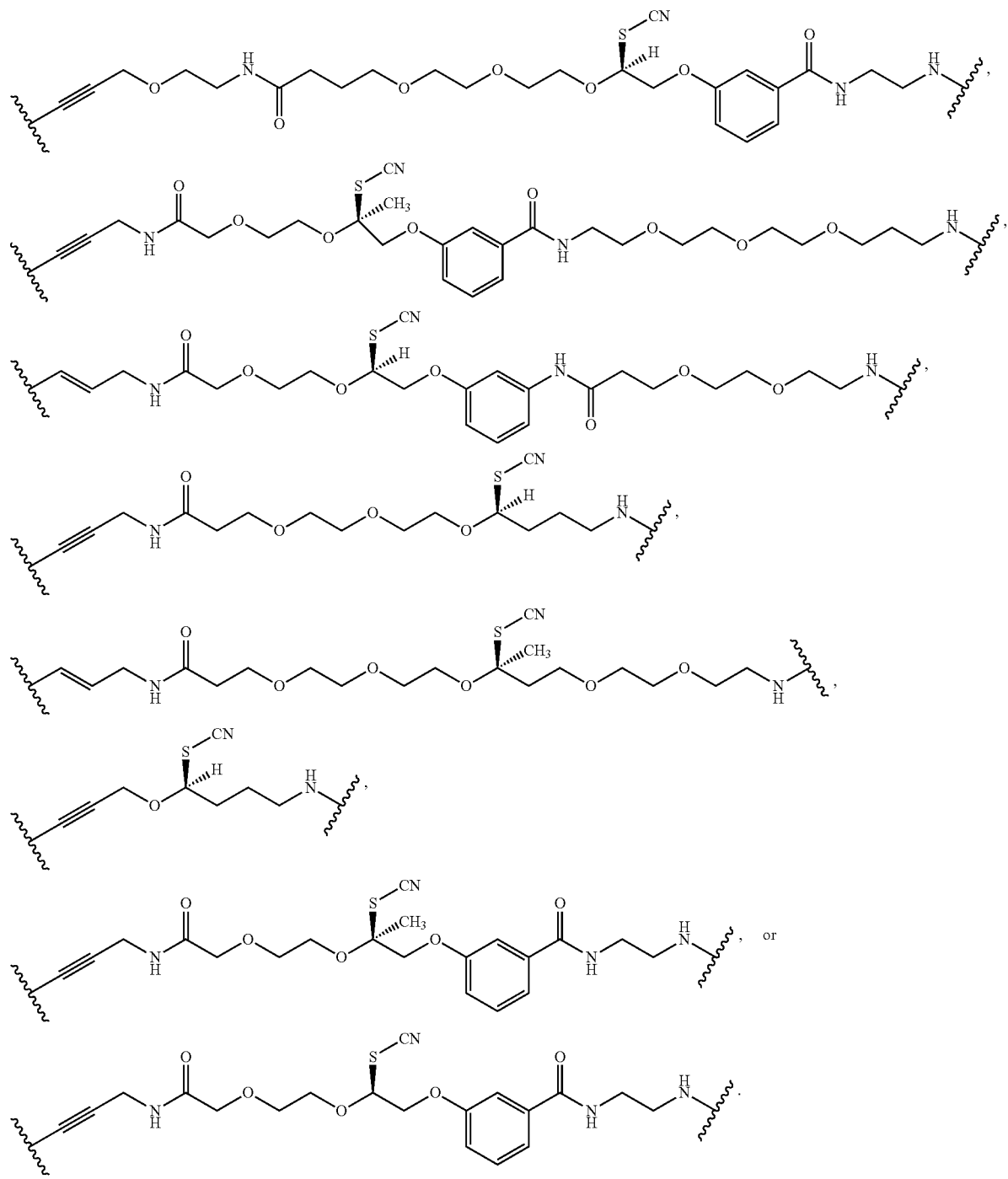

In embodiments, -(L$^{101}$)-OC(SSR$^{102}$)(R$^{102a}$)-(L$^{103}$)-(L$^{104}$)-(L$^{105}$)- is
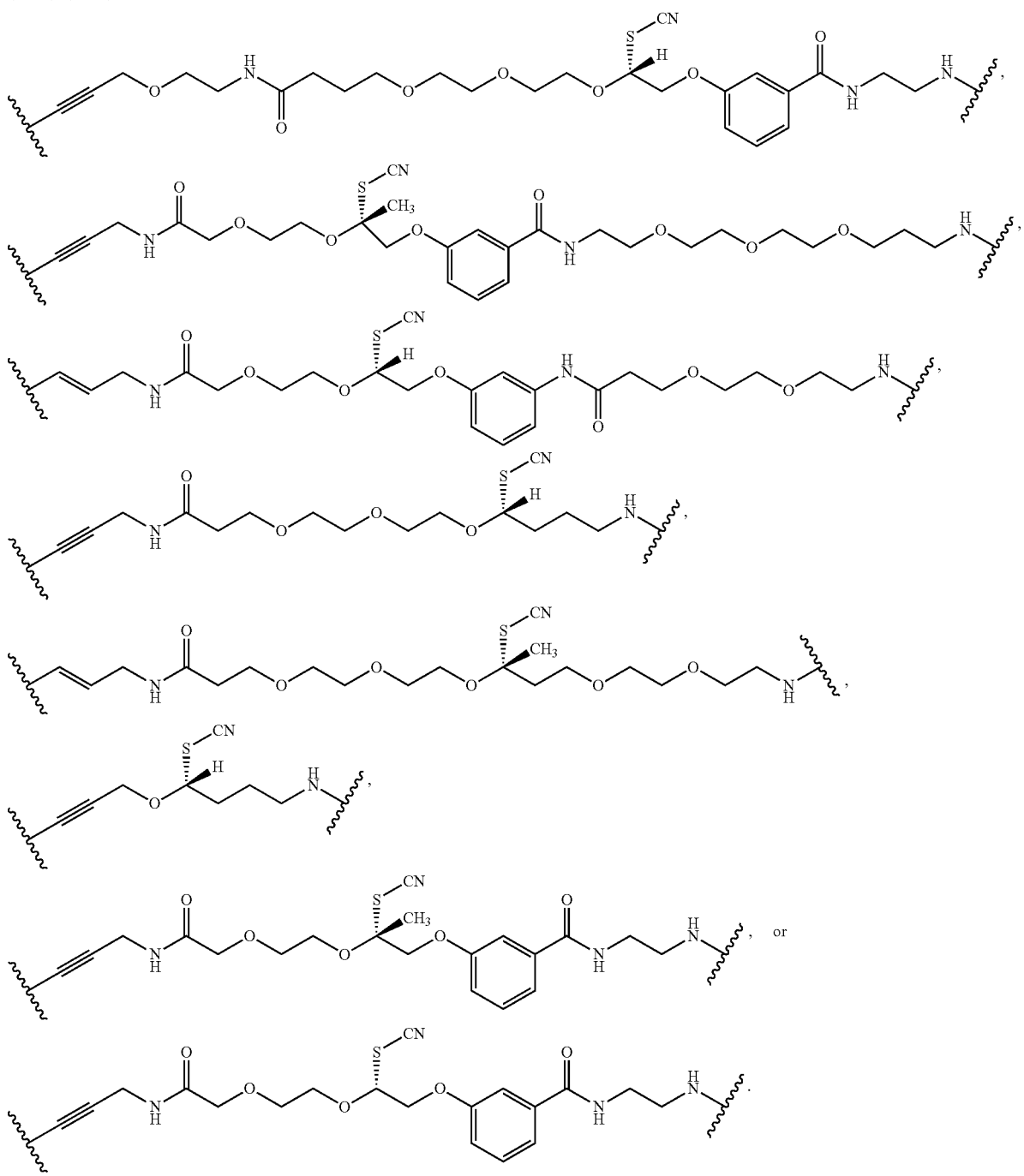
In embodiments, -(L$^{101}$)-OC(SSR$^{102}$)(R$^{102a}$)-(L$^{103}$)-(L$^{104}$)-(L$^{105}$)- is
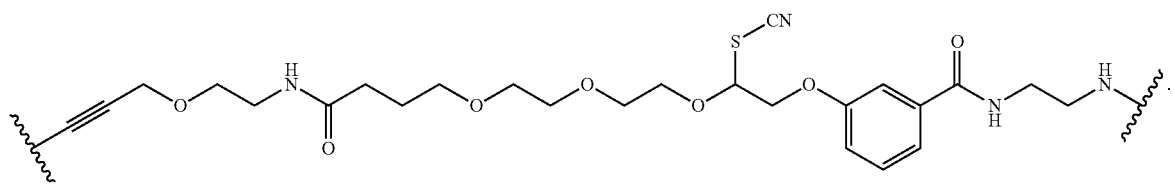 [SMILES: *C#CCOCCNC(=O)CCCOCCOCCOC(COc1cccc(C(=O)NCCN*)c1)SC#N]

In embodiments, -(L$^{101}$)-OC(SSR$^{102}$)(R$^{102a}$)-(L$^{103}$)-(L$^{104}$)-(L$^{105}$)- is
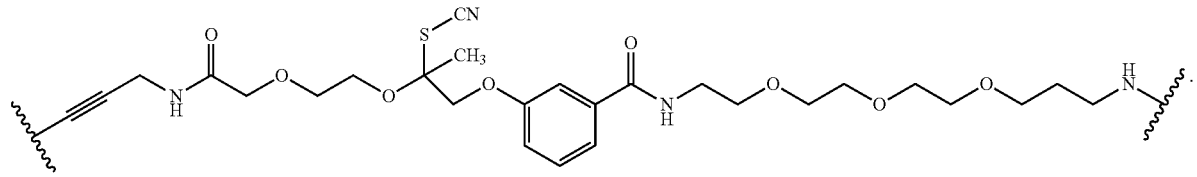 [SMILES: *C#CCNC(=O)COCCOC(C)(COc1cccc(C(=O)NCCOCCOCCOCCCN*)c1)SC#N]
In embodiments, -(L$^{101}$)-OC(SSR$^{102}$)(R$^{102a}$)-(L$^{103}$)-(L$^{104}$)-(L$^{105}$)- is
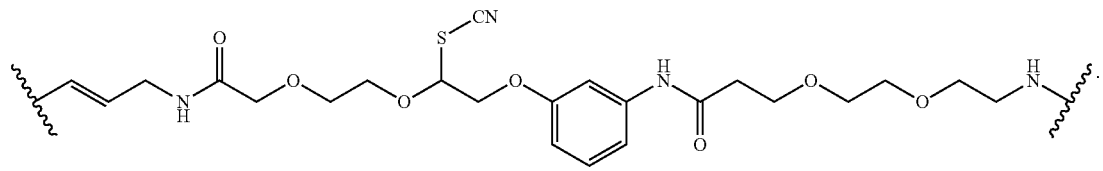 [SMILES: */C=C/CNC(=O)COCCOC(COc1cccc(NC(=O)CCOCCOCCN*)c1)SC#N]
In embodiments, -(L$^{101}$)-OC(SSR$^{102}$)(R$^{102a}$)-(L$^{103}$)-(L$^{104}$)-(L$^{105}$)- is
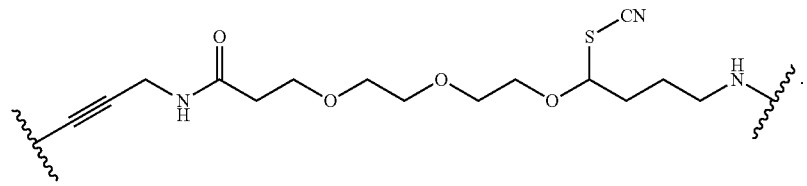 [SMILES: *C#CCNC(=O)CCOCCOCCOC(CCCN*)SC#N]
In embodiments, -(L$^{101}$)-OC(SSR$^{102}$)(R$^{102a}$)-(L$^{103}$)-(L$^{104}$)-(L$^{105}$)- is
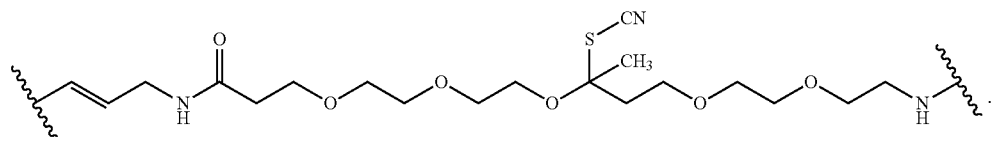 [SMILES: */C=C/CNC(=O)CCOCCOCCOC(C)(CCOCCOCCN*)SC#N]
In embodiments, -(L$^{101}$)-OC(SSR$^{102}$)(R$^{102a}$)-(L$^{103}$)-(L$^{104}$)-(L$^{105}$)- is
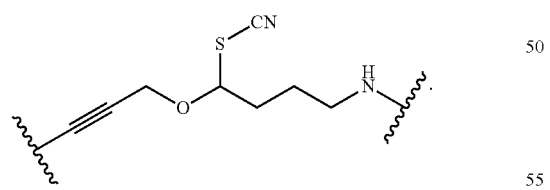
In embodiments, -(L$^{101}$)-OC(SSR$^{102}$)(R$^{102a}$)-(L$^{103}$)-(L$^{104}$)-(L$^{105}$)- is
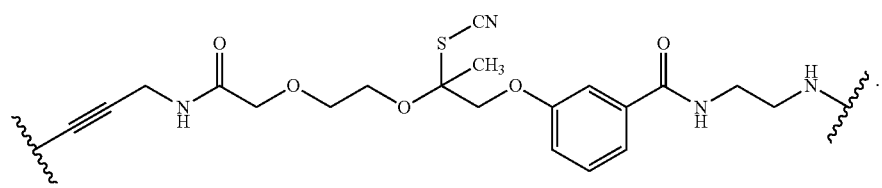 [SMILES: *C#CCNC(=O)COCCOC(C)(COc1cccc(C(=O)NCCN*)c1)SC#N]

In embodiments, -(L$^{101}$)-OC(SSR$^{102}$)(R$^{102a}$)-(L$^{103}$)-(L$^{104}$)-(L$^{105}$)- is
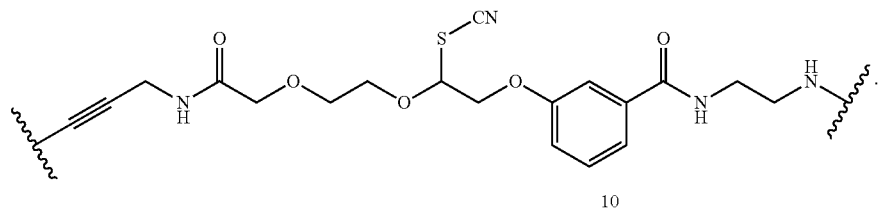
In embodiments, -(L$^{101}$)-OC(SSR$^{102}$)(R$^{102a}$)-(L$^{103}$)-(L$^{104}$)-(L$^{105}$)- is
In embodiments, -(L$^{101}$)-OC(SSR$^{102}$)(R$^{102a}$)-(L$^{103}$)-(L$^{104}$)-(L$^{105}$)- is
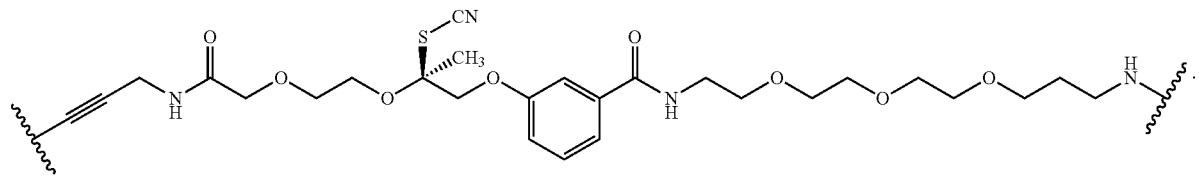 [SMILES: *C#CCNC(=O)COCCO[C@](C)(COc1cccc(C(=O)NCCOCCOCCOCCCN*)c1)SC#N]
In embodiments, -(L$^{101}$)-OC(SSR$^{102}$)(R$^{102a}$)-(L$^{103}$)-(L$^{104}$)-(L$^{105}$)- is
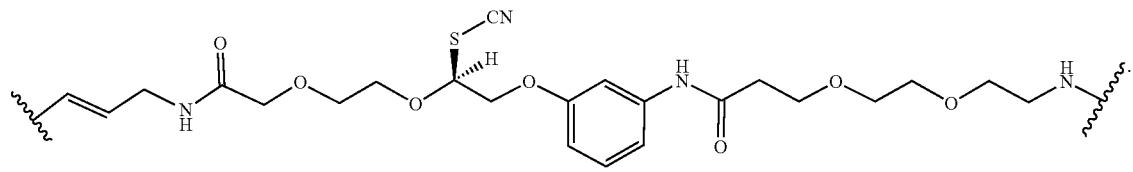 [SMILES: */C=C/CNC(=O)COCCO[C@H](COc1cccc(NC(=O)CCOCCOCCN*)c1)SC#N]
In embodiments, -(L$^{101}$)—OC(SSR$^{102}$)(R$^{102a}$)-(L$^{103}$)-(L$^{104}$)-(L$^{105}$)- is
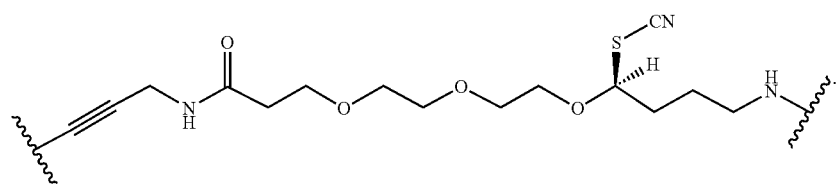 [SMILES: *C#CCNC(=O)CCOCCOCCO[C@H](CCCN*)SC#N]
In embodiments, -(L$^{101}$)-OC(SSR$^{102}$)(R$^{102a}$)-(L$^{103}$)-(L$^{104}$)-(L$^{105}$)- is
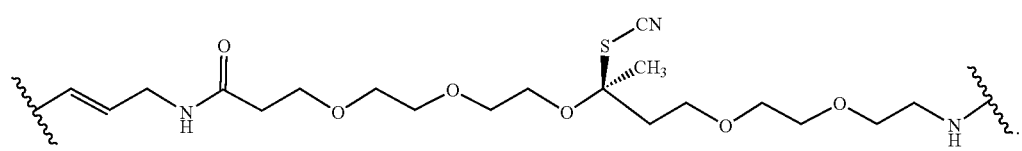 [SMILES: */C=C/CNC(=O)CCOCCOCCO[C@](C)(CCOCCOCCN*)SC#N]

In embodiments, -(L$^{101}$)-OC(SSR$^{102}$)(R$^{102a}$)-(L$^{103}$)-(L$^{104}$)-(L$^{105}$)- is
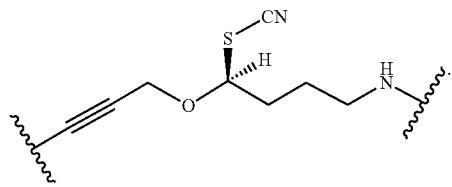 [SMILES: *C#CCO[C@H](CCCN*)SC#N]
In embodiments, -(L$^{101}$)-OC(SSR$^{102}$)(R$^{102a}$)-(L$^{103}$)-(L$^{104}$)-(L$^{105}$)- is
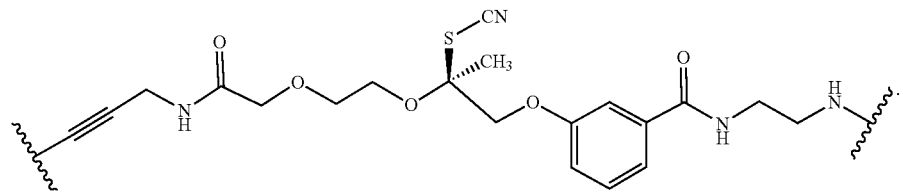 [SMILES: *C#CCNC(=O)COCCO[C@](C)(COc1cccc(C(=O)NCCN*)c1)SC#N]
In embodiments, -(L$^{101}$)-OC(SSR$^{102}$)(R$^{102a}$)-(L$^{103}$)-(L$^{104}$)-(L$^{105}$)- is
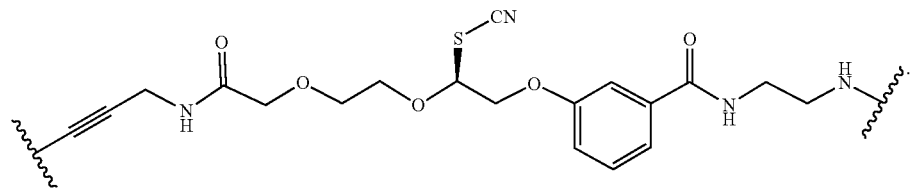 [SMILES: *C#CCNC(=O)COCCO[C@H](COc1cccc(C(=O)NCCN*)c1)SC#N]
In embodiments, -(L$^{101}$)-OC(SSR$^{102}$)(R$^{102a}$)-(L$^{103}$)-(L$^{104}$)-(L$^{105}$)- is
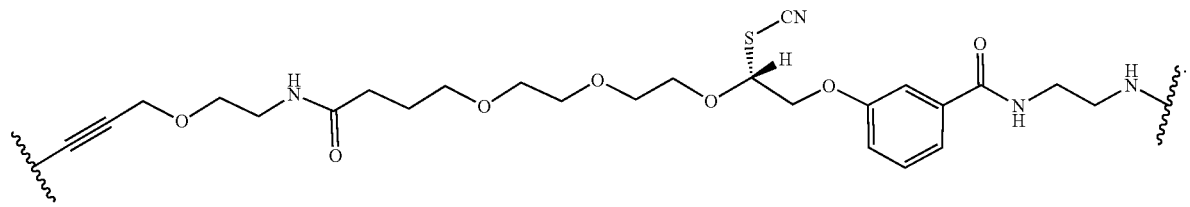 [SMILES: *C#CCOCCNC(=O)CCCOCCOCCO[C@@H](COc1cccc(C(=O)NCCN*)c1)SC#N]
In embodiments, -(L$^{101}$)-OC(SSR$^{102}$)(R$^{102a}$)-(L$^{103}$)-(L$^{104}$)-(L$^{105}$)- is
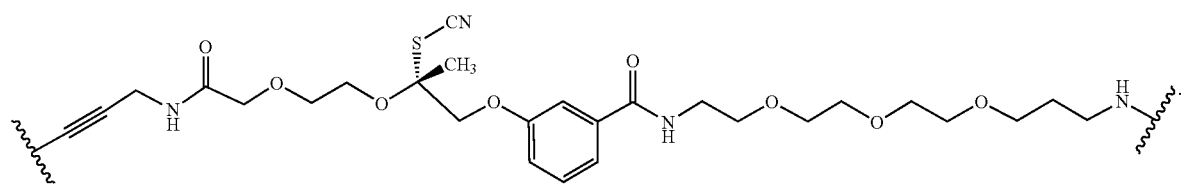 [SMILES: *C#CCNC(=O)COCCO[C@@](C)(COc1cccc(C(=O)NCCOCCOCCOCCCN*)c1)SC#N]

In embodiments, -(L$^{101}$)-OC(SSR$^{102}$)(R$^{102a}$)-(L$^{103}$)-(L$^{104}$)-(L$^{105}$)- is
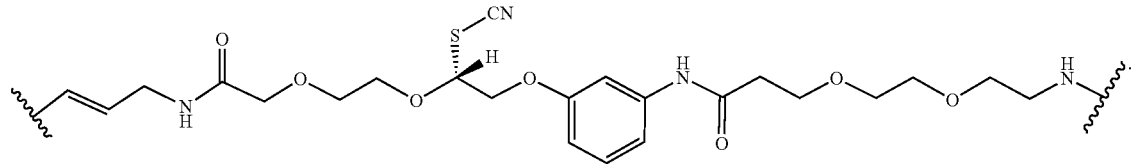 [SMILES: */C=C/CNC(=O)COCCO[C@@H](COc1cccc(NC(=O)CCOCCOCCN*)c1)SC#N]
In embodiments, -(L$^{101}$)-OC(SSR$^{102}$)(R$^{102a}$)-(L$^{103}$)-(L$^{104}$)-(L$^{105}$)- is
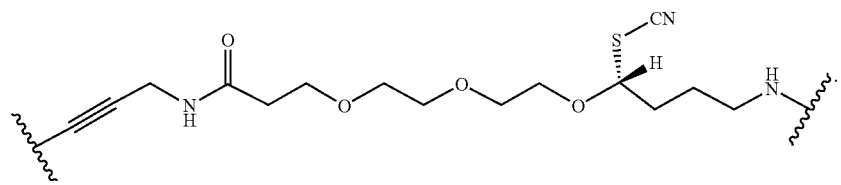 [SMILES: *C#CCNC(=O)CCOCCOCCO[C@@H](CCCN*)SC#N]
In embodiments, -(L$^{101}$)-OC(SSR$^{102}$)(R$^{102a}$)-(L$^{103}$)-(L$^{104}$)-(L$^{105}$)- is
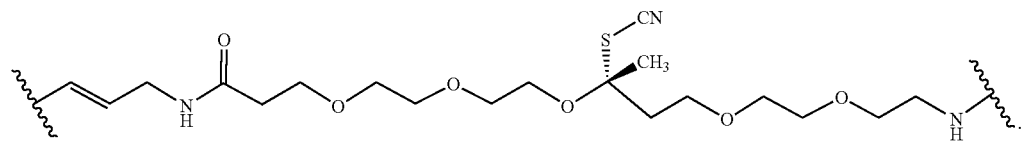 [SMILES: */C=C/CNC(=O)CCOCCOCCO[C@@](C)(CCOCCOCCN*)SC#N]
In embodiments, -(L$^{101}$)-OC(SSR$^{102}$)(R$^{102a}$)-(L$^{103}$)-(L$^{104}$)-(L$^{105}$)- is
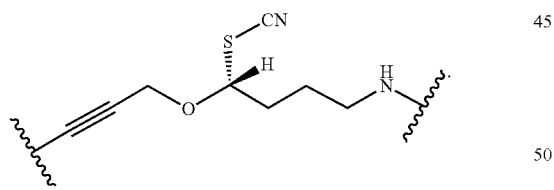
In embodiments, -(L$^{101}$)-OC(SSR$^{102}$)(R$^{102a}$)-(L$^{103}$)-(L$^{104}$)-(L$^{105}$)- is
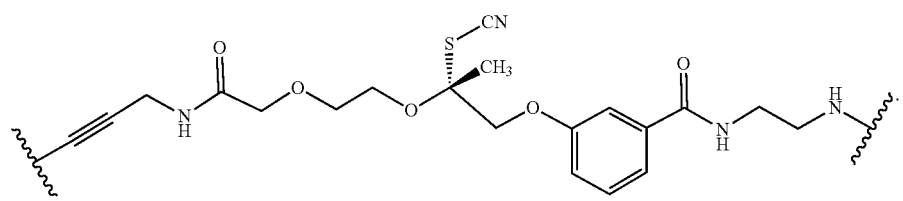 [SMILES: *C#CCNC(=O)COCCO[C@@](C)(COc1cccc(C(=O)NCCN*)c1)SC#N]

In embodiments, -(L$^{101}$)-OC(SSR$^{102}$)(R$^{102a}$)-(L$^{103}$)-(L$^{104}$)-(L$^{105}$)- is
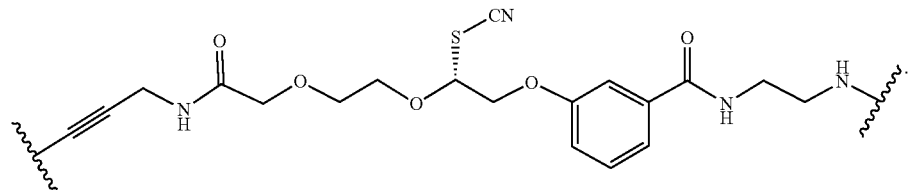 [SMILES: *C#CCNC(=O)COCCO[C@@H](COc1cccc(C(=O)NCCN*)c1)SC#N]
In embodiments, R$^4$ is a fluorescent dye moiety. In embodiments, R$^4$ is a detectable moiety described herein (e.g., Table 1). In embodiments, R$^4$ is a detectable moiety described in Table 1.
In embodiments, R$^4$ is
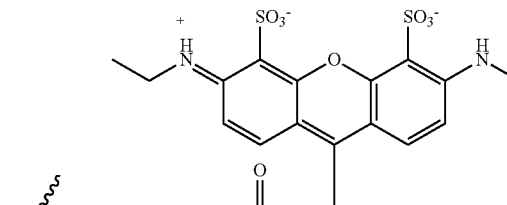
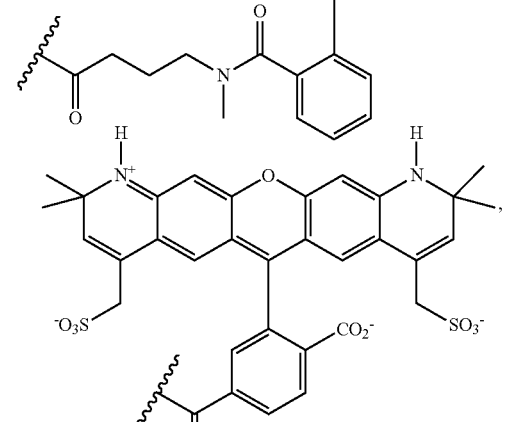
or
In embodiments, R$^4$ is
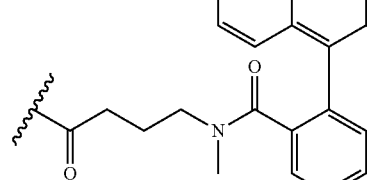
In embodiments, R$^4$ is
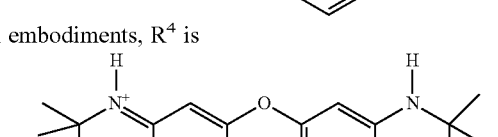
In embodiments, R$^4$ is
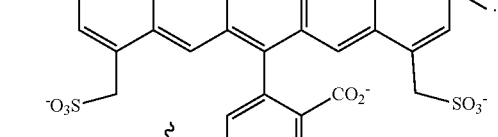
In embodiments, R$^4$ is
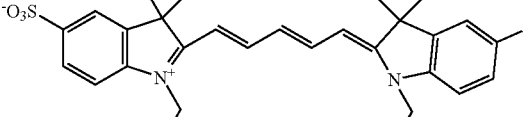

In embodiments, the compound has the formula:

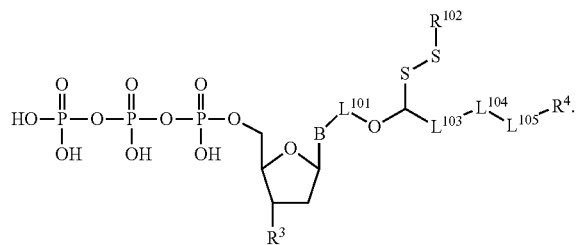

$R^3$, B, $L^{101}$, $L^{103}$, $L^{104}$, $L^{105}$, $R^{102}$ and $R^4$ are as described herein, including in embodiments. In embodiments, $R^3$ is an —O-polymerase-compatible cleavable moiety. In embodiments, $R^{102}$ is an unsubstituted $C_1$-$C_4$ alkyl.

In embodiments, the compound has the formula:

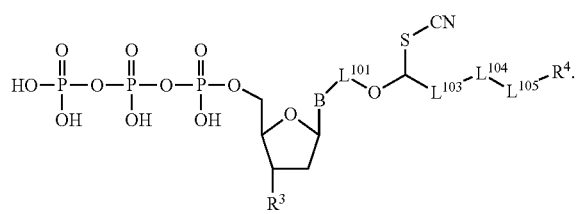

$R^3$, B, $L^{101}$, $L^{103}$, $L^{104}$, $L^{105}$, and $R^4$ are as described herein, including in embodiments. In embodiments, $R^3$ is an —O-polymerase-compatible cleavable moiety.

In embodiments, the compound has the formula:

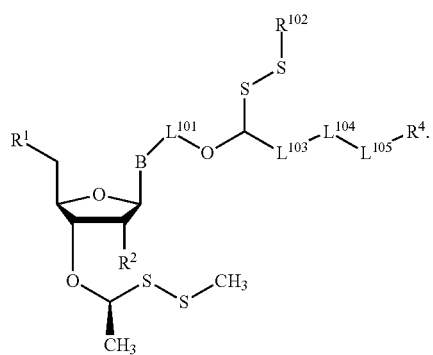

B, $R^1$, $R^2$, $L^{101}$, $L^{103}$, $L^{104}$, $L^{105}$, $R^{102}$, and $R^4$ are as described herein.

In embodiments, compound has the formula:

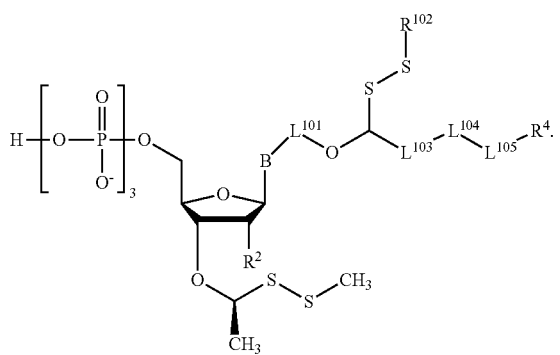

B, $R^2$, $L^{101}$, $L^{103}$, $L^{104}$, $L^{105}$, $R^{102}$, and $R^4$ are as described herein.

In embodiments, the compound has the formula:

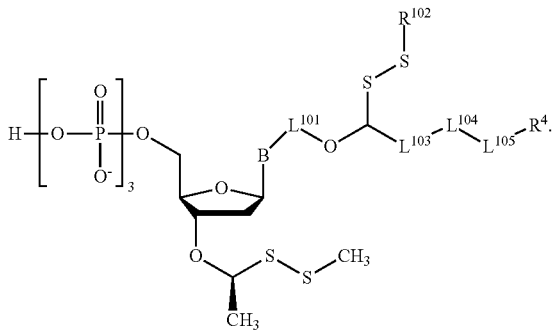

B, $L^{101}$, $L^{103}$, $L^{104}$, $L^{105}$, $R^{102}$, and $R^4$ are as described herein.

In embodiments, the compound has the formula:

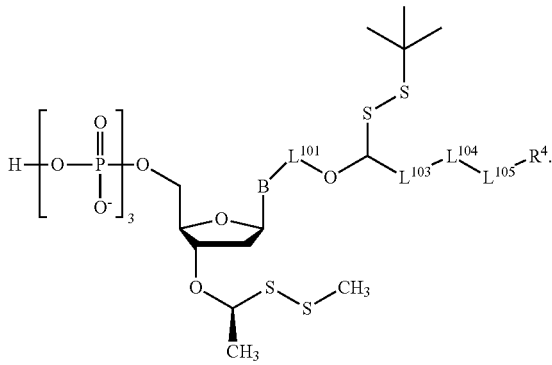

B, $L^{101}$, $L^{103}$, $L^{104}$, $L^{105}$, and $R^4$ are as described herein.

In embodiments, the compound has the formula:

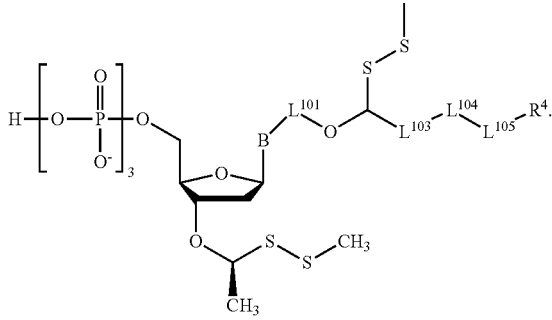

B, $L^{101}$, $L^{103}$, $L^{104}$, $L^{105}$, and $R^4$ are as described herein.

In embodiments, the compound has the formula:

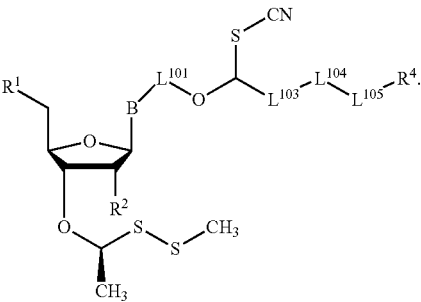

B, $R^1$, $R^2$, $L^{101}$, $L^{103}$, $L^{104}$, $L^{105}$, and $R^4$ are as described herein.

In embodiments, compound has the formula:

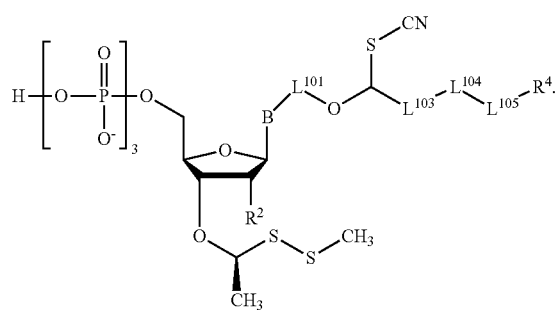

B, $R^2$, $L^{101}$, $L^{103}$, $L^{104}$, $L^{105}$, and $R^4$ are as described herein.

In embodiments, the compound has the formula:

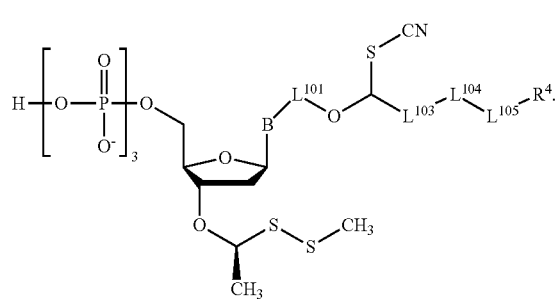

B, $L^{101}$, $L^{103}$, $L^{104}$, $L^{1050}$, and $R^4$ are as described herein.

In embodiments, the compound has the formula:

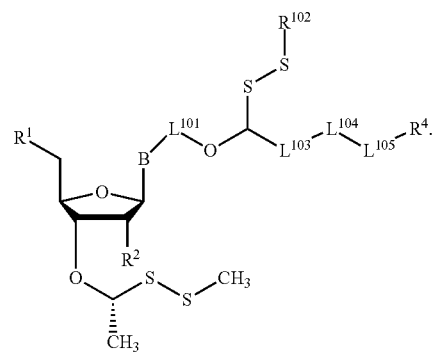

B, $R^1$, $R^2$, $L^{101}$, $L^{103}$, $L^{104}$, $L^{105}$, $R^{102}$, and $R^4$ are as described herein.

In embodiments, the compound has the formula:

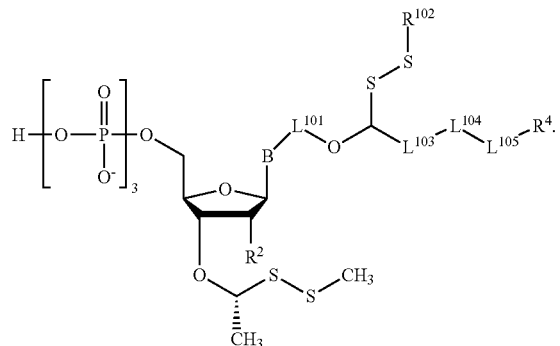

B, $R^2$, $L^{101}$, $L^{103}$, $L^{104}$, $L^{105}$, $R^{102}$ and $R^4$ are as described herein.

In embodiments, the compound has the formula:

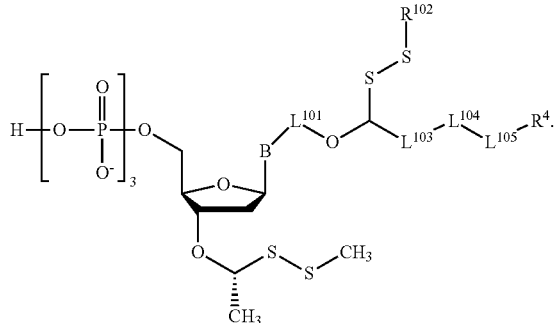

B, $L^{101}$, $L^{103}$, $L^{104}$, $L^{105}$, $R^{102}$, and $R^4$ are as described herein.

In embodiments, the compound has the formula:

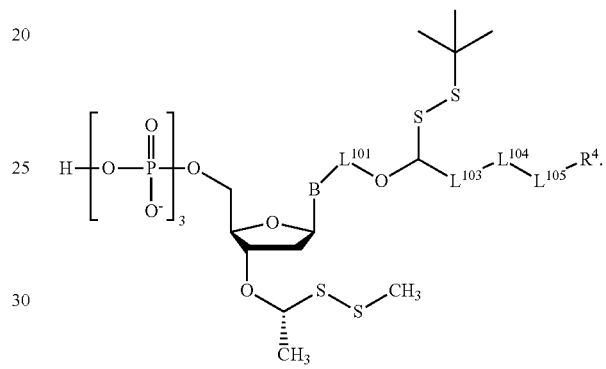

B, $L^{101}$, $L^{103}$, $L^{104}$, $L^{105}$, and $R^4$ are as described herein.

In embodiments, the compound has the formula:

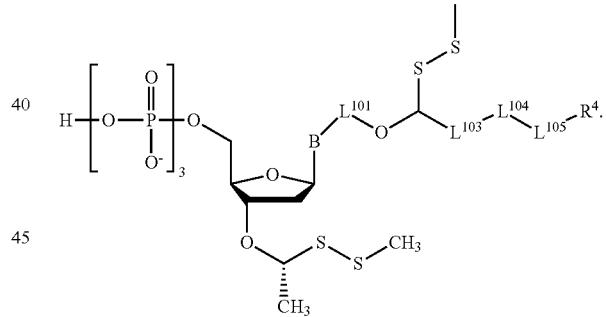

B, $L^{101}$, $L^{103}$, $L^{104}$, $L^{105}$, and $R^4$ are as described herein.

In embodiments, the compound has the formula:

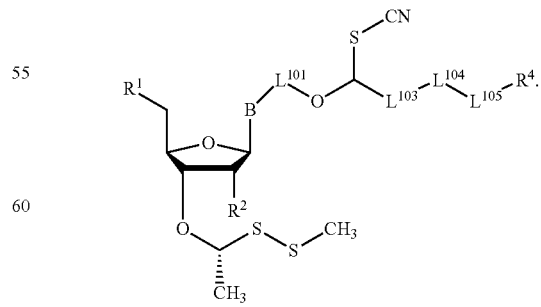

B, $R^1$, $R^2$, $L^{101}$, $L^{103}$, $L^{104}$, $L^{105}$, and $R^4$ are as described herein.

In embodiments, the compound has the formula:

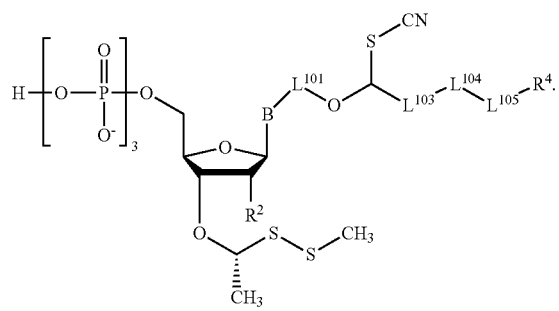

B, $R^2$, $L^{101}$, $L^{103}$, $L^{104}$, $L^{105}$, and $R^4$ are as described herein.

In embodiments, the compound has the formula:

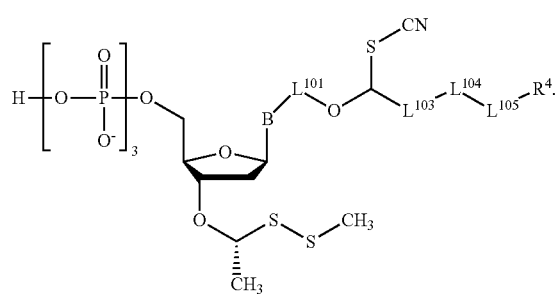

B, $L^{101}$, $L^{103}$, $L^{104}$, $L^{105}$, and $R^4$ are as described herein.

In embodiments, the compound has the formula:

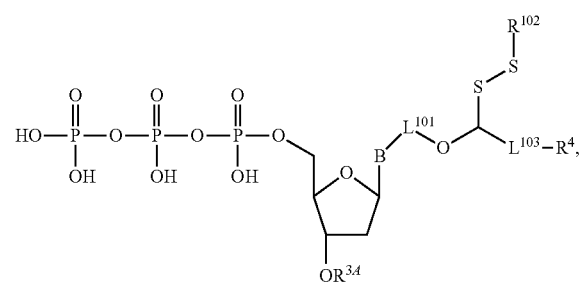

wherein $R^{3A}$, B, $L^{101}$, $L^{103}$, $R^{102}$, and $R^4$ are as described herein, including in embodiments. In embodiments, the compound has the formula:

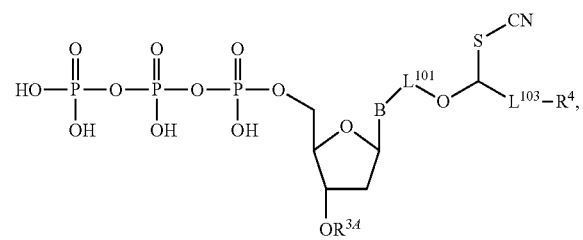

wherein $R^{3A}$, B, $L^{101}$, $L^{103}$, and $R^4$ are as described herein, including in embodiments. In embodiments $L^1$ is

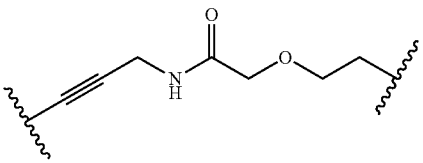

In embodiments, $L^1$ is

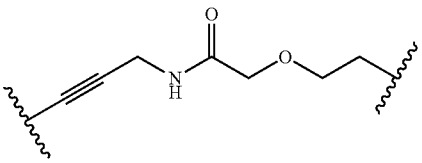

In embodiments, $L^1$ is

In embodiments, $R^{3A}$ is independently:

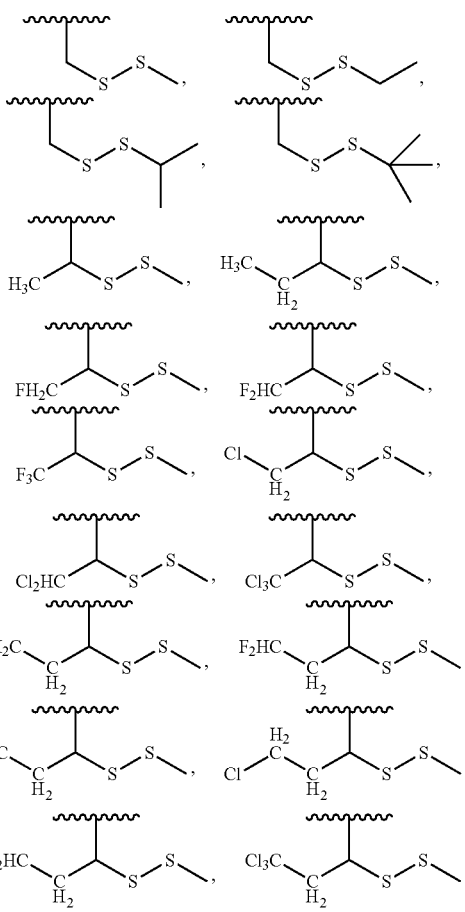

-continued
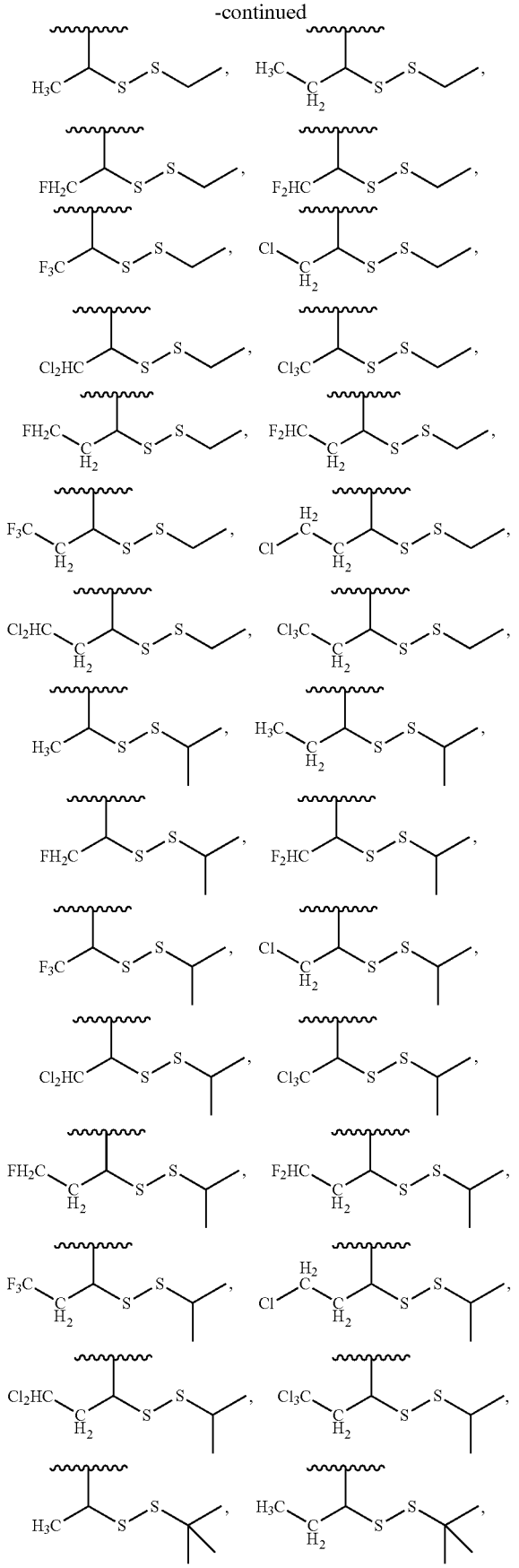
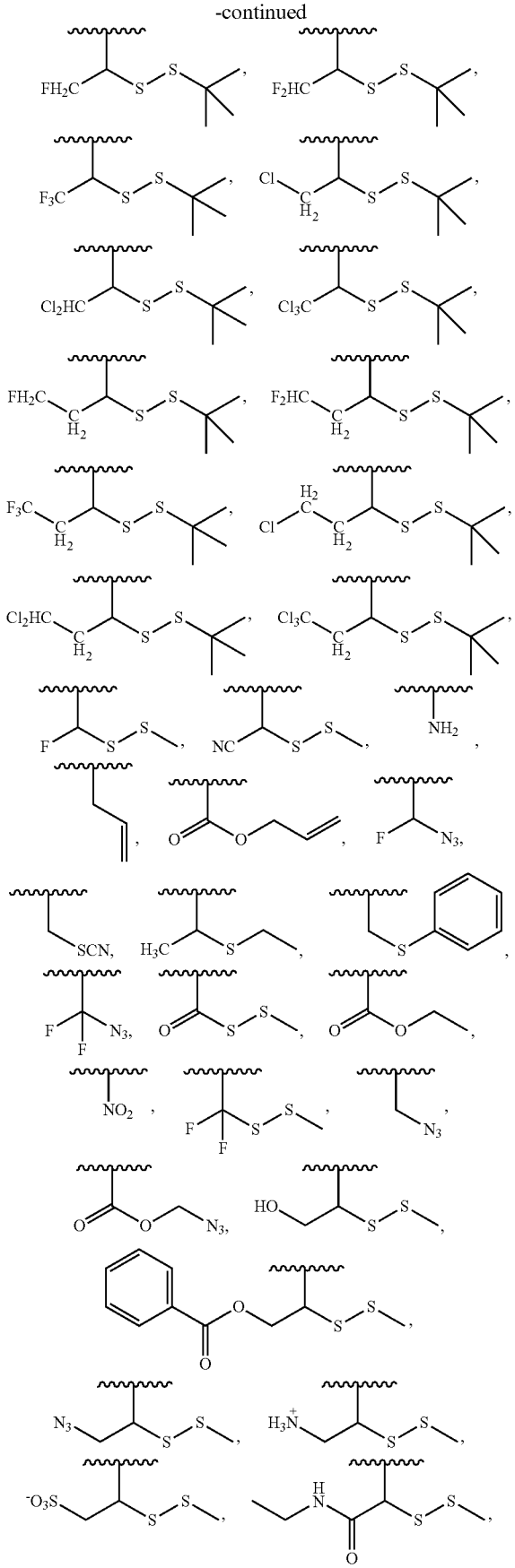

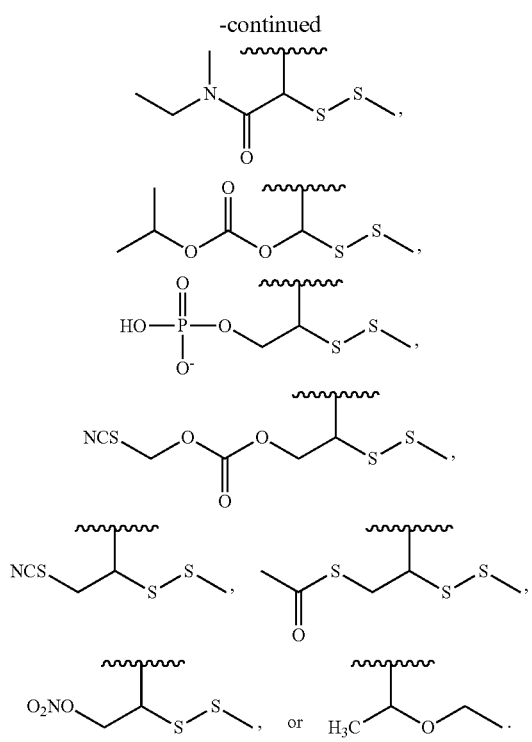

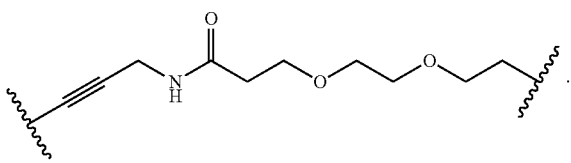 [SMILES: *C#CCNC(=O)CCOCCOCC*]

In embodiments, $R^2$ is hydrogen. In embodiments, $R^2$ is —OH.

In embodiments, $R^{102}$ is unsubstituted methyl. In embodiments, $R^{102}$ is unsubstituted ethyl. In embodiments, $R^{102}$ is unsubstituted propyl. In embodiments, $R^{102}$ is unsubstituted isopropyl. In embodiments, $R^{102}$ is unsubstituted butyl. In embodiments, $R^{102}$ is unsubstituted tert-butyl.

In embodiments, $L^{101}$ is

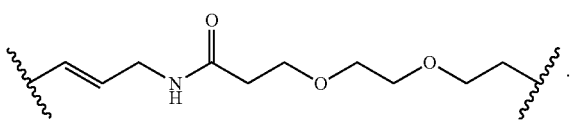 [SMILES: */C=C/CNC(=O)CCOCCOCC*]

In embodiments, $L^1$ is

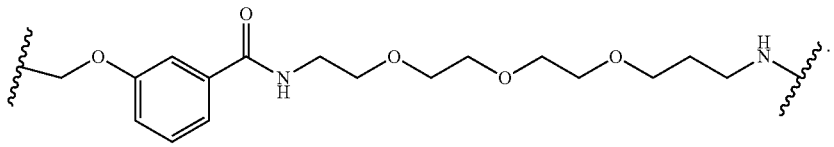

In embodiments $L^{101}$ is —CCCH$_2$—. In embodiments, $L^{101}$ is

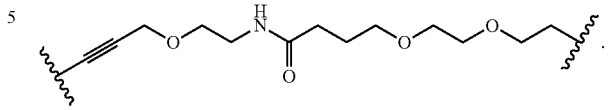

In embodiments, $L^{101}$ is

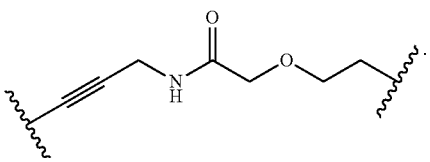 [SMILES: *C#CCNC(=O)COCC*]

In embodiments, $L^{101}$ is

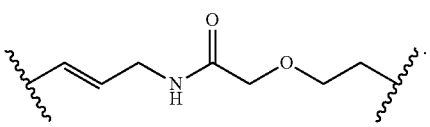 [SMILES: */C=C/CNC(=O)COCC*]

In embodiments, $L^{103}$ is

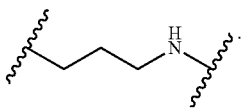 [SMILES: *CCCN*]

In embodiments $L^{103}$ is

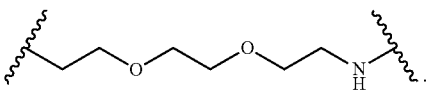 [SMILES: *CCOCCOCCN*]

In embodiments, $L^{103}$ is

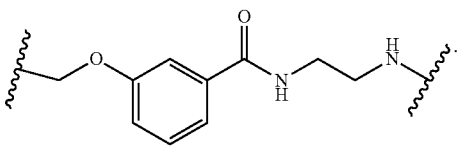 [SMILES: *COc1cccc(C(=O)NCCN*)c1]

In embodiments, $L^{103}$ is

In embodiments, $L^{103}$ is
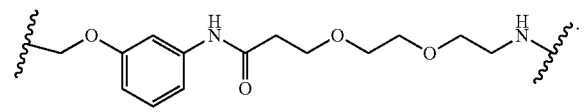 [SMILES: *COc1cccc(NC(=O)CCOCCOCCN*)c1]
In embodiments, $L^{103}$ is a bond.
In embodiments, $L^{104}$ is
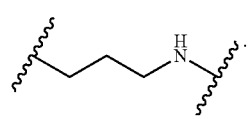 [SMILES: *CCCN*]
In embodiments, $L^{104}$ is
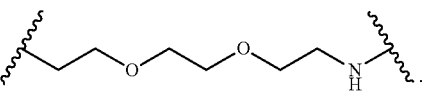 [SMILES: *CCOCCOCCN*]
In embodiments, $L^{104}$ is
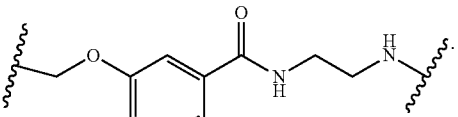
In embodiments, $L^{104}$ is
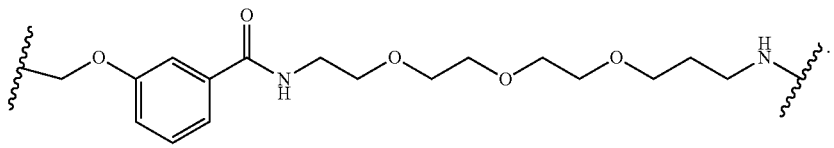 [SMILES: *COc1cccc(C(=O)NCCOCCOCCOCCCN*)c1]
In embodiments, $L^{104}$ is
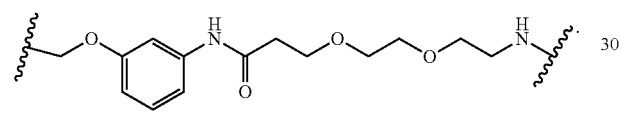
In embodiments, $L^{104}$ is a bond.
In embodiments, $L^{105}$ is
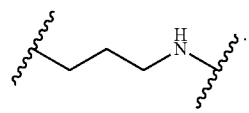 [SMILES: *CCCN*]
In embodiments, $L^{105}$ is
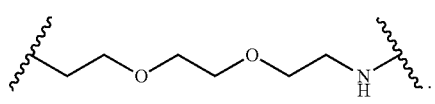 [SMILES: *CCOCCOCCN*]
H In embodiments, $L^{105}$ is
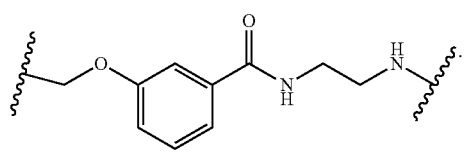 [SMILES: *COc1cccc(C(=O)NCCN*)c1]
In embodiments, $L^{105}$ is
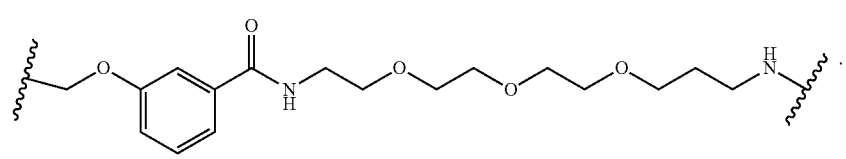 [SMILES: *COc1cccc(C(=O)NCCOCCOCCOCCCN*)c1]

In embodiments, $L^{105}$ is

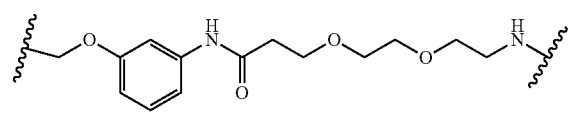

In embodiments, $L^{105}$ is a bond.

In embodiments, $L^{103}$-$L^{104}$-$L^{105}$- is

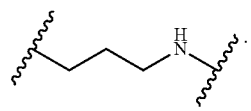

In embodiments, $L^{103}$-$L^{104}$-$L^{105}$- is

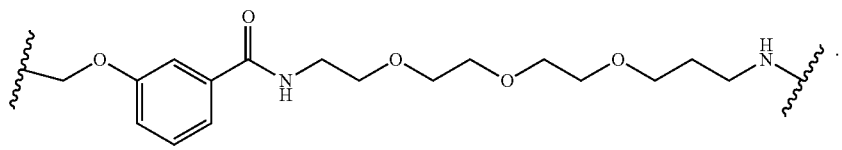

In embodiments, $L^{103}$-$L^{104}$-$L^{105}$- is

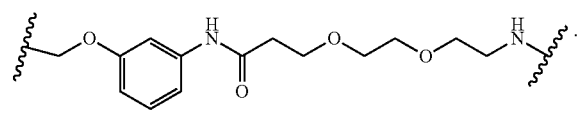 [SMILES: *COc1cccc(NC(=O)CCOCCOCCN*)c1]

In embodiments, $L^{103}$-$L^{104}$-$L^{105}$- is

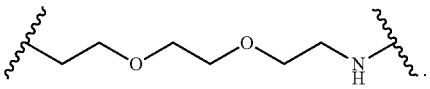 [SMILES: *CCOCCOCCN*]

In embodiments, $L^{103}$-$L^{104}$-$L^{105}$- is

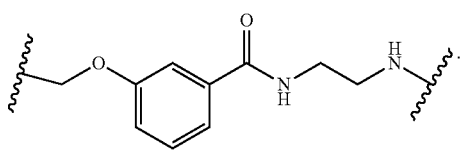 [SMILES: *COc1cccc(C(=O)NCCN*)c1]

In embodiments, the compound has the formula:

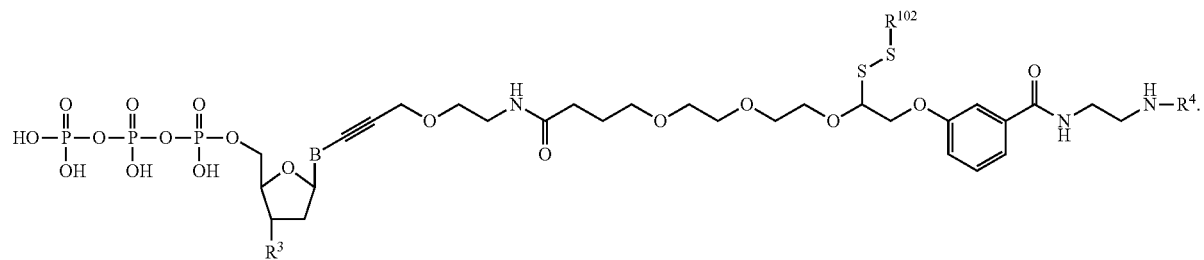

$R^3$, $R^4$, and $R^{102}$ are as described herein, including in embodiments. In embodiments, $R^3$ is an —O-polymerase-compatible cleavable moiety. In embodiments, $R^{102}$ is an unsubstituted $C_1$-$C_4$ alkyl.

In embodiments, the compound has the formula:

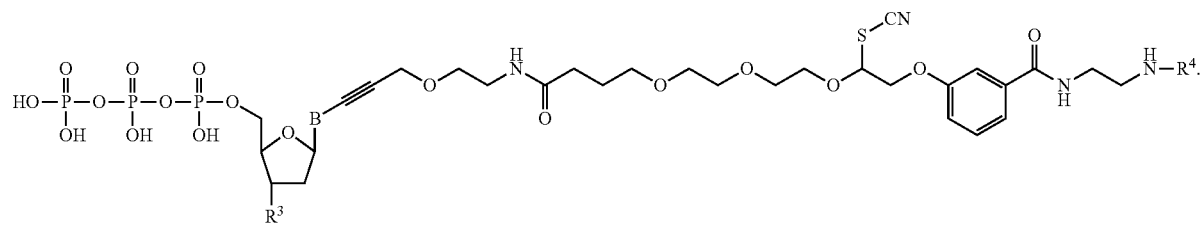

$R^3$ and $R^4$ are as described herein, including in embodiments. In embodiments, $R^3$ is an —O-polymerase-compatible cleavable moiety.

In embodiments, the compound has the formula:

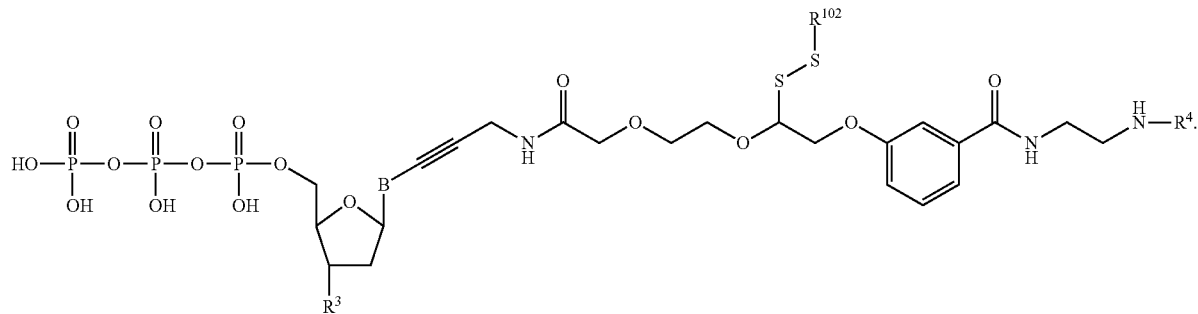

$R^3$, $R^4$, and $R^{102}$ are as described herein, including in embodiments. In embodiments, $R^3$ is an —O-polymerase-compatible cleavable moiety. In embodiments, $R^{102}$ is an unsubstituted $C_1$-$C_4$ alkyl.

In embodiments, the compound has the formula:

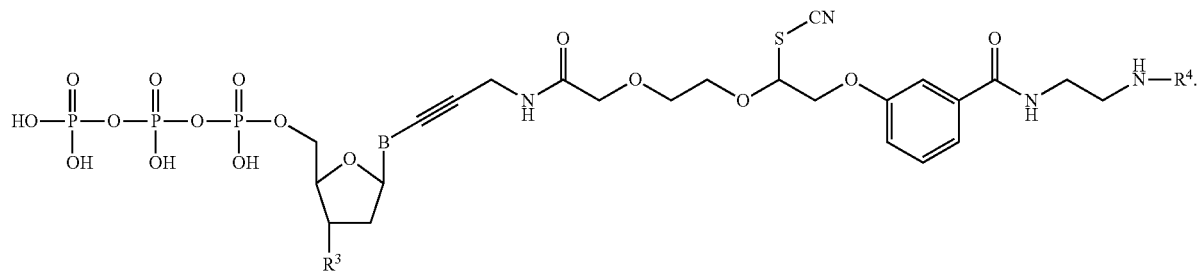

$R^3$ and $R^4$ are as described herein, including in embodiments. In embodiments, $R^3$ is an —O-polymerase-compatible cleavable moiety.

In embodiments, the compound has the formula:

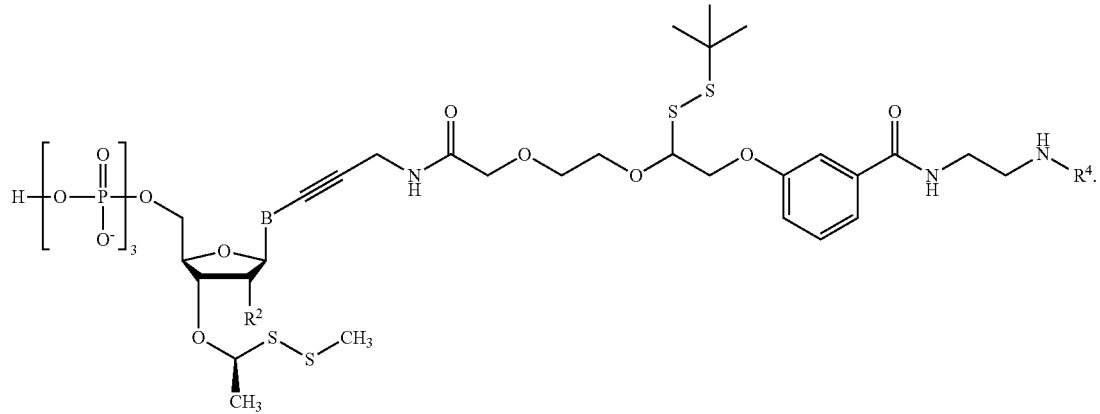

B, $R^2$ and $R^4$ are as described herein.

In embodiments, the compound has the formula:
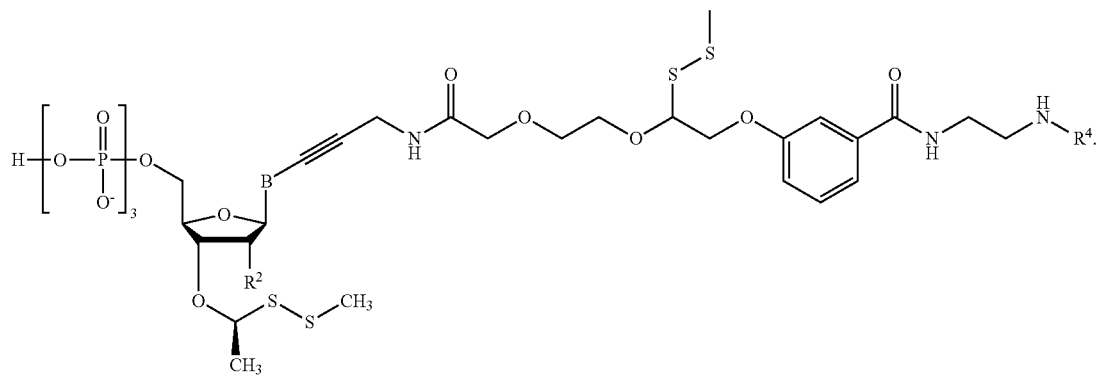
B, $R^2$ and $R^4$ are as described herein.
In embodiments, the compound has the formula:
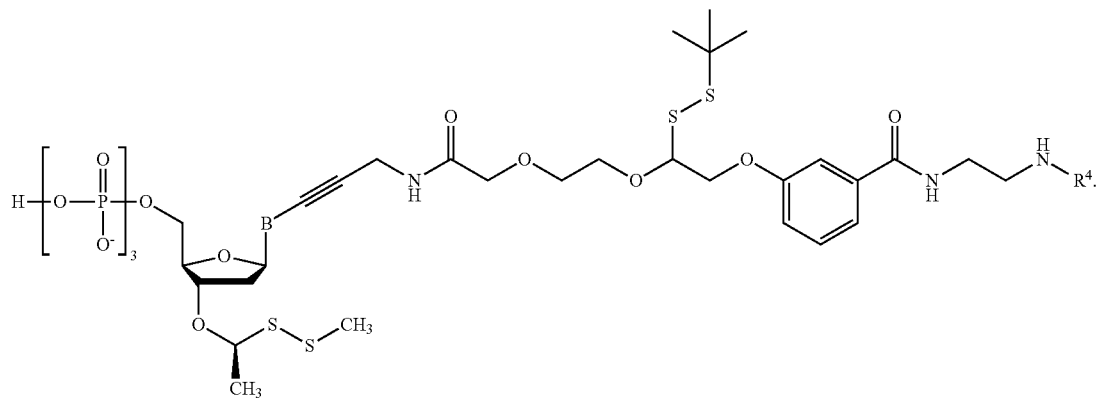
B and $R^4$ are as described herein.
In embodiments, the compound has the formula:
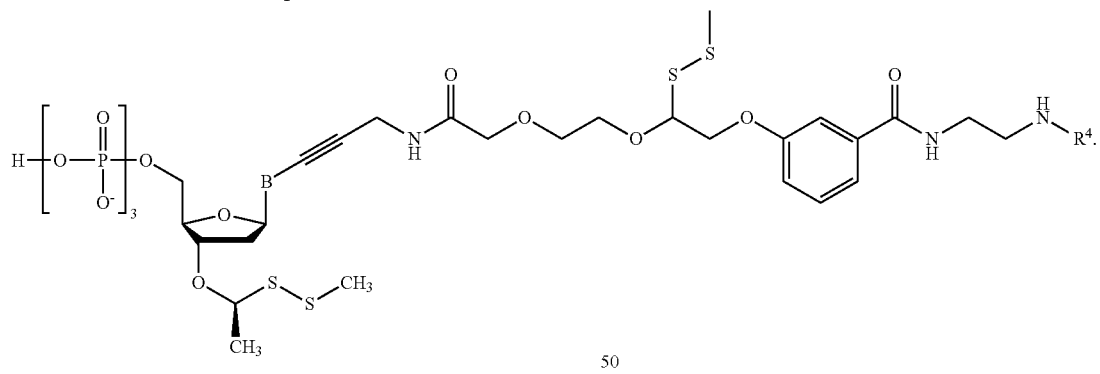
B and $R^4$ are as described herein.
In embodiments, the compound has the formula:
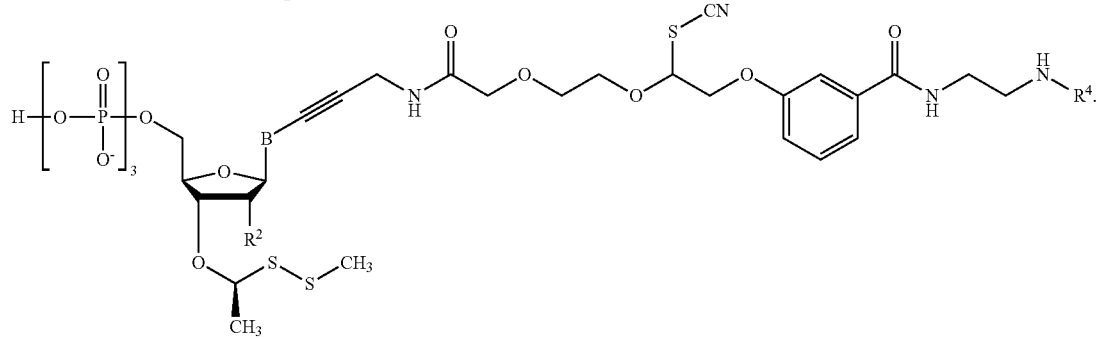
B, $R^2$, and $R^4$ are as described herein.

In embodiments, the compound has the formula:
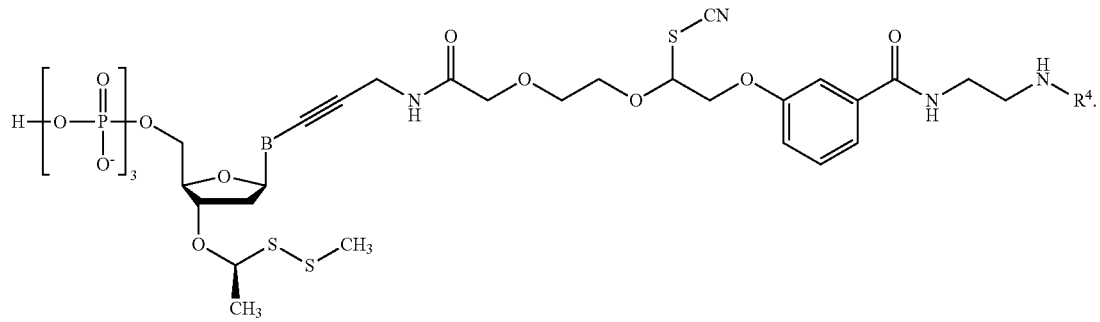
B and R⁴ are as described herein.
In embodiments, the compound has the formula:
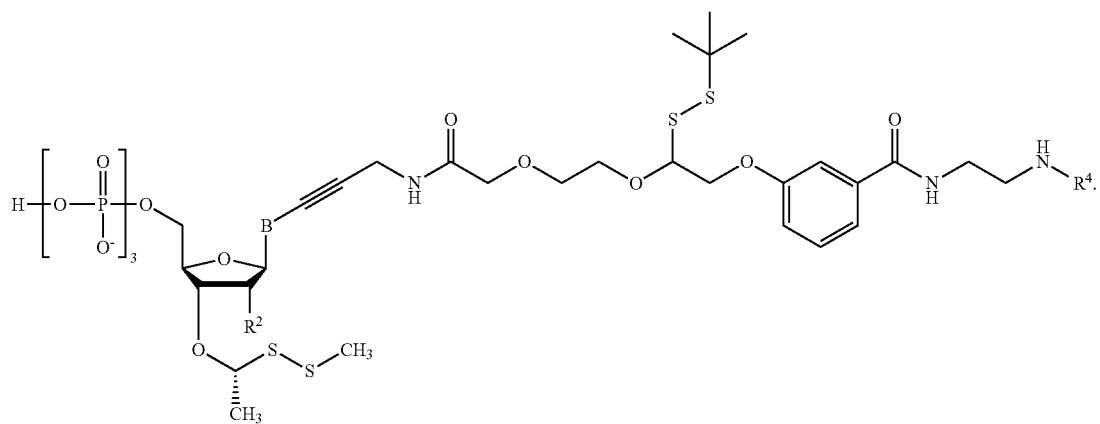
B, R², and R⁴ are as described herein.
In embodiments, the compound has the formula:
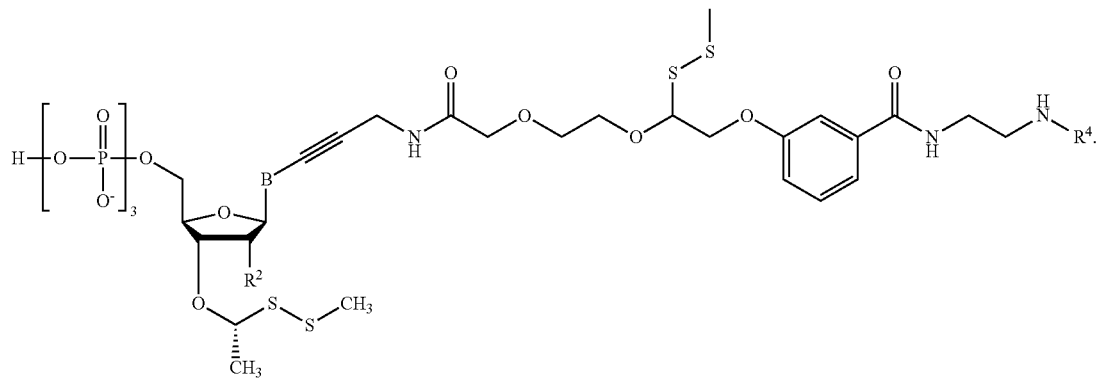
B, R², and R⁴ are as described herein.

In embodiments, the compound has the formula:
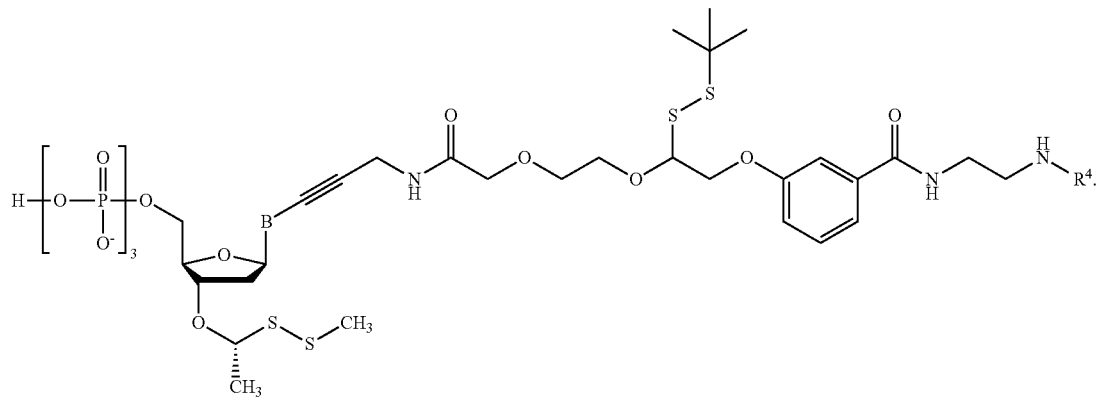
B and R⁴ are as described herein.
In embodiments, the compound has the formula:
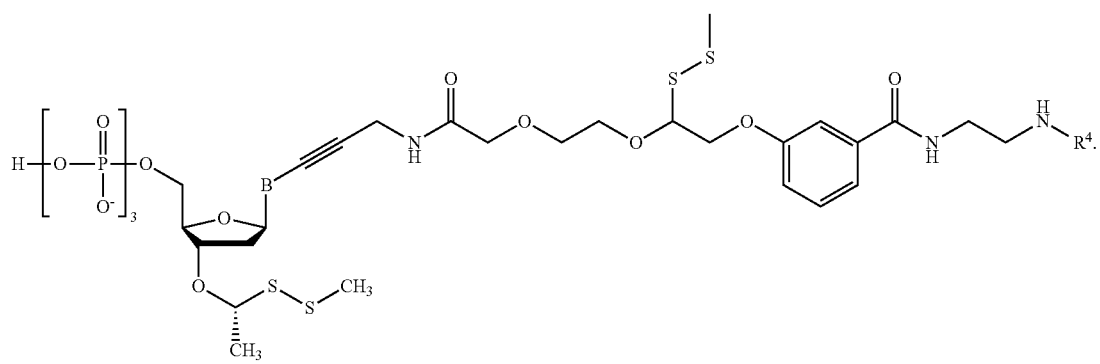
B and R⁴ are as described herein.
In embodiments, the compound has the formula:
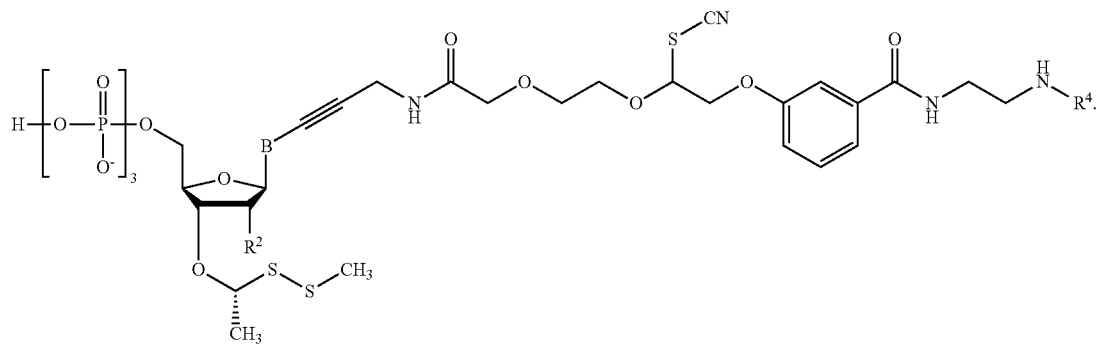
B, R², and R⁴ are as described herein.

In embodiments, the compound has the formula:

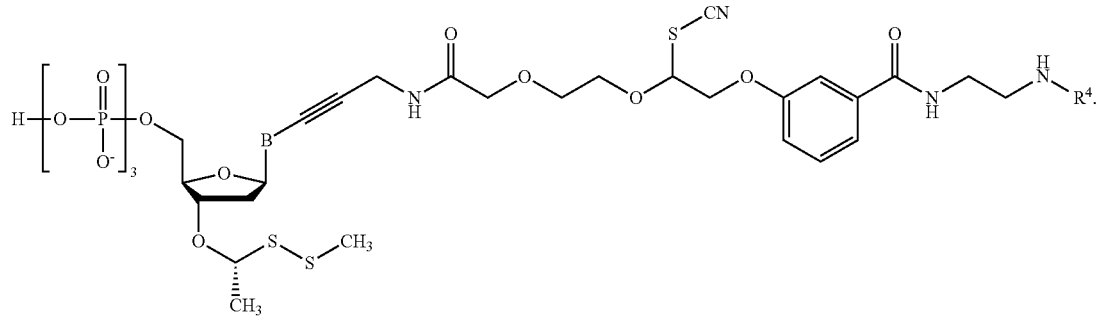

B and R⁴ are as described herein.

In embodiments, the compound has the formula:

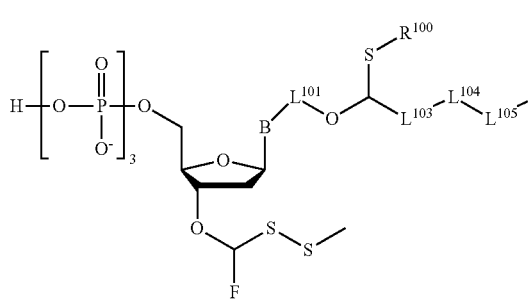

(IV)

B, $L^{101}$, $L^{103}$, $L^{104}$, $L^{105}$, and R⁴ are as described herein. In embodiments of Formula (IV), $R^{100}$ is —$SR^{102}$, and $R^{102}$ is as described herein (e.g., unsubstituted $C_1$-$C_4$ alkyl). In embodiments of Formula (IV), $R^{100}$ is —CN.

In embodiments, the compound has the formula:

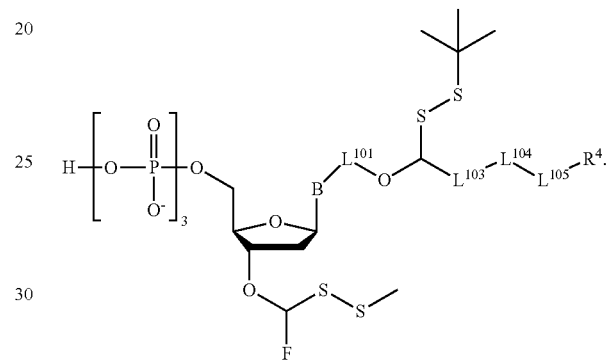

B, $L^{101}$, $L^{103}$, $L^{104}$, $L^{105}$, and R⁴ are as described herein.

In embodiments, the compound has the formula:

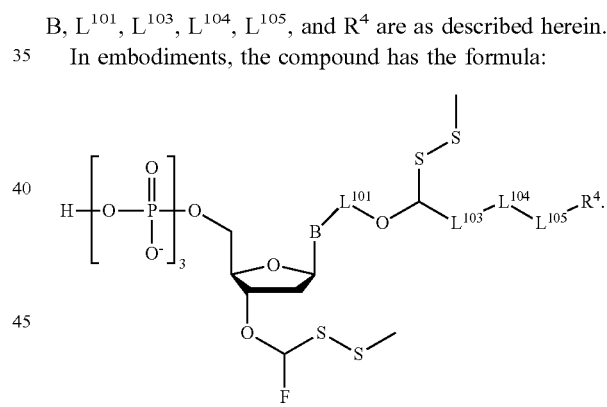

B, $L^{101}$, $L^{103}$, $L^{104}$, $L^{105}$, and R⁴ are as described herein.

In embodiments, the compound has the formula:

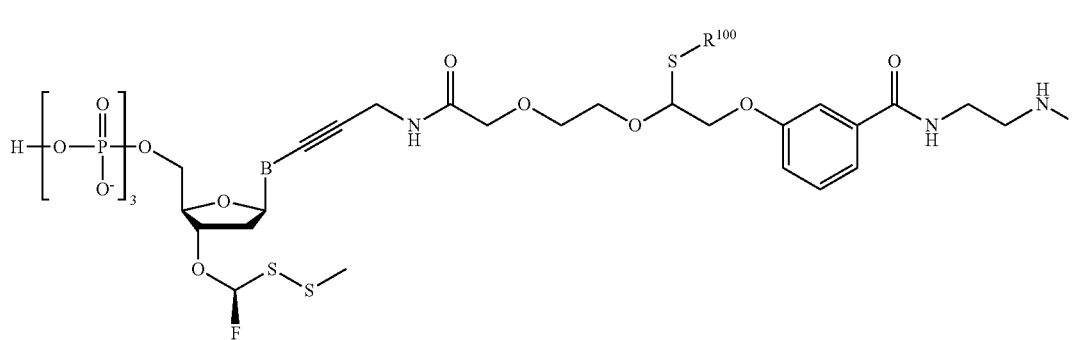

(V)

B and $R^4$ are as described herein. In embodiments of Formula (V), $R^{100}$ is $-SR^{102}$, and $R^{102}$ is as described herein. In embodiments of Formula (V), $R^{100}$ is $-CN$.

In embodiments, the compound has the formula:

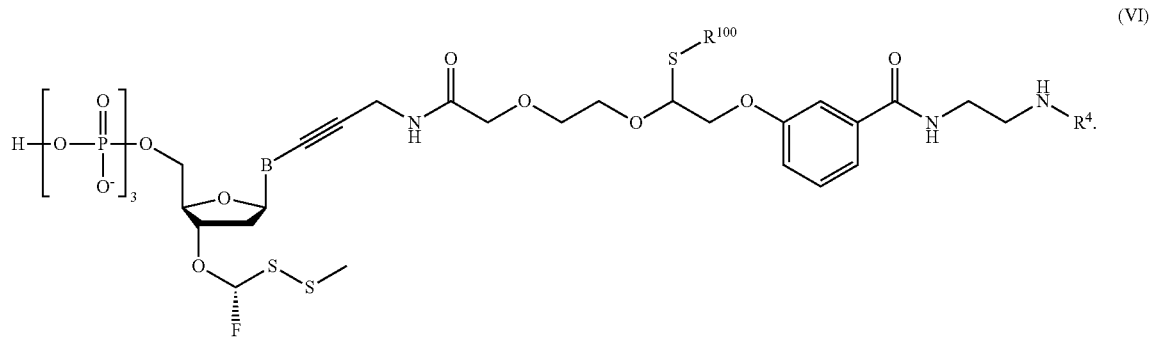

(VI)

B and $R^4$ are as described herein. In embodiments of Formula (VI), $R^{100}$ is $-SR^{102}$, and $R^{102}$ is as described herein. In embodiments of Formula (VI), $R^{100}$ is $-CN$.

In embodiments, the compound has the formula:

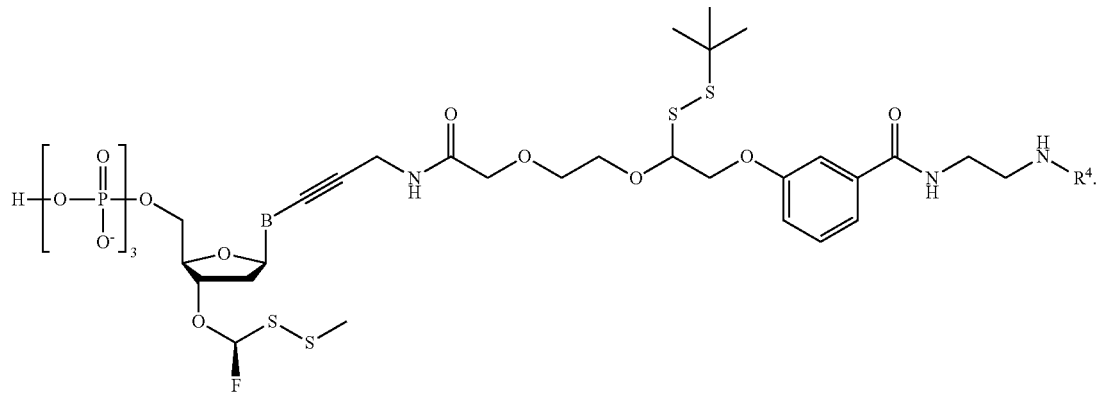

B and $R^4$ are as described herein.

In embodiments, the compound has the formula:

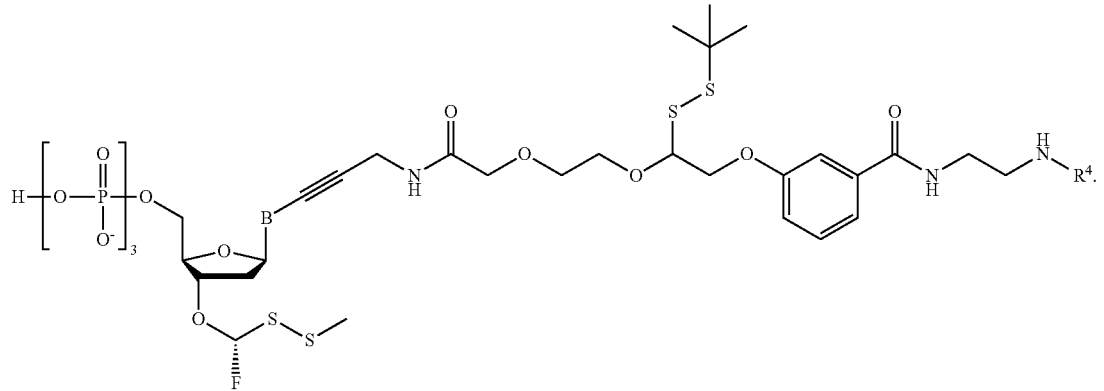

B and $R^4$ are as described herein.

In embodiments, the compound has the formula:

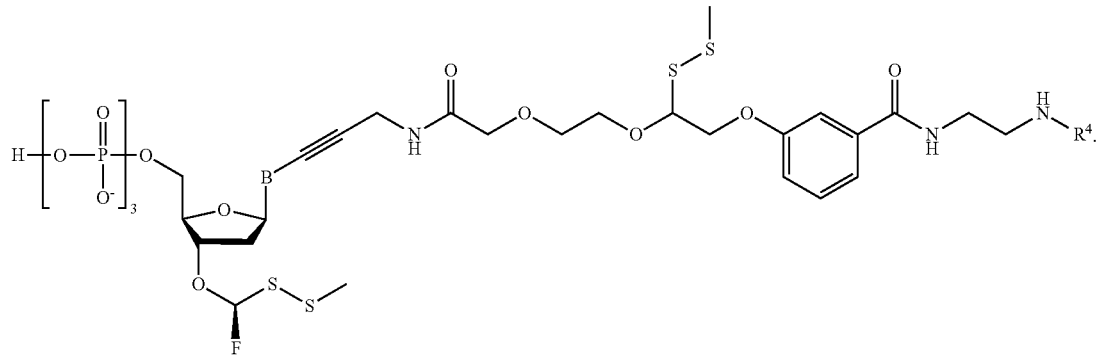

B and R⁴ are as described herein.

In embodiments, the compound has the formula:

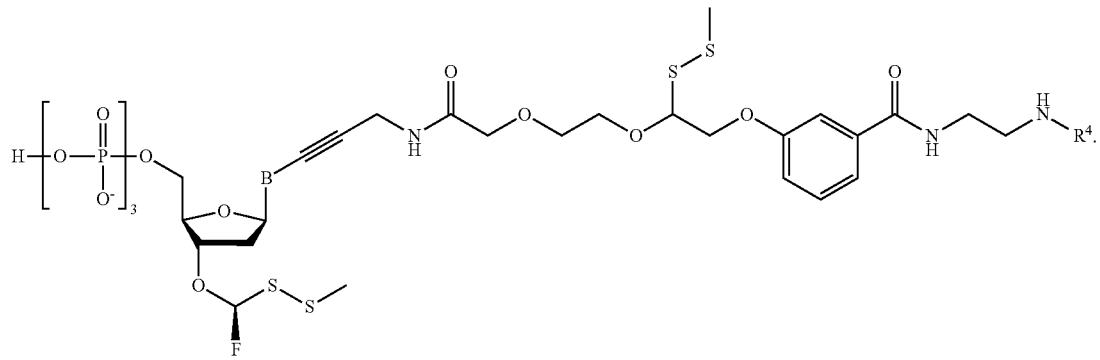

B and R⁴ are as described herein.

In embodiments, the compound has the formula:

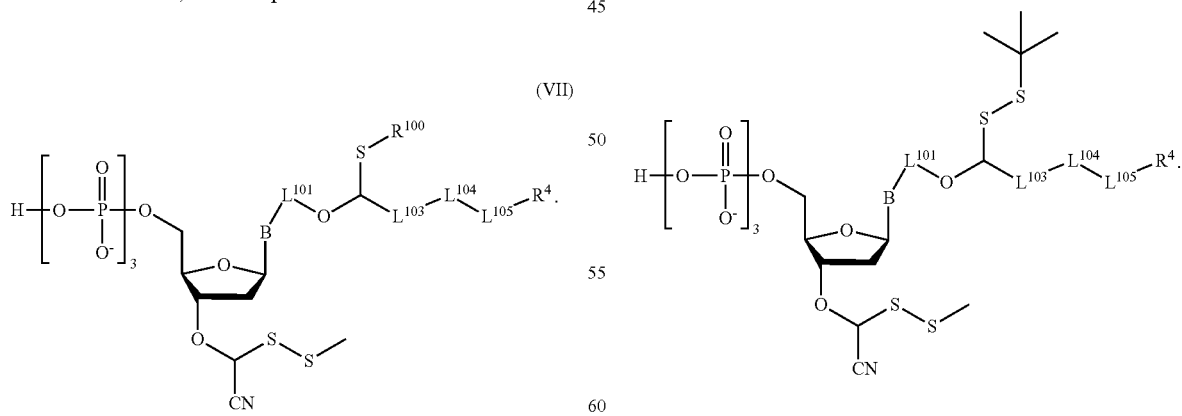

(VII)

B, $L^{101}$, $L^{103}$, $L^{104}$, $L^{105}$, and R⁴ are as described herein. In embodiments of Formula (VII), $R^{100}$ is —$SR^{102}$, and $R^{102}$ is as described herein (e.g., unsubstituted $C_1$-$C_4$ alkyl). In embodiments of Formula (VII), $R^{100}$ is —CN.

In embodiments, the compound has the formula:

B, $L^{101}$, $L^{103}$, $L^{104}$, $L^{105}$, and R⁴ are as described herein.

In embodiments, the compound has the formula:

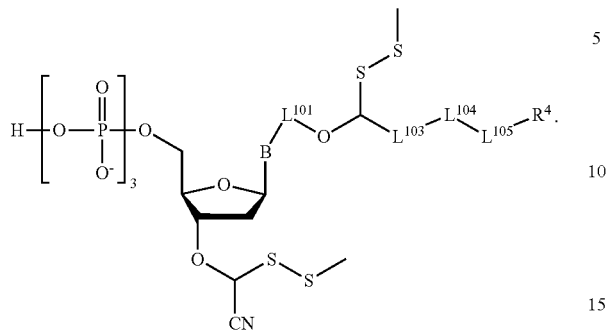

B, $L^{101}$, $L^{103}$, $L^{104}$, $L^{105}$, and $R^4$ are as described herein.

In embodiments, the compound has the formula:

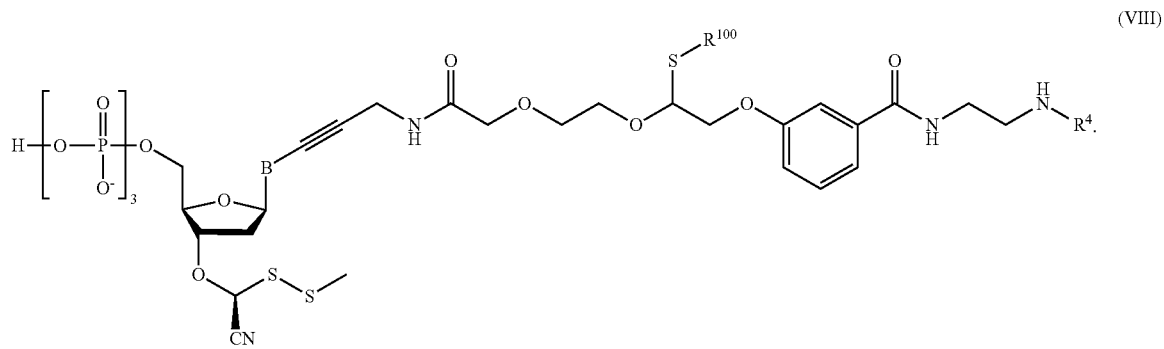

(VIII)

B and $R^4$ are as described herein. In embodiments of Formula (VIII), $R^{100}$ is —$SR^{102}$ and $R^{102}$ is as described herein. In embodiments of Formula (VIII), $R^{100}$ is —CN.

In embodiments, the compound has the formula:

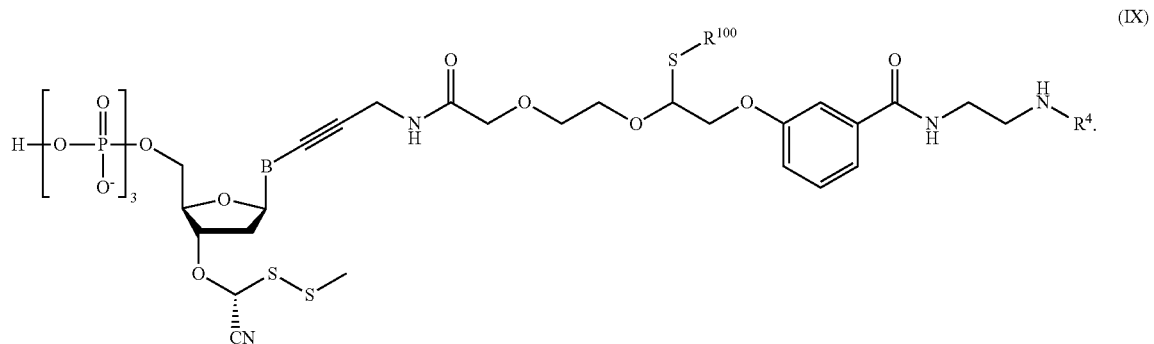

(IX)

B and $R^4$ are as described herein. In embodiments of Formula (IX), $R^{100}$ is —$SR^{102}$, and $R^{102}$ is as described herein. In embodiments of Formula (IX), $R^{100}$ is —CN.

In embodiments, the compound has the formula:
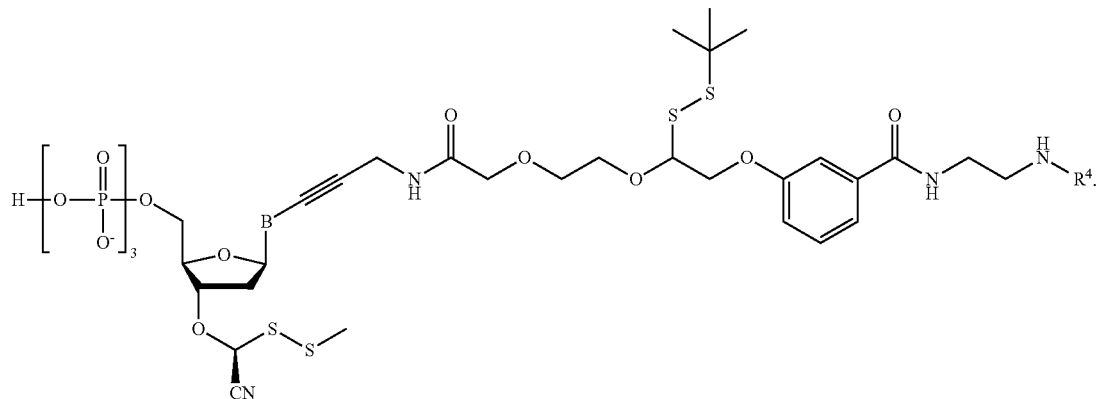
B and R⁴ are as described herein.
In embodiments, the compound has the formula:
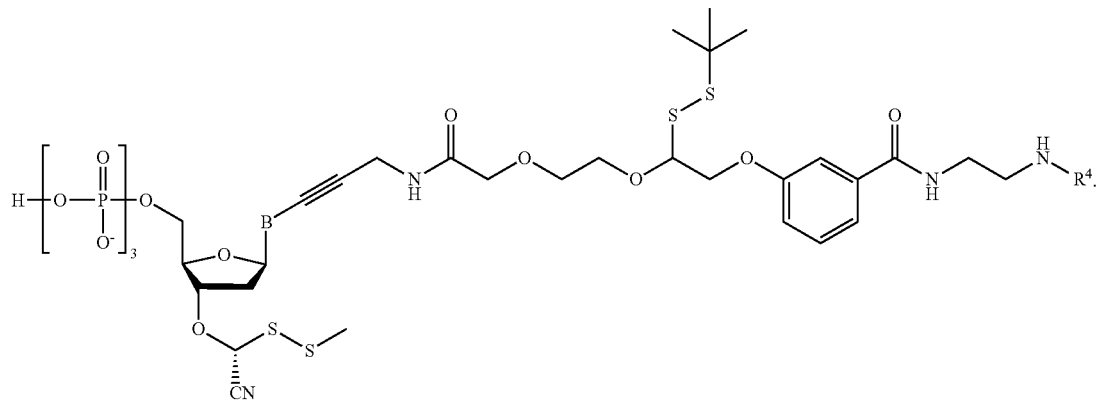
B and R⁴ are as described herein.
In embodiments, the compound has the formula:
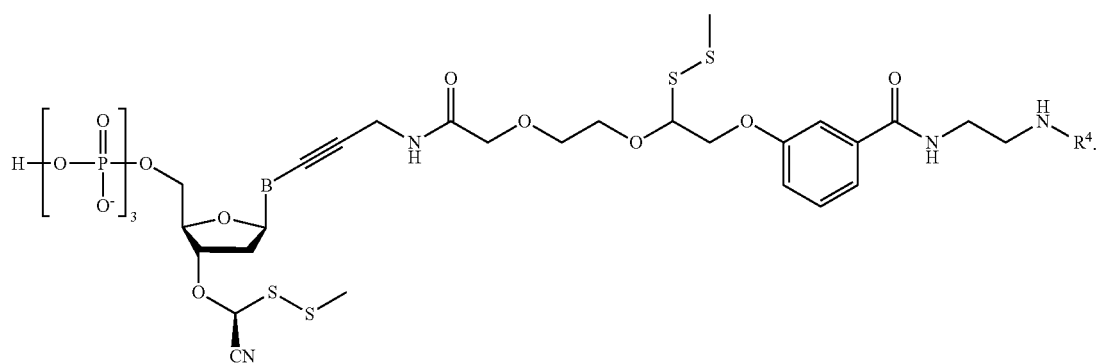
B and R⁴ are as described herein.

In embodiments, the compound has the formula:

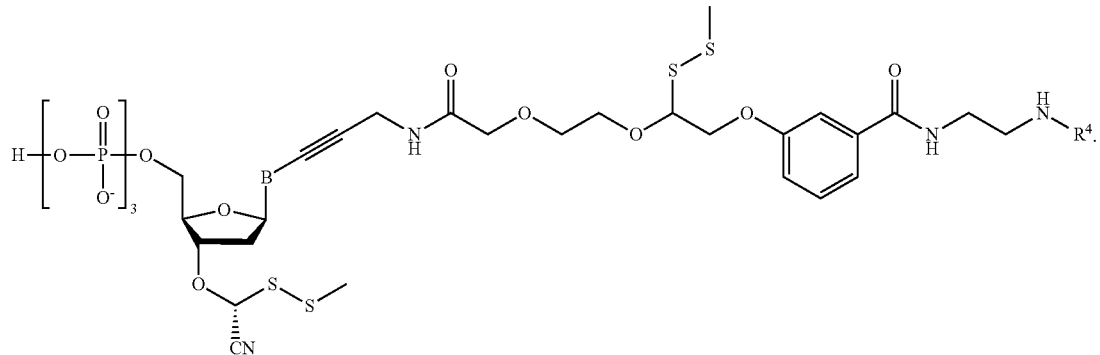

B and R⁴ are as described herein.

In embodiments, the compound has the formula:

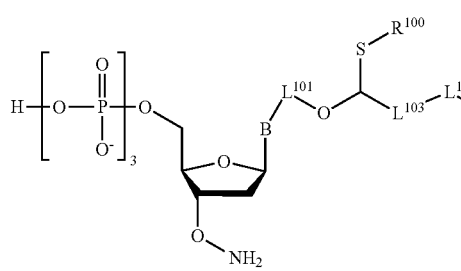

(X)

B, $L^{101}$, $L^{103}$, $L^{104}$, $L^{105}$, and R⁴ are as described herein. In embodiments of Formula (X), $R^{100}$ is —$SR^{102}$, and $R^{102}$ is as described herein (e.g., unsubstituted $C_1$-$C_4$ alkyl). In embodiments of Formula (X), $R^{100}$ is —CN.

In embodiments, the compound has the formula:

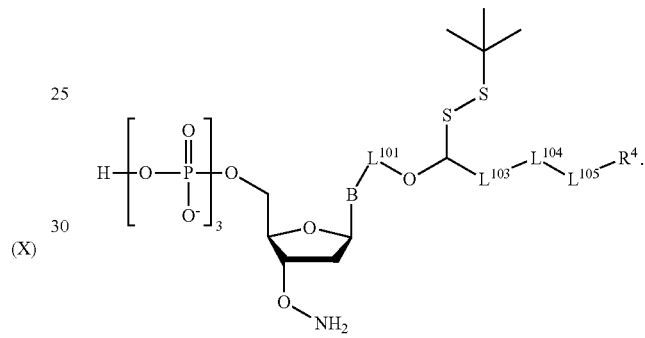

B, $L^{101}$, $L^{103}$, $L^{104}$, $L^{105}$, and R⁴ are as described herein.
In embodiments, the compound has the formula:

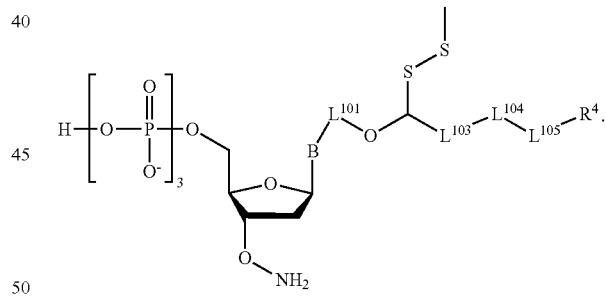

B, $L^{101}$, $L^{103}$, $L^{104}$, $L^{105}$, and R⁴ are as described herein.
In embodiments, the compound has the formula:

(XI)

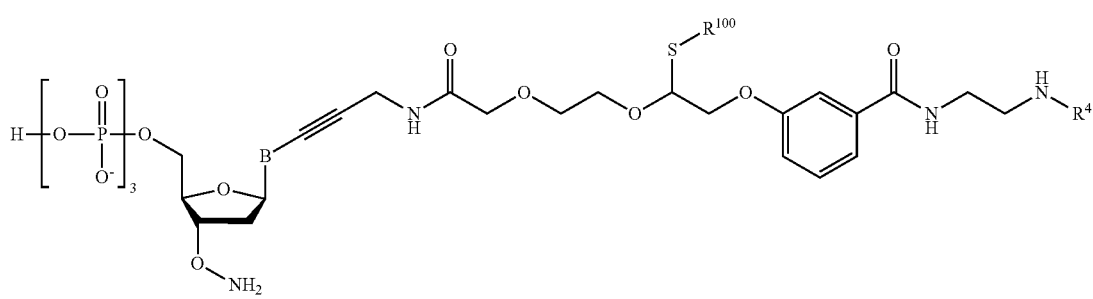

B and $R^4$ are as described herein. In embodiments of Formula (XI), $R^{100}$ is —$SR^{102}$, and $R^{102}$ is as described herein (e.g., unsubstituted $C_1$-$C_4$ alkyl). In embodiments of Formula (XI), $R^{100}$ is —CN.

In embodiments, the compound has the formula:

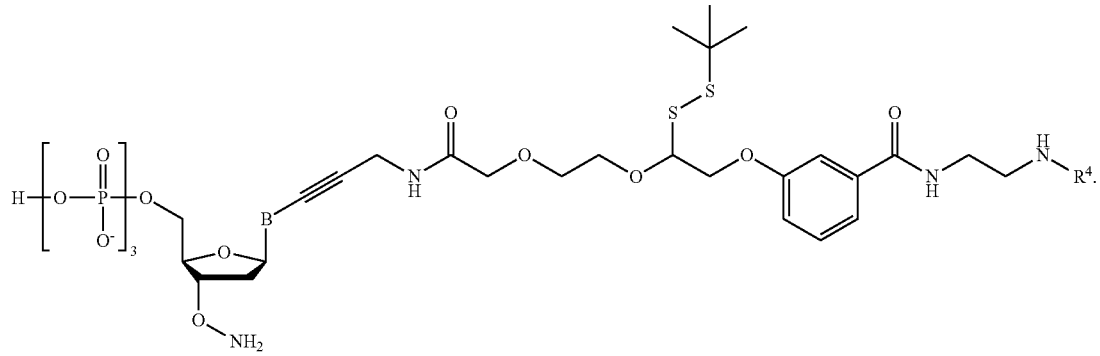

B and $R^4$ are as described herein.

In embodiments, the compound has the formula:

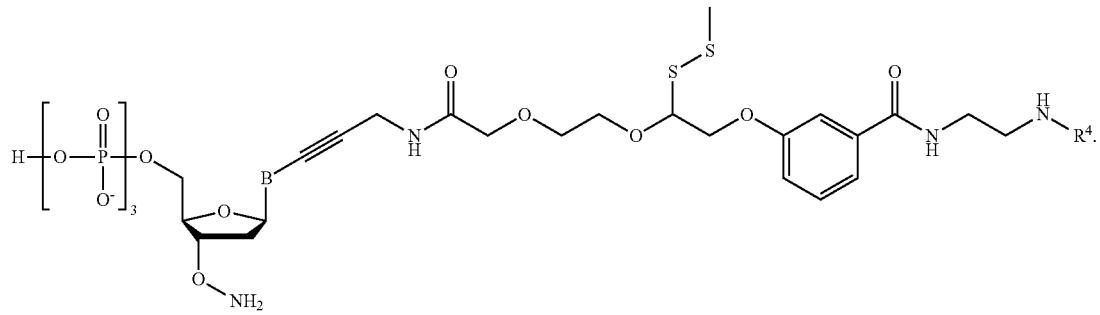

B and $R^4$ are as described herein.

In embodiments, the compound has the formula:

(XII)

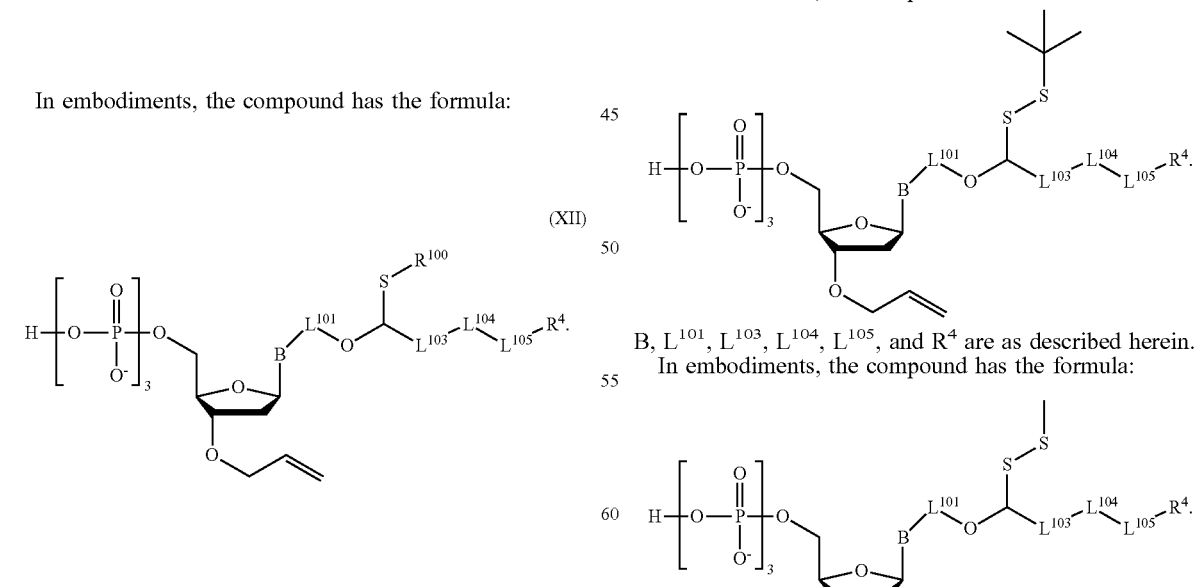

B, $L^{101}$, $L^{103}$, $L^{104}$, $L^{105}$, and $R^4$ as described herein. In embodiments of Formula (XII), $R^{100}$ is —$SR^{102}$, and $R^{102}$ is as described herein (e.g., unsubstituted $C_1$-$C_4$ alkyl). In embodiments of Formula (XII), $R^{100}$ is —CN.

In embodiments, the compound has the formula:

B, $L^{101}$, $L^{103}$, $L^{104}$, $L^{105}$, and $R^4$ are as described herein.

In embodiments, the compound has the formula:

B, $L^{101}$, $L^{103}$, $L^{104}$, $L^{105}$, and $R^4$ are as described herein.

In embodiments, the compound has the formula:

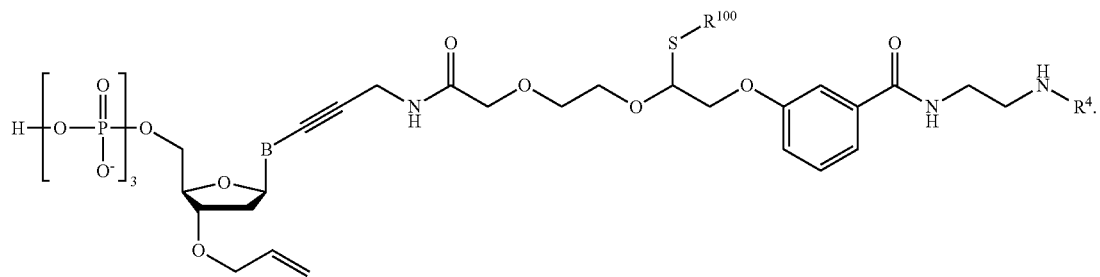
(XIII)

B and R⁴ are as described herein. In embodiments of Formula (XIII), $R^{100}$ is —$SR^{102}$, and $R^{102}$ is as described herein (e.g., unsubstituted $C_1$-$C_4$ alkyl). In embodiments of Formula (XIII), $R^{100}$ is —CN.

In embodiments, the compound has the formula:

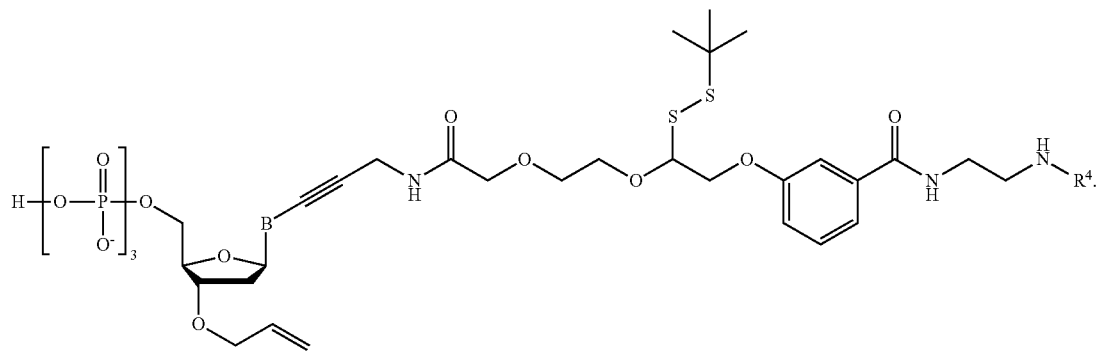

B and R⁴ are as described herein.

In embodiments, the compound has the formula:

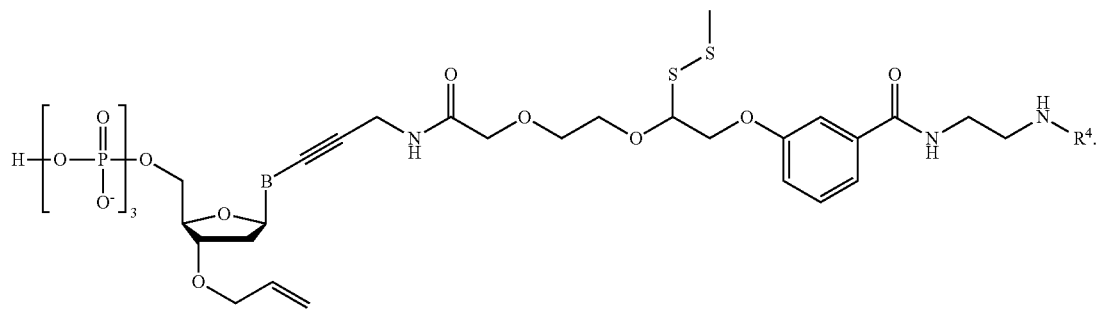

B and R⁴ are as described herein.

In embodiments, the compound has the formula:

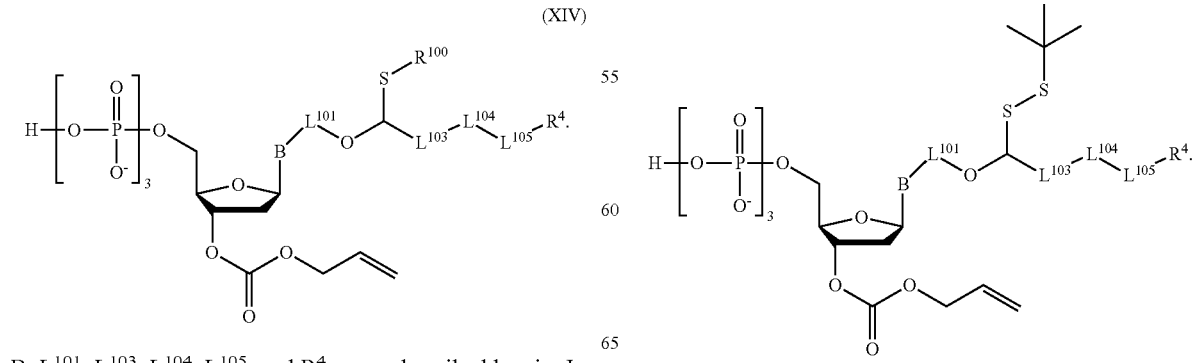
(XIV)

B, $L^{101}$, $L^{103}$, $L^{104}$, $L^{105}$, and R⁴ are as described herein. In embodiments of Formula (XIV), $R^{100}$ is —$SR^{102}$, and $R^{102}$ is as described herein (e.g., unsubstituted $C_1$-$C_4$ alkyl). In embodiments of Formula (XIV), $R^{100}$ is —CN.

In embodiments, the compound has the formula:

B, $L^{101}$, $L^{103}$, $L^{104}$, $L^{105}$, and R⁴ are as described herein.

In embodiments, the compound has the formula:

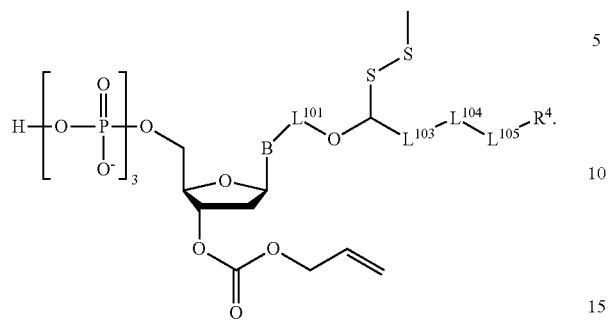

B, $L^{101}$, $L^{103}$, $L^{104}$, $L^{105}$, and $R^4$ are as described herein.

In embodiments, the compound has the formula:

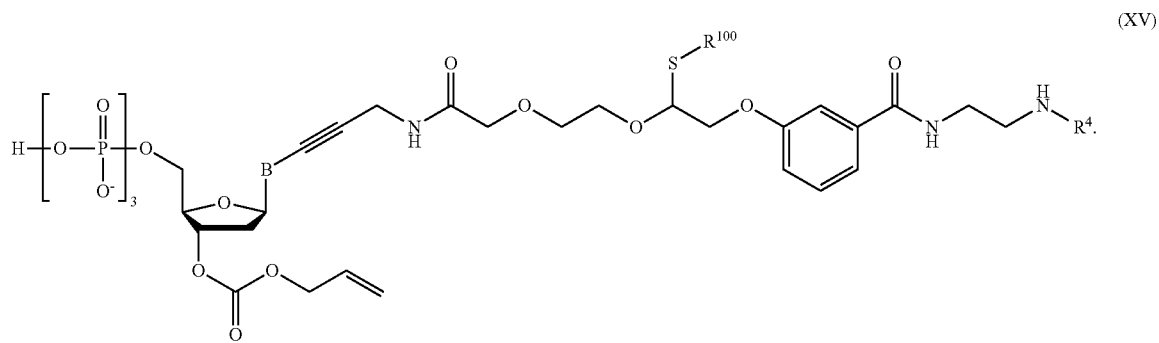

B and $R^4$ are as described herein. In embodiments of Formula (XV), $R^{100}$ is $-SR^{102}$, and $R^{102}$ is as described herein. In embodiments of Formula (XV), $R^{100}$ is $-CN$.

In embodiments, the compound has the formula:

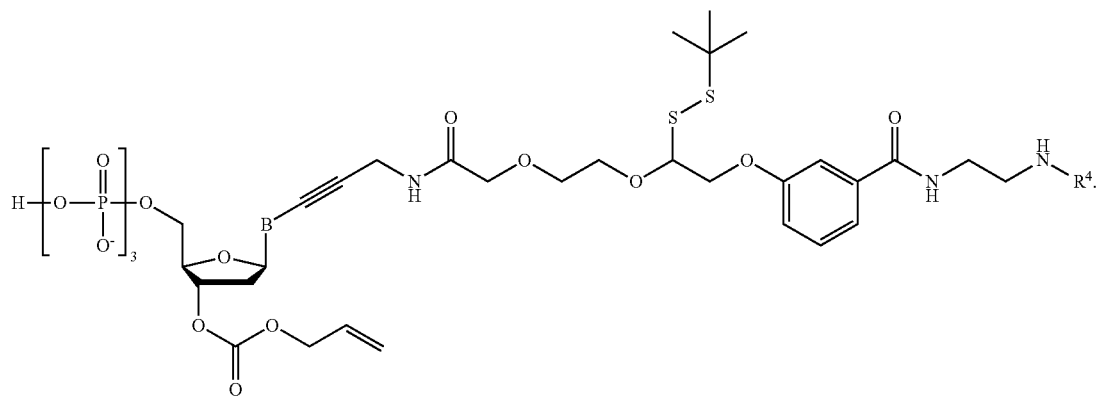

B and $R^4$ are as described herein.

In embodiments, the compound has the formula:

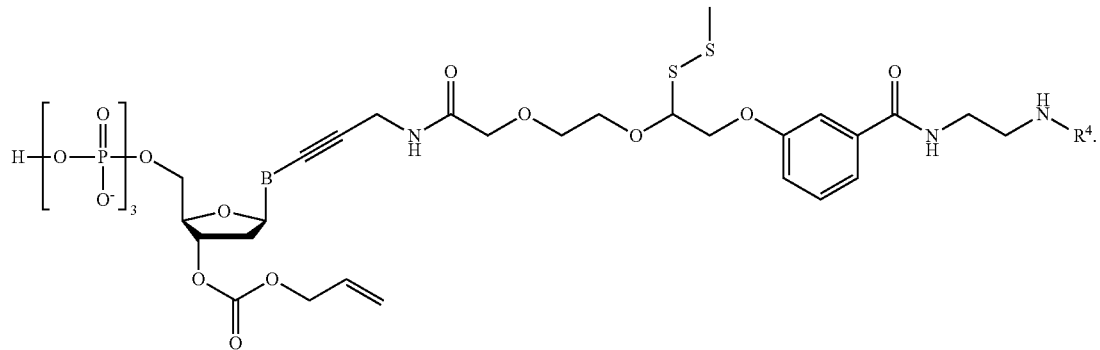

B and $R^4$ are as described herein.

In embodiments, the compound has the formula:

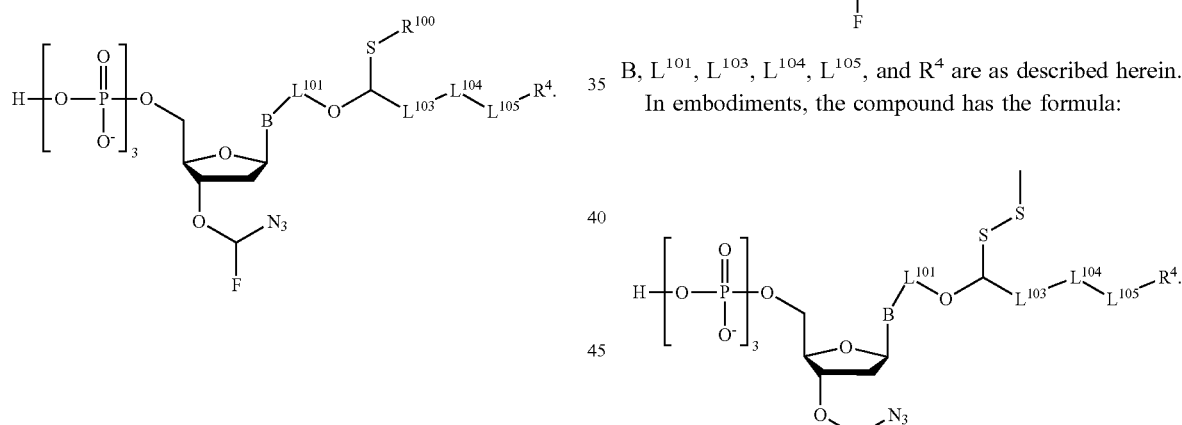

(XVI)

B, $L^{101}$, $L^{103}$, $L^{104}$, $L^{105}$, and $R^4$ are as described herein. In embodiments of Formula (XVI), $R^{100}$ is —$SR^{102}$, and $R^{102}$ is as described herein (e.g., unsubstituted $C_1$-$C_4$ alkyl). In embodiments of Formula (XVI), $R^{100}$ is —CN.

In embodiments, the compound has the formula:

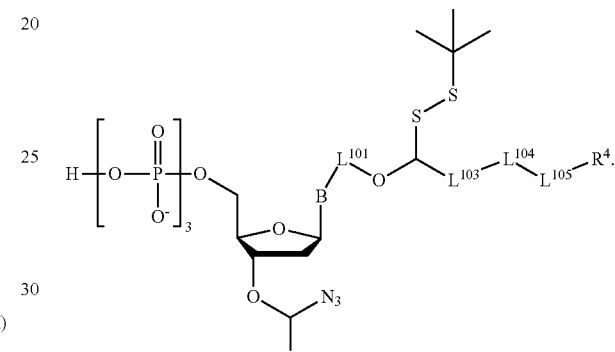

B, $L^{101}$, $L^{103}$, $L^{104}$, $L^{105}$, and $R^4$ are as described herein.

In embodiments, the compound has the formula:

B, $L^{101}$, $L^{103}$, $L^{104}$, $L^{105}$, and $R^4$ are as described herein.

In embodiments, the compound has the formula:

(XVII)

B and R⁴ are as described herein. In embodiments of Formula (XVII), $R^{100}$ is —$SR^{102}$, and $R^{102}$ is as described herein. In embodiments of Formula (XVII), $R^{100}$ is —CN.

In embodiments, the compound has the formula:

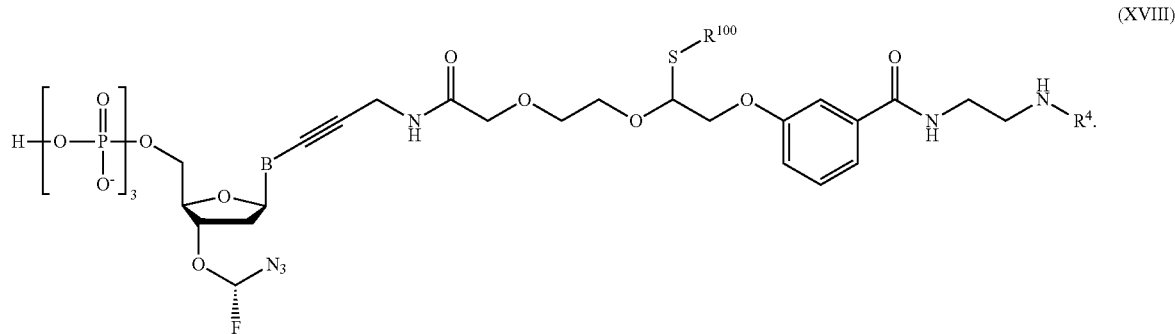

(XVIII)

B and R⁴ are as described herein. In embodiments of Formula (XVIII), $R^{100}$ is —$SR^{102}$, and $R^{102}$ is as described herein. In embodiments of Formula (XVIII), $R^{100}$ is —CN.

In embodiments, the compound has the formula:

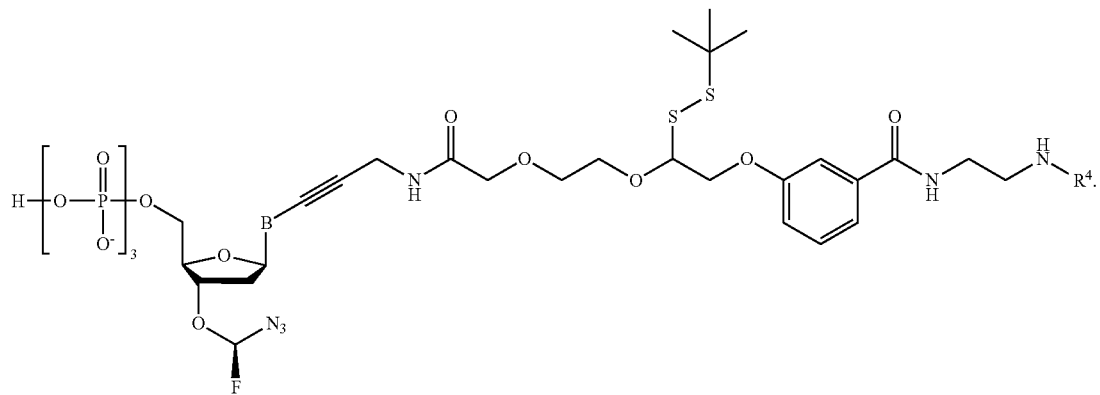

B and R⁴ are as described herein.

In embodiments, the compound has the formula:

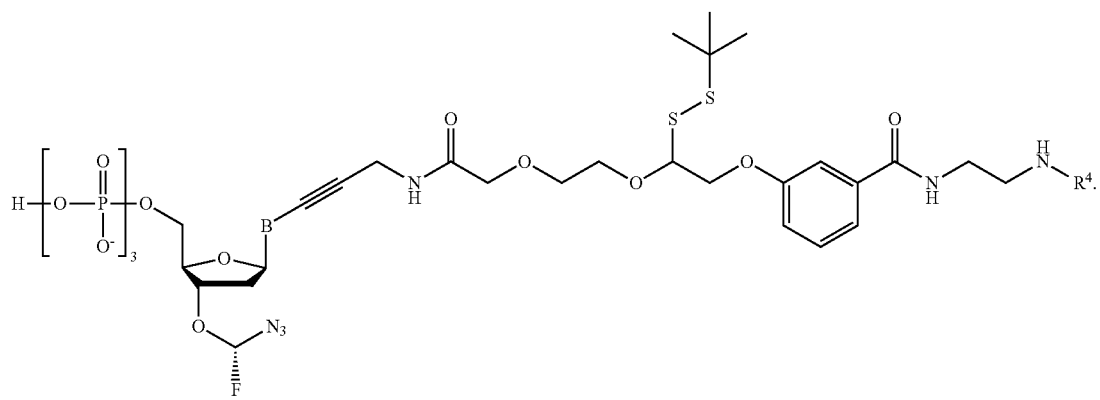

B and R⁴ are as described herein.

In embodiments, the compound has the formula:

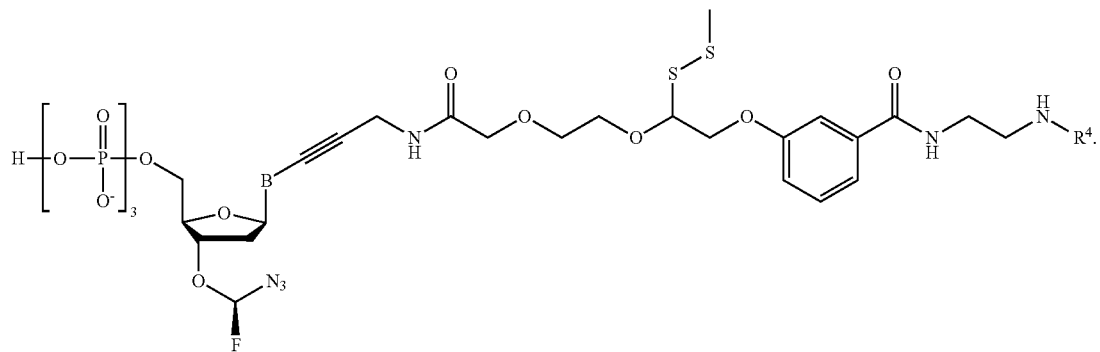

B and R⁴ are as described herein.

In embodiments, the compound has the formula:

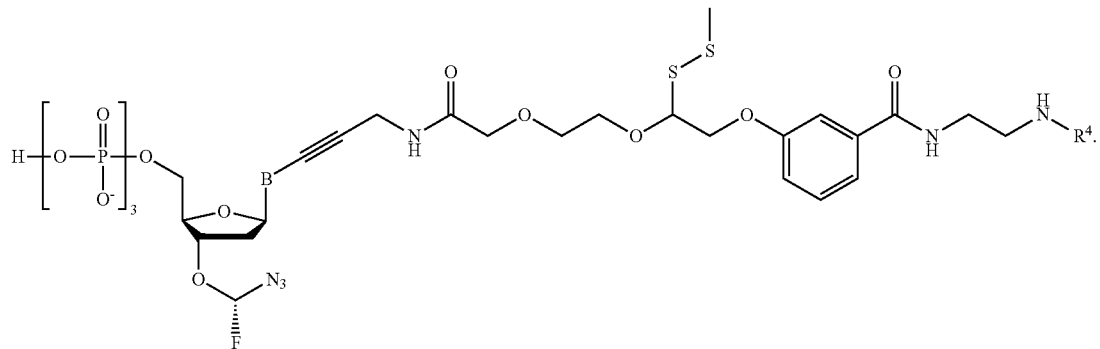

B and R⁴ are as described herein.

In embodiments, the compound has the formula:

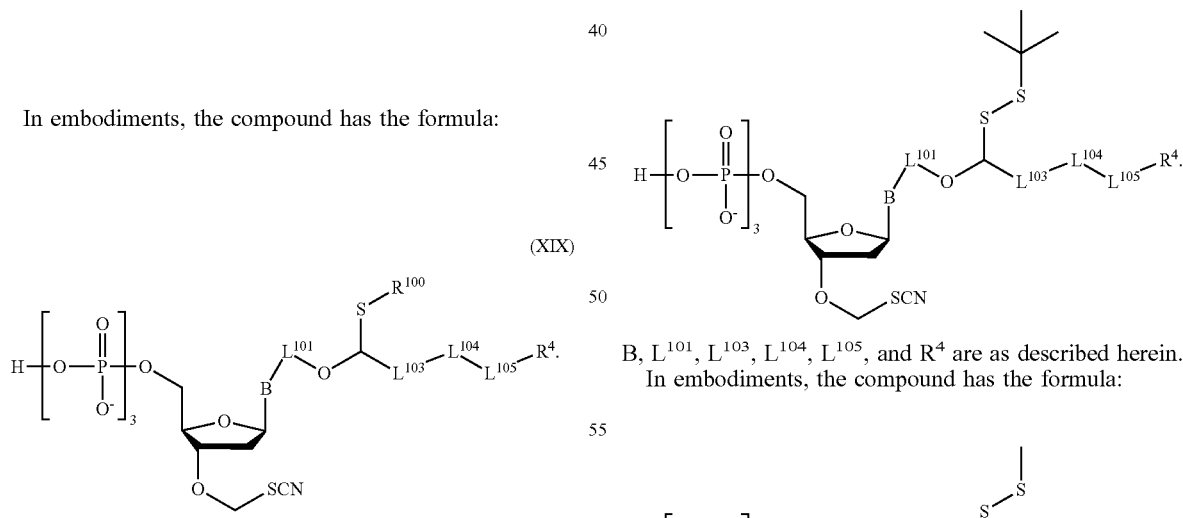

(XIX)

B, $L^{101}$, $L^{103}$, $L^{104}$, $L^{105}$, and R⁴ are as described herein. In embodiments of Formula (XIX), $R^{100}$ is —$SR^{102}$, and $R^{102}$ is as described herein (e.g., unsubstituted $C_1$-$C_4$ alkyl). In embodiments of Formula (XIX), $R^{100}$ is —CN.

B, $L^{101}$, $L^{103}$, $L^{104}$, $L^{105}$, and R⁴ are as described herein.

In embodiments, the compound has the formula:

B, $L^{101}$, $L^{103}$, $L^{104}$, $L^{105}$, and R⁴ are as described herein.

In embodiments, the compound has the formula:

B, $L^{101}$, $L^{103}$, $L^{104}$, $L^{105}$, and R⁴ are as described herein.

In embodiments, the compound has the formula:

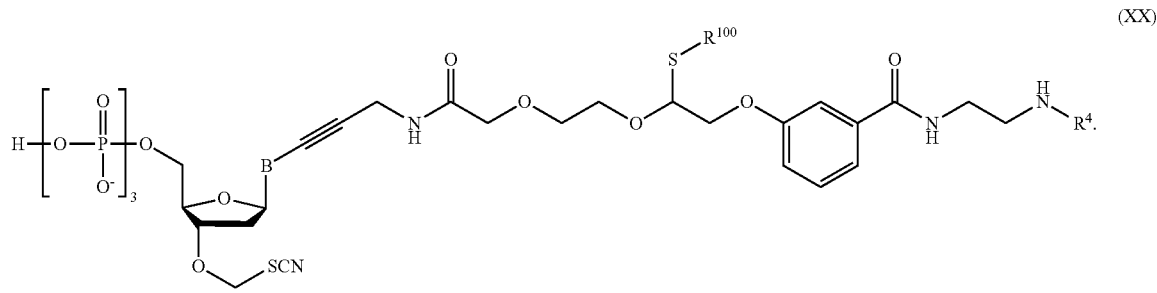

(XX)

B and R⁴ are as described herein. In embodiments of Formula (XX), $R^{100}$ is —$SR^{102}$, and $R^{102}$ is as described herein (e.g., unsubstituted $C_1$-$C_4$ alkyl). In embodiments of Formula (XX), $R^{100}$ is —CN.

In embodiments, the compound has the formula:

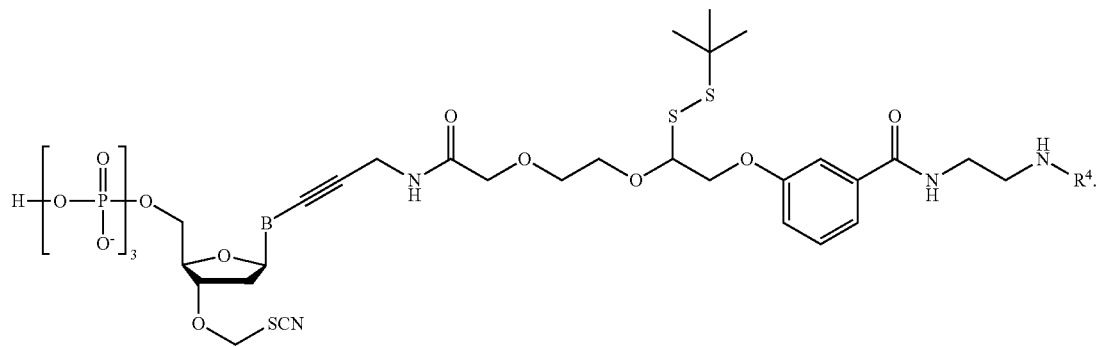

B and R⁴ are as described herein.

In embodiments, the compound has the formula:

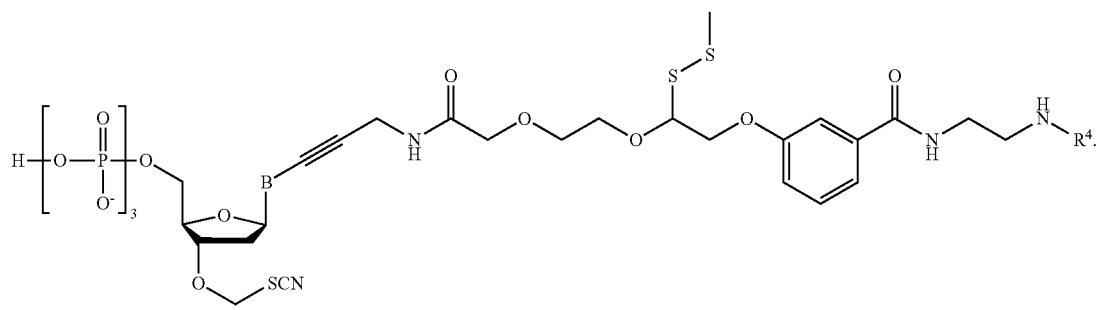

B and R⁴ are as described herein.

In embodiments, the compound has the formula:

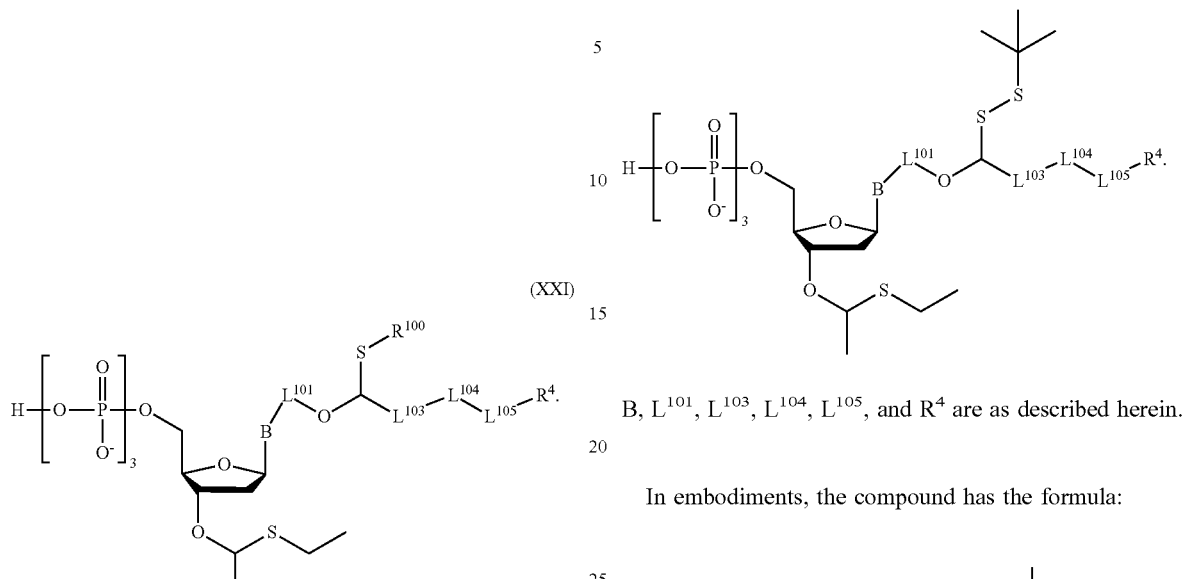

(XXI)

B, $L^{101}$, $L^{103}$, $L^{104}$, $L^{105}$, and $R^4$ are as described herein. In embodiments of Formula (XXI), $R^{100}$ is $-SR^{102}$, and $R^{102}$ is as described herein (e.g., unsubstituted $C_1$-$C_4$ alkyl). In embodiments of Formula (XXI), $R^{100}$ is —CN.

In embodiments, the compound has the formula:

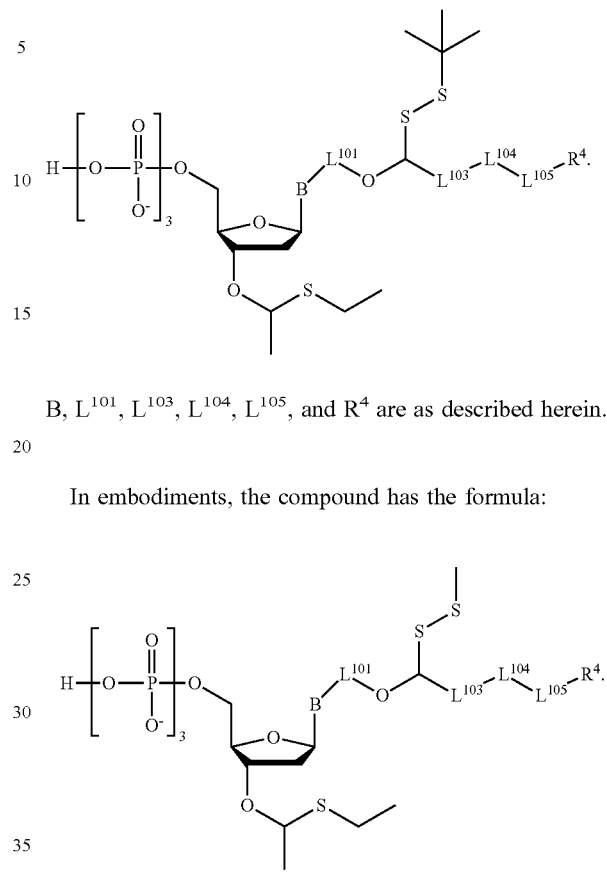

B, $L^{101}$, $L^{103}$, $L^{104}$, $L^{105}$, and $R^4$ are as described herein.

In embodiments, the compound has the formula:

B, $L^{101}$, $L^{103}$, $L^{104}$, $L^{105}$, and $R^4$ are as described herein.

In embodiments, the compound has the formula:

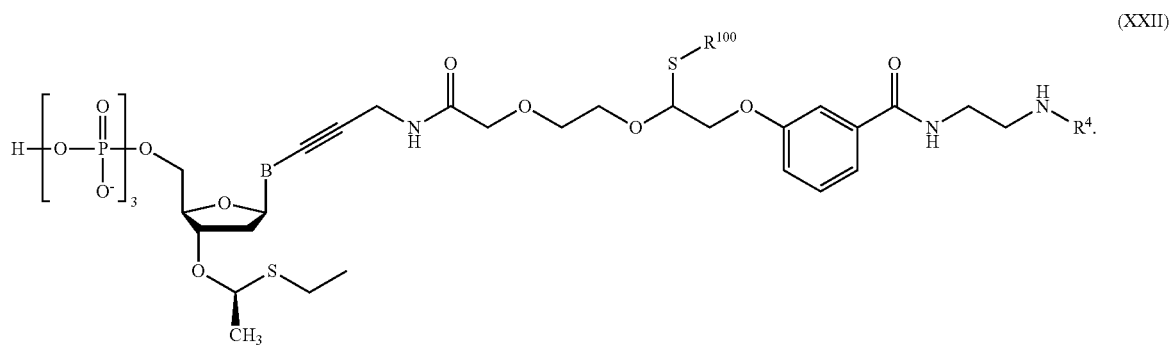

(XXII)

B and $R^4$ are as described herein. In embodiments of Formula (XXII), $R^{100}$ is $-SR^{102}$, and $R^{102}$ is as described herein (e.g., unsubstituted $C_1$-$C_4$ alkyl). In embodiments of Formula (XXII), $R^{100}$ is —CN.

In embodiments, the compound has the formula:

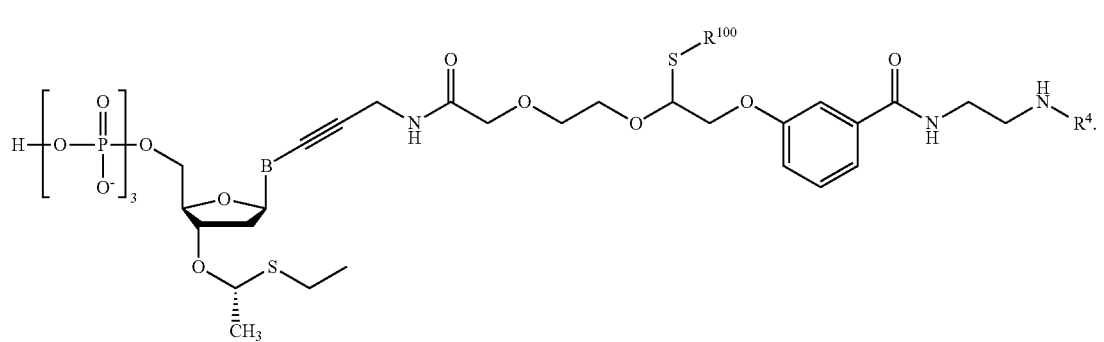
(XXIII)

B and R⁴ are as described herein. In embodiments of Formula (XXIII), $R^{100}$ is —$SR^{102}$, and $R^{102}$ is as described herein (e.g., unsubstituted $C_1$-$C_4$ alkyl). In embodiments of Formula (XXIII), $R^{100}$ is —CN.

In embodiments, the compound has the formula:

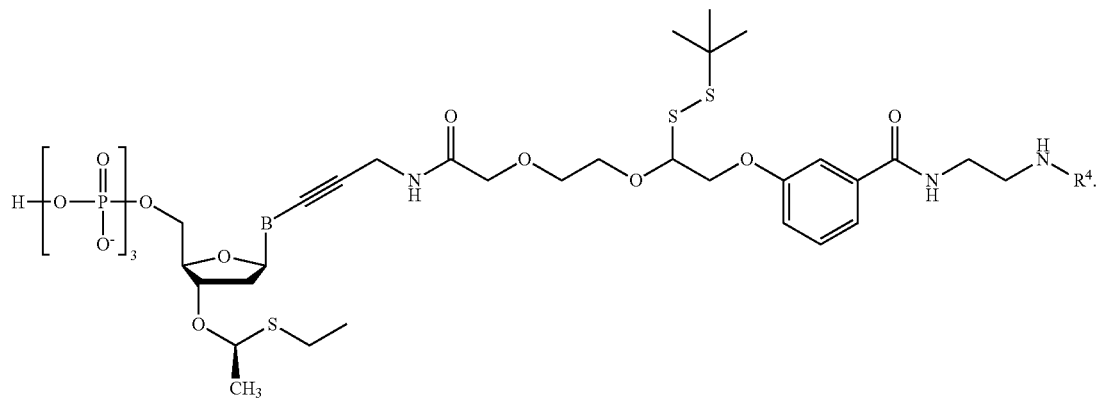

B and R⁴ are as described herein.

In embodiments, the compound has the formula:

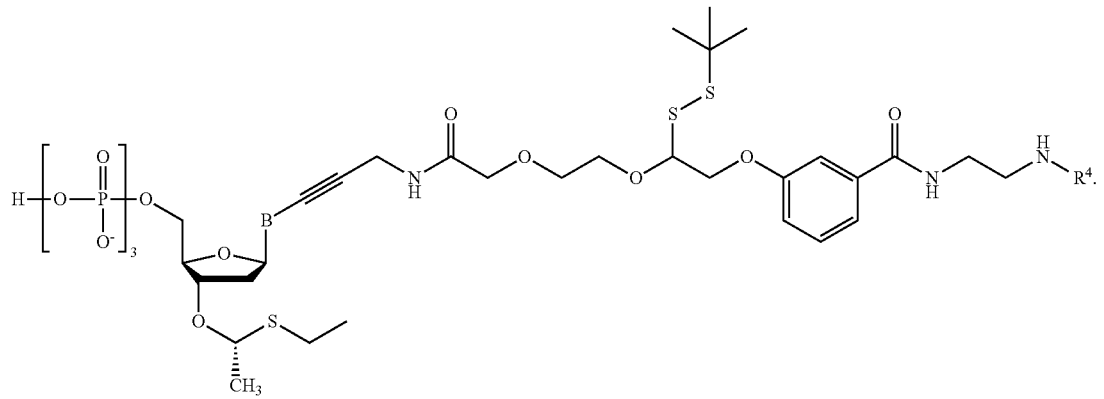

B and R⁴ are as described herein.

In embodiments, the compound has the formula:

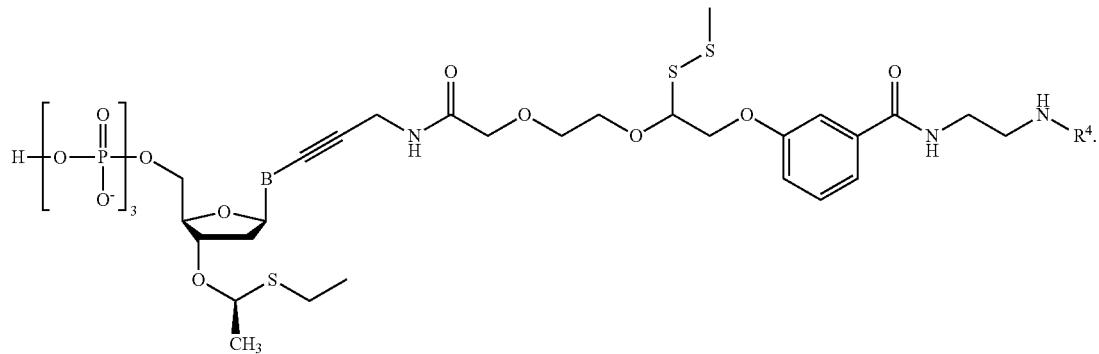

B and R⁴ are as described herein.

In embodiments, the compound has the formula:

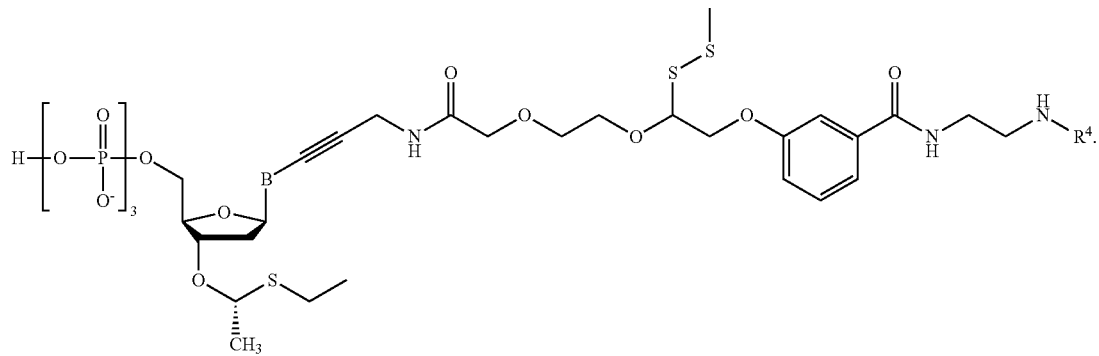

B and R⁴ are as described herein.

In embodiments, the compound has the formula:

(XXIV)

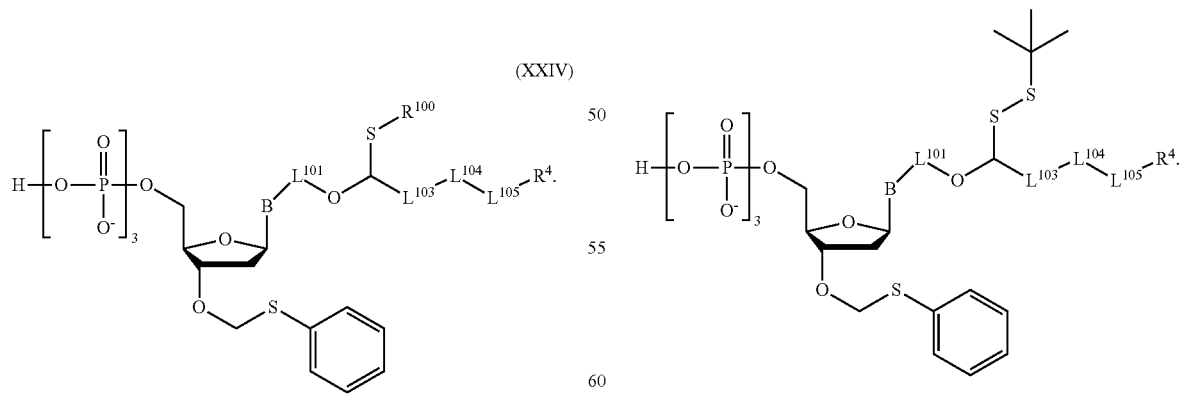

B, $L^{101}$, $L^{103}$, $L^{104}$, $L^{105}$, and R⁴ are as described herein. In embodiments of Formula (XXIV), $R^{100}$ is —$SR^{102}$, and $R^{102}$ is as described herein (e.g., unsubstituted $C_1$-$C_4$ alkyl). In embodiments of Formula (XXIV), $R^{100}$ is —CN.

In embodiments, the compound has the formula:

B, $L^{101}$, $L^{103}$, $L^{104}$, $L^{105}$, and R⁴ are as described herein.

In embodiments, the compound has the formula:

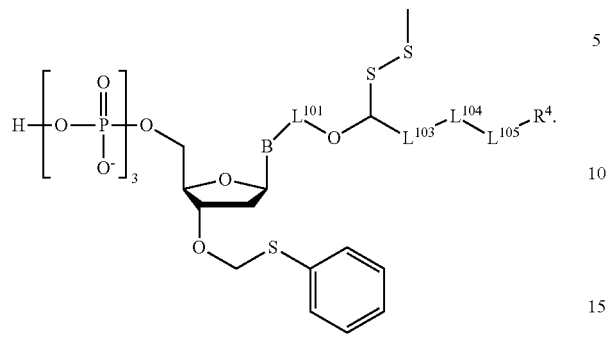

B, $L^{101}$, $L^{103}$, $L^{104}$, $L^{105}$, and $R^4$ are as described herein.

In embodiments, the compound has the formula:

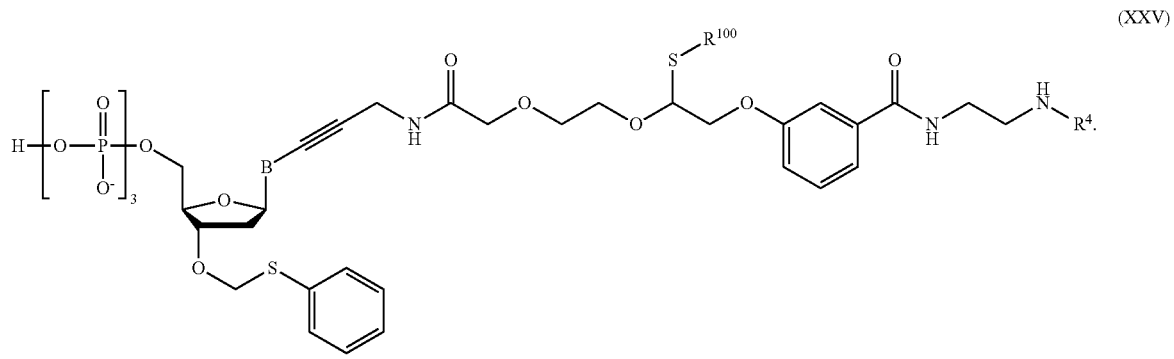

(XXV)

B and $R^4$ are as described herein. In embodiments of Formula (XXV), $R^{100}$ is —$SR^{102}$, and $R^{102}$ is as described herein (e.g., unsubstituted $C_1$-$C_4$ alkyl). In embodiments of Formula (XXV), $R^{100}$ is —CN.

In embodiments, the compound has the formula:

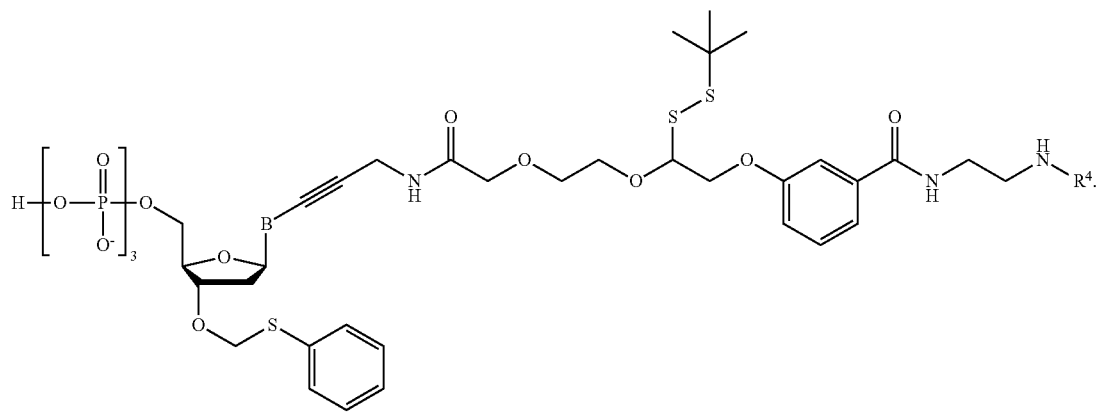

B and $R^4$ are as described herein.

In embodiments, the compound has the formula:

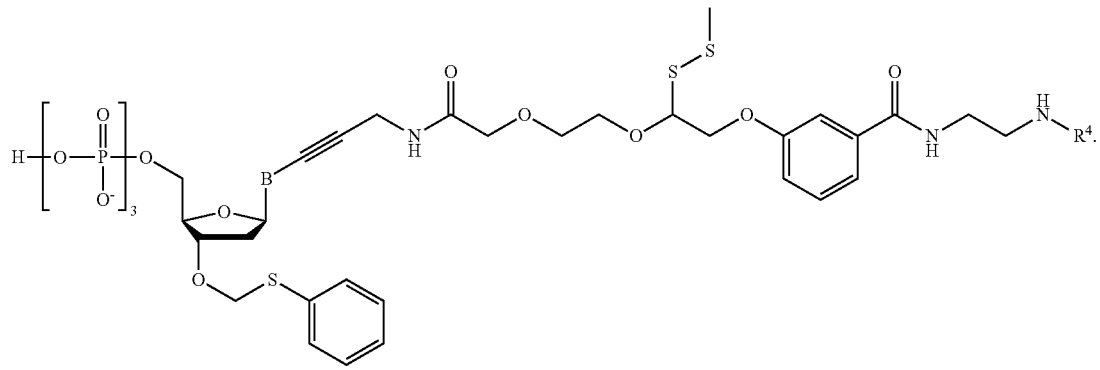

B and R⁴ are as described herein.

In embodiments, the compound has the formula:

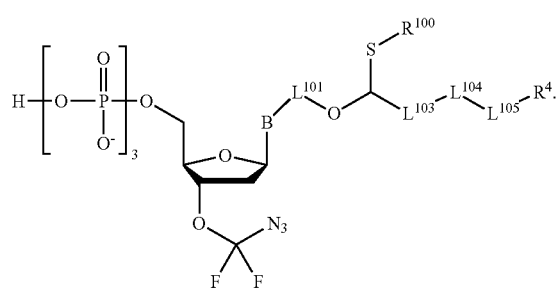

(XXVI)

B, $L^{101}$, $L^{103}$, $L^{104}$, $L^{105}$, and R⁴ are as described herein. In embodiments of Formula (XXVI), $R^{100}$ is —$SR^{102}$, and $R^{102}$ is as described herein (e.g., unsubstituted $C_1$-$C_4$ alkyl). In embodiments of Formula (XXVI), $R^{100}$ is —CN.

In embodiments, the compound has the formula:

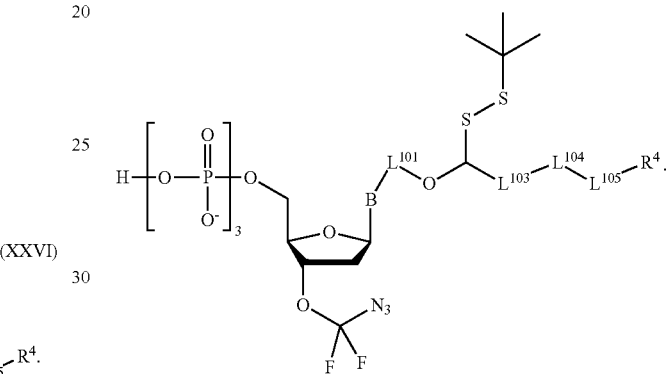

B, $L^{101}$, $L^{103}$, $L^{104}$, $L^{105}$, and R⁴ are as described herein.

In embodiments, the compound has the formula:

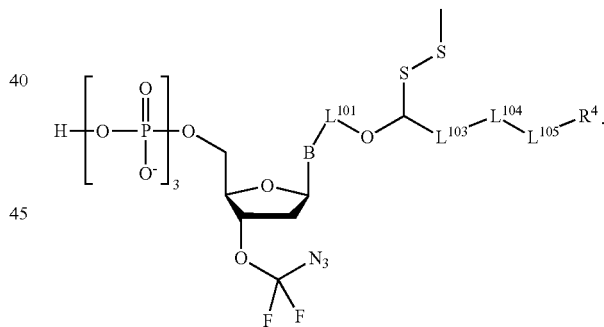

B, $L^{101}$, $L^{103}$, $L^{104}$, $L^{105}$, and R⁴ are as described herein.

In embodiments, the compound has the formula:

(XXVII)

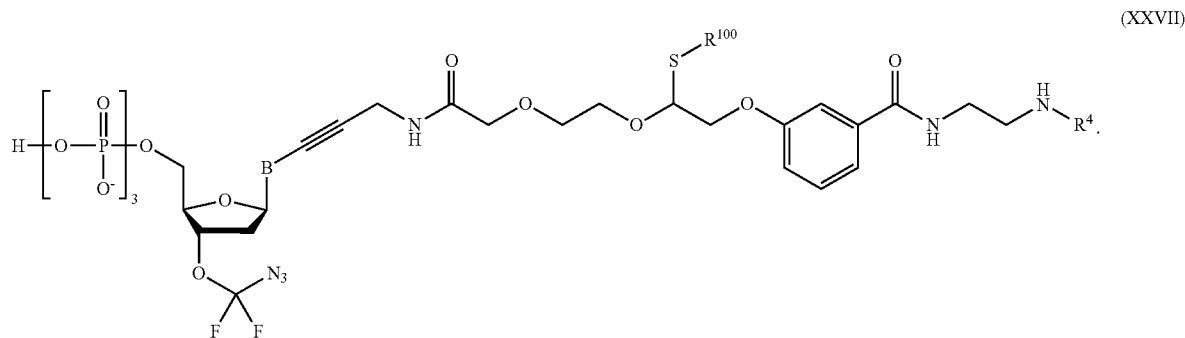

B and R⁴ are as described herein. In embodiments of Formula (XXVII), $R^{100}$ is —$SR^{102}$, and $R^{102}$ is as described herein (e.g., unsubstituted $C_1$-$C_4$ alkyl). In embodiments of Formula (XXVII), $R^{100}$ is —CN.

In embodiments, the compound has the formula:

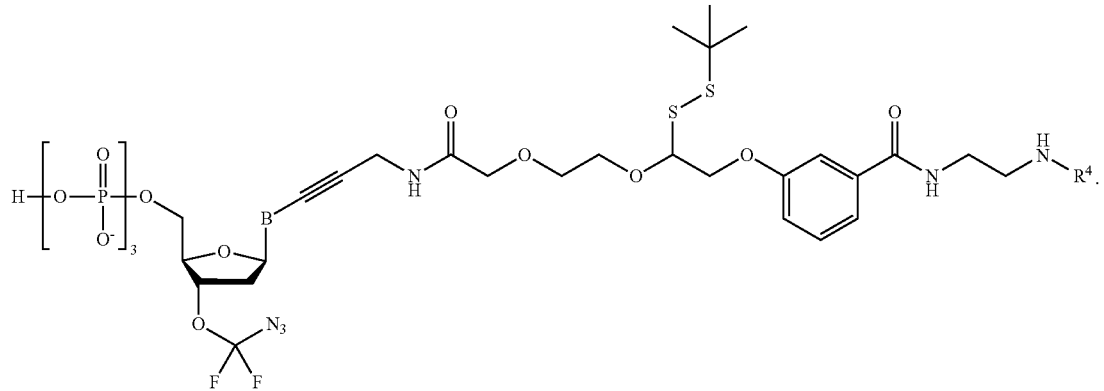

B and R⁴ are as described herein.

In embodiments, the compound has the formula:

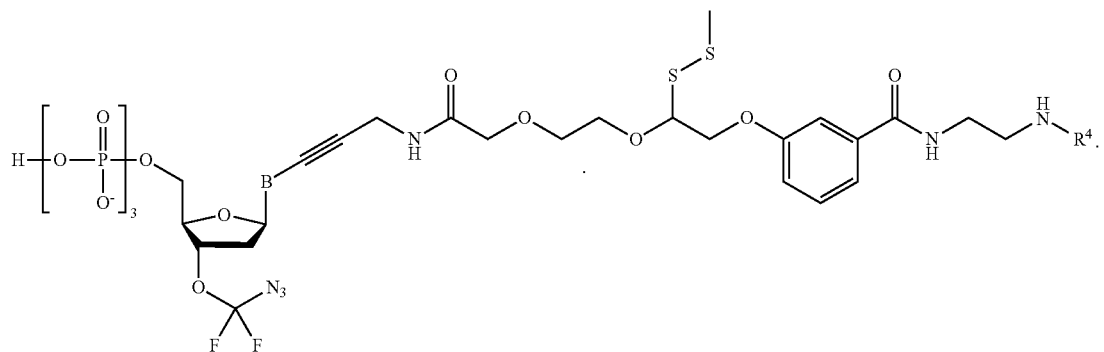

B and R⁴ are as described herein.

In embodiments, the compound has the formula:

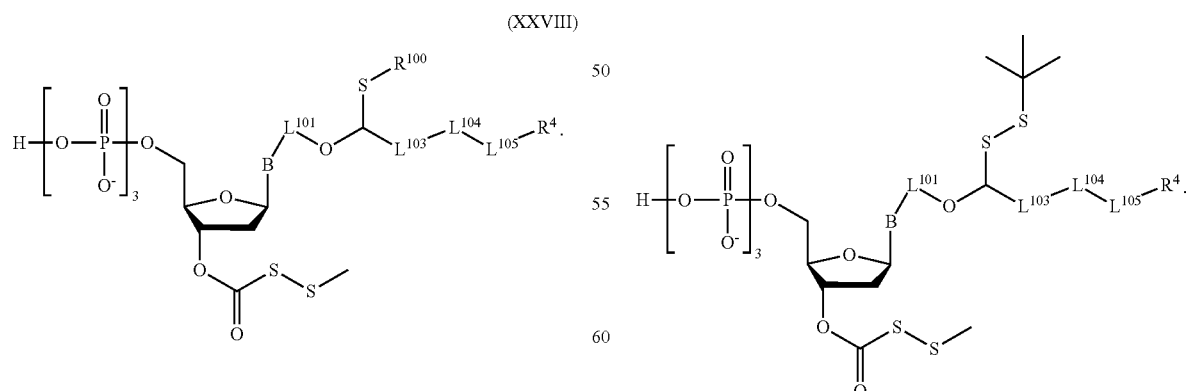

B, $L^{101}$, $L^{103}$, $L^{104}$, $L^{105}$, and R⁴ are as described herein. In embodiments of Formula (XXVIII), $R^{100}$ is —$SR^{102}$ and $R^{102}$ is as described herein (e.g., unsubstituted $C_1$-$C_4$ alkyl). In embodiments of Formula (XXVIII), $R^{100}$ is —CN.

B, $L^{101}$, $L^{103}$, $L^{104}$, $L^{105}$, and R⁴ are as described herein.

In embodiments, the compound has the formula:

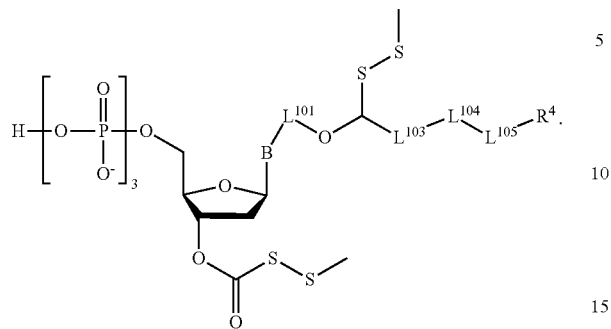

B, $L^{101}$, $L^{103}$, $L^{104}$, $L^{105}$, and $R^4$ are as described herein.

In embodiments, the compound has the formula:

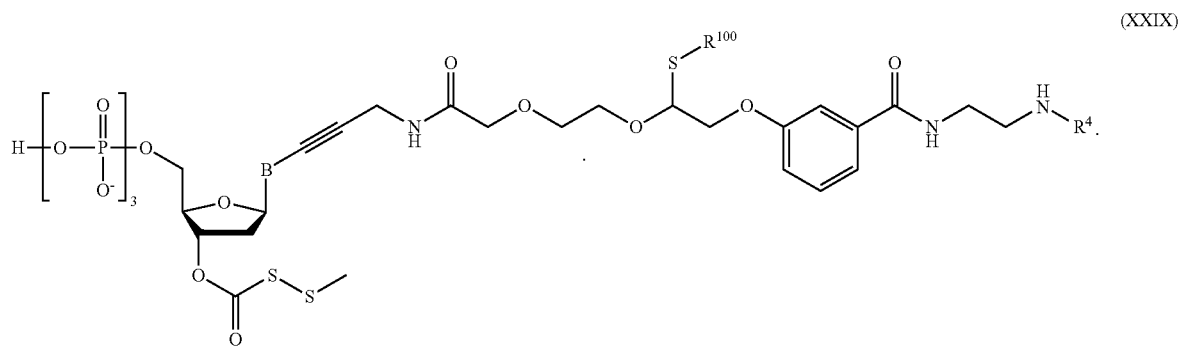

(XXIX)

B and $R^4$ are as described herein. In embodiments of Formula (XXIX), $R^{100}$ is —$SR^{102}$, and $R^{102}$ is as described herein (e.g., unsubstituted $C_1$-$C_4$ alkyl). In embodiments of Formula (XXIX), $R^{100}$ is —CN.

In embodiments, the compound has the formula:

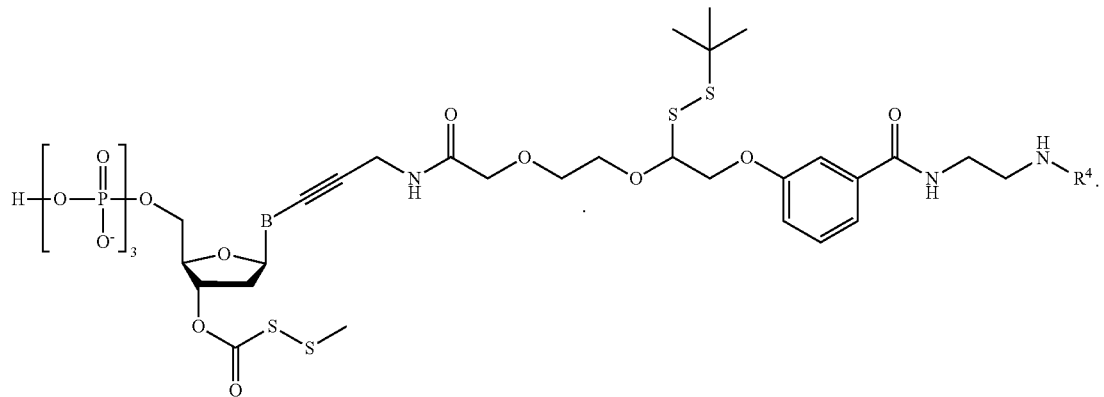

B and $R^4$ are as described herein.

In embodiments, the compound has the formula:

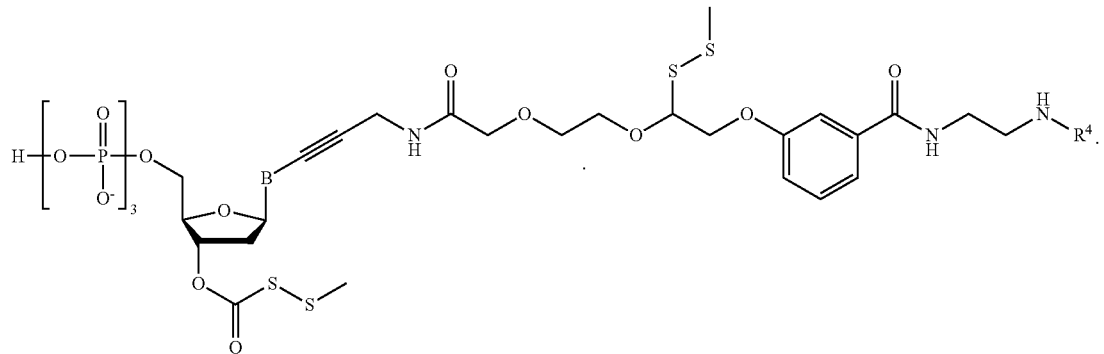

B and R⁴ are as described herein.

In embodiments, the compound has the formula:

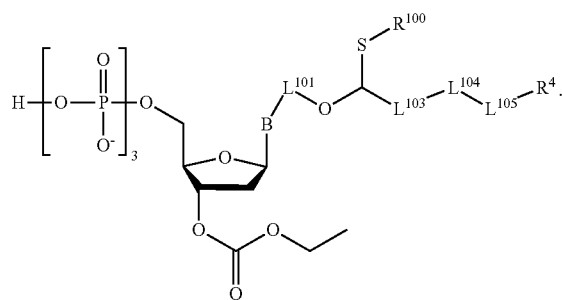

(XXX)

B, $L^{101}$, $L^{103}$, $L^{104}$, $L^{105}$, and R⁴ are as described herein. In embodiments of Formula (XXX), $R^{100}$ is —$SR^{102}$, and $R^{102}$ is as described herein (e.g., unsubstituted $C_1$-$C_4$ alkyl). In embodiments of Formula (XXX), $R^{100}$ is —CN.

In embodiments, the compound has the formula:

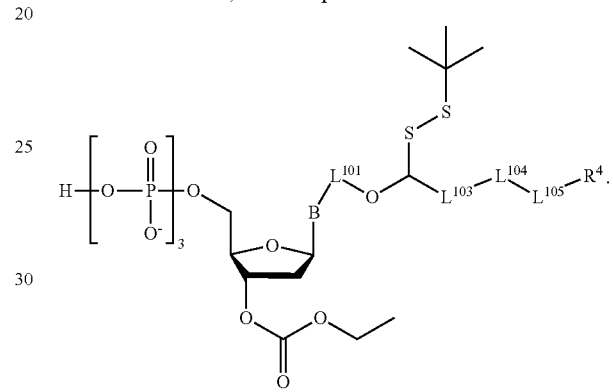

B, $L^{101}$, $L^{103}$, $L^{104}$, $L^{105}$, and R⁴ are as described herein.

In embodiments, the compound has the formula:

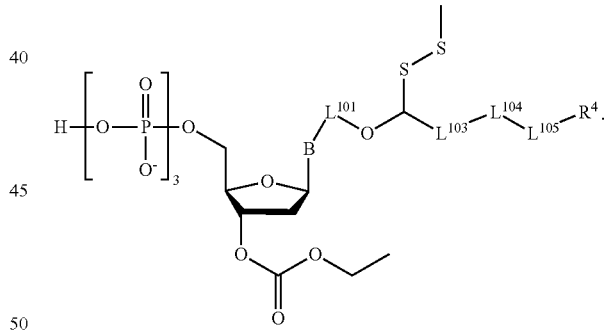

B, $L^{101}$, $L^{103}$, $L^{104}$, $L^{105}$, and R⁴ are as described herein.

In embodiments, the compound has the formula:

(XXXI)

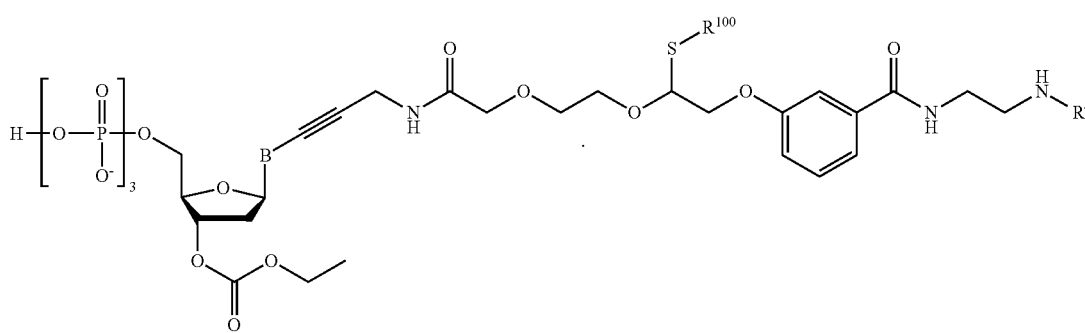

B and $R^4$ are as described herein. In embodiments of Formula (XXXI), $R^{100}$ is —$SR^{102}$, and $R^{102}$ is as described herein (e.g., unsubstituted $C_1$-$C_4$ alkyl). In embodiments of Formula (XXXI), $R^{100}$ is —CN.

In embodiments, the compound has the formula:

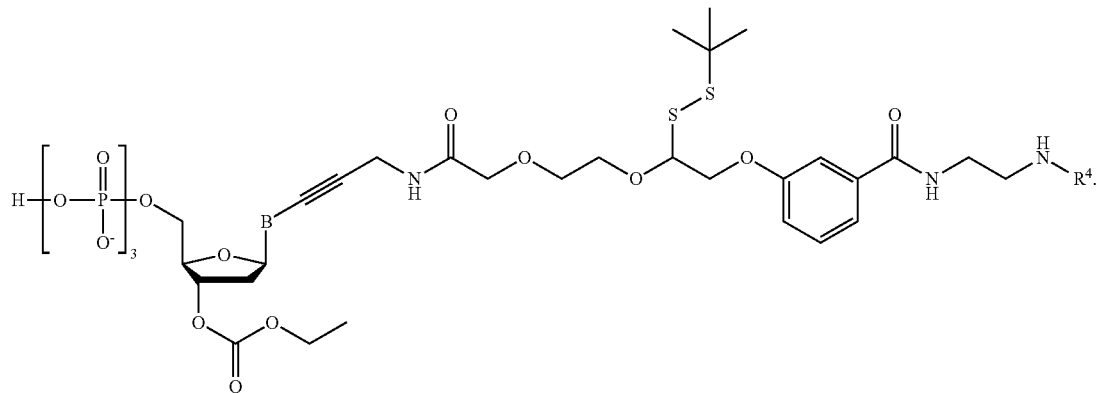

$R^4$ are as described herein.

In embodiments, the compound has the formula:

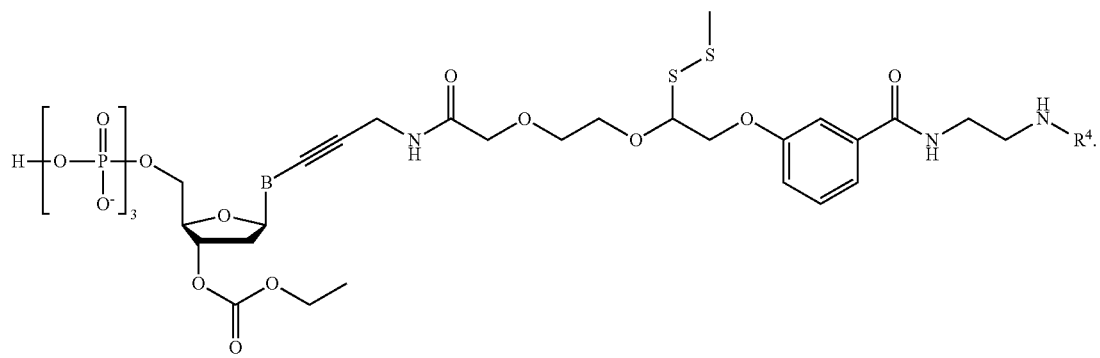

B and $R^4$ are as described herein.

In embodiments, the compound has the formula:

In embodiments, the compound has the formula:

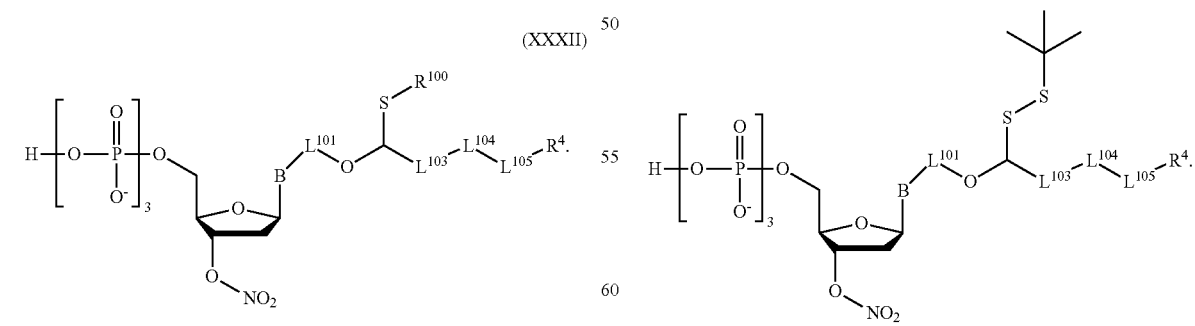

B, $L^{101}$, $L^{103}$, $L^{104}$, $L^{105}$, and $R^4$ are as described herein. In embodiments of Formula (XXXII), $R^{100}$ is —$SR^{102}$, and $R^{102}$ is as described herein (e.g. unsubstituted $C_1$-$C_4$ alkyl). In embodiments of Formula (XXXII), $R^{100}$ is —CN.

In embodiments, the compound has the formula:

B, $L^{101}$, $L^{103}$, $L^{104}$, $L^{105}$, and $R^4$ are as described herein.

In embodiments, the compound has the formula:

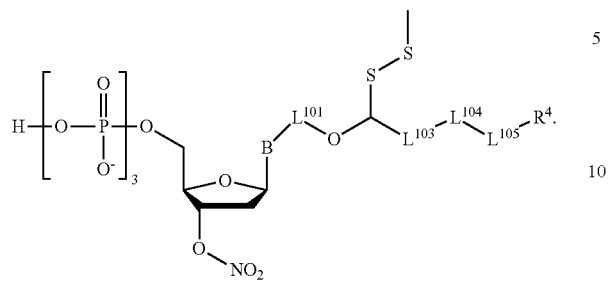

B, $L^{101}$, $L^{103}$, $L^{104}$, $L^{105}$, and $R^4$ are as described herein.

In embodiments, the compound has the formula:

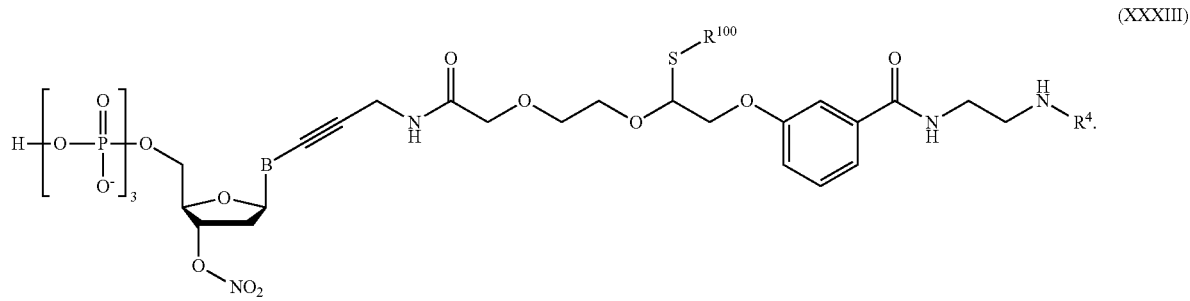

(XXXIII)

B and $R^4$ are as described herein. In embodiments of Formula (XXXIII), $R^{100}$ is $-SR^{102}$, and $R^{102}$ is as described herein (e.g., unsubstituted $C_1$-$C_4$ alkyl). In embodiments of Formula (XXXIII), $R^{100}$ is $-CN$.

In embodiments, the compound has the formula:

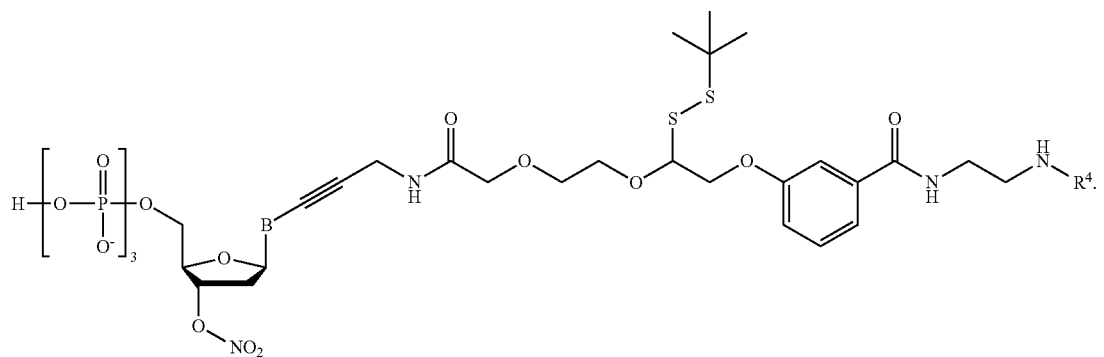

B and $R^4$ are as described herein.

In embodiments, the compound has the formula:

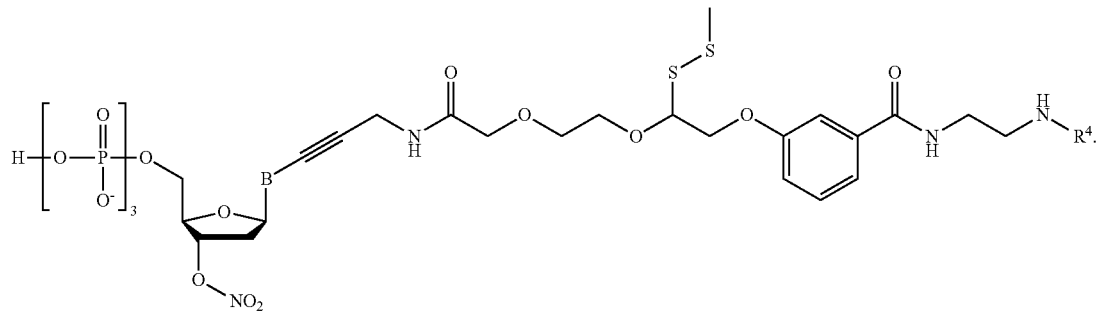

B and R⁴ are as described herein.

In embodiments, the compound has the formula:

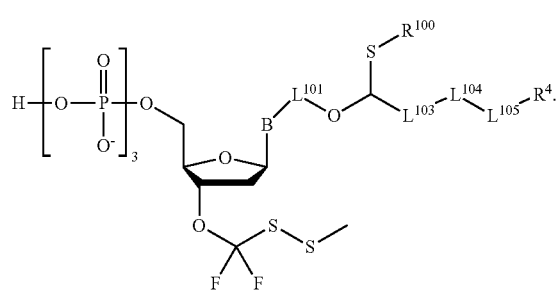

(XXXIV)

B, L¹⁰, L¹⁰³, L¹⁰⁴, L¹⁰⁵ and R⁴ are as described herein. In embodiments of Formula (XXXIV), R¹⁰⁰ is —SR¹⁰² and R¹⁰² is as described herein (e.g., unsubstituted C₁-C₄ alkyl). In embodiments of Formula (XXXIV), R¹⁰⁰ is —CN.

In embodiments, the compound has the formula:

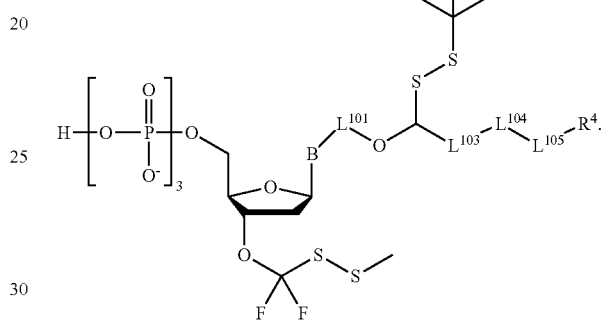

B, L¹⁰¹, L¹⁰³, L¹⁰⁴, L¹⁰⁵, and R⁴ are as described herein.

In embodiments, the compound has the formula:

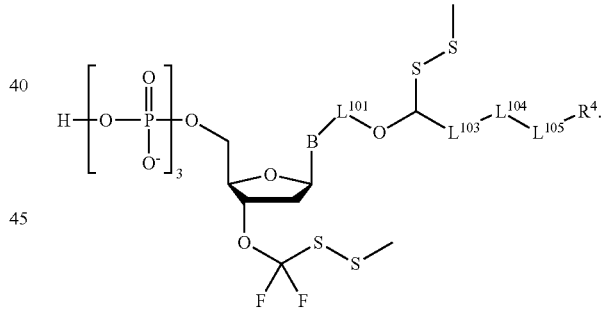

B, L¹⁰¹, L¹⁰³, L¹⁰⁴, L¹⁰⁵, and R⁴ are as described herein.

In embodiments, the compound has the formula:

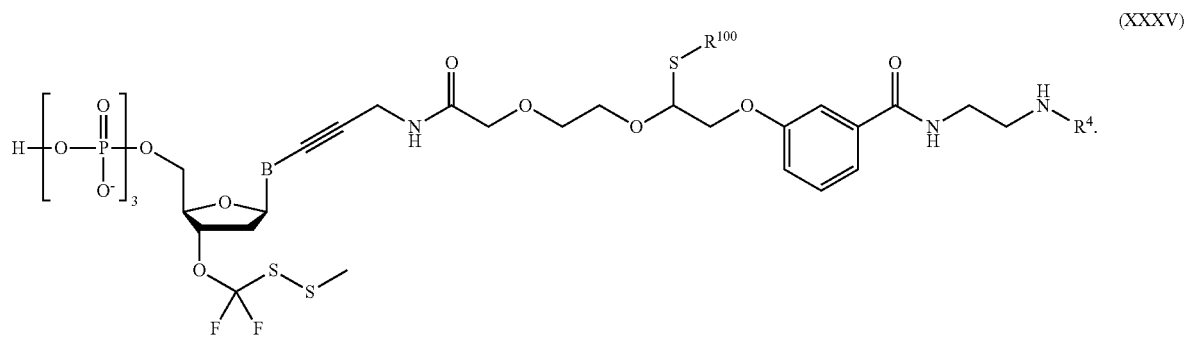

(XXXV)

B and R⁴ are as described herein. In embodiments of Formula (XXXV), R¹⁰⁰ is —SR¹⁰² and R¹⁰² is as described herein (e.g., unsubstituted $C_1$-$C_4$ alkyl). In embodiments of Formula (XXXV), R¹⁰⁰ is —CN.

In embodiments, the compound has the formula:

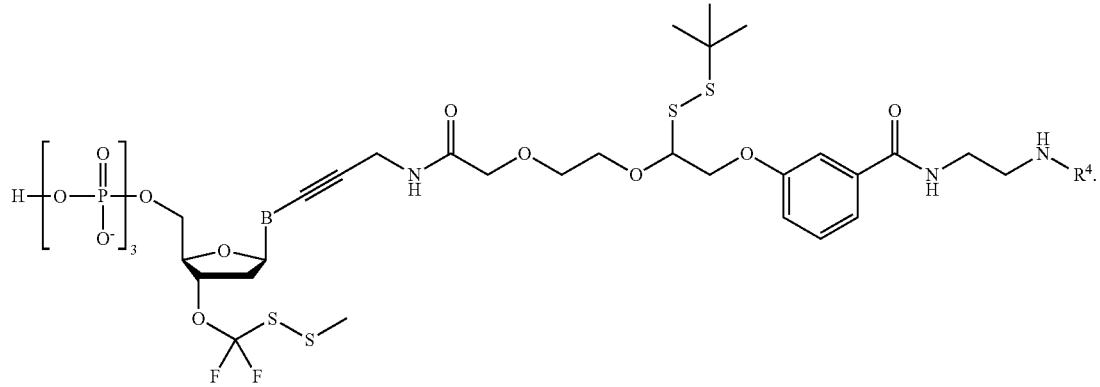

B and R⁴ are as described herein.

In embodiments, the compound has the formula:

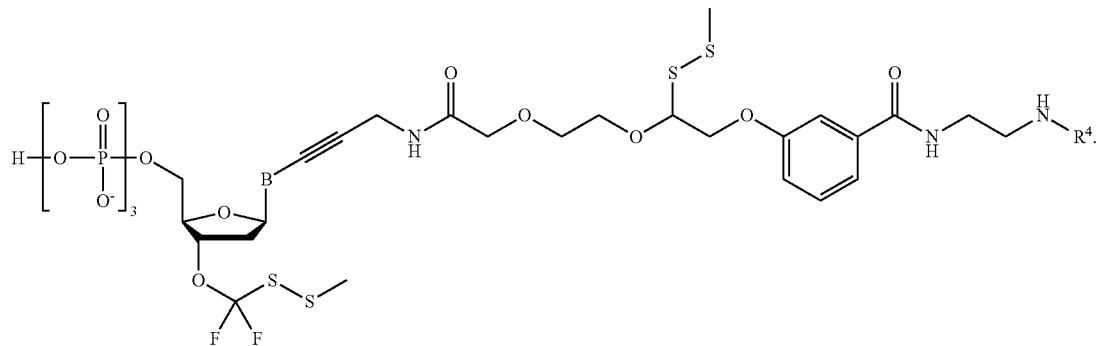

B and R⁴ are as described herein.

In embodiments, the compound has the formula:

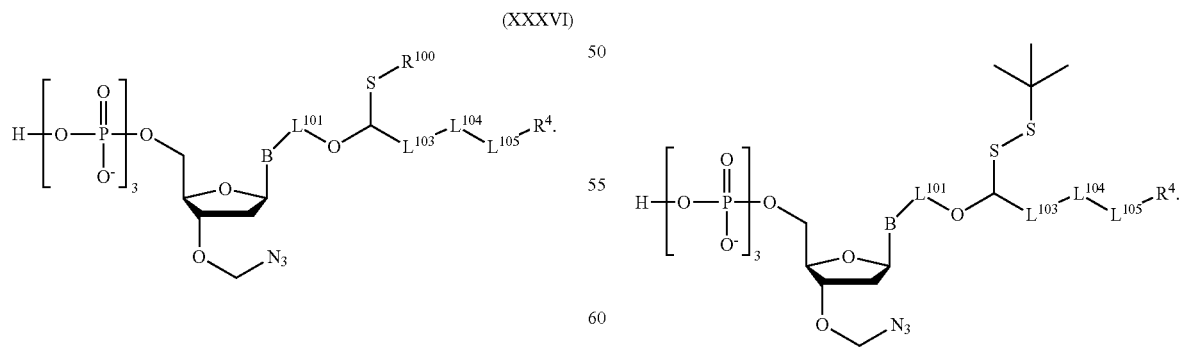

B, $L^{101}$, $L^{103}$, $L^{104}$, $L^{105}$ and R⁴ are as described herein. In embodiments of Formula (XXXVI), R¹⁰⁰ is —SR¹⁰² and R¹⁰² is as described herein (e.g., unsubstituted $C_1$-$C_4$ alkyl). In embodiments of Formula (XXXVI), R¹⁰⁰ is —CN.

In embodiments, the compound has the formula:

B, $L^{101}$, $L^{103}$, $L^{104}$, $L^{105}$, and R⁴ are as described herein.

In embodiments, the compound has the formula:

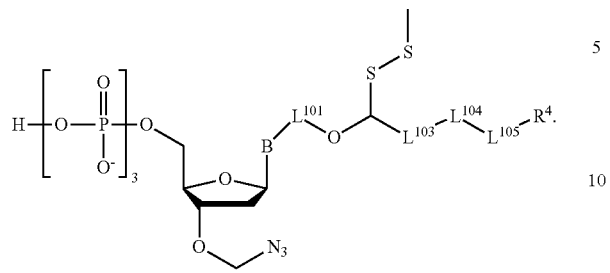

$B$, $L^{101}$, $L^{103}$, $L^{104}$, $L^{105}$, and $R^4$ are as described herein.

In embodiments, the compound has the formula:

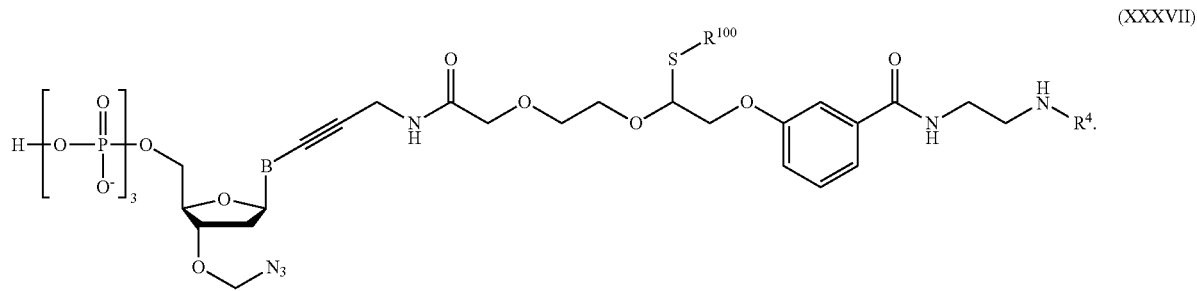

(XXXVII)

B and $R^4$ are as described herein. In embodiments of Formula (XXXVII), $R^{100}$ is $-SR^{102}$, and $R^{102}$ is as described herein (e.g., unsubstituted $C_1$-$C_4$ alkyl). In embodiments of Formula (XXXVII), $R^{100}$ is $-CN$.

In embodiments, the compound has the formula:

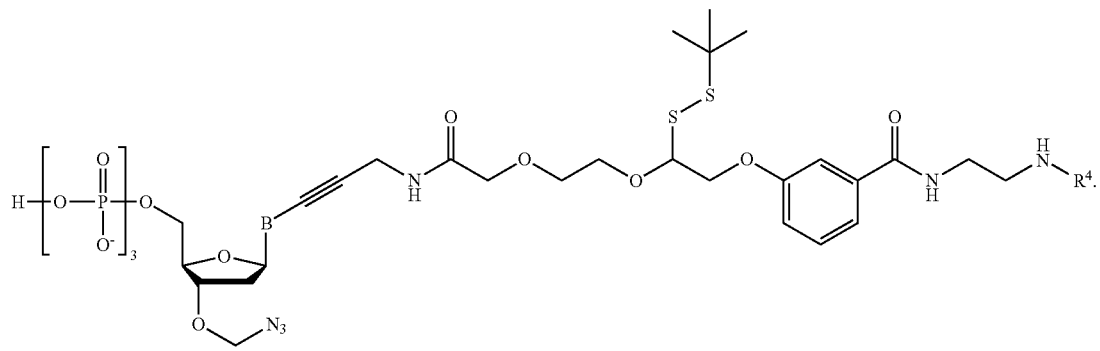

B and $R^4$ are as described herein.

In embodiments, the compound has the formula:

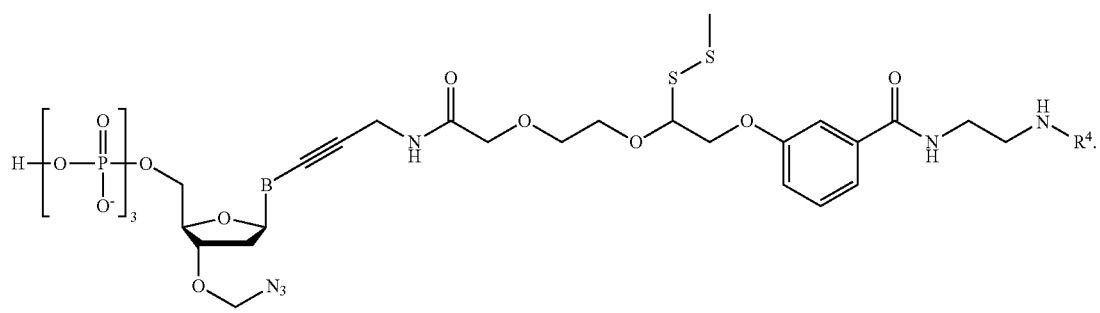

B and $R^4$ are as described herein.

In embodiments, the compound has the formula:

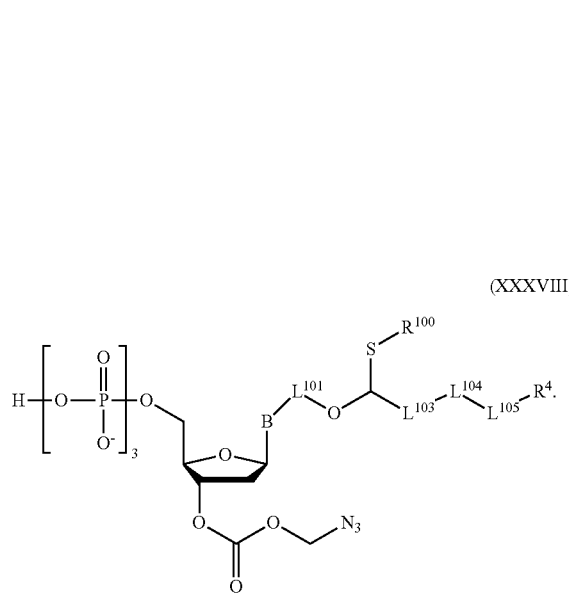

(XXXVIII)

B, L$^{101}$, L$^{103}$, L$^{104}$, L$^{105}$, and R$^4$ are as described herein. In embodiments of Formula (XXXVIII), R$^{100}$ is —SR$^{102}$ and R$^{102}$ is as described herein (e.g., unsubstituted C$_1$-C$_4$ alkyl). In embodiments of Formula (XXXVIII), R$^{100}$ is —CN.

In embodiments, the compound has the formula:

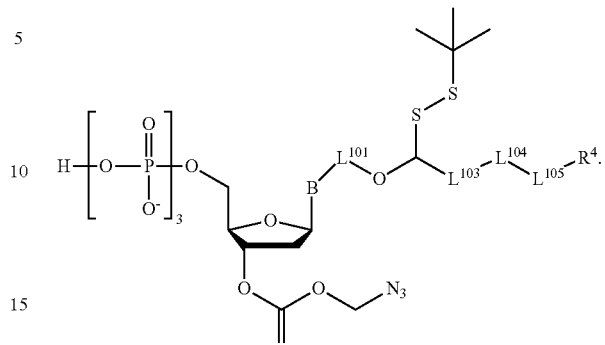

B, L$^{101}$, L$^{103}$, L$^{104}$, L$^{105}$, and R$^4$ are as described herein.

In embodiments, the compound has the formula:

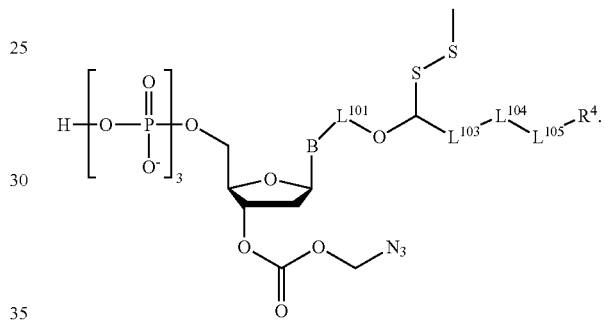

B, L$^{101}$, L$^{103}$, L$^{104}$, L$^{105}$, and R$^4$ are as described herein.

In embodiments, the compound has the formula:

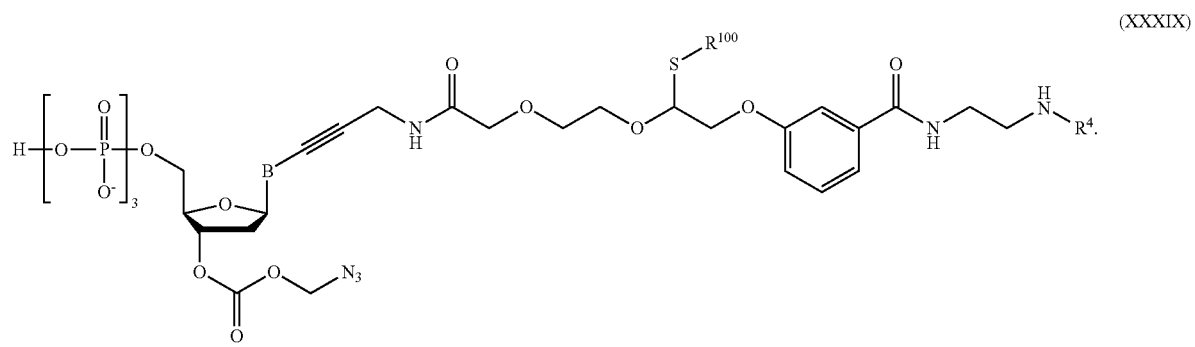

(XXXIX)

B and R$^4$ are as described herein. In embodiments of Formula (XXXIX), R$^{100}$ is —SR$^{102}$, and R$^{102}$ is as described herein (e.g., unsubstituted C$_1$-C$_4$ alkyl). In embodiments of Formula (XXXIX), R$^{100}$ is —CN.

In embodiments, the compound has the formula:

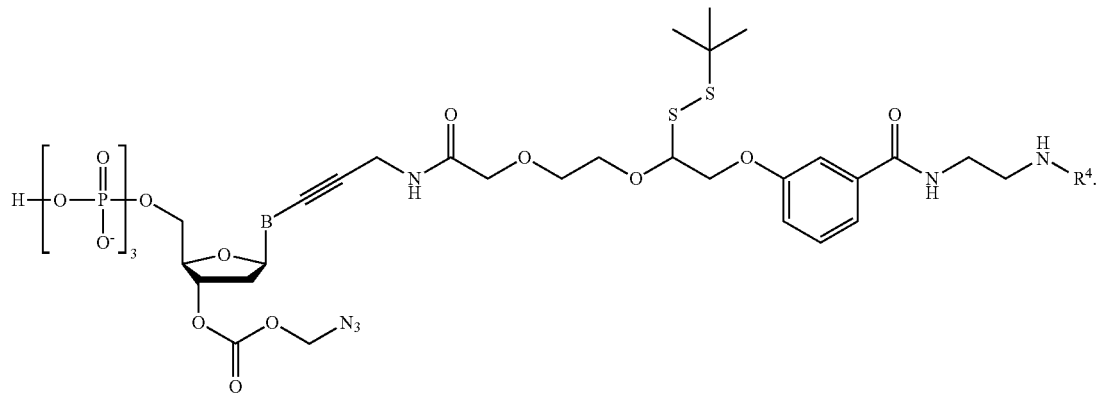

B and R⁴ are as described herein.

In embodiments, the compound has the formula:

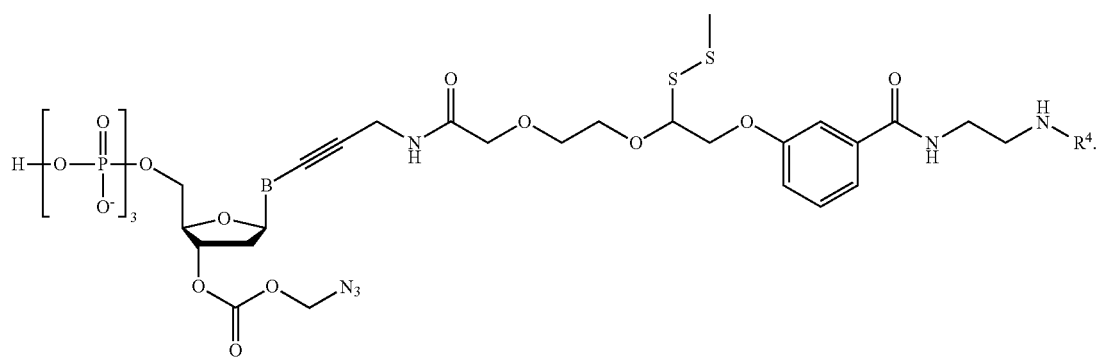

B and R⁴ are as described herein.

In embodiments, the compound has the formula:

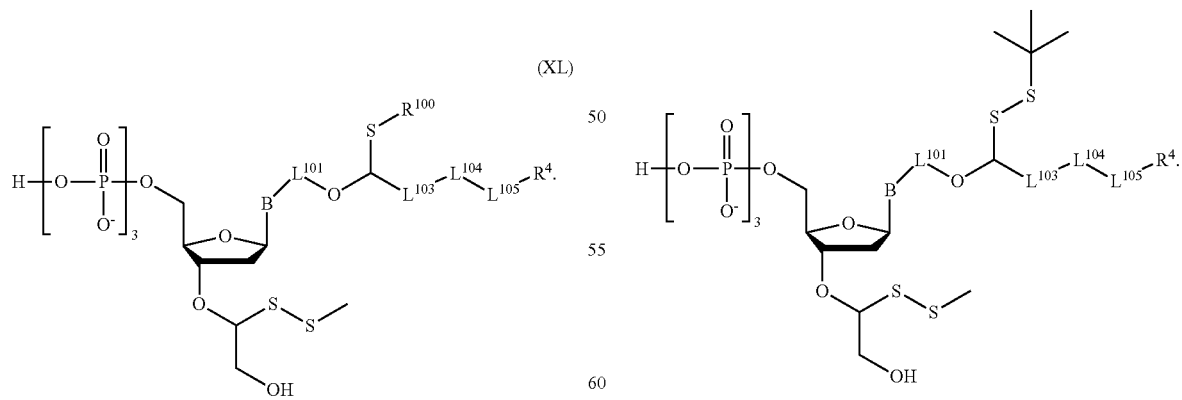

B, $L^1$, $L^{103}$, $L^{104}$, $L^{105}$, and $R^4$ are as described herein. In embodiments of Formula (XL), $R^{100}$ is —$SR^{102}$, and $R^{102}$ is as described herein (e.g., unsubstituted $C_1$-$C_4$ alkyl). In embodiments of Formula (XL), $R^{100}$ is —CN.

In embodiments, the compound has the formula:

B, $L^{101}$, $L^{103}$, $L^{104}$, $L^{105}$, and $R^4$ are as described herein.

In embodiments, the compound has the formula:

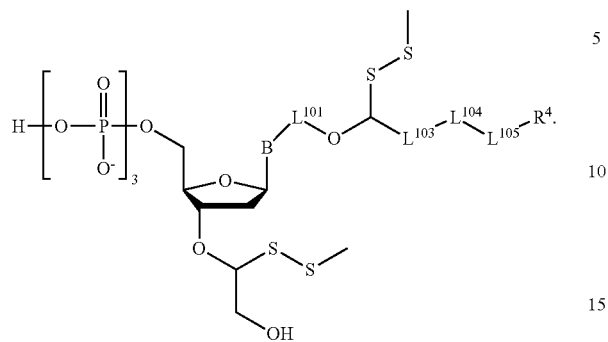

B, $L^{101}$, $L^{103}$, $L^{104}$, $L^{105}$, and $R^4$ are as described herein.

In embodiments, the compound has the formula:

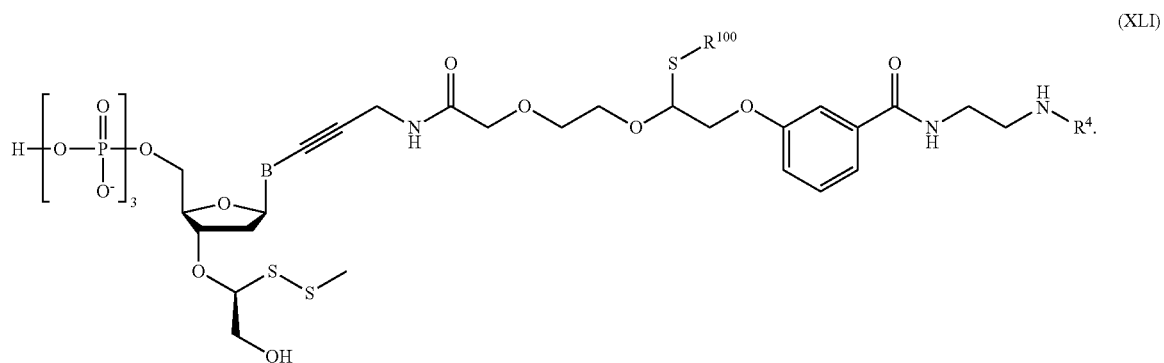

(XLI)

B and $R^4$ are as described herein. In embodiments of Formula (XLI), $R^{100}$ is $-SR^{102}$, and $R^{102}$ is as described herein. In embodiments of Formula (XLI), $R^{100}$ is $-CN$.

In embodiments, the compound has the formula:

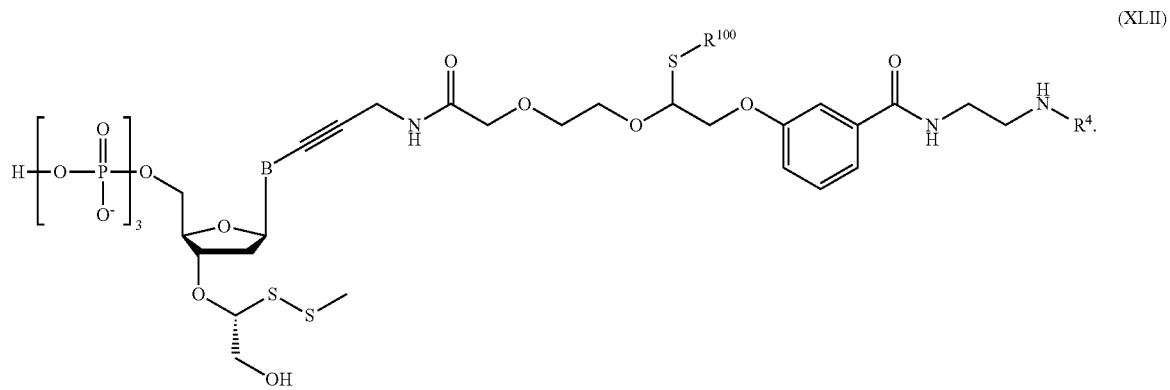

(XLII)

B and $R^4$ are as described herein. In embodiments of Formula (XLII), $R^{100}$ is $-SR^{102}$ and $R^{102}$ is as described herein. In embodiments of Formula (XLII), $R^{100}$ is $-CN$.

In embodiments, the compound has the formula:
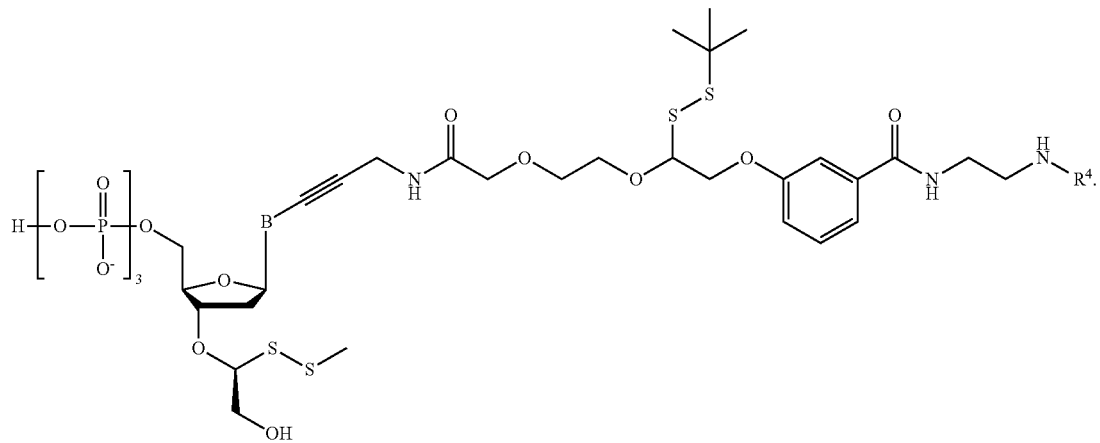
B and R⁴ are as described herein.
In embodiments, the compound has the formula:
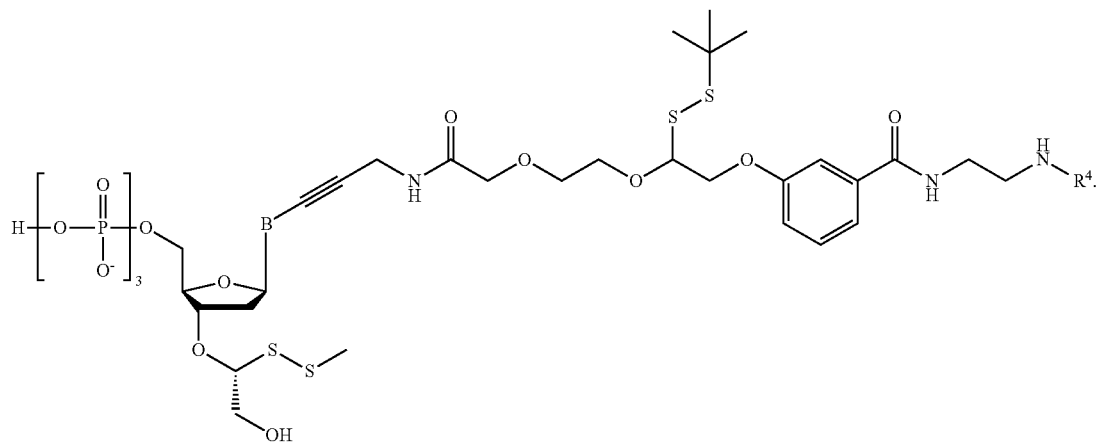
B and R⁴ are as described herein.
In embodiments, the compound has the formula:
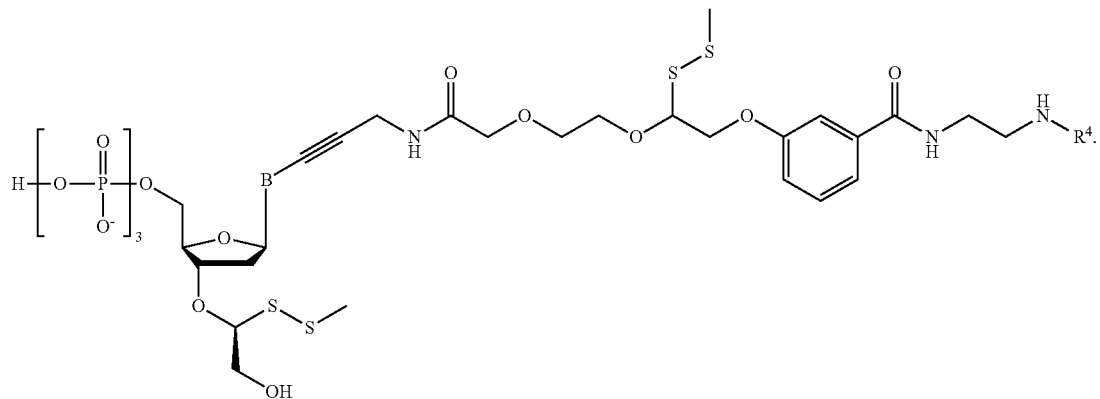
B and R⁴ are as described herein.

In embodiments, the compound has the formula:

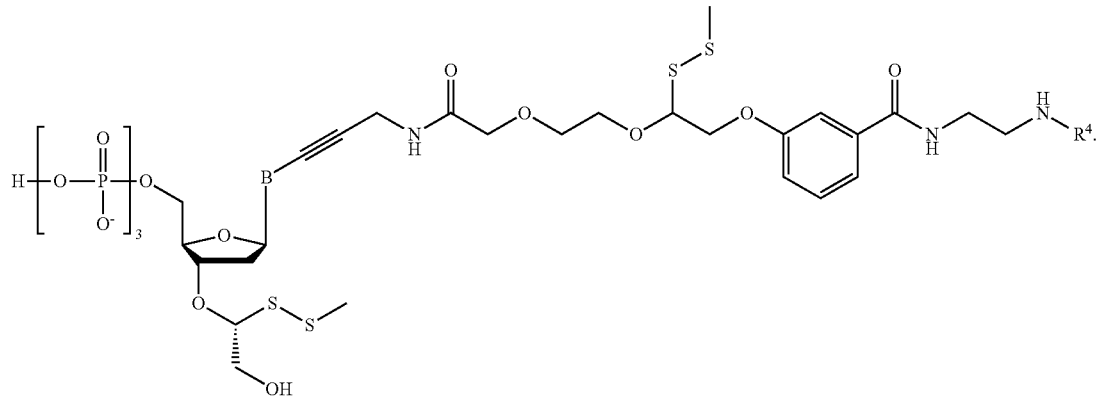

B and R⁴ are as described herein.

In embodiments, the compound has the formula:

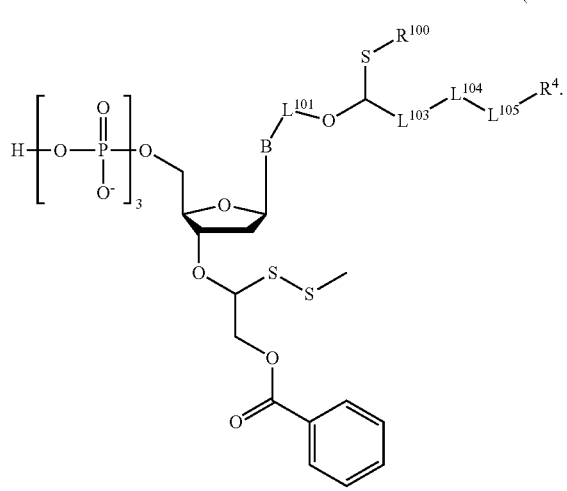

(XLIII)

B, $L^{101}$, $L^{103}$, $L^{104}$, $L^{105}$, and R⁴ are as described herein. In embodiments of Formula (XLIII), $R^{100}$ is —$SR^{102}$, and $R^{102}$ is as described herein (e.g., unsubstituted $C_1$-$C_4$ alkyl). In embodiments of Formula (XLIII), $R^{100}$ is —CN.

In embodiments, the compound has the formula.

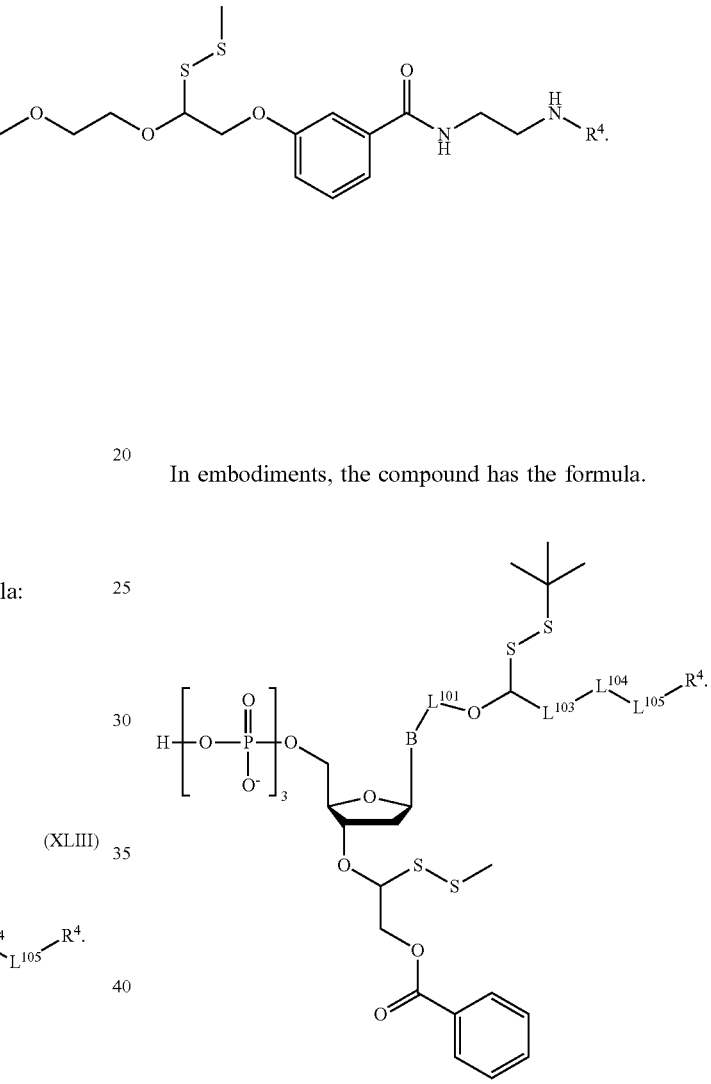

B, $L^{101}$, $L^{103}$, $L^{104}$, $L^{105}$, and R⁴ are as described herein.

In embodiments, the compound has the formula:

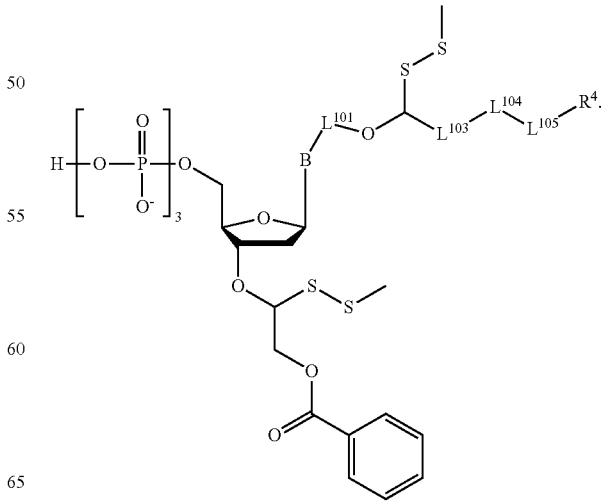

B, $L^{101}$, $L^{103}$, $L^{104}$, $L^{105}$, and R⁴ are as described herein.

In embodiments, the compound has the formula:

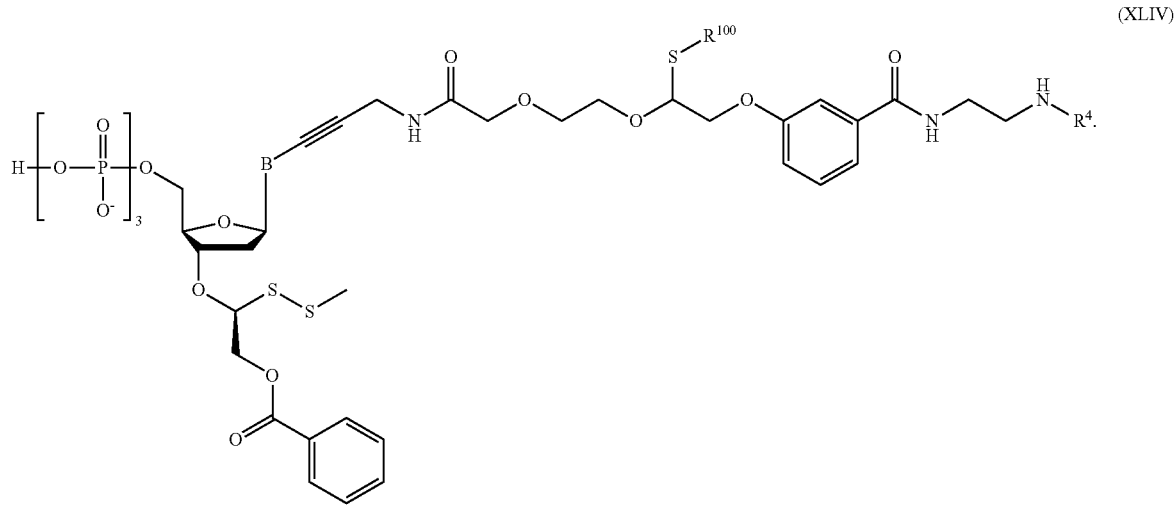

(XLIV)

B and R$^4$ are as described herein. In embodiments of Formula (XLIV), R$^{100}$ is —SR$^{102}$, and R$^{102}$ is as described herein (e.g., unsubstituted C$_1$-C$_4$ alkyl). In embodiments of Formula (XLIV), R$^{100}$ is —CN.

In embodiments, the compound has the formula:

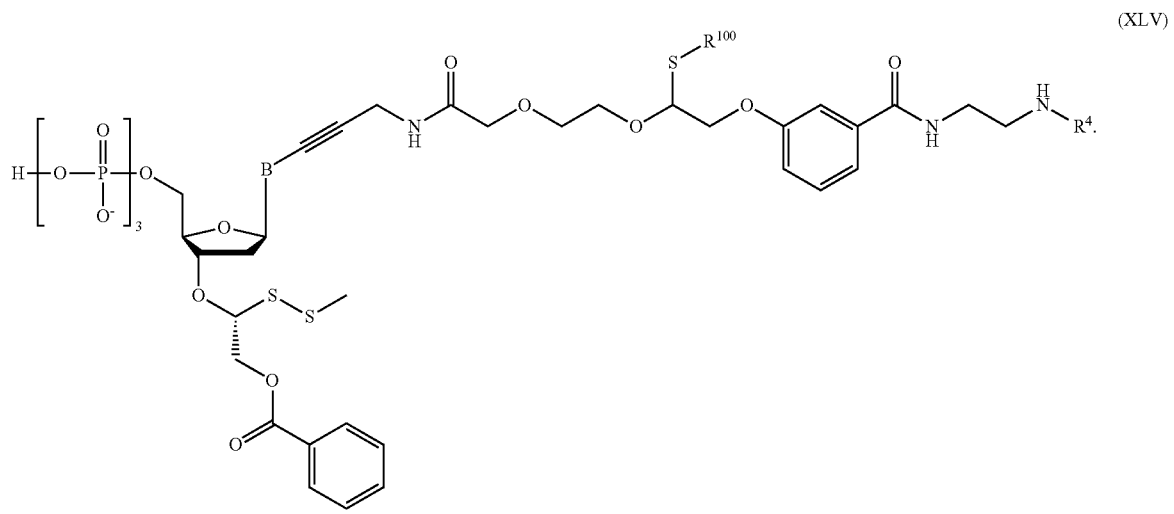

(XLV)

B and R$^4$ are as described herein. In embodiments of Formula (XLV), R$^{100}$ is —SR$^{100}$2, and R$^{102}$ is as described herein. In embodiments of Formula (XLV), R$^{100}$ is —CN.

In embodiments, the compound has the formula.
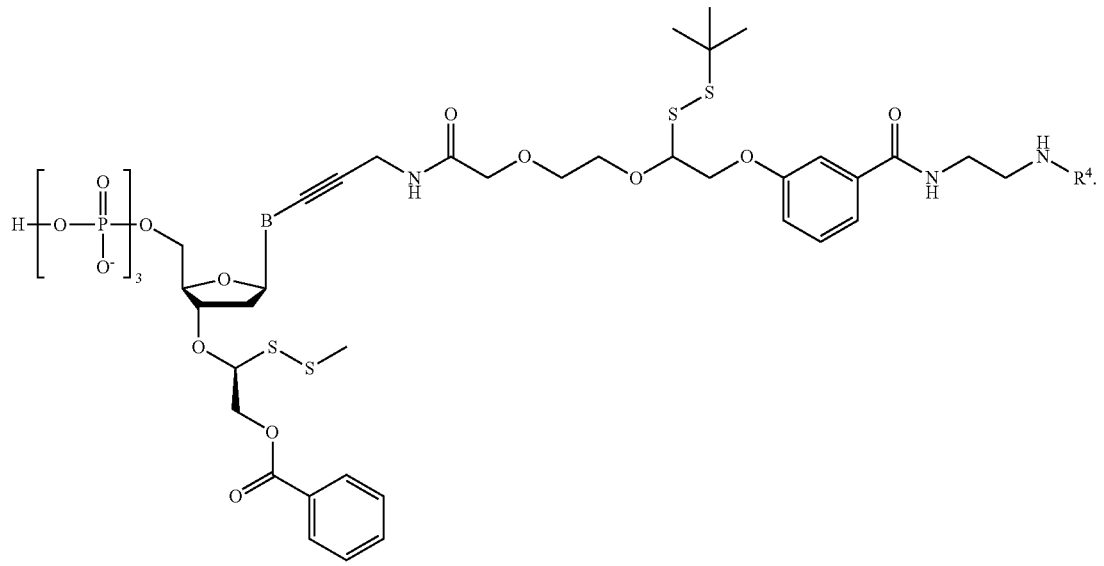
B and R⁴ are as described herein.
In embodiments, the compound has the formula:
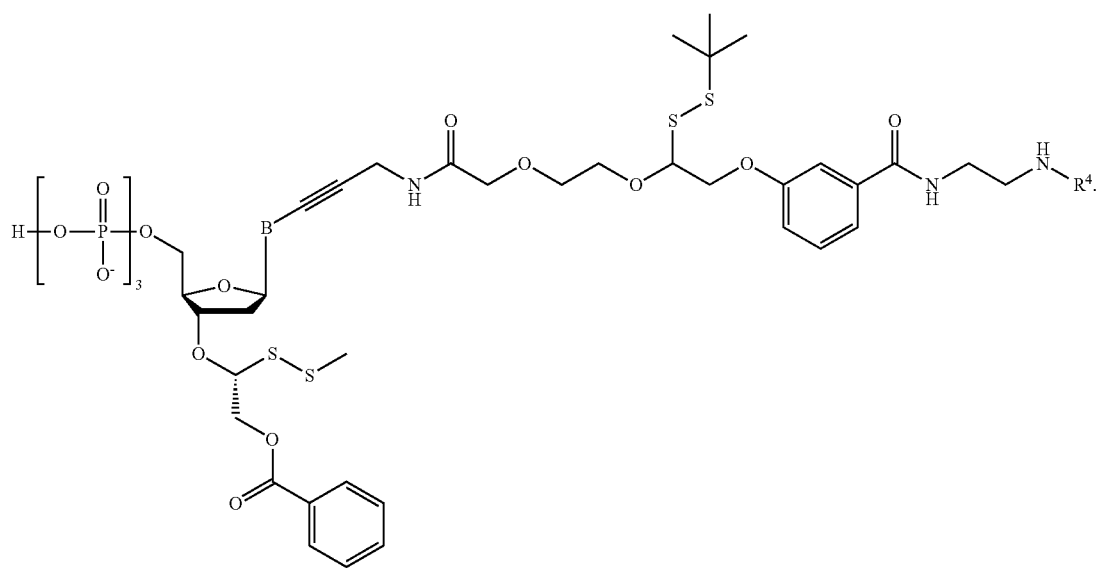
B and R⁴ are as described herein.

In embodiments, the compound has the formula:

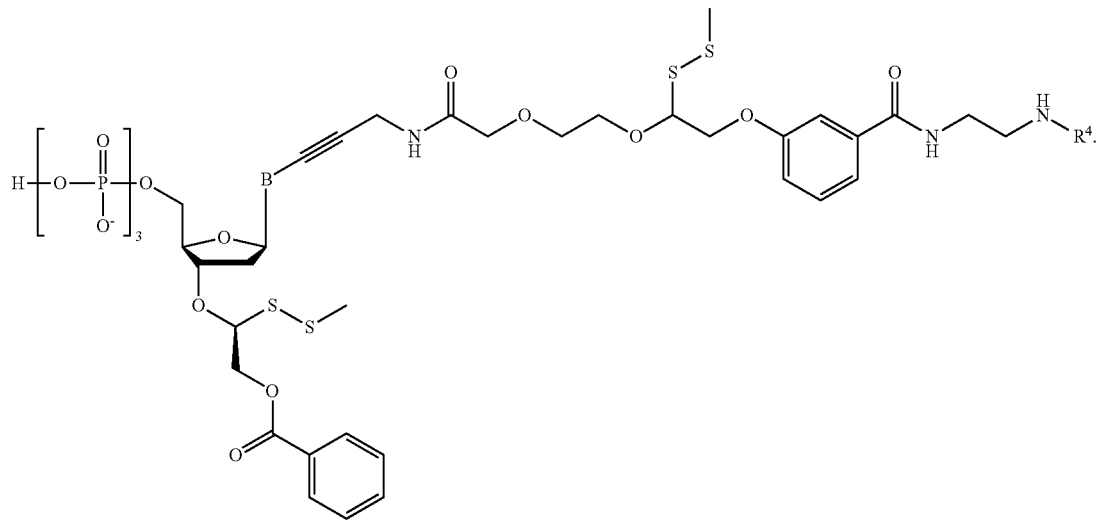

B and R are as described herein.

In embodiments, the compound has the formula:

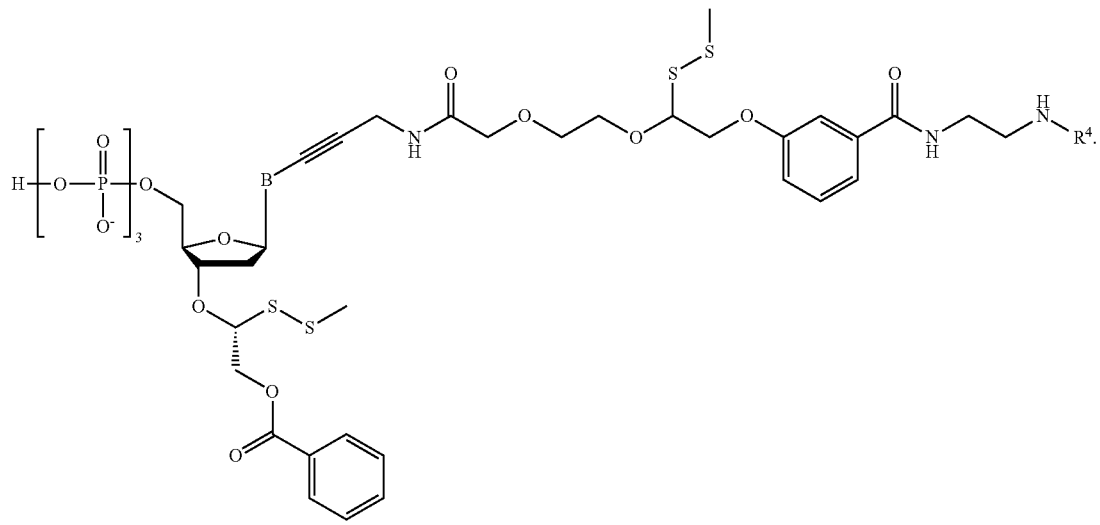

B and R⁴ are as described herein.

In embodiments, the compound has the formula:

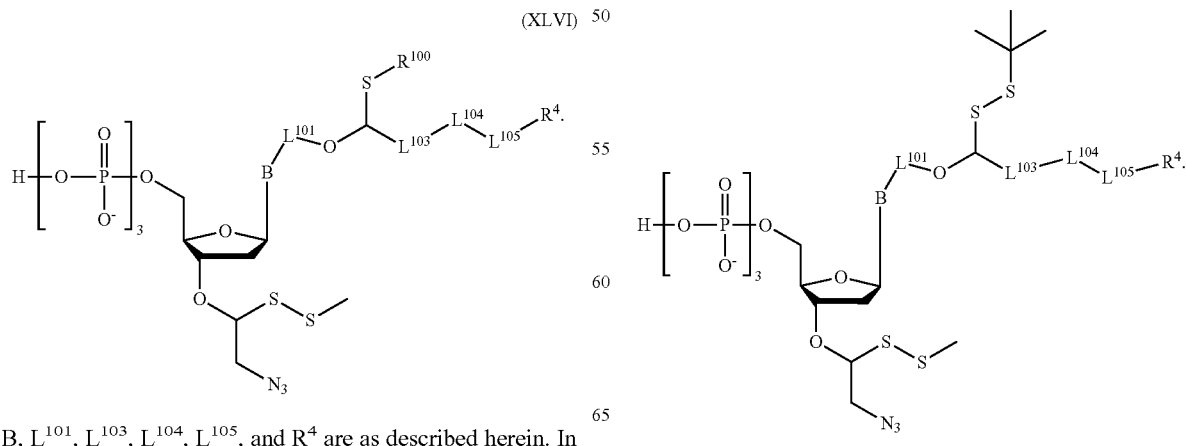

B, $L^{101}$, $L^{103}$, $L^{104}$, $L^{105}$, and $R^4$ are as described herein. In embodiments of Formula (XLVI), $R^{100}$ is —$SR^{102}$, and $R^{102}$ is as described herein (e.g., unsubstituted $C_1$-$C_4$ alkyl). In embodiments of Formula (XLVI), $R^{100}$ is —CN.

In embodiments, the compound has the formula:

B, $L^{101}$, $L^{103}$, $L^{104}$, $L^{105}$, and $R^4$ are as described herein.

In embodiments, the compound has the formula:

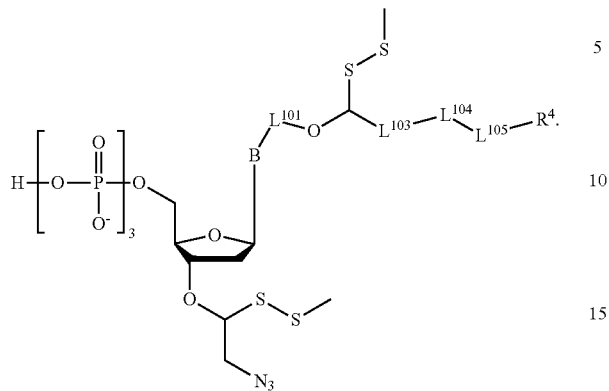

B, $L^{101}$, $L^{1033}$, $L^{104}$, $L^{105}$, and $R^4$ are as described herein.

In embodiments, the compound has the formula:

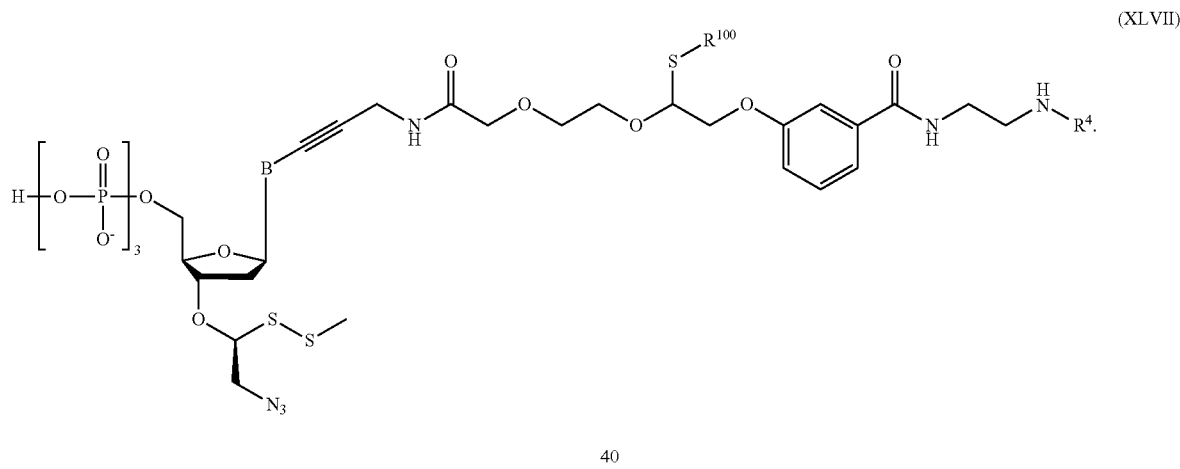

(XLVII)

B and $R^4$ are as described herein. In embodiments of Formula (XLVII), $R^{100}$ is —$SR^{102}$, and $R^{102}$ is as described herein. In embodiments of Formula (XLVII), $R^{100}$ is —CN.

In embodiments, the compound has the formula:

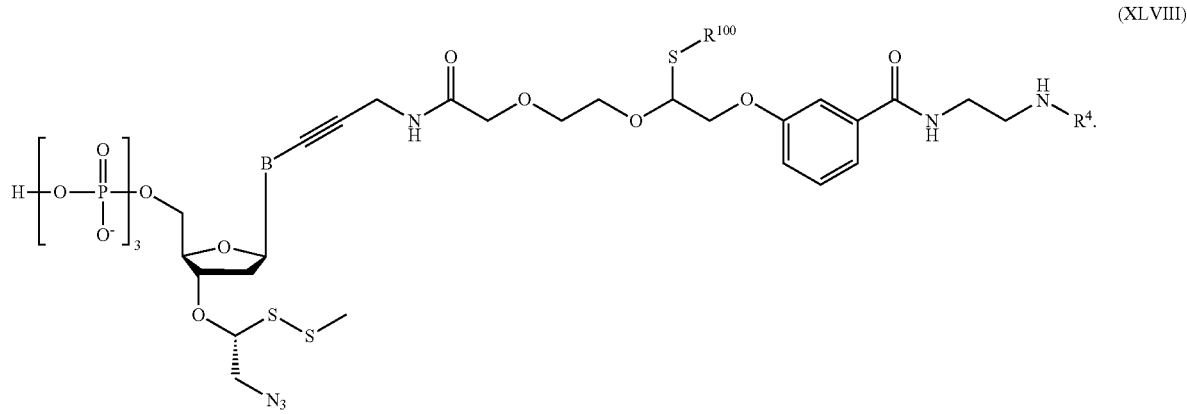

(XLVIII)

B and $R^4$ are as described herein. In embodiments of Formula (XLVIII), $R^{100}$ is —$SR^{102}$, and $R^{102}$ is as described herein. In embodiments of Formula (XLVIII), $R^{100}$ is —CN.

In embodiments, the compound has the formula:
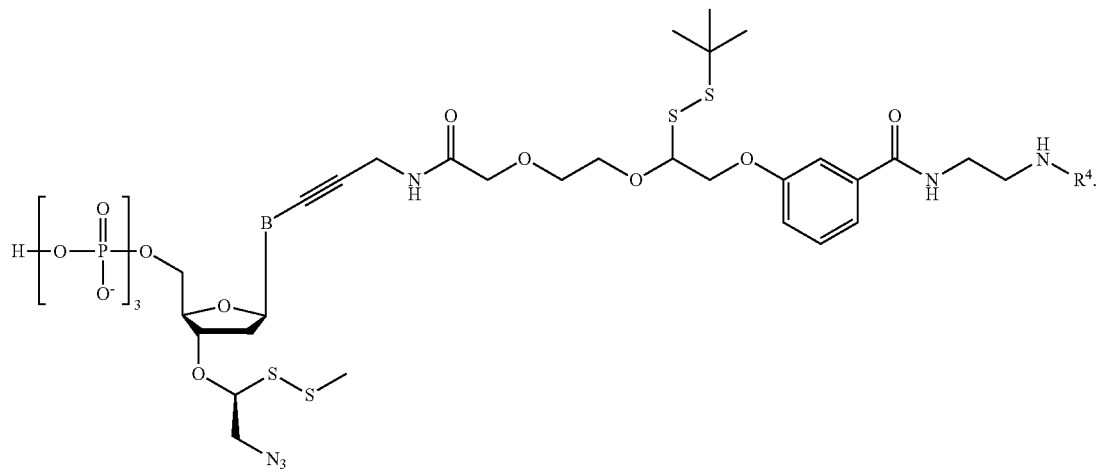
B and R⁴ are as described herein.
In embodiments, the compound has the formula:
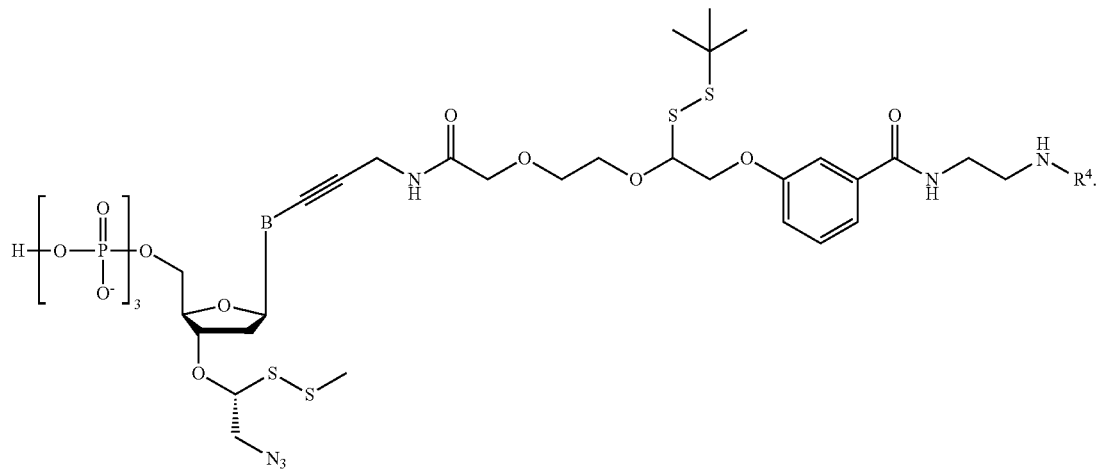
B and R⁴ are as described herein.
In embodiments, the compound has the formula:
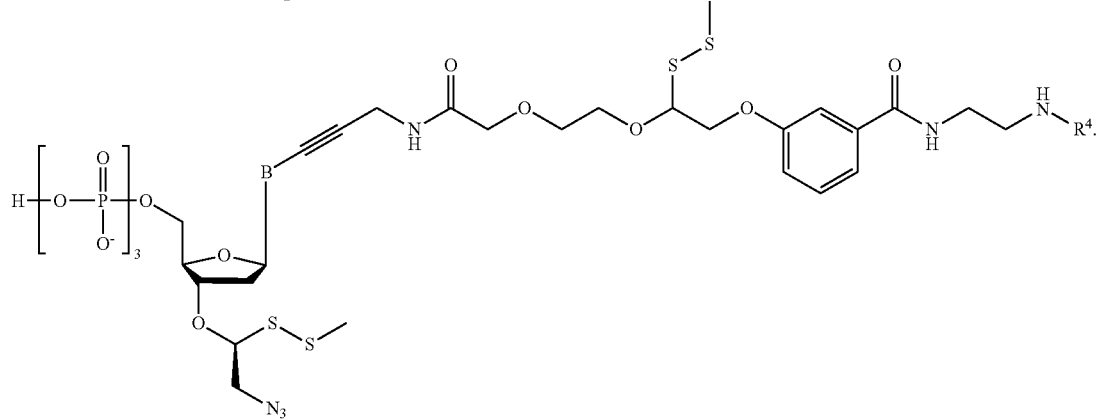
B and R⁴ are as described herein.

In embodiments, the compound has the formula:

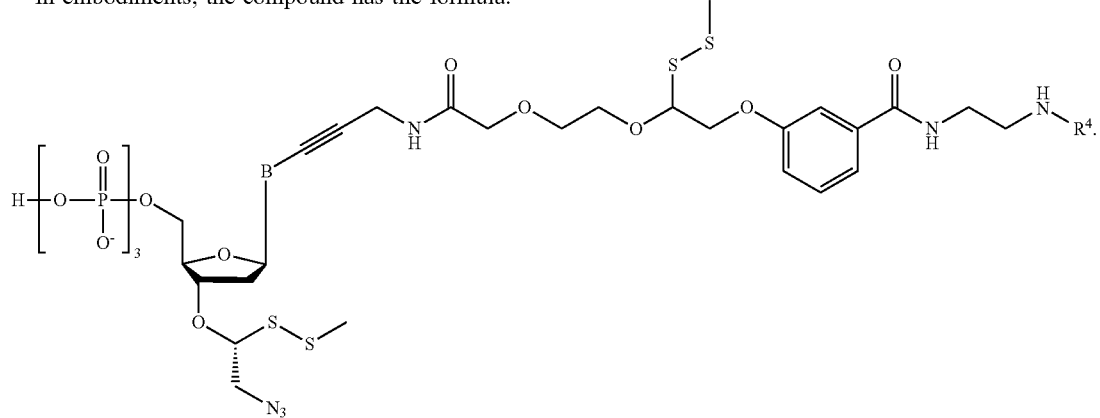

B and R⁴ are as described herein.

In embodiments, the compound has the formula:

(XLIX)

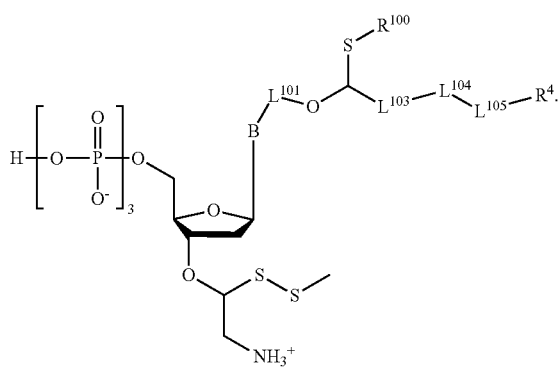

B, $L^{101}$, $L^{103}$, $L^{104}$, $L^{105}$, and R⁴ are as described herein. In embodiments of Formula (XLIX), $R^{100}$ is —$SR^{102}$, and $R^{102}$ is as described herein (e.g., unsubstituted $C_1$-$C_4$ alkyl). In embodiments of Formula (XLIX), $R^{100}$ is —CN.

In embodiments, the compound has the formula:

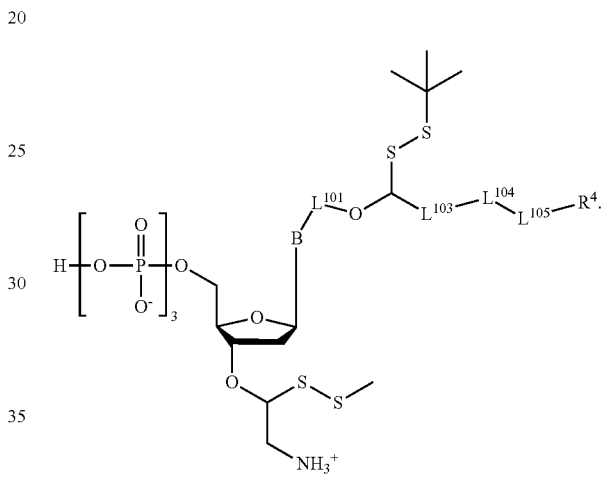

B, $L^{101}$, $L^{103}$, $L^{104}$, $L^{05}$, and R⁴ are as described herein.

In embodiments, the compound has the formula:

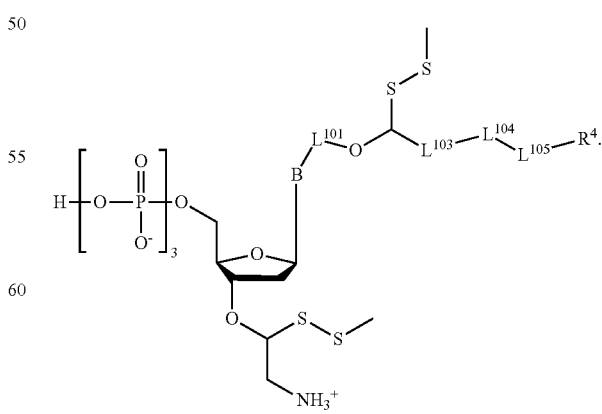

B, $L^{101}$, $L^{103}$, $L^{104}$, $L^{105}$, and R⁴ are as described herein.

In embodiments, the compound has the formula:

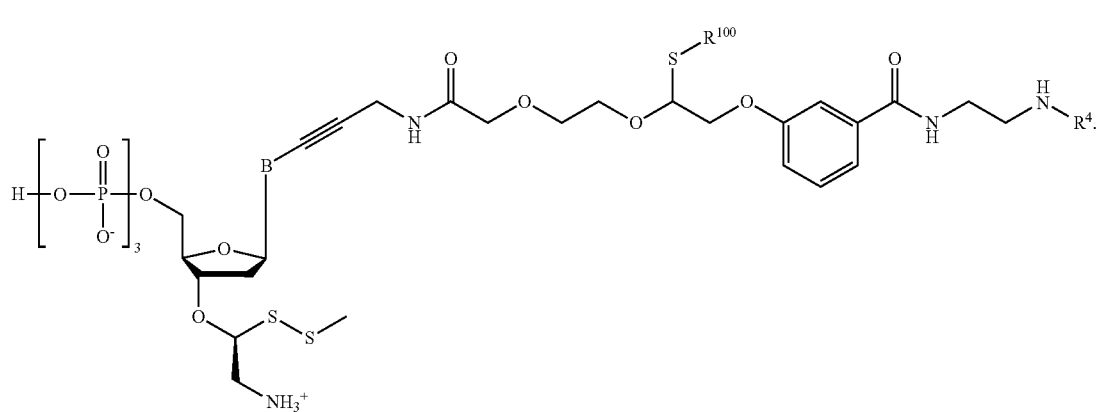

(L)

B and R⁴ are as described herein. In embodiments of Formula (L), $R^{100}$ is —$SR^{102}$, and $R^{102}$ is as described herein. In embodiments of Formula (L), $R^{100}$ is —CN.

In embodiments, the compound has the formula:

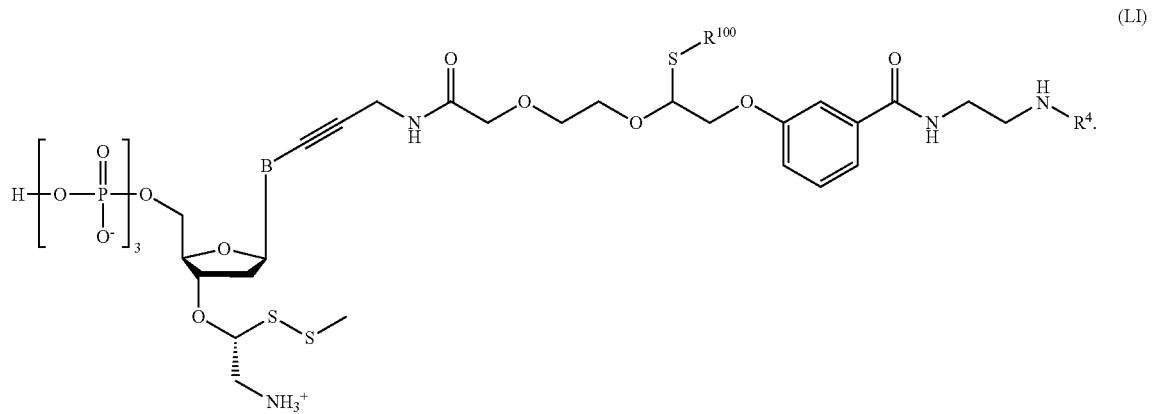

(LI)

B and R⁴ are as described herein. In embodiments of Formula (LI), $R^{100}$ is —$SR^{102}$, and $R^{102}$ is as described herein. In embodiments of Formula (LI), $R^{100}$ is —CN.

In embodiments, the compound has the formula:

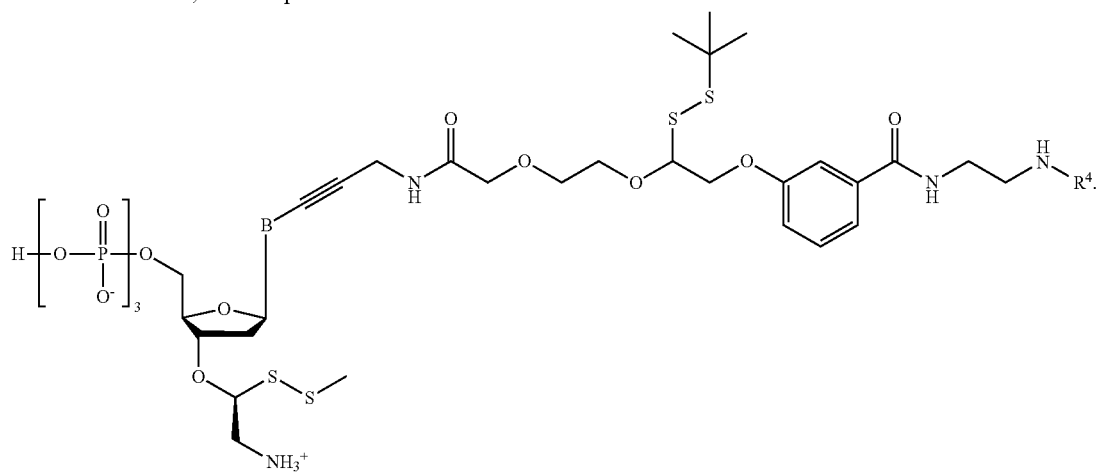

B and R⁴ are as described herein.

In embodiments, the compound has the formula:
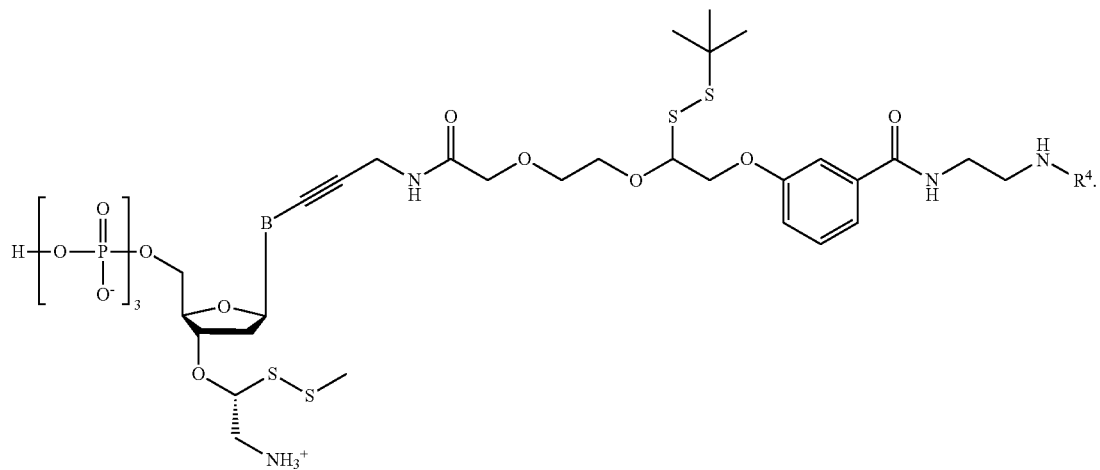
B and R⁴ are as described herein.
In embodiments, the compound has the formula:
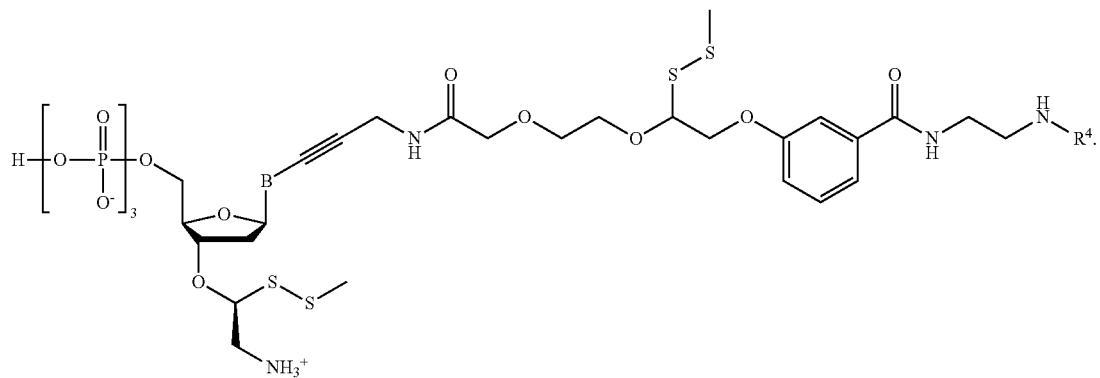
B and R⁴ are as described herein.
In embodiments, the compound has the formula:
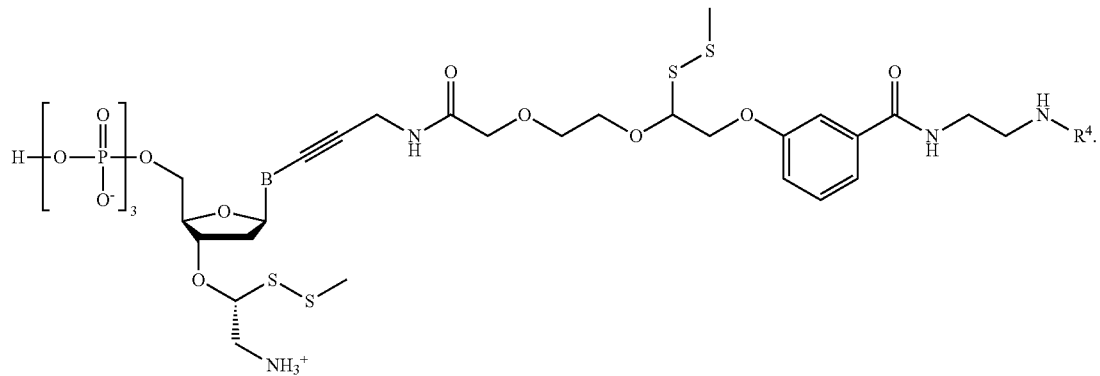
B and R⁴ are as described herein.

In embodiments, the compound has the formula:

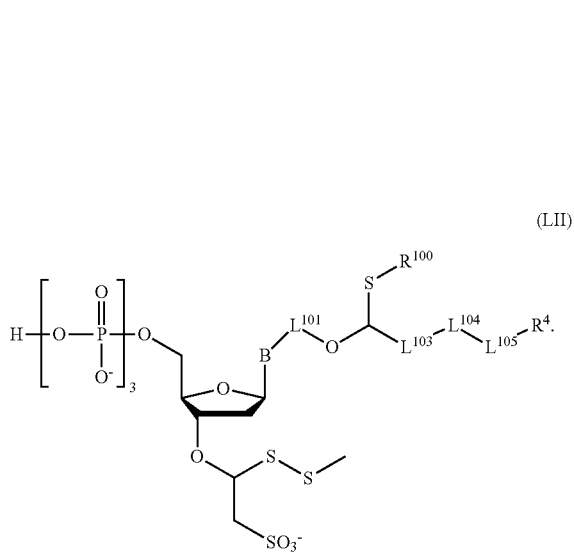

(LII)

B, $L^{101}$, $L^{103}$, $L^{104}$, $L^{105}$, and $R^4$ are as described herein. In embodiments of Formula (LII), $R^{100}$ is —$SR^{102}$, and $R^{102}$ is as described herein (e.g., unsubstituted $C_1$-$C_4$ alkyl). In embodiments of Formula (LII), $R^{100}$ is —CN.

In embodiments, the compound has the formula:

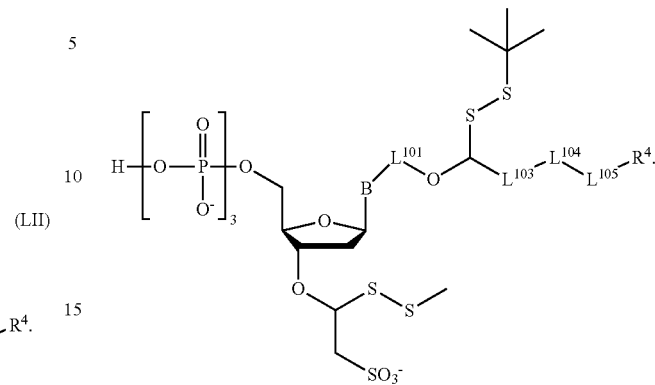

B, $L^{101}$, $L^{103}$, $L^{104}$, $L^{105}$, and $R^4$ are as described herein.
In embodiments, the compound has the formula:

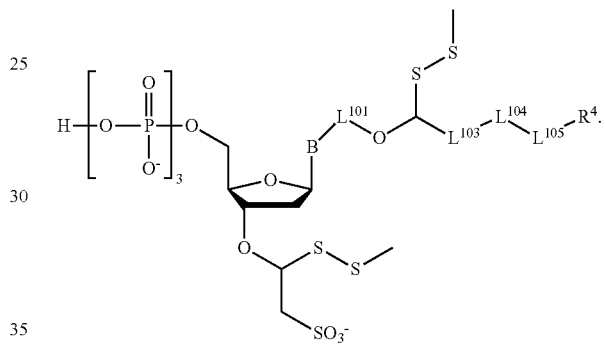

B, $L^{101}$, $L^{103}$, $L^{104}$, $L^{105}$, and $R^4$ are as described herein.
In embodiments, the compound has the formula:

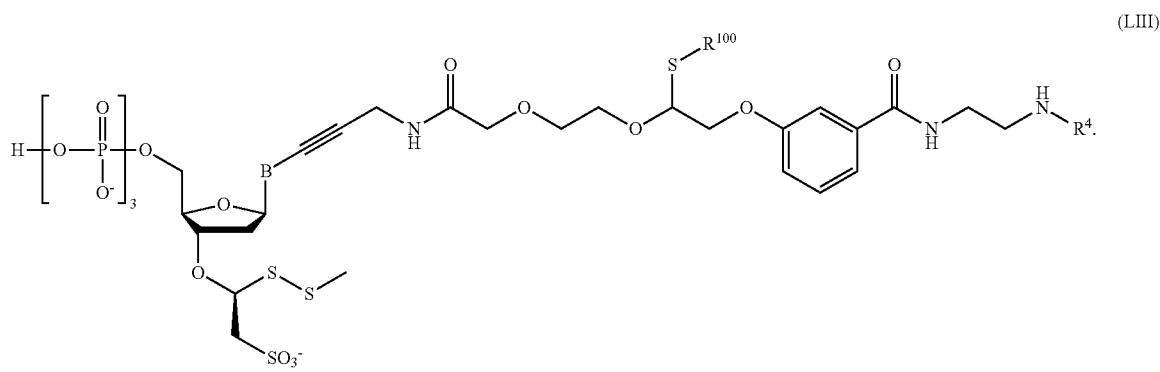

(LIII)

B and $R^4$ are as described herein. In embodiments of Formula (LIII), $R^{100}$ is —$SR^{102}$, and $R^{102}$ is as described herein. In embodiments of Formula (LIII), $R^{100}$ is —CN.

In embodiments, the compound has the formula:
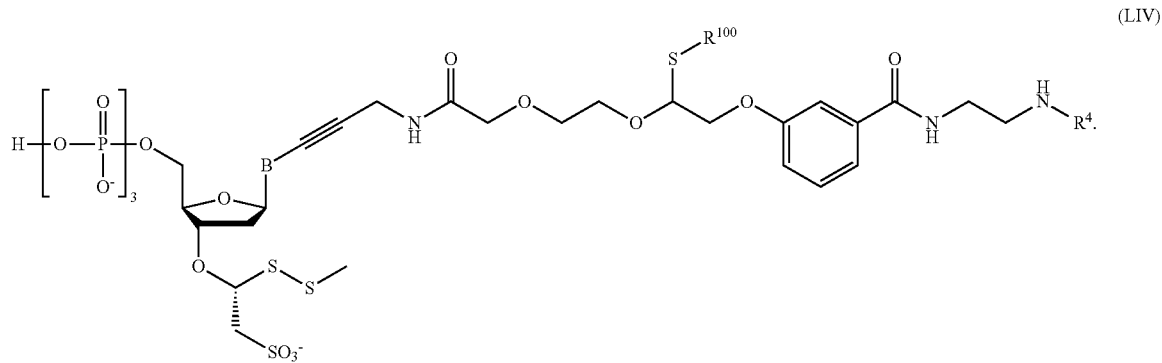
(LIV)
B and R⁴ are as described herein. In embodiments of Formula (LIV), $R^{100}$ is —$SR^{102}$, and $R^{102}$ is as described herein. In embodiments of Formula (LIV), $R^{100}$ is —CN.
In embodiments, the compound has the formula:
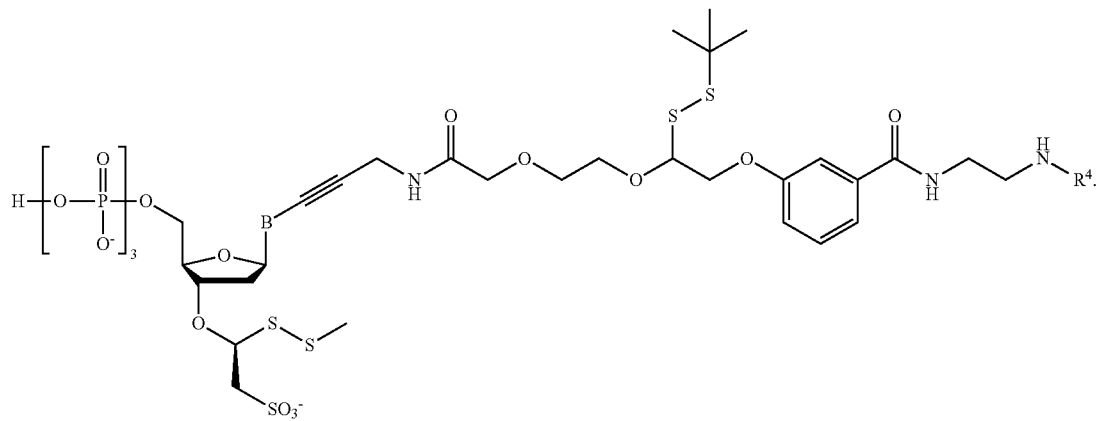
B and R⁴ are as described herein.
In embodiments, the compound has the formula.
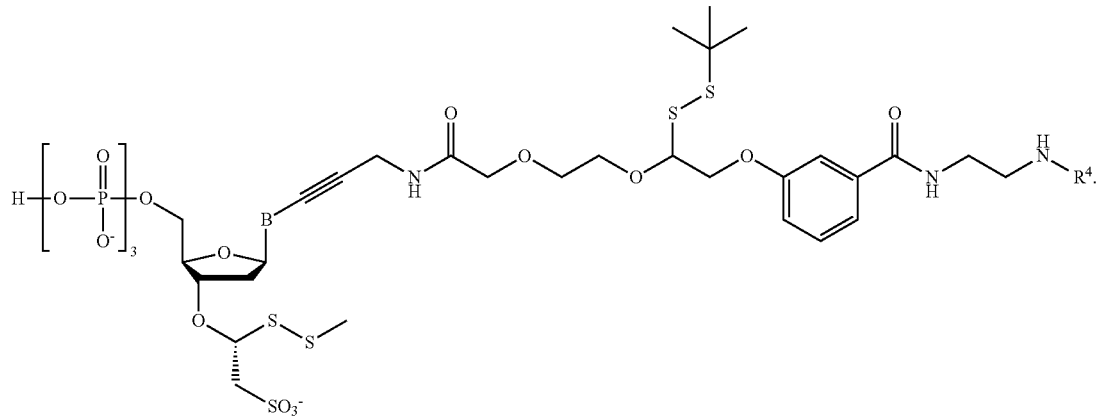
B and R⁴ are as described herein.

In embodiments, the compound has the formula:

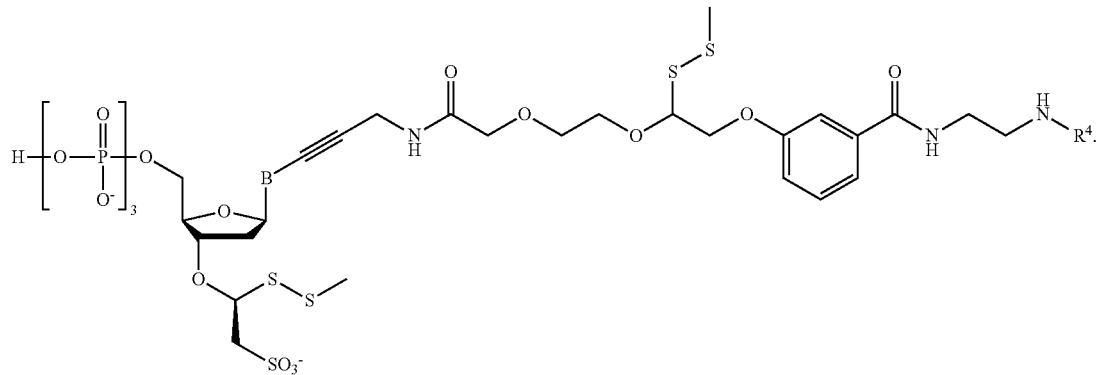

B and R⁴ are as described herein.

In embodiments, the compound has the formula:

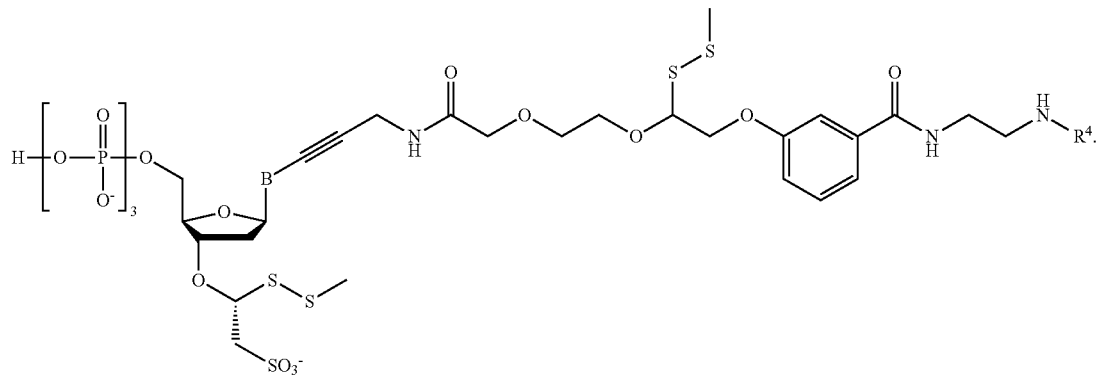

B and R⁴ are as described herein.

In embodiments, the compound has the formula:

In embodiments, the compound has the formula:

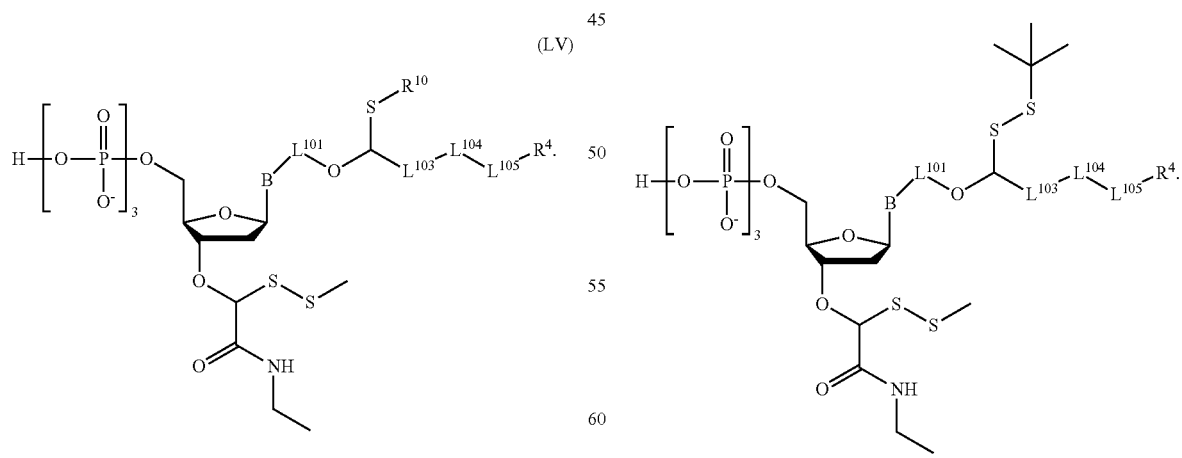

B, $L^{101}$, $L^{103}$, $L^{104}$, $L^{100}$, and $R^4$ are as described herein. In embodiments of Formula (LV), $R^{100}$ is —$SR^{102}$, and $R^{102}$ is as described herein (e.g., unsubstituted $C_1$-$C_4$ alkyl). In embodiments of Formula (LV), $R^{100}$ is —CN.

B, $L^{101}$, $L^{103}$, $L^{104}$, $L^{105}$, and $R^4$ are as described herein.

In embodiments, the compound has the formula:

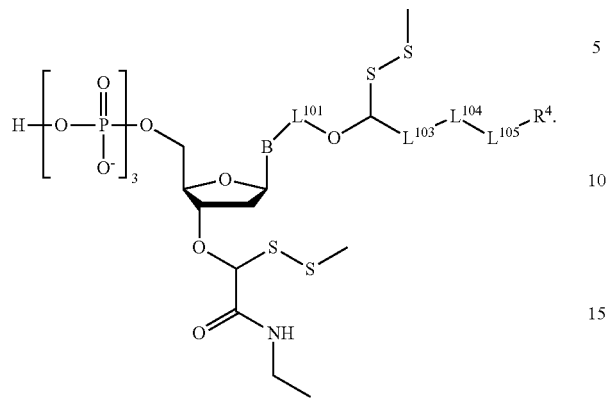

B, $L^{101}$, $L^{103}$, $L^{104}$, $L^{105}$, and $R^4$ are as described herein.

In embodiments, the compound has the formula:

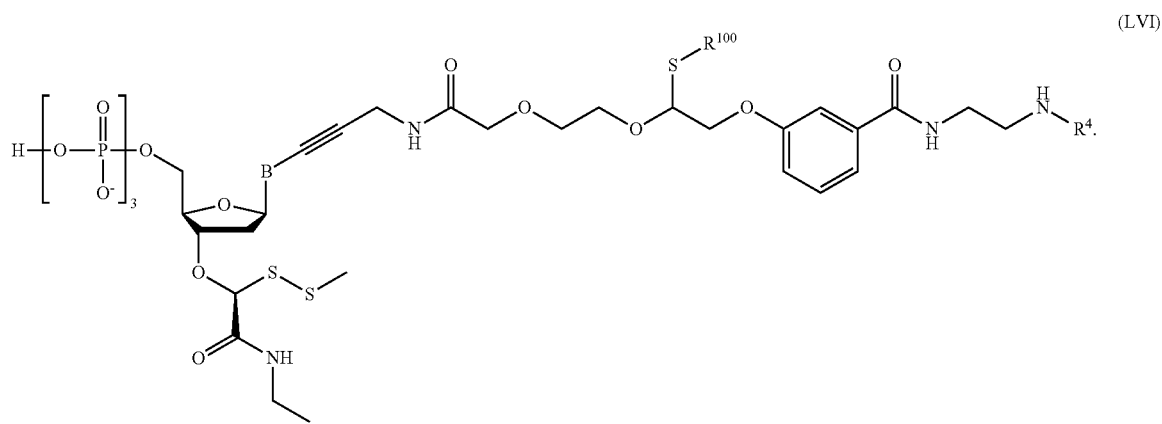

(LVI)

B and $R^4$ are as described herein. In embodiments of Formula (LVI), $R^{100}$ is $-SR^{102}$, and $R^{102}$ is as described herein. In embodiments of Formula (LVI), $R^{100}$ is —CN.

In embodiments, the compound has the formula:

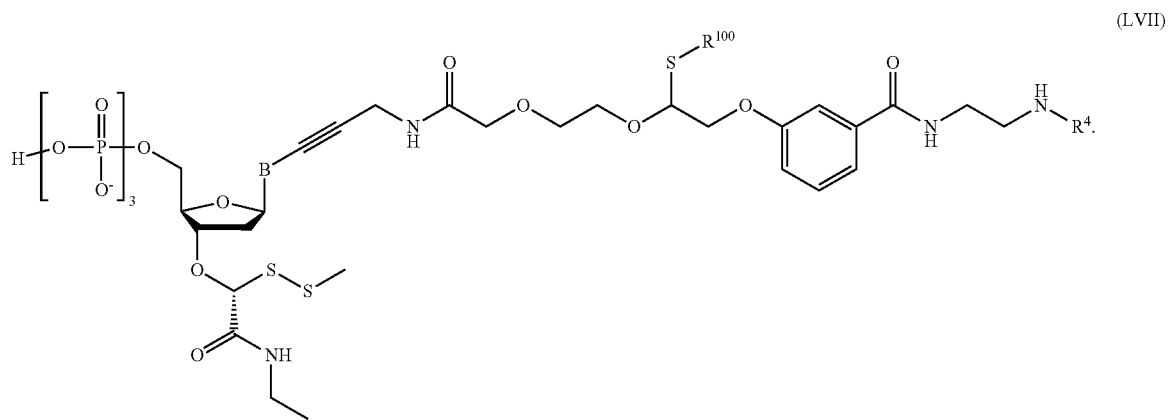

(LVII)

B and $R^4$ are as described herein. In embodiments of Formula (LVII), $R^{100}$ is $-SR^{102}$ and $R^{102}$ is as described herein. In embodiments of Formula (LVII), $R^{100}$ is —CN.

In embodiments, the compound has the formula:
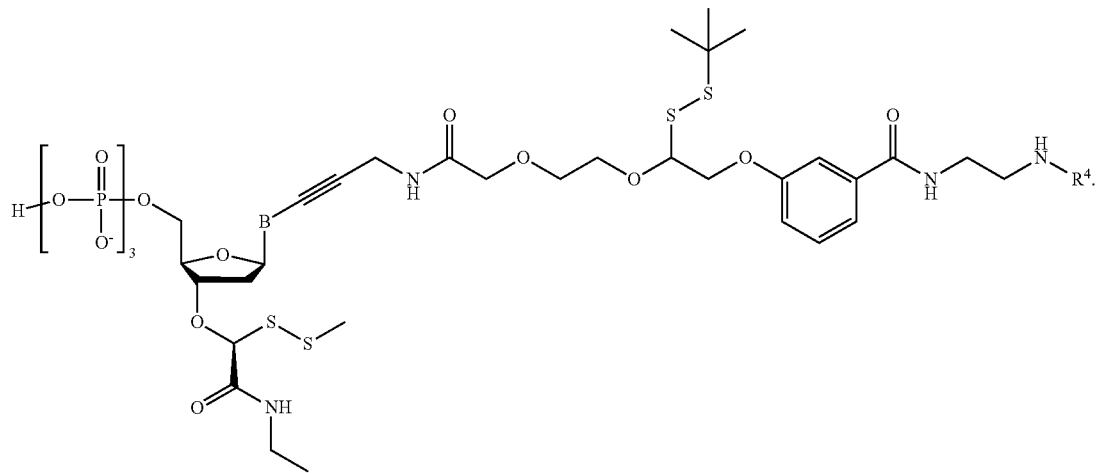
B and R⁴ are as described herein.
In embodiments, the compound has the formula:
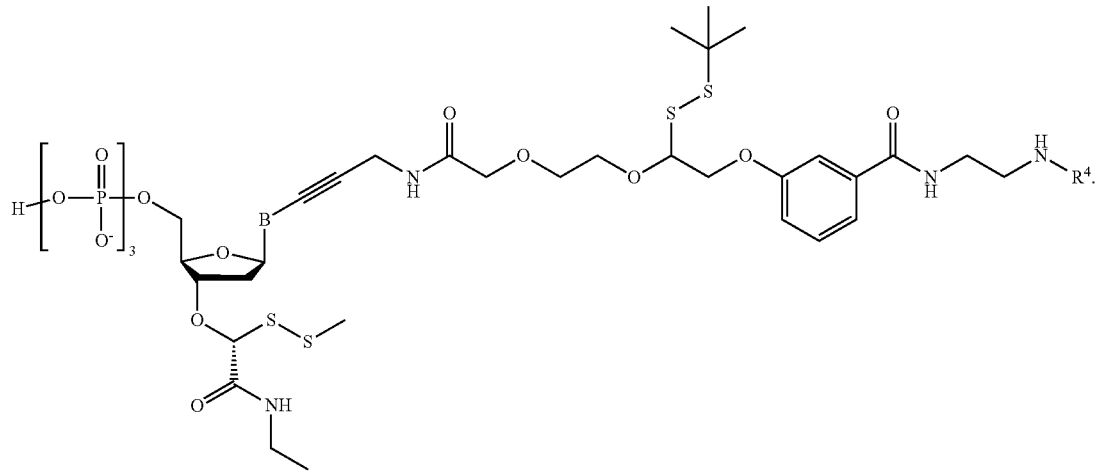
B and R⁴ are as described herein.
In embodiments, the compound has the formula:
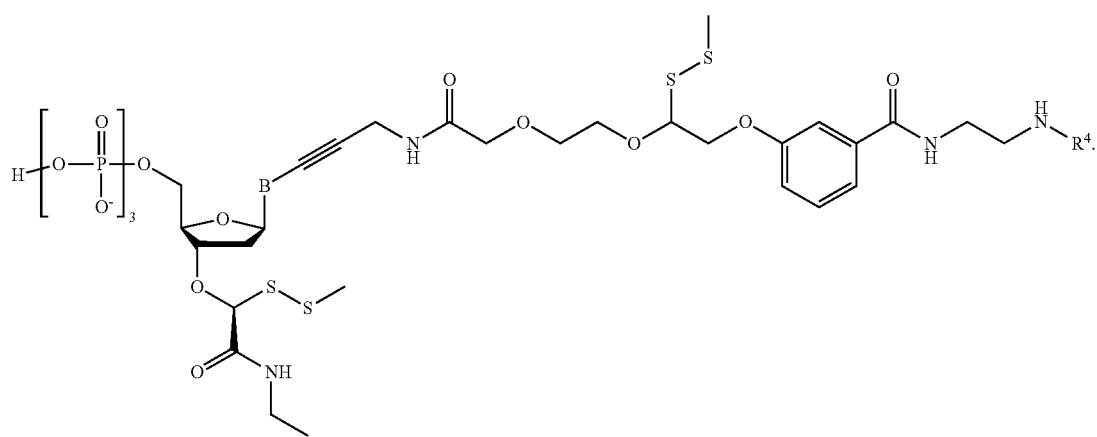
B and R⁴ are as described herein.

In embodiments, the compound has the formula:

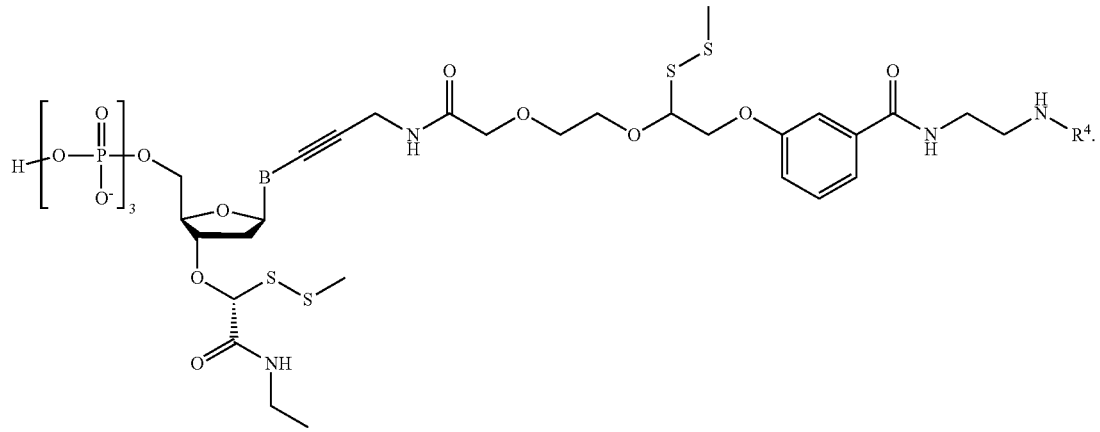

B and R$^4$ are as described herein.
In embodiments, the compound has the formula.

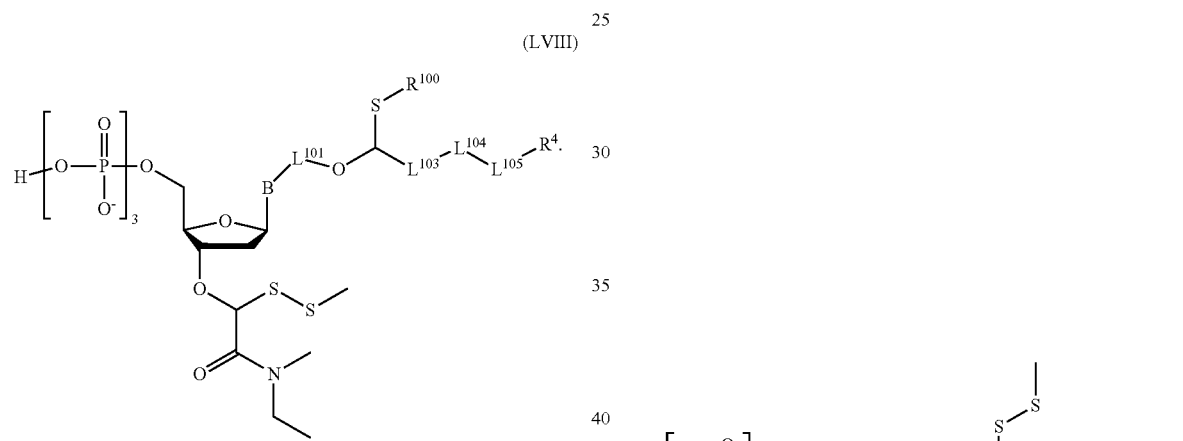

B, L$^{101}$, L$^{103}$, L$^{104}$, L$^{105}$, and R$^4$ are as described herein. In embodiments of Formula (LVIII), R$^{100}$ is —SR$^{102}$, and R$^{102}$ is as described herein (e.g., unsubstituted C$_1$-C$_4$ alkyl). In embodiments of Formula (LVIII), R$^{100}$ is —CN.
In embodiments, the compound has the formula:

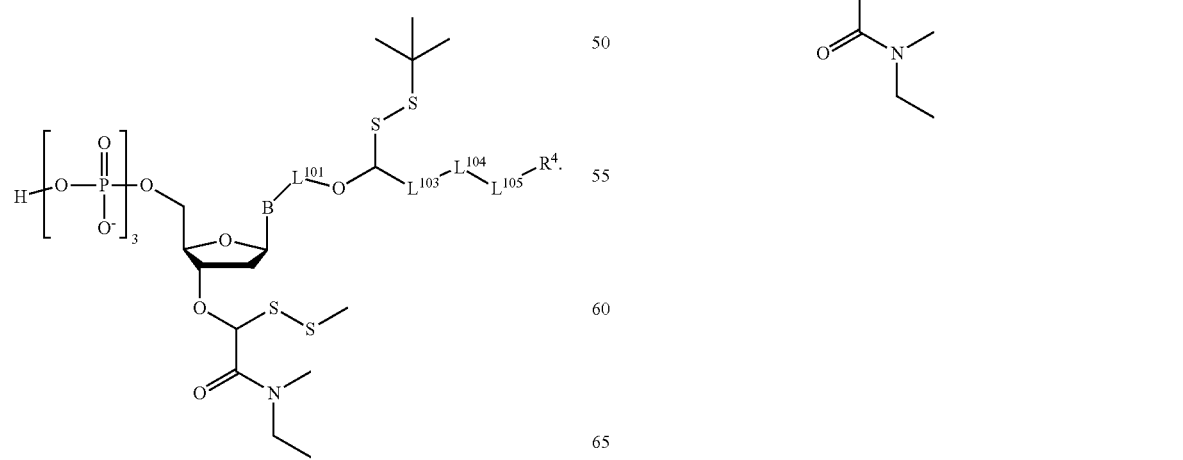

B, L$^{101}$, L$^{103}$, L$^{104}$, L$^{105}$, and R$^4$ are as described herein.

In embodiments, the compound has the formula:

B, L$^{101}$, L$^{103}$, L$^{104}$, L$^{105}$, and R$^4$ are as described herein.

In embodiments, the compound has the formula:

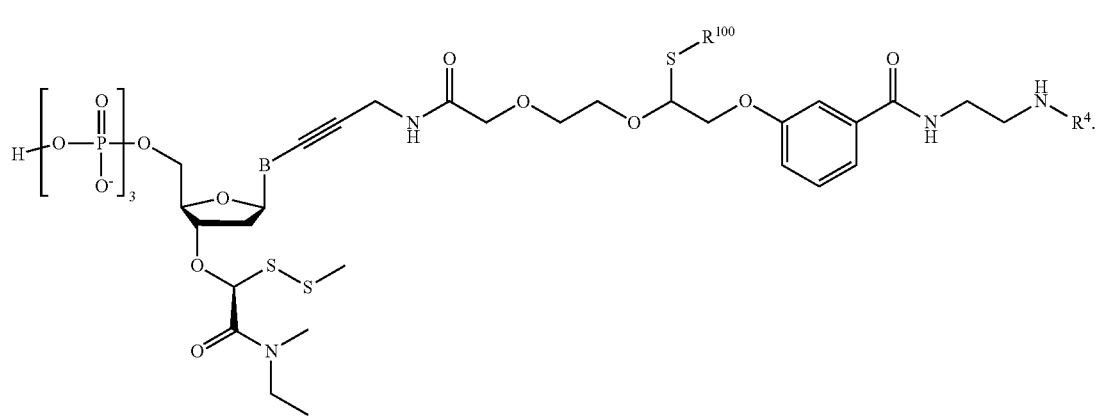

(LIX)

B and R⁴ are as described herein. In embodiments of Formula (LIX), $R^{100}$ is —$SR^{102}$ and $R^{102}$ is as described herein. In embodiments of Formula (LIX), $R^{100}$ is —CN.

In embodiments, the compound has the formula:

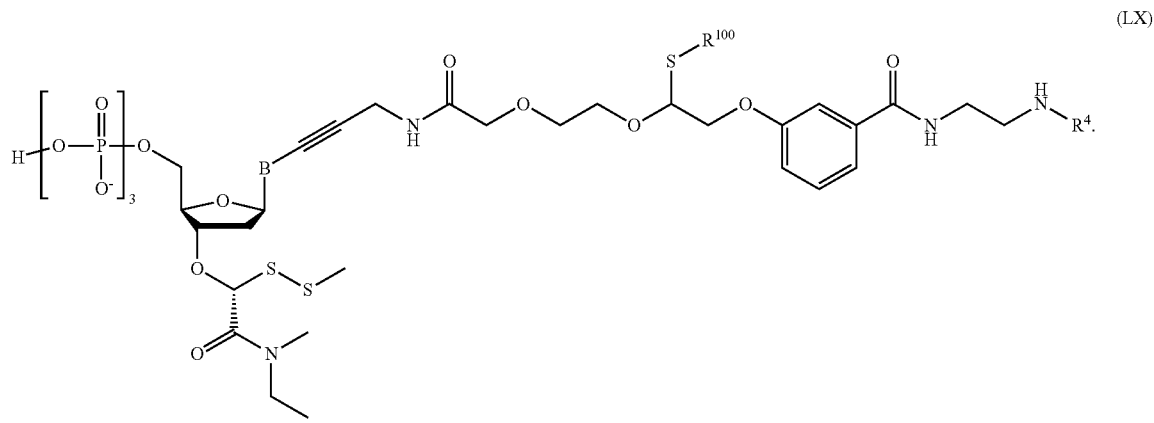

(LX)

B and R⁴ are as described herein. In embodiments of Formula (LX), $R^{100}$ is —$SR^{102}$, and $R^{102}$ is as described herein. In embodiments of Formula (LX), $R^{100}$ is —CN.

In embodiments, the compound has the formula:

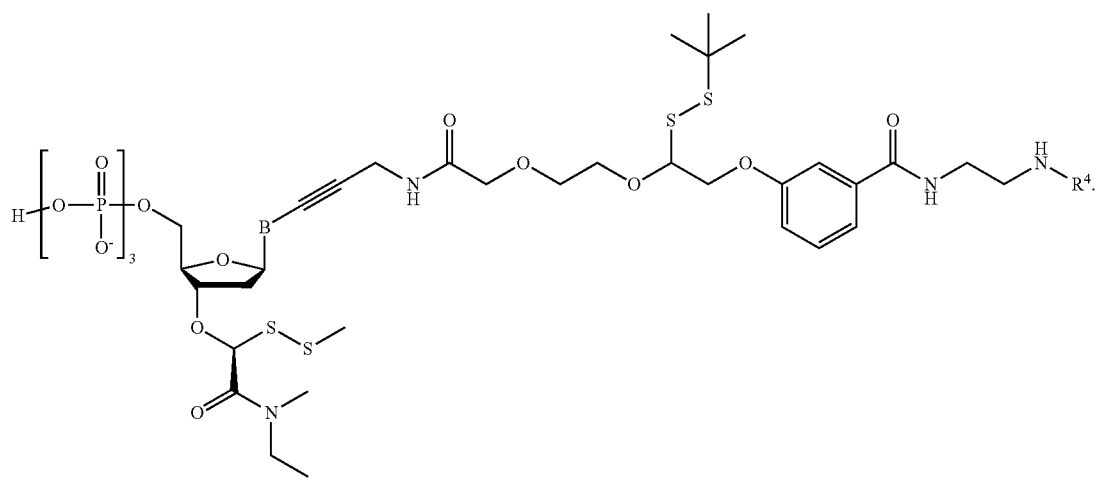

B and R⁴ are as described herein.

In embodiments, the compound has the formula:
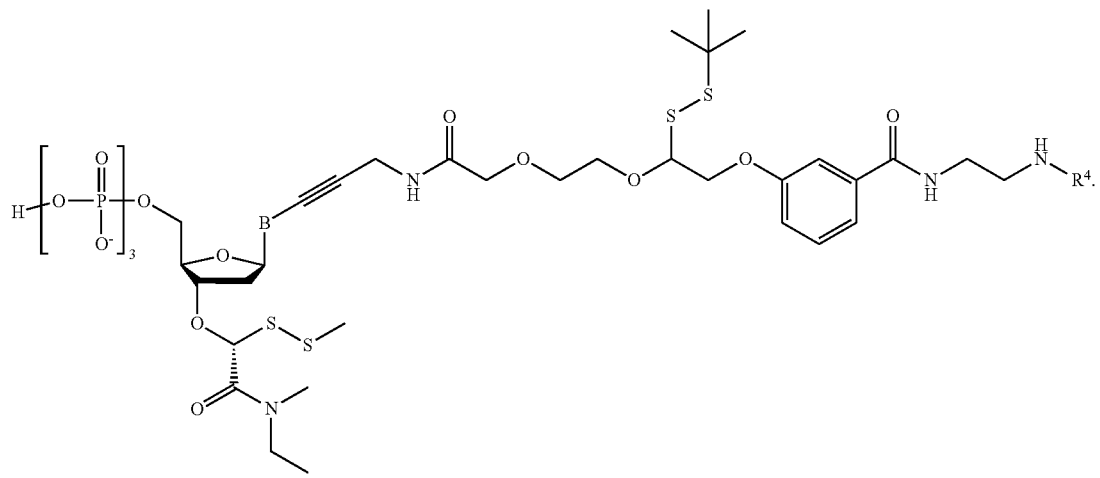
B and R⁴ are as described herein.
In embodiments, the compound has the formula:
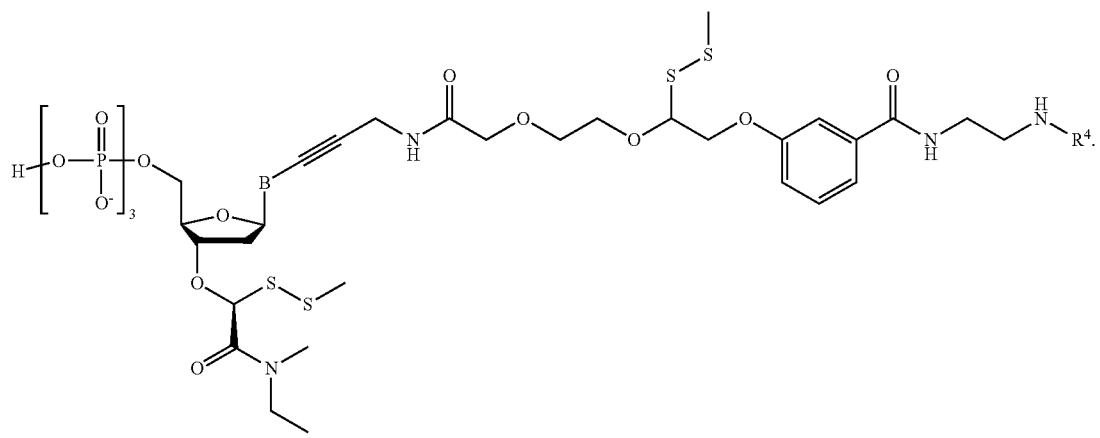
B and R⁴ are as described herein.
In embodiments, the compound has the formula:
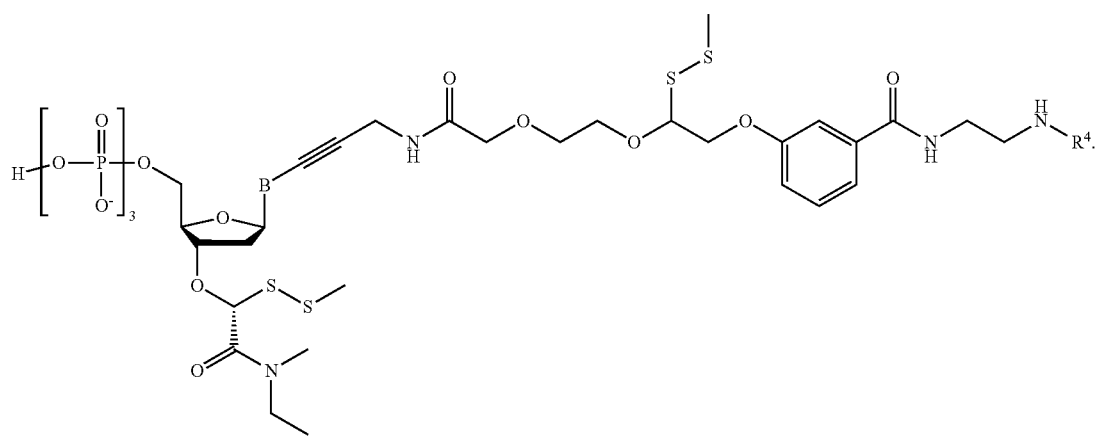
B and R⁴ are as described herein.

In embodiments, the compound has the formula:

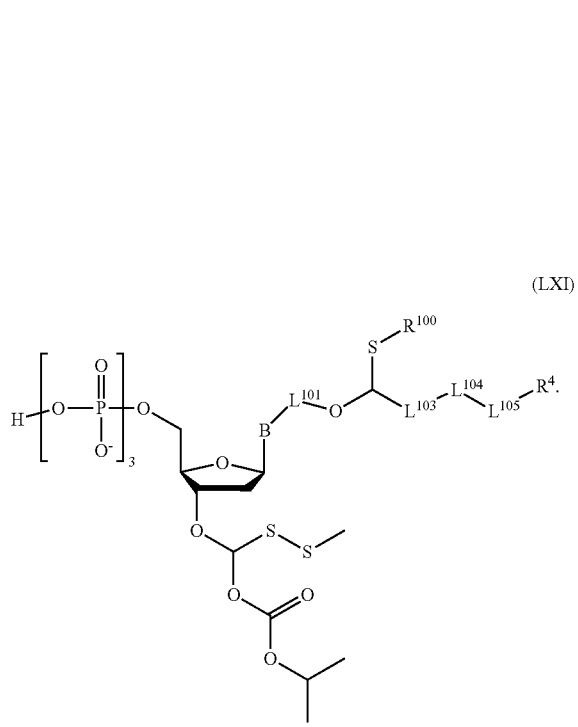

(LXI)

B, $L^{101}$, $L^{103}$, $L^{104}$, $L^{105}$, and $R^4$ are as described herein. In embodiments of Formula (LXI), $R^{100}$ is —$SR^{102}$, and $R^{102}$ is as described herein (e.g., unsubstituted $C_1$-$C_4$ alkyl). In embodiments of Formula (LXI), $R^{100}$ is —CN.

In embodiments, the compound has the formula:

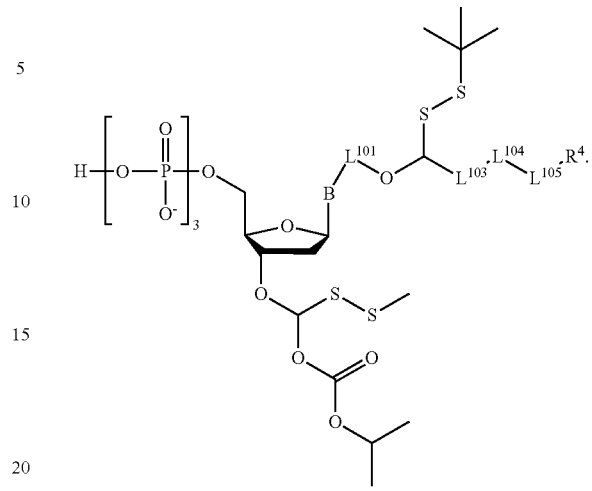

B, $L^{101}$, $L^{103}$, $L^{104}$, $L^{105}$, and $R^4$ are as described herein.

In embodiments, the compound has the formula:

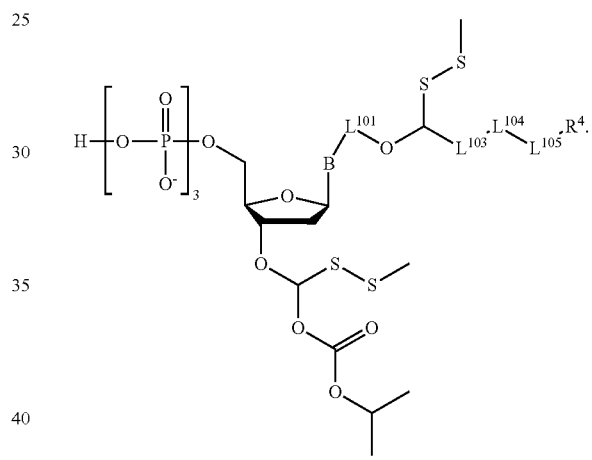

B, $L^{101}$, $L^{103}$, $L^{104}$, $L^{105}$, and $R^4$ are as described herein.

In embodiments, the compound has the formula:

(LXII)

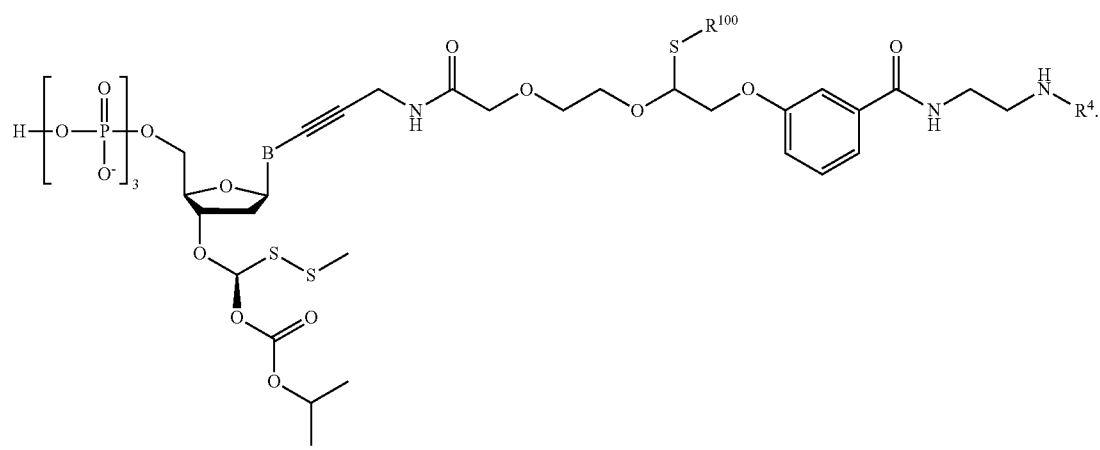

B and $R^4$ are as described herein. In embodiments of Formula (LXII), $R^{100}$ is —$SR^{102}$ and $R^{102}$ is as described herein. In embodiments of Formula (LXII), $R^{100}$ is —CN.

In embodiments, the compound has the formula:
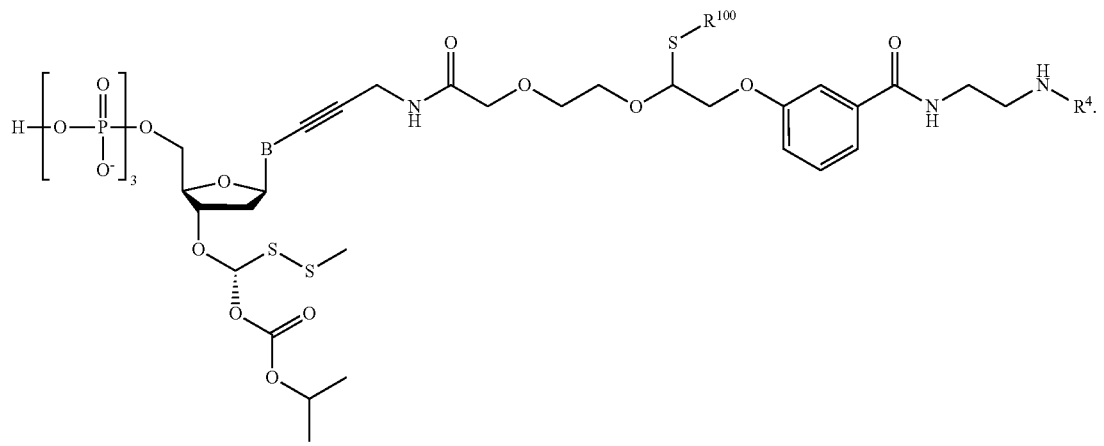
(LXIII)
B and R⁴ are as described herein. In embodiments of Formula (LXIII), $R^{100}$ is —$SR^{102}$, and $R^{102}$ is as described herein. In embodiments of Formula (LXIII), $R^{100}$ is —CN.
In embodiments, the compound has the formula:
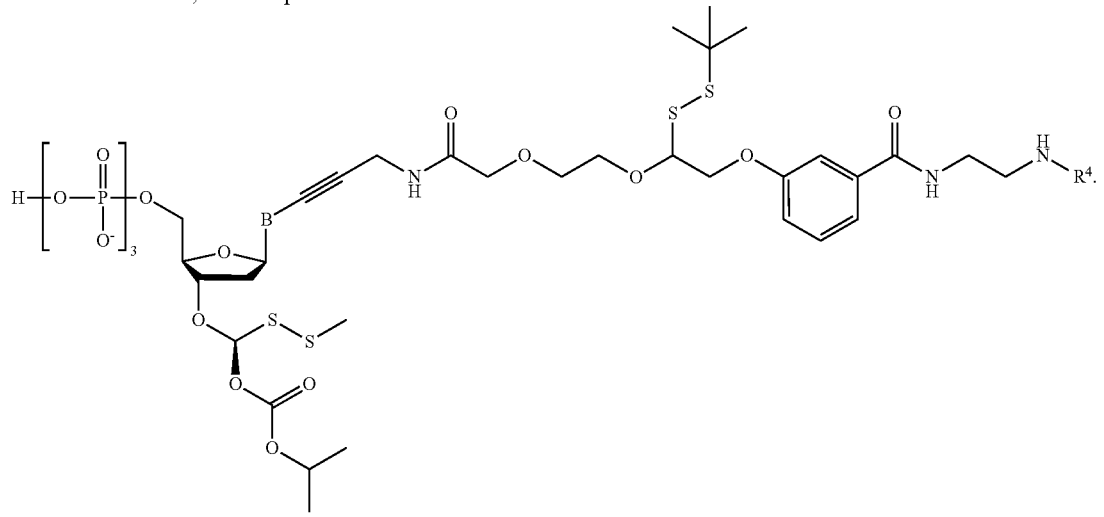
B and R⁴ are as described herein.
In embodiments, the compound has the formula:
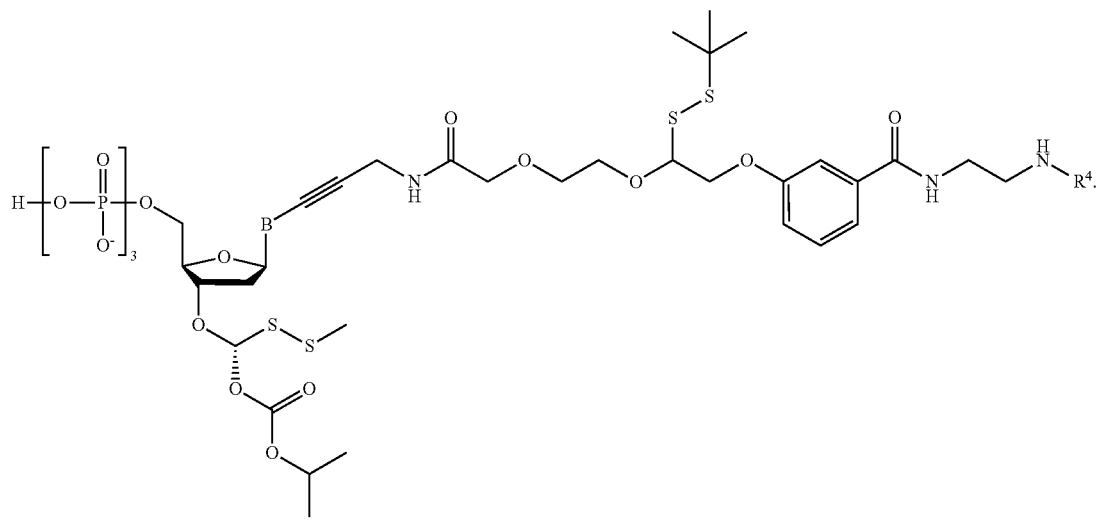
B and R⁴ are as described herein.

In embodiments, the compound has the formula:

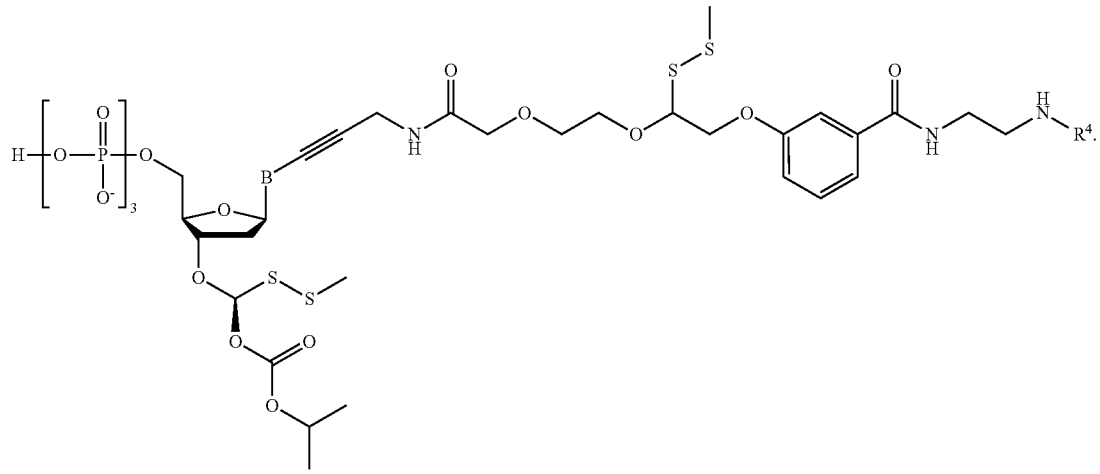

B and R⁴ are as described herein.

In embodiments, the compound has the formula:

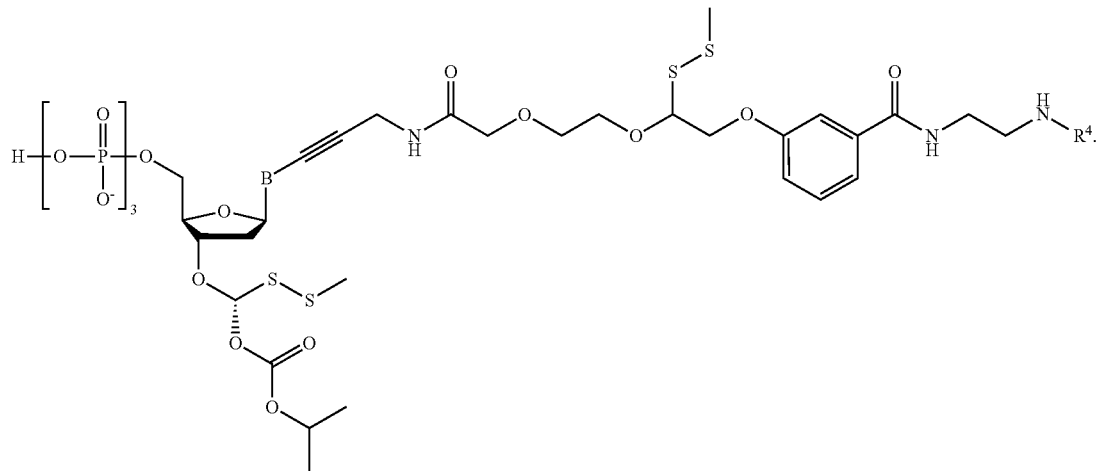

B and R⁴ are as described herein.

In embodiments, the compound has the formula:

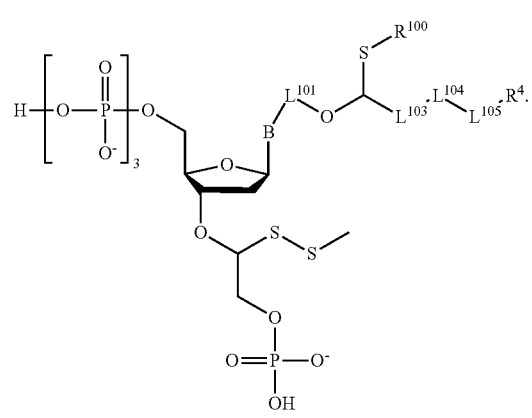

(LXIV)

B, $L^{101}$, $L^{103}$, $L^{104}$, $L^{105}$, and $R^4$ are as described herein. In embodiments of Formula (LXIV), $R^{100}$ is —$SR^{102}$, and $R^{102}$ is as described herein (e.g., unsubstituted $C_1$-$C_4$ alkyl). In embodiments of Formula (LXIV), $R^{100}$ is —CN.

327

In embodiments, the compound has the formula:

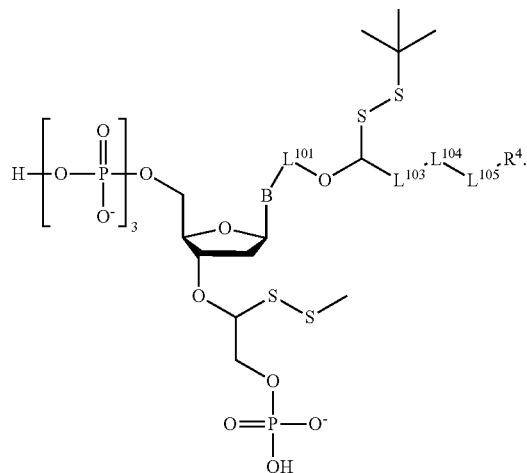

B, $L^{101}$, $L^{103}$, $L^{104}$, $L^{105}$, and $R^4$ are as described herein.

328

In embodiments, the compound has the formula:

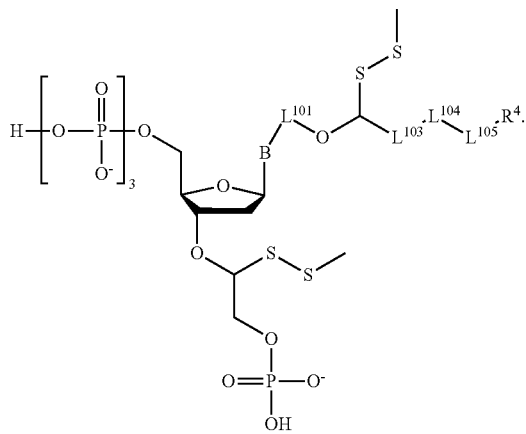

B, $L^{101}$, $L^{103}$, $L^{104}$, $L^{105}$, and $R^4$ are as described herein.

In embodiments, the compound has the formula:

(LXV)

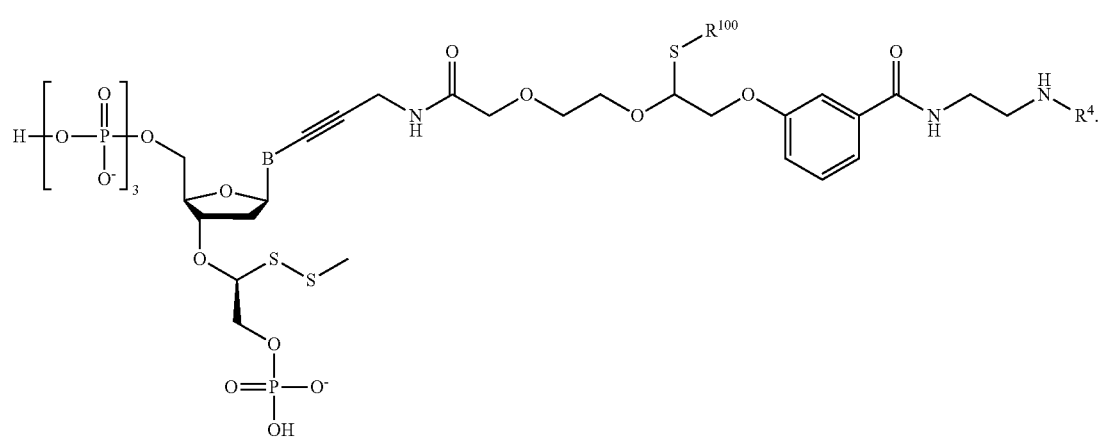

B and $R^4$ are as described herein. In embodiments of Formula (LXV), $R^{100}$ is —$SR^{102}$, and $R^{102}$ is as described herein. In embodiments of Formula (LXV), $R^{100}$ is —CN.

In embodiments, the compound has the formula:

(LXVI)

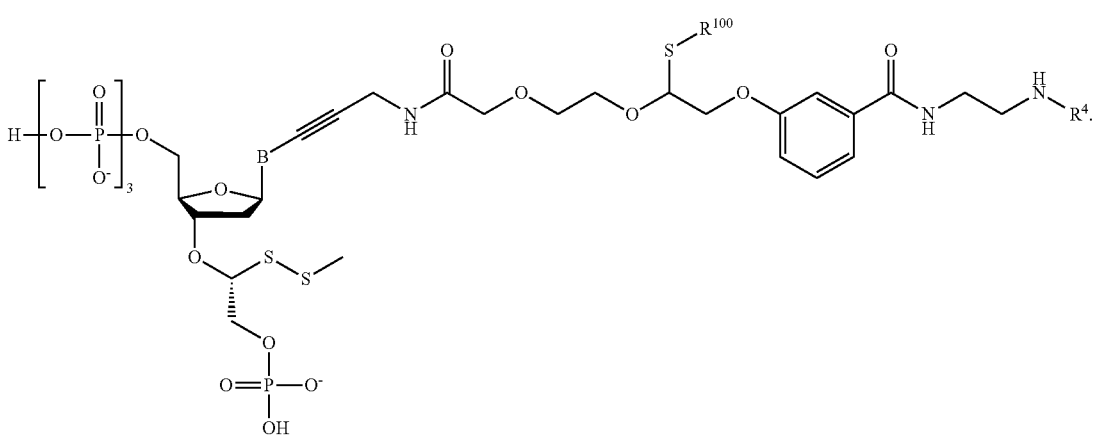

B and $R^4$ are as described herein. In embodiments of Formula (LXVI), $R^{100}$ is —$SR^{102}$, and $R^{102}$ is as described herein. In embodiments of Formula (LXVI), $R^{100}$ is —CN.

In embodiments, the compound has the formula:
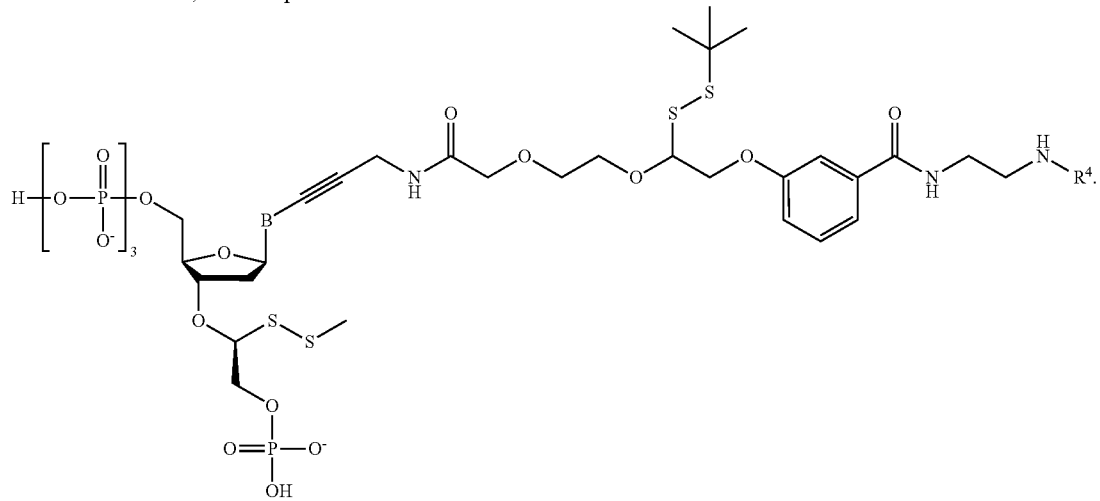
B and R⁴ are as described herein.
In embodiments, the compound has the formula:
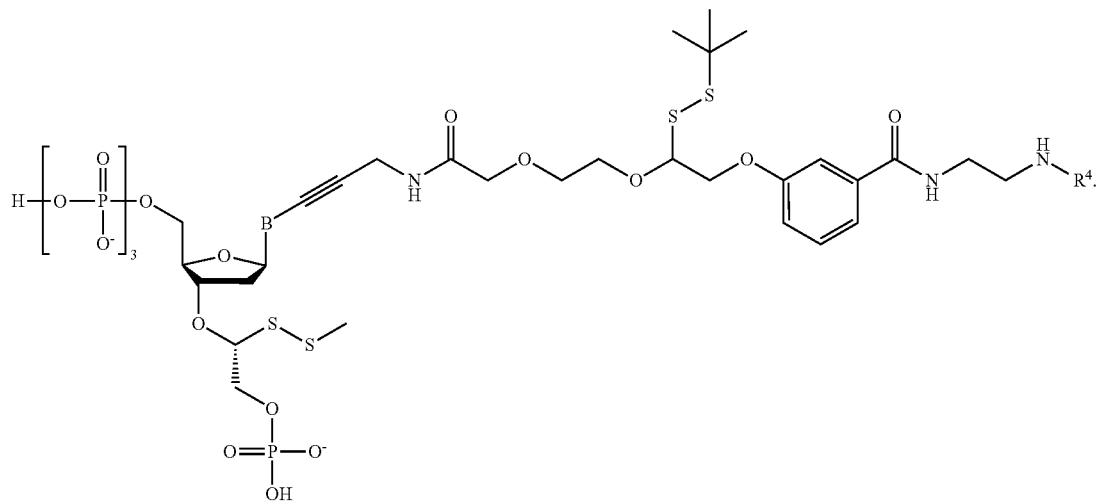
B and R⁴ are as described herein.
In embodiments, the compound has the formula:
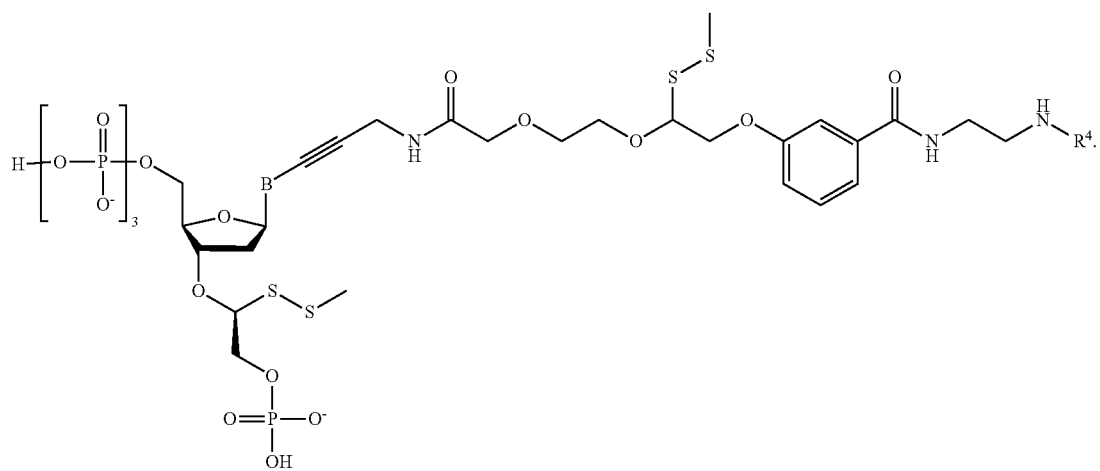
B and R⁴ are as described herein.

In embodiments, the compound has the formula:

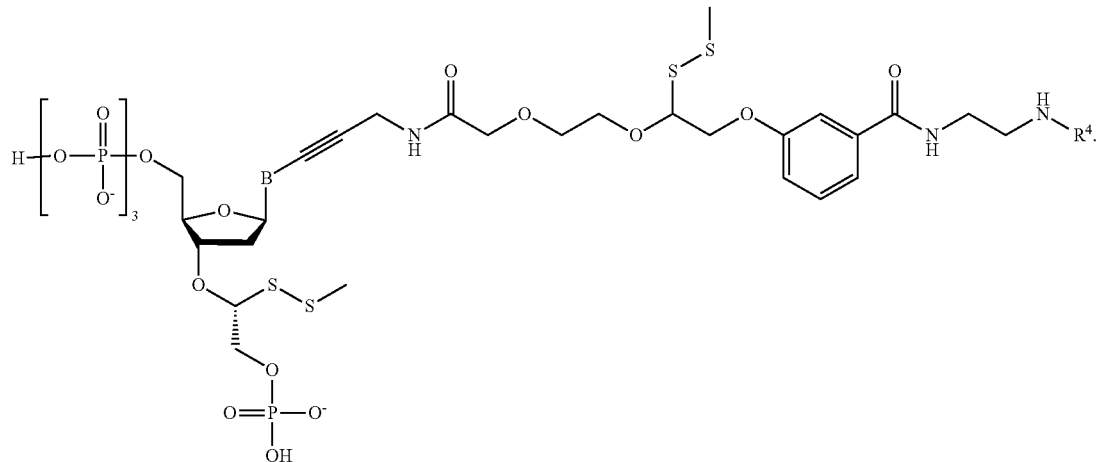

B and R⁴ are as described herein.

In embodiments, the compound has the formula:

(LXVII)

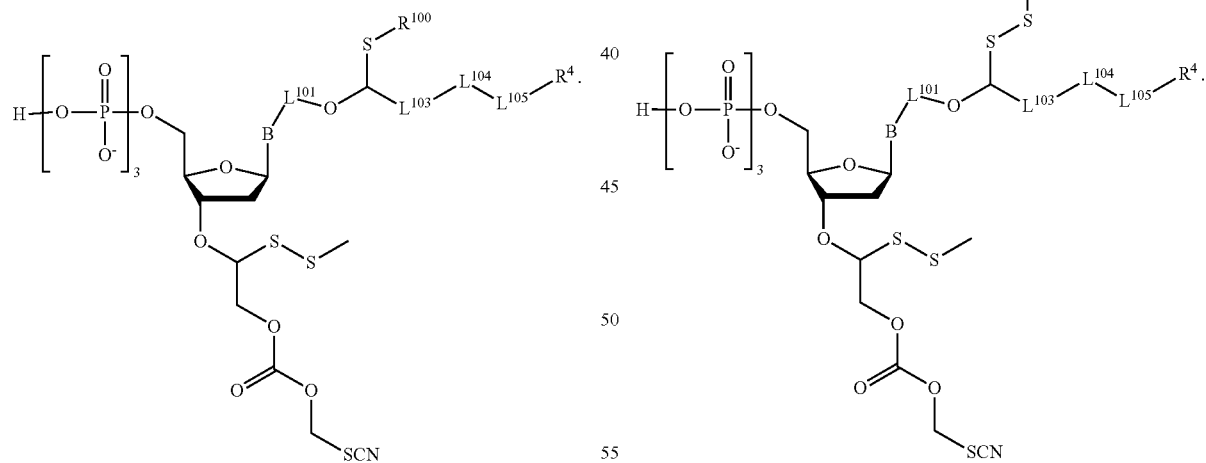

B, $L^{101}$, $L^{103}$, $L^{104}$, $L^{105}$, and R⁴ are as described herein. In embodiments of Formula (LXVII), $R^{100}$ is —$SR^{102}$, and $R^{102}$ is as described herein (e.g., unsubstituted $C_1$-$C_4$ alkyl). In embodiments of Formula (LXVII), $R^{100}$ is —CN.

In embodiments, the compound has the formula:

B, $L^{101}$, $L^{103}$, $L^{104}$, $L^{105}$, and R⁴ are as described herein.

In embodiments, the compound has the formula:

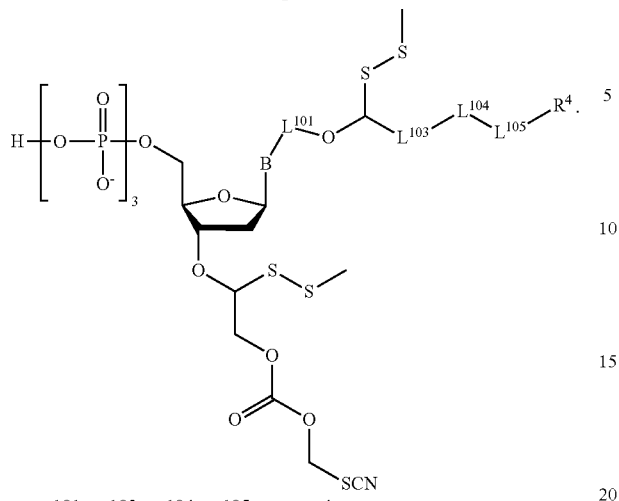

B, $L^{101}$, $L^{103}$, $L^{104}$, $L^{105}$, and $R^4$ are as described herein.

In embodiments, the compound has the formula:

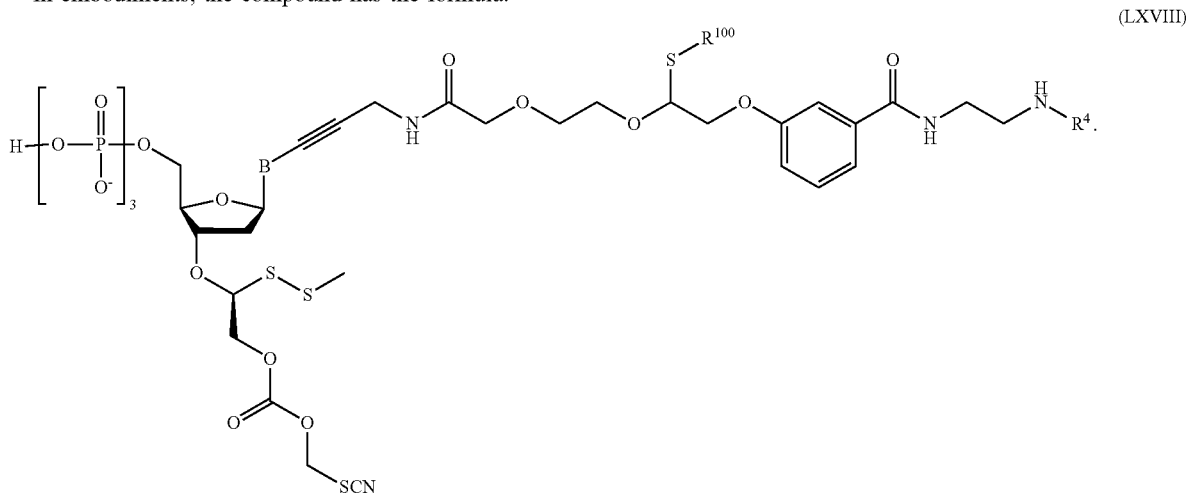

(LXVIII)

B and $R^4$ are as described herein. In embodiments of Formula (LXVIII), $R^{100}$ is —$SR^{102}$, and $R^{102}$ is as described herein. In embodiments of Formula (LXVIII), $R^{100}$ is —CN.

In embodiments, the compound has the formula:

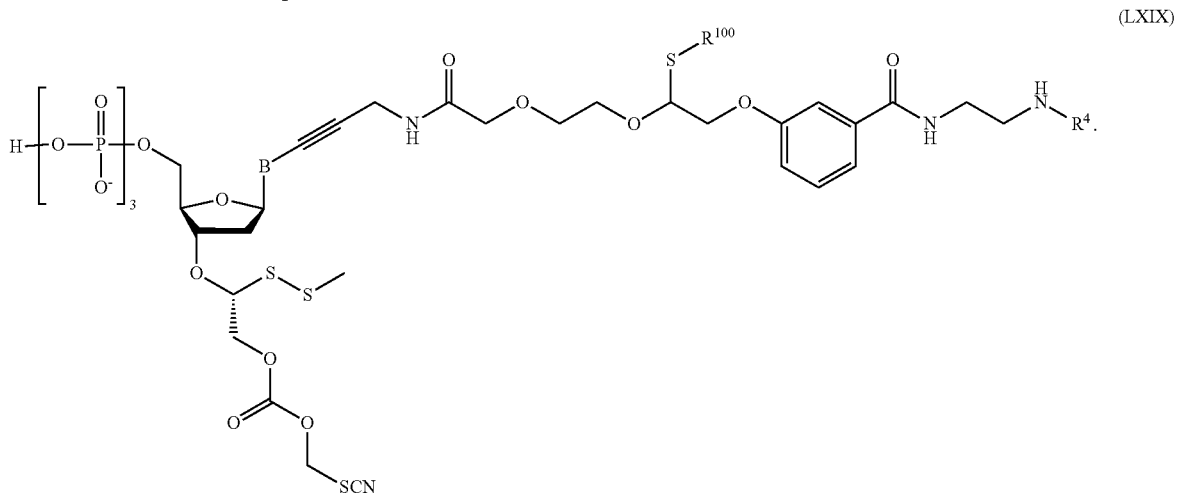

(LXIX)

B and $R^4$ are as described herein. In embodiments of Formula (LXIX), $R^{100}$ is —$SR^{102}$, and $R^{102}$ is as described herein. In embodiments of Formula (LXIX), $R^{100}$ is —CN.

In embodiments, the compound has the formula:
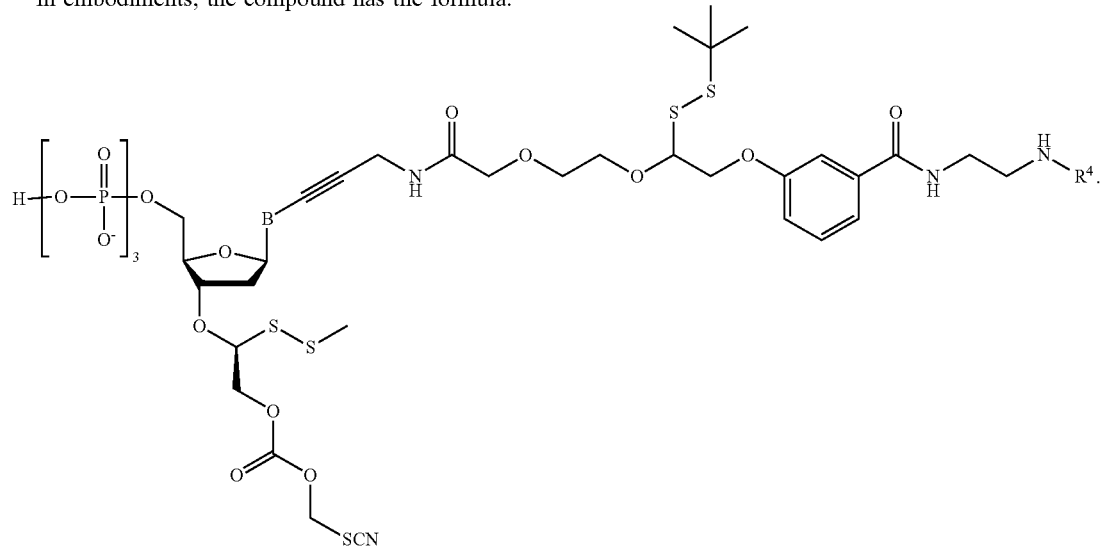
B and R⁴ are as described herein.
In embodiments, the compound has the formula:
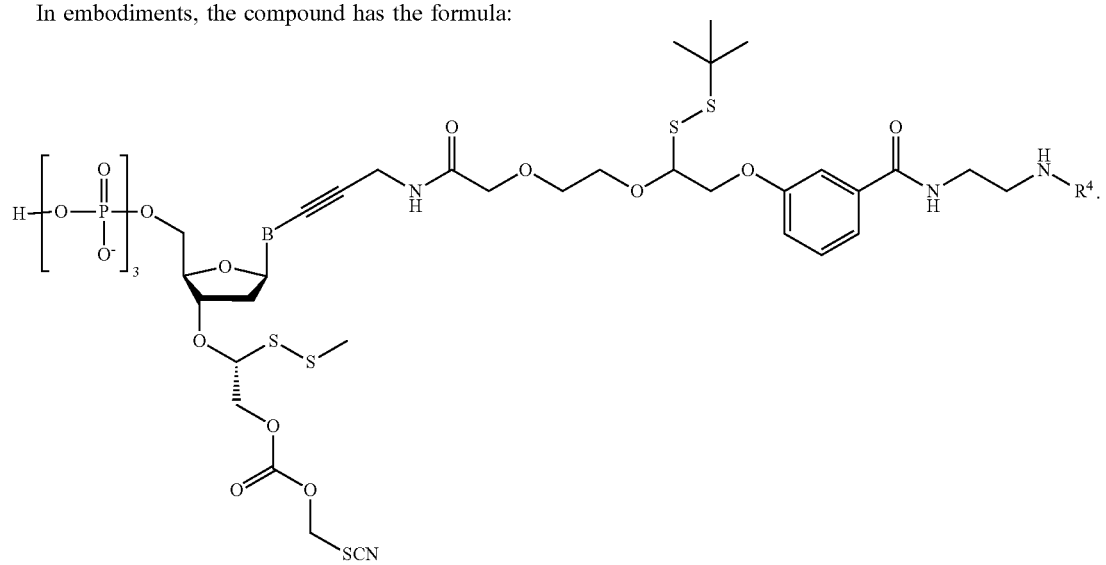
B and R⁴ are as described herein.
In embodiments, the compound has the formula:
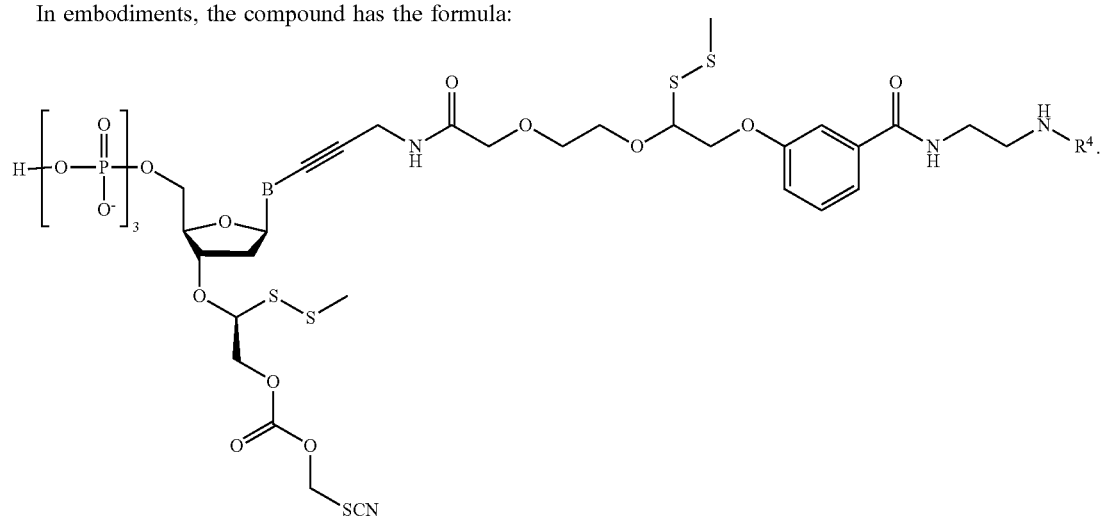
B and R⁴ are as described herein.

In embodiments, the compound has the formula:

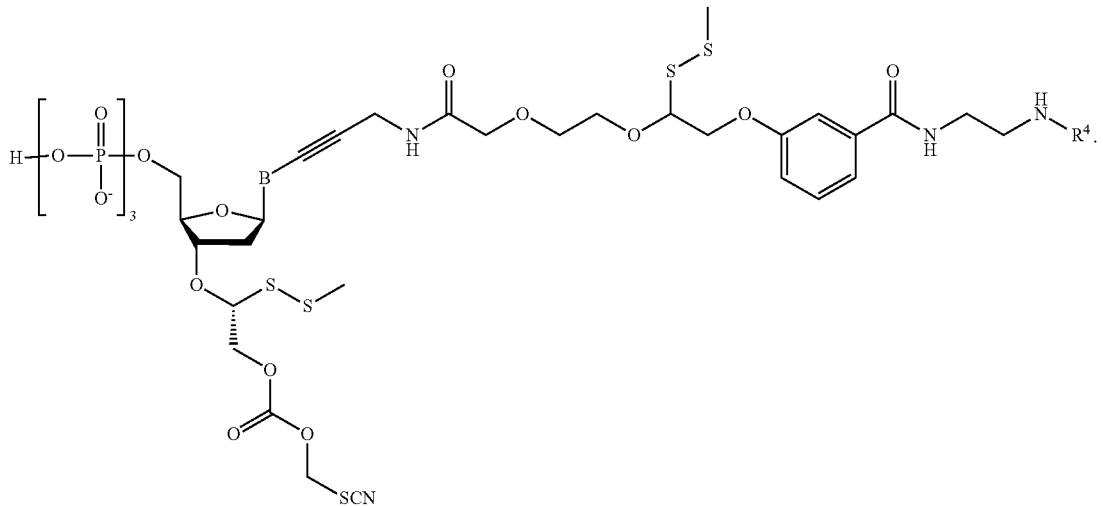

B and R⁴ are as described herein.

In embodiments, the compound has the formula:

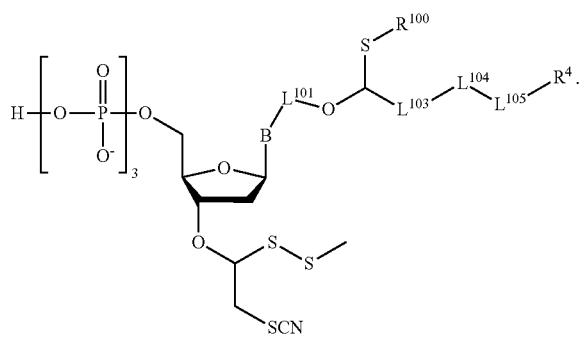

(LXX)

B, $L^1$, $L^{103}$, $L^{104}$, $L^{105}$, and R⁴ are as described herein. In embodiments of Formula (LXX), $R^{100}$ is —$SR^{102}$, and $R^{102}$ is as described herein (e.g., unsubstituted $C_1$-$C_4$ alkyl). In embodiments of Formula (LXX), $R^{100}$ is —CN.

In embodiments, the compound has the formula:

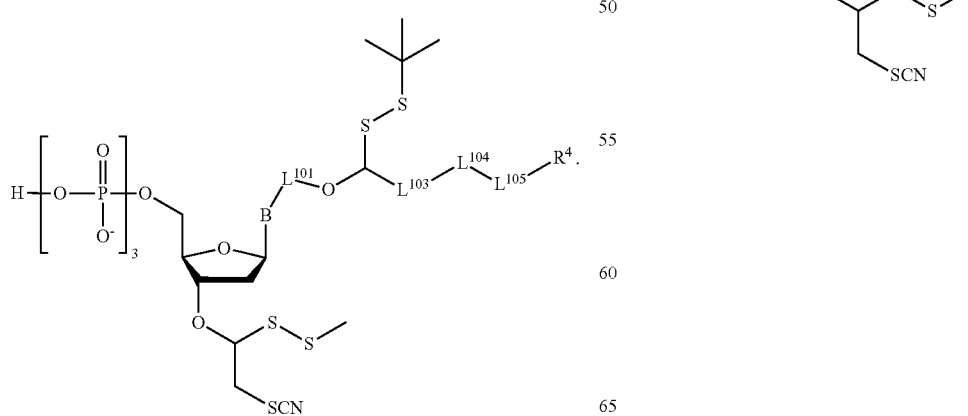

B, $L^{101}$, $L^{103}$, $L^{104}$, $L^{105}$, and R⁴ are as described herein.

In embodiments, the compound has the formula:

B, $L^{101}$, $L^{103}$, $L^{104}$, $L^{105}$, and R⁴ are as described herein.

In embodiments, the compound has the formula:

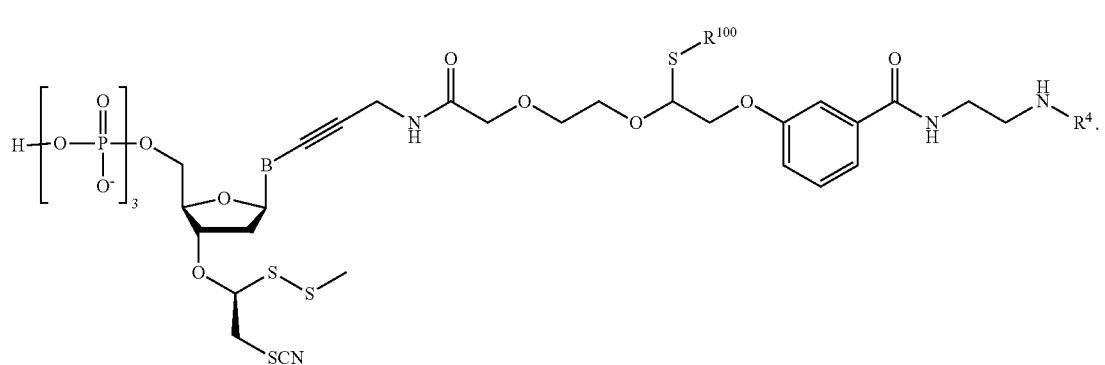

(LXXI)

B and R⁴ are as described herein. In embodiments of Formula (LXXI), $R^{100}$ is —SR$^{102}$, and $R^{102}$ is as described herein. In embodiments of Formula (LXXI), $R^{100}$ is —CN.

In embodiments, the compound has the formula:

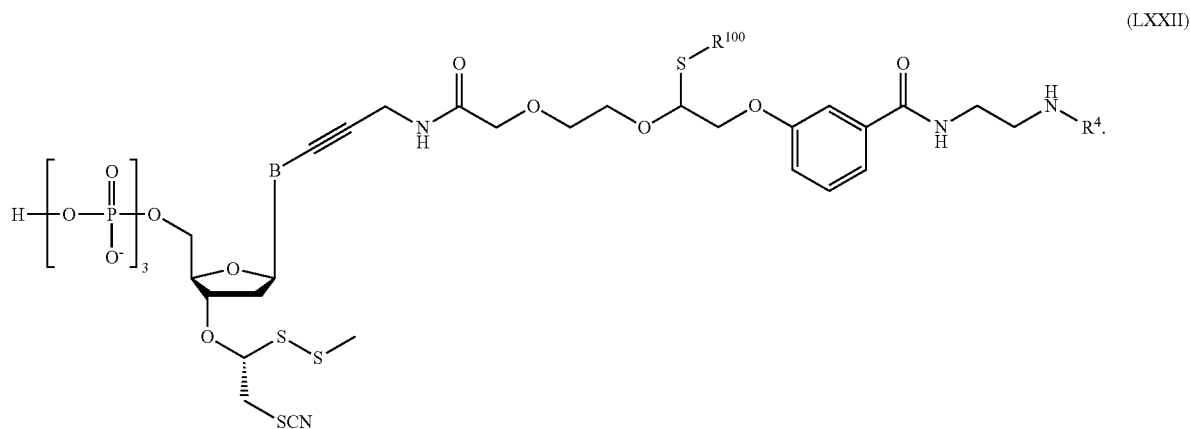

(LXXII)

B and R⁴ are as described herein. In embodiments of Formula (LXXII), $R^{100}$ is —SR$^{102}$, and $R^{102}$ is as described herein. In embodiments of Formula (LXXII), $R^{100}$ is —CN.

In embodiments, the compound has the formula:

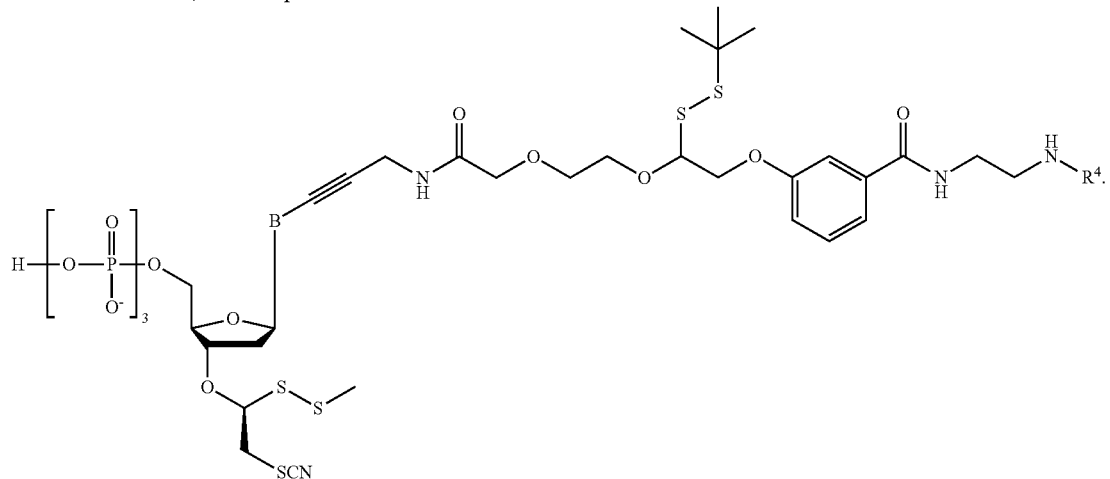

B and R⁴ are as described herein.

In embodiments, the compound has the formula:
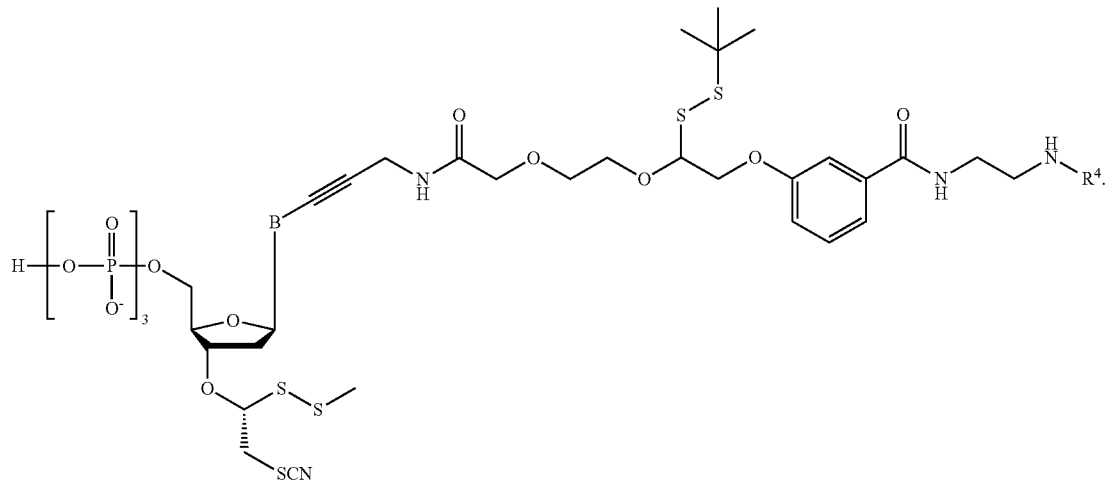
B and R⁴ are as described herein.
In embodiments, the compound has the formula:
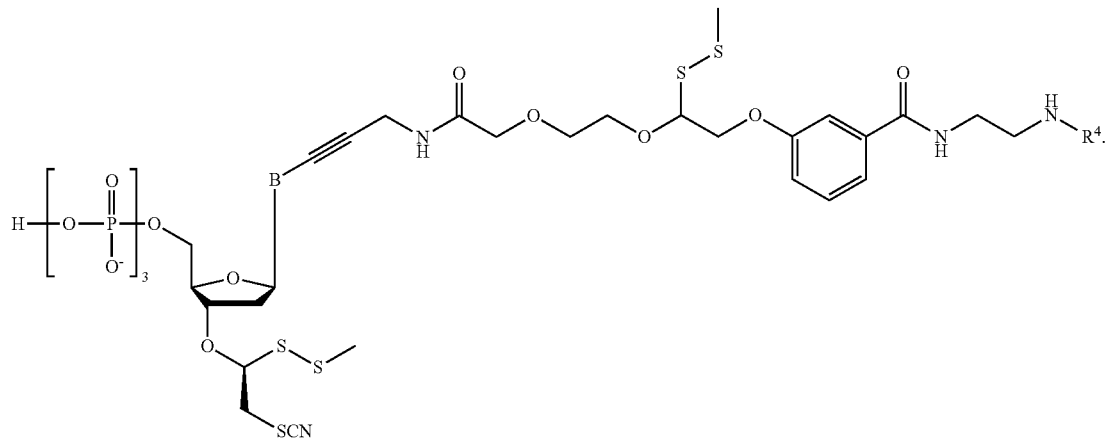
B and R⁴ are as described herein.
In embodiments, the compound has the formula:
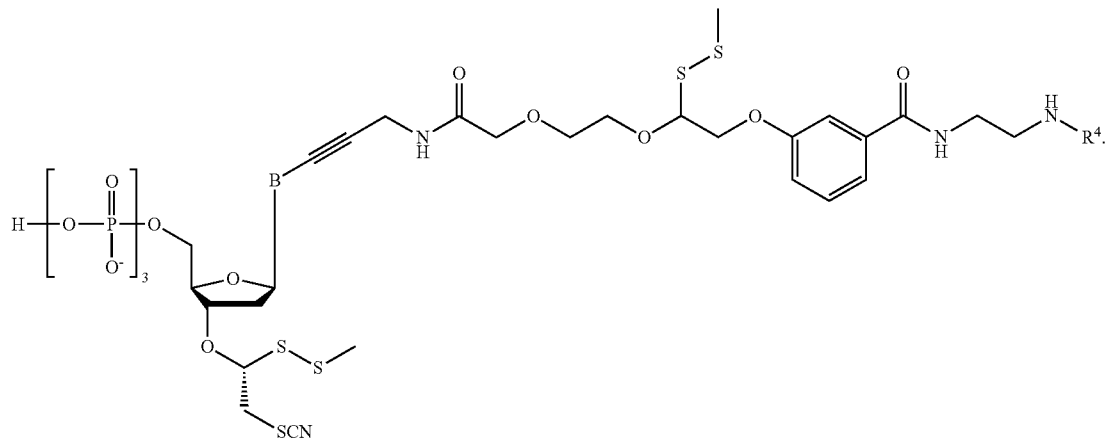
B and R⁴ are as described herein.

In embodiments, the compound has the formula:

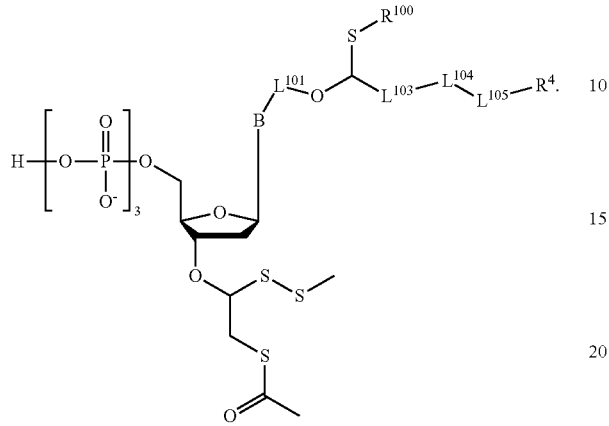

(LXXIII)

B, $L^{101}$, $L^{103}$, $L^{104}$, $L^{105}$, and $R^4$ are as described herein. In embodiments of Formula (LXXIII), $R^{100}$ is —$SR^{102}$, and $R^{102}$ is as described herein (e.g. unsubstituted $C_1$-$C_4$ alkyl). In embodiments of Formula (LXXIII), $R^{100}$ is —CN.

In embodiments, the compound has the formula:

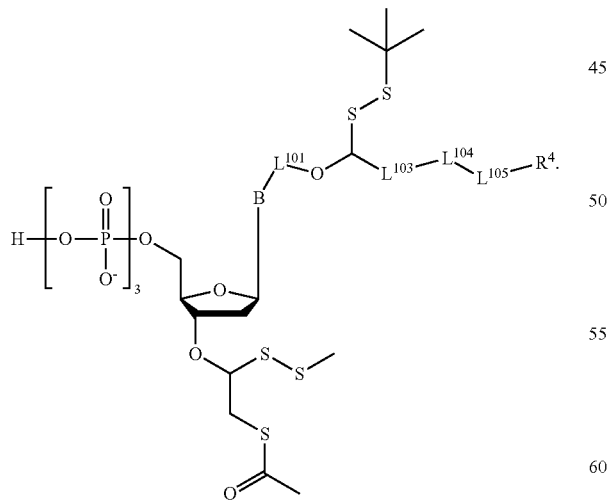

B, $L^{101}$, $L^{103}$, $L^{104}$, $L^{105}$, and $R^4$ are as described herein.

In embodiments, the compound has the formula.

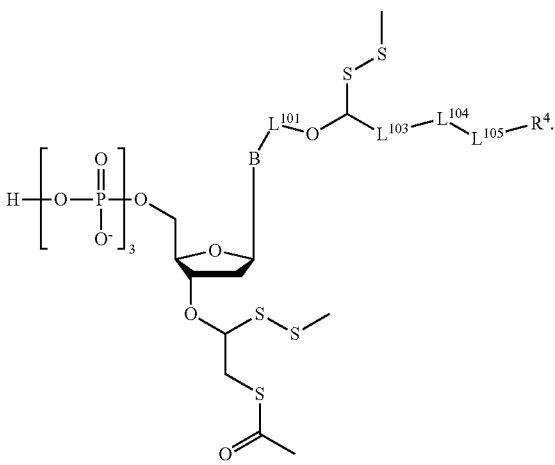

B, $L^{101}$, $L^{103}$, $L^{104}$, $L^{105}$, and $R^4$ are as described herein.

In embodiments, the compound has the formula:

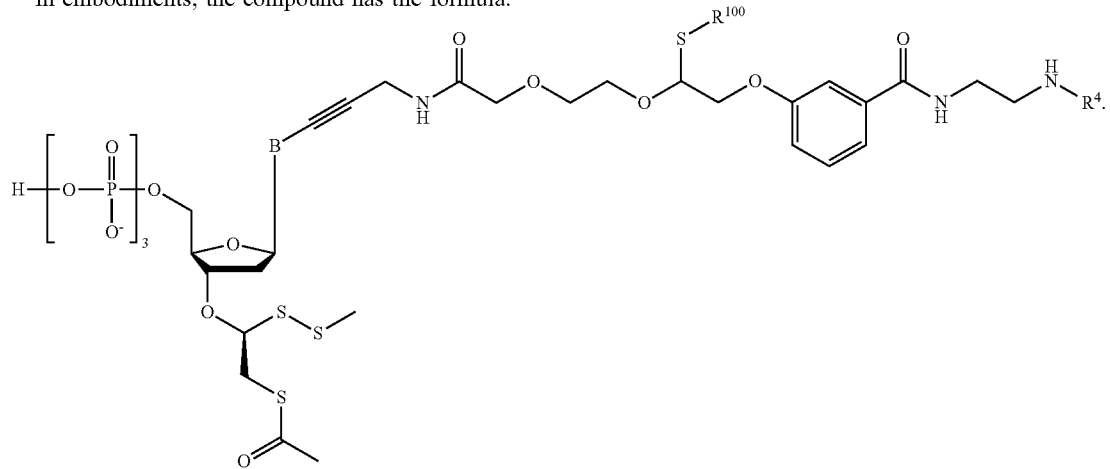

(LXXIV)

B and R⁴ are as described herein. In embodiments of Formula (LXXIV), $R^{100}$ is —$SR^{100}2$, and $R^{102}$ is as described herein. In embodiments of Formula (LXXIV), $R^{100}$ is —CN.

In embodiments, the compound has the formula:

(LXXV)

B and R⁴ are as described herein. In embodiments of Formula (LXXV), $R^{100}$ is —$SR^{100}2$, and $R^{102}$ is as described herein. In embodiments of Formula (LXXV), $R^{100}$ is —CN.

In embodiments, the compound has the formula:

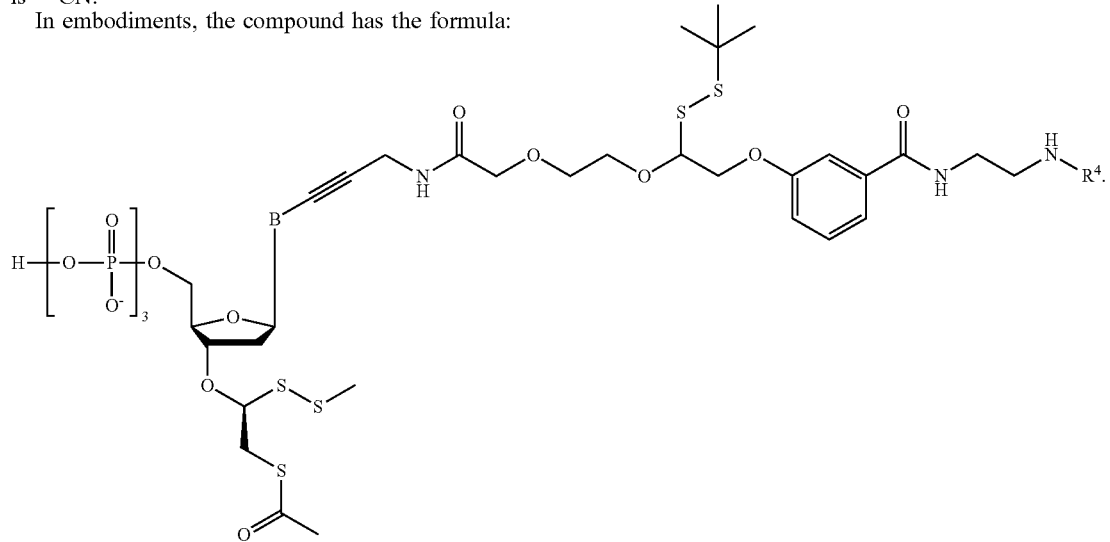

B and R⁴ are as described herein.

In embodiments, the compound has the formula:
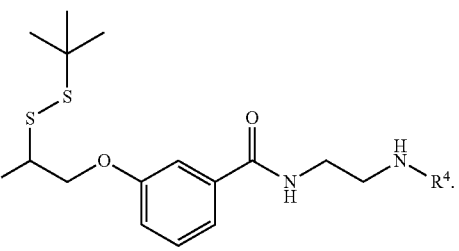
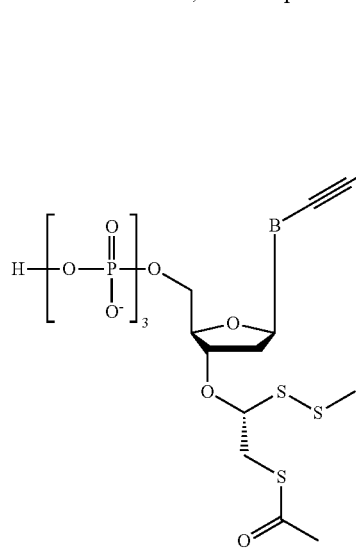
B and R⁴ are as described herein.
In embodiments, the compound has the formula:
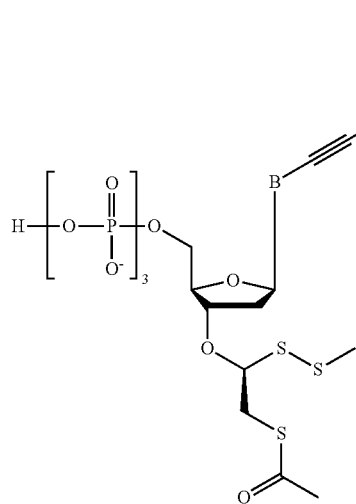
B and R⁴ are as described herein.
In embodiments, the compound has the formula:
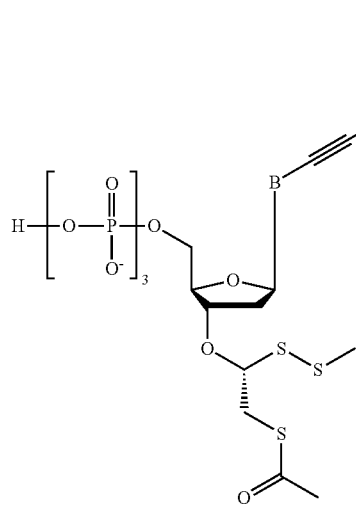
B and R⁴ are as described herein.

In embodiments, the compound has the formula:

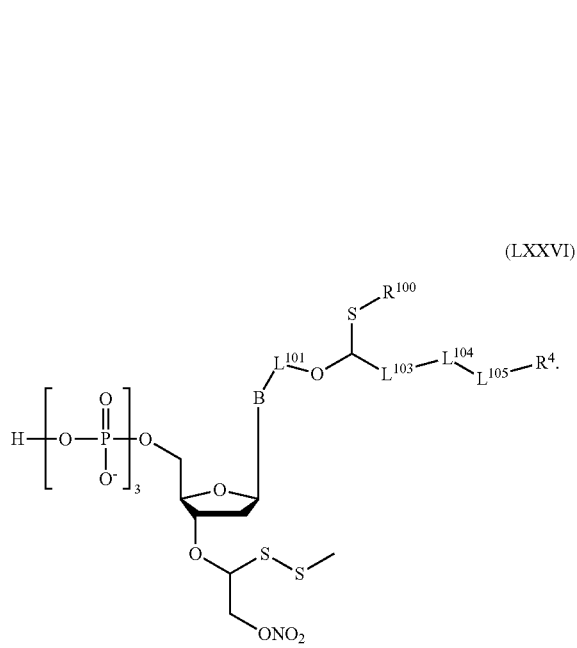

(LXXVI)

B, $L^{101}$, $L^{103}$, $L^{104}$, $L^{105}$, and $R^4$ are as described herein. In embodiments of Formula (LXXVI), $R^{100}$ is —$SR^{102}$, and $R^{102}$ is as described herein (e.g., unsubstituted $C_1$-$C_4$ alkyl). In embodiments of Formula (LXXVI), $R^{100}$ is —CN.

In embodiments, the compound has the formula.

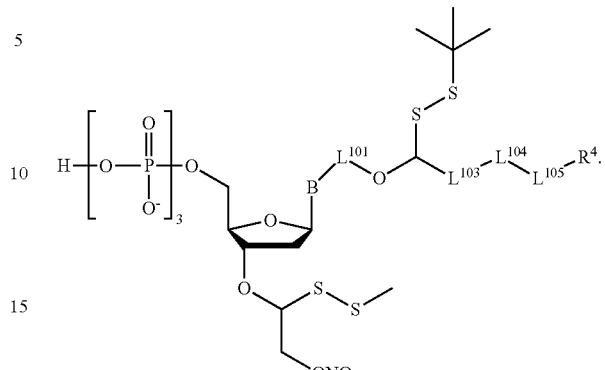

B, $L^{101}$, $L^{103}$, $L^{104}$, $L^{105}$, and $R^4$ are as described herein.

In embodiments, the compound has the formula:

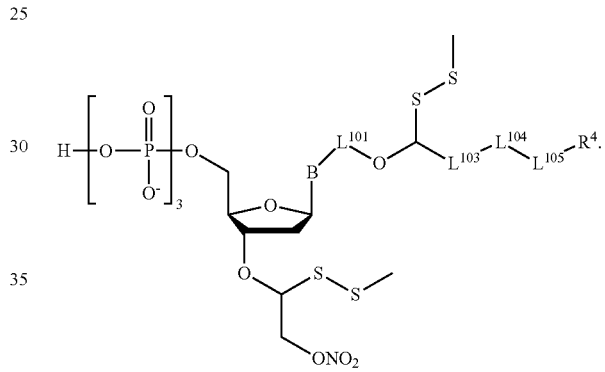

B, $L^{101}$, $L^{103}$, $L^{104}$, $L^{105}$, and $R^4$ are as described herein.

In embodiments, the compound has the formula:

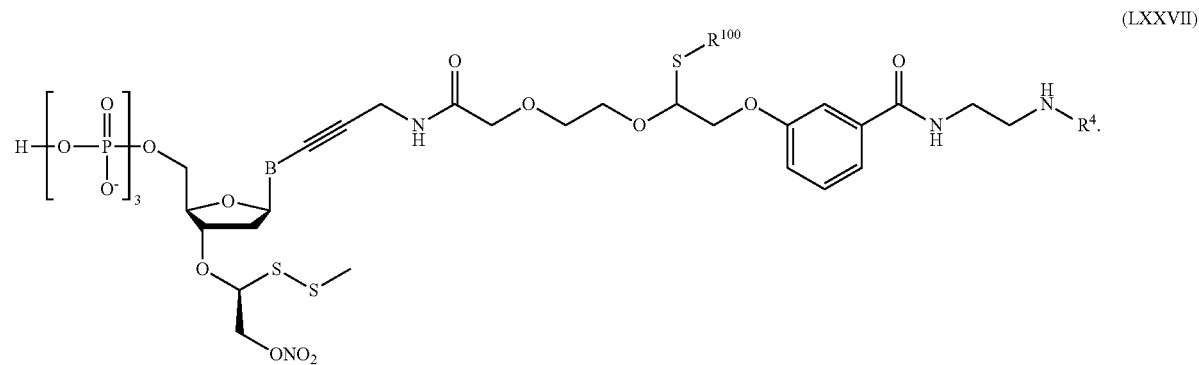

(LXXVII)

B and $R^4$ are as described herein. In embodiments of Formula (LXXVII), $R^{100}$ is —$SR^{100}2$, and $R^{102}$ is as described herein. In embodiments of Formula (LXXVII), $R^{100}$ is —CN.

In embodiments, the compound has the formula:
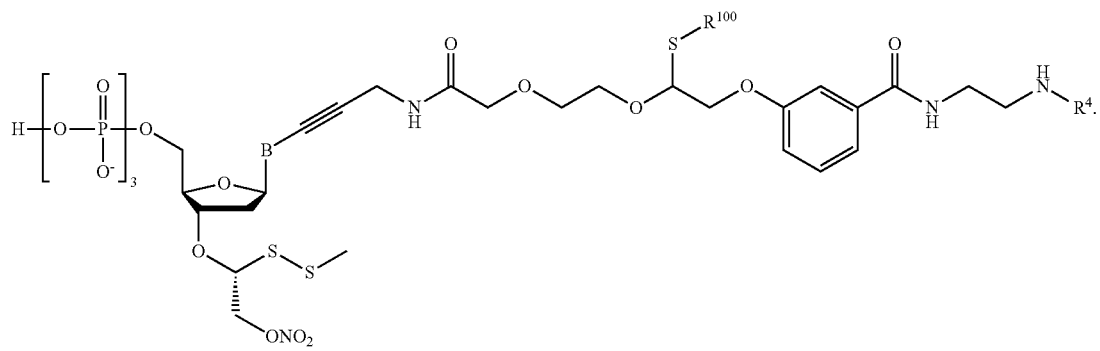
(LXXVIII)
B and R⁴ are as described herein. In embodiments of Formula (LXXVIII), $R^{100}$ is —$SR^{102}$, and $R^{102}$ is as described herein. In embodiments of Formula (LXXVIII), $R^{100}$ is —CN.
In embodiments, the compound has the formula:
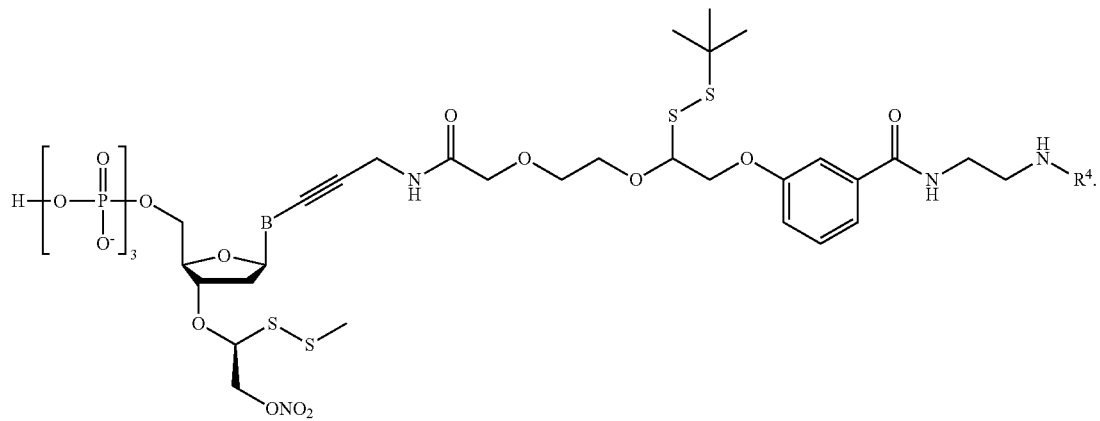
B and R⁴ are as described herein.
In embodiments, the compound has the formula:
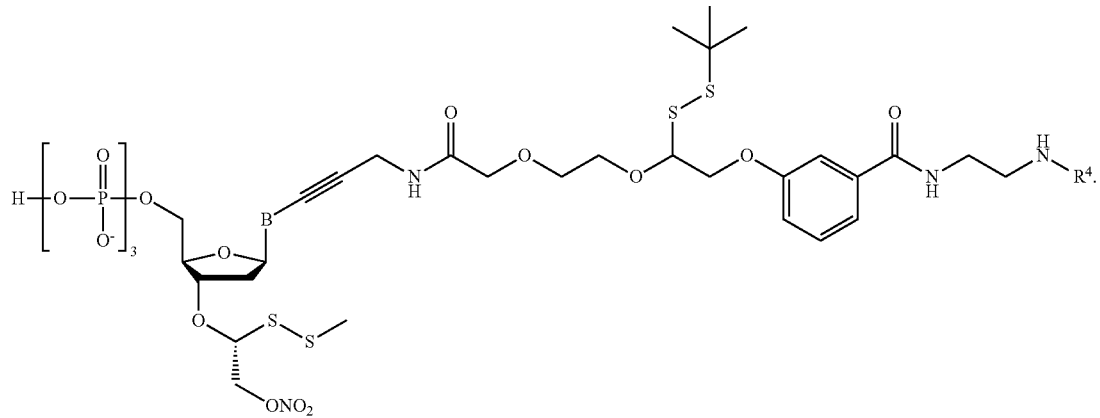
B and R⁴ are as described herein.

In embodiments, the compound has the formula:

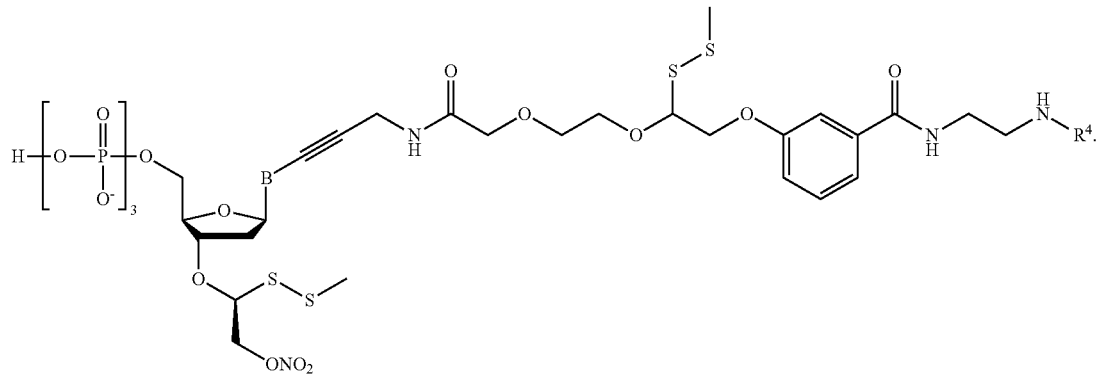

B and R⁴ are as described herein.

In embodiments, the compound has the formula.

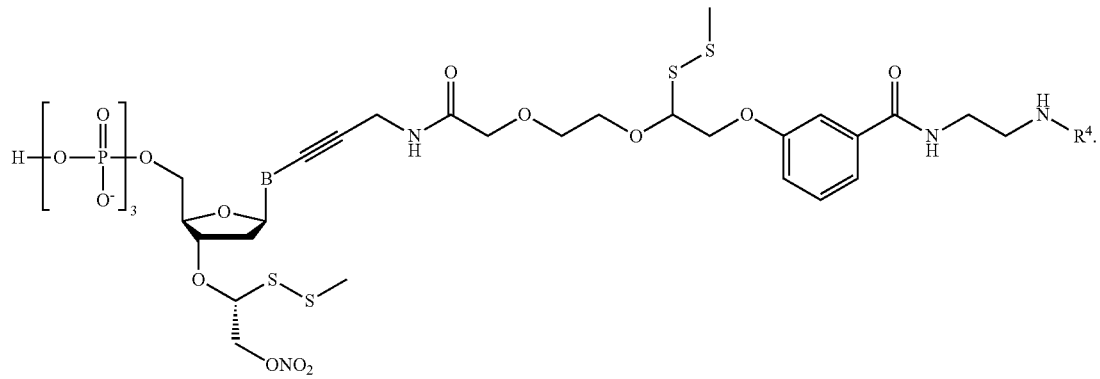

B and R⁴ are as described herein.

In an aspect is provided a nucleic acid polymerase complex, wherein the nucleic acid polymerase is bound (e.g., non-covalently bound) to a compound described herein, including embodiments. In another aspect is provided a modified nucleotide or nucleoside, the nucleotide or nucleoside including a sugar moiety (e.g., a ribose or deoxyribose sugar moiety) having a 3'-O-polymerase-compatible cleavable moiety and a base (e.g., a purine or pyrimidine base) linked via a covalent linker to a detectable moiety, wherein the covalent linker includes a thio-trigger moiety having the formula

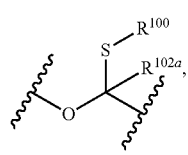

wherein $R^{100}$ is —$SR^{102}$ or —CN; and $R^{102}$ and $R^{102a}$ are as described herein, including embodiments. In embodiments, the thio-trigger moiety has the formula:

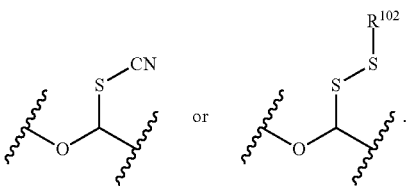

In embodiments, the thio-trigger moiety has the formula:

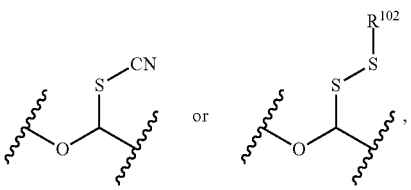

wherein $R^{102}$ is as described herein, including in embodiments. In embodiments, the thio-trigger moiety has the formula:

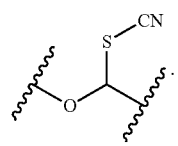 [SMILES: *OC(*)SC#N]

In embodiments, the thio-trigger moiety has the formula:

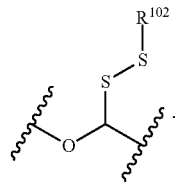

In embodiments, the thio-trigger moiety has the formula:

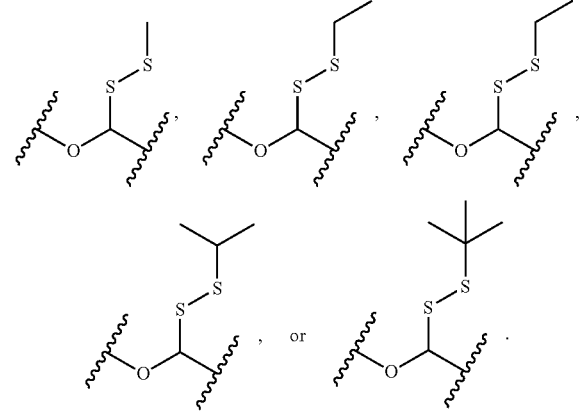, or

In embodiments, the thio-trigger moiety has the formula:

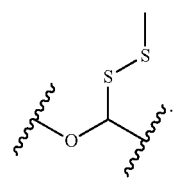 [SMILES: *OC(*)SSC]

In embodiments, the thio-trigger moiety has the formula:

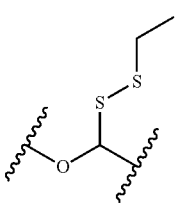

In embodiments, the thio-trigger moiety has the formula:

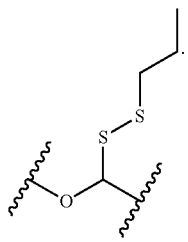 [SMILES: *OC(*)SSCCC]

In embodiments, the thio-trigger moiety has the formula:

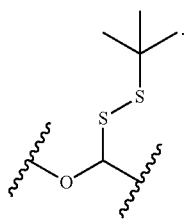 [SMILES: *OC(*)SSC(C)(C)C]

In embodiments, the thio-trigger moiety has the formula:

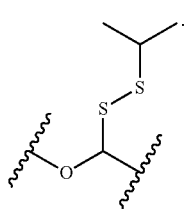 [SMILES: *OC(*)SSC(C)C]

In embodiments, the nucleic acid polymerase is a Taq polymerase, Therminator γ, 9° N polymerase (exo-), Therminator II, Therminator III, or Therminator IX. In embodiments, the nucleic acid polymerase is Therminator γ. In embodiments, the nucleic acid polymerase is 9° N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9° N and mutants thereof. In embodiments, the nucleic acid polymerase is Phi29 and mutants thereof.

In an aspect is provided a compound having the formula:

$$\text{HO}-\overset{\overset{\displaystyle O}{\|}}{\underset{\underset{\displaystyle OH}{|}}{P}}-O-\overset{\overset{\displaystyle O}{\|}}{\underset{\underset{\displaystyle OH}{|}}{P}}-O-\overset{\overset{\displaystyle O}{\|}}{\underset{\underset{\displaystyle OH}{|}}{P}}-O\diagdown\overset{B}{\underset{OR^{3A}}{\bigcirc}}\diagdown L^{101}\diagdown OH,$$

wherein $L^{101}$, B, and $R^{3A}$ are as described herein, including in embodiments. In embodiments, $L^1$ is In embodiments, $L^1$ is

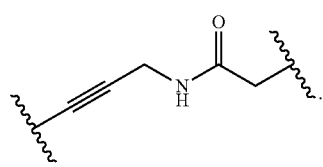 [SMILES: *C#CCNC(=O)C*]

In embodiments, $L^1$ is

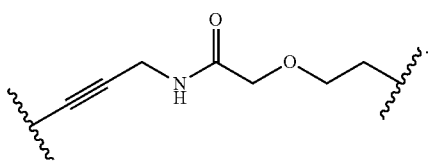 [SMILES: *C#CCNC(=O)COCC*]

In embodiments, $L^1$ is

In embodiments, the compound is a compound described herein.

Some embodiments disclosed herein relate to kits including a labeled nucleoside or nucleotide including a linker between the fluorophore and the nucleoside or nucleotide, wherein the linker comprises a thio-trigger moiety as described herein.

In an aspect, provided herein are kits for use in accordance with any of the methods disclosed herein, and including one or more elements thereof. In embodiments, a kit includes labeled nucleotides including four differently labeled nucleotides (e.g., compounds described herein). In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including four differently labeled nucleotides, wherein the label identifies the type of nucleotide. For example, each of an adenine nucleotide, or analog thereof; a thymine nucleotide; a cytosine nucleotide, or analog thereof, and a guanine nucleotide, or analog thereof may be labeled with a different fluorescent label.

In embodiments, the sequencing solution includes a buffer solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. Additionally, other buffer agents that can be used in enzyme reactions, hybridization reactions, and detection reactions are well known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$ and $Ca^{2+}$. In embodiments, the buffered solution can contain one or more divalent cations at a concentration sufficient to permit hybridization of a nucleic acid. In some embodiments, a concentration can be more than about 1 μM, more than about 2 μM, more than about 5 μM, more than about 10 μM, more than about 25 μM, more than about 50 μM, more than about 75 μM, more than about 100 μM, more than about 200 M, more than about 300 μM, more than about 400 μM, more than about 500 μM, more than about 750 μM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1 M.

III. Methods of Use

In an aspect is provided a method for sequencing a nucleic acid, including: (i) incorporating in series with a nucleic acid polymerase, within a reaction vessel, one of four different labeled nucleoside analogues into a primer to create an extension strand, wherein the primer is hybridized to the nucleic acid and wherein each of the four different labeled nucleoside analogues include a unique detectable label; and (ii) detecting the unique detectable label of each incorporated nucleoside analogue, so as to thereby identify each incorporated nucleoside analogue in the extension strand, thereby sequencing the nucleic acid; wherein each of the four different labeled nucleoside analogues is independently a compound described herein.

In an aspect is provided a method for sequencing a nucleic acid, including: (i) incorporating in series with a nucleic acid polymerase, within a reaction vessel, one of four different labeled nucleoside analogues into a primer to create an extension strand, wherein the primer is hybridized to the nucleic acid and wherein each of the four different labeled nucleoside analogues include a unique detectable label; and (ii) detecting the unique detectable label of each incorporated nucleoside analogue, so as to thereby identify each incorporated nucleoside analogue in the extension strand, thereby sequencing the nucleic acid; wherein each of the four different labeled nucleoside analogues is independently a compound described herein, including in embodiments.

In an aspect is provided a method for sequencing a nucleic acid, including: (i) incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues include a unique detectable label; and (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues is independently a compound described herein, including in embodiments.

In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base. In embodiments, the primer is immobilized on a substrate. In embodiments, the nucleic acid is immobilized on a substrate. In embodiments, the sequencing methods are performed with the primer arrayed on a solid substrate. Multiple nucleic acids can be immobilized on the solid support through linker molecules, or can be attached to particles, e.g., microspheres, which can also be attached to a solid substrate. The solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, diamond, silver, metal, or polypropylene. This invention also provides the instant method, wherein the solid substrate is porous.

In embodiments, the method includes performing a plurality of sequencing cycles. In embodiments, the methods of sequencing a template nucleic acid include a total number of sequencing cycles of about 1 to about 100, or about 20 to about 50. In embodiments, the total number of sequencing cycles is about 1, 2, 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles. In embodiments, the total number of sequencing cycles is about 50 cycles. In embodiments, the total number of sequencing cycles is about 100 cycles. In embodiments, the total number of sequencing cycles is about 150 cycles. In embodiments, the total number of sequencing cycles is about 200 cycles. In embodiments, the total number of sequencing cycle is greater than 50 cycles. In embodiments, the total number of sequencing cycle is greater than 100 cycles. In embodiments, the total number of sequencing cycle is greater than 150 cycles. In embodiments, the total number of sequencing cycle is greater than 200 cycles.

In embodiments, the nucleic acid can include any nucleic acid of interest. The nucleic acid can include DNA, RNA, peptide nucleic acid, morpholino nucleic acid, locked nucleic acid, glycol nucleic acid, threose nucleic acid, mixtures thereof, and hybrids thereof. In embodiments, the nucleic acid is obtained from one or more source organisms. As used herein the term "organism" is not necessarily limited to a particular species of organism but can be used to refer to the living or self replicating particle at any level of classification, which comprises the template nucleic acid. For example, the term "organism" can be used to refer collectively to all of the species within the genus *Salmonella* or all of the bacteria within the kingdom Eubacteria. In some embodiments, the nucleic acid can include a selected sequence or a portion of a larger sequence. In embodiments, sequencing a portion of a nucleic acid or a fragment thereof can be used to identify the source of the nucleic acid. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides or at least 100 consecutive nucleotides.

In embodiments, the methods of sequencing a nucleic acid include a extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Terminator γ, 9° N polymerase (exo-), Terminator II, Terminator III, or Terminator IX). In embodiments, the DNA polymerase is a thermophilic nucleic acid polymerase. In embodiments, the DNA polymerase is a modified archaeal DNA polymerase.

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step.

In embodiments, the methods of sequencing a template nucleic acid include a sequencing solution. The sequencing solution includes (a) an adenine nucleotide, or analog thereof; (b) (i) a thymine nucleotide, or analog thereof, or (ii) a uracil nucleotide, or analog thereof; (c) a cytosine nucleotide, or analog thereof, and (d) a guanine nucleotide, or analog thereof.

In another aspect is provided a method of incorporating a nucleoside analogue into a primer, the method including combining a polymerase, a primer hybridized to nucleic acid template and a nucleoside analogue within a reaction vessel and allowing the polymerase to incorporate the nucleoside analogue into the primer thereby forming an extended primer, wherein the nucleoside analogue is a compound described herein, including embodiments.

In another aspect is provided a method of incorporating a nucleotide analogue into a primer, the method including combining a polymerase, a primer hybridized to nucleic acid template and a nucleotide analogue within a reaction vessel and allowing the polymerase to incorporate the nucleotide analogue into the primer thereby forming an extended primer, wherein the nucleotide analogue is a compound described herein, including embodiments.

In an aspect is provided a method for sequencing a nucleic acid, including: incorporating in series with a nucleic acid polymerase, within a reaction vessel, one of four different compounds into a primer to create an extension strand, wherein the primer is hybridized to the nucleic acid and wherein each of the four different compounds includes a unique detectable label; detecting the unique detectable label of each incorporated compound, so as to thereby identify each incorporated compound in the extension strand, thereby sequencing the nucleic acid; wherein each of the four different compounds is independently a compound described herein.

In an aspect is provided a method for sequencing a nucleic acid, including: incorporating in series with a nucleic acid polymerase, within a reaction vessel, one of four different compounds into a primer to create an extension strand, wherein the primer is hybridized to the nucleic acid and wherein each of the four different compounds includes a unique detectable label; detecting the unique detectable label of each incorporated compound, so as to thereby identify each incorporated compound in the extension strand, thereby sequencing the nucleic acid; wherein each of the four different compounds is independently a compound described herein, including in embodiments.

In an aspect is provided a method for sequencing a nucleic acid, including: incorporating in series with a nucleic acid polymerase, within a reaction vessel, a compound into a primer to create an extension strand, wherein the primer is hybridized to the nucleic acid and wherein the compound includes a detectable label; detecting the detectable label of the incorporated compound, so as to thereby identify the incorporated compound in the extension strand, thereby sequencing the nucleic acid; wherein the compound is independently a compound described herein. In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In an aspect is provided a method for sequencing a nucleic acid, including: incorporating in series with a nucleic acid polymerase, within a reaction vessel, a compound into a primer to create an extension strand, wherein the primer is hybridized to the nucleic acid and wherein the compound includes a detectable label; detecting the detectable label of the incorporated compound, so as to thereby identify the incorporated compound in the extension strand, thereby sequencing the nucleic acid; wherein the compound is independently a compound described herein, including in embodiments. In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In an aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein.

In an aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein, including in embodiments.

In an aspect is provided a nucleic acid polymerase complex including a nucleic acid polymerase, wherein the nucleic acid polymerase is bound to a compound described herein.

In an aspect is provided a nucleic acid polymerase complex including a nucleic acid polymerase, wherein the nucleic acid polymerase is bound (e.g., non-covalently bound) to a compound described herein.

In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof. In embodiments, the nucleic acid polymerase is a *Pyrococcus abyssi* polymerase and mutants thereof.

In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof.

In embodiments, the method includes simultaneously sequencing a plurality of different nucleic acids, including: a) extending a plurality of priming DNA strands hybridized to template DNAs, each of which includes one of the priming DNA strands, by incorporating a labeled nucleotide; and b) identifying each labeled nucleotide, so as to simultaneously sequence the plurality of different nucleic acids. In embodiments, the labeled nucleotide is a compound described herein.

In embodiments, the method includes simultaneously sequencing a plurality of different nucleic acids, including: a) extending a plurality of priming DNA strands hybridized to template DNAs, each of which includes one of the priming DNA strands, by incorporating a labeled nucleotide; and b) identifying each labeled nucleotide, so as to simultaneously sequence the plurality of different nucleic acids. In embodiments, the labeled nucleotide is a compound described herein, including in embodiments.

In embodiments, the method further including, after the incorporating, cleaving the linker (e.g., the thio-trigger containing linker, -($L^{101}$)-OC($SR^{100}$)($R^{102a}$)-($L^{103}$)-($L^{104}$)-($L^{105}$)-) with a cleaving reagent (e.g., a water-soluble phosphine, such as tris(hydroxypropyl)phosphine (THPP)). In embodiments, the cleaving reagent is a reducing agent. In embodiments, the cleaving agent is a phosphine containing agent. In embodiments, the cleaving agent is a thiol containing agent. In embodiments, the cleaving agent is di-mercaptopropane sulfonate (DMPS). In embodiments, the cleaving reagent is Tris-(2-carboxyethyl)phosphines trisodium salt (TCEP), tris(hydroxypropyl)phosphine (THPP), guanidine, urea, cysteine, 2-mercaptoethylamine, or dithiothreitol (DTT). In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the cleaving reagent is in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

In embodiments, the method further including, after the incorporating, cleaving the linker (e.g., the thio-trigger containing linker, -($L^{101}$)-OC($SR^{100}$)($R^{102a}$)-($L^{103}$)-($L^{104}$)-($L^{105}$)-) with a cleaving reagent (e.g., a water-soluble phosphine, such as tris(hydroxypropyl)phosphine (THPP)). In embodiments, the cleaving reagent is a reducing agent. In embodiments, the cleaving agent is a phosphine containing agent. In embodiments, the cleaving agent is a thiol containing agent. In embodiments, the cleaving agent is di-mercaptopropane sulfonate (DMPS). In embodiments, the cleaving reagent is Tris-(2-carboxyethyl)phosphines trisodium salt (TCEP), tris(hydroxypropyl)phosphine (THPP), guanidine, urea, cysteine, 2-mercaptoethylamine, or dithiothreitol (DTT). In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the reducing agent is dithiothreitol (DTT), or a phosphine reagent such as tris(2-carboxyethyl)phosphine (TCEP), tris(hydroxymethyl)phosphine (THP), tris(3-hydroxypropyl)phosphine (THPP), 1,3,5-triaza-7-phosphaadamantane (PTA), 1,4,7-triaza-9-phosphatricyclo[5.3.2.1]-tridecane (CAP), proazaphosphatrane, trialkylphosphines, or aminophosphines. In embodiments, the reducing agent is $Na_2S_2O_3$, $Na_2SO_3$, $NaN_3$, $EtNO_2$, $CH_2(CN)_2$, or $NEt_3$. In embodiments, the reducing agent is a thiol-containing agent, such as di-mercaptopropanesulfonate, di-mercaptopropanephosphonate, di-mercaptopropanol, cysteine, cysteamine, dithio-succinic acid, dithiothreitol (DTT), dithiobutylamine, meso-2,5-dimercapto-N,N,N',N'-tetramethyladipamide (DTA), Bis (2-mercaptoethyl)sulfone (BMS), or N,N'-dimethyl, N,N'-bis(mercaptoacetyl)-hydrazine (DMH). In embodiments, the cleaving agent is a cleaving agent described in US 2017/0211134. In embodiments, the cleaving reagent is in a buffer. In embodiments, the buffer includes an acetate buffer, 3-(N-morpholino)propanesulfonic acid (MOPS) buffer, N-(2-Ac-etamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

In embodiments, the method includes contacting the compound (e.g., a compound described herein) with a reducing agent. In embodiments, the method further including, after the incorporating, cleaving the linker at about 55° C. In embodiments, the method further including, after the incorporating, cleaving the linker at about 55° C. to about 80° C. In embodiments, the method further including, after the incorporating, cleaving the linker at about 60° C. to about 70° C. In embodiments, the method further including, after the incorporating, cleaving the linker at about 65° C. to about 75° C. In embodiments, the method further including, after the incorporating, cleaving the linker at about 65° C. In embodiments, the method further including, after the incorporating, cleaving the linker at about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or about 80° C. In embodiments, the method further including, after the incorporating, cleaving the linker at a pH at about 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is between 9.0 and 11.0, and the temperature is about 60° C. to about 70° C.

In embodiments, the cleaving reagent cleaves both the linker and the polymerase-compatible cleavable moiety simultaneously.

In embodiments, the cleaving reagent cleaves both the linker and the polymerase-compatible cleavable moiety simultaneously. In embodiments, the linker is cleaved prior to cleavage of the polymerase-compatible cleavable moiety. In embodiments, the linker is cleaved after to cleavage of the polymerase-compatible cleavable moiety.

In embodiments, the thermophilic nucleic acid polymerase is a Taq polymerase, Therminator γ, 9° N polymerase (exo-), Therminator II, Therminator III, or Therminator IX. In embodiments, the thermophilic nucleic acid polymerase is Therminator γ. In embodiments, the thermophilic nucleic acid polymerase is 9° N polymerase (exo-). In embodiments, the thermophilic nucleic acid polymerase is Therminator II. In embodiments, the thermophilic nucleic acid polymerase is Therminator III. In embodiments, the thermophilic nucleic acid polymerase is Therminator IX. In embodiments, the thermophilic nucleic acid polymerase is a Taq polymerase. In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof. In embodiments, the polymerase is a non-thermophilic nucleic acid polymerase.

In embodiments, chemical cleavage of a compound (e.g., cleavage of a polymerase-compatible cleavable moiety or cleavage of the thio-trigger containing linker of a compound described herein) described herein (e.g., in an aspect or embodiment) includes contacting the compound with a reducing agent. In embodiments, chemical cleavage of a (e.g., cleavage of a polymerase-compatible cleavable moiety or cleavage of the thio-trigger containing linker of a compound described herein) described herein (e.g., in an aspect or embodiment) includes contacting the compound with THPP (e.g., about 10 mM THPP, at least 10 mM THPP). In embodiments, chemical cleavage of a compound (e.g., cleavage of a polymerase-compatible cleavable moiety or cleavage of the thio-trigger containing linker of a compound described herein) described herein (e.g., in an aspect or embodiment) is performed at about 55 degrees Celsius. In embodiments, chemical cleavage of a compound (e.g., cleavage of a polymerase-compatible cleavable moiety or cleavage of the thio-trigger containing linker of a compound described herein) described herein (e.g., in an aspect or embodiment) is performed at a temperature of at least 55 degrees Celsius. In embodiments, chemical cleavage of a compound (e.g., cleavage of a polymerase-compatible cleavable moiety or cleavage of the thio-trigger containing linker of a compound described herein) described herein (e.g., in an aspect or embodiment) is performed at about pH 9.5-10.0. In embodiments, chemical cleavage of a compound (e.g., cleavage of a polymerase-compatible cleavable moiety or cleavage of the thio-trigger containing linker of a compound described herein) described herein (e.g., in an aspect or embodiment) is performed at pH 9.5.

The methods and kits of the present disclosure may be applied, mutatis mutandis, to the sequencing of RNA, or to determining the identity of a ribonucleotide.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

IV. Embodiments

Embodiment P1. A compound having the formula:

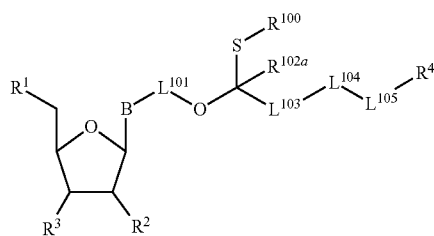

wherein,

B is a divalent nucleobase;

$R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and $R^2$ and $R^3$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or a —O-polymerase-compatible cleavable moiety;

$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is —$SR^{102}$ or —CN;

$R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^4$ is a detectable moiety.

Embodiment P2. The compound of embodiment P1, wherein $R^3$ is an —O-polymerase-compatible cleavable moiety.

Embodiment P3. The compound of embodiment P2, wherein the -polymerase-compatible cleavable moiety is independently -(substituted or unsubstituted alkylene)-SS-(unsubstituted alkyl).

Embodiment P4. The compound of embodiment P2, wherein the -polymerase-compatible cleavable moiety is independently -(halo-substituted or unsubstituted $C_1$-$C_3$ alkylene)-SS-(unsubstituted $C_1$-$C_4$ alkyl).

Embodiment P5. The compound of embodiment P2, wherein the -polymerase-compatible cleavable moiety is independently:

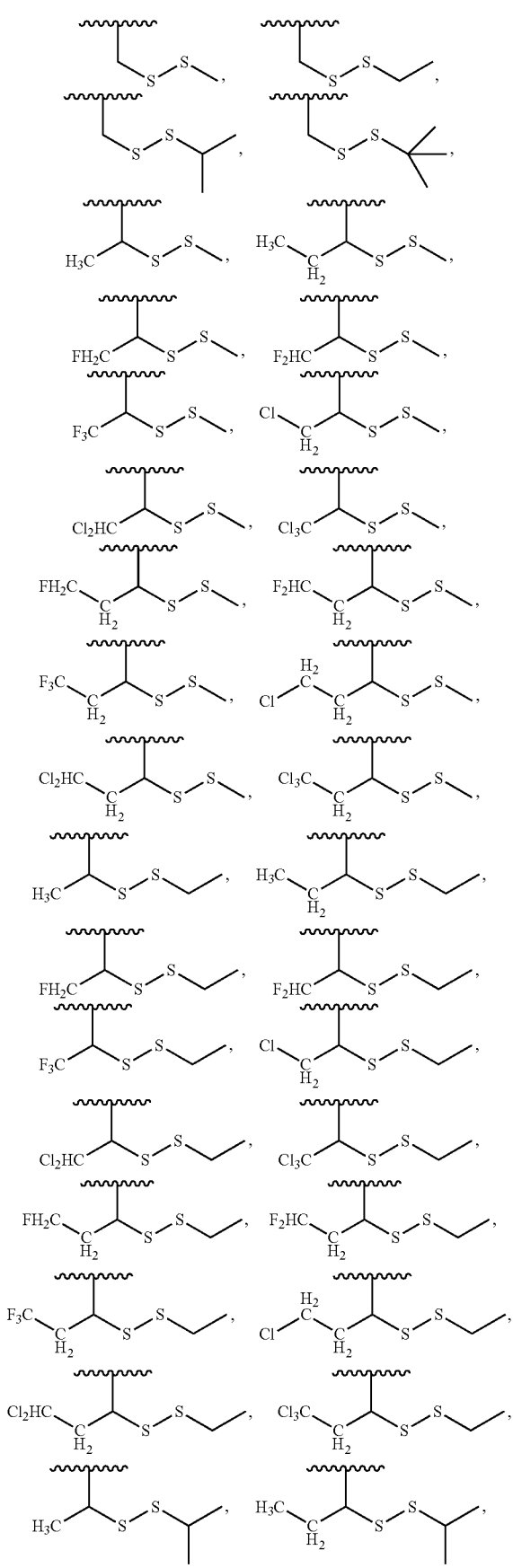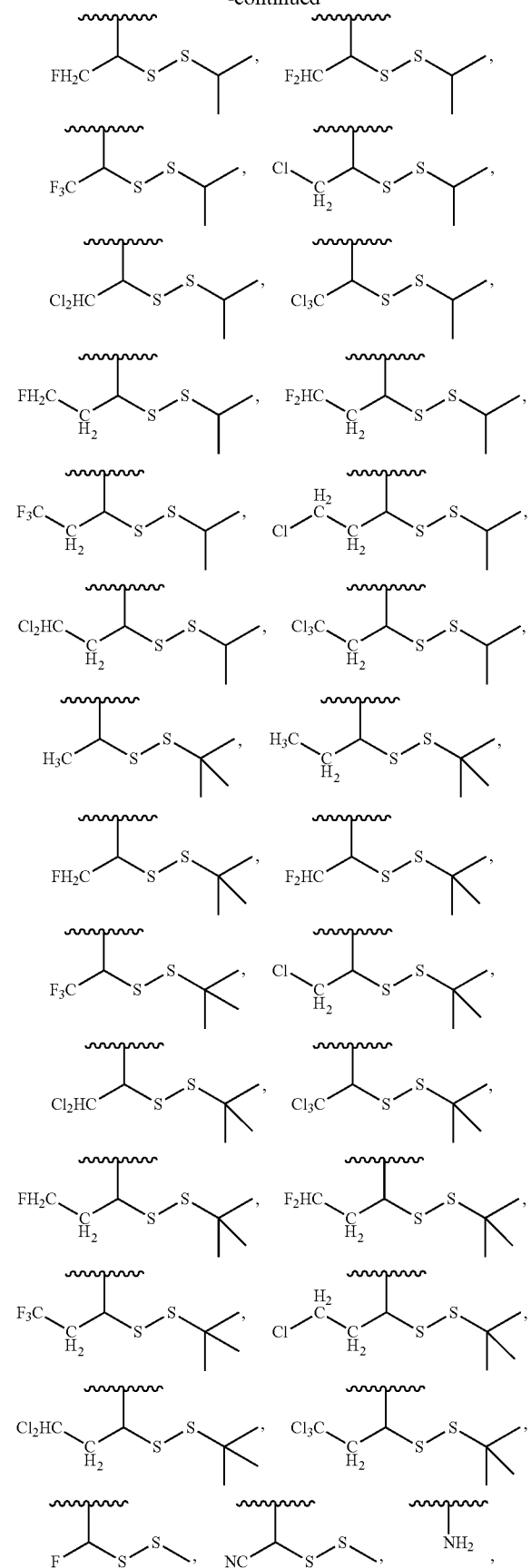

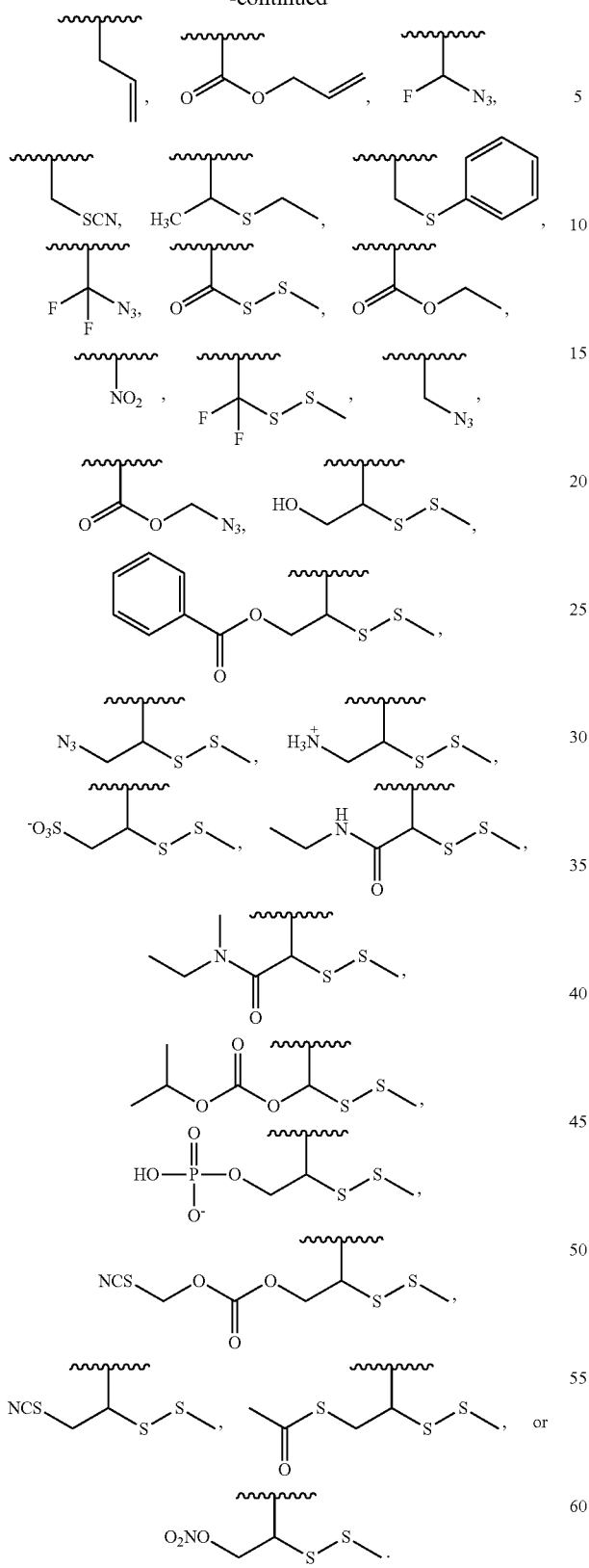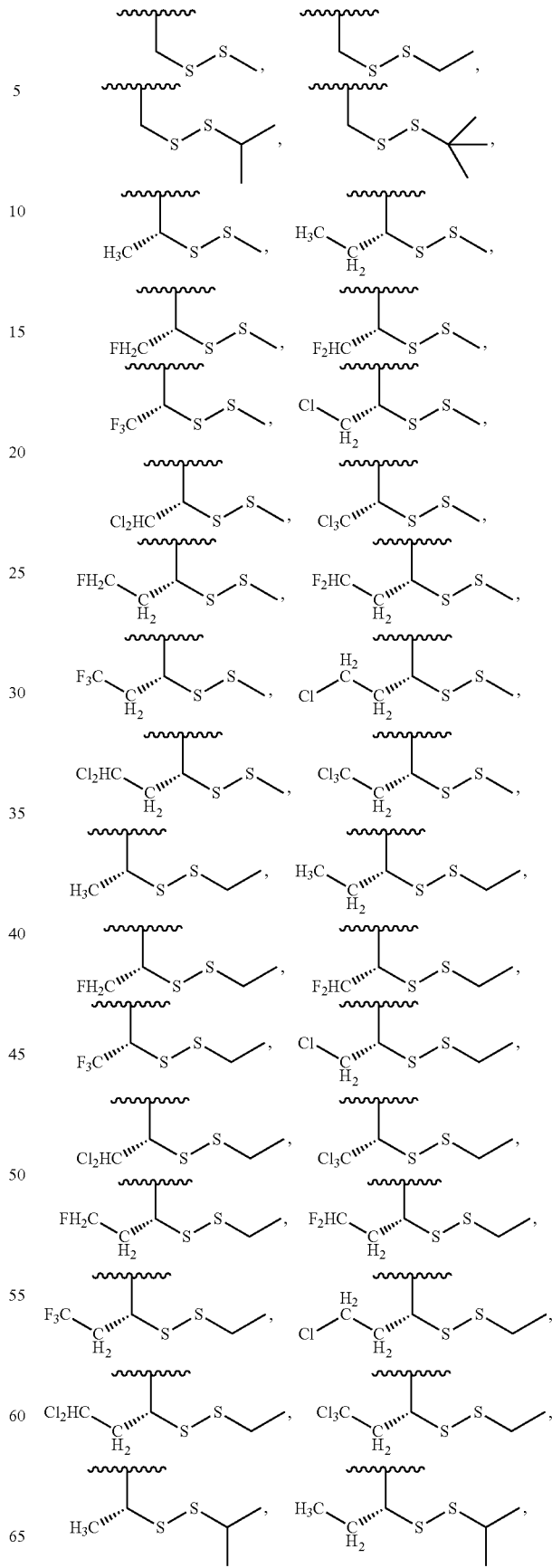
Embodiment P6. The compound of embodiment P2, wherein the -polymerase-compatible cleavable moiety is independently:

371
-continued
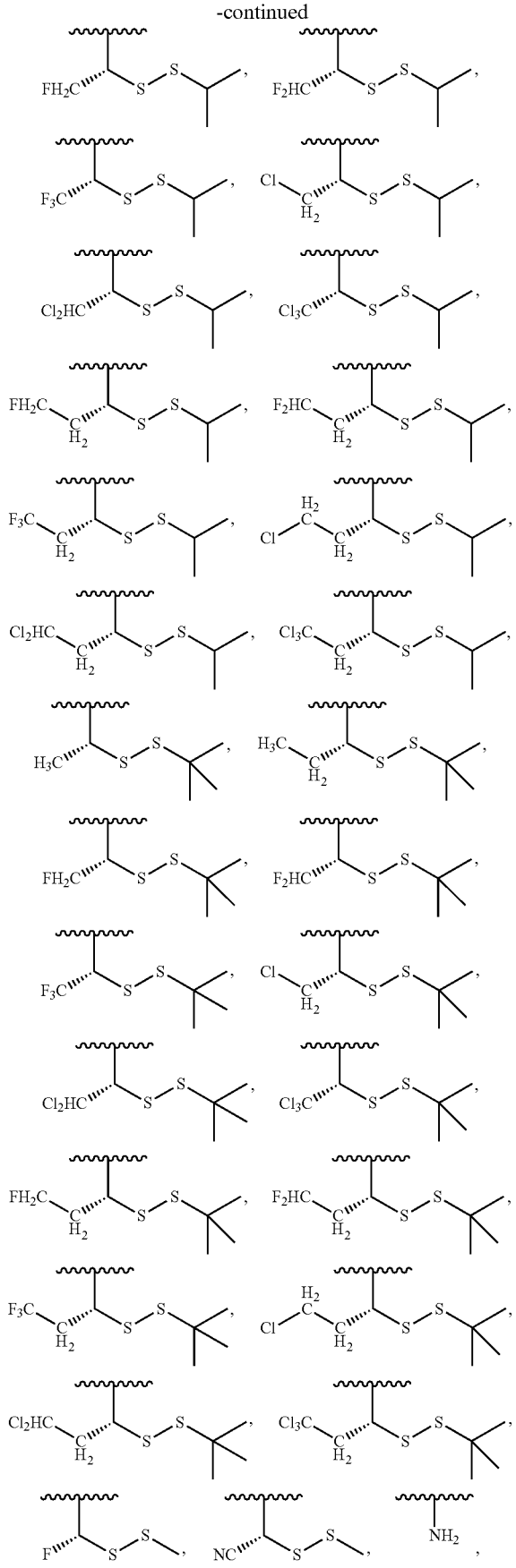
372
-continued
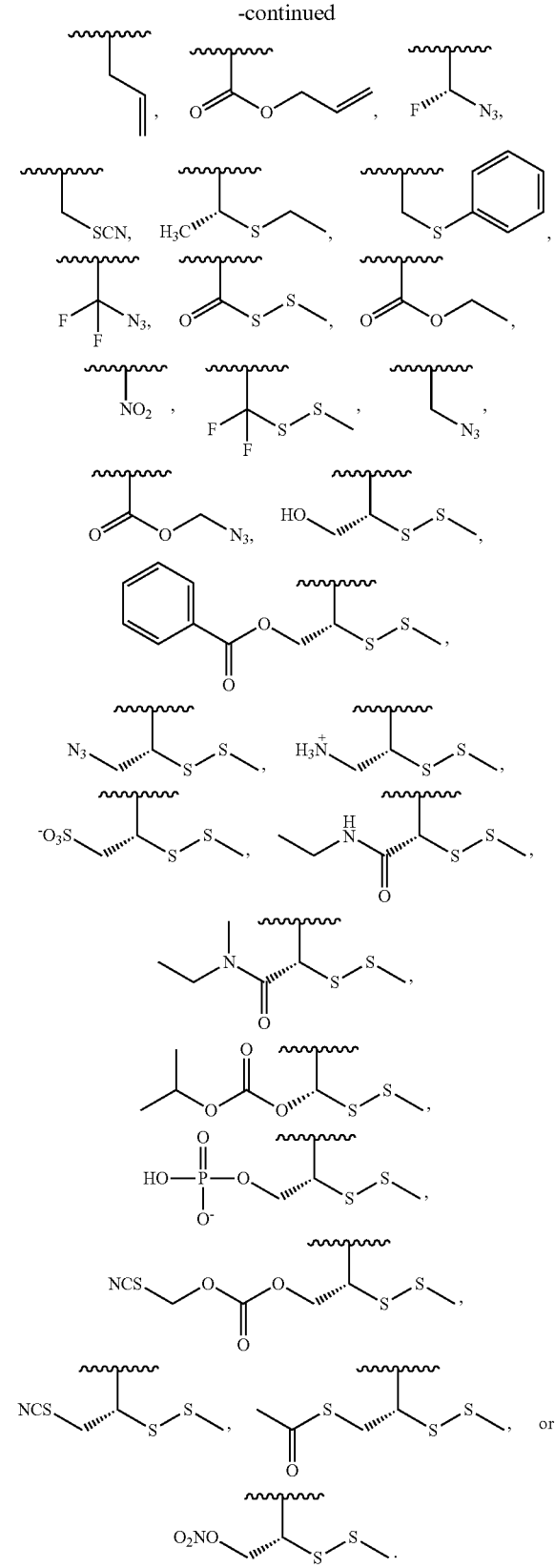
Embodiment P7. The compound of embodiment P2, wherein the -polymerase-compatible cleavable moiety is independently:

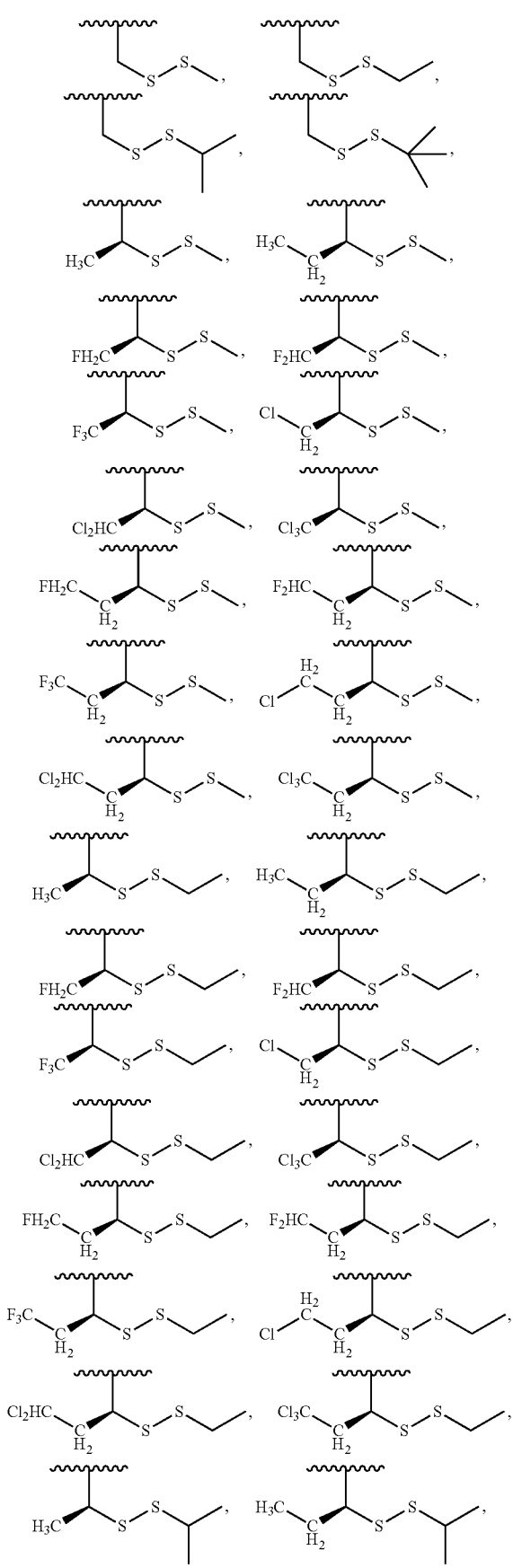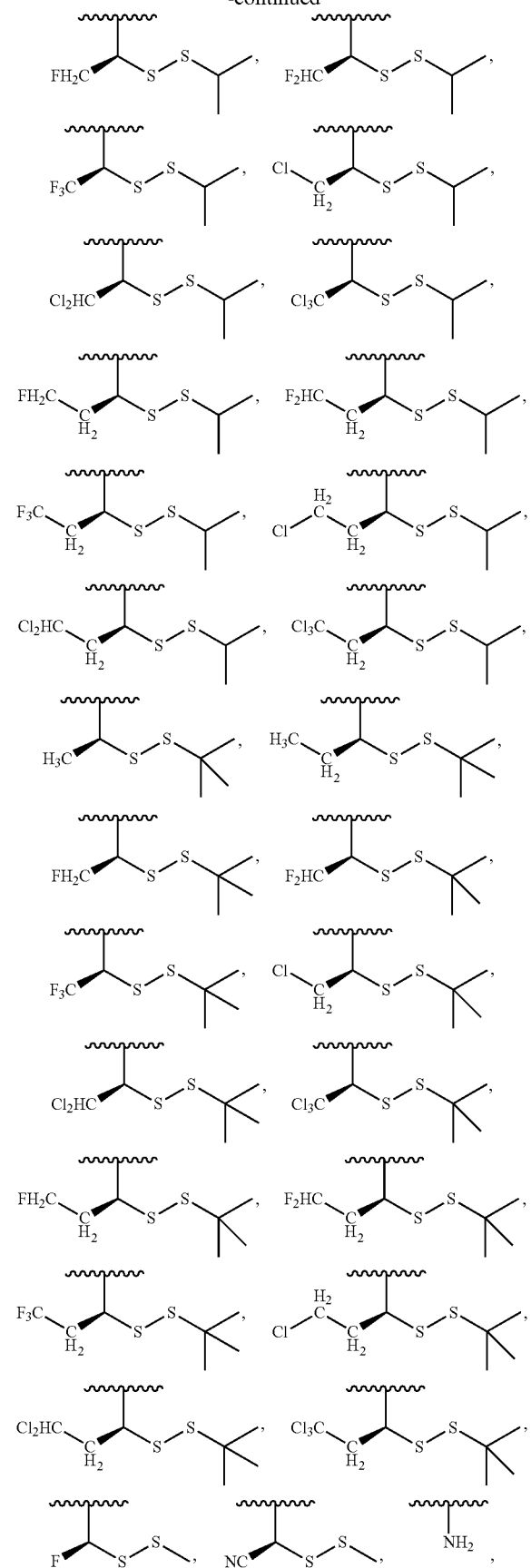

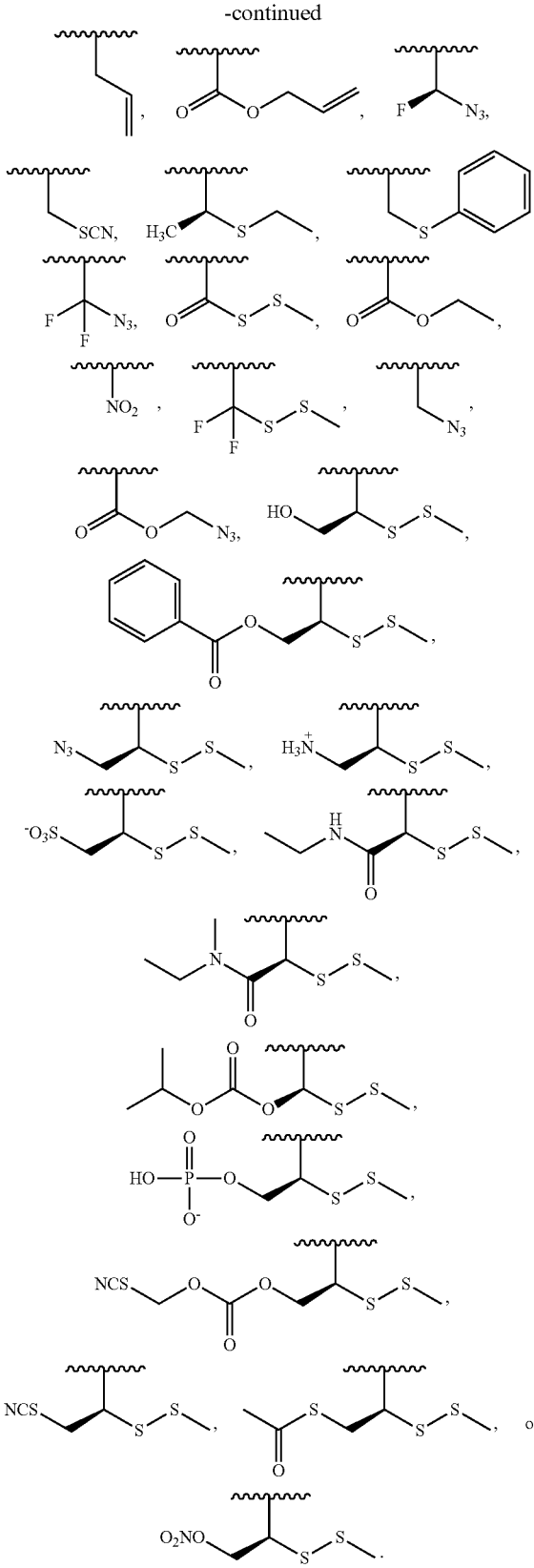

Embodiment P8. The compound of embodiment P2, wherein the -polymerase-compatible cleavable moiety is independently:

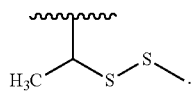

Embodiment P9. The compound of embodiment P2, wherein the -polymerase-compatible cleavable moiety is independently:

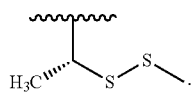

Embodiment P10. The compound of embodiment P2, wherein the -polymerase-compatible cleavable moiety is independently:

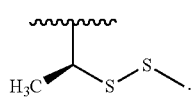

Embodiment P11. The compound of one of embodiments P1 to P10, wherein $R^2$ is hydrogen.
Embodiment P12. The compound of one of embodiments P1 to P10, wherein $R^2$ is —OH.
Embodiment P13. The compound of one of embodiments P1 to P10, wherein $R^2$ is —O-polymerase-compatible cleavable moiety.
Embodiment P14. The compound of one of embodiments P1 to P13, wherein $R^1$ is hydrogen.
Embodiment P15. The compound of one of embodiments P1 to P13, wherein $R^1$ is a monophosphate moiety.
Embodiment P16. The compound of one of embodiments P1 to P13, wherein $R^1$ is a polyphosphate moiety.
Embodiment P17. The compound of one of embodiments P1 to P13, wherein $R^1$ is a triphosphate moiety.
Embodiment P18. The compound of one of embodiments P1 to P13, wherein $R^1$ is a nucleic acid moiety.
Embodiment P19. The compound of one of embodiments P1 to P18, wherein
B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.
Embodiment P20. The compound of embodiment P19, wherein B is

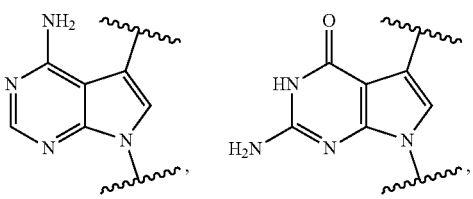

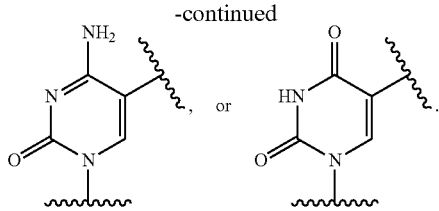

Embodiment P21. The compound of one of embodiments P1 to P20, wherein, $R^{100}$ is —$SR^{102}$.

Embodiment P22. The compound of one of embodiments P1 to P21, wherein;
- $L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
- $R^{102}$ and $R^{102a}$ are independently hydrogen or unsubstituted alkyl.

Embodiment P23. The compound of one of embodiments P1 to P21, wherein
- $L^{101}$ is independently a substituted or unsubstituted $C_1$-$C_4$ alkylene or substituted or unsubstituted 8 to 20 membered heteroalkylene;
- $L^{103}$ is independently a bond or substituted or unsubstituted 2 to 10 membered heteroalkylene;
- $L^{104}$ is independently a bond, substituted or unsubstituted 4 to 18 membered heteroalkylene, or substituted or unsubstituted phenylene;
- $L^{105}$ is independently bond or substituted or unsubstituted 4 to 18 membered heteroalkylene; and
- $R^{102}$ is unsubstituted $C_1$-$C_4$ alkyl; and
- $R^{102a}$ is hydrogen or unsubstituted methyl.

Embodiment P24. The compound of one of embodiments P1 to P21, wherein
- $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
- $L^{104}$ is unsubstituted phenylene; and
- $R^{102}$ and $R^{102a}$ are independently hydrogen or unsubstituted alkyl.

Embodiment P25. The compound of one of embodiments P1 to P21, wherein
- $L^{101}$ is independently a substituted or unsubstituted $C_1$-$C_4$ alkylene or substituted or unsubstituted 8 to 20 membered heteroalkylene;
- $L^{103}$ is independently a bond or substituted or unsubstituted 2 to 10 membered heteroalkylene;
- $L^{104}$ is independently an unsubstituted phenylene;
- $L^{105}$ is independently bond or substituted or unsubstituted 4 to 18 membered heteroalkylene; and
- $R^{102}$ is unsubstituted $C_1$-$C_4$ alkyl; and
- $R^{102a}$ is hydrogen or unsubstituted methyl.

Embodiment P26. The compound of one of embodiments P1 to P21, wherein -($L^{101}$)-OC(SS$R^{102}$)($R^{102a}$)-($L^{103}$)-($L^{104}$)-($L^{105}$)- is

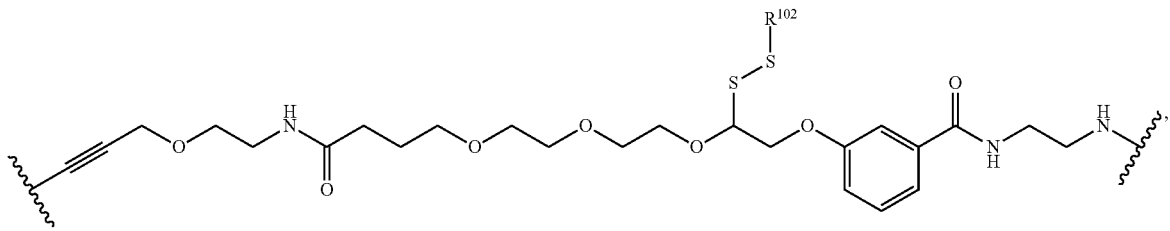

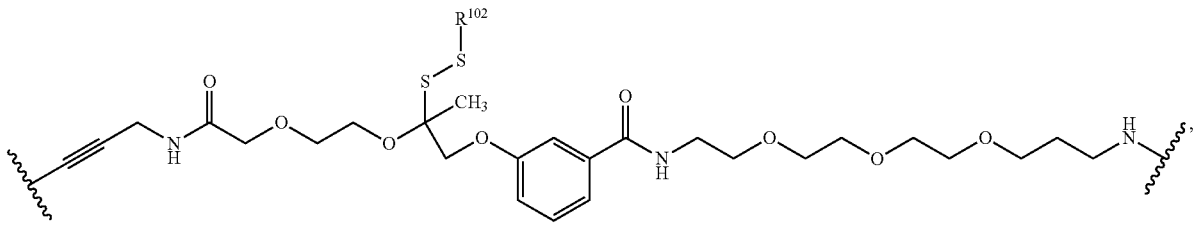

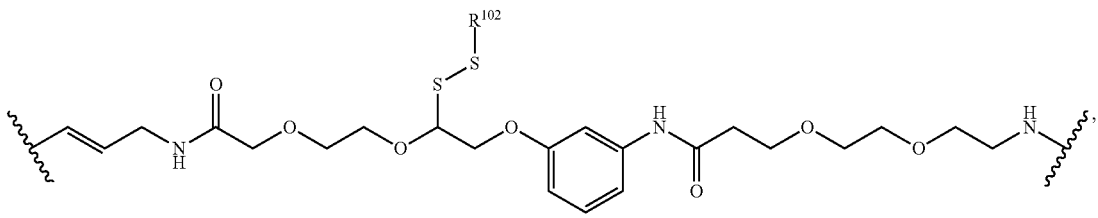

-continued
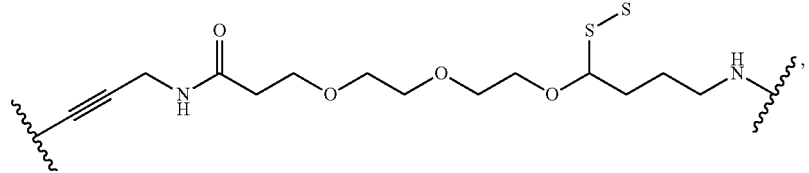
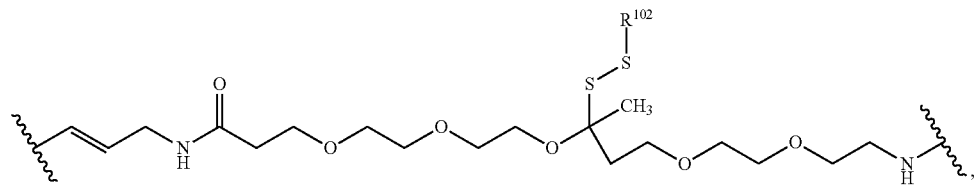
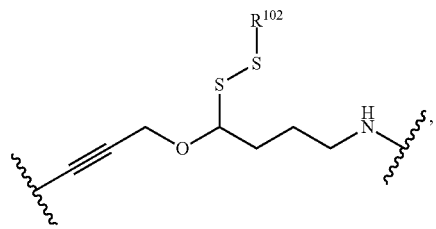
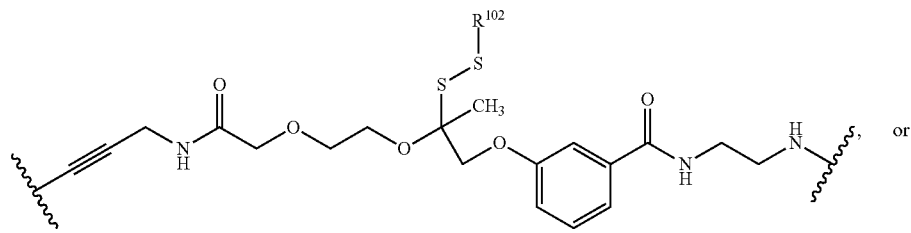   or
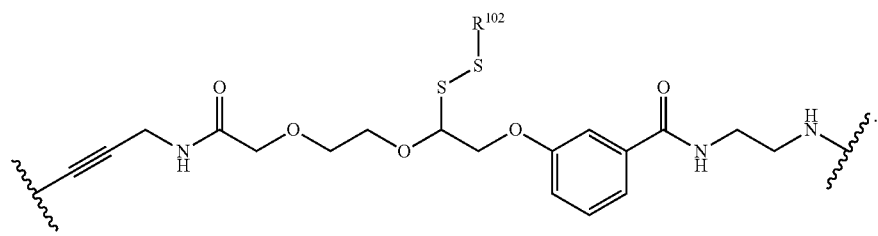
50
Embodiment P27. The compound of one of embodiments P1 to P21, wherein -($L^{101}$)-OC(SS$R^{102}$)($R^{102a}$)-($L^{103}$)-($L^{104}$)-($L^{105}$)- is
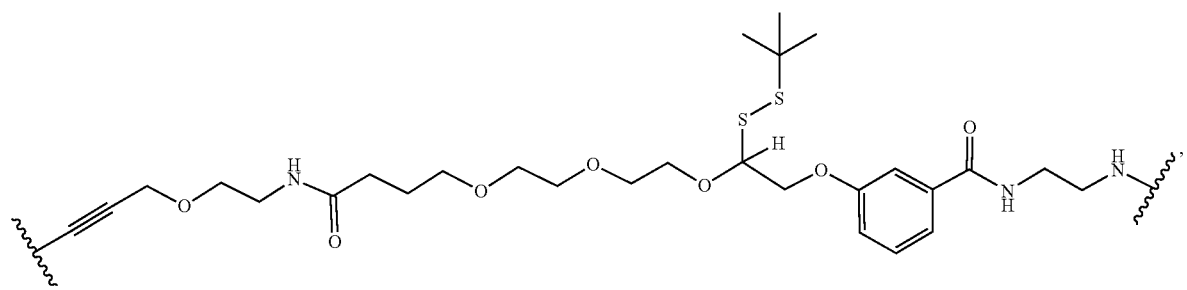

-continued
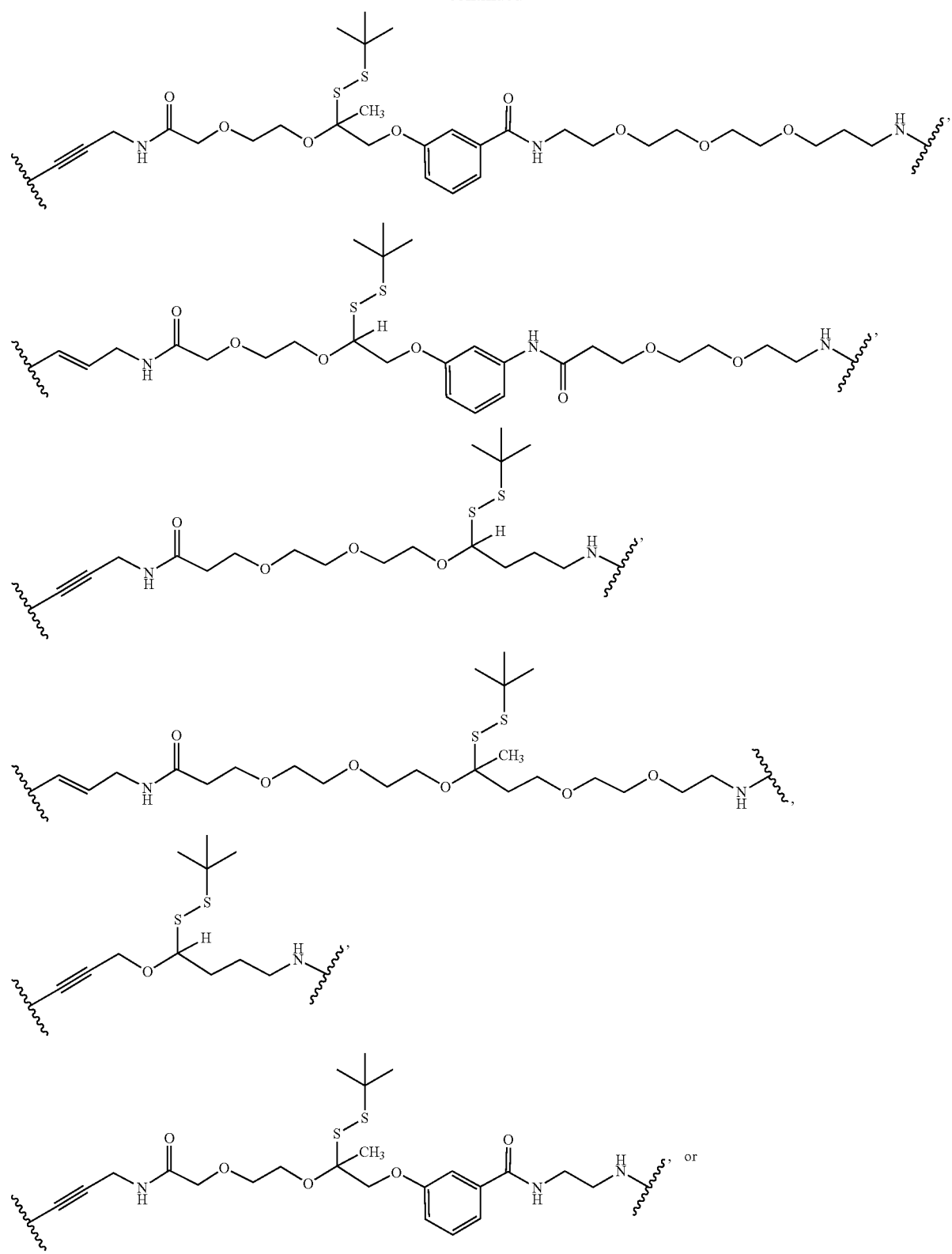

-continued

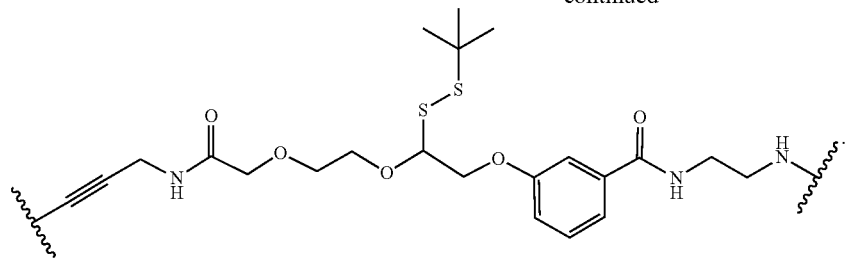

Embodiment P28. The compound of one of embodiments P1 to P20, wherein $R^{100}$ is —CN.

Embodiment P29. The compound of embodiment P28, wherein;
$L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
$R^{102a}$ is independently hydrogen or unsubstituted alkyl.

Embodiment P30. The compound of embodiment P28, wherein
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently a bond, substituted or unsubstituted 4 to 18 membered heteroalkylene, or substituted or unsubstituted phenylene;
$L^{105}$ is independently bond or substituted or unsubstituted 4 to 18 membered heteroalkylene; and
$R^{102a}$ is hydrogen or unsubstituted methyl.

Embodiment P31. The compound of embodiment P28, wherein
$L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$L^{104}$ is unsubstituted phenylene; and
$R^{102a}$ is independently hydrogen or unsubstituted alkyl.

Embodiment P32. The compound of embodiment P28, wherein
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently an unsubstituted phenylene;
$L^{105}$ is independently bond or substituted or unsubstituted 4 to 18 membered heteroalkylene; and
$R^{102a}$ is hydrogen or unsubstituted methyl.

Embodiment P33. The compound of embodiment P28, wherein -($L^{101}$)—OC(SCN)($R^{102a}$)-($L^{103}$)-($L^{104}$)-($L^{105}$)- is

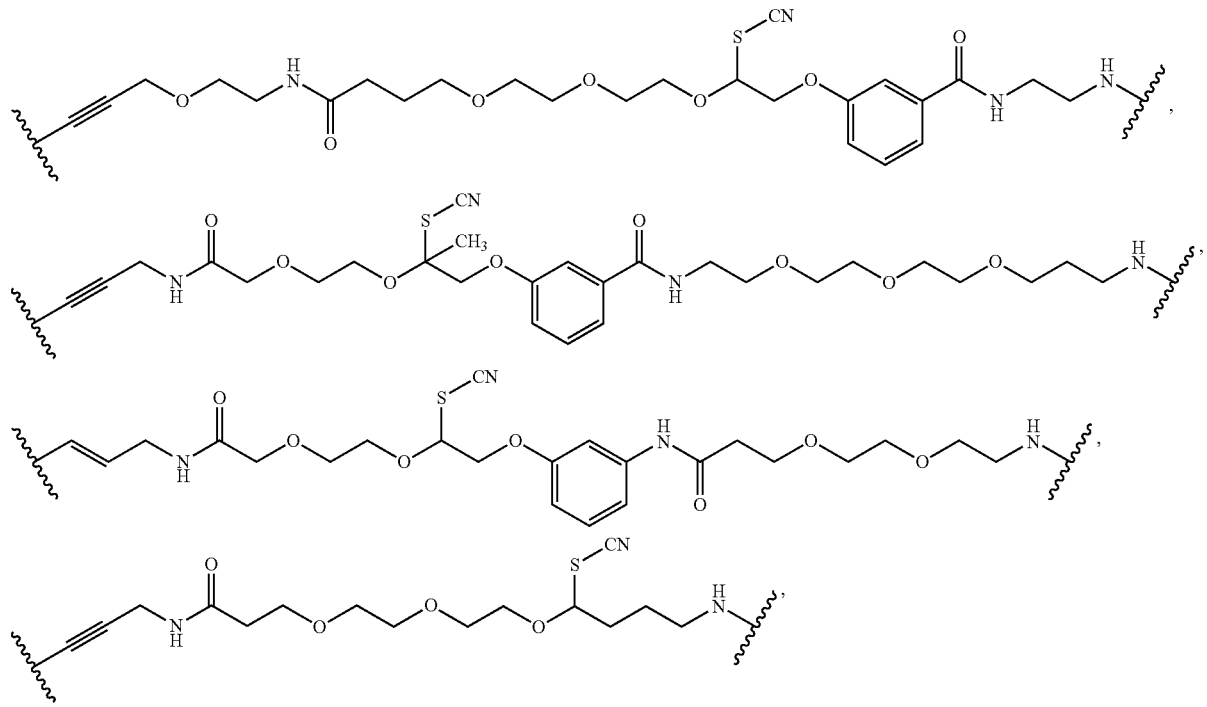

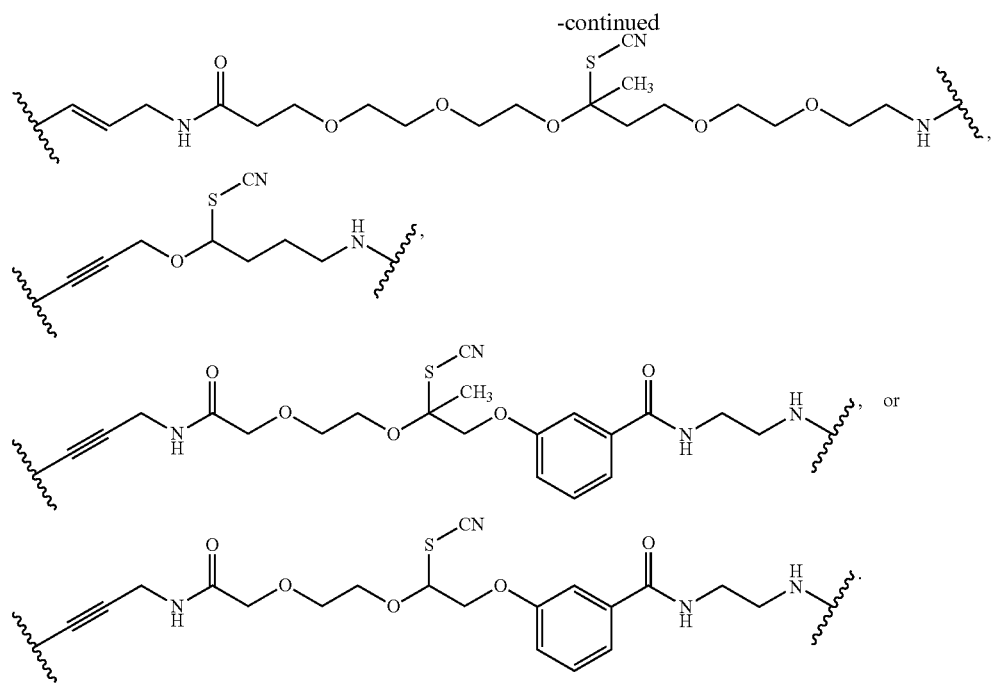
Embodiment P34. The compound of one of embodiments P1 to P33, wherein $R^4$ is a fluorescent dye moiety.
Embodiment P35. The compound of one of embodiments P1 to P33, wherein $R^4$ is
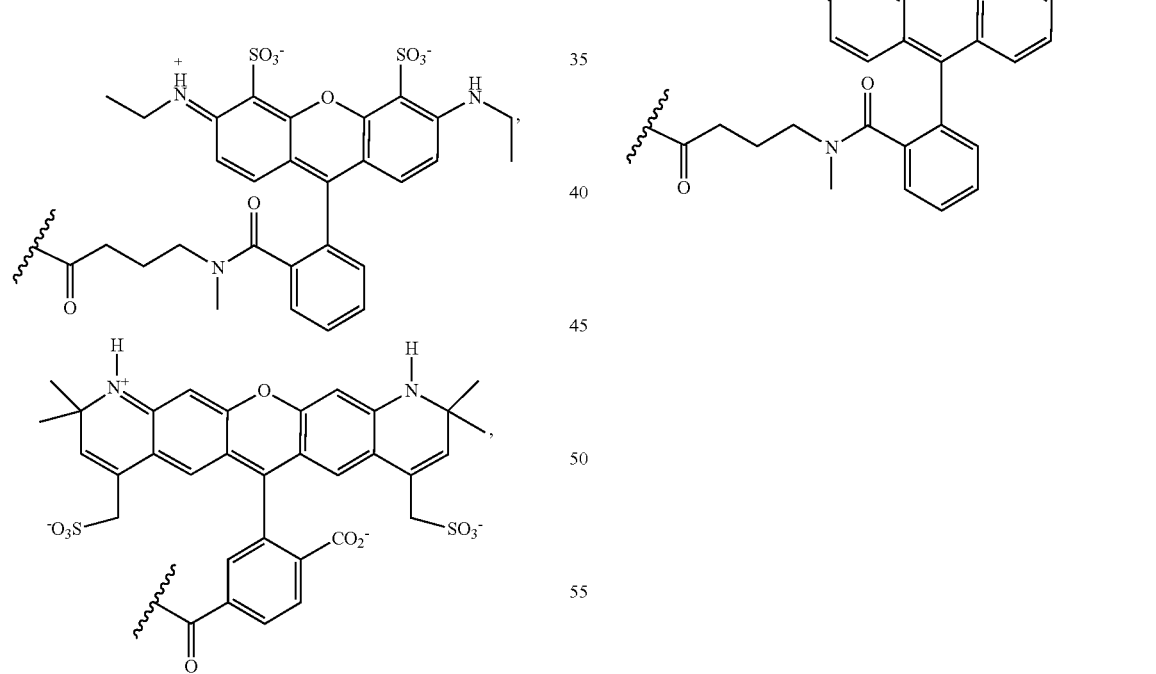

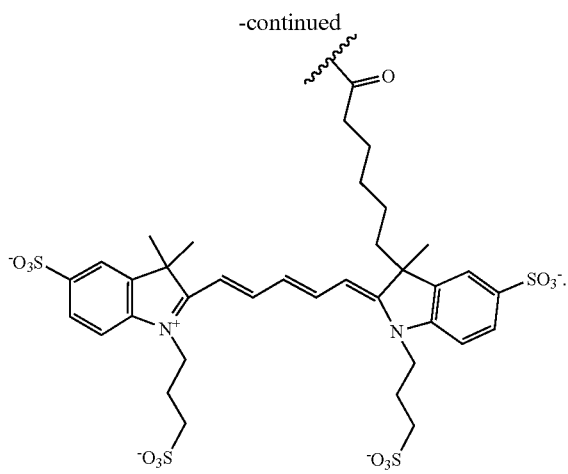

Embodiment P36. A method for sequencing a nucleic acid, comprising:
(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
(ii) detecting said unique detectable label of each incorporated compound, so as to thereby identify each incorporated compound in said extension strand, thereby sequencing the nucleic acid;
wherein each of said four different compounds is independently a compound of one of embodiments P1 to P35.

Embodiment P37. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments P1 to P35.

Embodiment P38. A nucleic acid polymerase complex comprising a nucleic acid polymerase, wherein said nucleic acid polymerase is bound to a compound of one of embodiments P1 to P35.

Embodiment Q1. A compound having the formula:

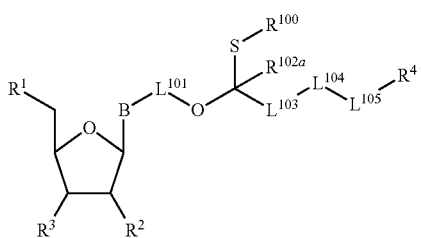

wherein,
B is a divalent nucleobase;
$R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and
$R^2$ and $R^3$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety;
$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{100}$ is —$SR^{102}$ or —CN;
$R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^4$ is a detectable moiety.

Embodiment Q2. The compound of embodiment Q1, wherein $R^3$ is an —O-polymerase-compatible cleavable moiety.

Embodiment Q3. The compound of one of embodiments Q1 to Q2, wherein the polymerase-compatible cleavable moiety is independently -(substituted or unsubstituted alkylene)-SS-(unsubstituted alkyl).

Embodiment Q4. The compound of one of embodiments Q1 to Q2, wherein the polymerase-compatible cleavable moiety is independently -(halo-substituted or unsubstituted $C_1$-$C_3$ alkylene)-SS-(unsubstituted $C_1$-$C_4$ alkyl).

Embodiment Q5. The compound of one of embodiments Q1 to Q2, wherein the polymerase-compatible cleavable moiety is independently:

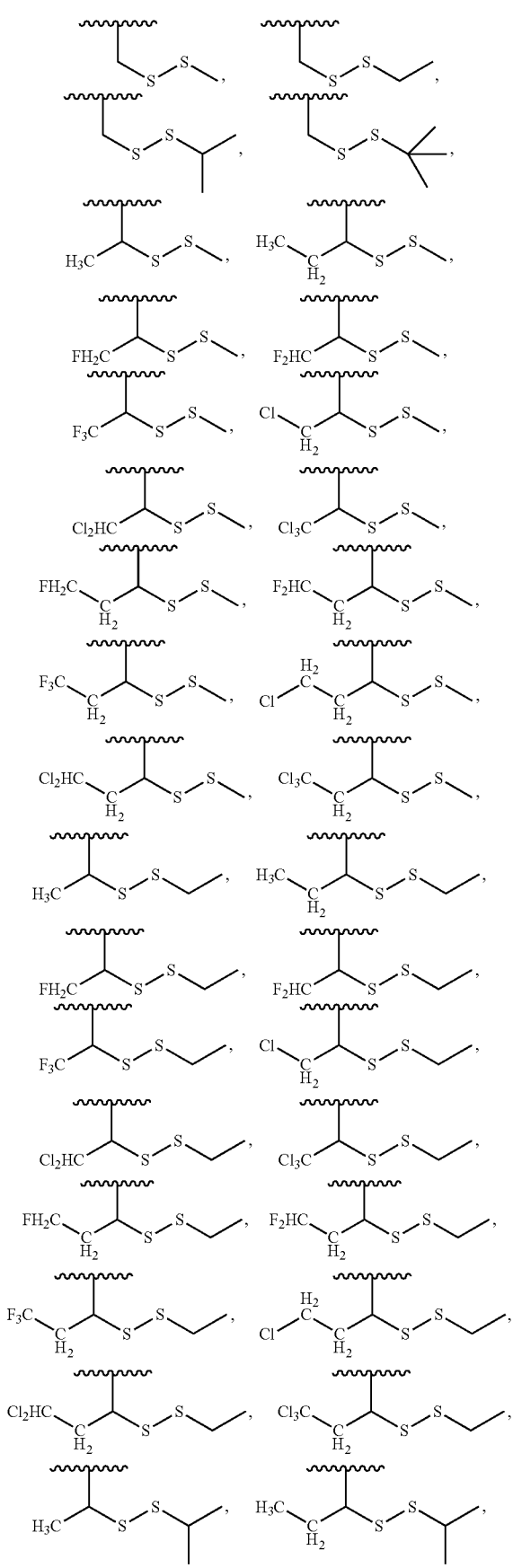
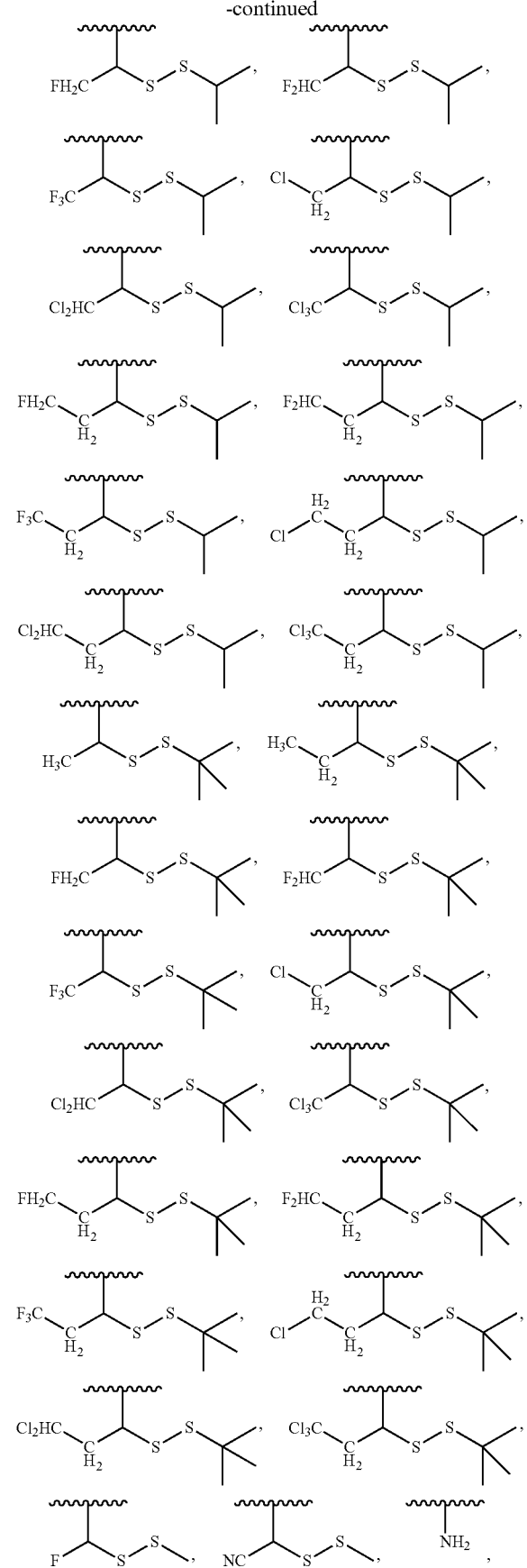

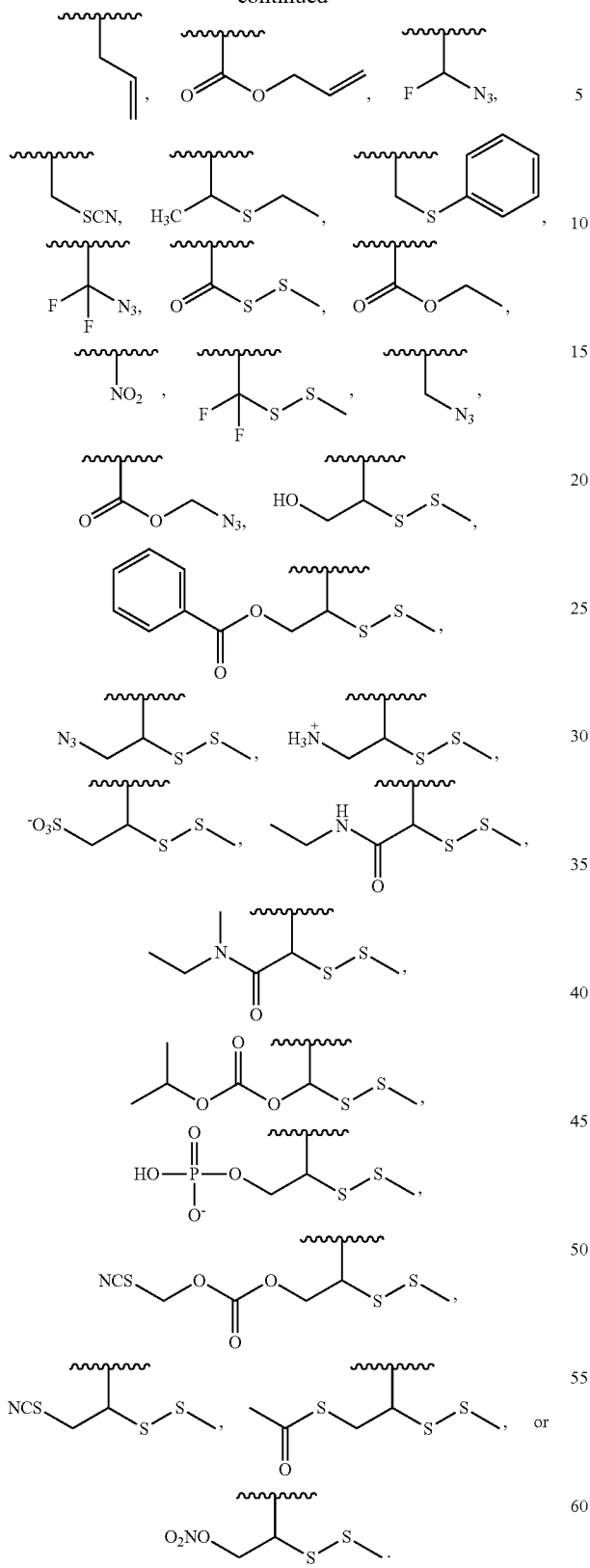
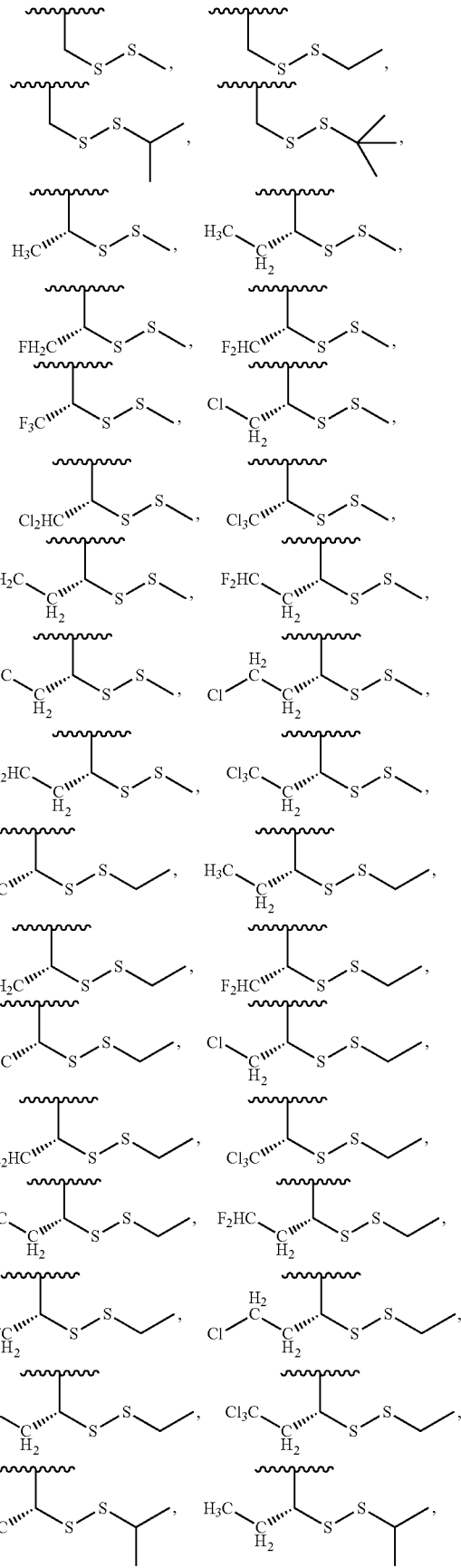
Embodiment Q6. The compound of one of embodiments Q1 to Q2, wherein the -polymerase-compatible cleavable moiety is independently:

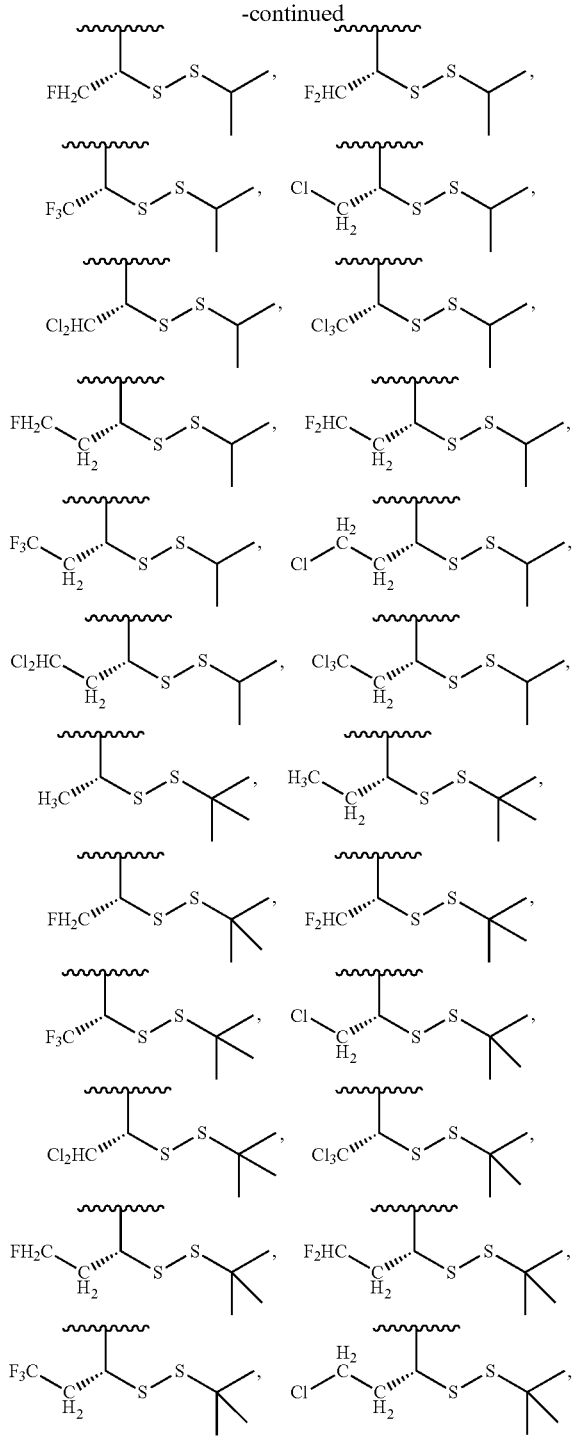
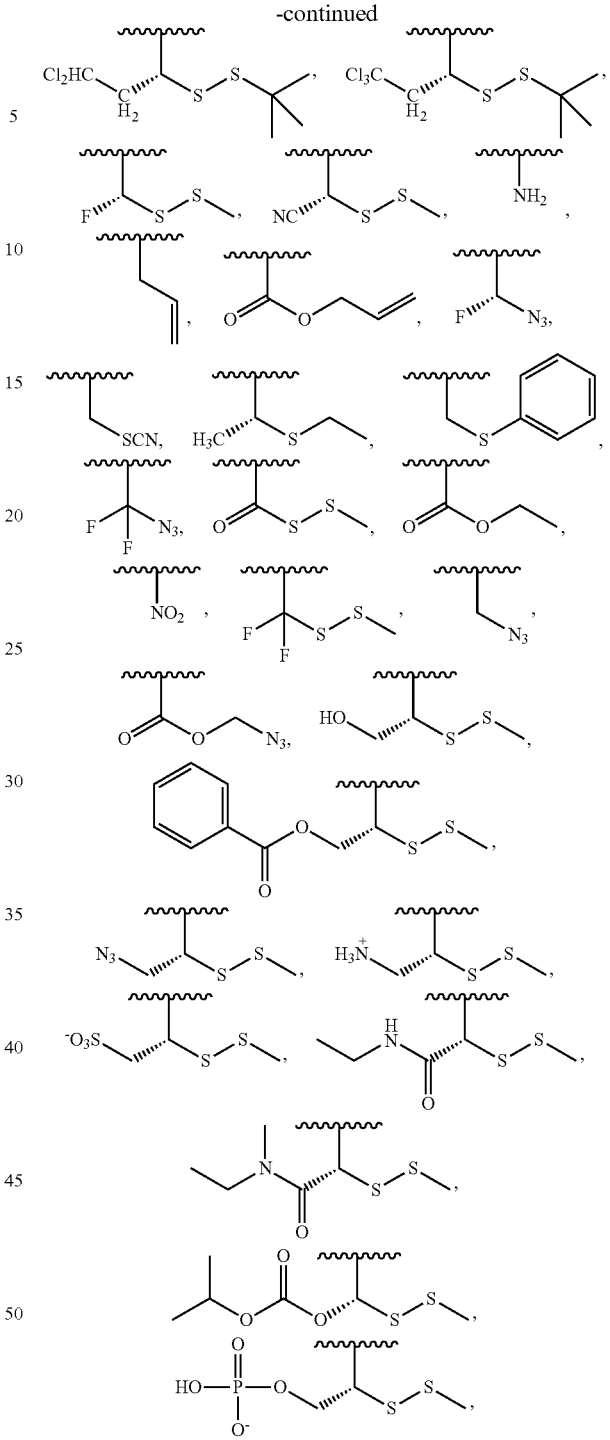

Embodiment Q7. The compound of one of embodiments Q1 to Q2, wherein the polymerase-compatible cleavable moiety is independently:
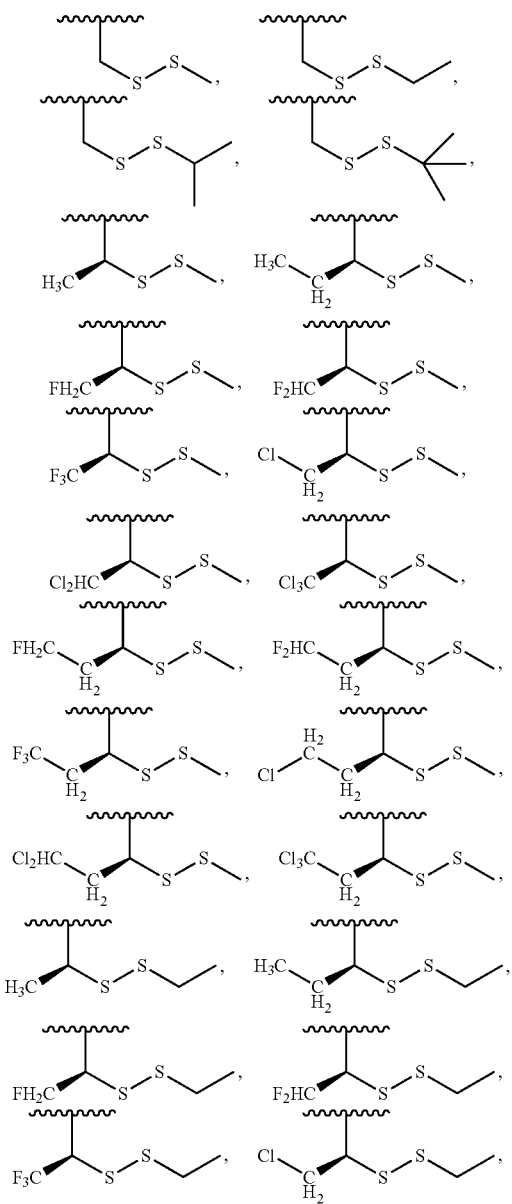

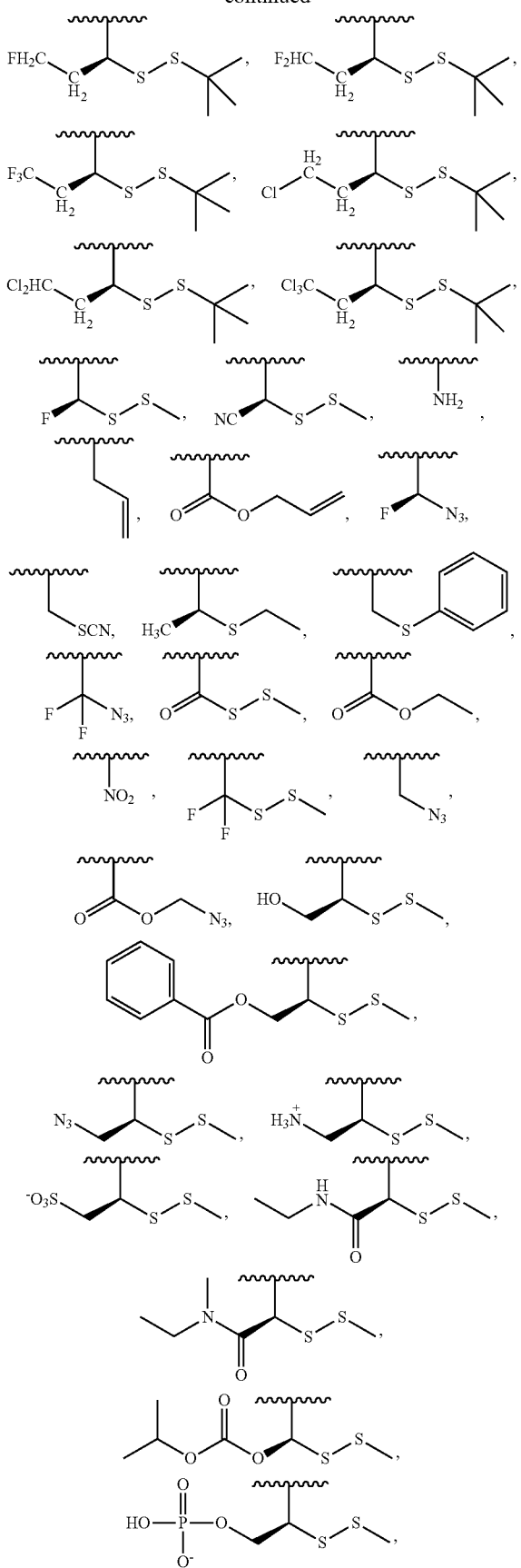

Embodiment Q8. The compound of one of embodiments Q1 to Q2, wherein the polymerase-compatible cleavable moiety is independently:

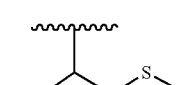

Embodiment Q9. The compound of one of embodiments Q1 to Q2, wherein the polymerase-compatible cleavable moiety is independently:

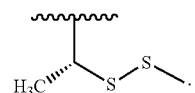

Embodiment Q10. The compound of one of embodiments Q1 to Q2, wherein the polymerase-compatible cleavable moiety is independently:

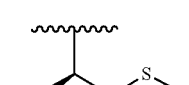

Embodiment Q11. The compound of one of embodiments Q1 to Q10, wherein $R^2$ is hydrogen.
Embodiment Q12. The compound of one of embodiments Q1 to Q10, wherein $R^2$ is —OH.
Embodiment Q13. The compound of one of embodiments Q1 to Q10, wherein $R^2$ is an —O-polymerase-compatible cleavable moiety.
Embodiment Q14. The compound of one of embodiments Q1 to Q13, wherein $R^1$ is hydrogen.
Embodiment Q15. The compound of one of embodiments Q1 to Q13, wherein $R^1$ is a monophosphate moiety.
Embodiment Q16. The compound of one of embodiments Q1 to Q13, wherein $R^1$ is a polyphosphate moiety.
Embodiment Q17. The compound of one of embodiments Q1 to Q13, wherein $R^1$ is a triphosphate moiety.
Embodiment Q18. The compound of one of embodiments Q1 to Q13, wherein $R^1$ is a nucleic acid moiety.
Embodiment Q19. The compound of one of embodiments Q1 to Q18, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment Q20. The compound of embodiment Q19, wherein B is

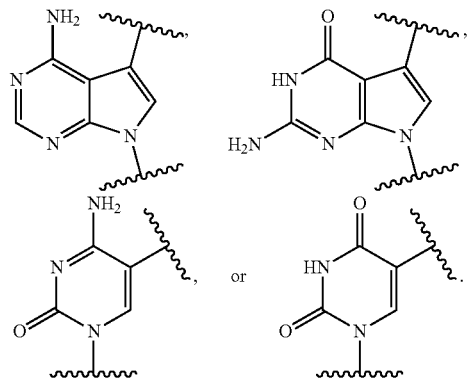

Embodiment Q21. The compound of one of embodiments Q1 to Q20, wherein, $R^{100}$ is $-SR^{102}$.

Embodiment Q22. The compound of one of embodiments Q1 to Q21, wherein;
  $L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
  $R^{102}$ and $R^{102a}$ are independently hydrogen or unsubstituted alkyl.

Embodiment Q23. The compound of one of embodiments Q1 to Q21, wherein
  $L^{101}$ is independently a substituted or unsubstituted $C_1$-$C_4$ alkylene or substituted or unsubstituted 8 to 20 membered heteroalkylene;
  $L^{103}$ is independently a bond or substituted or unsubstituted 2 to 10 membered heteroalkylene;
  $L^{104}$ is independently a bond, substituted or unsubstituted 4 to 18 membered heteroalkylene, or substituted or unsubstituted phenylene;
  $L^{105}$ is independently bond or substituted or unsubstituted 4 to 18 membered heteroalkylene; and
  $R^{102}$ is unsubstituted $C_1$-$C_4$ alkyl; and
  $R^{102a}$ is hydrogen or unsubstituted methyl.

Embodiment Q24. The compound of one of embodiments Q1 to Q21, wherein
  $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
  $L^{104}$ is unsubstituted phenylene; and
  $R^{102}$ and $R^{102a}$ are independently hydrogen or unsubstituted alkyl.

Embodiment Q25. The compound of one of embodiments Q1 to Q21, wherein
  $L^{101}$ is independently a substituted or unsubstituted $C_1$-$C_4$ alkylene or substituted or unsubstituted 8 to 20 membered heteroalkylene;
  $L^{103}$ is independently a bond or substituted or unsubstituted 2 to 10 membered heteroalkylene;
  $L^{104}$ is independently an unsubstituted phenylene;
  $L^{105}$ is independently bond or substituted or unsubstituted 4 to 18 membered heteroalkylene; and
  $R^{102}$ is unsubstituted $C_1$-$C_4$ alkyl; and
  $R^{102a}$ is hydrogen or unsubstituted methyl.

Embodiment Q26. The compound of one of embodiments Q1 to Q21, wherein -($L^{101}$)-OC(SS$R^{102}$)($R^{102a}$)-($L^{103}$)-($L^{104}$)-($L^{105}$)- is

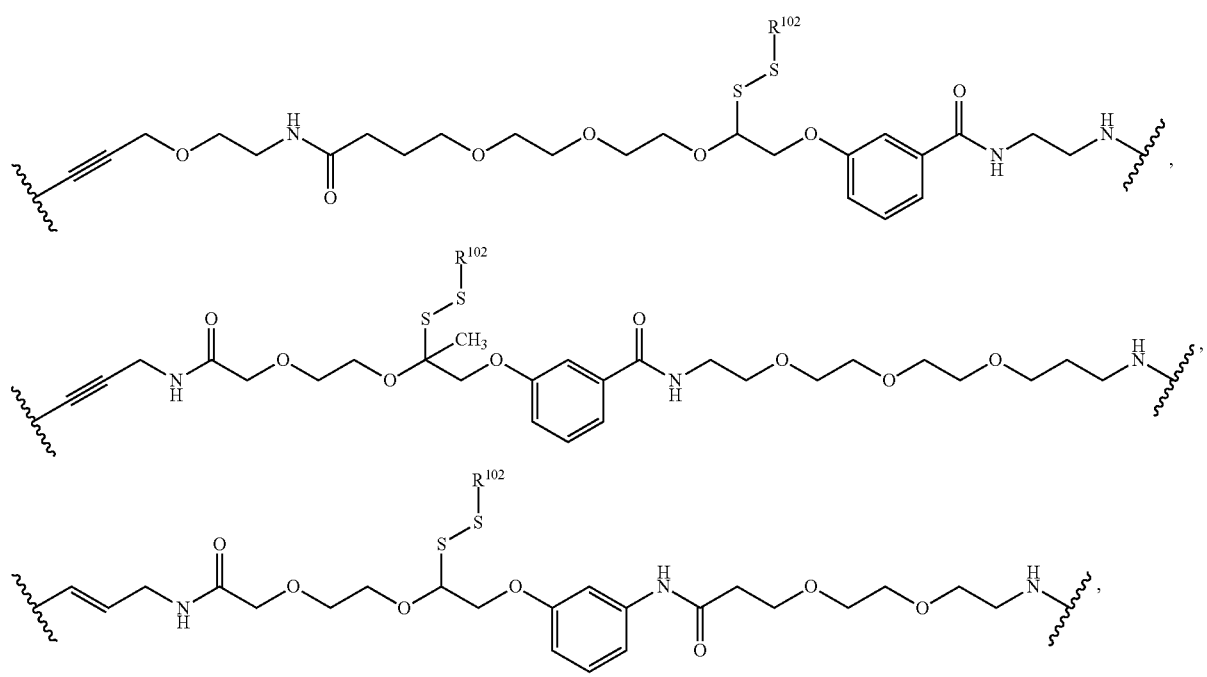

-continued
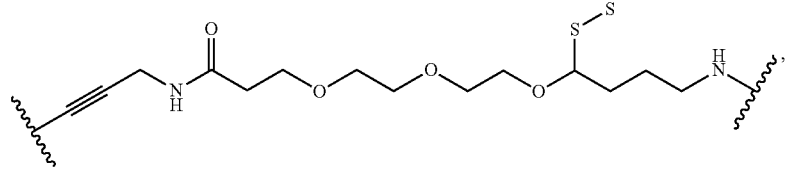
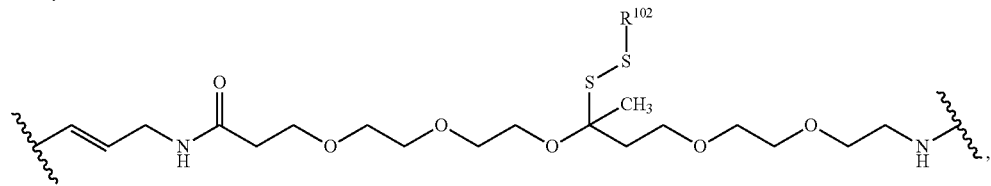
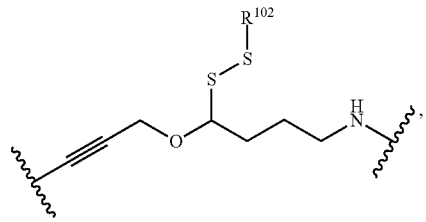
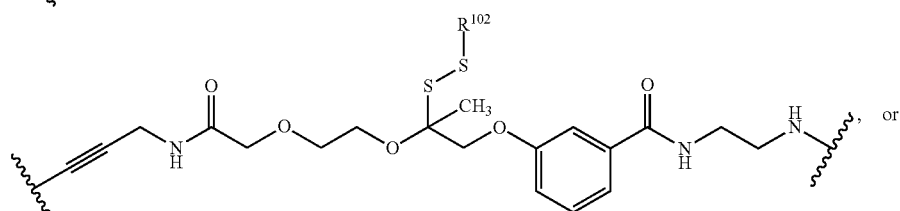
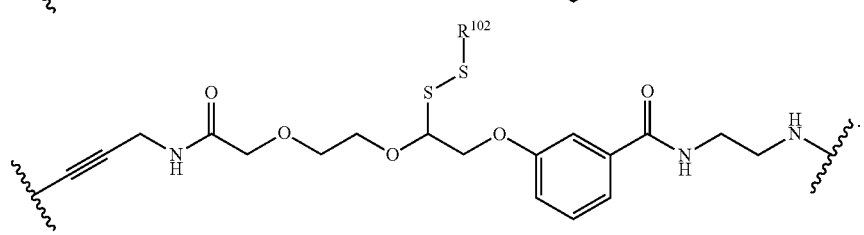
Embodiment Q27. The compound of one of embodiments Q1 to Q21, wherein -(L$^{101}$)-OC(SSR$^{102}$)(R$^{102a}$)-(L$^{103}$)-(L$^{104}$)-(L$^{105}$)- is
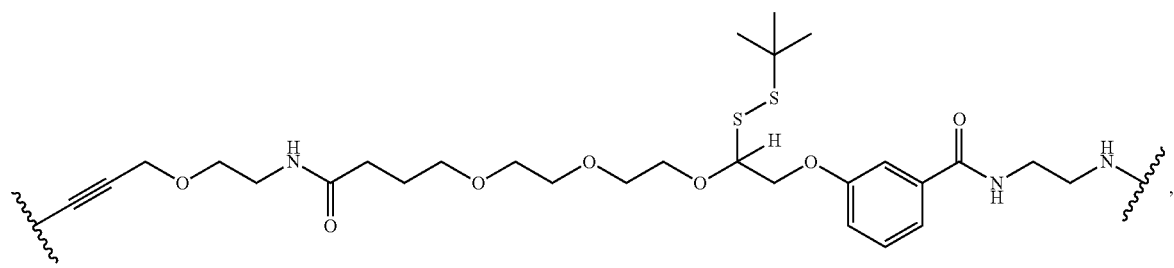

-continued
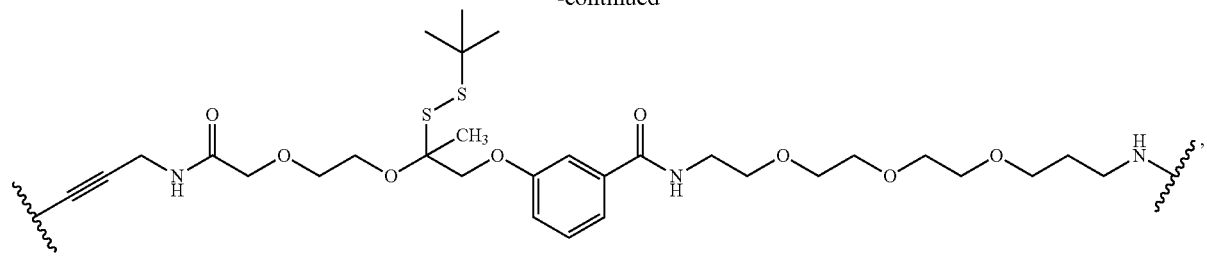
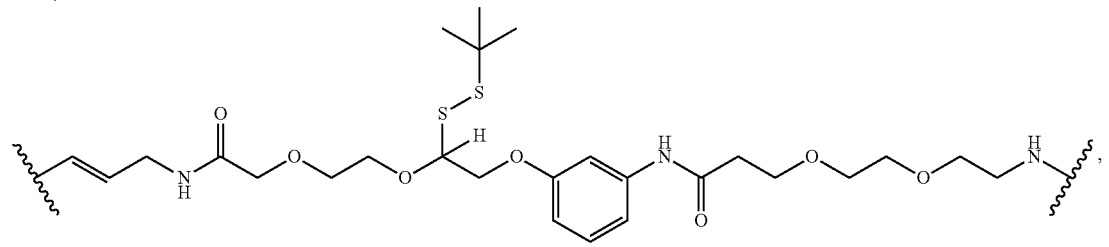
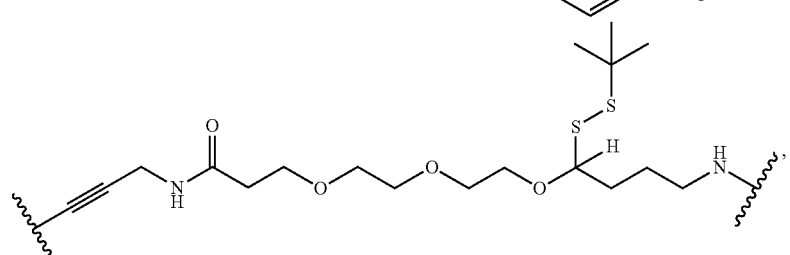
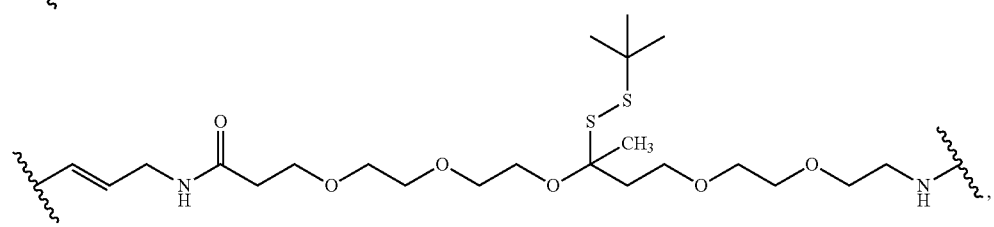
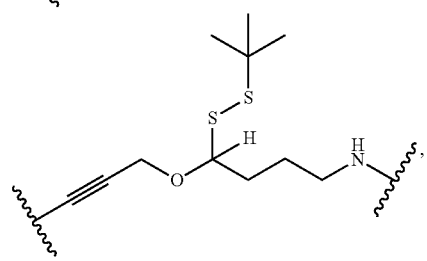
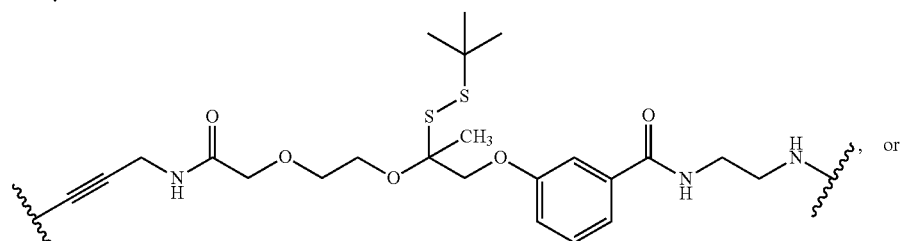, or
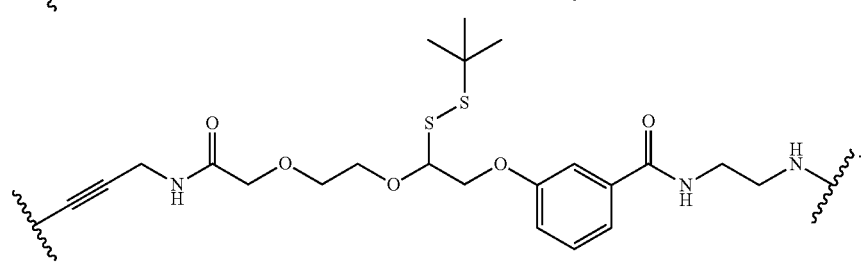

Embodiment Q28. The compound of one of embodiments Q1 to Q20, wherein $R^{00}$ is —CN.

Embodiment Q29. The compound of embodiment Q28, wherein;
$L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
$R^{102a}$ is independently hydrogen or unsubstituted alkyl.

Embodiment Q30. The compound of embodiment Q28, wherein
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently a bond, substituted or unsubstituted 4 to 18 membered heteroalkylene, or substituted or unsubstituted phenylene;
$L^{105}$ is independently bond or substituted or unsubstituted 4 to 18 membered heteroalkylene; and
$R^{102a}$ is hydrogen or unsubstituted methyl.

Embodiment Q31. The compound of embodiment Q28, wherein
$L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$L^{104}$ is unsubstituted phenylene; and
$R^{102a}$ is independently hydrogen or unsubstituted alkyl.

Embodiment Q32. The compound of embodiment Q28, wherein
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently an unsubstituted phenylene;
$L^{105}$ is independently bond or substituted or unsubstituted 4 to 18 membered heteroalkylene; and
$R^{102a}$ is hydrogen or unsubstituted methyl.

Embodiment Q33. The compound of embodiment Q28, wherein -($L^{101}$)-OC($SSR^{102}$)($R^{102a}$)-($L^{103}$)-($L^{104}$)-($L^{105}$)- is

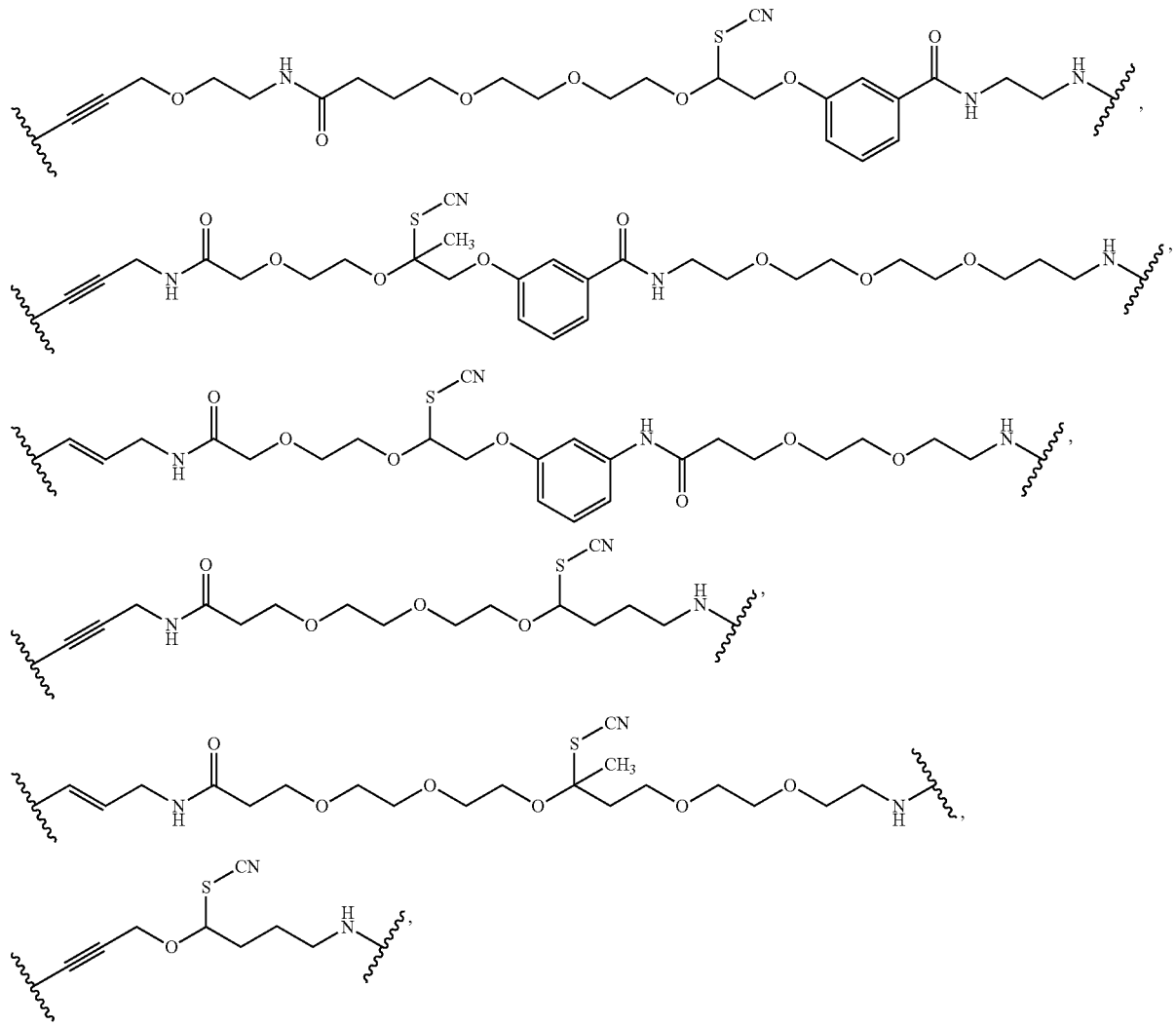

-continued

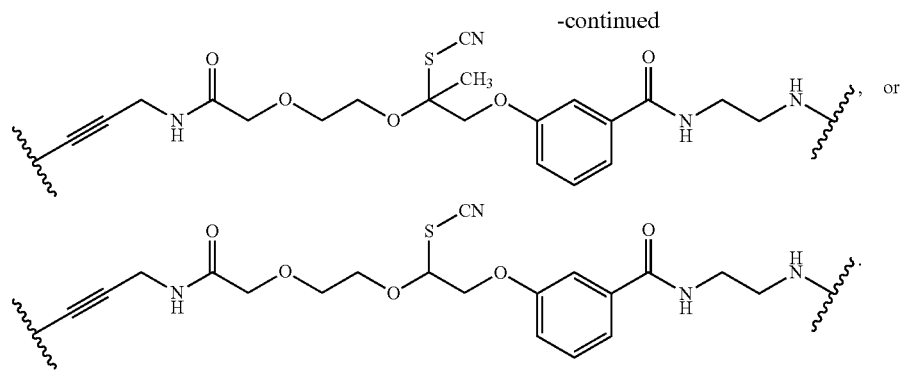

Embodiment Q34. The compound of one of embodiments Q1 to Q33, wherein $R^4$ is a fluorescent dye moiety.

Embodiment Q35. The compound of one of embodiments Q1 to Q33, wherein $R^4$

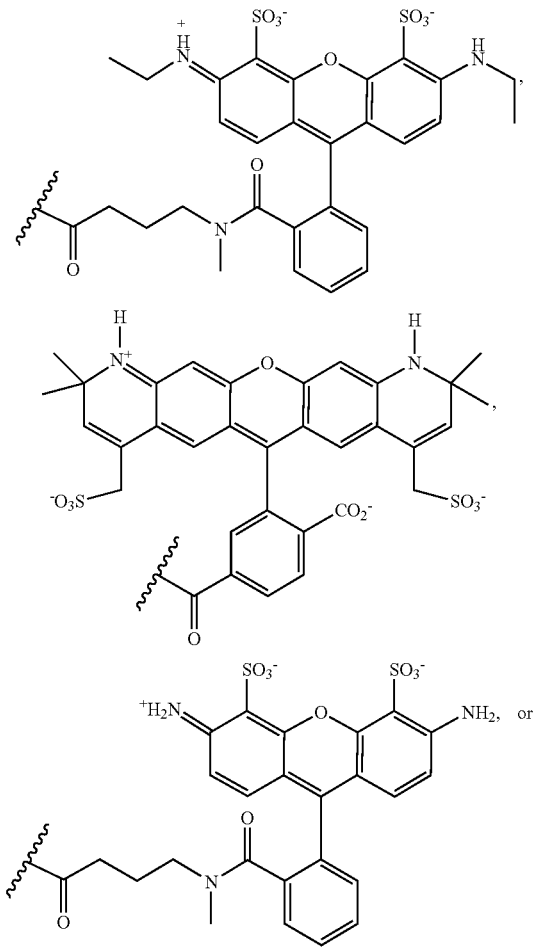

-continued

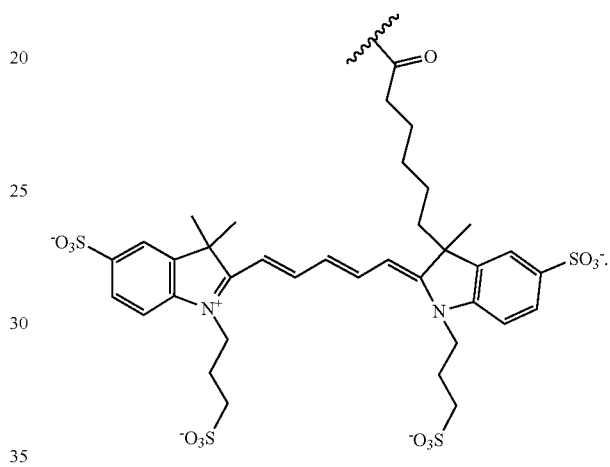

Embodiment Q36. A method for sequencing a nucleic acid, comprising:

(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;

(ii) detecting said unique detectable label of each incorporated compound, so as to thereby identify each incorporated compound in said extension strand, thereby sequencing the nucleic acid;

wherein each of said four different compounds is independently a compound of one of embodiments Q1 to Q35.

Embodiment Q37. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments Q1 to Q35.

Embodiment Q38. A nucleic acid polymerase complex comprising a nucleic acid polymerase, wherein said nucleic acid polymerase is bound to a compound of one of embodiments Q1 to Q35.

V. Additional Embodiments

Embodiment 1. A compound having the formula:

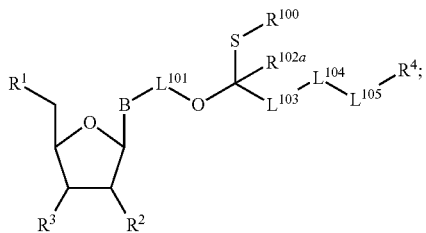

(I)

wherein
B is a divalent nucleobase;
$R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and
$R^2$ and $R^3$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety;
$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{100}$ is —SR$^{102}$ or —CN;
$R^{102}$ and $R^{102a}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^4$ is a detectable moiety.

Embodiment 2. The compound of embodiment 1, wherein $R^3$ is an —O-polymerase-compatible cleavable moiety.

Embodiment 3. The compound of one of embodiments 1 to 2, wherein the polymerase-compatible cleavable moiety is independently -(substituted or unsubstituted alkylene)-SS-(unsubstituted alkyl).

Embodiment 4. The compound of one of embodiments 1 to 2, wherein the polymerase-compatible cleavable moiety is independently -(halo-substituted or unsubstituted $C_1$-$C_3$ alkylene)-SS-(unsubstituted $C_1$-$C_4$ alkyl).

Embodiment 5. The compound of one of embodiments 1 to 2, wherein the polymerase-compatible cleavable moiety is independently:

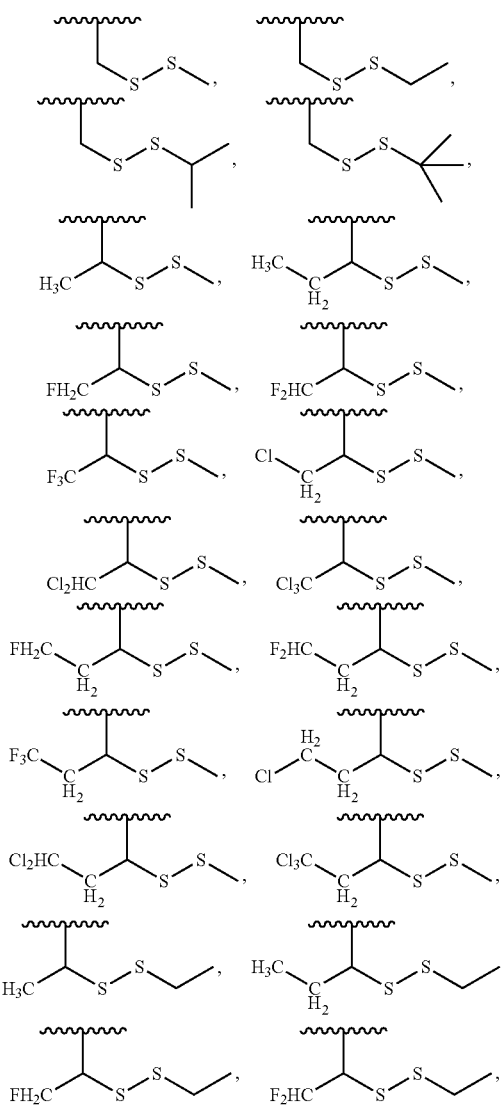

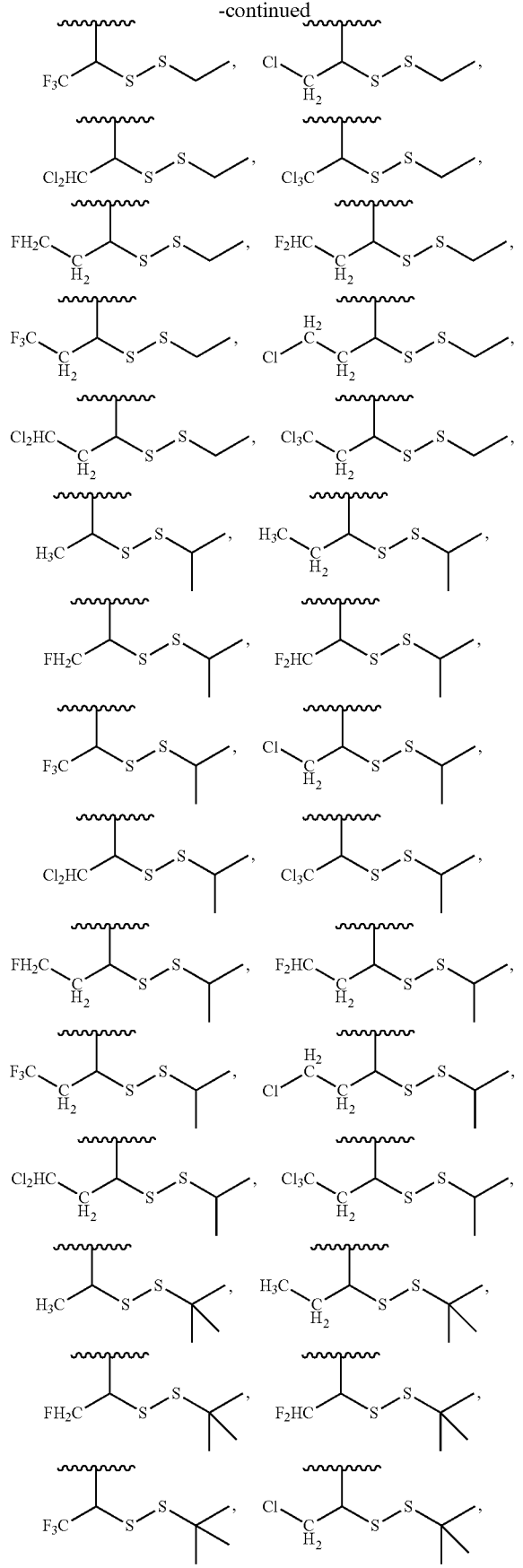
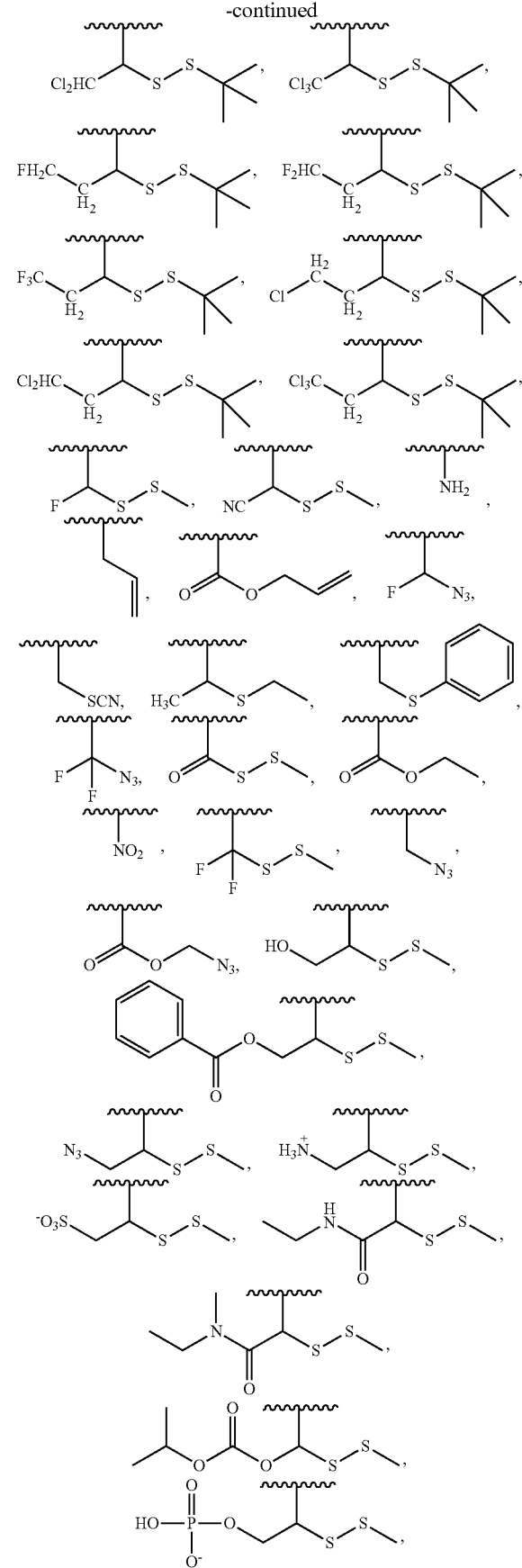

413
-continued
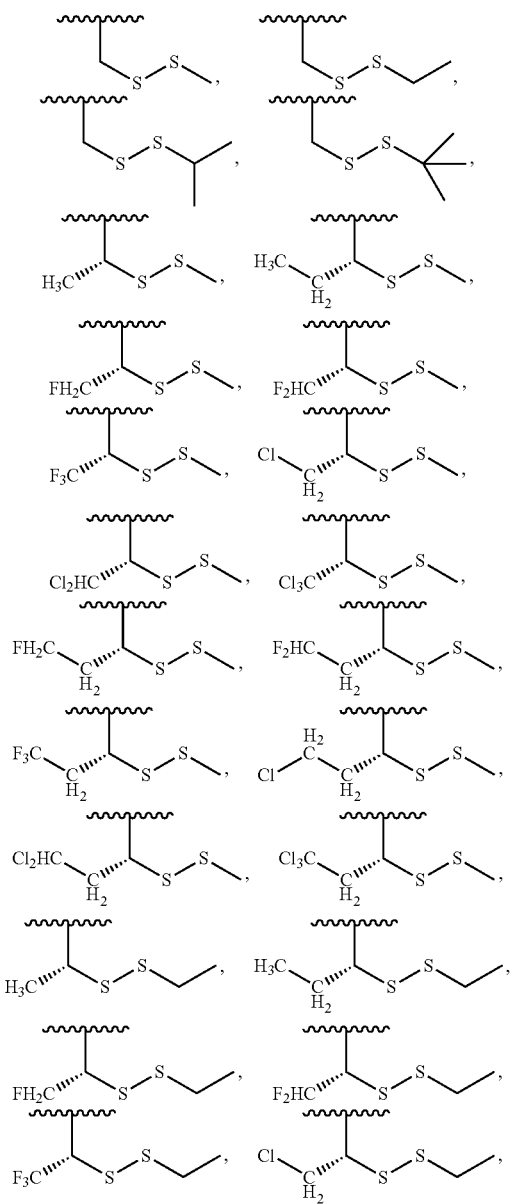
Embodiment 6. The compound of one of embodiments 1 to 2, wherein the -polymerase-compatible cleavable moiety is independently:

415
-continued
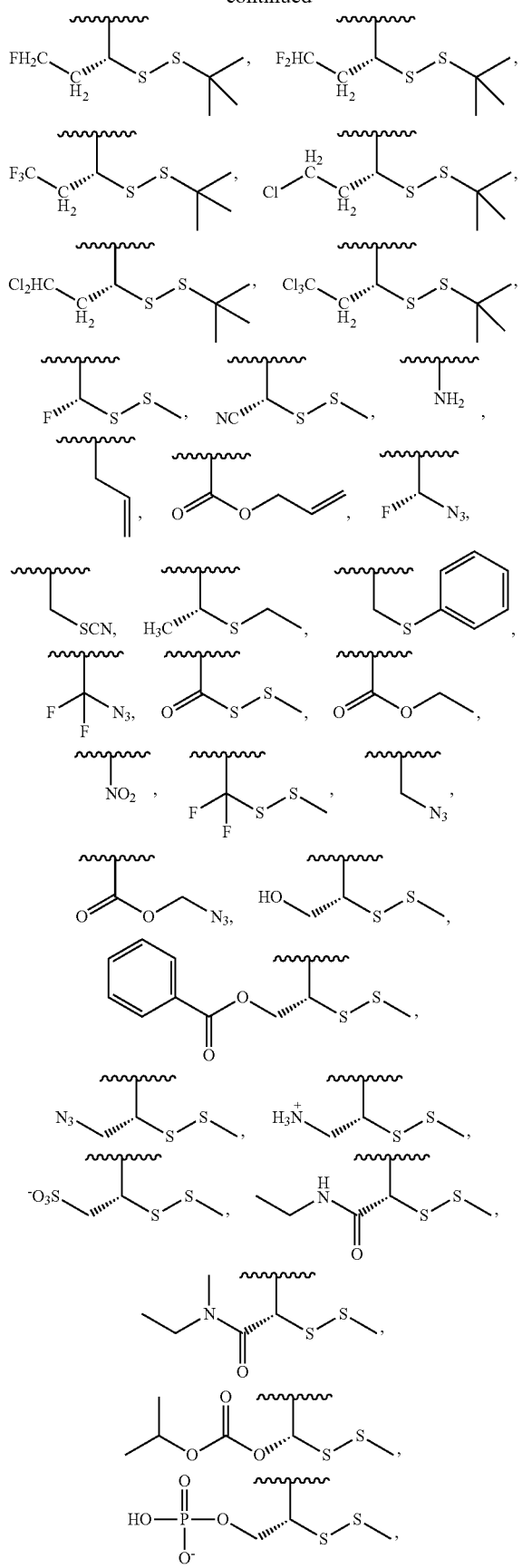
416
-continued
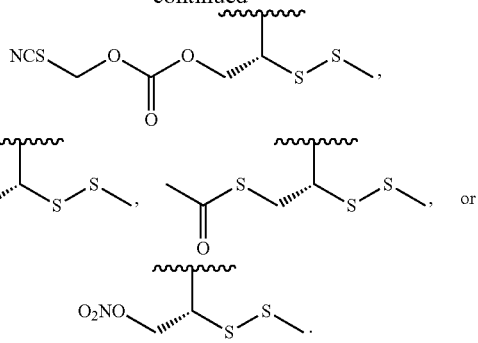
Embodiment 7. The compound of one of embodiments 1 to 2, wherein the polymerase-compatible cleavable moiety is independently:
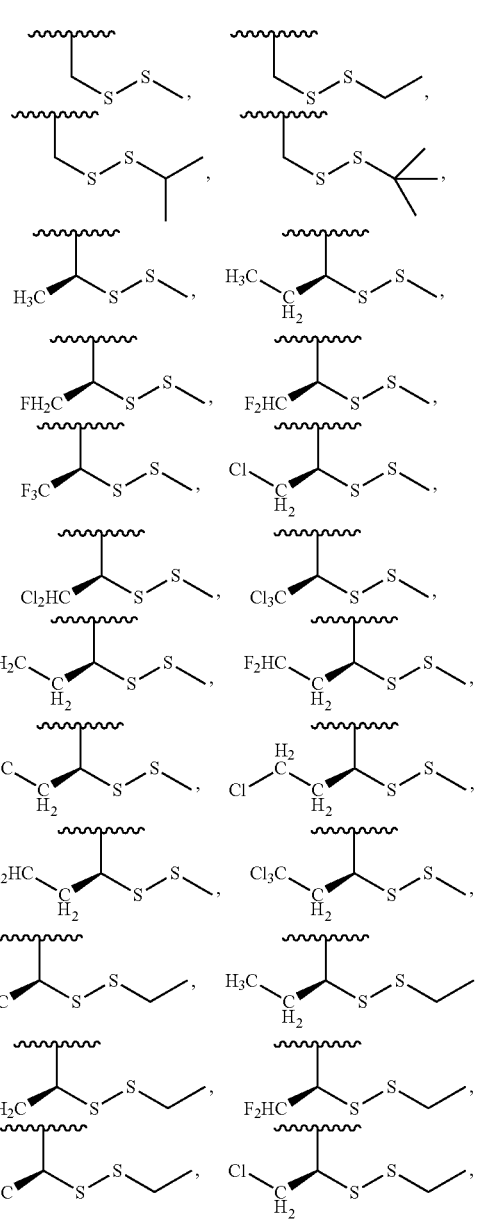

417
-continued
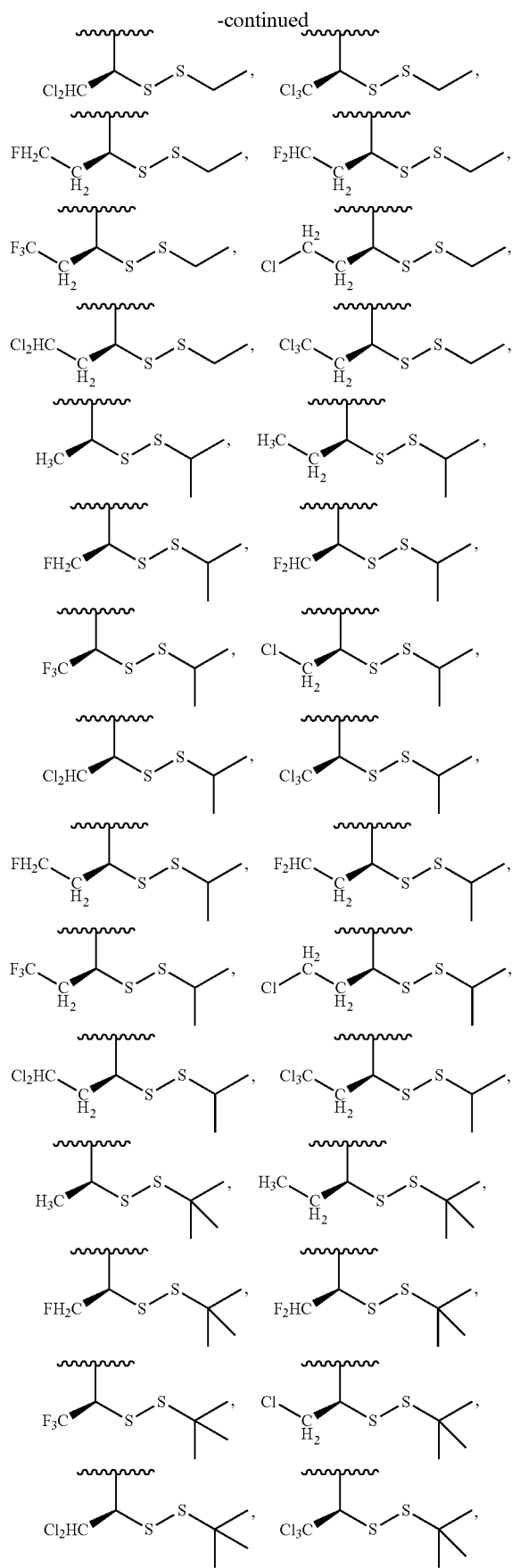
418
-continued
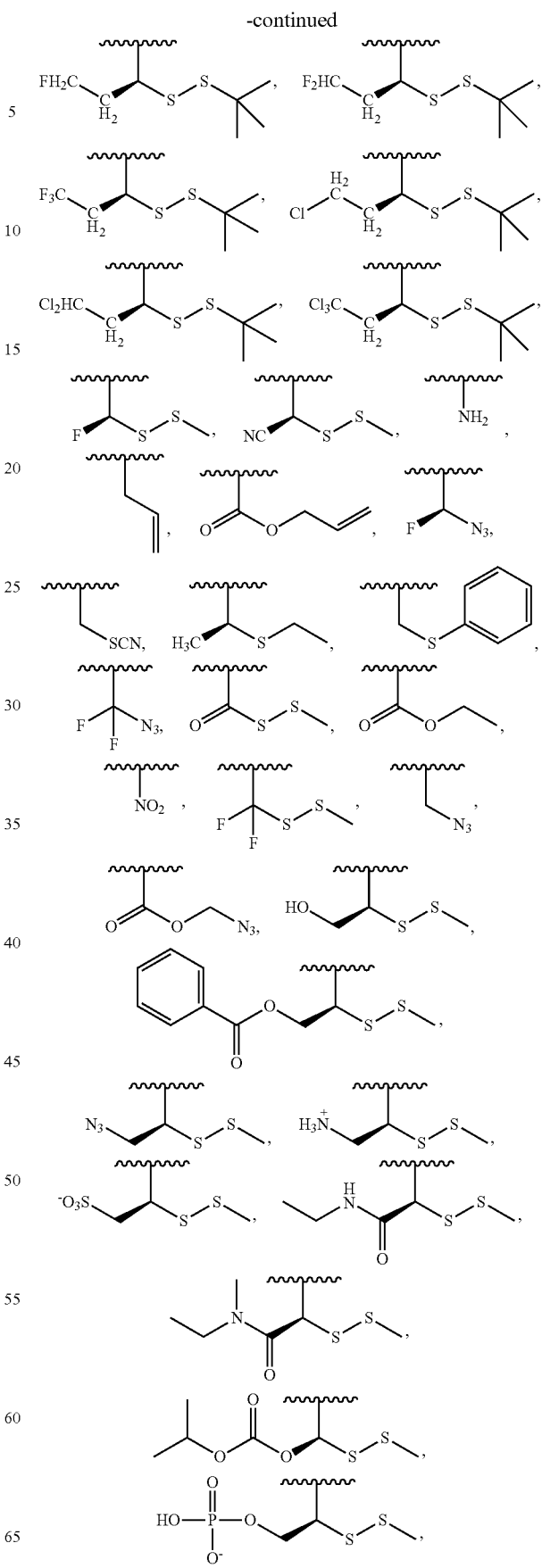

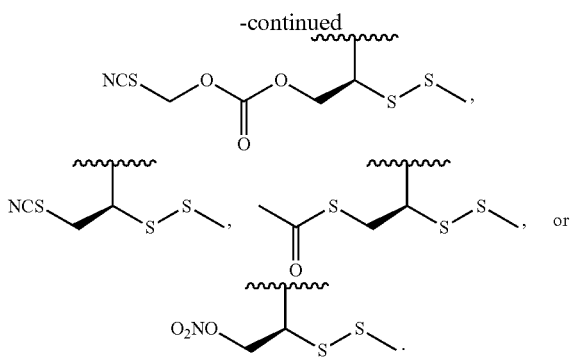

Embodiment 8. The compound of one of embodiments 1 to 2, wherein the polymerase-compatible cleavable moiety is independently:

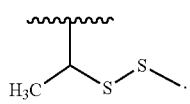

Embodiment 9. The compound of one of embodiments 1 to 2, wherein the polymerase-compatible cleavable moiety is independently:

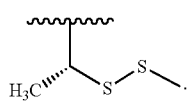

Embodiment 10. The compound of one of embodiments 1 to 2, wherein the polymerase-compatible cleavable moiety is independently:

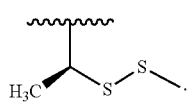

Embodiment 11. The compound of one of embodiments 1 to 10, wherein $R^2$ is hydrogen.

Embodiment 12. The compound of one of embodiments 1 to 10, wherein $R^2$ is —OH.

Embodiment 13. The compound of one of embodiments 1 to 10, wherein $R^2$ is an —O-polymerase-compatible cleavable moiety.

Embodiment 14. The compound of one of embodiments 1 to 13, wherein $R^1$ is hydrogen.

Embodiment 15. The compound of one of embodiments 1 to 13, wherein $R^1$ is a monophosphate moiety.

Embodiment 16. The compound of one of embodiments 1 to 13, wherein $R^1$ is a polyphosphate moiety.

Embodiment 17. The compound of one of embodiments 1 to 13, wherein $R^1$ is a triphosphate moiety.

Embodiment 18. The compound of one of embodiments 1 to 13, wherein $R^1$ is a nucleic acid moiety.

Embodiment 19. The compound of one of embodiments 1 to 18, wherein

B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment 20. The compound of embodiment 19, wherein B is

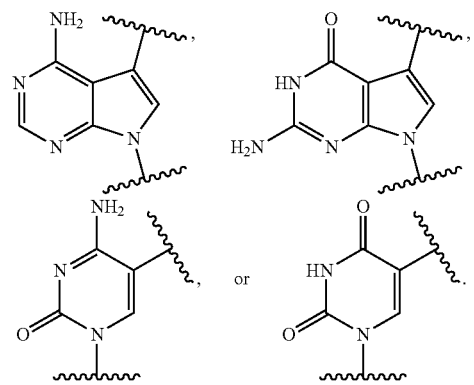

Embodiment 21. The compound of one of embodiments 1 to 20, wherein, $R^{100}$ is —$SR^{102}$.

Embodiment 22. The compound of one of embodiments 1 to 21, wherein;

$L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ and $R^{102a}$ are independently hydrogen or unsubstituted alkyl.

Embodiment 23. The compound of one of embodiments 1 to 21, wherein $L^{101}$ is independently a substituted or unsubstituted $C_1$-$C_4$ alkylene or substituted or unsubstituted 8 to 20 membered heteroalkylene;

$L^{103}$ is independently a bond or substituted or unsubstituted 2 to 10 membered heteroalkylene;

$L^{104}$ is independently a bond, substituted or unsubstituted 4 to 18 membered heteroalkylene, or substituted or unsubstituted phenylene;

$L^{105}$ is independently bond or substituted or unsubstituted 4 to 18 membered heteroalkylene; and $R^{102}$ is unsubstituted $C_1$-$C_4$ alkyl; and $R^{102a}$ is hydrogen or unsubstituted methyl.

Embodiment 24. The compound of one of embodiments 1 to 21, wherein $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{104}$ is unsubstituted phenylene; and $R^{102}$ and $R^{102a}$ are independently hydrogen or unsubstituted alkyl.

421

Embodiment 25. The compound of one of embodiments 1 to 21, wherein
- $L^{101}$ is independently a substituted or unsubstituted $C_1$-$C_4$ alkylene or substituted or unsubstituted 8 to 20 membered heteroalkylene;
- $L^{103}$ is independently a bond or substituted or unsubstituted 2 to 10 membered heteroalkylene;
- $L^{104}$ is independently an unsubstituted phenylene;

422

- $L^{105}$ is independently bond or substituted or unsubstituted 4 to 18 membered heteroalkylene;
- $R^{102}$ is unsubstituted $C_1$-$C_4$ alkyl; and
- $R^{102a}$ is hydrogen or unsubstituted methyl.

Embodiment 26. The compound of one of embodiments 1 to 21, wherein -($L^{101}$)-OC(SSR$^{102}$)(R$^{102a}$)-($L^{103}$)-($L^{104}$)-($L^{105}$)- is

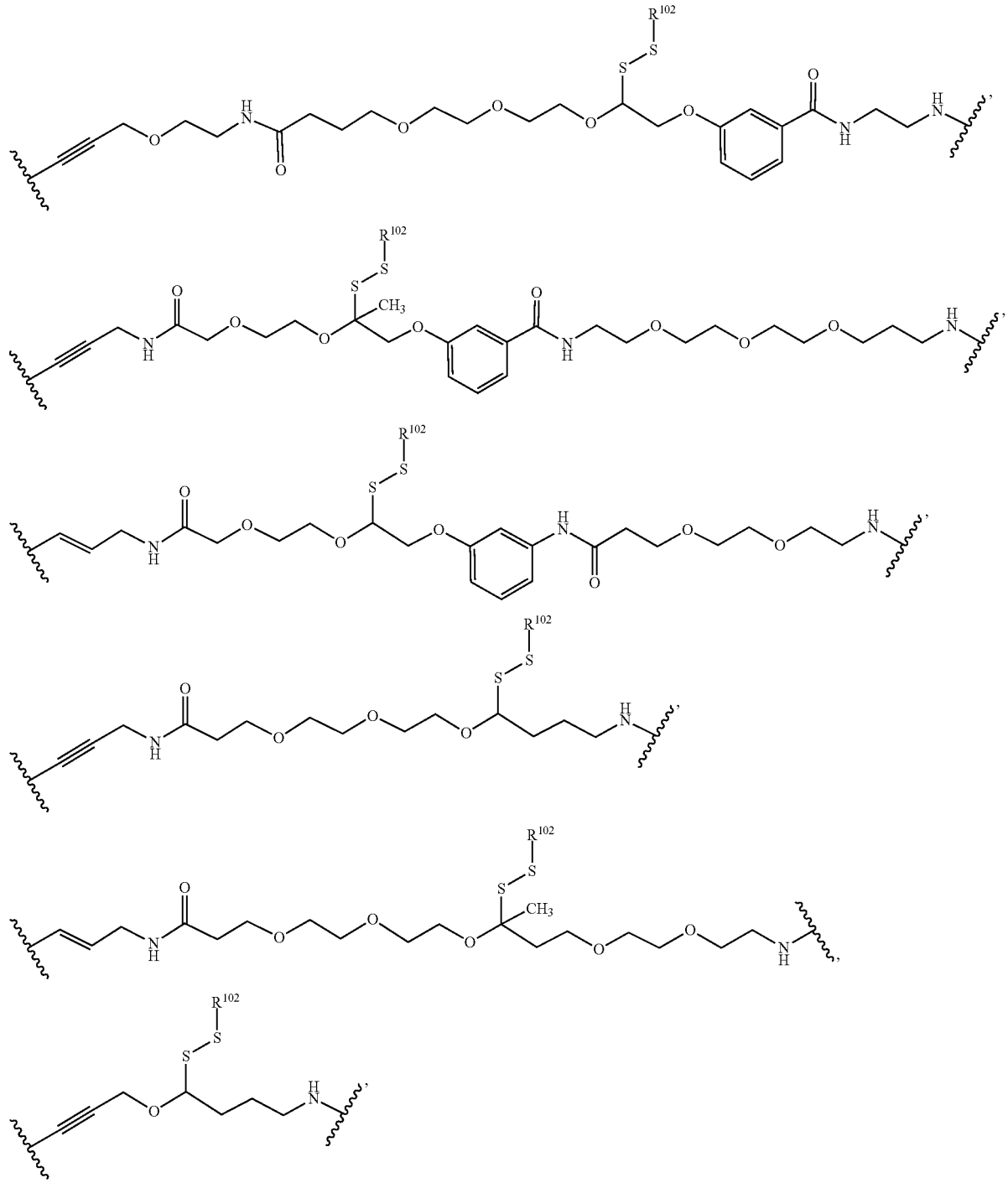

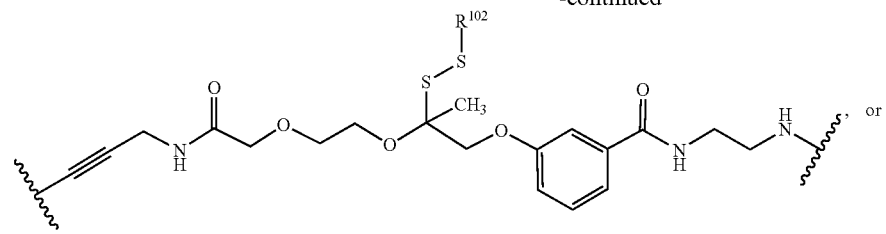
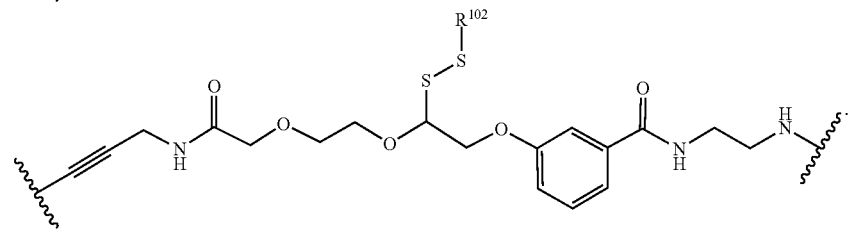
Embodiment 27. The compound of one of embodiments 1 to 21, wherein -($L^{101}$)-OC(SS$R^{102}$)($R^{102a}$)-($L^{103}$)-($L^{104}$)-($L^{105}$)- is
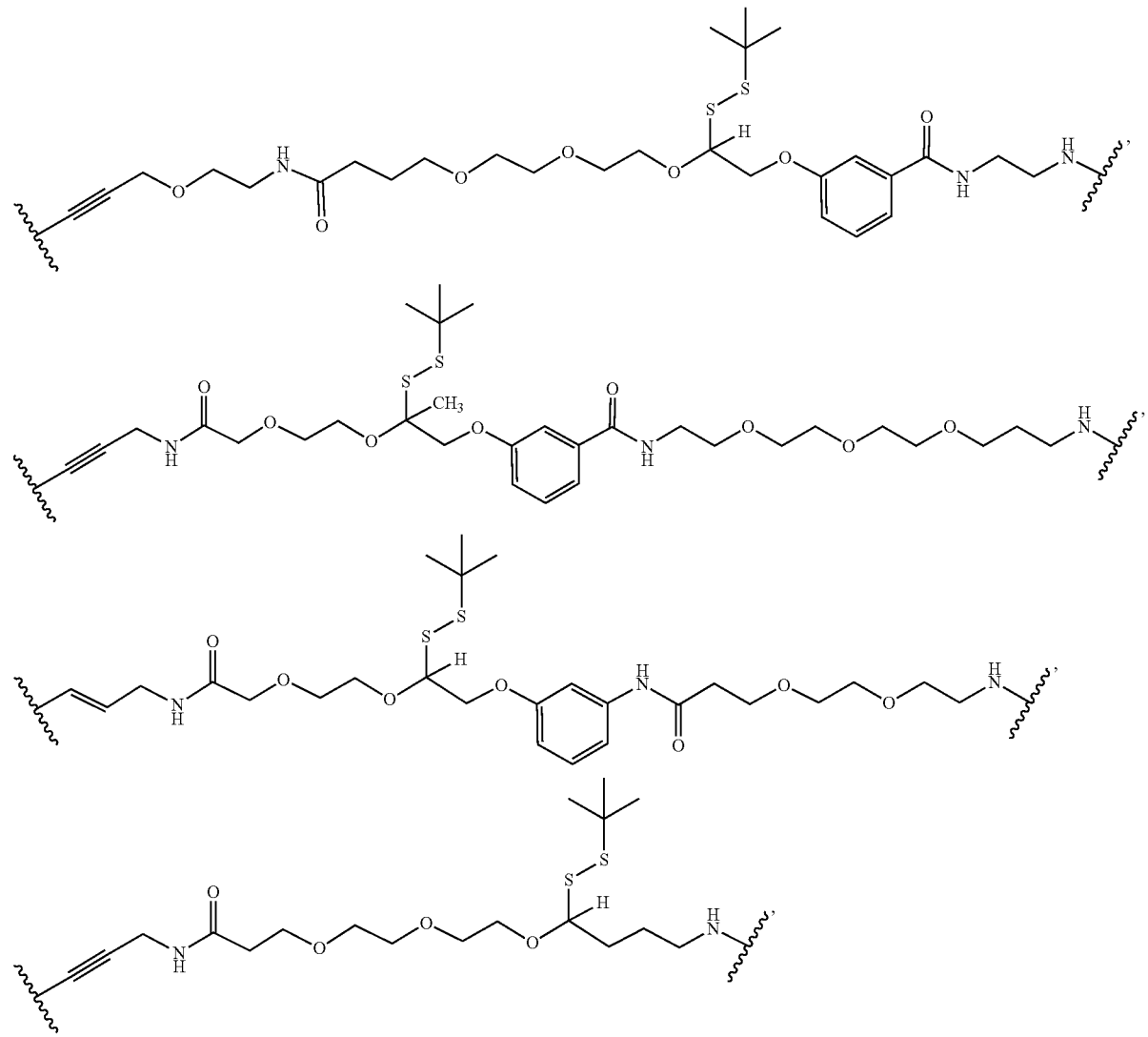

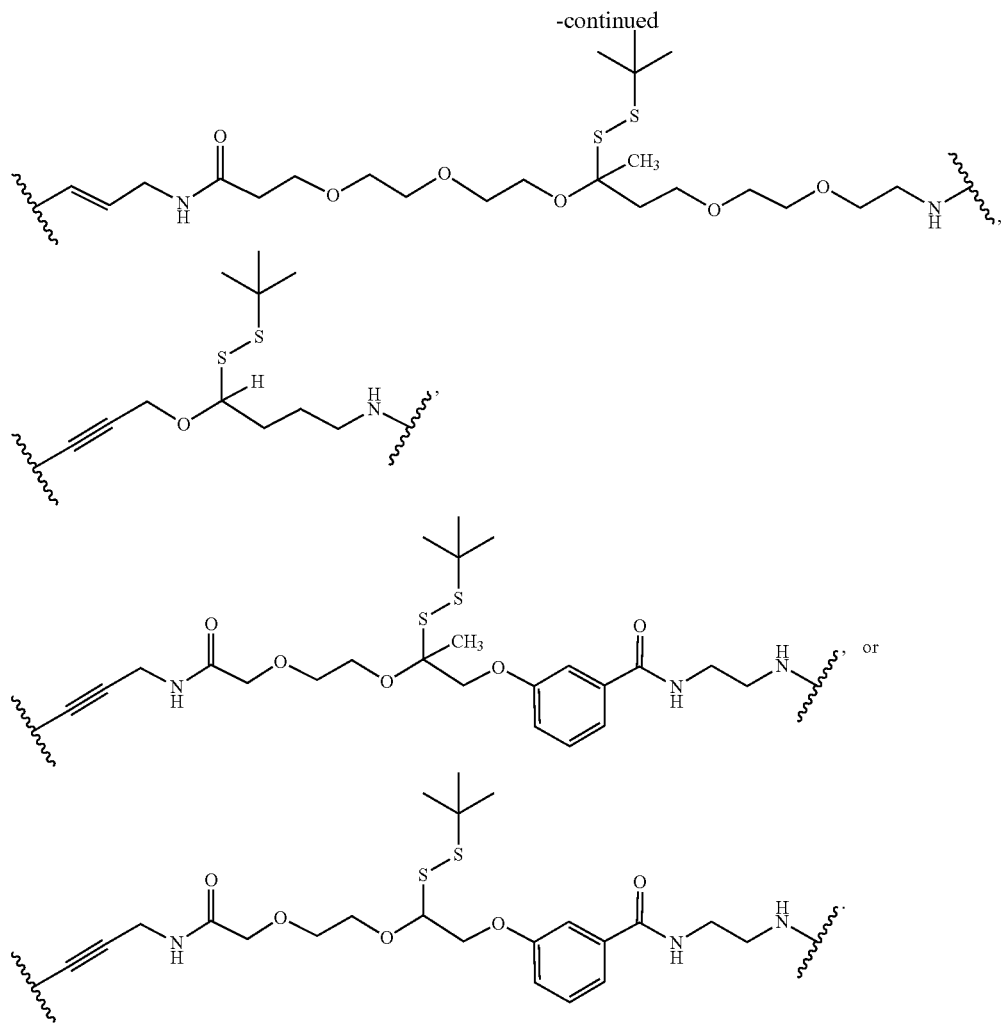

Embodiment 28. The compound of one of embodiments 1 to 20, wherein $R^{100}$ is —CN.

Embodiment 29. The compound of embodiment 28, wherein;
$L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
$R^{102a}$ is independently hydrogen or unsubstituted alkyl.

Embodiment 30. The compound of embodiment 28, wherein
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently a bond, substituted or unsubstituted 4 to 18 membered heteroalkylene, or substituted or unsubstituted phenylene;
$L^{105}$ is independently bond or substituted or unsubstituted 4 to 18 membered heteroalkylene; and
$R^{102a}$ is hydrogen or unsubstituted methyl.

Embodiment 31. The compound of embodiment 28, wherein
$L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$L^{104}$ is unsubstituted phenylene; and
$R^{102a}$ is independently hydrogen or unsubstituted alkyl.

Embodiment 32. The compound of embodiment 28, wherein
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently an unsubstituted phenylene;
$L^{105}$ is independently bond or substituted or unsubstituted 4 to 18 membered heteroalkylene; and
$R^{102a}$ is hydrogen or unsubstituted methyl.

Embodiment 33. The compound of embodiment 28, wherein -($L^{101}$)-OC(SS$R^{102}$)($R^{102a}$)-($L^{103}$)-($L^{104}$)-($L^{105}$)- is 427
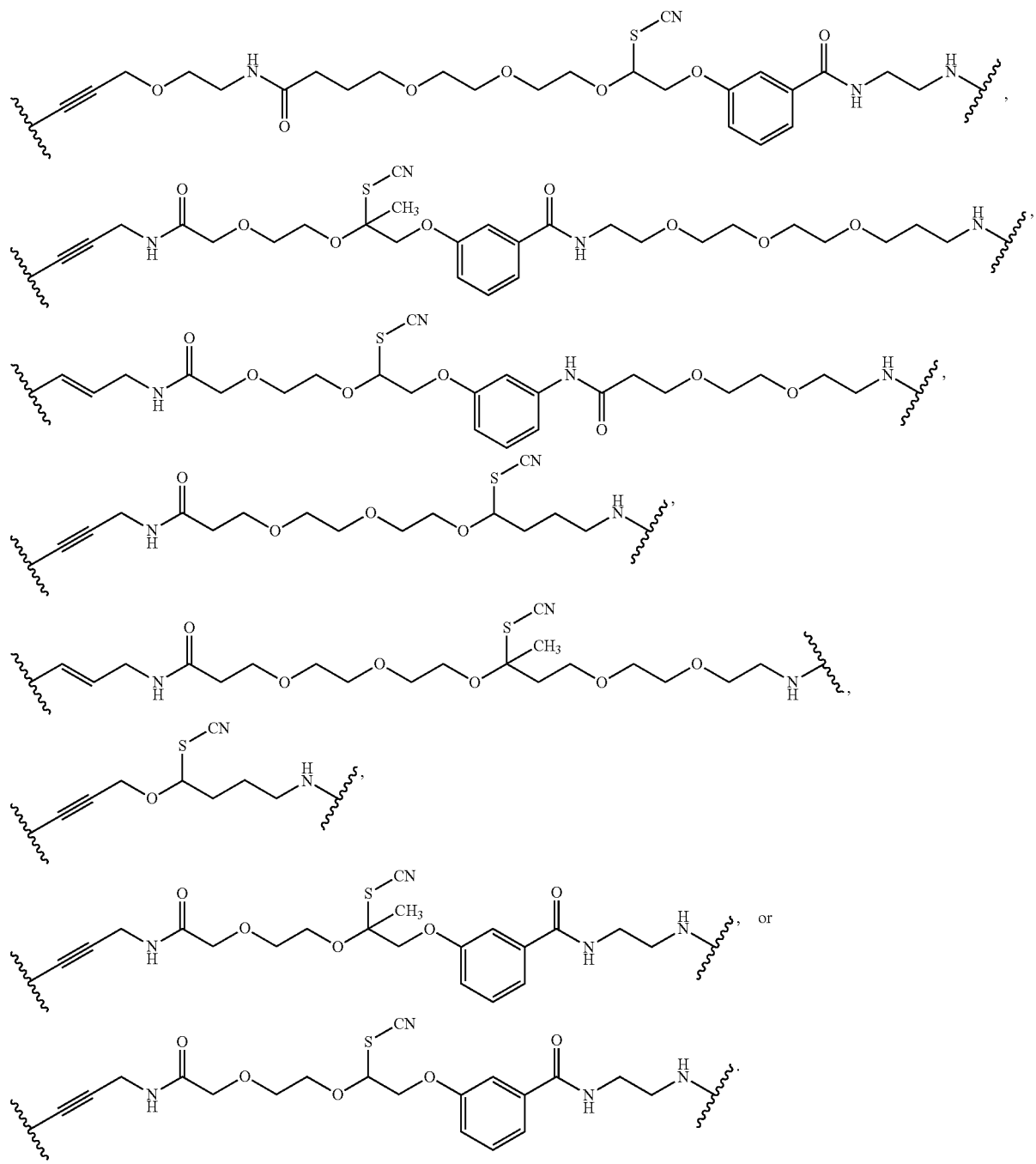
Embodiment 34. The compound of one of embodiments 1 to 33, wherein R⁴ is a fluorescent dye moiety.
Embodiment 35. The compound of one of embodiments 1 to 33, wherein R⁴ is
428
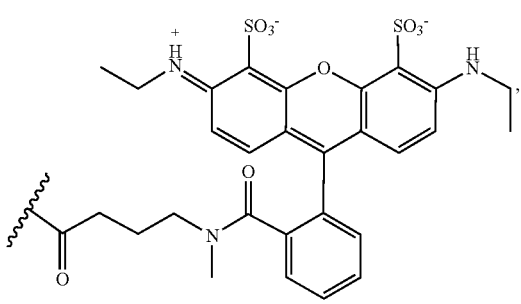

429
-continued

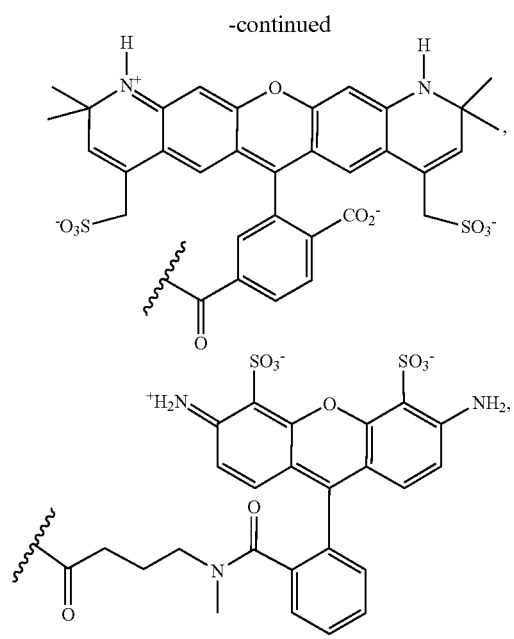

430
-continued

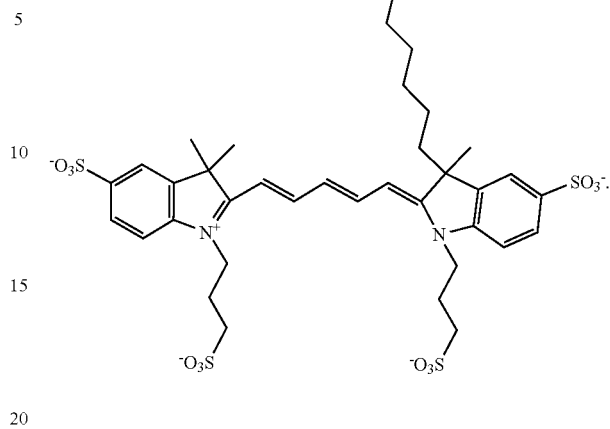

Embodiment 36. The compound of one of embodiments 1 to 35, having the formula:

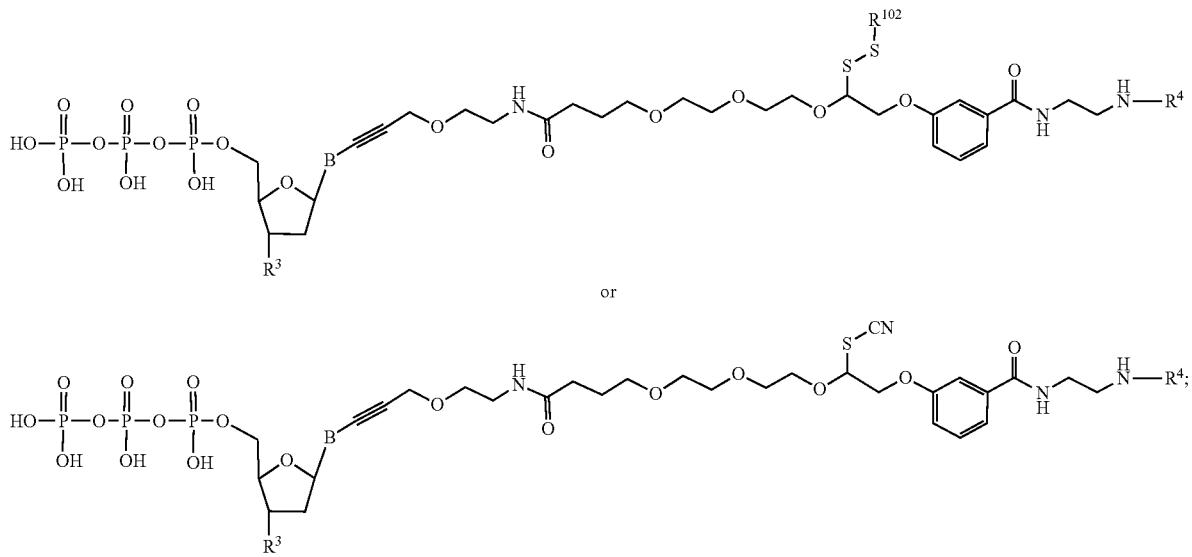

wherein
$R^3$ is an —O-polymerase-compatible cleavable moiety.

Embodiment 37. A method for sequencing a nucleic acid, comprising:
(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
(ii) detecting said unique detectable label of each incorporated compound, so as to thereby identify each incorporated compound in said extension strand, thereby sequencing the nucleic acid;
wherein each of said four different compounds is independently a compound of one of embodiments 1 to 36.

Embodiment 38. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments 1 to 36.

Embodiment 39. A nucleic acid polymerase complex comprising a nucleic acid polymerase, wherein said nucleic acid polymerase is bound to a compound of one of embodiments 1 to 36.

Embodiment 40. A modified nucleotide or nucleoside, the nucleotide or nucleoside comprising a sugar moiety having a 3'-O-polymerase-compatible cleavable moiety and a base linked via a covalent linker to a detectable moiety, wherein the covalent linker includes a thio-trigger moiety having the formula

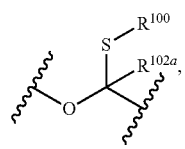

wherein $R^{100}$ is $-SR^{102}$ or $-CN$; $R^{102}$ and $R^{102a}$ are independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 41. The modified nucleotide or nucleoside of embodiment 40, wherein the thio-trigger moiety has the formula

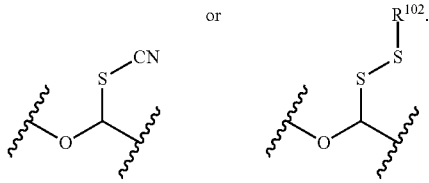

Embodiment 42. The modified nucleotide or nucleoside of embodiment 40, wherein the thio-trigger moiety has the formula

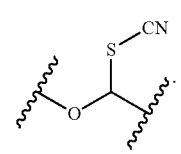 [SMILES: *OC(*)SC#N]

Embodiment 43. The modified nucleotide or nucleoside of embodiment 40, wherein the thio-trigger moiety has the formula

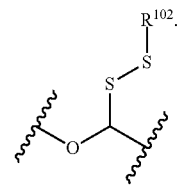

Embodiment 44. The modified nucleotide or nucleoside of embodiment 40, wherein the thio-trigger moiety has the formula

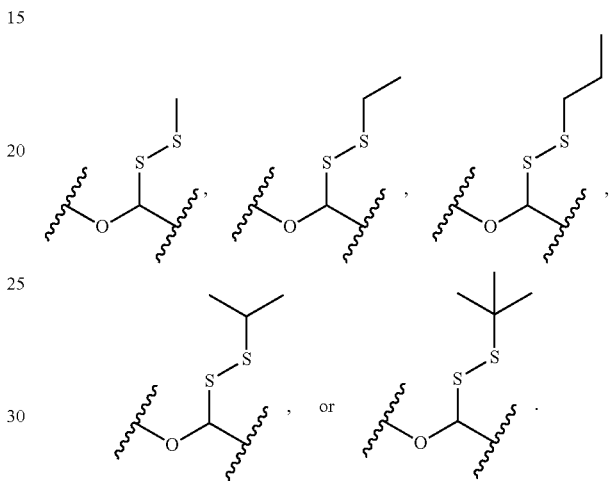

EXAMPLES

Example 1. Synthesis of Labeled Nucleosides

DNA sequencing is a fundamental tool in biological and medical research; it is an essential technology for the paradigm of personalized precision medicine. Sanger sequencing, where the sequence of a nucleic acid is determined by selective incorporation and detection of dideoxynucleotides, enabled the mapping of the first human reference genome. While this methodology is still useful for validating newer sequencing technologies, efforts to sequence and assemble genomes using the Sanger method are an expensive and laborious undertaking, requiring specialized equipment and expertise. Certain new sequencing methodologies make use of simultaneously sequencing millions of fragments of nucleic acids, resulting in a 50,000-fold drop in the costs associated with sequencing.

Traditional sequencing-by-synthesis (SBS) methodologies employ serial incorporation and detection of labeled nucleotide analogues. For example, high-throughput SBS technology uses cleavable fluorescent nucleotide reversible terminator (NRT) sequencing chemistry. These cleavable fluorescent NRTs were designed based on the following rationale: each of the four nucleotides (A, C, G, T, and/or U) is modified by attaching a unique cleavable fluorophore to the specific location of the nucleobase and capping the 3'-OH group of the nucleotide sugar with a small reversible moiety (also referred to herein as a reversible terminator) so that they are still recognized by DNA polymerase as substrates. The reversible terminator temporarily halts the polymerase reaction after nucleotide incorporation while the fluorophore signal is detected. After incorporation and signal detection, the fluorophore and the reversible terminator are cleaved to resume the polymerase reaction in the next cycle. A balance needs to be found between efficient incorporation of the labeled nucleotides, efficient cleavage to remove all the incorporated labels, and efficient incorporation of the next nucleotide. Described herein in are optimized nucleotide structures and synthetic schemes that improve the performance of nucleotides in Sequencing-by-Synthesis (SBS) cycles.

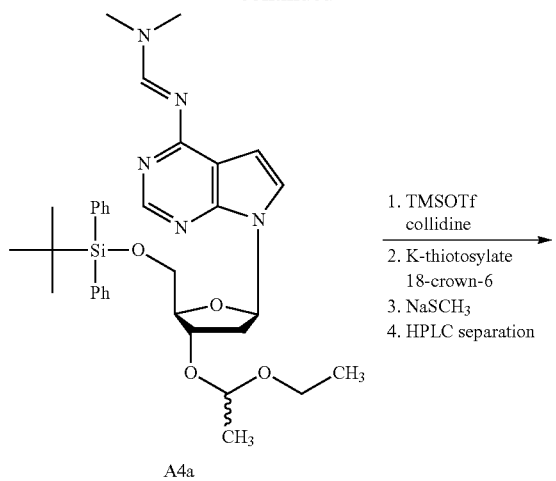

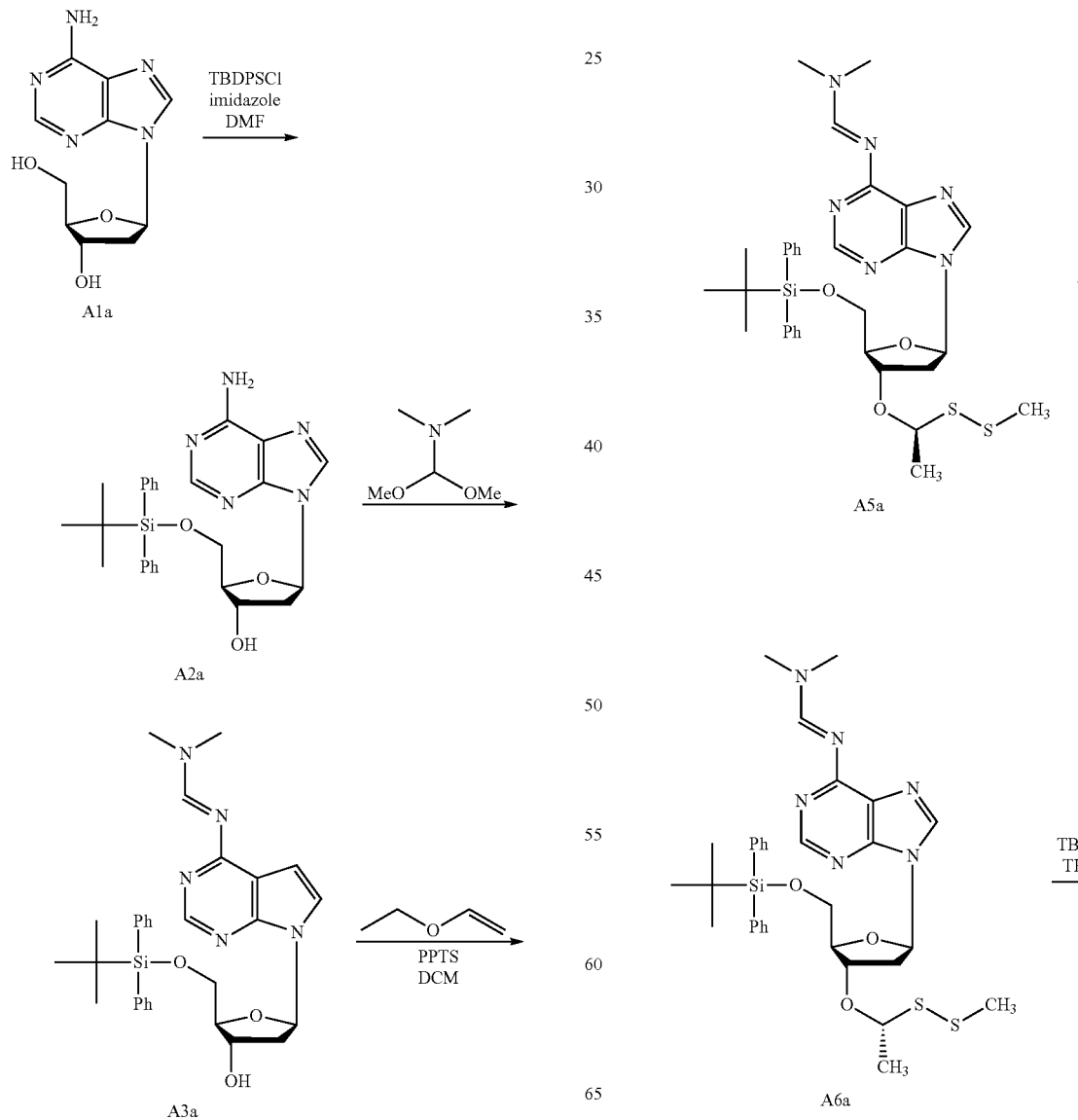

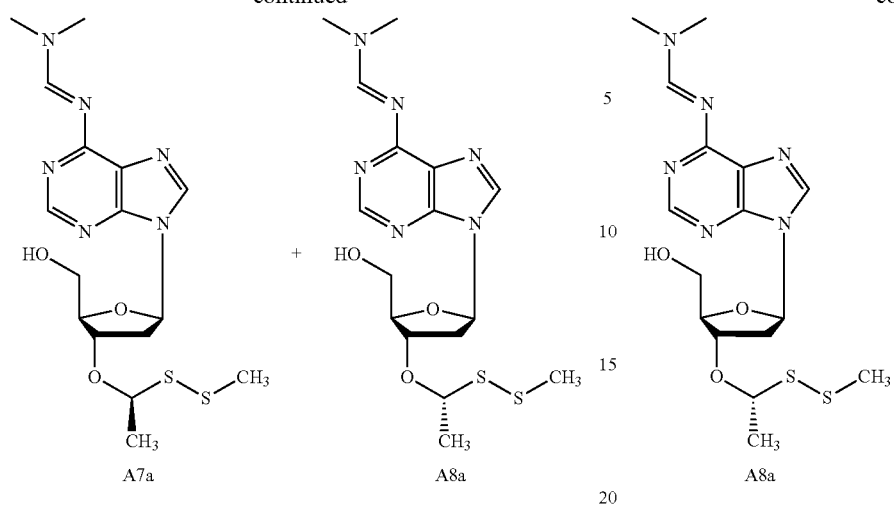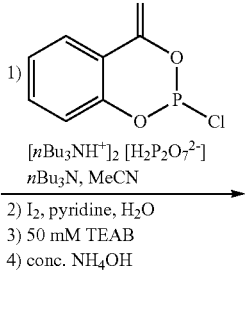

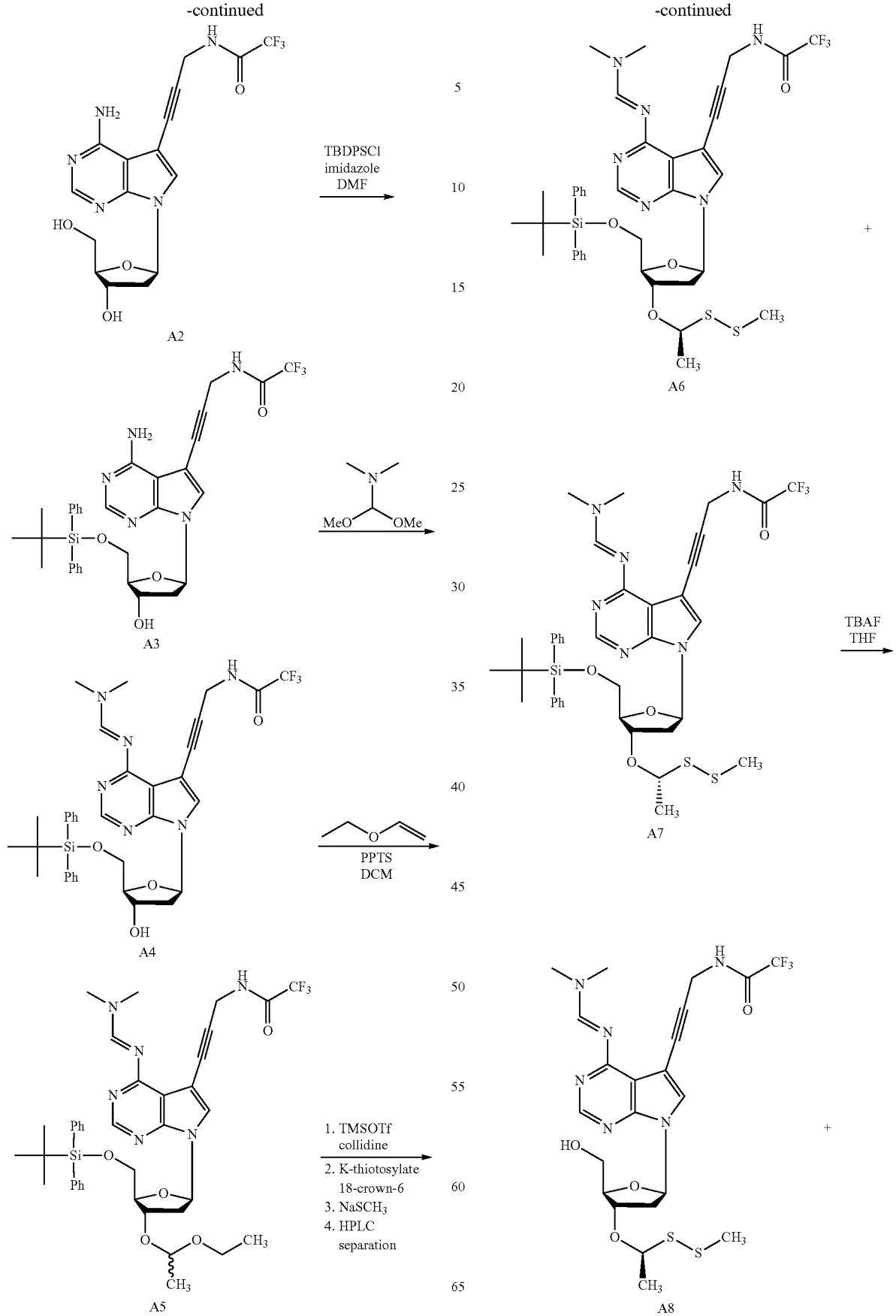

-continued
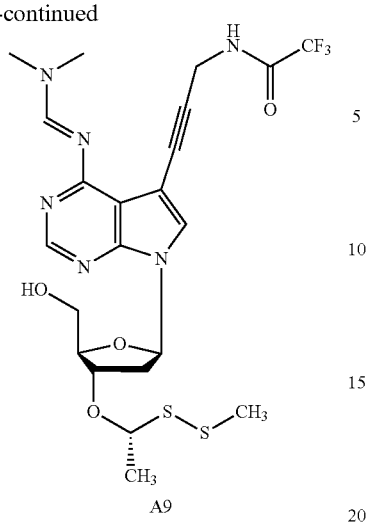
A9
Scheme 4. Part 2 of 3 MeSS_CHCH3_dATP_thio-trigger containing linker scheme
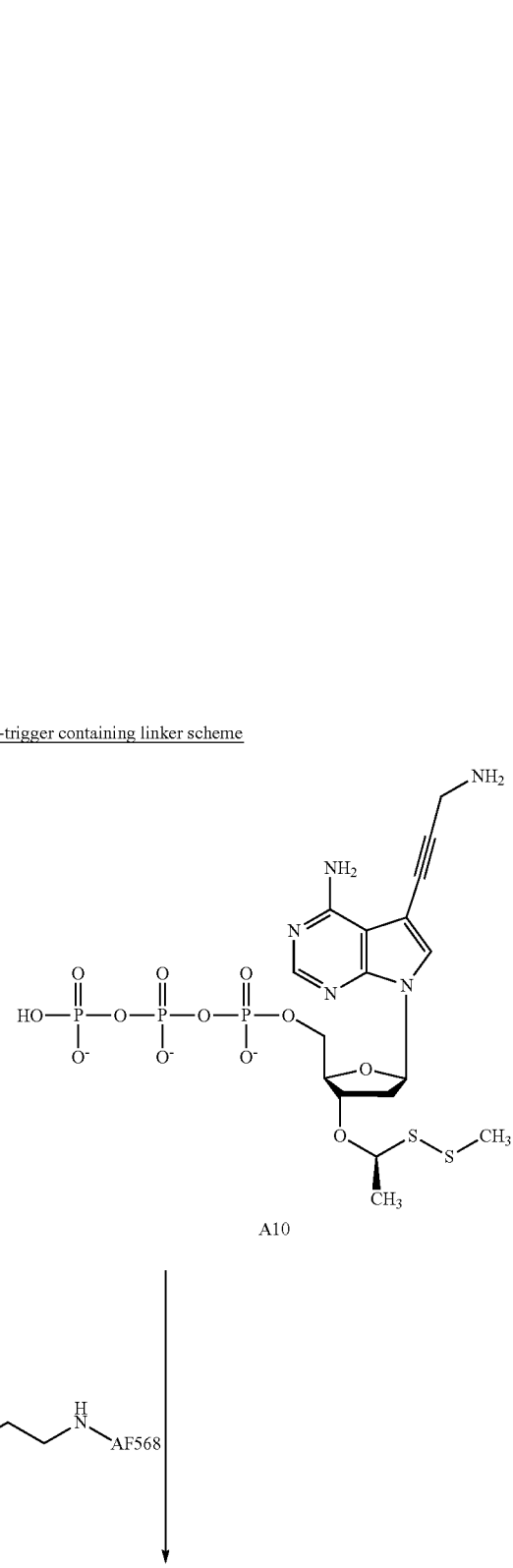

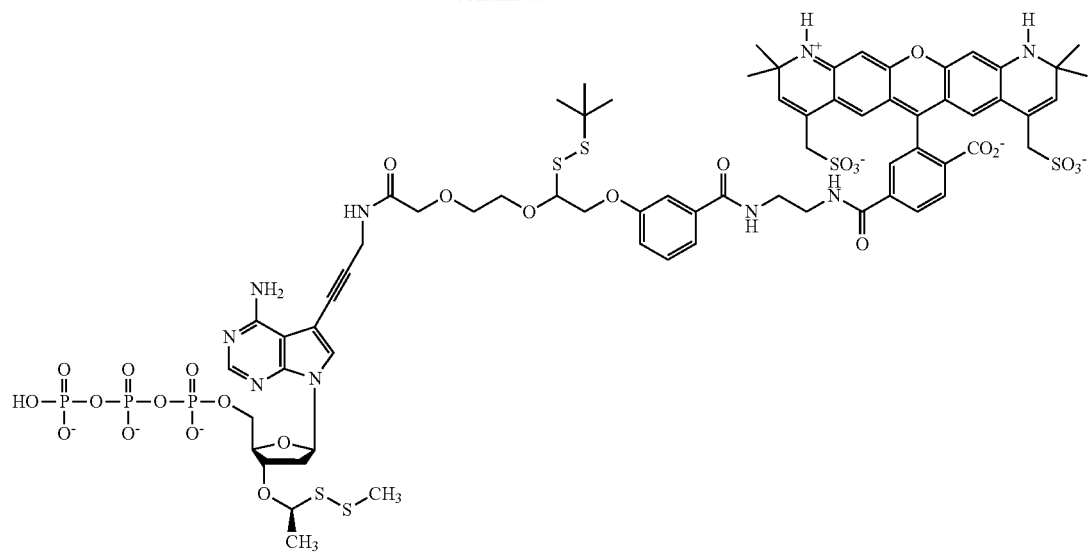
A14
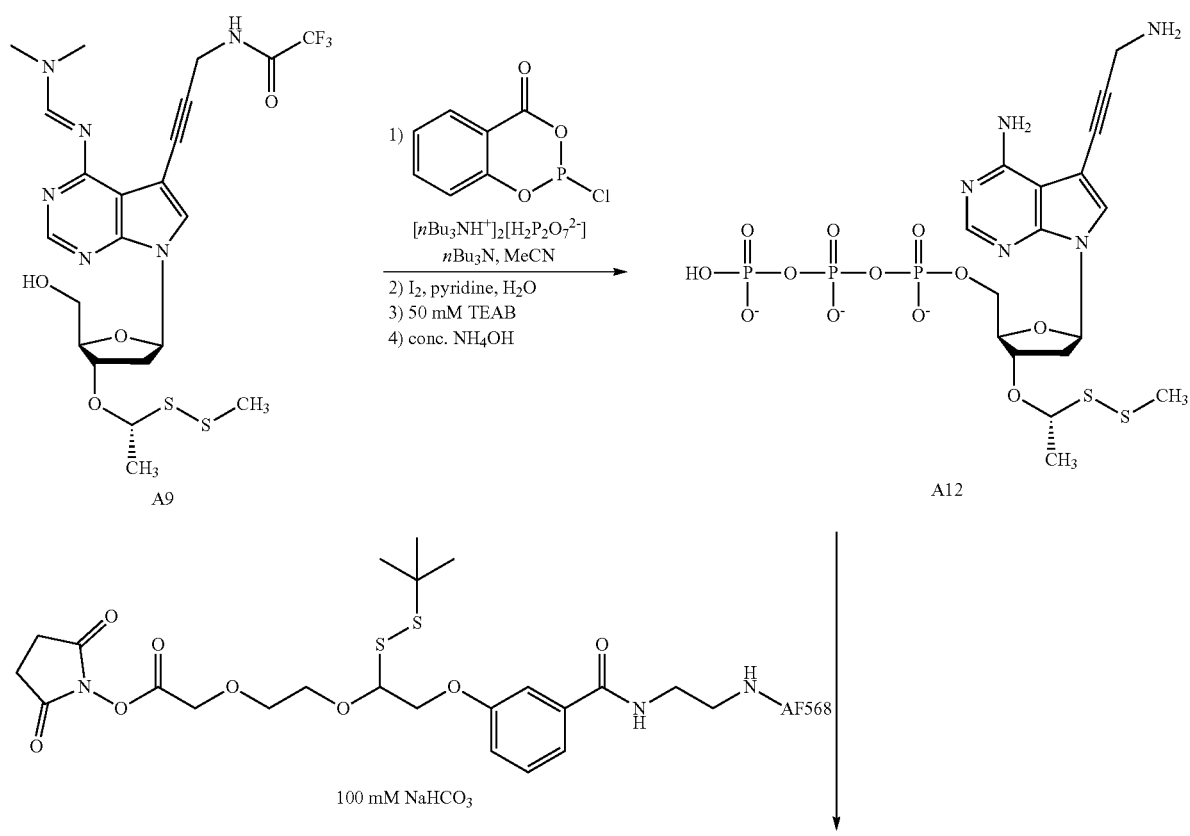
Scheme 5. Part 3 of 3 MeSS_CHCH3_dATP_thio-trigger containing linker scheme

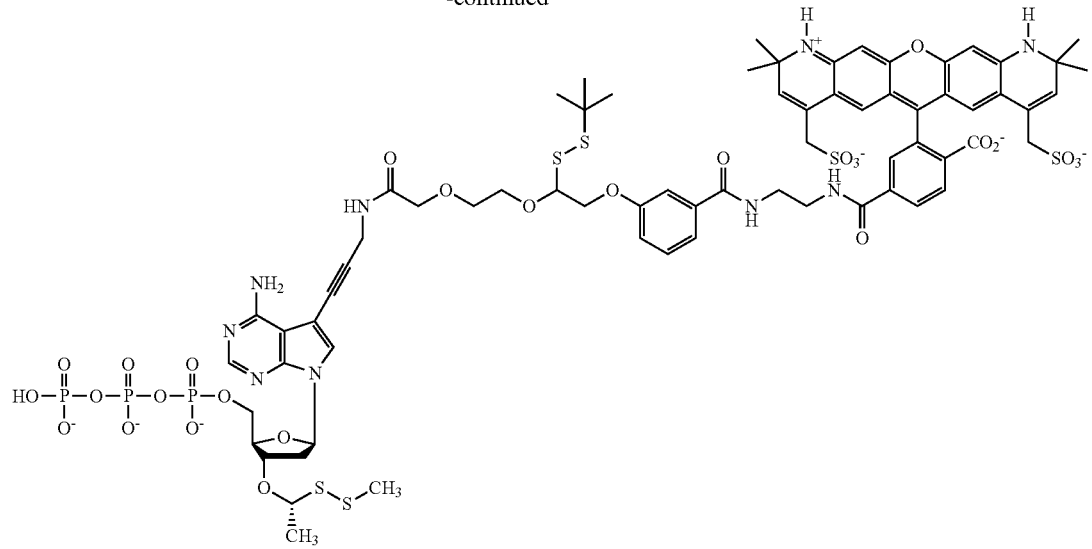
A15
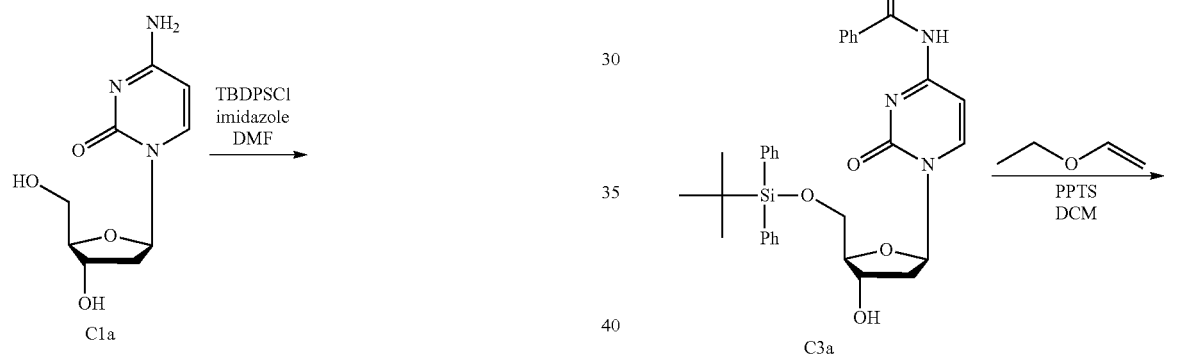
Scheme 6. Part 1 of 2 MeSS_CHCH3_dCTP scheme
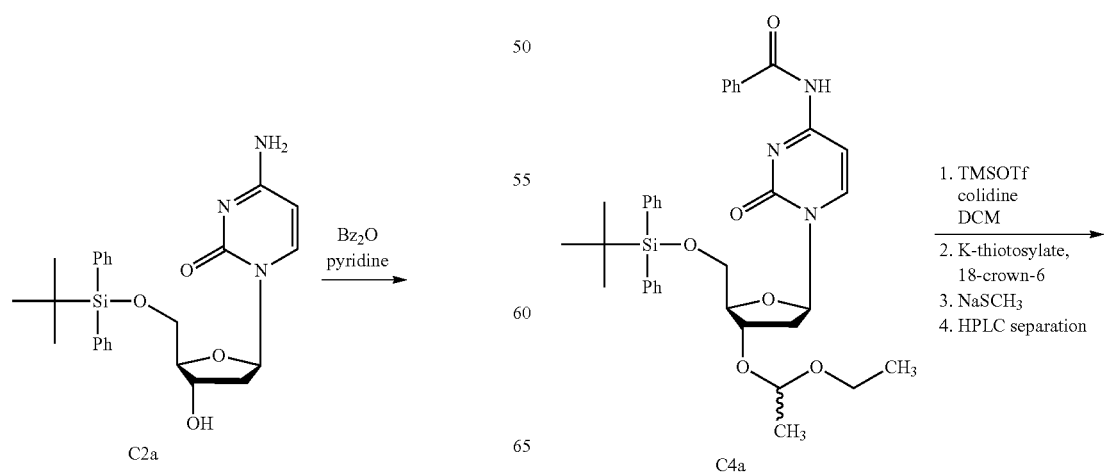

Scheme 7. Part 2 of 2 MeSS_CHCH3_dCTP scheme
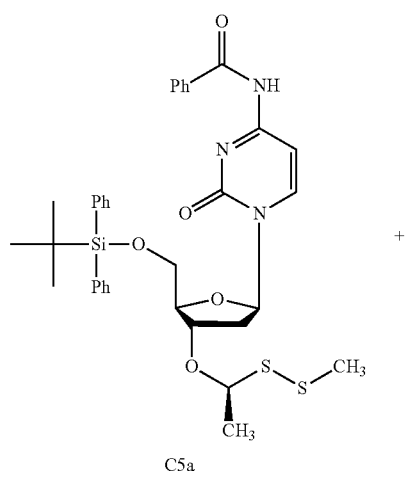
C5a
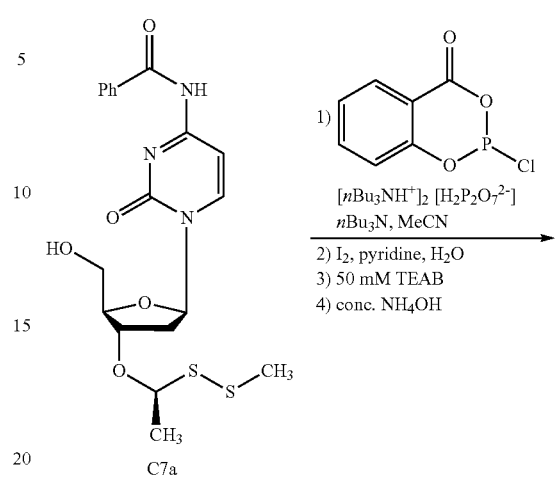
C7a
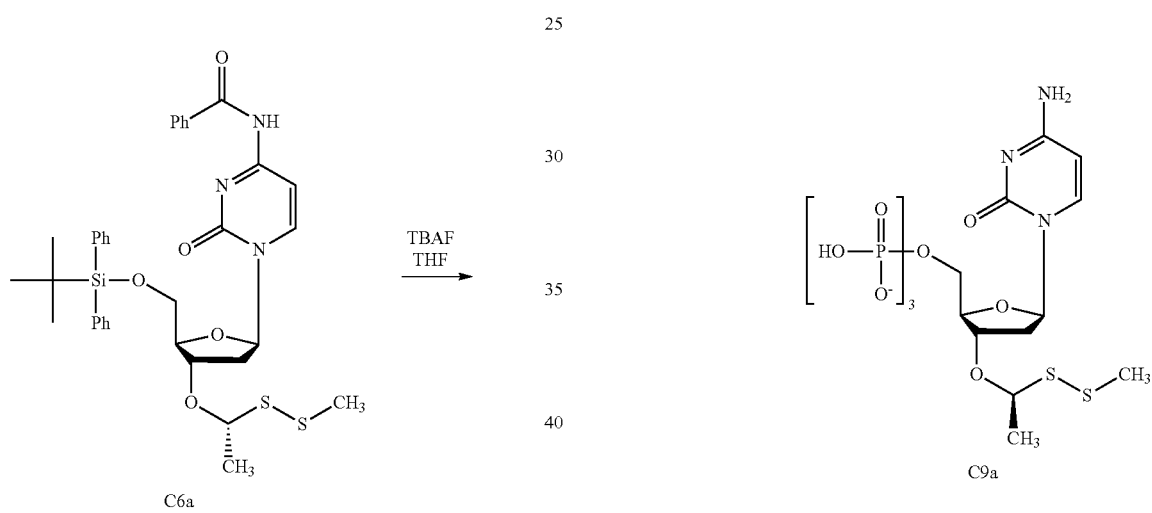
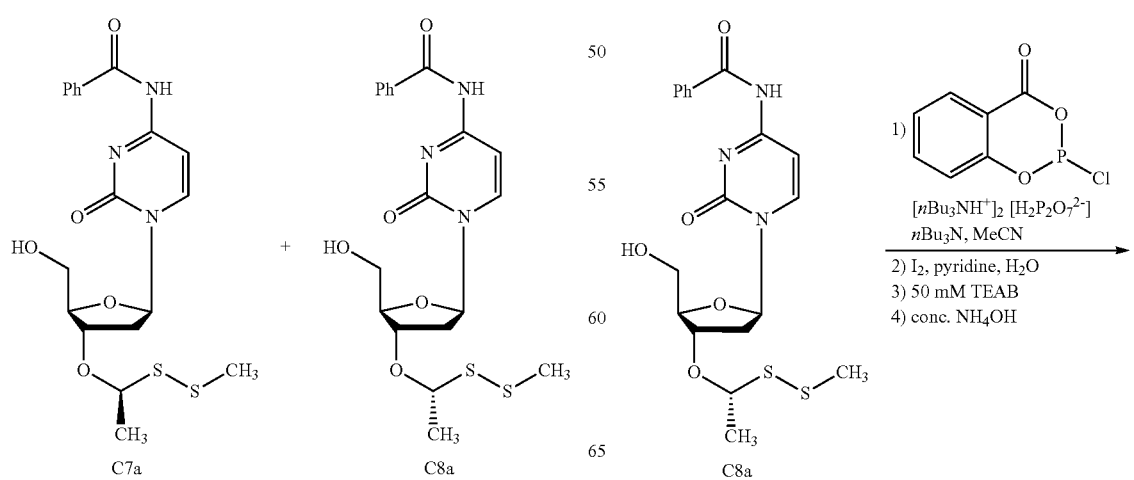

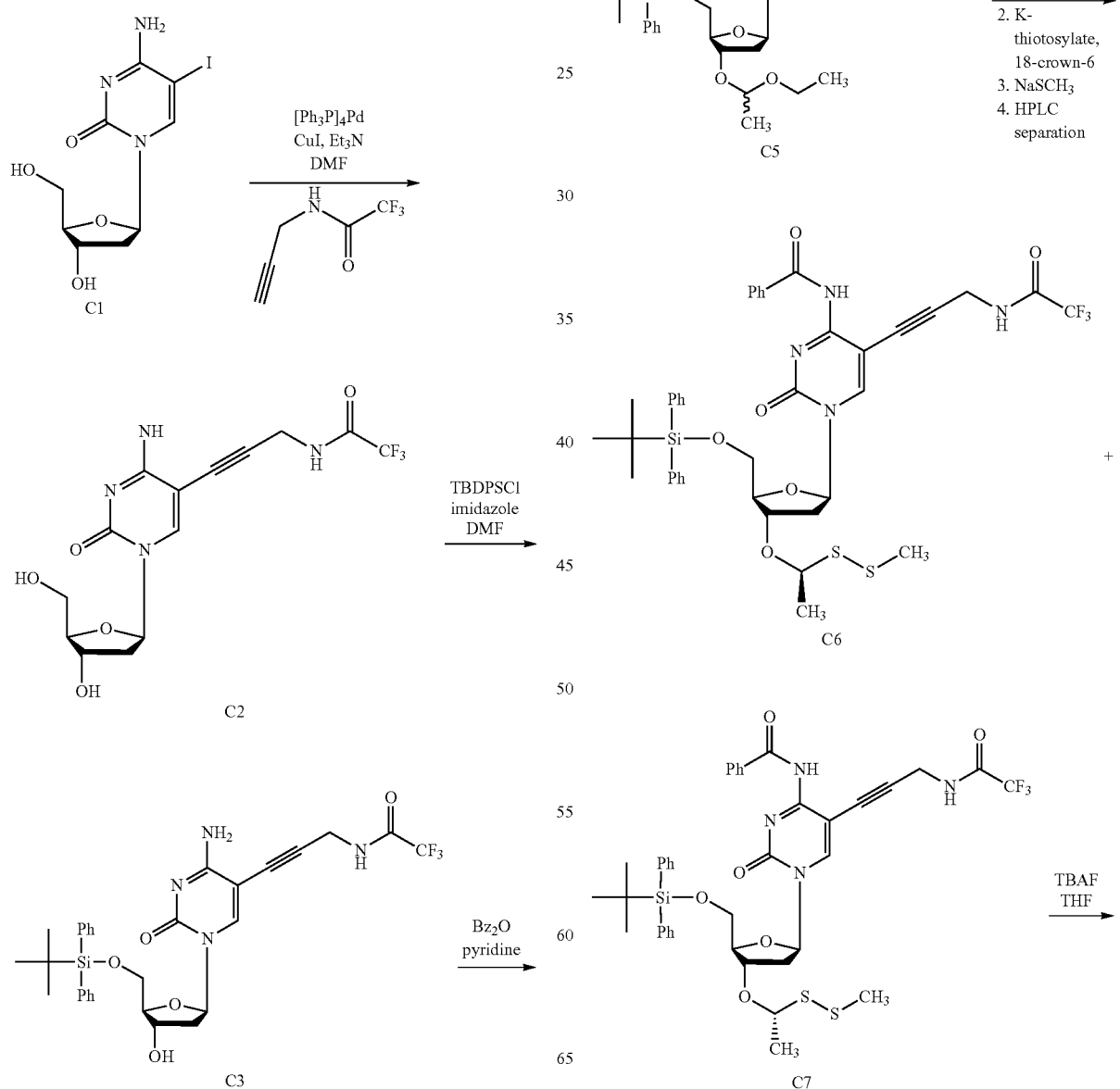

449
-continued
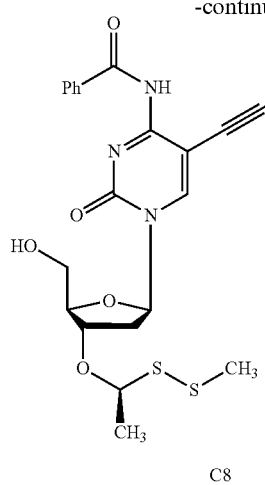
450
-continued
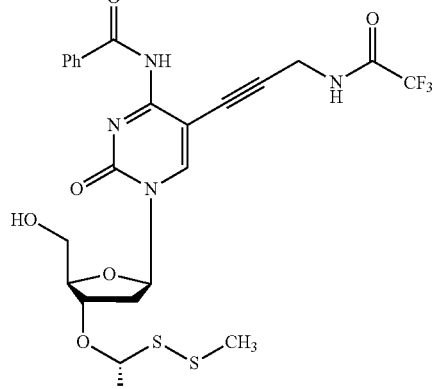
Scheme 9. Part 2 of 3 MeSS_CHCH3_dCTP_thio-trigger containing linker scheme
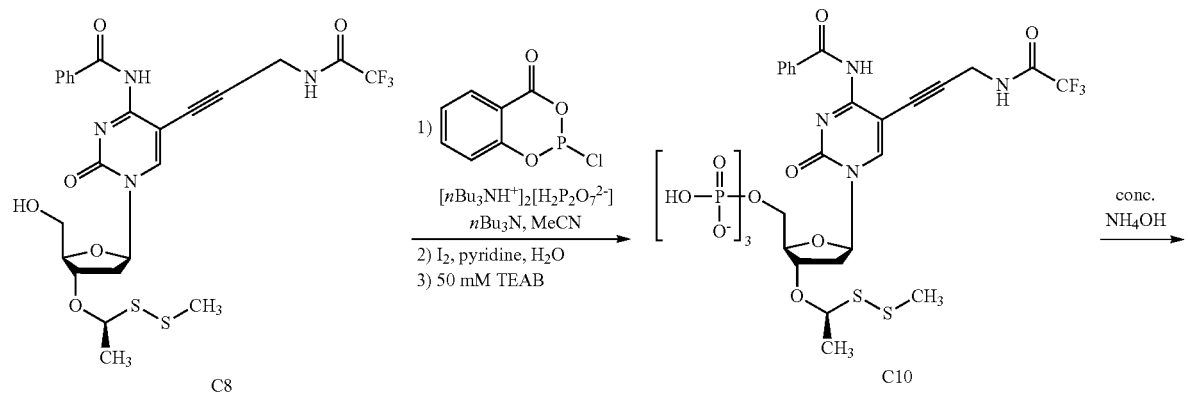
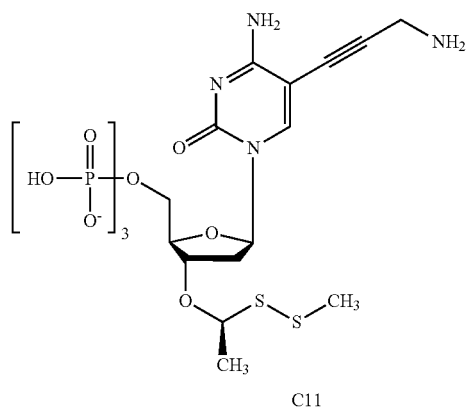
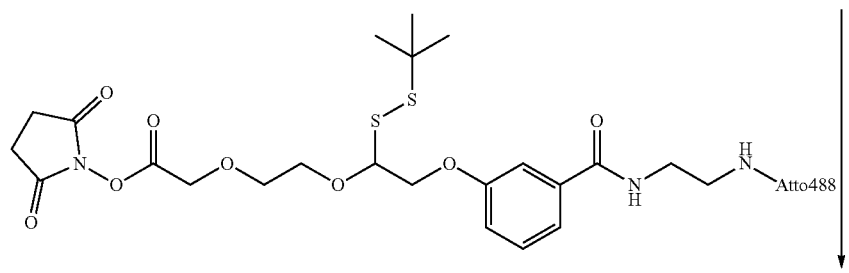

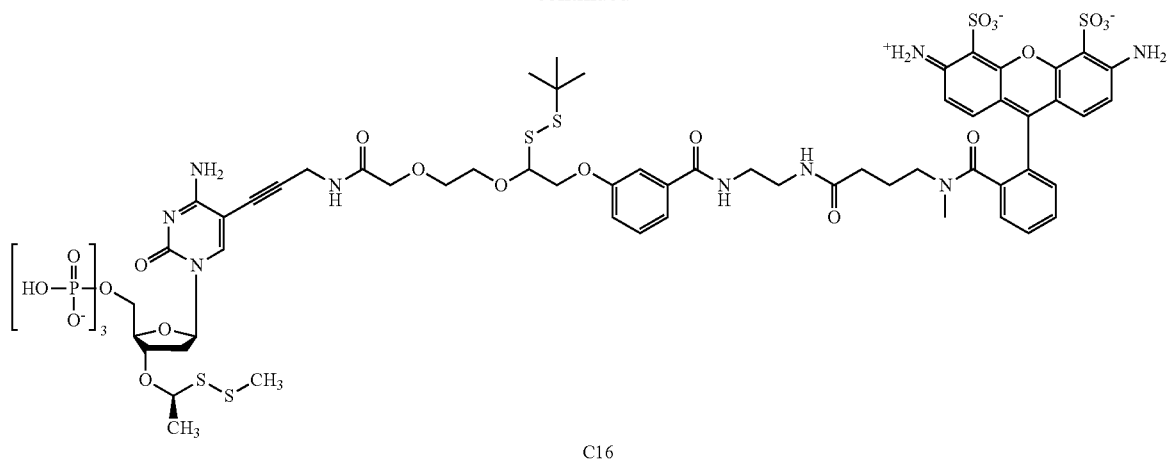
C16
Scheme 10. Part 3 of 3 MeSS_CHCH3_dCTP_thio-trigger containing linker scheme
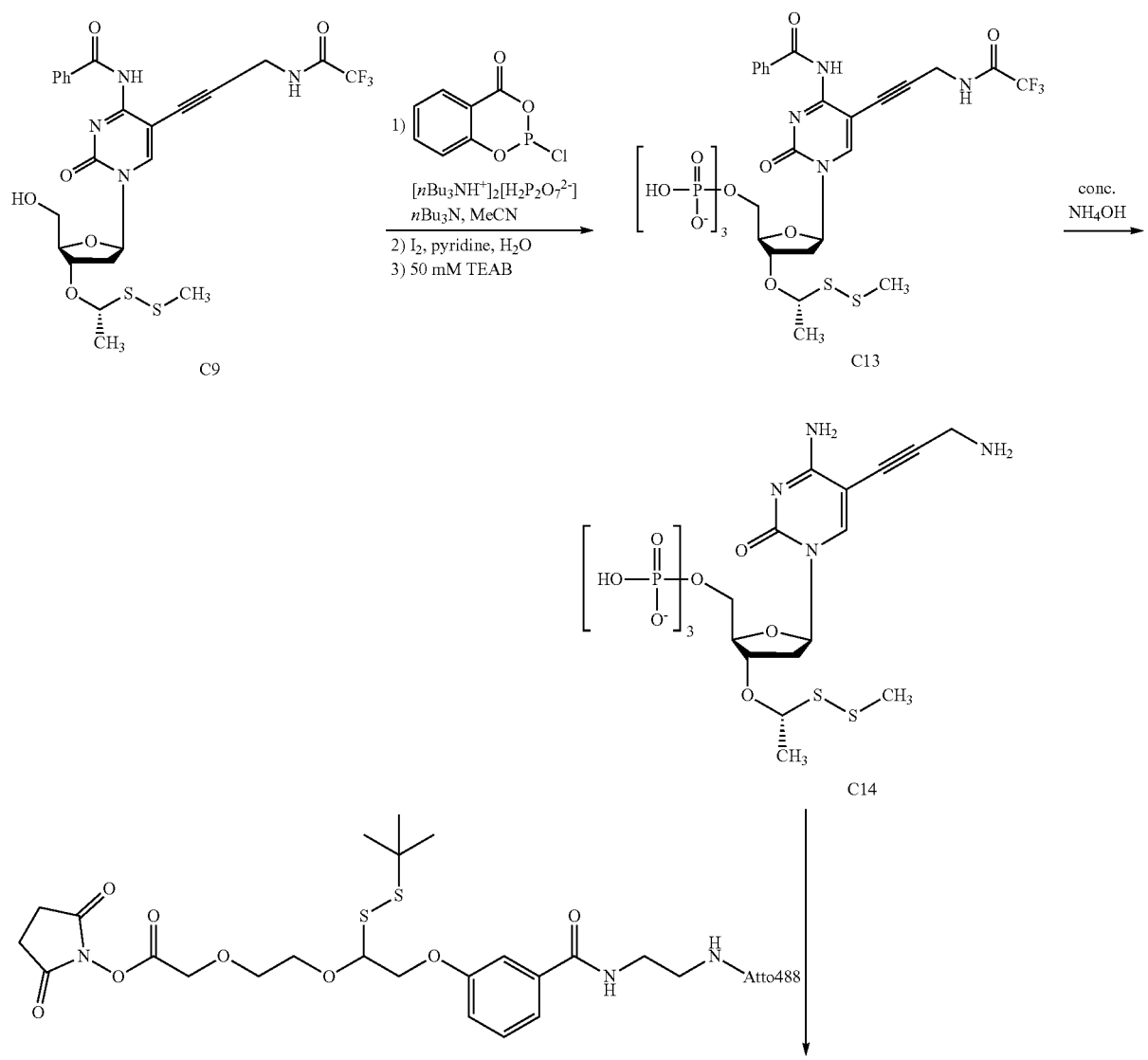

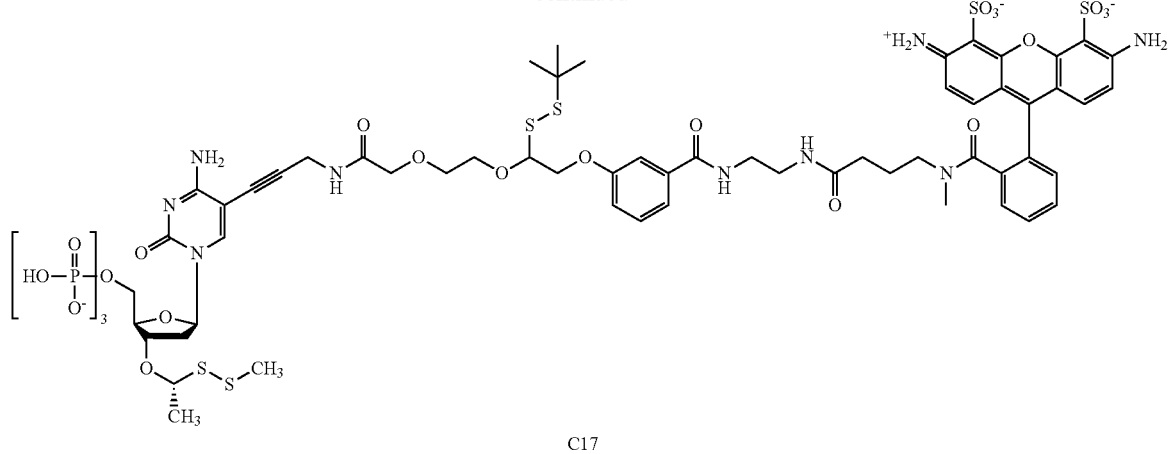
C17
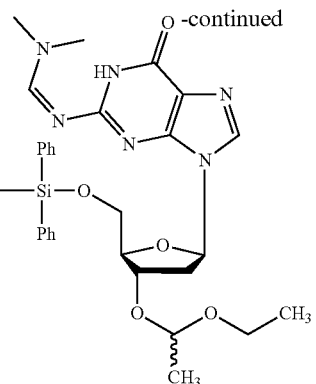
1. TMSOTf collidine
2. K-thiotosylate 18-crown-6
3. NaSCH₃
4. HPLC separation
Scheme 11. Part 1 of 2 MeSS_CHCH3_dGTP scheme
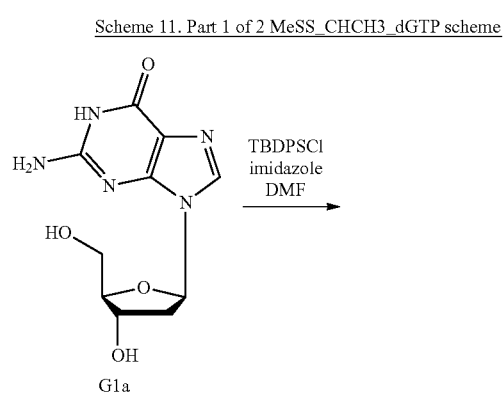
G1a
TBDPSCl
imidazole
DMF
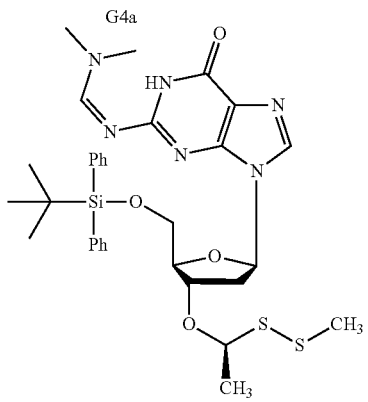
G4a
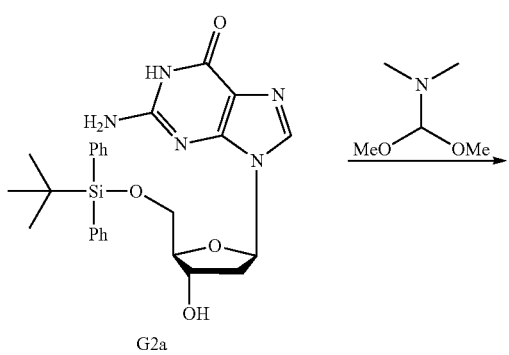
G2a
MeO—N(CH₃)₂—OMe
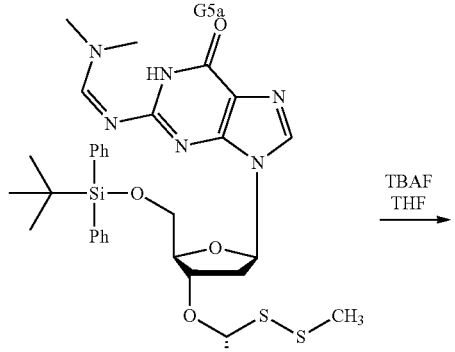
G5a
TBAF
THF
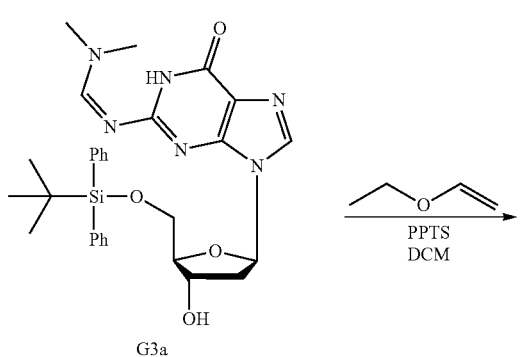
G3a
ethyl vinyl ether
PPTS
DCM
G6a 455
-continued
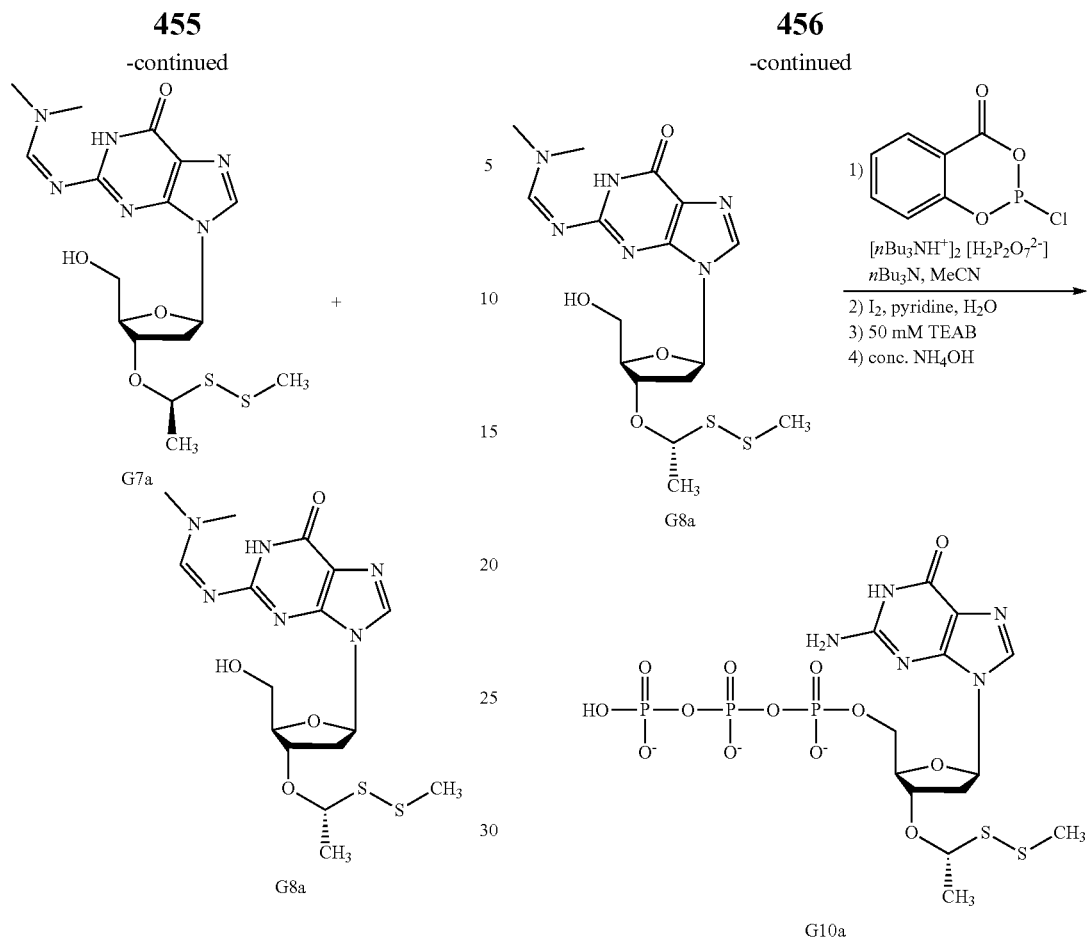
Scheme 12. Part 2 of 2 MeSS_CHCH3_dGTP scheme
456
-continued
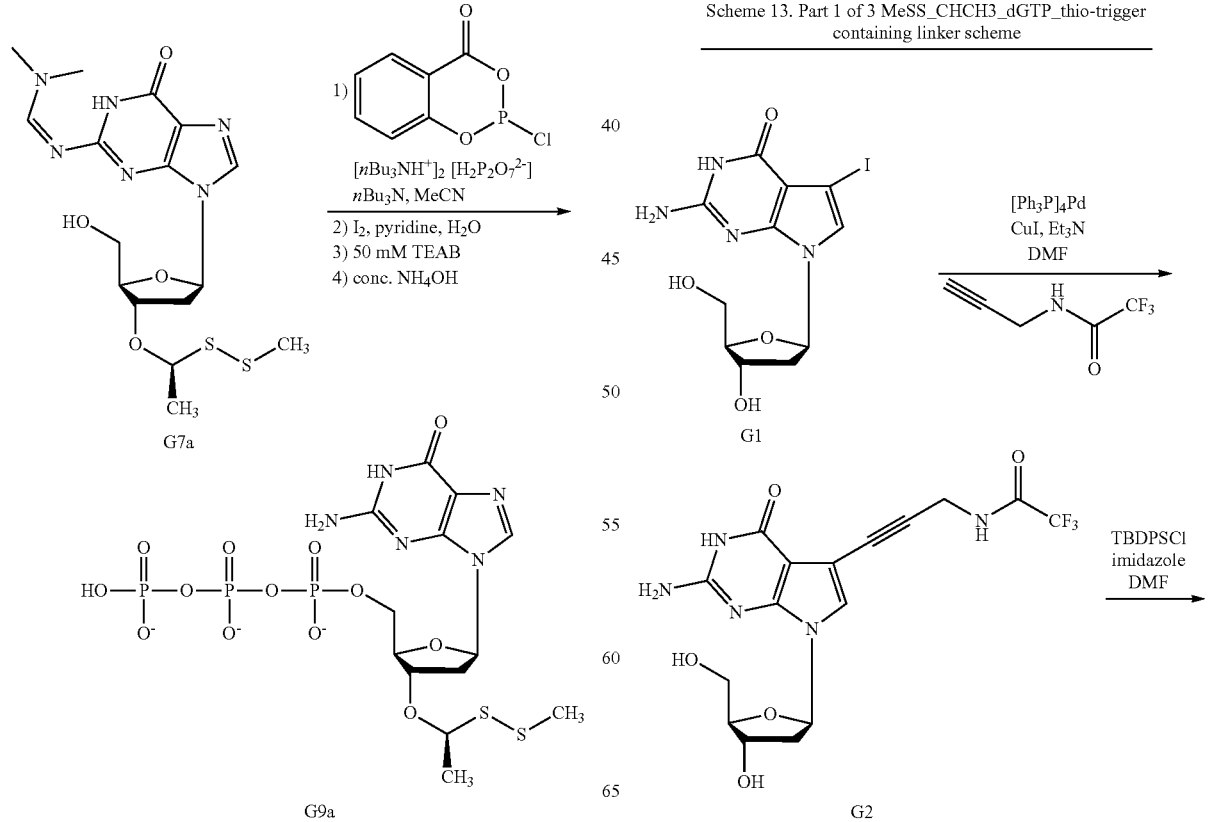
Scheme 13. Part 1 of 3 MeSS_CHCH3_dGTP_thio-trigger containing linker scheme

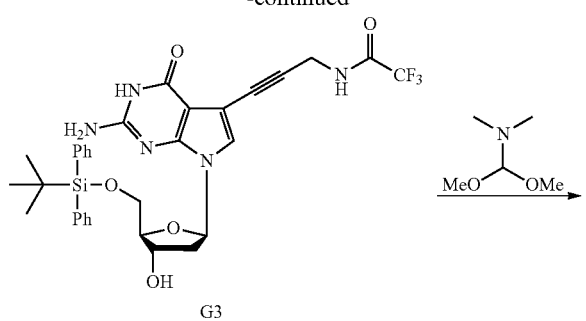
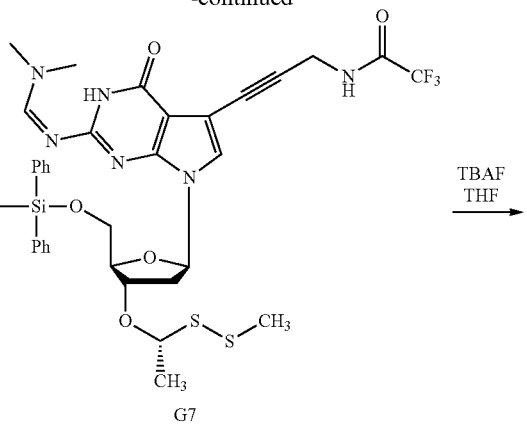
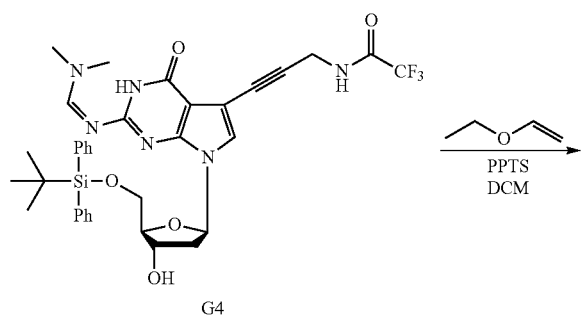
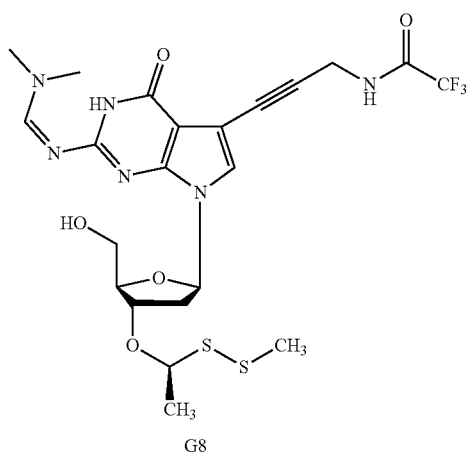
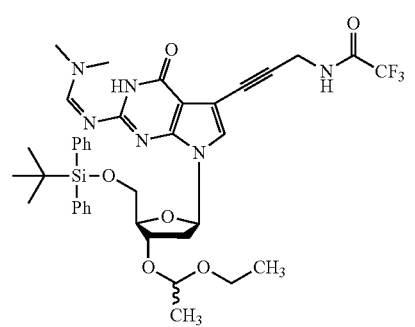
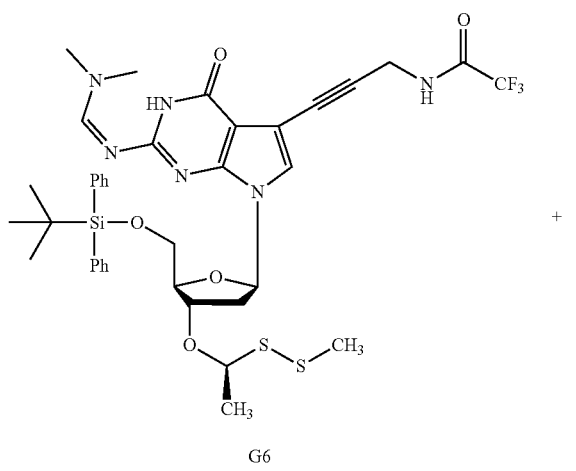
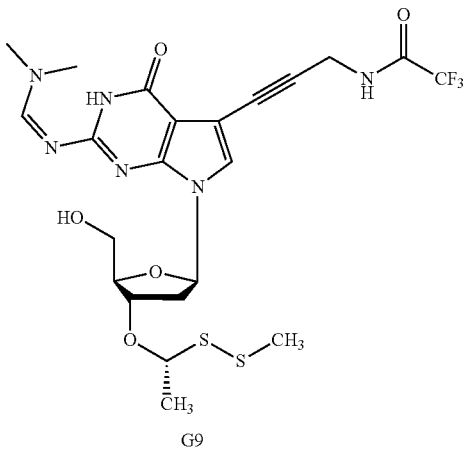

Scheme 14. Part 2 of 3 MeSS_CHCH3_dGTP_thio-trigger containing linker scheme
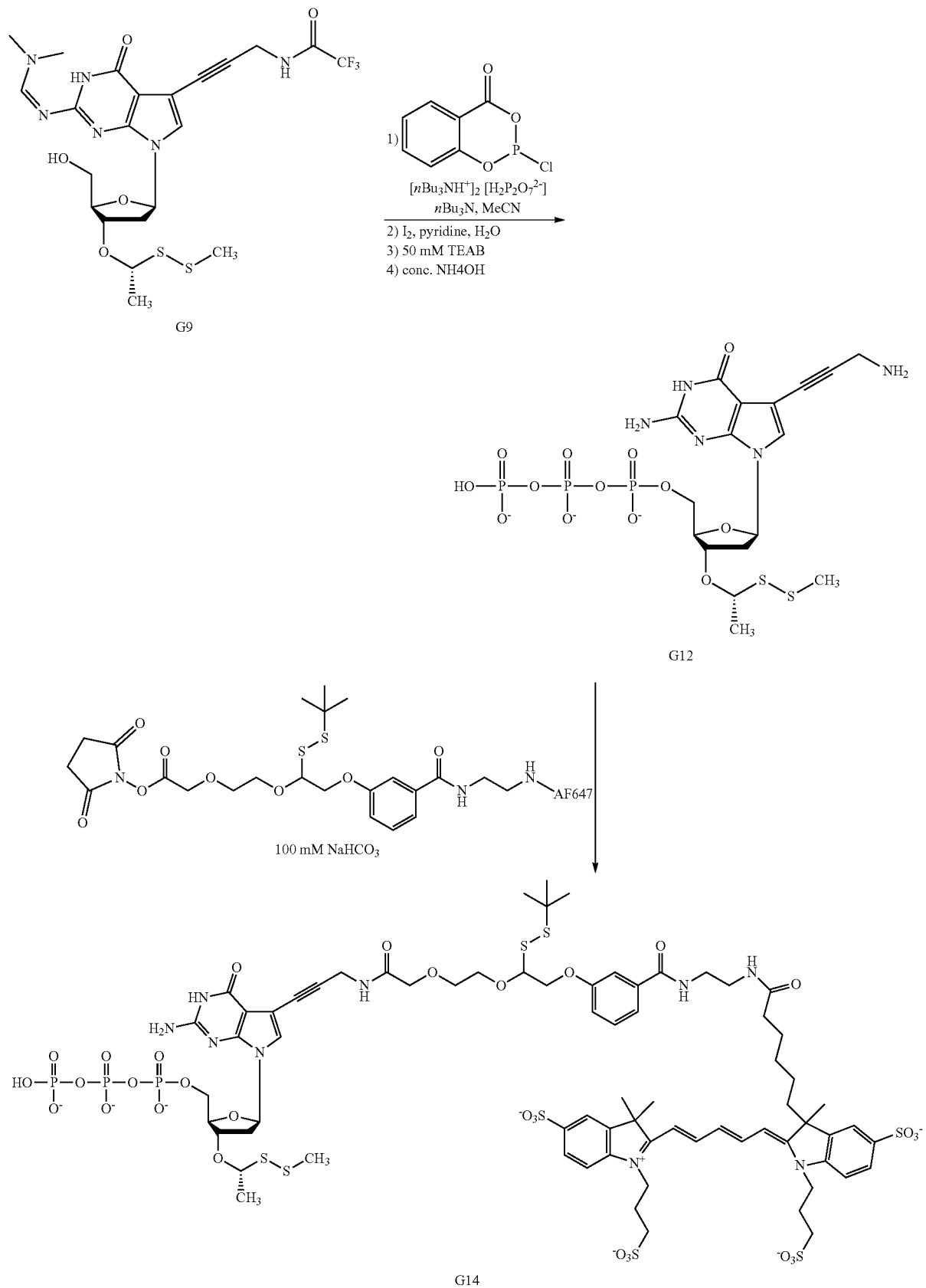

Scheme 15. Part 3 of 3 MeSS_CHCH3_dGTP_thio-trigger containing linker scheme
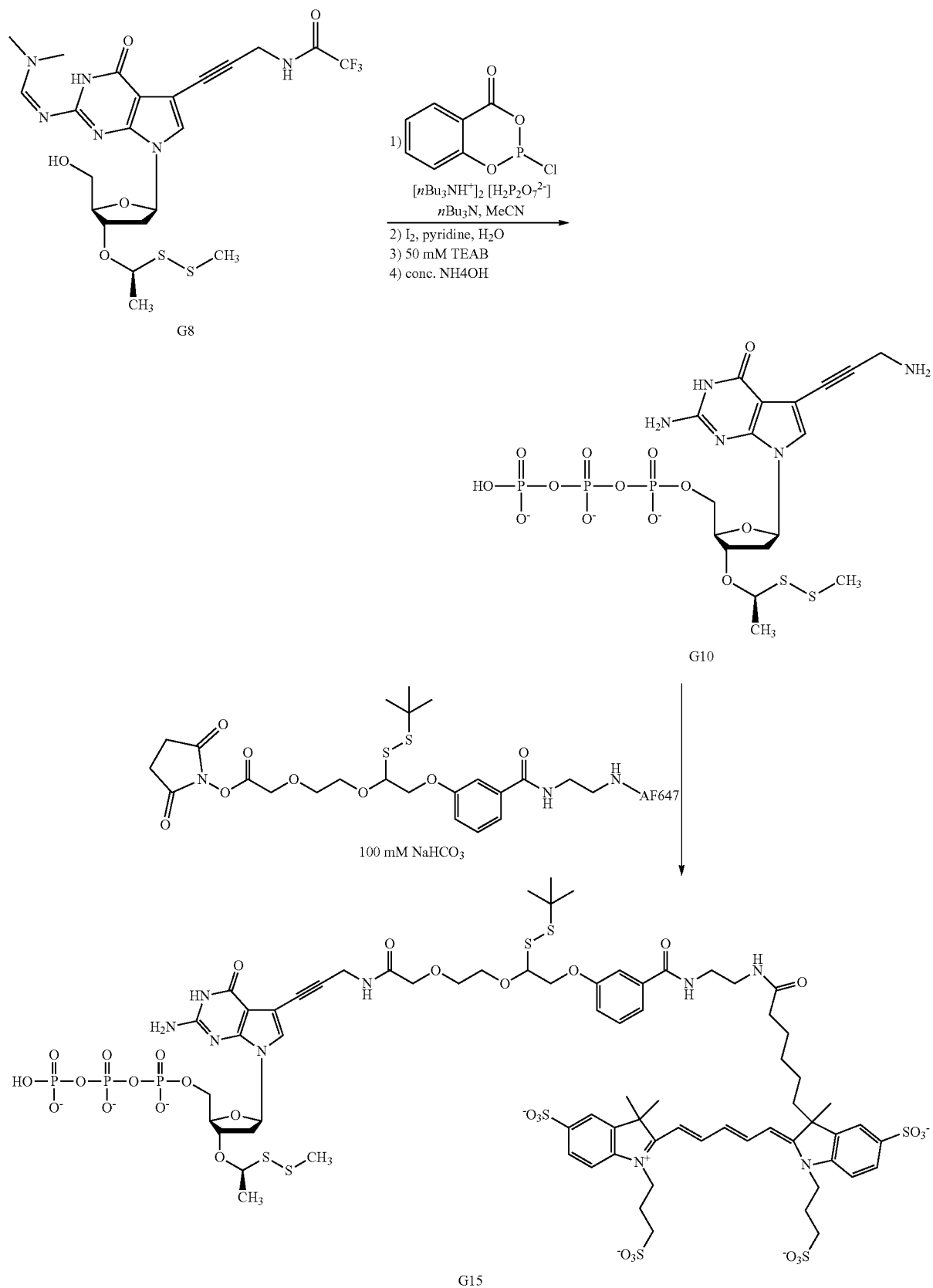

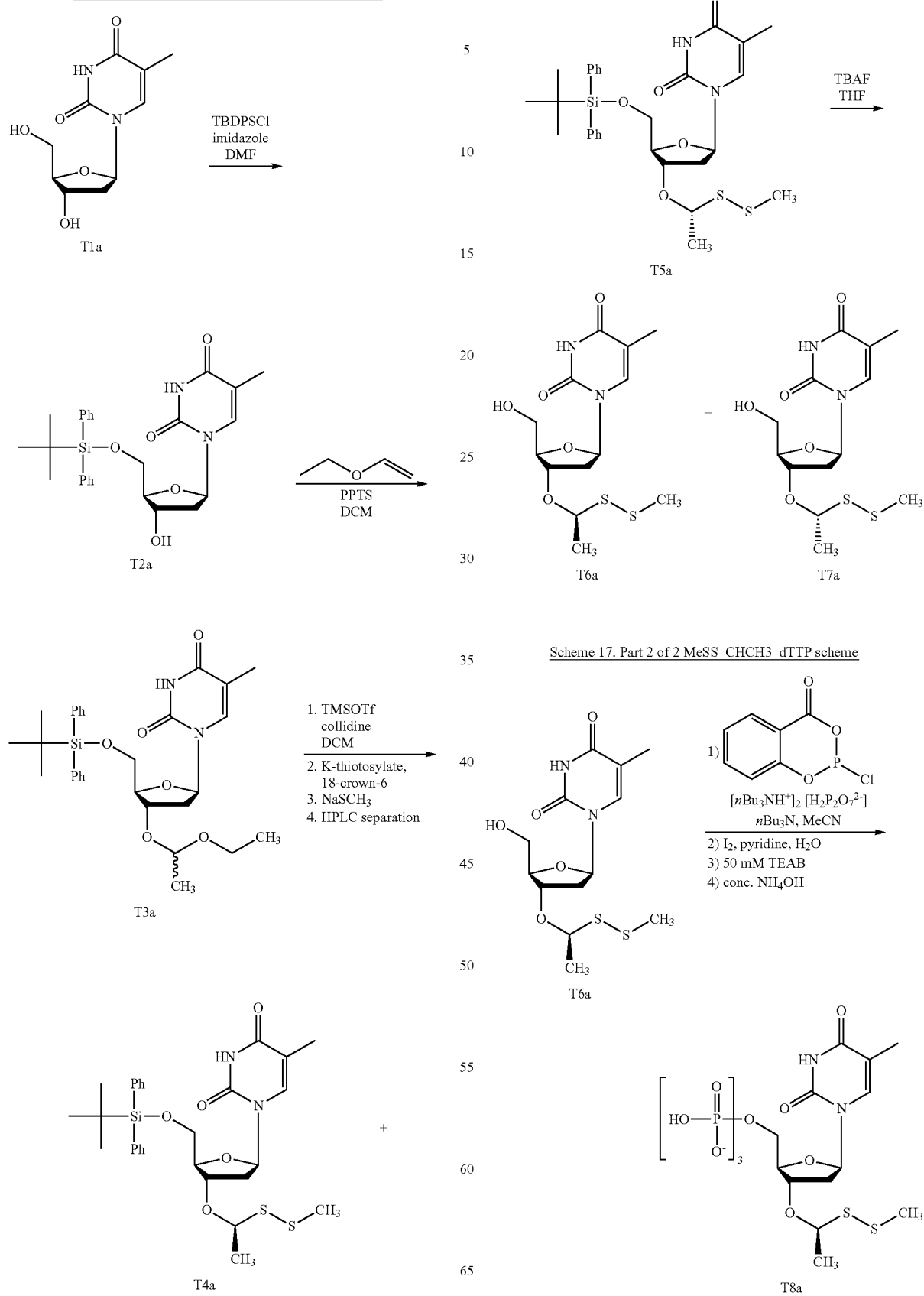

465
-continued
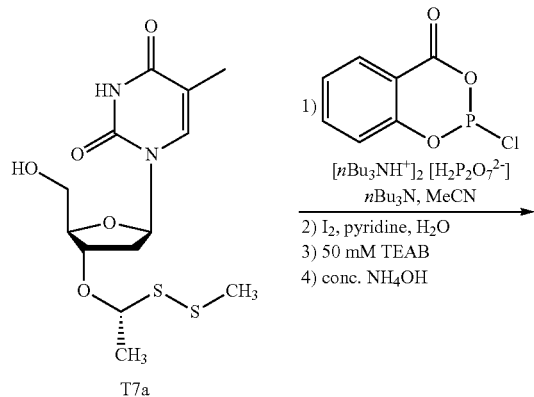
T7a
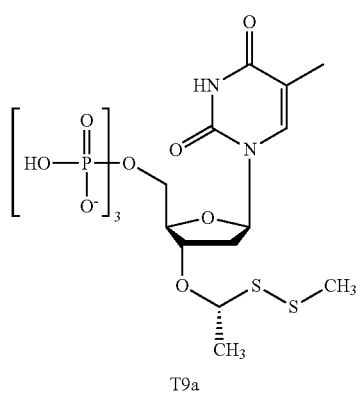
T9a
Scheme 18. Part 1 of 3 MeSS_CHCH3_dTTP_thio-trigger containing linker scheme
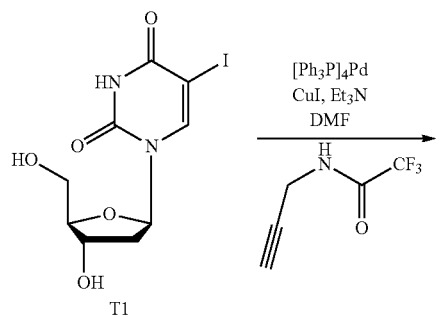
T1
466
-continued
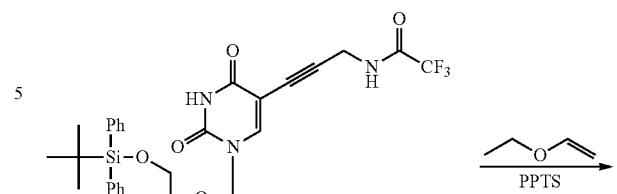
T3
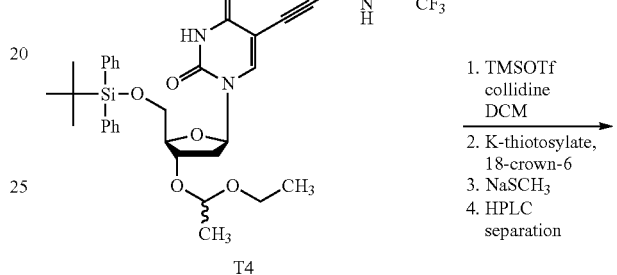
T4
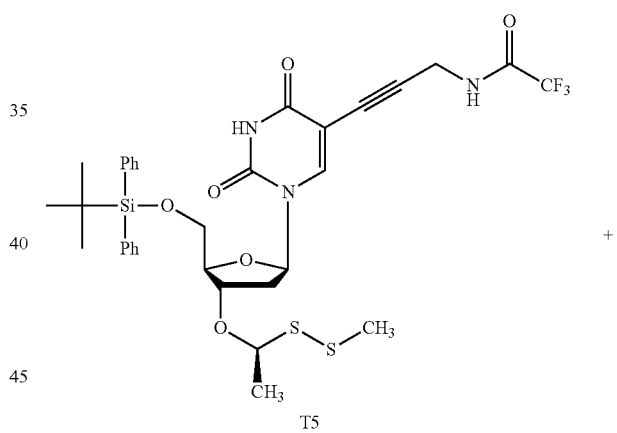
T5
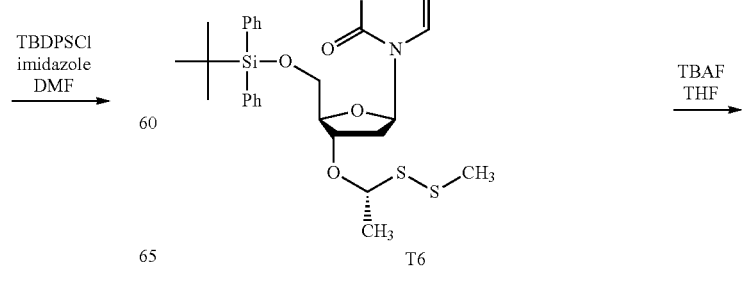
T6

467
-continued
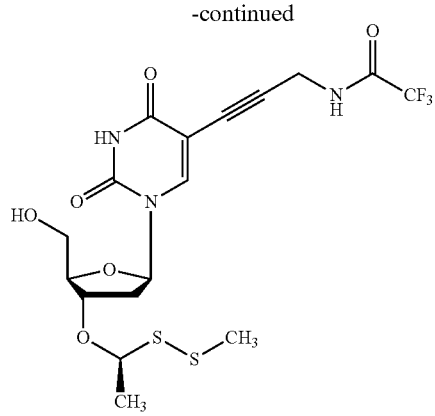
T7
+
468
-continued
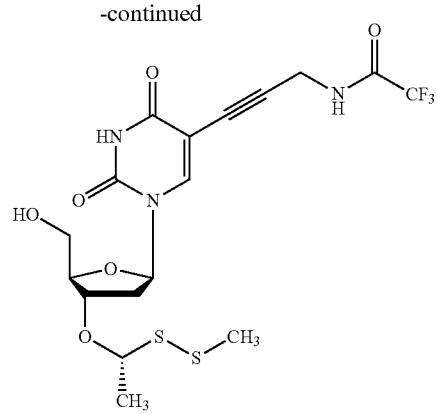
T8
Scheme 19. Part 2 of 3 MeSS_CHCH3_dTTP_thio-trigger containing linker scheme
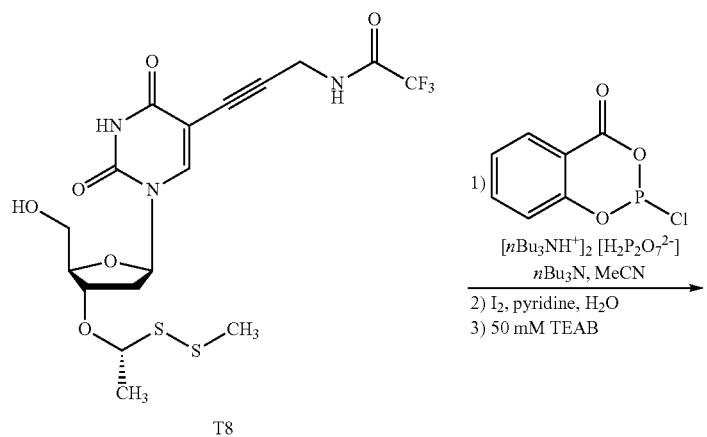
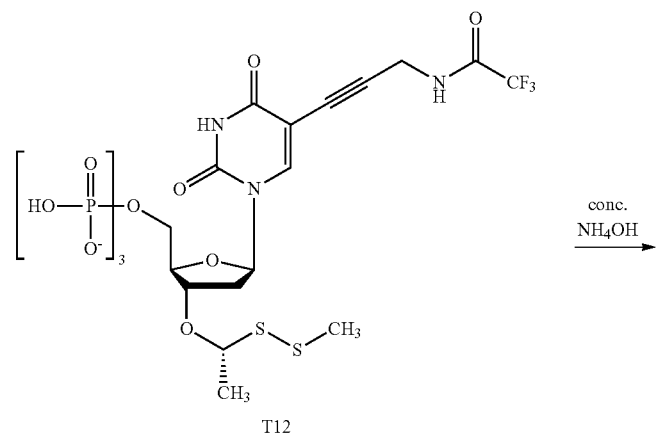
T12

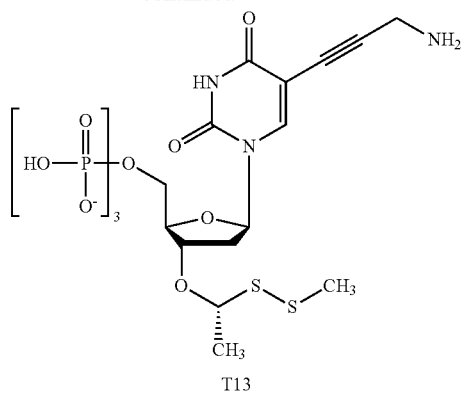
T13
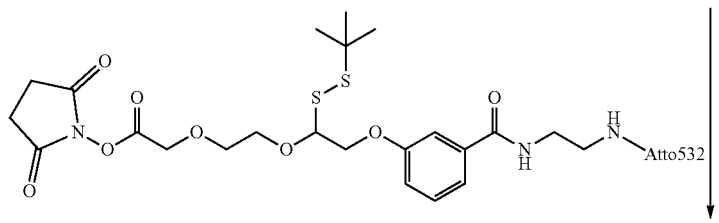
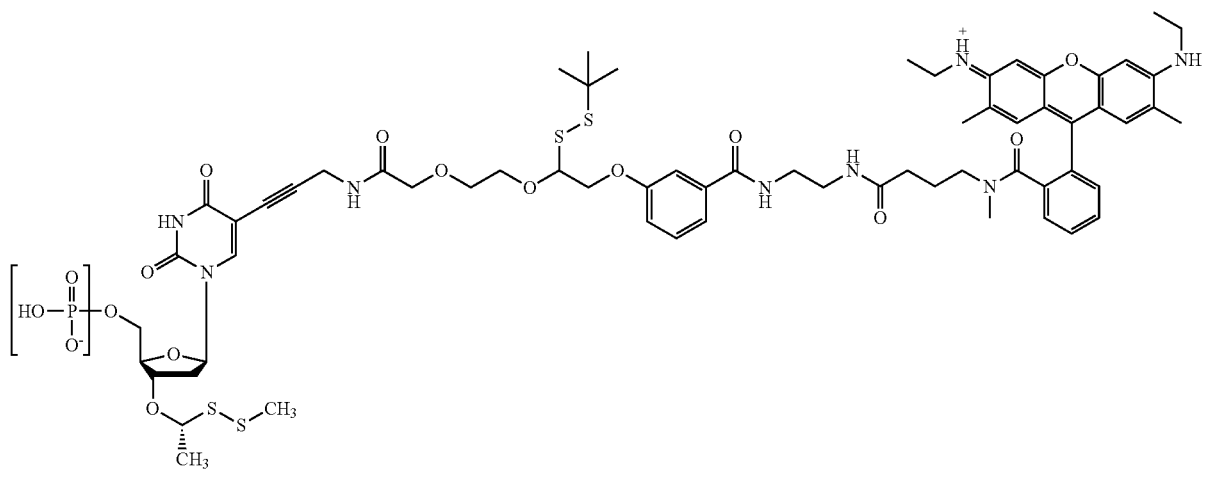
T15
Scheme 20. Part 3 of 3 MeSS_CHCH3_dTTP_thio-trigger containing linker scheme
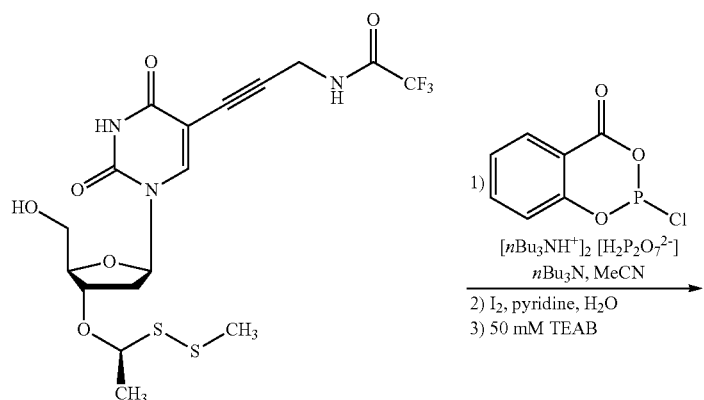
T7

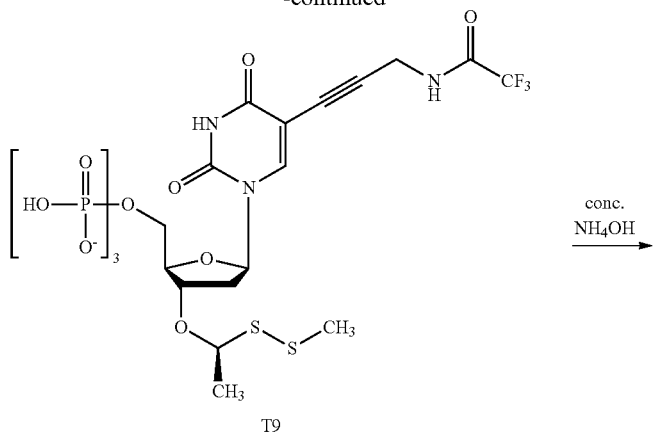
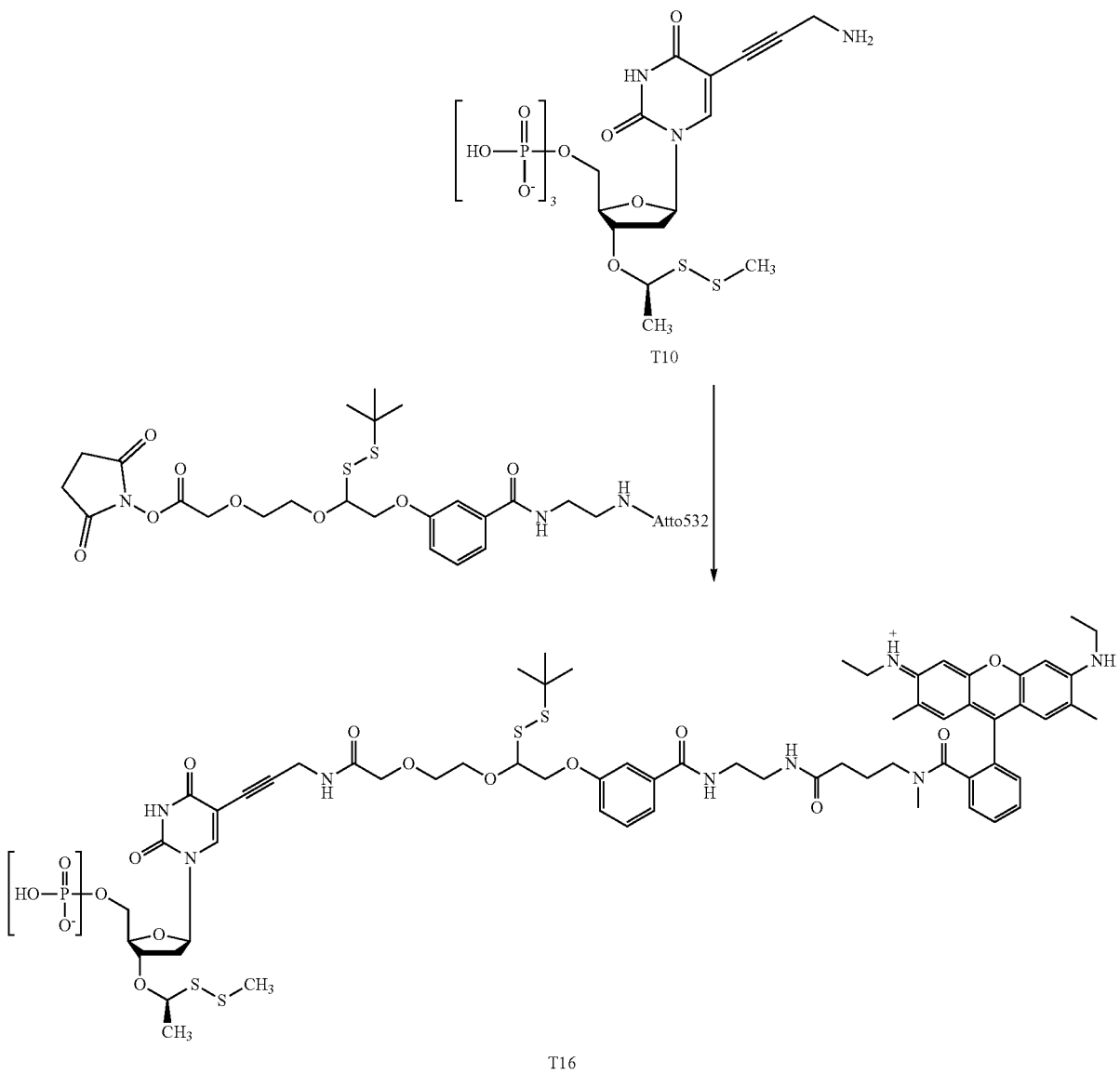
Preparation of T3a. T2a (1.0 g, 2.08 mmol) was suspended in dichloromethane (4 mL) and ethyl vinyl ether (2 mL). Pyridinium p-toluenesulfonate (26 mg, 0.1 mmol) was added and the reaction mixture was stirred at ambient temperature. After 1 hour the reaction mixture was clear, and the solvent was evaporated. The residue was dissolved in ether (25 mL) and washed with 0.1 M NaHCO₃ (2×25 mL) followed by brine (25 mL) and dried over magnesium sulfate. The crude product was purified by chromatography on silica gel eluting with dichloromethane/methanol (98:2) to afford T3a as a white foam (0.92 g, 1.66 mmol, 80%). LCMS observed m/z 552 calculated m/z 552. $^1$H NMR (500 MHz, CDCl₃) δ 9.80 (q, J=3.0 Hz, 1H), 7.99 (br s, 1H), 7.67-7.64 (m, 4H), 7.48-7.39 (m, 7H), 6.37 (dd, J=8.0, 5.5 Hz, 1H), 4.58-4.57 (m, 1H), 4.05-3.96 (m, 2H), 3.88-3.85 (m, 1H), 2.40-2.36 (m, 1H), 2.24-2.17 (m, 1H), 2.21 (d, J=3.0 Hz, 3H), 1.65 (d, J=1.0 Hz, 3H), 1.21 (d, J=6.5 Hz, 6H), 1.09 (s, 9H).

Preparation of T4a and T5a. T3a (542 mg, 0.982 mmol) was dissolved in anhydrous dichloromethane (4 mL) and cooled in an ice bath. Collidine (583 μL, 4.42 mmol) was added followed by dropwise addition of trimethylsilyl triflate (533 μL, 2.95 mmol). After stirring 30 min, 18-crown-6 (528 mg, 2 mmol) was added followed by potassium p-toluenethiosulfonate (452 mg, 2 mmol). The reaction mixture was warmed to room temperature and stirred for 30 min. Sodium thiomethoxide (210 mg, 3 mmol) was added and the reaction mixture was stirred at room temperature for 1 hour. The reaction mixture was added directly to a silica gel column and eluted with dichloromethane/methanol (97:3). The product was further purified by reverse phase HPLC eluting with acetonitrile/water 60:40 to 98:2 over 40 min. The fraction eluting between 23 and 27 minutes contained a mixture of T4a and T5a (209 mg, 36%). LCMS observed m/z 586 calculated m/z 586.

Preparation of T6a and T7a. A mixture of T4a and T5a (209 mg, 0.357 mmol) was dissolved in anhydrous tetrahydrofuran (2 mL). Tetrabutylammonium fluoride (0.536 mL, 1 M in THF) was added and the reaction mixture was left to sit for 1 hour at room temperature. The tetrahydrofuran was evaporated, and the crude product was triturated with ethyl ether (3×10 mL) and then purified by reverse phase HPLC eluting with acetonitrile/water (20:80 to 30:70 over 40 min). The fraction eluting between 22 and 26 minutes contained a mixture of T6a and T7a (81 mg, 0.233 mmol, 65%). LCMS observed m/z 348 calculated m/z 348. $^1$H NMR (500 MHz, CDCl₃) δ 9.28 (br s, 2H), 7.45 (d, J=1.5 Hz, 1H), 7.36 (d, J=1.0 Hz, 1H), 6.16-6.13 (m, 2H), 4.73 (q, J=6.0 Hz, 1H), 4.69 (q, J=6.0 Hz, 1H), 4.10-4.09 (m, 1H), 4.06-4.04 (m, 1H), 3.94-3.90 (m, 2H), 3.83-3.75 (m, 2H), 3.03 (br s, 1H), 2.85 (br s, 1H), 2.429 (s, 1H), 2.425 (s, 1H), 2.41-2.38 (m, 4H), 1.89 (s, 3H), 1.88 (s, 3H), 1.62 (d, J=6.0 Hz, 3H), 1.61 (d, J=6.0 Hz, 3H). $^{13}$C NMR (125 MHz, CDCl3) δ 164.1, 150.7, 137.1, 136.9, 111.3, 87.2, 86.7, 86.2, 86.0, 85.5, 85.0, 77.4, 76.9, 62.9, 62.4, 38.3, 37.2, 24.7, 24.6, 22.9, 22.8, 12.7.

Preparation of T8a and T9a. A solution of 2-chloro-4-H-1,3,2-benzodioxaphosphorin-4-one (44 mg, 0.216 mmol) in anhydrous acetonitrile (0.12 mL) was added dropwise to a solution of tributylammonium pyrophosphate (158 mg, 0.287 mmol) in anhydrous tributylamine (137 μL, 0.575 mmol) and anhydrous acetonitrile (0.3 mL). After stirring for 20 min at room temperature the solution was transferred to a solution of T6a and T7a (25 mg, 72 μmol) in anhydrous acetonitrile (0.2 mL). The reaction mixture was stirred for 30 minutes and then iodine solution (1 mL, 50 mM in 9:1 pyridine/water) was added. After 30 minutes water (1 mL) was added and the reaction mixture was stirred for 1 hour. The reaction mixture was concentrated to near dryness and the residue was triturated with ether (3×5 mL). The crude product was purified by reverse phase HPLC eluting with acetonitrile/50 mM TEAB (2:98 to 30:70 over 40 min). The fraction eluting at 22 minutes contained T8a (5 μmol, 7%) and the fraction eluting at 24 minutes contained T9a (4.4 μmol, 6%). LCMS observed m/z 587 calculated m/z 587.

Experimental Procedures for Thio-Trigger Containing Linker

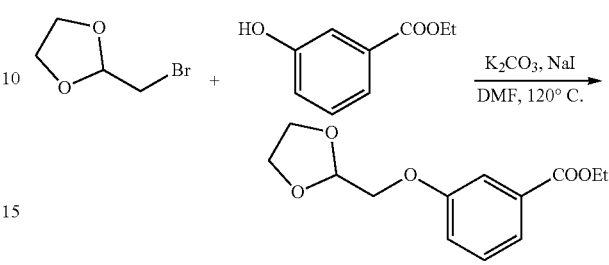

Sodium iodide (1.5 g, 10.0 mmol) and potassium carbonate (6.9 g, 50 mmol) were added to a stirred solution of ethyl 3-hydroxybenzoate (4.15 g, 25 mmol), 2-bromomethyl-1,3-dioxolane (10.4 mL, 100 mmol) in DMF (15 mL) and was heated to 120° C. The progress of the reaction was monitored by HPLC (100 mM TEAA/MeCN, 60% to 100% over 15 min, hold for 5 min at 100%). The reaction mixture was cooled to room temperature when the amount of ethyl-3-hydroxybenzoate was less than 5%. The suspension was filtered and washed with ether (2×50 mL). The combined filtrates were washed with water (3×50 mL) and brine (50 mL), dried over sodium sulfate and concentrated in vacuo. The crude product was purified by silica gel chromatography (hexanes/ethyl acetate, 80:20) to obtain the desired compound, ethyl 3-((1,3-dioxolan-2-yl)methoxy)benzoate as colorless clear liquid (5.57 g, 88%). $^1$H NMR (500 MHz, DMSO) δ 7.59-7.52 (m, 1H), 7.48-7.39 (m, 2H), 7.25 (ddd, J=8.3, 2.7, 1.0 Hz, 1H), 5.22 (t, J=3.9 Hz, 1H), 4.35-4.25 (m, 2H), 4.07 (d, J=3.9 Hz, 2H), 4.01-3.91 (m, 2H), 3.86 (ddd, J=15.2, 9.1, 5.6 Hz, 2H), 1.31 (q, J=7.2 Hz, 3H); MS: calc'd for [$C_{13}H_{16}O_5$+Na]: 275.1, found 275.3.

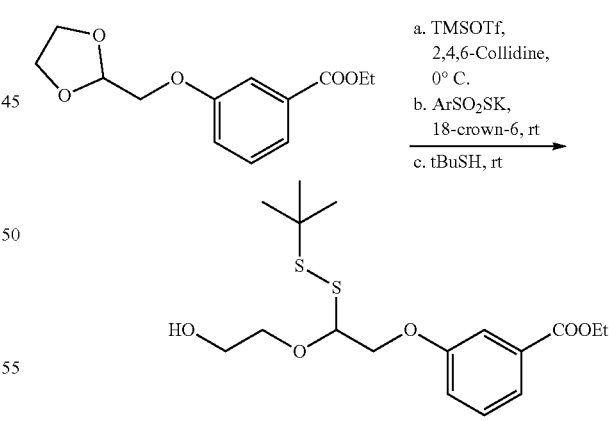

2,4,6-Collidine (2.38 mmol, 3.0 equiv.) was added to a stirred solution of ethyl 3-((1,3-dioxolan-2-yl)methoxy)benzoate (0.2 g, 0.79 mmol) in DCM (0.1 M) at 0° C. under Ar atmosphere followed by the addition of trimethylsilyl triflate (1.59 mmol, 2.0 equiv.). The mixture was stirred at the same temperature until the disappearance of an acetal on TLC and formation of highly polar compound was observed, after which potassium thiotosylate (1.59 mmol, 2.0 equiv.) and 18-crown-6 (1.59 mmol, 2.0 equiv.) were added to the reaction mixture. Disappearance of the polar component was confirmed by TLC, after which tert-butyl thiol (1.59 mmol, 2.0 equiv.) was added. The reaction mixture was loaded on to silica gel column upon completion of the reaction and the desired product, ethyl 3-(2-(tert-butyldisulfaneyl)-2-(2-hydroxyethoxy)ethoxy)benzoate was eluted with 20% ethyl acetate and hexanes mixture as a colorless oil (235.6 mg, 63% yield). $^1$H NMR (500 MHz, DMSO) δ 7.57 (dd, J=6.6, 1.2 Hz, 1H), 7.51-7.42 (m, 2H), 7.27 (ddd, J=8.2, 2.7, 0.8 Hz, 1H), 4.92 (t, J=5.4 Hz, 1H), 4.69 (t, J=5.4 Hz, 1H), 4.35-4.25 (m, 4H), 3.89-3.80 (m, 1H), 3.61-3.49 (m, 3H), 1.37-1.28 (m, 12H). MS: calc'd for [$C_{17}H_{26}O_5S_2$+Na]: 397.1, found 397.3.

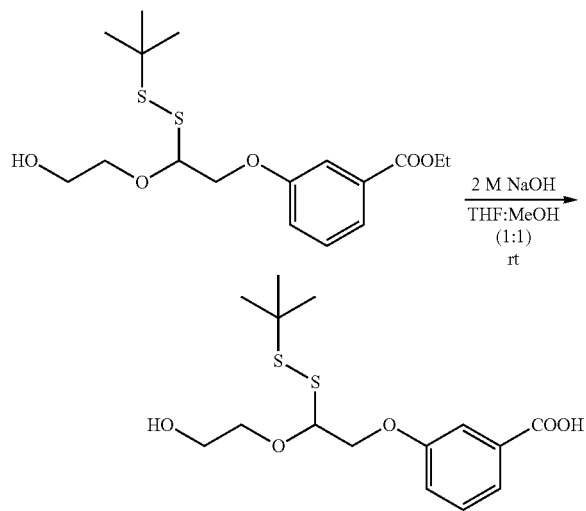

Sodium hydroxide (0.7 mL, 2 M) was added to a stirred solution of ethyl 3-(2-(tert-butyldisulfaneyl)-2-(2-hydroxyethoxy)ethoxy)benzoate (131 mg, 0.35 mmol) in 1:1 methanol (0.33 mL) and THF (0.33 mL) mixture. The solution was initially heterogeneous but became homogenous after 1 hour of stirring. The reaction progress was monitored by HPLC (100 mM TEAA/MeCN, 60% to 100% over 15 min, hold for 5 min at 100%). Upon completion, the reaction mixture was concentrated and HCl (1 M, 1.382 mL) was added dropwise with stirring until the milky swirl persisted. The aqueous suspension was extracted with DCM (3×15 mL) and the extracts were dried over sodium sulfate. The crude product was purified using silica gel chromatography (50% ethyl acetate:hexanes) and 3-(2-(tert-butyldisulfaneyl)-2-(2-hydroxyethoxy)ethoxy)benzoic acid was obtained as a colorless oil (87 mg, 72% yield). $^1$H NMR (500 MHz, DMSO) δ 13.00 (s, 1H), 7.58-7.52 (m, 1H), 7.47 (dt, J=11.9, 6.1 Hz, 1H), 7.42 (t, J=7.9 Hz, 1H), 7.21-7.19 (m, 1H), 4.92 (t, J=5.4 Hz, 1H), 4.69 (s, 1H), 4.34-4.24 (m, 2H), 3.88-3.82 (m, 1H), 3.61-3.50 (m, 3H), 1.35-1.26 (m, 9H). MS: calc'd for [$C_{15}H_{22}O_5S_2$+Na]: 369.1, found 369.2.

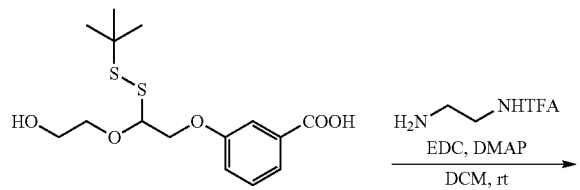

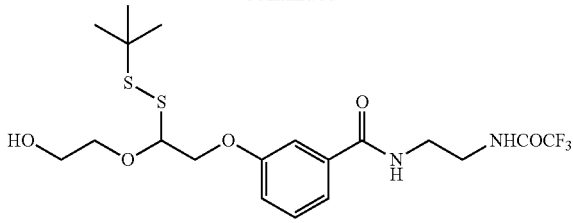

To a mixture of 3-(2-(tert-butyldisulfaneyl)-2-(2-hydroxyethoxy)ethoxy)benzoic acid (43 mg, 0.124 mmol), N-(2-aminoethyl)-2,2,2-trifluoroacetamide (28.6 mg, 0.148 mmol, 1.2 equiv.), 4-N,N-dimethylaminopyridine (4.5 mg, 0.037 mmol, 0.3 equiv.) in DCM (0.2 mL, 0.6 M) at 0° C., was added N-(3-dimethylaminopropyl)-N'-ethylcarbodiimide hydrochloride (33 mg, 0.174 mmol, 1.4 equiv.) in DCM dropwise. The reaction was stirred at room temperature until the disappearance of the starting material as monitored by HPLC (100 mM TEAA/MeCN, 60% to 100% over 15 min, hold for 5 min at 100%). The reaction mixture was diluted with water and extracted with ethyl acetate (3×15 mL) and dried over sodium sulfate. The crude was purified by silica gel chromatography (60% ethyl acetate:hexanes) and 3-(2-(tert-butyldisulfaneyl)-2-(2-hydroxyethoxy)ethoxy)-N-(2-(2,2,2-trifluoroacetamido)ethyl)benzamide was obtained as colorless liquid (38 mg, 63.3% yield). $^1$H NMR (500 MHz, DMSO) δ 9.49 (d, J=5.5 Hz, 1H), 8.59 (t, J=5.5 Hz, 1H), 7.40 (dq, J=22.8, 7.7 Hz, 3H), 7.12 (dd, J=8.0, 1.6 Hz, 1H), 4.92 (t, J=5.4 Hz, 1H), 4.70 (t, J=5.3 Hz, 1H), 4.35-4.19 (m, 2H), 3.87 (dt, J=9.6, 4.3 Hz, 1H), 3.62-3.50 (m, 3H), 3.43-3.33 (m, 4H), 1.31 (s, 9H). MS: calc'd for [$C_{19}H_{27}F_3N_2O_5S_2$+Na]: 507.1, found 507.2.

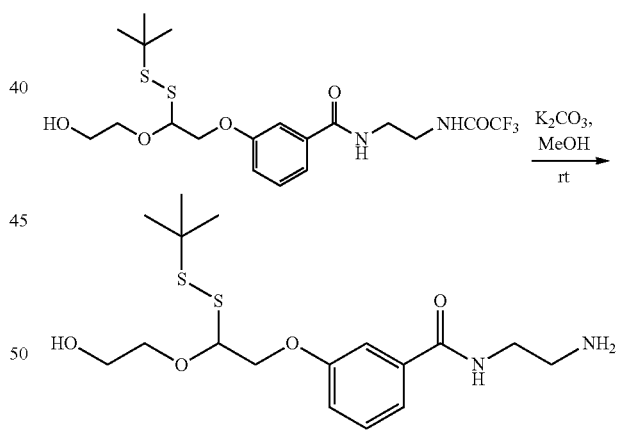

To a stirred solution of 3-(2-(tert-butyldisulfaneyl)-2-(2-hydroxyethoxy)ethoxy)-N-(2-(2,2,2-trifluoroacetamido)ethyl)benzamide (55 mg, 0.115 mmol) in methanol (0.5 mL), potassium carbonate (45.5 mg, 0.329 mmol, 2.9 equiv.) was added. The reaction progress was monitored by HPLC (100 mM TEAA/MeCN, 60% to 100% over 15 min, hold for 5 min at 100%) and upon completion, the reaction mixture was diluted with water and extracted with ethyl acetate (3×5 mL). The organic fractions were collected, dried over sodium sulfate and purified by HPLC to obtain N-(2-aminoethyl)-3-(2-(tert-butyldisulfaneyl)-2-(2-hydroxyethoxy)ethoxy)benzamide as colorless liquid. $^1$H NMR (500 MHz, DMSO) δ 8.43 (d, J=5.0 Hz, 1H), 7.45 (t, J=5.8 Hz, 2H), 7.37 (t, J=7.8 Hz, 1H), 7.11 (dd, J=7.8, 2.1 Hz, 1H), 4.92 (t, J=5.3 Hz, 1H), 4.71 (s, 1H), 4.28 (d, J=5.9 Hz, 2H), 3.87 (dt, J=9.4, 4.2 Hz, 1H), 3.63-3.50 (m, 3H), 3.32-3.22 (m, 4H), 2.71 (t, J=6.5 Hz, 2H), 1.31 (s, 9H). MS: calc'd for $[C_{17}H_{28}N_2O_4S_2+H]$: 389.2, found 389.4.

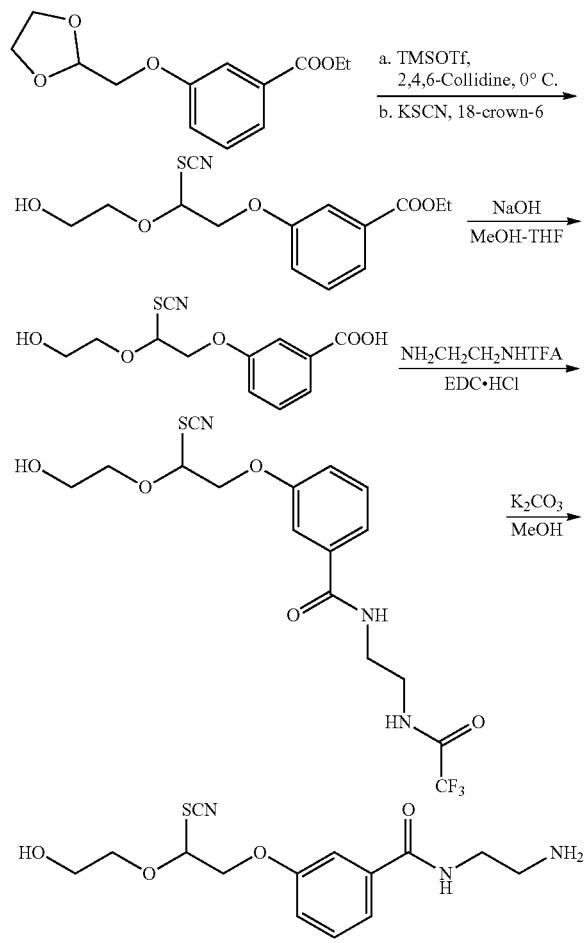

Scheme 21. Additional thio-trigger (SCN) containing linker scheme

Experimental Procedures for Thio-Trigger Containing Linker

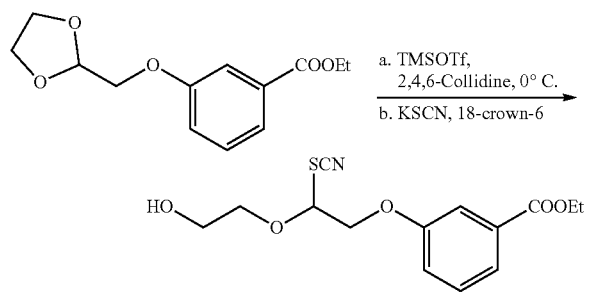

2,4,6-Collidine (0.59 mmol, 3.0 equiv.) was added to a stirred solution of ethyl 3-((1,3-dioxolan-2-yl)methoxy)benzoate (0.05 g, 0.79 mmol) in DCM (0.1 M) at 0° C. under Ar atmosphere followed by the addition of trimethylsilyl triflate (0.4 mmol, 2.0 equiv.). The mixture was stirred at the same temperature until the disappearance of an acetal on TLC and formation of highly polar compound was observed, after which a solution of potassium thiocyanate (0.99 mmol, 5.0 equiv.) and 18-crown-6 (0.99 mmol, 5.0 equiv.) in acetone (0.2 mL) was added to it. Disappearance of the polar component was confirmed by TLC. The product formation was confirmed by mass analysis, MS: calc'd for $[C_{14}H_{17}NO_5S—H]^-$: 311.0, found 310.0.

TABLE 1

Detectable moieties to be used in selected embodiments.

| Nucleoside/nucleotide abbreviation | Dye name | λmax (nm) |
|---|---|---|
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

Example 2. Thio-Trigger Containing Linkers

In the context of nucleic acid sequencing reactions it is desirable to increase the rate of nucleotide incorporation during sequencing by synthesis and eliminate any potential side reactions so that the efficiency of the sequencing method can be improved.

The compounds described herein utilize a covalent linker between the base moiety (e.g., a purine or pyrimidine base) of the nucleoside or nucleotide and the detectable label. Often in sequencing by synthesis (SBS) techniques, the detectable label is removed by breaking apart, or cleaving, the linker. The use of a cleavable linker ensures that the label can, if required, be removed after detection, avoiding any interfering signal with any labelled nucleotide incorporated subsequently. Suitable linkers can be adapted from standard chemical blocking groups, as disclosed in Greene & Wuts, Protective Groups in Organic Synthesis, John Wiley & Sons and in Guillier et al. (Chem. Rev. 100:2092-2157, 2000).

For example, a linker used in SBS methodologies is a disulfide linker (referred to herein as an SS linker) having the formula:

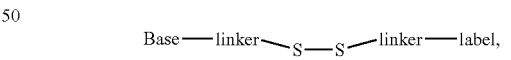

wherein the SS linker is linear (i.e., continuous) within the linker. Upon exposure to a reducing agent, the intermediate forms a reactive thiol capable of interacting with the polymerase or other reactive moieties and decreasing the efficiency. In contrast, compounds described herein include a thio-trigger containing linker, which forms non-reactive products and cleaves approximately 5× faster than the SS linker under similar conditions. Additionally, in embodiments, the thio-trigger containing linker and the polymerase-compatible cleavable moiety are cleaved simultaneously under the given reaction conditions (e.g., cleaved under the same reaction conditions but not necessarily at the exact same time or rate). In embodiments, modifying the reaction conditions (e.g., elevating the temperature to 65° C., increasing the pH) results in faster cleavage.

Scheme 22. Thio-trigger containing linker reaction

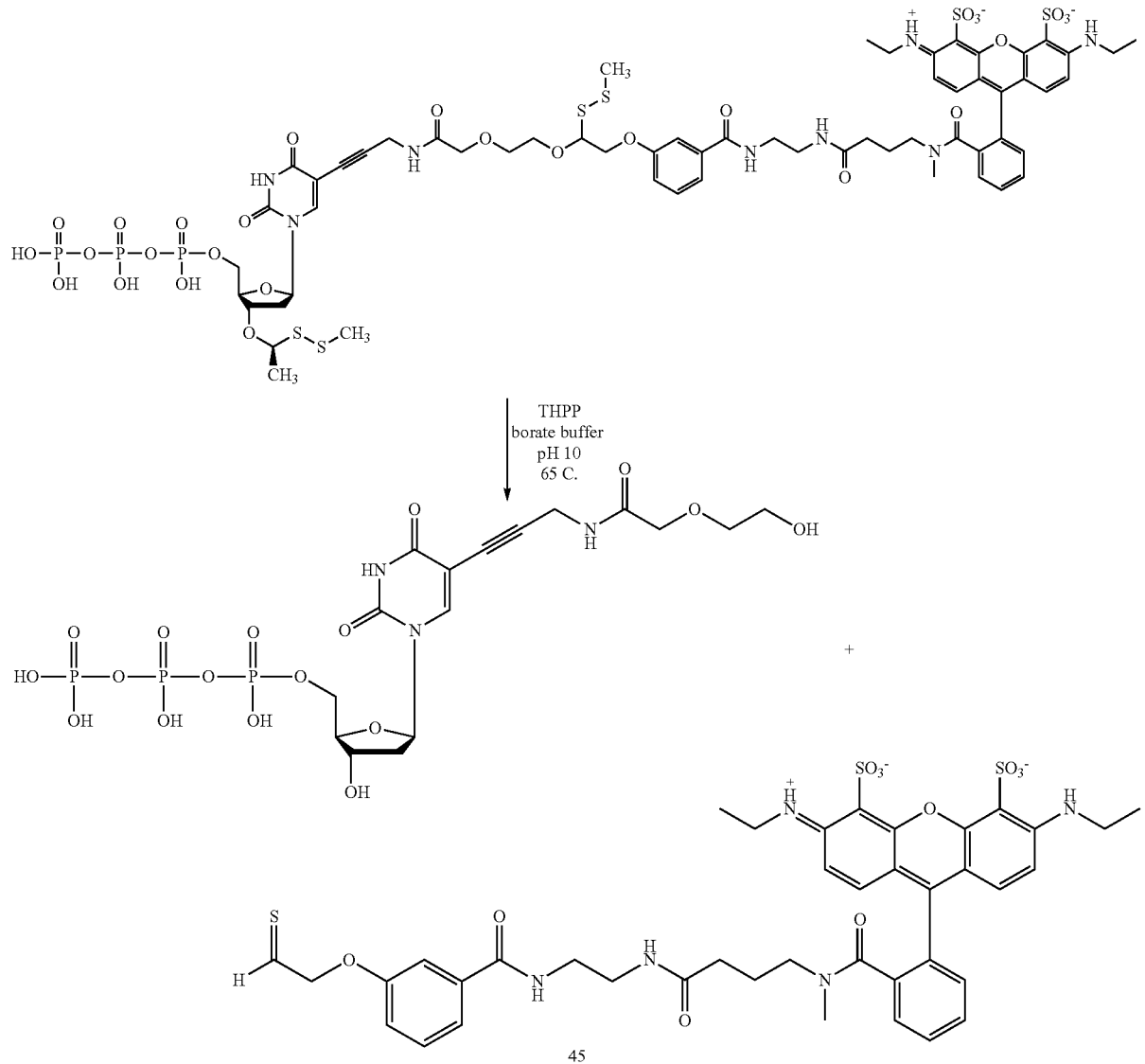

Minimal scar nucleotides. Following detecting and identifying the incorporated nucleotide (e.g., the nucleotide as described herein), the linker can be cleaved thus allowing the fluorophore to be removed. Cleavage may result in a "scar" moiety located on each of the detected nucleotides which may negatively impact incorporation of the subsequent nucleotide. Minimizing the scar length can improve sequencing results by allowing for more efficient nucleotide incorporation.

What is claimed is:

1. A compound having the formula:

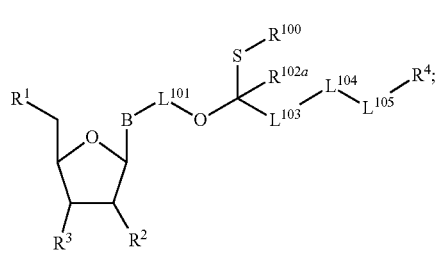

(I)

wherein

B is a divalent nucleobase;

$R^1$ is a polyphosphate moiety, a monophosphate moiety, or a nucleic acid moiety;

$R^2$ is a hydrogen or —OH;

$R^3$ is an —O-polymerase-compatible cleavable moiety, —OH, —ONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F;

$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is —SR$^{102}$ or —CN;

$R^{102}$ is substituted or unsubstituted alkyl, hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{102a}$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^4$ is a detectable moiety.

2. The compound of claim 1, wherein R$^3$ is an —O-polymerase-compatible cleavable moiety.

3. The compound of claim 1, wherein the polymerase-compatible cleavable moiety is -(substituted or unsubstituted alkylene)-SS-(unsubstituted alkyl).

4. The compound of claim 1, wherein the polymerase-compatible cleavable moiety is -(halo-substituted or unsubstituted C$_1$-C$_3$ alkylene)-SS-(unsubstituted C$_1$-C$_4$ alkyl).

5. The compound of claim 1, wherein the polymerase-compatible cleavable moiety is:

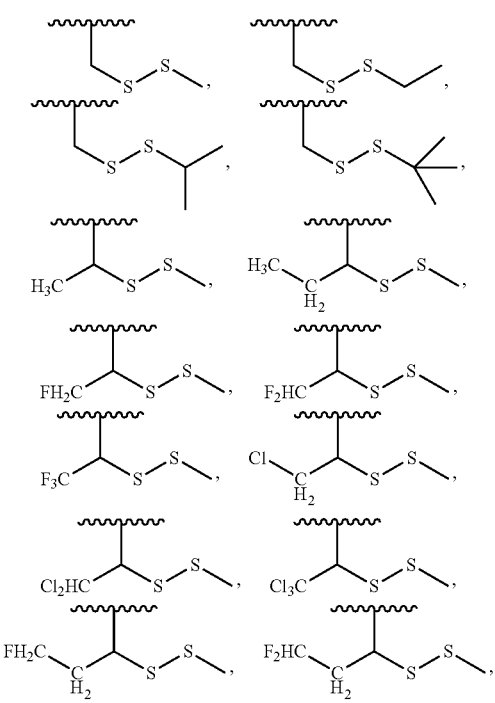

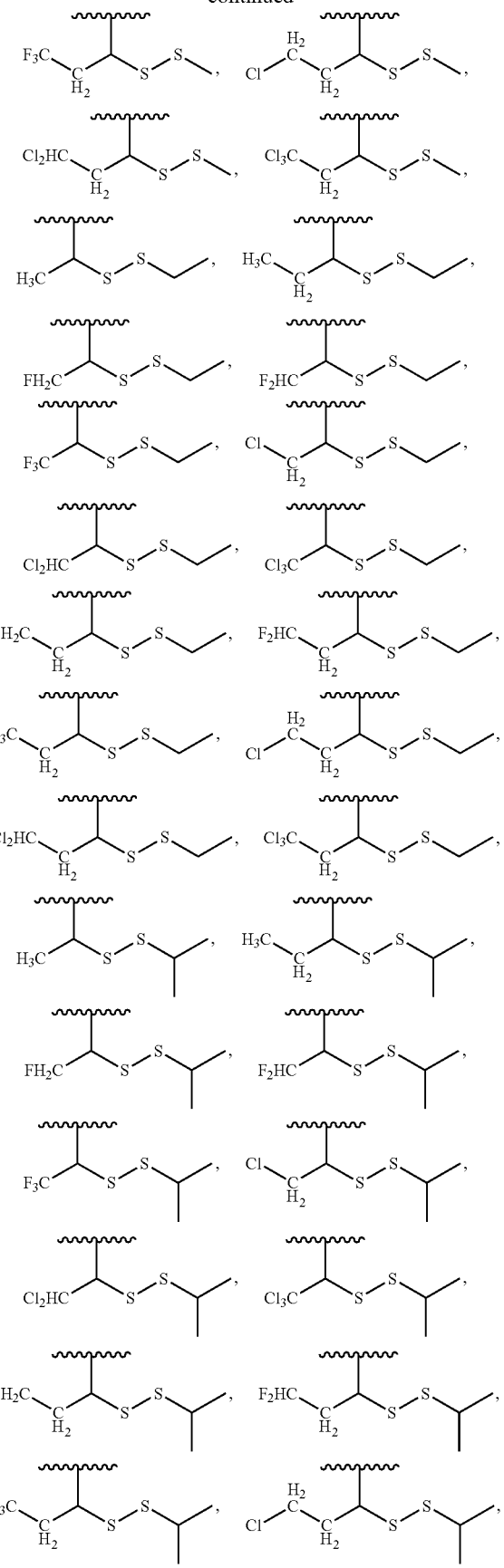

-continued

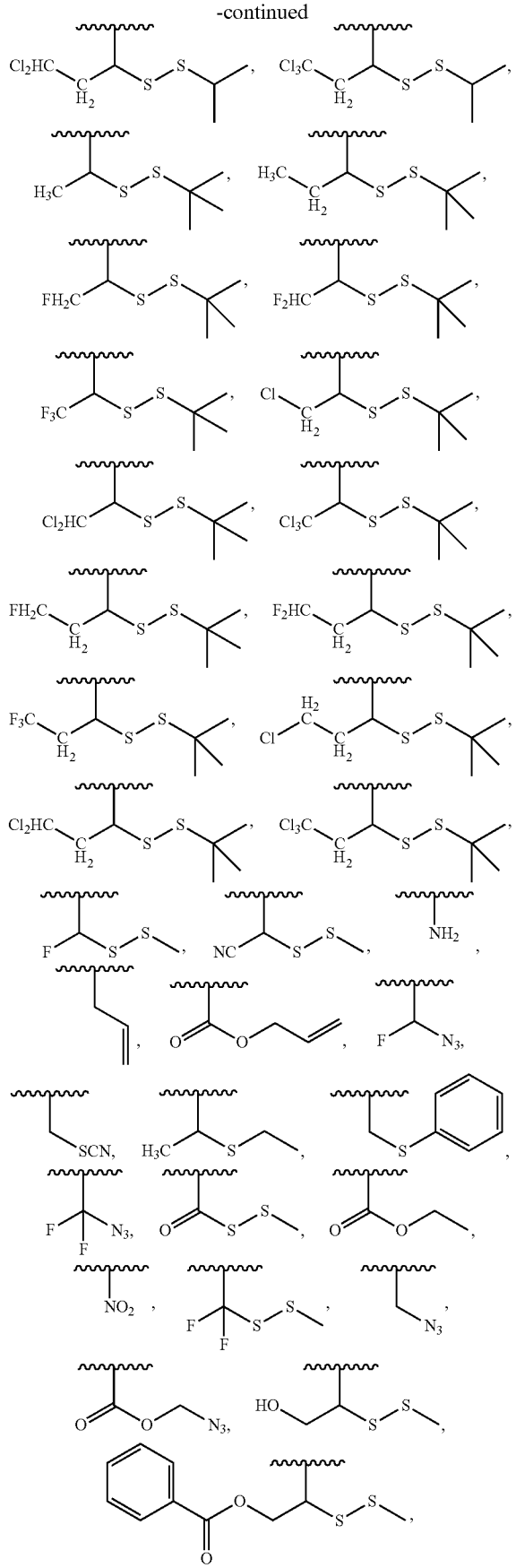

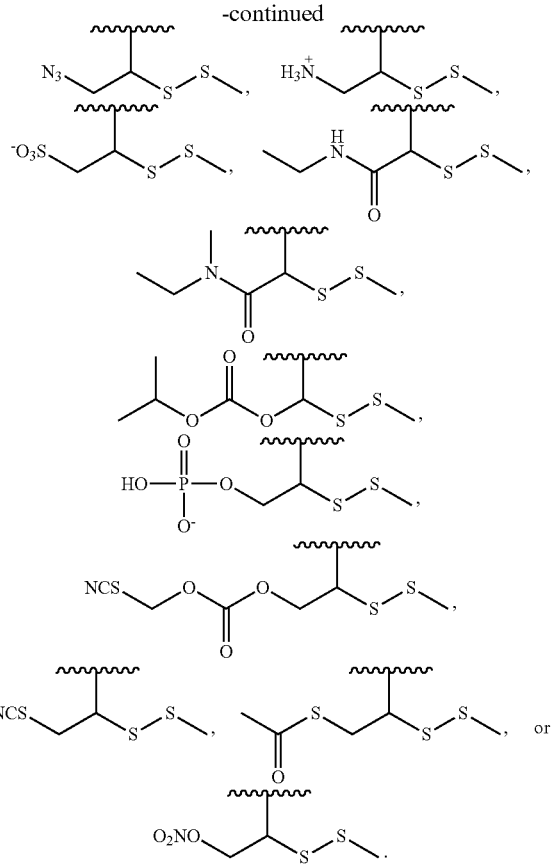

6. The compound of claim 1, wherein the polymerase-compatible cleavable moiety is:

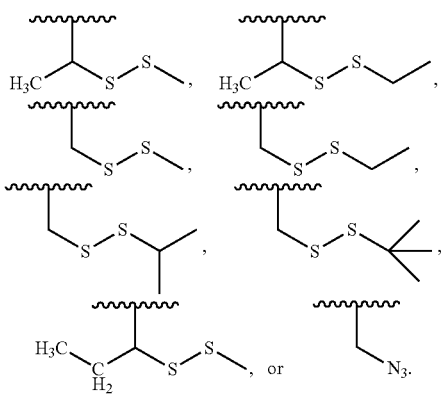

7. The compound of claim 1, wherein $R^1$ is a monophosphate moiety or a polyphosphate moiety.

8. The compound of claim 1, wherein
B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

9. The compound of claim 1, wherein;

$L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ and $R^{102a}$ are independently hydrogen or unsubstituted alkyl.

10. The compound of claim 1, wherein $L^{101}$ is a substituted or unsubstituted $C_1$-$C_4$ alkylene or substituted or unsubstituted 8 to 20 membered heteroalkylene;

$L^{103}$ is a bond or substituted or unsubstituted 2 to 10 membered heteroalkylene;

$L^{104}$ is a bond, substituted or unsubstituted 4 to 18 membered heteroalkylene, or substituted or unsubstituted phenylene;

$L^{105}$ is a bond or substituted or unsubstituted 4 to 18 membered heteroalkylene;

$R^{102}$ is unsubstituted $C_1$-$C_4$ alkyl; and $R^{102a}$ is hydrogen or unsubstituted methyl.

11. The compound of claim 1, wherein $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{104}$ is unsubstituted phenylene; and $R^{102}$ and $R^{102a}$ are independently hydrogen or unsubstituted alkyl.

12. The compound of claim 1, wherein $L^{101}$ is a substituted or unsubstituted $C_1$-$C_4$ alkylene or substituted or unsubstituted 8 to 20 membered heteroalkylene;

$L^{103}$ is a bond or substituted or unsubstituted 2 to 10 membered heteroalkylene;

$L^{104}$ is an unsubstituted phenylene;

$L^{105}$ is a bond or substituted or unsubstituted 4 to 18 membered heteroalkylene;

$R^{102}$ is unsubstituted $C_1$-$C_4$ alkyl; and $R^{102a}$ is hydrogen or unsubstituted methyl.

13. The compound of claim 1, wherein -($L^{101}$)-OC(SSR$^{102}$)(R$^{102a}$)-($L^{103}$)-($L^{104}$)-($L^{105}$)- is

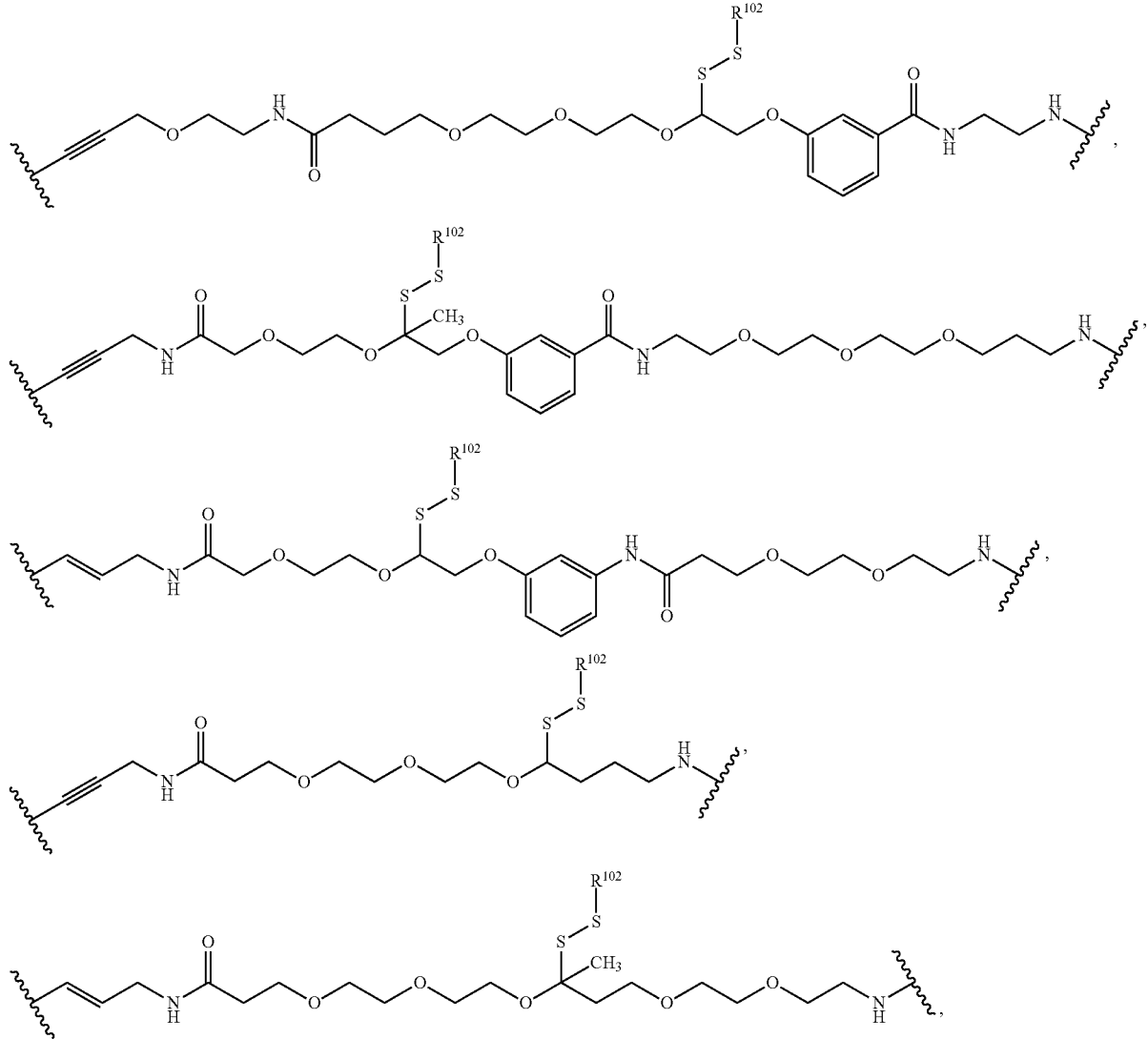

-continued
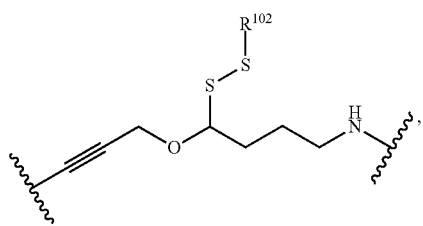
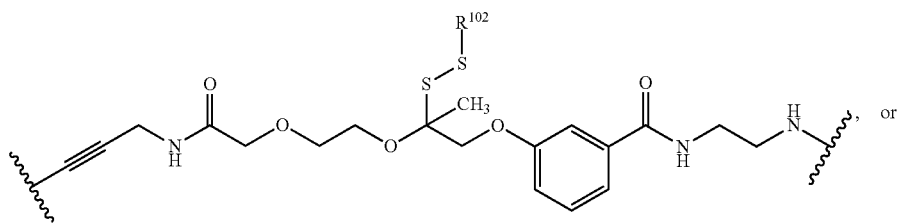, or
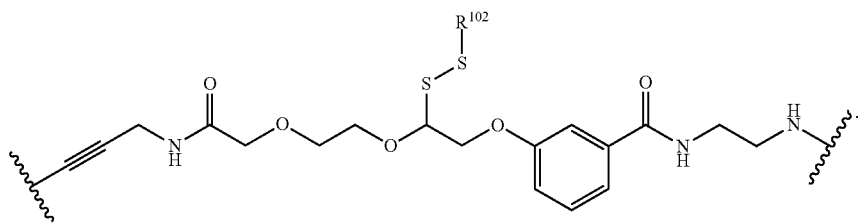
14. The compound of claim 1, wherein -(L$^{101}$)-OC(SSR$^{102}$)(R$^{102a}$)-(L$^{103}$)-(L$^{104}$)-(L$^{105}$)- is
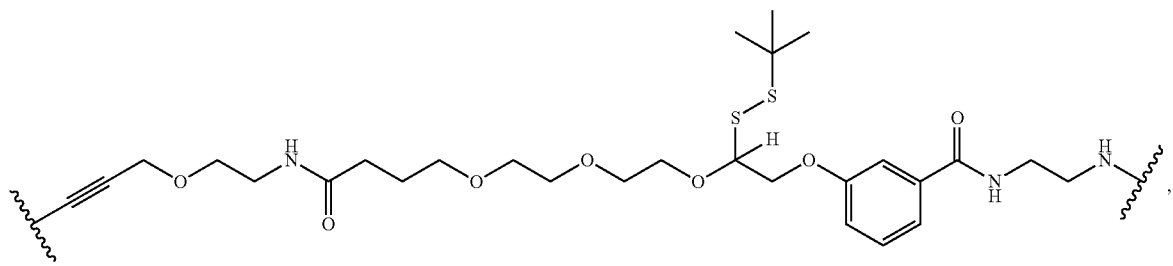,
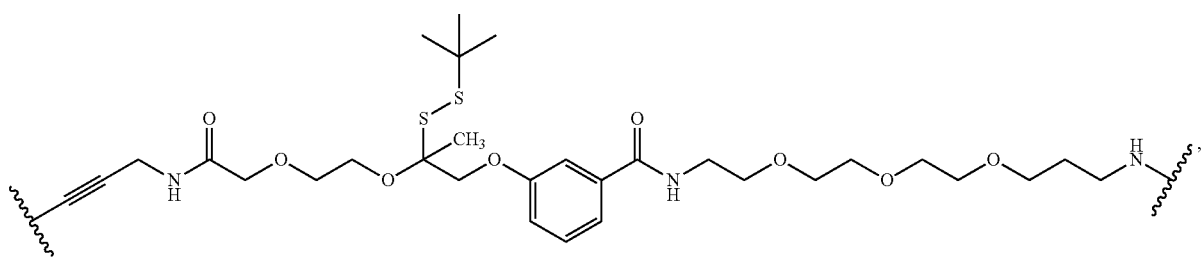,
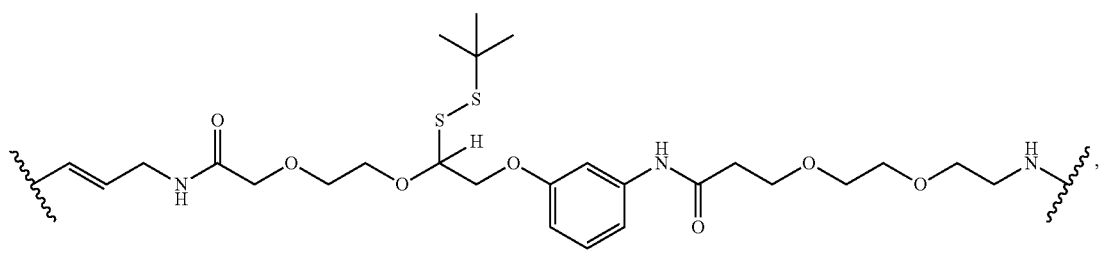, -continued

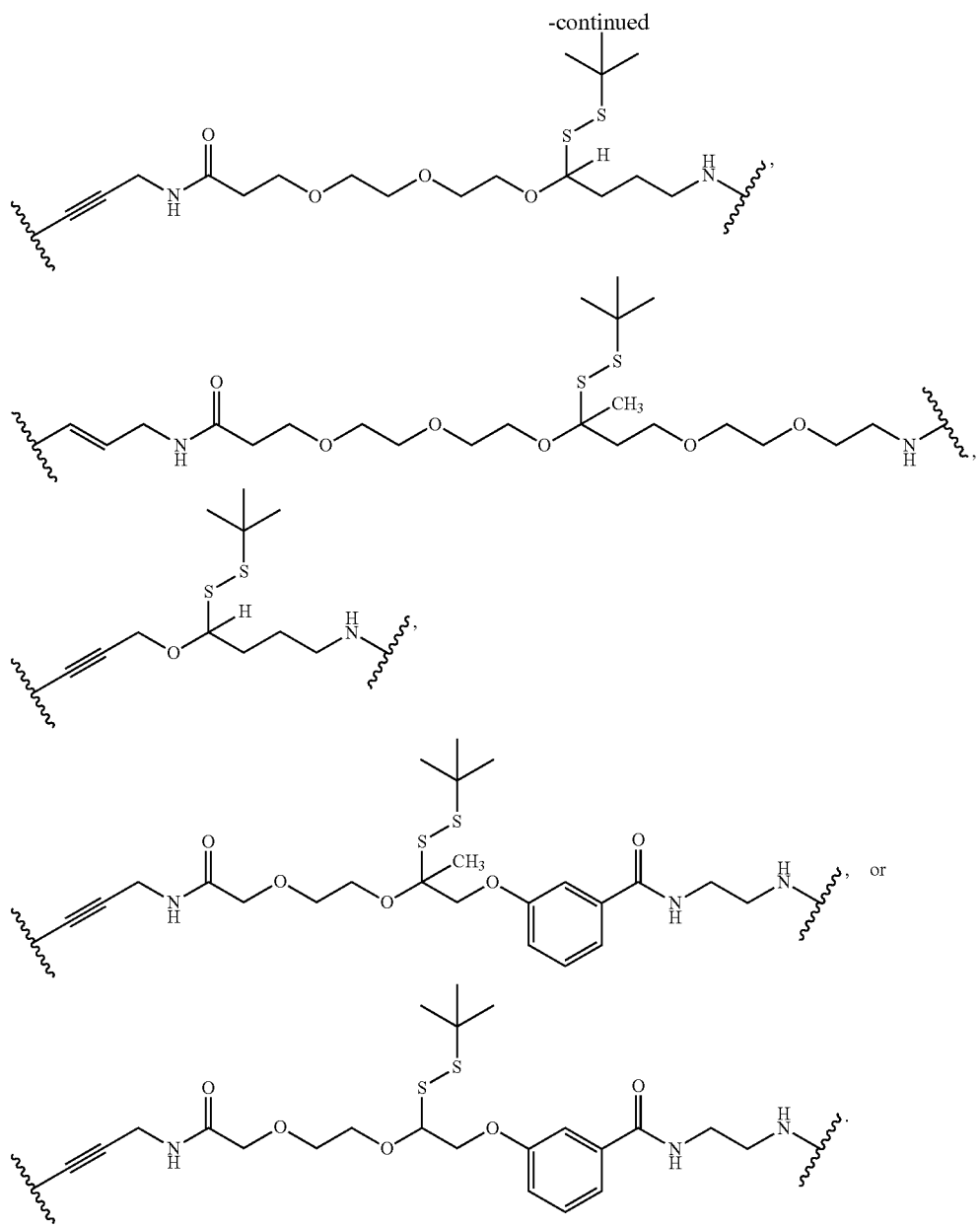

15. The compound of claim 1, wherein $R^4$ is a fluorescent dye moiety.

16. A method for sequencing a nucleic acid, comprising:
(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
(ii) detecting said unique detectable label of each incorporated compound, so as to thereby identify each incorporated compound in said extension strand, thereby sequencing the nucleic acid;
wherein each of said four different compounds is independently a compound of claim 1.

17. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of claim 1.

18. A nucleic acid polymerase complex comprising a nucleic acid polymerase, wherein said nucleic acid polymerase is bound to a compound of claim 1.

19. The compound of claim 1, having the formula

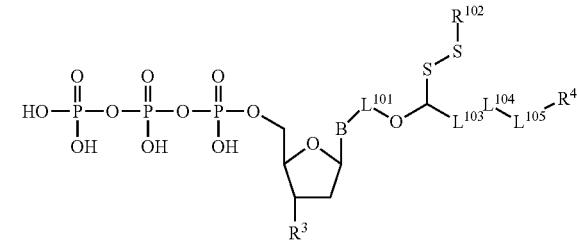

wherein $R^3$ is an —O-polymerase compatible cleavable moiety selected from the group consisting of

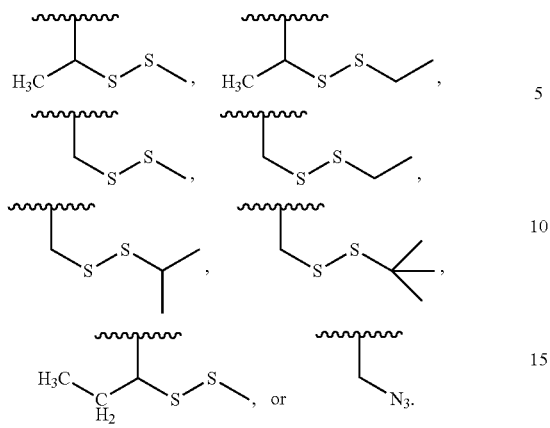
20. The compound of claim 19, wherein
$L^{101}$ is —CCCH$_2$—NHC(O)—(CH$_2$)$_c$(OCH$_2$CH$_2$)$_b$— wherein c is 1 and b is 1;
$L^{103}$ is —(CH$_2$CH$_2$O)$_d$— wherein d is 1, 2 or 3;
$L^{104}$ is an unsubstituted phenylene;
$L^{105}$ is C(O)NH—(CH$_2$)$_g$—NH wherein g is 0, 1, 2 or 3; and
$R^{102}$ is hydrogen or unsubstituted C$_1$-C$_4$ alkyl.
* * * * *